US008252810B2

(12) United States Patent  
Ozaki et al.

(10) Patent No.: US 8,252,810 B2  
(45) Date of Patent: Aug. 28, 2012

(54) BICYCLOAMINE DERIVATIVES

(75) Inventors: Fumihiro Ozaki, Tsukuba (JP); Motohiro Soejima, Tsukuba (JP); Tasuku Ishida, Tsukuba (JP); Yoshihiko Norimine, Tsukuba (JP); Nobuyuki Kurusu, Tsukuba (JP); Eriko Doi, Tsukuba (JP); Toshihiko Kaneko, Tsukuba (JP); Daiju Hasegawa, Tsukuba (JP); Kiyoaki Kobayashi, Tsukuba (JP); Noboru Yamamoto, London (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 635 days.

(21) Appl. No.: 12/368,069

(22) Filed: Feb. 9, 2009

(65) Prior Publication Data  
US 2009/0270369 A1 Oct. 29, 2009

Related U.S. Application Data

(60) Provisional application No. 61/028,378, filed on Feb. 13, 2008.

(30) Foreign Application Priority Data

Feb. 13, 2008 (JP) ................ P2008-031939

(51) Int. Cl.  
*A01N 43/42* (2006.01)  
*A61K 31/44* (2006.01)  
*C07D 221/02* (2006.01)  
(52) U.S. Cl. .................. 514/299; 546/112  
(58) Field of Classification Search .......... 546/112; 514/299  
See application file for complete search history.

(56) References Cited

U.S. PATENT DOCUMENTS

2003/0220368 A1 11/2003 Ozaki et al.  
2005/0020564 A1 1/2005 Atkinson et al.

FOREIGN PATENT DOCUMENTS

| EP | 1 908 752 A1 | 4/2008 |
|---|---|---|
| WO | WO 01/32179 * | 5/2001 |
| WO | WO-01/32179 A1 | 5/2001 |
| WO | WO-01/53288 A1 | 7/2001 |
| WO | WO-03/037274 A2 | 5/2003 |
| WO | WO-03/037890 A2 | 5/2003 |
| WO | WO-03/037900 A2 | 5/2003 |
| WO | WO 2004/076448 * | 9/2004 |
| WO | WO-2004/076448 A1 | 9/2004 |
| WO | WO-2005/080389 A1 | 9/2005 |
| WO | WO-2006/069125 A1 | 6/2006 |
| WO | WO-2006/082354 A1 | 8/2006 |
| WO | WO-2006/113875 A2 | 10/2006 |
| WO | WO-2006/132192 A1 | 12/2006 |
| WO | WO-2006/133104 A2 | 12/2006 |
| WO | WO 2007/007069 A1 | 1/2007 |
| WO | WO-2007/052123 A2 | 5/2007 |
| WO | WO-2007/083239 A1 | 7/2007 |
| WO | WO-2008/016811 A2 | 2/2008 |

OTHER PUBLICATIONS

Extended European Search Report dated Oct. 12, 2011 for the European Application No. 09710649.6.  
Soren H. Sindrup et al.; Efficacy of pharmacological treatments . . . ; Pain; No. 83, pp. 389-400, 1999.  
E. Kalso et al.; Systemic local-anaesthetic-type . . . ; European Journal of Pain; No. 2; pp. 3-14; 1998.  
Wade S. Kingery; A critical review of controlled clinical trials for . . . ; Pain; No. 73; pp. 123-139; 1997.  
Patrick Kwan et al.; The mechanisms of action of commonly used . . . ; Pharmacology & Therapeutics; No. 90; pp. 21-34; 2001.  
Gabriela V. Obrocea et al.; Clinical Predictors of Response to Lamotrigine . . . ; Society of Biogical Psychiatry; No. 51; pp. 253-260; 2002.  
Masaki Sakurai et al.; Positive symptoms in multiple sclerosis . . . ; Journal of the Neurological Sciences; No. 162; pp. 162-168; 1999.  
M. K. Atikeler et al.; Optimum usage of prilocaine-lidocaine . . . ; Andrologia; No. 34, pp. 356-359; 2002.  
M. Nieto-Barrera et al.; A comparison of monotherapy with lamotrigine . . . ; Epilepsy Research; No. 46; pp. 145-155; 2001.  
Keri Wellington et al.; Oxcarbazepine—An update of its efficacy in . . . ; CNS Drugs; No. 15; pp. 137-163; 2001.  
Charles P. Taylor et al.; Na$^+$ channels as targets for . . . ; Trends Pharmacol. Sci.; No. 16; pp. 309-316; 1995.  
J. M. Stutzmann et al.; The Na++ Channel Blocker . . . ; 31st Annual Meeting of Society for Neuroscience; Abstract 199.16; 2001. Armen N. Akopian et al.; A tetrodotoxin-resistant . . . ; Nature; vol. 379; pp. 257-262; 1996.  
Douglas K. Rabert et al.; A tetrodotoxin-resistant voltage-gated . . . ; Pain; No. 78; pp. 107-114; 1998.  
Armen N. Akopian et al.; The tetrodotoxin-resistant sodium channel SNS has a . . . ; Nature Neuroscience; vol. 2; No. 6; pp. 541-548; 1999.  
Response filed Jun. 25, 2012, in reply to the First Office Action issued in Chinese Patent Application No. 200980101797.1, with English translation.

* cited by examiner

*Primary Examiner* — Paul V. Ward  
(74) *Attorney, Agent, or Firm* — Birch, Stewart, Kolasch & Birch, LLP

(57) ABSTRACT

Compounds represented by formula (I) and pharmaceutically acceptable salts thereof have excellent sodium channel inhibitory action and are useful as therapeutic agents and analgesics for various kinds of neuralgia, neuropathy, epilepsy, insomnia, premature ejaculation and the like.

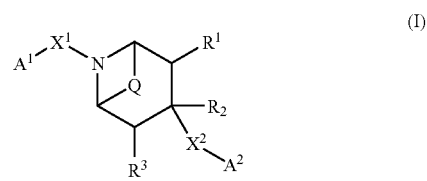

(I)

wherein Q represents ethylene, etc., $R^1$, $R^2$ and $R^3$ represent hydrogen, etc., $X^1$ represents $C_{1-6}$ alkylene, etc., $X^2$ represents $C_{1-6}$ alkylene, etc., $A^1$ represents a 5- to 6-membered heterocyclic group, etc., and $A^2$ represents $C_{6-14}$ aryl, etc.

9 Claims, No Drawings

BICYCLOAMINE DERIVATIVES

RELATED APPLICATIONS

This application claims priority to U.S. provisional application 61/028,378 filed on Feb. 13, 2008 as well as Japanese Patent Application 2008-031,939 filed on Feb. 13, 2008, both of which are herein incorporated by reference by in their entireties.

BACKGROUND OF THE INVENTION

1. Field of the Invention

The present invention relates to bicycloamine derivatives having sodium channel inhibitory action, and particularly 8-azabicyclo[3.2.1]octane or 9-azabicyclo[3.3.1]nonane derivatives or pharmaceutically acceptable salts thereof.

2. Related Background Art

Compounds having sodium channel inhibitory action are known to be useful as treatment for various types of neuralgia (for example, postherpetic neuralgia, diabetic neuralgia, HIV-induced neuralgia and the like).

Compounds having sodium channel inhibitory action include Lidocaine, Carbamazepine, Mexiletine, Amitriptyline and the like, which are already used as therapeutic agents for various types of neuralgia. For example, Lidocaine is used as a treatment for postherpetic neuralgia, and Carbamazepine is used as a treatment for trigeminal neuralgia.

It has also been reported that Mexiletine and Lidocaine are effective as analgesics (see Non-patent documents 1-3, for example).

The following pharmacological activity and therapeutic effects have also been reported for compounds having sodium channel inhibitory action, for diseases other than neuralgia.

(i) Compounds having sodium channel inhibitory action are used as treatments for epilepsy (Non-patent document 4).

(ii) Carbamazepine, used as an anticonvulsant, is effective as a treatment for manic-depressive psychosis (Non-patent document 5).

(iii) Lidocaine and Mexiletine are effective for various symptoms of multiple sclerosis (Non-patent document 6).

(iv) Lidocaine is effective as a treatment for premature ejaculation (Non-patent document 7).

(v) Carbamazepine and Oxocarbazepine used as anticonvulsants also have somnolent action (Non-patent documents 8 and 9), and sodium channel inhibitors can be used as treatments for insomnia.

(vi) Various animal neuropathy models have demonstrated action by sodium channel inhibitors, and suggested protective action against cerebrovascular disease and against neuropathy associated with head injury or spinal cord injury (Non-patent document 10).

(vii) The effectiveness of sodium channel inhibitors in animal models of Parkinson's disease has been reported at an academic meeting (Non-patent document 11).

While sodium channel inhibitors are thus effective as treatments for the diseases mentioned above, sodium channels are also present in non-neuronal tissue such as in the muscles and heart, such that they exhibit side-effects when systemically administered.

Progress in molecular biology has brought to light 10 different sodium channel subtypes with different α-subunits that form the pores of voltage-gated sodium channels. Of these subtypes, Nav1.8 is a tetrodotoxin (TTX)-resistant sodium channel localized in the small neurons of the dorsal root ganglion (C-fibers) that are associated with nerve sensation, and it is referred to as sensory neuron specific sodium channel (SNS) SCN10A or PN3 (Non-patent documents 12 and 13). It has been reported that Nav1.8 knockout mice have an increased nociception threshold for mechanical stimulation (Non-patent document 14), and that administration of antisense DNA for Nav1.8 to neurogenic pain or inflammatory pain models attenuates hyperesthesia and dysesthesia. Therefore, Nav1.8 inhibitors are promising as drugs capable of exhibiting analgesic effects against diseases of neurogenic pain including pain, numbness, burning sensation and dull pain, or nociceptive pain, in which C-fibers are involved. Also, since Nav1.8 is not expressed in non-neuronal tissue or central nerve, drugs that selectively inhibit Nav1.8 are considered to have potential as drugs with no side-effects in non-neuronal tissue or central nerve.

Low molecular compounds having sodium channel inhibitory action have been reported as Nav1.8 inhibitors, but these compounds have different structures than the compounds of the invention (see Patent documents 2-10, for example).

Also, the following 3-azabicyclo[3.3.1]nonane derivative has been reported, and it has a structure similar to a compound of the invention (Patent document 1, Example 129).

[Chemical Formula 1]

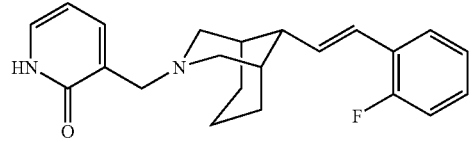

This compound has an inhibitory activity against sodium channels in cultured rat hippocampus but its inhibitory activity against ectopic firing is described as inadequate. No bicycloamine compounds other than the 3-azabicyclo[3.3.1]nonane derivative are disclosed in the patent document. Moreover, 8-azabicyclo[3.2.1]octane derivatives and 9-azabicyclo[3.3.1]nonane derivatives having sodium channel inhibitory action are still unknown.

[Patent document 1] WO01/053288
[Patent document 2] US20050020564
[Patent document 3] WO03/037274
[Patent document 4] WO03/037890
[Patent document 5] WO03/037900
[Patent document 6] WO06/082354
[Patent document 7] WO06/113875
[Patent document 8] WO06/132192
[Patent document 9] WO07/052,123
[Patent document 10] WO07/083,239
[Non-patent document 1] Sindrup et al., Pain, 83:389-400, 1999
[Non-patent document 2] Kalso et al., Eur. J. Pain, 2:3-14, 1998
[Non-patent document 3] Kingery et al., Pain, 73:123-139, 1997
[Non-patent document 4] Kwan et al., Pharmacol. Ther., 90:21-34, 2001
[Non-patent document 5] Obrocea et al., Biol. Psychiatry, 51:253-260, 2002
[Non-patent document 6] Sakurai et al., J. Neurol. Sci., 162: 162-168, 1999
[Non-patent document 7] Atikeler et al., Andrologia, 34:356-359, 2002
[Non-patent document 8] Nieto-Barrera et al., Epilepsy, 46:145-155, 2002

[Non-patent document 9] Wellington et al., CNS Drugs, 15:137-163, 2001
[Non-patent document 10] Taylor et al., Trends Pharmacol. Sci., 16:309-316, 1995
[Non-patent document 11] Stutzmann et al., 31st Annual Meeting of Society for Neuroscience, Abstract 199.16, 2001
[Non-patent document 12] Akopian et al., Nature, 379:257-262, 1996
[Non-patent document 13] Rabert et al., Pain, 78:107-114, 1998
[Non-patent document 14] Akopian et al., Nat. Neurosci., 2:541-548, 1999

SUMMARY OF THE INVENTION

As mentioned above, a demand exists for drugs that exhibit excellent sodium channel inhibitory action, satisfactory pharmacological activity as drugs, and clinical efficacy. It is therefore an object of the present invention to find and discover compounds with such excellent sodium channel inhibitory action.

[Means For Solving The Problem]

The present inventors have conducted a great deal of diligent and avid research in light of the circumstances described above, and as a result novel bicycloamine compounds that are safe and exhibit excellent sodium channel inhibitory action have been discovered.

Specifically, the present invention provides the following [1]-[22].

[1] A compound represented by the formula (I) or pharmaceutically acceptable salt thereof:

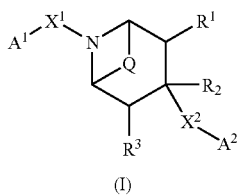

(I)

wherein

Q represents ethylene or trimethylene, $R^1$, $R^2$ and $R^3$ each independently represents hydrogen, halogen or hydroxy, or $C_{1-6}$ alkyl or $C_{1-6}$ alkoxy each optionally having one or more substituents selected from Group A, $X^1$ represents cyclopropane-1,2-dimethylene, or $C_{1-6}$ alkylene or $C_{2-6}$ alkenylene each optionally having one or more substituents selected from Group B, $X^2$ represents $C_{1-6}$ alkylene, $C_{1-6}$ alkyleneoxy, Oxy-$C_{1-6}$ alkylene, $C_{1-6}$ alkylenethio, thio-$C_{1-6}$ alkylene, $C_{1-6}$ alkyleneoxy-$C_{1-6}$ alkylene, $C_{2-6}$ alkenylene, oxycarbonyl, carbonyloxy, $C_{1-6}$ alkyleneamino, amino-$C_{1-6}$ alkylene, aminocarbonyl, carbonylamino, $C_{1-6}$ alkyleneaminocarbonyl, carbonylamino-$C_{1-6}$ alkylene, oxycarbonylamino, aminocarbonyloxy or ureylene each optionally having one or more substituents selected from Group C, $A^1$ represents a 5- to 6-membered heterocyclic group or an 8- to 11-membered fused heterocyclic group each optionally having one or more substituents selected from Group D, $A^2$ represents $C_{3-8}$ cycloalkyl, $C_{6-14}$ aryl, a 5- to 6-membered aromatic heterocyclic group or a 9- to 11-membered benzo-fused heterocyclic group each optionally having one or more substituents selected from Group E, Group A consists of halogen, hydroxy and $C_{1-6}$ alkoxy, Group B consists of halogen, hydroxy, oxo, cyano, amino, $C_{1-6}$ alkyl, halo-$C_{1-6}$ alkyl, hydroxy-$C_{1-6}$ alkyl, $C_{1-6}$ alkoxy-$C_{1-6}$ alkyl, $C_{1-6}$ alkoxy, $C_{1-6}$ alkylcarbonylamino, $C_{1-6}$ alkoxycarbonylamino, $C_{1-6}$ alkylsulfonylamino, hydroxyimino and $C_{1-6}$ alkoxyimino, Group C consists of halogen, hydroxy, $C_{1-6}$ alkoxy, oxo and $C_{1-6}$ alkyl, Group D consists of halogen, hydroxy, and amino optionally having one or two $C_{1-6}$ alkyl, and $C_{1-6}$ alkyl, $C_{2-6}$ alkenyl, $C_{3-8}$ cycloalkyl, $C_{3-8}$ cycloalkylmethyl, $C_{1-6}$ alkylthio, C, 6 alkylsulfonyl, $C_{6-10}$ aryl, $C_{7-11}$ aralkyl and a 5- to 6-membered aromatic heterocyclic group each optionally having one or more substituents selected from Group D1, Group D1 consists of halogen, hydroxy, $C_{1-6}$ alkyl and $C_{1-6}$ alkoxy, Group E consists of halogen, cyano, hydroxy, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl, and $C_{6-10}$ aryl, a 5- to 6-membered heterocyclic group and a 5- to 6-membered aromatic heterocyclic group each optionally having one or more substituents selected from Group E1, and Group E1 consists of halogen, $C_{1-6}$ alkyl, halo-$C_{1-6}$ alkyl, $C_{1-6}$ alkoxy and halo-$C_{1-6}$ alkoxy.

[2] The compound or pharmaceutically acceptable salt thereof of [1], wherein $A^1$ is a group represented by the formula:

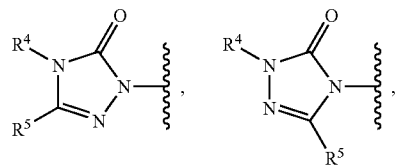

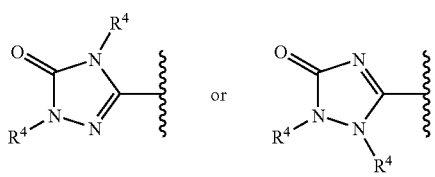

wherein $R^4$ represents hydrogen or $C_{1-6}$ alkyl, $C_{2-6}$ alkenyl, $C_{3-8}$ cycloalkyl, $C_{3-8}$ cycloalkylmethyl, $C_{6-10}$ aryl, $C_{7-11}$ aralkyl or a 5- to 6-membered aromatic heterocyclic group each optionally having one or more substituents selected from Group D1, and $R^5$ represents hydrogen, halogen, hydroxy, or amino optionally having one or two $C_{1-6}$ alkyl, or $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl or a 5- to 6-membered aromatic heterocyclic group each optionally having one or more substituents selected from Group D1, or a group represented by the formula each optionally having one or more substituents selected from Group D1:

[Chemical Formula 4]

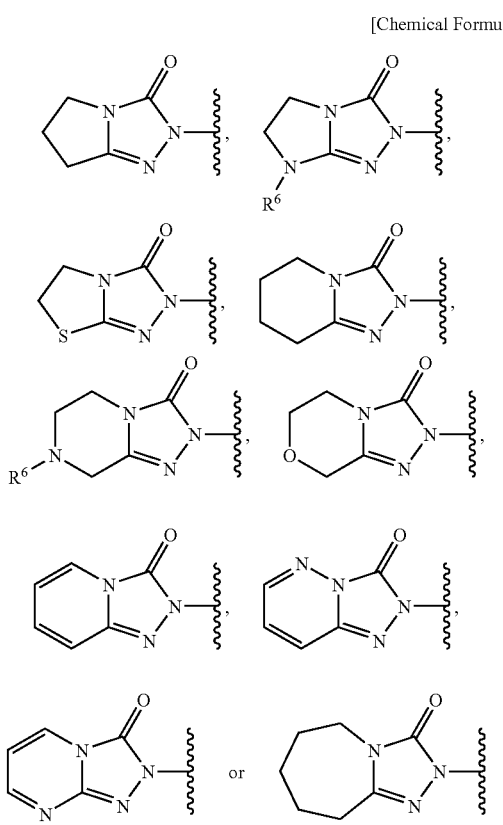

wherein $R^6$ represents hydrogen or $C_{1-6}$ alkyl, and

Group D1 consists of halogen, hydroxy, $C_{1-6}$ alkyl and $C_{1-6}$ alkoxy.

[3] The compound or pharmaceutically acceptable salt thereof of [1], wherein $A^1$ is a group represented by the formula:

[Chemical Formula 5]

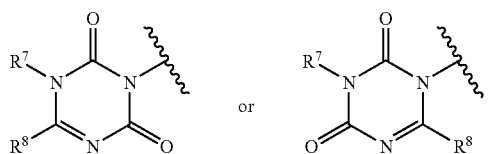

wherein $R^7$ represents hydrogen or $C_{1-6}$ alkyl, $C_{2-6}$ alkenyl, $C_{3-8}$ cycloalkyl, $C_{3-8}$ cycloalkylmethyl, $C_{6-10}$ aryl, $C_{7-11}$ aralkyl or a 5- to 6-membered aromatic heterocyclic group each optionally having one or more substituents selected from Group D1, and $R^8$ represents hydrogen, halogen, hydroxy or amino optionally having one or two $C_{1-6}$ alkyl, or $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl or a 5- to 6-membered aromatic heterocyclic group each optionally having one or more substituents selected from Group D1, or a group represented by the formula each optionally having one or more substituents selected from Group D1:

[Chemical Formula 6]

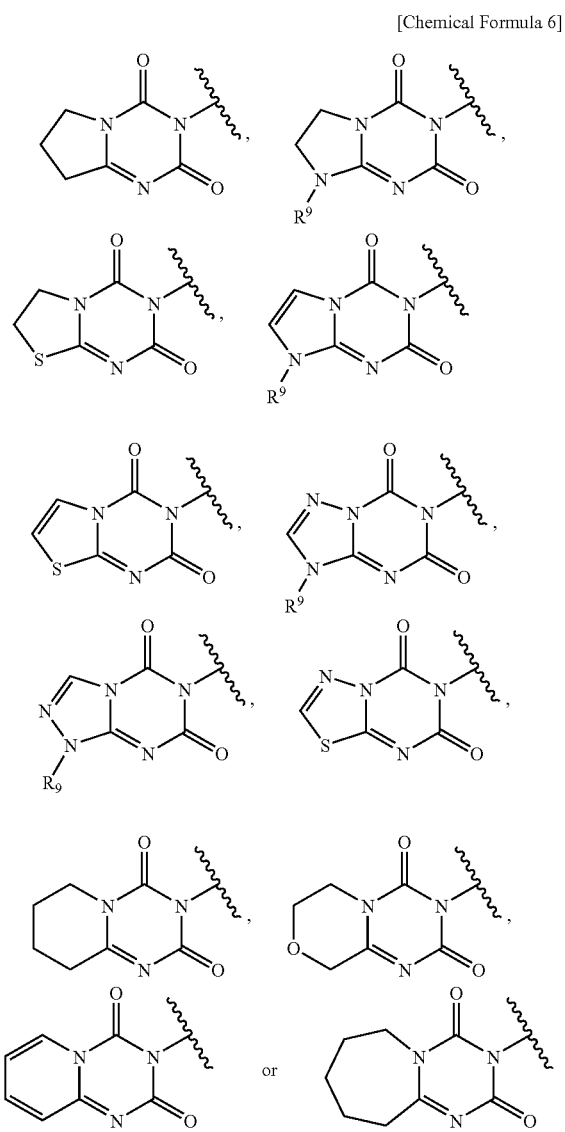

wherein $R^9$ represents hydrogen or $C_{1-6}$ alkyl, and

Group D1 consists of halogen, hydroxy, $C_{1-6}$ alkyl and $C_{1-6}$ alkoxy.

[4] The compound or pharmaceutically acceptable salt thereof of [1], wherein $A^1$ is a group represented by the formula:

[Chemical Formula 7]

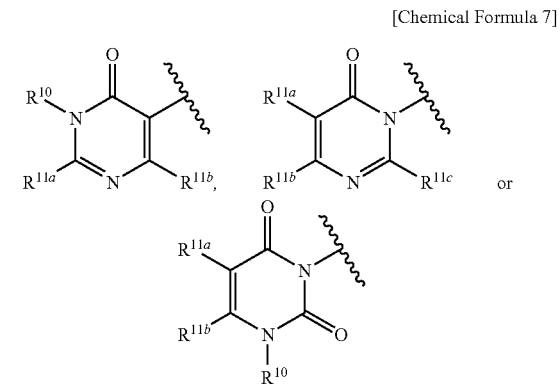

wherein $R^{10}$ represents hydrogen or $C_{1-6}$ alkyl, $C_{2-6}$ alkenyl, $C_{3-8}$ cycloalkyl, $C_{3-8}$ cycloalkylmethyl, $C_{6-10}$ aryl, $C_{7-11}$ aralkyl or a 5- to 6-membered aromatic heterocyclic group each optionally having one or more substituents selected from Group D1, and $R^{11a}$, $R^{11b}$ and $R^{11c}$ each independently represents hydrogen, halogen, hydroxy or amino optionally having one or two $C_{1-6}$ alkyl, or $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl or a 5- to 6-membered aromatic heterocyclic group each optionally having one or more substituents selected from Group D1, or a group represented by the formula optionally having one or more substituents selected from Group D1:

[Chemical Formula 8]

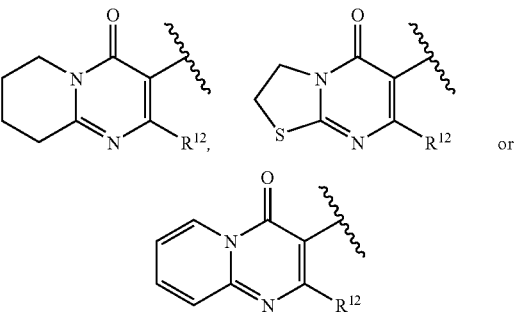

wherein $R^{12}$ represents hydrogen or $C_{1-6}$ alkyl, and

Group D1 consists of halogen, hydroxy, $C_{1-6}$ alkyl and $C_{1-6}$ alkoxy.

[5] The compound or pharmaceutically acceptable salt thereof of [1], wherein $A^1$ is a group represented by the formula optionally having one or more substituents selected from Group D1:

[Chemical Formula 9]

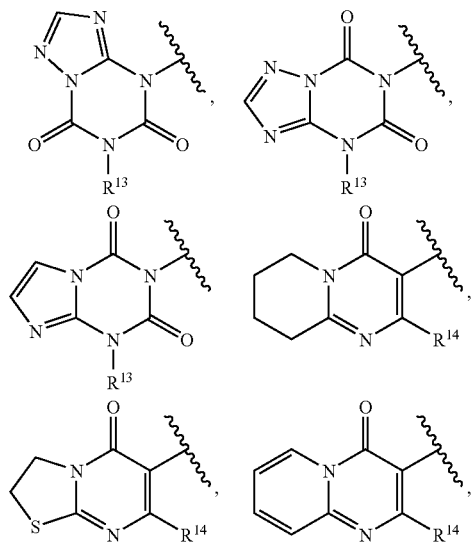

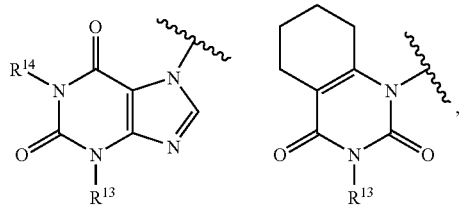

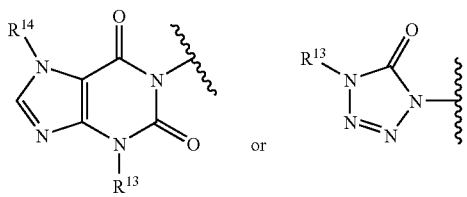

wherein $R^{13}$ and $R^{14}$ each independently represent hydrogen, $C_{1-6}$ alkyl or $C_{6-10}$ aryl, and Group D1 consists of halogen, hydroxy, $C_{1-6}$ alkyl and $C_{1-6}$ alkoxy.

[6] The compound or pharmaceutically acceptable salt thereof of [1], wherein $A^2$ is phenyl, thienyl, benzothienyl or naphthyl each optionally having one or more substituents selected from Group E2, Group E2 consists of halogen, cyano, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl, and phenyl, furyl, pyridyl, pyrazinyl, pyrrolidinyl, piperidinyl and morpholinyl each optionally having one or more substituents selected from Group E3, and Group E3 consists of halogen, $C_{1-6}$ alkyl, halo-$C_{1-6}$ alkyl, $C_{1-6}$ alkoxy and halo-$C_{1-6}$ alkoxy.

[7] The compound or pharmaceutically acceptable salt thereof of [1], wherein $X^2$ is $C_{1-6}$ alkylene, $C_{1-6}$ alkyleneoxy or oxy-$C_{1-6}$ alkylene each optionally having one or more substituents selected from Group C1, and Group C1 consists of halogen, hydroxy, $C_{1-6}$ alkoxy, oxo and $C_{1-6}$ alkyl.

[8] The compound or pharmaceutically acceptable salt thereof of [1], wherein Q is ethylene.

[9] The compound or pharmaceutically acceptable salt thereof of [1], wherein $A^1$ is a group represented by the formula:

[Chemical Formula 10]

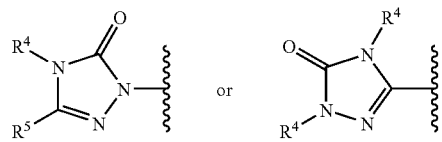

wherein $R^4$ and $R^5$ have the same definitions as in [2],
or a group represented by the formula optionally having one or more substituents selected from Group D1:

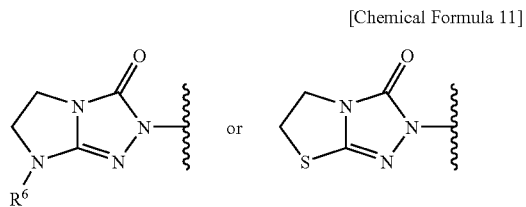

[Chemical Formula 11]

wherein $R^6$ has the same definition as in [2], and
Group D1 consists of halogen, hydroxy, $C_{1-6}$ alkyl and $C_{1-6}$ alkoxy.

[10] The compound or pharmaceutically acceptable salt thereof of [9], wherein
$X^1$ is $C_{2-6}$ alkylene optionally having one or more substituents selected from Group B1,
Group B1 consists of halogen, amino, acetamide, methoxyacetamide, methanesulfonylamide, hydroxy, oxo, cyano, $C_{1-6}$ alkyl, hydroxy-$C_{1-6}$ alkyl, halo-$C_{1-6}$ alkyl, $C_{1-6}$ alkoxy-$C_{1-6}$ alkyl and $C_{1-6}$ alkoxy,
$X^2$ is $C_{1-6}$ alkylene, $C_{1-6}$ alkyleneoxy or oxy-$C_{1-6}$ alkylene each optionally having one or more substituents selected from Group C1,
Group C1 consists of halogen, hydroxy, $C_{1-6}$ alkoxy, oxo and $C_{1-6}$ alkyl,
$A^2$ is phenyl or thienyl each optionally having one or more substituents selected from Group E2, and
Group E2 consists of halogen, cyano, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl.

[11] The compound or pharmaceutically acceptable salt thereof of [1], wherein
$A^1$ is a group represented by the formula:

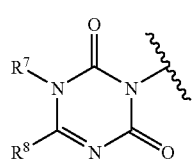

[Chemical Formula 12]

wherein $R^7$ and $R^8$ have the same definitions as in [3],
or a group represented by the formula optionally having one or more substituents selected from Group D1:

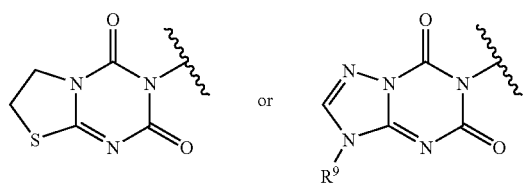

[Chemical Formula 13]

wherein $R^9$ has the same definition as in [3], and
Group D1 consists of halogen, hydroxy, $C_{1-6}$ alkyl and $C_{1-6}$ alkoxy.

[12] The compound or pharmaceutically acceptable salt thereof of [11], wherein
$X^1$ is $C_{2-6}$ alkylene optionally having one or more substituents selected from Group B1,
Group B1 consists of halogen, amino, acetamide, methoxyacetamide, methanesulfonylamide, hydroxy, oxo, cyano, $C_{1-6}$ alkyl, hydroxy-$C_{1-6}$ alkyl, halo-$C_{1-6}$ alkyl, $C_{1-6}$ alkoxy-$C_{1-6}$ alkyl and $C_{1-6}$ alkoxy,
$X^2$ is $C_{1-6}$ alkylene, $C_{1-6}$ alkyleneoxy or oxy-$C_{1-6}$ alkylene each optionally having one or more substituents selected from Group C1,
Group C1 consists of halogen, hydroxy, $C_{1-6}$ alkoxy, oxo and $C_{1-6}$ alkyl,
$A^2$ is phenyl or thienyl each optionally having one or more substituents selected from Group E2,
Group E2 consists of halogen, cyano, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and C2-7 acyl.

[13] The compound or pharmaceutically acceptable salt thereof of [1], wherein the compound represented by formula (I) is a compound represented by the formula:

[Chemical Formula 14]

wherein
$Y^1$ and $Y^2$ each independently represents hydrogen, halogen, hydroxy, $C_{1-6}$ alkyl, halo-$C_{1-6}$ alkyl, $C_{1-6}$ alkoxy-$C_{1-6}$ alkyl, $C_{1-6}$ alkoxy or halo-$C_{1-6}$ alkoxy,
$X^1$ represents $C_{2-6}$ alkylene optionally having one or more substituents selected from the group consisting of halogen, amino, acetamide, methoxyacetamide, methanesulfonylamide, hydroxy, oxo, cyano, $C_{1-6}$ alkyl, hydroxy-$C_{1-6}$ alkyl, halo-$C_{1-6}$ alkyl, $C_{1-6}$ alkoxy-$C_{1-6}$ alkyl and $C_{1-6}$ alkoxy,
$X^2$ represents $C_{1-6}$ alkylene, $C_{1-6}$ alkyleneoxy or oxy-$C_{1-6}$ alkylene each optionally having one or more substituents selected from the group consisting of halogen, hydroxy, $C_{1-6}$ alkoxy, oxo and $C_{1-6}$ alkyl, and
$R^4$ and $R^5$ have the same definitions as in [2].

[14] The compound or pharmaceutically acceptable salt thereof of [1], wherein the compound represented by formula (I) is a compound represented by the formula:

[Chemical Formula 15]

wherein $Y^1$, $Y^2$, $X^1$ and $X^2$ have the same definitions as in [13], and
$R^7$ and $R^8$ have the same definitions as in [3].

[15] The compound or pharmaceutically acceptable salt thereof of [13], wherein
$X^1$ is $C_{2-6}$ alkylene optionally having one or more substituents selected from Group B2, and
Group B2 consists of halogen and hydroxy.

[16] The compound or pharmaceutically acceptable salt thereof of [14], wherein
$X^1$ is $C_{2-6}$ alkylene optionally having one or more substituents selected from Group B2, and
Group B2 consists of halogen and hydroxy.
[17] A pharmaceutical composition comprising the compound or pharmaceutically acceptable salt thereof of [1] and a pharmaceutically acceptable carrier.
[18] The pharmaceutical composition of [17], which is a sodium channel inhibitor.
[19] The pharmaceutical composition of [17], which is an analgesic agent.
[20] The pharmaceutical composition of [17], which is a therapeutic agent for neuralgia.
[21] The pharmaceutical composition of [17], which is a therapeutic agent for diabetic neuralgia, HIV-induced neuralgia, postherpetic neuralgia, trigeminal neuralgia, stump pain, post-spinal cord injury pain, thalamic pain or post-apoplectic pain.
[22] The pharmaceutical composition of [17], which is a therapeutic agent for neuropathy, epilepsy, insomnia or premature ejaculation.

EFFECT OF THE INVENTION

The compounds represented by formula (I) of the invention have excellent sodium channel inhibitory action, and the invention can therefore provide novel bicycloamine compounds and pharmaceutically acceptable salts thereof that have high utility as drugs when comprehensively considered from the viewpoint of pharmacological activity, as well as novel pharmaceutical compositions comprising the same. The compounds of the invention and pharmaceutical compositions comprising the same can exhibit excellent therapeutic effect for diseases for which sodium channel inhibition is effective, and are promising as therapeutic agents and analgesics for various kinds of neuralgia (for example, diabetic neuralgia, HIV-induced neuralgia, postherpetic neuralgia, trigeminal neuralgia, stump pain, post-spinal cord injury pain, thalamic pain and post-apoplectic pain), neuropathy, epilepsy, insomnia, premature ejaculation and the like.

DESCRIPTION OF THE PREFERRED EMBODIMENTS

The meanings of the terms and symbols used throughout the present specification will now be explained, followed by a more detailed description of the invention.

Throughout the present specification, the structural formulas for the compounds will show only one specific isomer for convenience, but the invention includes all isomers such as geometric isomers, optical isomers based on asymmetric carbons, stereoisomers, tautomers and the like, that are implied by the compound structures, as well as isomer mixtures thereof, and the compounds may therefore be any of the isomers or mixtures thereof, without being limited to the formulas shown for convenience. Thus, the compounds of the invention may have asymmetric carbon atoms in the molecule and thus exist as optically active or racemic forms, all of which are included without limitations according to the invention. Polymorphic crystals may also exist, and there may be used any simple crystal form or crystal mixture without any restrictions, while the compounds of the invention also include both anhydrate and hydrate forms. In addition, so-called metabolites produced by in vivo decomposition of the compounds of the invention are also included within the scope of the claims of the invention.

The term "halogen" represents fluorine, chlorine, bromine and iodine.

The term "$C_{1-6}$ alkyl" represents an alkyl group of straight or branched chain having a carbon number of 1 to 6, which is a monovalent group derived by removing one hydrogen from aliphatic hydrocarbon having a carbon number of 1 to 6, and as specific examples there may be mentioned methyl, ethyl, 1-propyl, 2-propyl, 2-methyl-1-propyl, 2-methyl-2-propyl, 1-butyl, 2-butyl, 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl and 2,3-dimethyl-2-butyl, among which $C_{1-3}$ alkyl such as methyl, ethyl and n-propyl are preferred.

The term "halo-$C_{1-6}$ alkyl" represents "$C_{1-6}$ alkyl" as defined above wherein 1-5 hydrogen atoms have been replaced with "halogen" as defined above, and as specific examples there may be mentioned fluoromethyl, difluoromethyl, trifluoromethyl, trichloromethyl, 1-fluoroethyl, 2-fluoroethyl, 2-chloroethyl, 1,2-difluoroethyl, 2,2-difluoroethyl, 2,2,2-trifluoroethyl, 1-fluoropropyl, 2-fluoropropyl, 3-fluoropropyl, 3-chloropropyl, 2-fluoro-2-propyl, 4-fluorobutyl, 5-fluoropentyl and 6-fluorohexyl.

The term "hydroxy-$C_{1-6}$ alkyl" represents "$C_{1-6}$ alkyl" as defined above wherein 1-2 hydrogen atoms have been replaced with hydroxy, and as specific examples there may be mentioned hydroxymethyl, 1-hydroxyethyl, 2-hydroxyethyl, 1,2-dihydroxyethyl, 1-hydroxypropyl, 2-hydroxypropyl, 3-hydroxypropyl, 2-hydroxy-2-propyl, 1,2-dihydroxypropyl, 1,3-dihydroxypropyl, 2,3-dihydroxypropyl, 4-hydroxybutyl, 5-hydroxypentyl and 6-hydroxyhexyl.

The term "$C_{2-6}$ alkenyl" represents an alkenyl group of straight or branched chain having a carbon number of 2 to 6, with one double bond, and as specific examples there may be mentioned ethenyl (vinyl), 1-propenyl, 2-propenyl (allyl), 1-butenyl, 2-butenyl, 3-butenyl, pentenyl and hexenyl.

The term "$C_{3-8}$ cycloalkyl" represents a cyclic aliphatic hydrocarbon group having a carbon number of 3 to 8, and as specific examples there may be mentioned cyclopropyl, cyclobutyl, cyclopentyl, cyclohexyl, cycloheptyl and cyclooctyl.

The term "$C_{3-8}$ cycloalkylmethyl" represents a methyl group wherein "$C_{3-8}$ cycloalkyl" as defined above is bonded thereto, and as specific examples there may be mentioned cyclopropylmethyl, cyclobutylmethyl, cyclopentylmethyl, cyclohexylmethyl, cycloheptylmethyl and cyclooctylmethyl.

The term "$C_{1-6}$ alkylene" represents a divalent group derived by removing any hydrogen from "$C_{1-6}$ alkyl" as defined above, and as specific examples there may be mentioned methylene, 1,2-ethylene, 1,1-ethylene, 1,3-propylene, tetramethylene, pentamethylene and hexamethylene. The term "$C_{2-6}$ alkylene" refers to $C_{2-6}$ groups among "$C_{1-6}$ alkylene" groups as defined above, and as specific examples there may be mentioned 1,2-ethylene, 1,1-ethylene, 1,3-propylene, tetramethylene, pentamethylene and hexamethylene.

The term "$C_{2-6}$ alkenylene." represents a divalent group derived by removing any hydrogen from "$C_{2-6}$ alkenyl" as defined above, and as specific examples there may be mentioned vinylene, propenylene, butenylene, pentenylene and hexenylene.

The term "cyclopropane-1,2-dimethylene" represents a divalent group derived by removing one hydrogen from each of the two methyl groups of 1,2-dimethylcyclopropane.

The term "$C_{1-6}$ alkoxy" represents an oxy group bonded to "$C_{1-6}$ alkyl" as defined above, and as specific examples there may be mentioned methoxy, ethoxy, 1-propyloxy, 2-propyloxy, 2-methyl-1-propyloxy, 2-methyl-2-propyloxy, 1-butyloxy, 2-butyloxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butyloxy, 3,3-dimethyl-1-butyloxy, 2,2-dimethyl-1-butyloxy, 2-ethyl-1-butyloxy, 3,3-dimethyl-2-butyloxy and 2,3-dimethyl-2-butyloxy.

The term "halo-$C_{1-6}$ alkoxy" represents "$C_{1-6}$ alkoxy" as defined above wherein 1-5 hydrogen atoms have been replaced by "halogen" as defined above, and as specific examples there may be mentioned fluoromethoxy, difluoromethoxy, trifluoromethoxy, 1-fluoroethoxy, 2-fluoroethoxy, 2-chloroethoxy, 1,2-difluoroethoxy, 2,2-difluoroethoxy, 2,2,2-trifluoroethoxy, 1-fluoropropyloxy, 2-fluoropropyloxy, 3-fluoropropyloxy, 3-chloropropyloxy, 2-fluoro-2-propyloxy, 4-fluorobutyloxy, 5-fluoropentyloxy and 6-fluorohexyloxy.

The term "$C_{1-6}$ alkoxy-$C_{1-6}$ alkyl" represents "$C_{1-6}$ alkyl" as defined above wherein "$C_{1-6}$ alkoxy" as defined above is bonded thereto, and as specific examples there may be mentioned methoxymethyl, 1-methoxyethyl, 2-methoxyethyl, 1-methoxypropyl, 2-methoxypropyl, 3-methoxypropyl, 2-methoxy-2-propyl, (1-propyloxy)methyl, (2-propyloxy) methyl, 1-(1-propyloxy)ethyl, 2-(1-propyloxy)ethyl, 1-(2-propyloxy)ethyl, 2-(2-propyloxy)ethyl, 1-(1-propyloxy)propyl, 2-(1-propyloxy)propyl, 3-(1-propyloxy)propyl, 2-(1-propyloxy)-2-propyl, 1-(2-propyloxy)propyl, 2-(2-propyloxy)propyl, 3-(2-propyloxy)propyl and 2-(2-propyloxy)-2-propyl.

The term "$C_{1-6}$ alkyleneoxy" or "oxy-$C_{1-6}$ alkylene" represents a divalent group derived by further removing any hydrogen from "$C_{1-6}$ alkoxy" as defined above, and as specific examples there may be mentioned methyleneoxy, ethyleneoxy, trimethyleneoxy, tetramethyleneoxy, pentamethyleneoxy and hexamethyleneoxy.

The term "$C_{1-6}$ alkylthio" represents a thio group bonded to "$C_{1-6}$ alkyl" as defined above, and as specific examples there may be mentioned methylthio, ethylthio, 1-propylthio, 2-propylthio, butylthio and pentylthio.

The term "$C_{1-6}$ alkylenethio" or "thio-$C_{1-6}$ alkylene" represents a divalent group derived by further removing any hydrogen from "$C_{1-6}$ alkylthio" as defined above, and as specific examples there may be mentioned methylenethio, ethylenethio, trimethylenethio and tetramethylenethio.

The term "$C_{1-6}$ alkyleneoxy-$C_{1-6}$ alkylene" represents a divalent group wherein two "$C_{1-6}$ alkylene" groups as defined above bonded to an oxy group, and as specific examples there may be mentioned methyleneoxymethylene, methyleneoxyethylene, methyleneoxypropylene, ethyleneoxymethylene, ethyleneoxyethylene, ethyleneoxypropylene, propyleneoxymethylene, propyleneoxyethylene and propyleneoxypropylene.

The term "$C_{1-6}$ alkyleneamino" or "amino-$C_{1-6}$ alkylene" represents a divalent group wherein "$C_{1-6}$ alkylene" as defined above is bonded to an amino group, and as specific examples there may be mentioned methyleneamino, ethyleneamino and propyleneamino.

The term "$C_{1-6}$ alkyleneaminocarbonyl" or "carbonylamino-$C_{1-6}$ alkylene" represents a divalent group wherein a carbonyl group is bonded to the amino group of "$C_{1-6}$ alkyleneamino" as defined above, and as specific examples there may be mentioned methyleneaminocarbonyl, ethyleneaminocarbonyl and propyleneaminocarbonyl.

The term "$C_{1-6}$ alkylsulfonyl" represents a sulfonyl group wherein "$C_{1-6}$ alkyl" as defined above is bonded thereto, and as specific examples there may be mentioned methylsulfonyl, ethylsulfonyl, 1-propylsulfonyl, 2-propylsulfonyl, butylsulfonyl and pentylsulfonyl.

The term "$C_{2-7}$ acyl" represents a carbonyl group wherein "$C_{1-6}$ alkyl" as defined above is bonded thereto, and as specific examples there may be mentioned acetyl, propionyl, isopropionyl, butyryl, isobutyryl, valeryl, isovaleryl and pivaloyl.

The term "$C_{1-6}$ alkoxycarbonyl" represents a carbonyl group wherein "$C_{1-6}$ alkoxy" as defined above is bonded thereto, and as specific examples there may be mentioned methoxycarbonyl, ethoxycarbonyl, 1-propyloxycarbonyl and 2-propyloxycarbonyl.

The term "$C_{1-6}$ alkylcarbonylamino" represents a carbonylamino group wherein "$C_{1-6}$ alkyl" as defined above is bonded thereto, and as specific examples there may be mentioned methylcarbonylamino, ethylcarbonylamino and propylcarbonylamino.

The term "$C_{1-6}$ alkoxycarbonylamino" represents a carbonylamino group wherein "$C_{1-6}$ alkoxy" as defined above is bonded thereto, and as specific examples there may be mentioned methoxycarbonylamino, ethoxycarbonylamino and propyloxycarbonylamino.

The term "$C_{1-6}$ alkylsulfonylamino" represents an amino group wherein "$C_{1-6}$ alkylsulfonyl" as defined above is bonded thereto, and as specific examples there may be mentioned methylsulfonylamino, ethylsulfonylamino and propylsulfonylamino.

The term "$C_{1-6}$ alkoxyimino" represents an imino group wherein "$C_{1-6}$ alkoxy" as defined above is bonded thereto, and as specific examples there may be mentioned methoxyimino, ethoxyimino and propylimino.

The term "amino optionally having one or two $C_{1-6}$ alkyl" represents amino, mono-$C_{1-6}$ alkylamino and di-$C_{1-6}$ alkylamino, where $C_{1-6}$ alkyl has the same definition as above. As specific examples of mono-$C_{1-6}$ alkylamino there may be mentioned methylamino, ethylamino, 1-propylamino, 2-propylamino, 2-methyl-1-propylamino, 2-methyl-2-propylamino, 1-butylamino, 2-butylamino, 1-pentylamino, 2-pentylamino, 3-pentylamino, 2-methyl-1-butylamino, 3-methyl-1-butylamino, 2-methyl-2-butylamino, 3-methyl-2-butylamino, 2,2-dimethyl-1-propylamino, 1-hexylamino, 2-hexylamino, 3-hexylamino, 2-methyl-1-pentylamino, 3-methyl-1-pentylamino, 4-methyl-1-pentylamino, 2-methyl-2-pentylamino, 3-methyl-2-pentylamino, 4-methyl-2-pentylamino, 2-methyl-3-pentylamino, 3-methyl-3-pentylamino, 2,3-dimethyl-1-butylamino, 3,3-dimethyl-1-butylamino, 2,2-dimethyl-1-butylamino, 2-ethyl-1-butylamino, 3,3-dimethyl-2-butylamino and 2,3-dimethyl-2-butylamino. As specific examples of di-$C_{1-6}$ alkylamino there may be mentioned N,N-dimethylamino, N,N-diethylamino, N,N-di-n-propylamino, N,N-di-1-propylamino, N,N-di-n-butylamino, N,N-di-1-butylamino, N,N-di-s-butylamino, N,N-di-t-butylamino, N-ethyl-N-methylamino, N-n-propyl-N-methylamino, N-i-propyl-N-methylamino, N-n-butyl-N-methylamino, N-i-butyl-N-methylamino, N-s-butyl-N-methylamino and N-t-butyl-N-methylamino.

The term "$C_{6-14}$ aryl" represents an aromatic hydrocarbon ring group having a carbon number of 6 to 14, and as specific examples there may be mentioned phenyl, naphthyl and anthryl.

The term "C$_{6-10}$ aryl" represents an aromatic hydrocarbon ring group having a carbon number of 6 to 10, and as specific examples there may be mentioned phenyl and naphthyl.

The term "C$_{7-11}$ aralkyl" represents an alkyl group of straight-chain or branched having a carbon number of 1 to 5 wherein "C$_{6-10}$ aryl" as defined above is bonded thereto, and as specific examples there may be mentioned benzyl and naphthylmethyl.

The term "heteroatom" represents nitrogen atom, oxygen atom or sulfur atom.

The term "5- to 6-membered aromatic heterocycle" represents an aromatic ring having 5 or 6 atoms composing the ring and containing one or more heteroatoms among the atoms composing the ring, and as specific examples there may be mentioned thiophene, furan, pyrrole, oxazole, isoxazole, thiazole, isothiazole, imidazole, triazole, pyrazole, furazan, thiadiazole, oxadiazole, pyridine, pyridazine, pyrimidine, pyrazine and triazine.

The term "5- to 6-membered aromatic heterocyclic group" represents a monovalent group derived by removing one hydrogen at any position from "5- to 6-membered aromatic heterocycle" as defined above.

The term "5- to 6-membered heterocycle" represents a non-aromatic monocycle having 5 or 6 atoms composing the ring, containing 1-4 heteroatoms among the atoms composing the ring, optionally containing 1-2 double bonds in the ring and optionally containing 1-3 carbonyl groups in the ring, and as specific examples there may be mentioned pyrrolidine, piperidine, tetrahydrofuran, tetrahydropyran, morpholine, thiomorpholine, piperazine, thiazolidine, dioxane, imidazoline, thiazoline, 2,4-dihydro-[1,2,4]-triazol-3-one, 3H-pyrimidin-4-one, 1H-pyrimidine-2,4-dione, 1H-[1,3,5]-triazine-2,4-dione and tetrazolone.

The term "5- to 6-membered aromatic heterocyclic group" represents a monovalent or divalent group derived by removing 1 or 2 hydrogen from any position of "5- to 6-membered aromatic heterocycle" as defined above.

The term "8- to 1-membered fused heterocycle" represents a fused non-aromatic ring having 8-11 atoms composing the ring, containing 2-5 heteroatoms among the atoms composing the ring, optionally containing 1-2 double bonds in the ring and optionally containing 1-3 carbonyl groups in the ring, and as specific examples there may be mentioned 1,2,4-triazol-3-one-containing fused heterocycle such as:

[Chemical Formula 16]

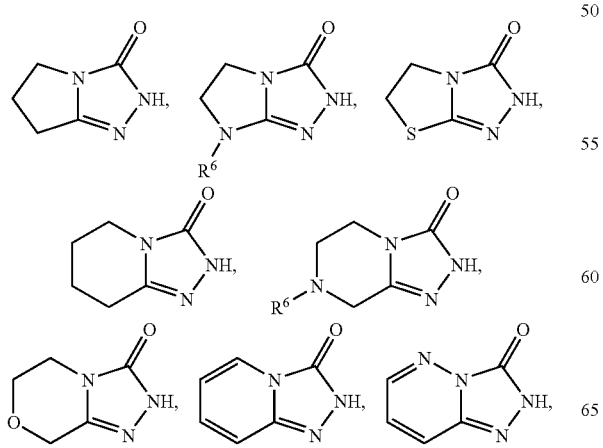

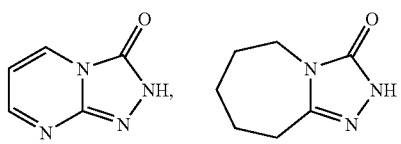

wherein R$^6$ represents hydrogen or C$_{1-6}$ alkyl, 1,3,5-triazine-2,4-dione-containing fused heterocycle such as:

[Chemical Formula 17]

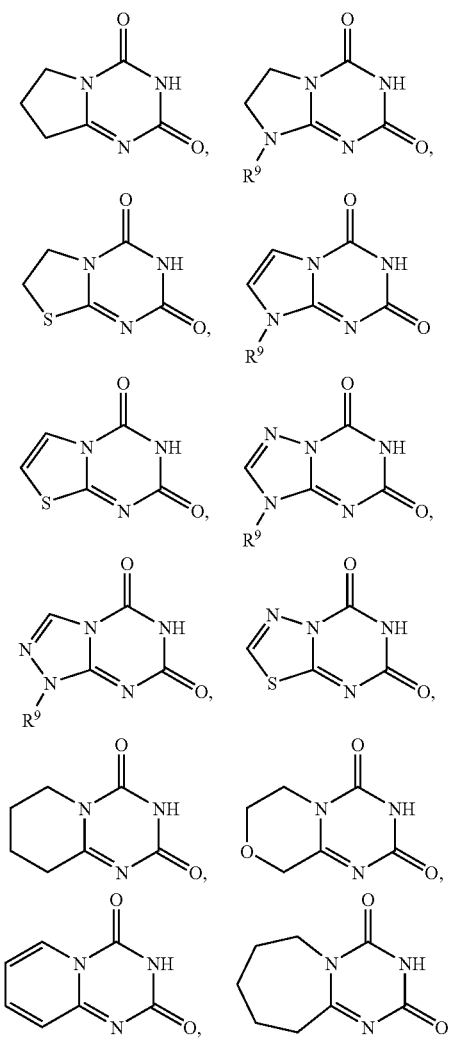

wherein R$^9$ represents hydrogen or C$_{1-6}$ alkyl, pyrimidin-4-one-containing fused heterocycle such as:

[Chemical Formula 18]

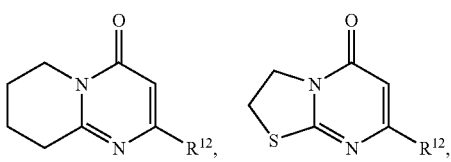

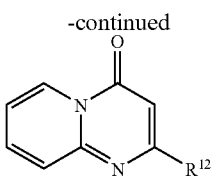

wherein $R^{12}$ represents hydrogen or $C_{1-6}$ alkyl, and the following groups:

[Chemical Formula 19]

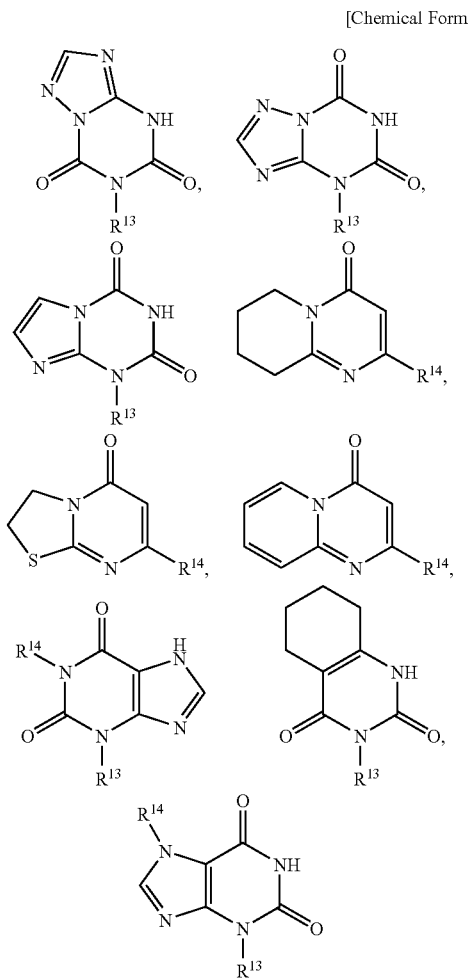

wherein $R^{13}$ and $R^{14}$ independently represent hydrogen, $C_{1-6}$ alkyl or $C_{6-10}$ aryl.

The term "8- to 11-membered fused heterocyclic group" represents a monovalent group derived by removing one hydrogen at any position from "8- to 11-membered fused heterocycle" as defined above.

The term "9- to 11-membered benzo-fused heterocycle" represents a bicyclic ring where a 5- to 7-membered aromatic or non-aromatic heterocycle is fused with a benzene ring, and as specific examples there may be mentioned indole, isoindole, indazole, chromene, quinoline, isoquinoline, cinnoline, quinazoline, quinoxaline, naphthylidine, phthalazine, purine, pteridine, thienofuran, imidazothiazole, benzofuran, benzothiophene, benzoxazole, benzothiazole, benzothiadiazole, benzimidazole, imidazopyridine, pyrrolopyridine, pyrrolopyrimidine, pyridopyrimidine, benzoazepine and benzodiazepine, among which indole, quinoline and benzothiophene are preferred.

The term "9- to 11-membered benzo-fused heterocyclic group" represents a monovalent or divalent group derived by removing 1 or 2 hydrogen from any position of "9- to 11-membered benzo-fused heterocycle" as defined above.

The term "optionally having a substituent" means optionally having 1-3 substituents selected as desired from the substituents in the relevant substituent group.

The substituents for the compounds represented by general formula (I) will now be explained.

[Definition of Q]

Q represents ethylene or trimethylene, and preferably ethylene.

[Definitions of $R^1$, $R^2$ and $R^3$]

$R^1$, $R^2$ and $R^3$ each independently represents hydrogen, halogen or hydroxy, or $C_{1-6}$ alkyl or $C_{1-6}$ alkoxy each optionally having one or more substituents selected from Group A.

As preferred examples of $R^1$, $R^2$ and $R^3$ there may be mentioned hydrogen for $R^1$ and $R^3$, and hydrogen, methyl or methoxymethyl for $R^2$.

More preferably, $R^1$, $R^2$ and $R^3$ are all hydrogen.

[Definition of $X^1$]

$X^1$ represents cyclopropane-1,2-dimethylene, or $C_{1-6}$ alkylene or $C_{2-6}$ alkenylene each optionally having one or more substituents selected from Group B.

As preferred examples of $X^1$ there may be mentioned $C_{2-6}$ alkylene optionally having one or more substituents selected from Group B1.

As more preferred examples of $X^1$ there may be mentioned $C_{2-6}$ alkylene optionally having one or more substituents selected from the group consisting of halogen, amino, acetamide, methoxyacetamide, methanesulfonylamide, hydroxy, oxo, cyano, $C_{1-6}$ alkyl, hydroxy-$C_{1-6}$ alkyl, halo-$C_{1-6}$ alkyl, $C_{1-6}$ alkoxy-$C_{1-6}$ alkyl and $C_{1-6}$ alkoxy.

[Definition of $X^2$]

$X^2$ represents $C_{1-6}$ alkylene, $C_{1-6}$ alkyleneoxy, oxy-$C_{1-6}$ alkylene, $C_{1-6}$ alkylenethio, thio-$C_{1-6}$ alkylene, $C_{1-6}$ alkyleneoxy-$C_{1-6}$ alkylene, $C_{2-6}$ alkenylene, oxycarbonyl, carbonyloxy, $C_{1-6}$ alkyleneamino, amino-$C_{1-6}$ alkylene, aminocarbonyl, carbonylamino, $C_{1-6}$ alkyleneaminocarbonyl, carbonylamino-$C_{1-6}$ alkylene, oxycarbonylamino, aminocarbonyloxy or ureylene each optionally having one or more substituents selected from Group C.

When $X^2$ represents $C_{1-6}$ alkyleneoxy, the $C_{1-6}$ alkylene portion of $X^2$ is bonded to 8-azabicyclo[3.2.1]octane or 9-azabicyclo[3.3.1]nonane (hereinafter also referred to as "azabicyclo"), and the oxy portion is bonded to $A^2$. When $X^2$ represents oxy-$C_{1-6}$ alkylene, the oxy portion of $X^2$ is bonded to azabicyclo and the $C_{1-6}$ alkylene portion of $X^2$ is bonded to $A^2$.

When $X^2$ is $C_{1-6}$ alkylenethio, the $C_{1-6}$ alkylene portion of $X^2$ is bonded to azabicyclo and the thio portion is bonded to $A^2$. When $X^2$ is thio-$C_{1-6}$ alkylene, the thio portion of $X^2$ is bonded to azabicyclo and the $C_{1-6}$ alkylene portion of $X^2$ is bonded to $A^2$.

When $X^2$ is oxycarbonyl, the oxy portion of $X^2$ is bonded to azabicyclo, and the carbonyl portion is bonded to $A^2$. When $X^2$ is carbonyloxy, the carbonyl portion of $X^2$ is bonded to azabicyclo, and the oxy portion of $X^2$ is bonded to $A^2$.

When $X^2$ is $C_{1-6}$ alkyleneamino, the $C_{1-6}$ alkylene portion of $X^2$ is bonded to azabicyclo and the amino portion is bonded to $A^2$. When $X^2$ is amino-$C_{1-6}$ alkylene, the amino portion of $X^2$ is bonded to azabicyclo and the $C_{1-6}$ alkylene portion of $X^2$ is bonded to $A^2$.

When $X^2$ is aminocarbonyl, the amino portion of $X^2$ is bonded to azabicyclo, and the carbonyl portion is bonded to $A^2$. When $X^2$ is carbonylamino, the carbonyl portion of $X^2$ is bonded to azabicyclo, and the amino portion of $X^2$ is bonded to $A^2$.

When $X^2$ is $C_{1-6}$ alkyleneaminocarbonyl, the $C_{1-6}$ alkylene portion of $X^2$ is bonded to azabicyclo and the carbonyl portion is bonded to $A^2$. When $X^2$ is carbonylamino-$C_{1-6}$ alkylene, the carbonyl portion of $X^2$ is bonded to azabicyclo and the $C_{1-6}$ alkylene portion of $X^2$ is bonded to $A^2$.

When $X^2$ is oxycarbonylamino, the oxy portion of $X^2$ is bonded to azabicyclo, and the amino portion is bonded to $A^2$. When $X^2$ is aminocarbonyloxy, the amino portion of $X^2$ is bonded to azabicyclo, and the oxy portion of $X^2$ is bonded to $A^2$.

$X^2$ may be in either the endo form or the exo form with regard to 8-azabicyclo[3.2.1]octane or 9-azabicyclo[3.3.1]nonane, but preferably in the endo form.

As preferred examples of $X^2$ there may be mentioned $C_{1-6}$ alkylene, $C_{1-6}$ alkyleneoxy or oxy-$C_{1-6}$ alkylene each optionally having one or more substituents selected from Group C1.

As more preferred examples of $X^2$ there may be mentioned $C_{1-6}$ alkylene, $C_{1-6}$ alkyleneoxy or oxy-$C_{1-6}$ alkylene each optionally having one or more substituents selected from the group consisting of halogen, hydroxy, $C_{1-6}$ alkoxy, oxo and $C_{1-6}$ alkyl.

[Definition of $A^1$]

$A^1$ represents a 5- to 6-membered heterocyclic group or a 8- to 11-membered fused heterocyclic group each optionally having one or more substituents selected from Group D.

As preferred examples of $A^1$ there may be mentioned groups represented by the formula:

[Chemical Formula 20]

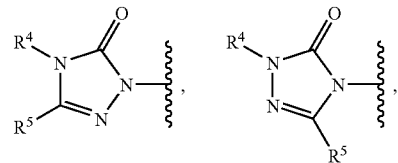

or

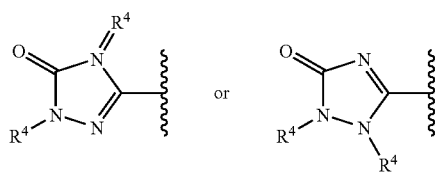

wherein $R^4$ represents hydrogen or $C_{1-6}$ alkyl, $C_{2-6}$ alkenyl, $C_{3-8}$ cycloalkyl, $C_{3-8}$ cycloalkylmethyl, $C_{6-10}$ aryl, $C_{7-11}$ aralkyl or a 5- to 6-membered aromatic heterocyclic group each optionally having one or more substituents selected from Group D1, and $R^5$ represents hydrogen, a halogen, hydroxy, or amino optionally having one or two $C_{1-6}$ alkyl, or $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl or a 5- to 6-membered aromatic heterocyclic group each optionally having one or more substituents selected from Group D1, groups represented by the formula optionally having one or more substituents group selected from Group D1:

[Chemical Formula 21]

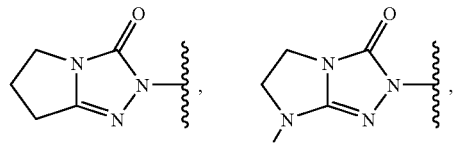

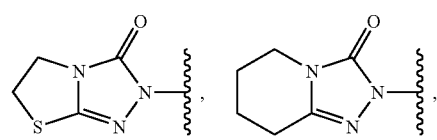

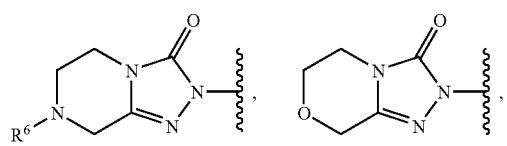

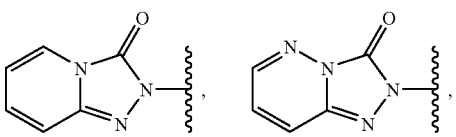

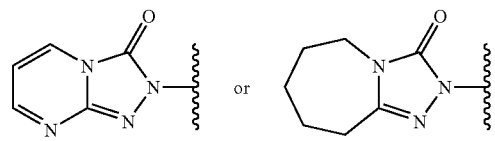

or wherein $R^6$ represents hydrogen or $C_{1-6}$ alkyl, groups represented by the formula:

[Chemical Formula 22]

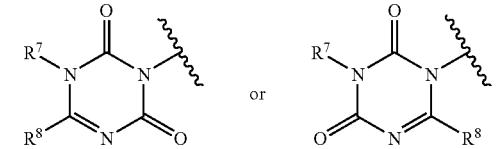

or wherein $R^7$ represents hydrogen or $C_{1-6}$ alkyl, $C_{2-6}$ alkenyl, $C_{3-8}$ cycloalkyl, $C_{3-8}$ cycloalkylmethyl, $C_{6-10}$ aryl, $C_{7-11}$ aralkyl or a 5- to 6-membered aromatic heterocyclic group each optionally having one or more substituents selected from Group D1, and $R^8$ represents hydrogen, halogen, hydroxy, or amino optionally having one or two $C_{1-6}$ alkyl, or $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl or a 5- to 6-membered aromatic heterocyclic group each optionally having one or more substituents selected from Group D1, groups represented by the formula optionally having one or more substituents selected from Group D1:

[Chemical Formula 23]

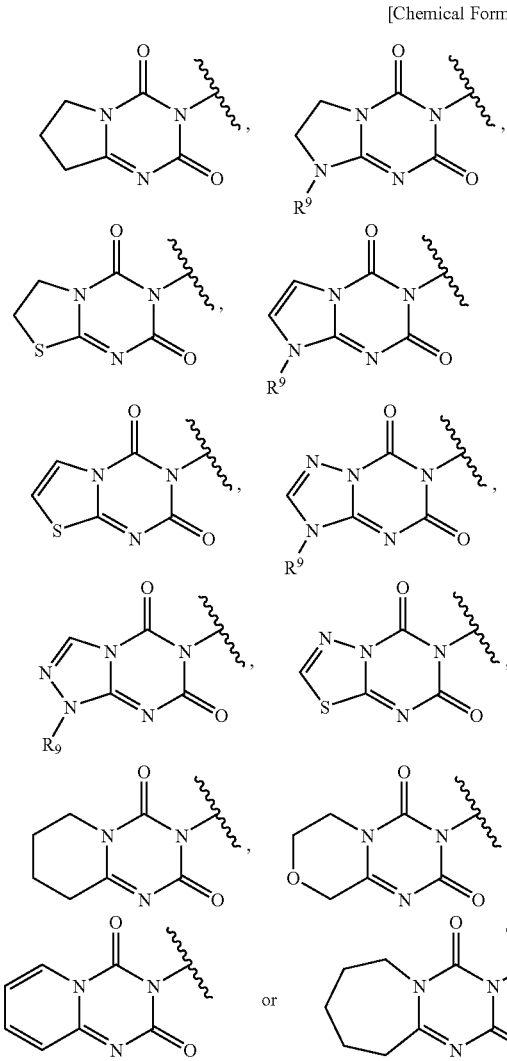

wherein R⁹ represents hydrogen or $C_{1-6}$ alkyl,
groups represented by the formula:

[Chemical Formula 24]

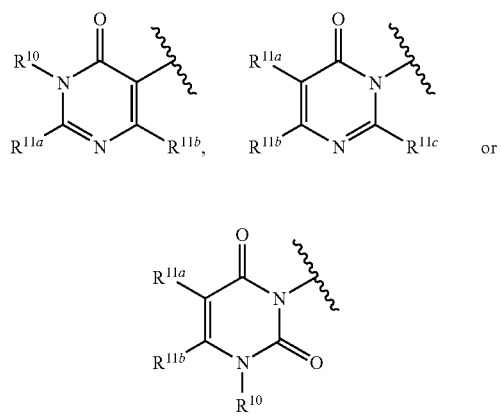

wherein
$R^{10}$ represents hydrogen or $C_{1-6}$ alkyl, $C_{2-6}$ alkenyl, $C_{3-8}$ cycloalkyl, $C_{3-8}$ cycloalkylmethyl, $C_{6-10}$ aryl, $C_{7-11}$ aralkyl or a 5- to 6-membered aromatic heterocyclic group each optionally having one or more substituents selected from Group D1, and $R^{11a}$, $R^{11b}$ and $R^{11c}$ each independently represents hydrogen, halogen, hydroxy, or amino optionally having one or two $C_{1-6}$ alkyl, or $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl or a 5- to 6-membered aromatic heterocyclic group each optionally having one or more substituents selected from Group D1, groups represented by the formula optionally having one or more substituents selected from Group D1:

[Chemical Formula 25]

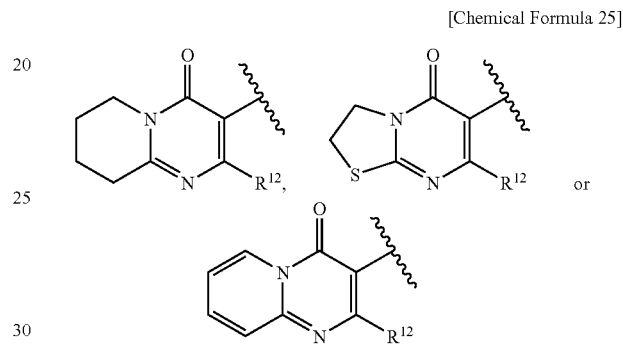

wherein $R^{12}$ represents hydrogen or $C_{1-6}$ alkyl,
and groups represented by the formula optionally having one or more substituents selected from Group D1:

[Chemical Formula 26]

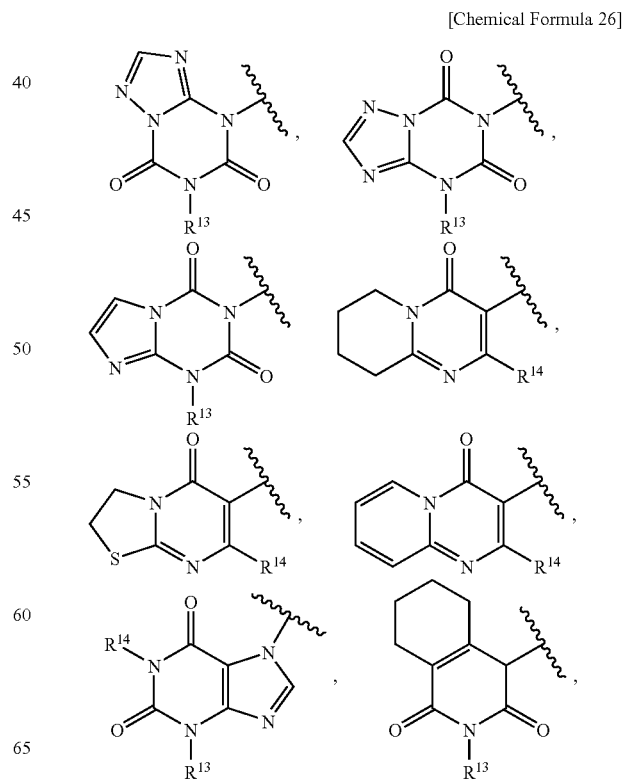

-continued

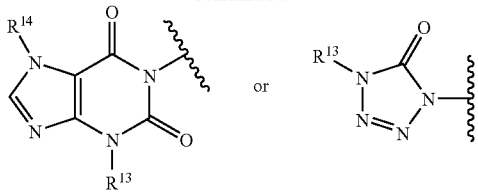

wherein $R^{13}$ and $R^{14}$ each independently represent hydrogen, $C_{1-6}$ alkyl or $C_{6-10}$ aryl.

As more preferred examples of $A^1$ there may be mentioned groups represented by the formula:

[Chemical Formula 27]

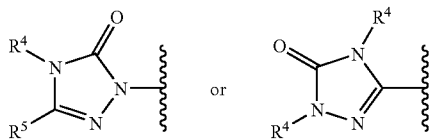

wherein $R^4$ and $R^5$ have the same definitions as above, groups represented by the formula optionally having one or more substituents group selected from Group D1:

[Chemical Formula 28]

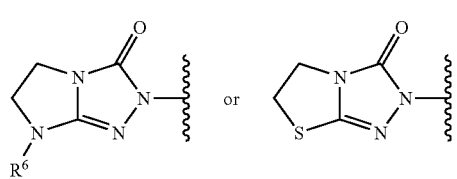

wherein $R^6$ has the same definition as above, groups represented by the formula:

[Chemical Formula 29]

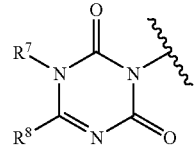

wherein $R^7$ and $R^8$ have the same definitions as above, and groups represented by the formula optionally having one or more substituents group selected from Group D1:

[Chemical Formula 30]

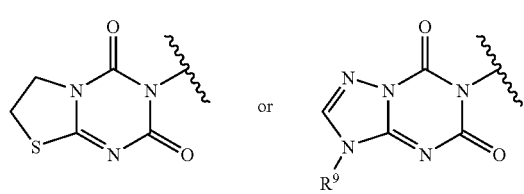

wherein $R^9$ has the same definition as above.

As even more preferred examples of $A^1$ there may be mentioned groups represented by the formula:

[Chemical Formula 31]

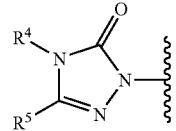

wherein $R^4$ and $R^5$ have the same definitions as above, and groups represented by the formula:

[Chemical Formula 32]

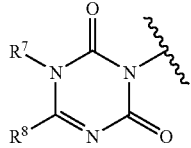

wherein $R^7$ and $R^8$ have the same definitions as above.

[Definition of $A^2$]

$A^2$ represents $C_{3-8}$ cycloalkyl, $C_{6-14}$ aryl, a 5- to 6-membered aromatic heterocyclic group or a 9- to 11-membered benzo-fused heterocyclic group each optionally having one or more substituents selected from Group E.

As more preferred examples of $A^2$ there may be mentioned phenyl, thienyl, benzothienyl and naphthyl each optionally having one or more substituents selected from Group E2.

As even more preferred examples of $A^2$ there may be mentioned phenyl and thienyl each optionally having one or more substituents selected from Group E2.

As yet more preferred examples of $A^2$ there may be mentioned groups represented by the formula:

[Chemical Formula 33]

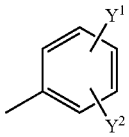

wherein $Y^1$ and $Y^2$ each independently represents hydrogen, halogen, hydroxy, $C_{1-6}$ alkyl, halo-$C_{1-6}$ alkyl, $C_{1-6}$ alkoxy-$C_{1-6}$ alkyl, $C_{1-6}$ alkoxy or halo-$C_{1-6}$ alkoxy.

[Definition of Group A]

Group A is the group consisting of halogen, hydroxy and $C_{1-6}$ alkoxy.

[Definition of Group B]

Group B is the group consisting of halogen, hydroxy, oxo, cyano, amino, $C_{1-6}$ alkyl, halo-$C_{1-6}$ alkyl, hydroxy-$C_{1-6}$ alkyl, $C_{1-6}$ alkoxy-$C_{1-6}$ alkyl, $C_{1-6}$ alkoxy, $C_{1-6}$ alkylcarbonylamino, $C_{1-6}$ alkoxycarbonylamino, $C_{1-6}$ alkylsulfonylamino, hydroxyimino and $C_{1-6}$ alkoxyimino.

[Definition of Group B1]

Group B1 is the group consisting of halogen, amino, acetamide, methoxyacetamide, methanesulfonylamide, hydroxy, oxo, cyano, $C_{1-6}$ alkyl, hydroxy-$C_{1-6}$ alkyl, halo-$C_{1-6}$ alkyl, $C_{1-6}$ alkoxy-$C_{1-6}$ alkyl and $C_{1-6}$ alkoxy.

[Definition of Group B2]

Group B2 is the group consisting of halogen and hydroxy.

[Definition of Group C]

Group C is the group consisting of halogen, hydroxy, $C_{1-6}$ alkoxy, oxo and $C_{1-6}$ alkyl.

[Definition of Group C1]

Group C1 is the group consisting of halogen, hydroxy, $C_{1-6}$ alkoxy, oxo and $C_{1-6}$ alkyl.

[Definition of Group D]

Group D is the group consisting of halogen, hydroxy and amino optionally having one or two $C_{1-6}$ alkyl, and $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl and a 5- to 6-membered aromatic heterocyclic group each optionally having one or more substituents selected from Group D1.

[Definition of Group D1]

Group D1 is the group consisting of halogen, hydroxy, $C_{1-6}$ alkyl and $C_{1-6}$ alkoxy.

[Definition of Group E]

Group E is the group consisting of halogen, cyano, hydroxy, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl, and $C_{6-10}$ aryl, a 5- to 6-membered heterocyclic group and a 5- to 6-membered aromatic heterocyclic group each optionally having one or more substituents selected from Group E1.

[Definition of Group E1]

Group E1 is the group consisting of halogen, $C_{1-6}$ alkyl, halo-$C_{1-6}$ alkyl, $C_{1-6}$ alkoxy and halo-$C_{1-6}$ alkoxy.

[Definition of Group E2]

Group E2 is the group consisting of halogen, cyano, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl, and phenyl, furyl, pyridyl, pyrazinyl, pyrrolidinyl, piperidinyl and morpholinyl each optionally having one or more substituents selected from Group E3.

[Definition of Group E3]

Group E3 is the group consisting of halogen, $C_{1-6}$ alkyl, halo-$C_{1-6}$ alkyl, $C_{1-6}$ alkoxy and halo-$C_{1-6}$ alkoxy.

A "pharmaceutically acceptable salt" as referred to throughout the present specification is not particularly restricted so long as it is formed with a compound of the invention and is pharmaceutically acceptable, and as examples there may be mentioned inorganic acid salts, organic acid salts, inorganic base salts, organic base salts and acidic or basic amino acid salts.

As preferred examples of inorganic acid salts there may be mentioned hydrochloride, hydrobromide, sulfate, nitrate, phosphate and the like, and as preferred examples of organic acid salts there may be mentioned acetate, succinate, fumarate, maleate, tartrate, citrate, lactate, stearate, benzoate, methanesulfonate, p-toluenesulfonate, oxalate and the like.

As preferred examples of inorganic base salts there may be mentioned alkali metal salts such as sodium salt and potassium salt, alkaline earth metal salts such as calcium salt and magnesium salt, and aluminum salt, ammonium salt and the like.

As preferred examples of acidic amino acid salts there may be mentioned aspartate, glutamate and the like, and as preferred examples of basic amino acid salts there may be mentioned arginine salt, lysine salt, ornithine salt and the like.

Typical processes for production of compounds represented by the general formula (I) according to the invention (hereinafter also referred to as compound (I)) will now be described.

In the following production schemes, n represents an integer of 0-4.

Boc represents a tert-butoxycarbonyl group.

$L^1$ and $L^2$ represent chlorine, bromine or iodine, $L^3$ represents a leaving group such as methanesulfonyloxy, trifluoromethanesulfonyloxy, p-toluenesulfonyloxy or p-nitrobenzenesulfonyloxy, $L^4$ represents a leaving group such as methanesulfonyloxy, p-toluenesulfonyloxy or p-nitrobenzenesulfonyloxy, and $L^5$ represents a leaving group such as chlorine, bromine, p-toluenesulfonyloxy or m-nitrobenzenesulfonyloxy.

$Met^1$ represents the formula —$SnR^M_3$ or —$B(OR^M)_2$, wherein $R^M$ represents hydrogen, $C_{1-6}$ alkyl, phenyl or the like, and $Met^2$ represents lithium, the formula —Mg—Br or the like.

$P^1$ represents a protecting group such as tert-butyldimethylsilyl, tert-butyldiphenylsilyl or benzyl.

$T^1$ represents nitrogen or CH, and $T^2$ represents sulfur or the formula —$NR^T$—, wherein $R^T$ represents hydrogen or $C_{1-6}$ alkyl.

Ts represents p-toluenesulfonyl.

X represents chlorine or bromine.

$X^3$ represents a group wherein a methylene group has been removed from $X^1$, $X^4$ and $X^5$ represent $C_{1-4}$ alkylene, $X^6$ represents a bond or $C_{1-6}$ alkylene, and $X^7$ represents $C_{1-6}$ alkylene.

$Y^3$ represents hydrogen, $C_{1-6}$ alkyl, $C_{1-6}$ alkoxy, fluorine or the like, $Y^4$ represents pyridyl, pyrazinyl, furyl or the like, $Y^5$ represents morpholino, pyridyl, pyrazinyl, furyl or the like, and $Y^6$ represents methanesulfonyl, trifluoromethanesulfonyl, p-toluenesulfonyl, p-nitrobenzenesulfonyl or the like.

$Z^1$ and $Z^2$ represent $C_{1-6}$ alkyl, $C_{7-11}$ aralkyl or the like, $Z^3$ represents methanesulfonyl, p-toluenesulfonyl, p-nitrobenzenesulfonyl or the like, $Z^4$ and $Z^5$ represent hydrogen, $C_{1-6}$ alkyl, $C_{7-11}$ aralkyl or the like and $Z^6$ represents methyl or tert-butoxycarbonyl.

$A^1$, $A^2$, $X^1$, $X^2$, Q, $R^1$, $R^2$, $R^3$, $R^4$, $R^5$, $R^6$, $R^7$ and $R^8$ have the same definitions as above.

The term "room temperature" used in the following description refers to a temperature around 15-30° C.

[Production Process A]

[Chemical Formula 34]

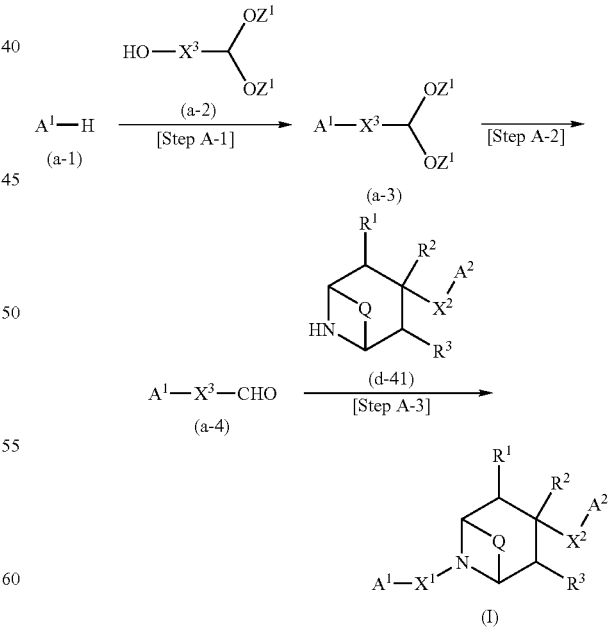

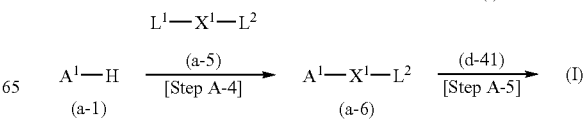

-continued

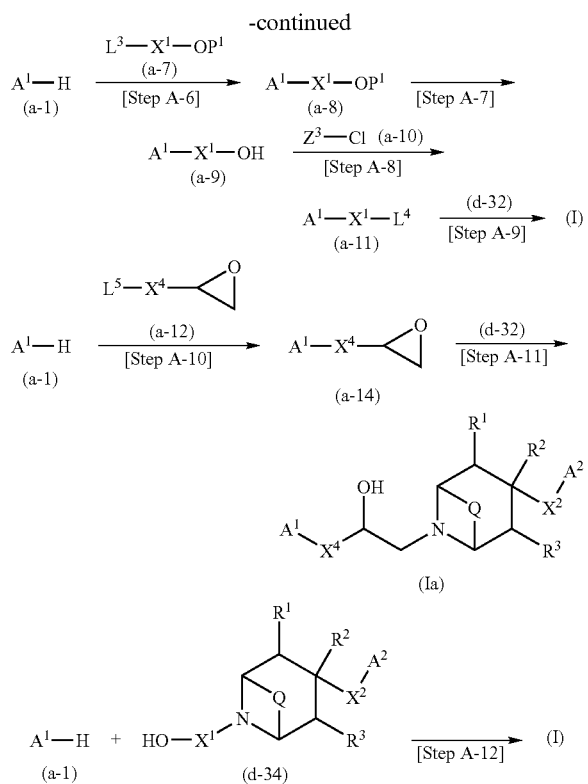

Production Process A is a process in which a compound (a-1) is used as starting material to produce a compound (I) or compound (Ia) according to the invention.

Compound (a-1) may be a commercially available material, or it may be produced by a process known to those skilled in the art from a commercially available material according to the method described in [Production Process E] or [Production Process F] below.

Compound (a-5) and compound (a-7) may be commercially available materials, or they may be produced by a process known to those skilled in the art from commercially available materials according to the method described in [Production Process G] below.

Compound (d-32) is the general formula for compounds (d-4), (d-4-a), (d-8), (d-18), (d-21), (d-23), (d-27), (d-30), (d-31), (d-46) described in [Production Process D] below, and compound (d-32) and compound (d-34) may be produced by processes known to those skilled in the art from commercially available materials according to the method described in [Production Process D].

[Step A-1]

Step A-1 is a step in which compound (a-1) and compound (a-2) are subjected to Mitsunobu reaction to obtain compound (a-3).

This reaction may be carried out under the same conditions as commonly employed for Mitsunobu reaction (for example, the conditions described in O. Mitsunobu, Synthesis, 1 (1981), D. L. Hughes, Organic Reactions, 42, 335 (1992)).

The reaction is conducted using a phosphine derivative such as triphenylphosphine and an azodicarboxylic acid diester such as diethyl azodicarboxylate or diisopropyl azodicarboxylate. The solvent used for the reaction is not particularly restricted so long as it dissolves the starting materials to some extent without inhibiting the reaction, and as examples there may be used tetrahydrofuran, benzene, toluene and N,N-dimethylformamide. The reaction temperature is not particularly restricted but will normally be from ice-cold to room temperature.

[Step A-2]

Step A-2 is a step in which compound (a-3) is subjected to hydrolysis under acidic conditions to obtain compound (a-4).

The reaction may be carried out under the same conditions as commonly employed for hydrolysis of acetal compounds (for example, the conditions described in T. W. Green and P. G. M. Wuts, "Protective Groups in Organic Synthesis, Third Edition", John Wiley & Sons (1999), p. 297-307).

The acid used for this step may be any commonly employed acid, and for example, it may be an acid such as hydrogen chloride, hydrochloric acid, hydrobromic acid, sulfuric acid, nitric acid, trifluoroacetic acid, formic acid or the like, or an acidic ion exchange resin such as Dowex 50W-X8 or Amberlyst-15. The reaction solvent is not particularly restricted so long as it dissolves the starting materials to some extent without inhibiting the reaction, and as examples there may be used methanol, ethanol, acetone, tetrahydrofuran, 1,4-dioxane, water, and mixtures of the foregoing.

The reaction temperature is not particularly restricted but will normally be from ice-cold to the reflux temperature of the solvent.

[Step A-3]

Step A-3 is a step in which compound (a-4) and compound (d-32) are subjected to reductive amination reaction to obtain compound (I).

The reaction may be carried out under the same conditions as commonly used for reductive amination reaction of carbonyl compounds and amine compounds. The reduction reaction used for this step is not particularly restricted, and there may be mentioned reductive amination reaction with reducing agents such as borane, boron hydride complexes and formic acid, and catalytic reduction reaction under a hydrogen atmosphere using metal catalysts.

Examples of reductive amination reaction using boron hydride complexes are described in the literature, such as W. S. Emerson, Organic Reactions, 4, 174 (1948), C. F. Lane, Synthesis, 135 (1975), J. C. Stowell and S. J. Pedegimas, Synthesis, 127 (1974), and A. F. Abdel-Magid, K. G. Carson, B. D. Harris, C. A. Maryanoff, and R. D. Shah, Journal of Organic Chemistry, 61, 3849 (1996), for example.

Compound (d-32) may be used in free form or as a salt, and preferably hydrochloride or hydrobromide of compound (d-32) is used.

As boron hydride complexes there may be used sodium borohydride, sodium cyanoborohydride and sodium triacetoxyborohydride.

When a boron hydride complex is used as the reducing agent, the solvent is not particularly restricted so long as it dissolves the starting materials to some extent without inhibiting the reaction, and as specific examples there may be mentioned methanol, ethanol, tetrahydrofuran, dichloromethane and 1,2-dichloroethane. The reaction may be carried out in the copresence of an acid for more favorable results, such as increased yield. There are no particular restrictions on such an acid, and it may be a mineral acid such as hydrochloric acid, an organic acid such as acetic acid, or a Lewis acid such as zinc chloride, boron trifluoride-diethyl ether complex or titanium (IV) tetraisopropoxide. The reaction temperature is not particularly restricted but will normally be from −78° C. to the reflux temperature of the solvent, and is preferably from ice-cold to room temperature.

When formic acid is used as the reducing agent, the solvent is not particularly restricted so long as it does not inhibit the reaction, and an excess of formic acid may even be used as the solvent. The reaction temperature is not particularly restricted but will normally be from 50° C. to the reflux temperature of the solvent. In addition, high-temperature heating at 150-250° C. with a sealed pressure-resistant container can produce satisfactory results such as a shortened reaction time.

The solvent used for catalytic reduction reaction under a hydrogen atmosphere is not particularly restricted so long as it does not inhibit the reaction, and methanol, ethanol, tetrahydrofuran, 1,4-dioxane, ethyl acetate may be mentioned. As metal catalysts for the reaction there may be mentioned palladium on carbon, palladium hydroxide on carbon, platinum oxide, Raney nickel and the like. The reaction conditions are not particularly restricted and may be a temperature between room temperature and the reflux temperature of the solvent and a pressure of between atmospheric pressure and 150 atm, and preferably a temperature from room temperature to 60° C. and a pressure from atmospheric pressure to 5 atm. The reaction may be carried out in the copresence of an acid for more favorable results, such as increased yield. There are no particular restrictions on such an acid, and mineral acids such as hydrochloric acid and organic acids such as acetic acid are preferred.

[Step A-4]

Step A-4 is a step in which compound (a-1) and compound (a-5) are subjected to nucleophilic substitution reaction to obtain compound (a-6). Specifically, for example, compound (a-1) may be reacted with a base to form an anion, which is then reacted with compound (a-5) to obtain compound (a-6).

Compound (a-5) will normally be used at about 1 equivalent to an excess, and preferably 3-10 equivalents, with respect to compound (a-1).

The solvent for the reaction is not particularly restricted so long as it does not inhibit the reaction, and a suitable base may be reacted at 1 equivalent to an excess, in an organic solvent such as diethyl ether, tetrahydrofuran, 1,4-dioxane, N,N-dimethylformamide or dimethyl sulfoxide. As bases used there may be mentioned sodium hydroxide, potassium hydroxide, sodium hydride, potassium hydride, sodium methoxide, sodium ethoxide, potassium tert-butoxide and the like.

The reaction temperature is not particularly restricted but will normally be from −78° C. to the reflux temperature of the solvent, and is preferably from ice-cold to 100° C.

[Step A-5]

Step A-5 is a step in which compound (a-6) and compound (d-32) are subjected to nucleophilic substitution reaction to obtain a compound of formula (I).

The reaction may be carried out under the same conditions as commonly employed for reaction between secondary amines and halogenated compounds (for example, the conditions described in Y. Hiraki, T. Terada, Y. Okaji, T. Yamazaki, Tetrahedron Letters, 31, 4755 (1990)). Compound (d-32) may be used in free form or as a salt.

The solvent used for the reaction in this step is not particularly restricted so long as it dissolves the starting materials to some extent without inhibiting the reaction, and as examples there may be mentioned methanol, ethanol, propanol, tetrahydrofuran, benzene, toluene, xylene, acetonitrile, dichloromethane, chloroform, N,N-dimethylformamide and dimethyl sulfoxide.

The reaction temperature will normally be from room temperature to the reflux temperature of the solvent, and is preferably from room temperature to 100° C.

Favorable results in the reaction, such as increased yield, can often be obtained by addition of a base. Such a base is not particularly restricted so long as it does not inhibit the reaction, and as examples there may be mentioned sodium carbonate, potassium carbonate, cesium carbonate, sodium hydroxide, potassium hydroxide, sodium hydride, potassium hydride, sodium methoxide, potassium methoxide, potassium tert-butoxide, triethylamine, diisopropylethylamine and diazabicycloundecene.

Favorable results such as increased yield may also be achieved by addition of sodium iodide, benzyltri-n-butylammonium iodide, tetra-n-butylammonium iodide or the like.

[Step A-6]

Step A-6 is a step in which compound (a-1) and compound (a-7) are subjected to nucleophilic substitution reaction to obtain compound (a-8).

Specifically, for example, compound (a-1) may be reacted with a base to form an anion, which is then reacted with compound (a-7) to obtain compound (a-8).

The solvent for the reaction is not particularly restricted so long as it does not inhibit the reaction, and a suitable base may be reacted at 1 equivalent to an excess, in an organic solvent such as diethyl ether, tetrahydrofuran, 1,4-dioxane, N,N-dimethylformamide or dimethyl sulfoxide. As suitable bases there may be mentioned sodium hydroxide, potassium hydroxide, sodium hydride, potassium hydride, sodium methoxide, sodium ethoxide, potassium tert-butoxide and the like.

The reaction temperature is not particularly restricted but will normally be from −78° C. to the reflux temperature of the solvent, and is preferably from ice-cold to 100° C.

[Step A-7]

Step A-7 is a step in which the protecting group for the hydroxyl of compound (a-8) is deprotected to obtain compound (a-9).

When $P^1$ is a tert-butyldimethylsilyl or tert-butyldiphenylsilyl group, the reaction may be carried out under the same conditions as commonly employed for silyl group deprotecting reaction (for example, the conditions described in T. W. Green and P. G. M. Wuts, "Protective Groups in Organic Synthesis, Third Edition", John Wiley & Sons (1999), p. 113-148). Specifically, for example, tetra-n-butylammonium fluoride may be reacted therewith in an organic solvent such as tetrahydrofuran or hydrochloric acid reacted therewith in ethanol, to obtain compound (a-9). The solvent used for the reaction is not particularly restricted so long as it does not inhibit the reaction, but dichloromethane, methanol, ethanol, propanol, ethyl acetate, tetrahydrofuran, 1,4-dioxane or the like is preferred. Addition of acetic acid can often produce satisfactory results such as increased yield.

When $P^1$ is benzyl, the reaction may be carried out under the same conditions as commonly employed for benzyl group deprotecting reaction (for example, the conditions described in T. W. Green and P. G. M. Wuts, "Protective Groups in Organic Synthesis, Third Edition", John Wiley & Sons (1999), p. 76-86). Specifically, for example, it may be carried out by a catalytic reduction process under a hydrogen atmosphere, using palladium on carbon, palladium hydroxide on carbon or the like as the catalyst in an organic solvent such as ethanol.

The solvent used for the reaction is not particularly restricted so long as it does not inhibit the reaction, and there may be mentioned methanol, ethanol, propanol, ethyl acetate, tetrahydrofuran, 1,4-dioxane and the like. The reaction conditions are not particularly restricted and may be a temperature between room temperature and the reflux temperature of the solvent and a pressure of between atmospheric pressure and 150 atm, and preferably a temperature from room temperature to 60° C. and a pressure from atmospheric pressure to 5 atm.

[Step A-8]

Step A-8 is a step in which compound (a-9) and compound (a-10) are reacted to obtain compound (a-11).

The reaction may be carried out under the same conditions as commonly employed for conversion of hydroxyl to leaving groups such as p-toluenesulfonyloxy (for example, the conditions described in Y. Yoshida, Y. Sakakura, N. Aso, S. Okada, and Y. Tanabe, Tetrahedron, 55, 2183 (1999)).

Specifically, for example, compound (a-9) may be reacted with methanesulfonyl chloride, p-toluenesulfonyl chloride, p-nitrobenzenesulfonyl chloride or the like to produce compound (a-11).

The solvent used for the reaction is not particularly restricted so long as it dissolves the starting materials to some extent without inhibiting the reaction, and as specific examples there may be mentioned dichloromethane, chloroform, tetrahydrofuran, toluene, xylene, acetonitrile, N,N-dimethylformamide and the like.

The reaction temperature will normally be from −78° C. to the reflux temperature of the solvent, and is preferably from −78° C. to room temperature. The reaction is preferably carried out in the presence of a base. The base used is not particularly restricted so long as it does not inhibit the reaction, and as preferred examples there may be mentioned sodium carbonate, potassium carbonate, triethylamine, diisopropylethylamine, pyridine and the like. Preferred results such as increased yield may be obtained if the reaction is conducted in the presence of trimethylammonium chloride.

[Step A-9]

Step A-9 is a step in which compound (a-11) and compound (d-32) are subjected to nucleophilic substitution reaction to obtain a compound of formula (I).

This step may be carried out under the same conditions as [Step A-5] described above.

[Step A-10]

Step A-10 is a step in which compound (a-1) and compound (a-12) are subjected to nucleophilic substitution reaction to obtain compound (a-14).

The reaction may be carried out under the same conditions as commonly employed for reaction between amide compounds and halogenated compounds or sulfonic acid esters (for example, the conditions described in K. Ogawa, Y. Matsushita, Chemical and Pharmaceutical Bulletin, 40, 2442 (1992)).

The solvent used for the reaction is not particularly restricted so long as it dissolves the starting materials to some extent without inhibiting the reaction, and as examples there may be mentioned methanol, ethanol, propanol, tetrahydrofuran, benzene, toluene, xylene, acetonitrile, dichloromethane, chloroform, N,N-dimethylformamide, dimethyl sulfoxide and the like.

The reaction is preferably carried out in the presence of a base. Such a base is not particularly restricted so long as it does not inhibit the reaction, and as preferred examples there may be mentioned sodium carbonate, potassium carbonate, cesium carbonate, sodium hydroxide, potassium hydroxide, sodium hydride, potassium hydride, sodium methoxide, potassium methoxide, potassium tert-butoxide, triethylamine, diisopropylethylamine, diazabicycloundecene and the like.

The reaction temperature will normally be from ice-cold to the reflux temperature of the solvent, and is preferably from ice-cold to 50° C. Favorable results such as increased yield may also be achieved by addition of sodium iodide, benzyltri-n-butylammonium iodide, tetra-n-butylammonium iodide or the like.

[Step A-11]

Step A-11 is a step in which compound (a-14) and compound (d-32) are reacted to obtain a compound of formula (Ia).

The reaction may be carried out under the same conditions as commonly employed for reaction between epoxy compounds and amine compounds (for example, the conditions described in K. Kulig, U. Holzgrabe, B. Malawska, Tetrahedron: Asymmetry, 12, 2533 (2001)). Compound (d-32) may be used in free form or as a salt.

The solvent used for the reaction is not particularly restricted so long as it dissolves the starting materials to some extent without inhibiting the reaction, and as examples there may be mentioned methanol, ethanol, propanol, tetrahydrofuran, benzene, toluene, xylene, acetonitrile, dichloromethane, chloroform, N,N-dimethylformamide, dimethyl sulfoxide and the like.

Favorable results in the reaction, such as increased yield, can often be obtained by addition of a base. Such a base is not particularly restricted so long as it does not inhibit the reaction, and as preferred examples there may be mentioned sodium carbonate, potassium carbonate, cesium carbonate, sodium hydroxide, potassium hydroxide, sodium hydride, potassium hydride, sodium methoxide, potassium methoxide, potassium tert-butoxide, triethylamine, diisopropylethylamine, diazabicycloundecene and the like.

The reaction temperature will normally be from ice-cold to the reflux temperature of the solvent, and is preferably from room temperature to 100° C.

[Step A-12]

Step A-12 is a step in which compound (a-1) and compound (d-34) are subjected to Mitsunobu reaction to obtain a compound of formula (I).

This step may be carried out under the same conditions as [Step A-1] described above.

[Production Process B]

[Chemical Formula 35]

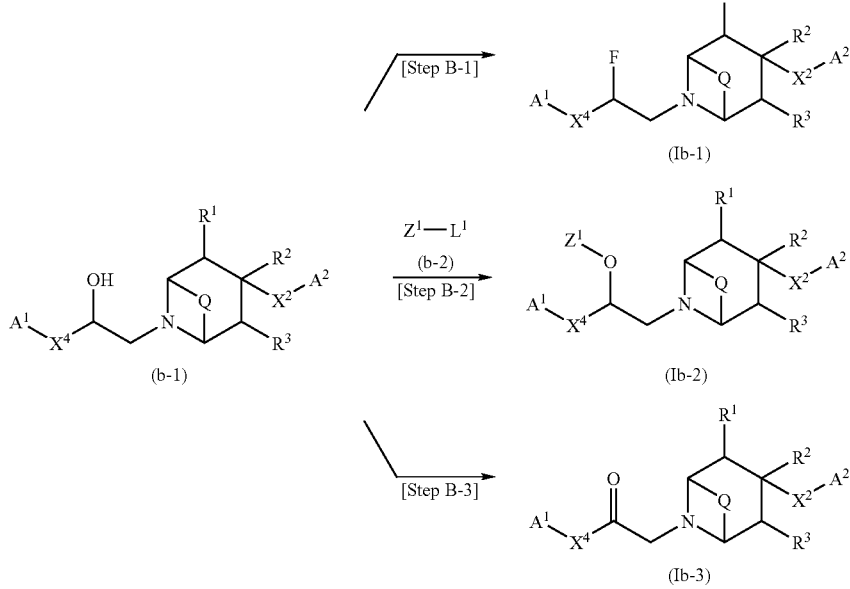

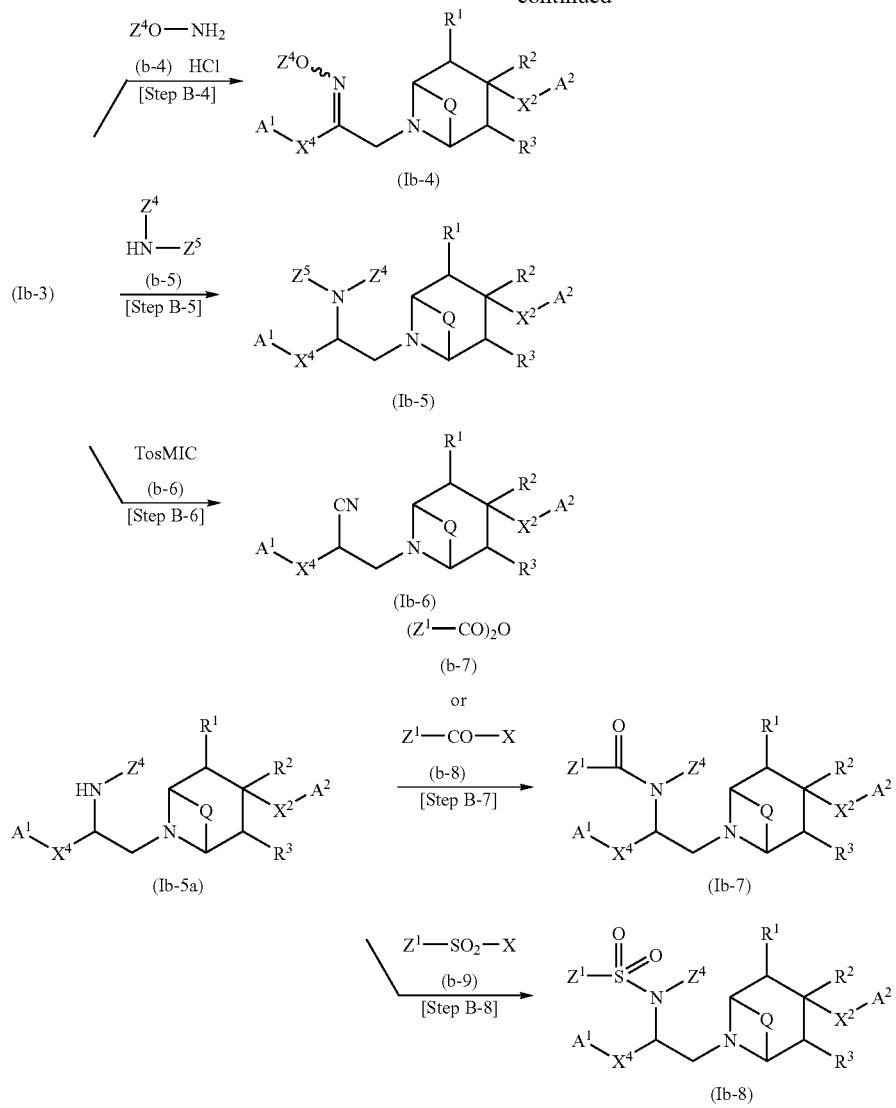

Production Process B is a process in which a compound (b-1) is used as starting material to produce any of compounds (Ib-1) to (Ib-8) according to the invention.

Compound (b-1) may be produced according to the method for compound (Ia) described in [Production Process A] above.

[Step B-1]

Step B-1 is a step in which compound (b-1) is reacted with a fluorinating agent to obtain compound (Ib-1).

The reaction may be carried out under the same conditions as commonly employed for conversion of hydroxyl to fluorine (for example, the conditions described in M. Hudliky, Organic Reactions, 35, 513 (1988)).

As fluorinating agents there may be mentioned dimethylaminosulfur-trifluoride, hydrogen fluoride, sulfur tetrafluoride, (2-chloro-1,1,2-trifluoroethyl)diethylamine, 1,1,2,3,3,3-hexafluoro-1-diethylaminopropane, 2,2-difluoro-1,3-dimethylimidazolidine, [bis(2-methoxyethyl)amino]sulfur trifluoride, difluorotriphenylphosphorane, trifluorodiphenylphosphorane and the like, among which dimethylaminosulfur-trifluoride is preferred.

The solvent used for the reaction is not particularly restricted so long as it does not inhibit the reaction, and as examples there may be mentioned 1,4-dioxane, tetrahydrofuran, dichloromethane, 1,2-dichloroethane, chloroform and the like.

The reaction temperature is not particularly restricted and the reaction may be conducted at a temperature between −78° C. and room temperature.

[Step B-2]

Step B-2 is a step in which compound (b-1) and compound (b-2) are subjected to nucleophilic substitution reaction to obtain a compound of formula (Ib-2).

This step may be carried out under the same conditions as [Step A-6] described for [Production Process A] above.

[Step B-3]

Step B-3 is a step in which compound (b-1) is subjected to oxidation reaction to obtain compound (Ib-3).

The reaction may be carried out under the same conditions as commonly employed for oxidation from secondary alcohol compounds to ketone compounds (for example, the conditions described in A. J. Mancuso and D. Swern, Synthesis, 165 (1981)).

The method for oxidizing the secondary alcohol to a ketone may be, for example, (a) a method using a metal salt such as chromic acid, (b) Swern oxidation using DMSO (dimethyl sulfoxide), or a modified form of the method, (c) a method using a ruthenium oxide (tetrapropylammonium perruthenate), or (d) a method using hypervalent iodine.

The solvent used for the Swern oxidation reaction is not particularly restricted so long as it dissolves the starting materials to some extent without inhibiting the reaction, and dimethyl sulfoxide, acetone, dichloromethane, chloroform or the like may be used, for example. The reaction temperature is not particularly restricted and the reaction may normally be conducted at a temperature between −78° C. and room temperature.

[Step B-4]

Step B-4 is a step in which compound (Ib-3) and compound (b-4) are reacted to obtain compound (Ib-4).

The reaction may be carried out under the same conditions as commonly employed for synthesis of oximes from ketones (for example, the conditions described in P. R. Dave, M. Ferraro, H. L. Ammon and C. S. Choi, Journal of Organic Chemistry, 55, 4459 (1990)).

The solvent is not particularly restricted so long as it dissolves the starting materials to some extent without inhibiting the reaction, and as specific examples there may be used methanol, ethanol, propanol and pyridine. Compound (b-4) may be used in free form or as a salt, and preferably a hydrochloride or hydrobromide of compound (b-4) is used. The reaction temperature is not particularly restricted but will normally be from ice-cold to the reflux temperature of the solvent, and is preferably from room temperature to the reflux temperature of the solvent. Favorable results in the reaction, such as increased yield, can be obtained by addition of a base. The base is not particularly restricted so long as it does not inhibit the reaction, and there may be mentioned as preferable sodium carbonate, potassium carbonate, sodium acetate, potassium acetate and the like.

[Step B-5]

Step B-5 is a step in which compound (Ib-3) and compound (b-5) are subjected to reductive amination reaction to obtain compound (Ib-5).

The reaction in this step may be carried out under the same conditions as [Step A-3] described for [Production Process A] above.

[Step B-6]

Step B-6 is a step in which compound (Ib-3) and TosMIC (tosylmethylisocyanide) (b-6) are reacted to obtain compound (Ib-6).

The reaction may be carried out under the same conditions as commonly employed for synthesis of nitriles from ketones (for example, the conditions described in Organic Synthesis Coll. Vol., 6, 41 (1988)).

The solvent is not particularly restricted so long as it dissolves the starting materials to some extent without inhibiting the reaction, and as specific examples there may be used solvents such as methanol, ethanol, propanol, tert-butanol, 1,2-dimethoxyethane and the like, or mixtures thereof.

The reaction is preferably carried out in the presence of a base. As suitable bases there may be mentioned sodium hydroxide, potassium hydroxide, sodium hydride, potassium hydride, sodium methoxide, sodium ethoxide, potassium tert-butoxide and the like. The reaction temperature is not particularly restricted but will normally be from ice-cold to the reflux temperature of the solvent, and is preferably from room temperature to the reflux temperature of the solvent.

[Step B-7]

Step B-7 is a step in which compound (Ib-5a) and compound (b-7) or compound (b-8) are reacted in the presence of a base to obtain compound (Ib-7).

The reaction may be carried out under the same conditions as commonly employed for synthesis of amides from amines (for example, the conditions described in T. W. Green and P. G. M. Wuts, "Protective Groups in Organic Synthesis, Third Edition", John Wiley & Sons (1999), p. 550-561).

The solvent used for the reaction is not particularly restricted so long as it dissolves the starting materials to some extent without inhibiting the reaction, and as examples there may be mentioned methanol, ethanol, propanol, tetrahydrofuran, benzene, toluene, xylene, acetonitrile, dichloromethane, chloroform, N,N-dimethylformamide, dimethyl sulfoxide and the like.

The reaction is preferably carried out in the presence of a base. Such a base is not particularly restricted so long as it does not inhibit the reaction, and as preferred examples there may be mentioned sodium carbonate, potassium carbonate, cesium carbonate, sodium hydroxide, potassium hydroxide, sodium hydride, potassium hydride, sodium methoxide, potassium methoxide, potassium tert-butoxide, triethylamine, diisopropylethylamine, diazabicycloundecene and the like.

The reaction temperature will normally be from ice-cold to the reflux temperature of the solvent, and is preferably from ice-cold to room temperature.

[Step B-8]

Step B-8 is a step in which compound (Ib-5a) and compound (b-9) are reacted in the presence of a base to obtain compound (Ib-8).

The reaction in this step may be carried out under the same conditions as [Step B-7] described above.

[Production Process C]

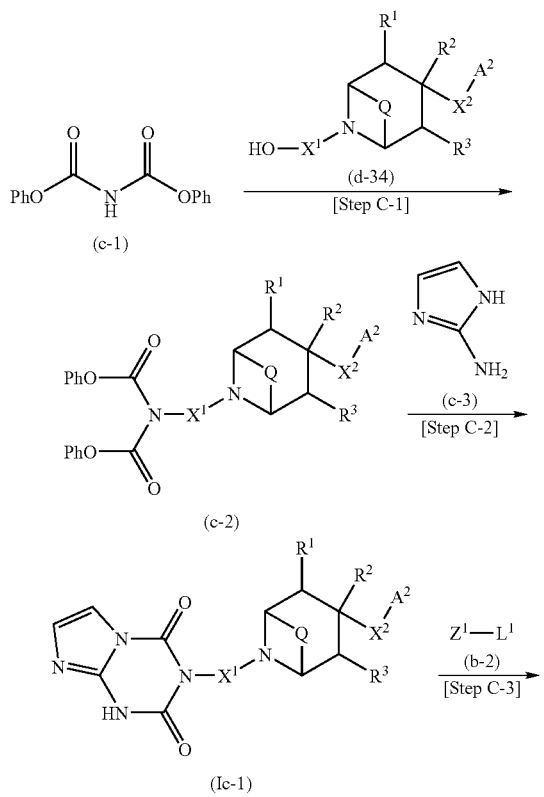

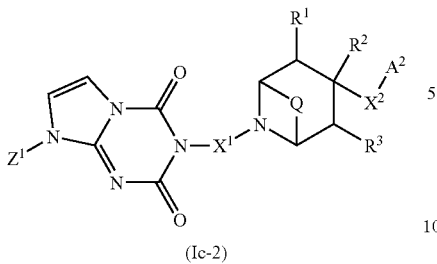

(Ic-2)

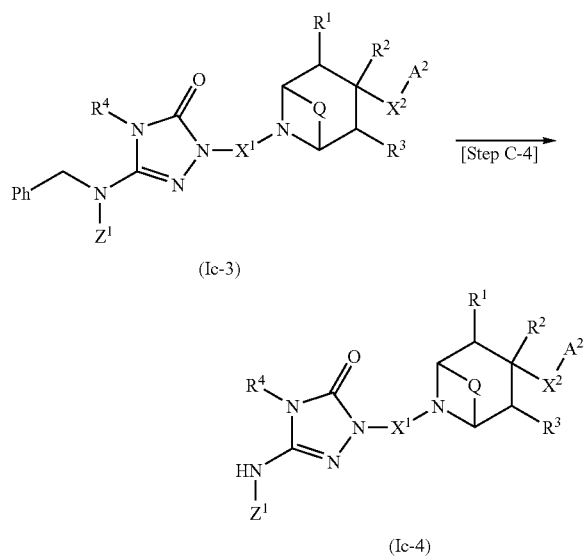

(Ic-3)

(Ic-4)

(Ic-5)

(Ic-6)

(Ic-7)

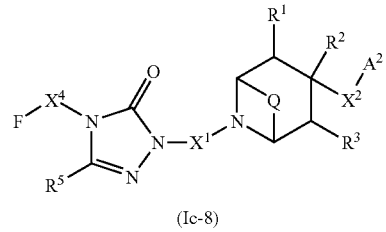

(Ic-8)

Production Process C is a process for production of compound (Ic-1), compound (Ic-2), compound (Ic-4), compound (Ic-6) and compound (Ic-8) according to the invention.

Compound (Ic-3), compound (Ic-5) and compound (Ic-7) used as starting materials may be produced according to the method described in [Production Process A] above.

Compound (d-34) may be produced by a process known to those skilled in the art from a commercially available material according to the method described in [Production Process D] above.

[Step C-1]

Step C-1 is a step in which compound (c-1) and compound (d-34) are subjected to Mitsunobu reaction to obtain compound (c-2).

This step may be carried out under the same conditions as [Step A-1] described for [Production Process A] above.

[Step C-2]

Step C-2 is a step in which compound (c-2) and compound (c-3) are reacted to obtain compound (Ic-1).

The reaction may be carried out under the same conditions described in the literature, such as in H. Usui, Y. Watanabe, M. Kanao, Journal of Heterocyclic Chemistry, 30, 551 (1993), for example.

The solvent used for the reaction is not particularly restricted so long as it dissolves the starting materials to some extent without inhibiting the reaction, and as examples there may be mentioned tetrahydrofuran, benzene, toluene, xylene, acetonitrile, dichloromethane, chloroform, N,N-dimethylformamide, dimethyl sulfoxide and the like.

The reaction temperature will normally be from ice-cold to the reflux temperature of the solvent, and is preferably from room temperature to the reflux temperature of the solvent.

[Step C-3]

Step C-3 is a step in which compound (Ic-1) and compound (b-2) are subjected to nucleophilic substitution reaction to obtain compound (Ic-2).

This step may be carried out under the same conditions as [Step A-4] described for [Production Process A] above.

[Step C-4]

Step C-4 is a step in which compound (Ic-3) is debenzylated by catalytic reduction to obtain a compound of general formula (Ic-4).

The reaction may be carried out under the same conditions as commonly employed for debenzylation under a hydrogen atmosphere (for example, the conditions described in T. W. Green and P. G. M. Wuts, "Protective Groups in Organic Synthesis, Third Edition", John Wiley & Sons (1999), p. 579-581).

The solvent used for the reaction is not particularly restricted so long as it does not inhibit the reaction, and methanol, ethanol, tetrahydrofuran, 1,4-dioxane, ethyl acetate may be mentioned. As metal catalysts for the reaction there may be mentioned palladium on carbon, palladium hydroxide on carbon, platinum oxide, Raney nickel and the like. The reaction conditions are not particularly restricted

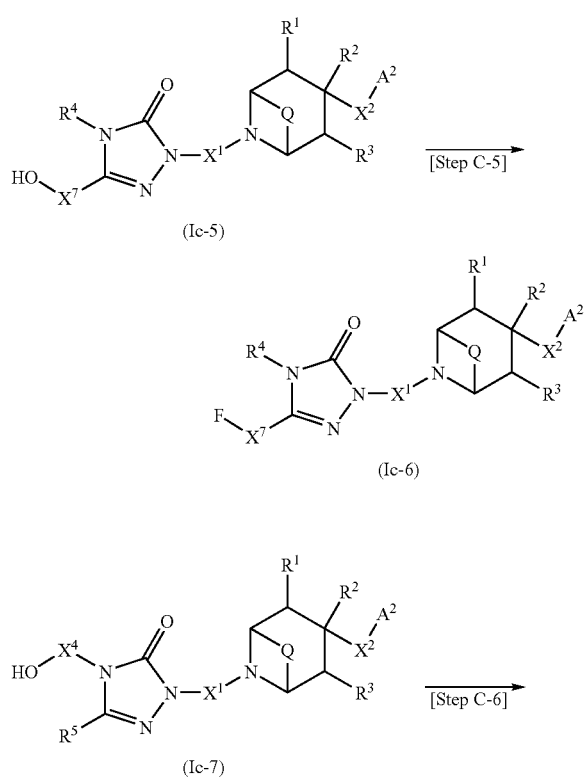

and may be a temperature between room temperature and the reflux temperature of the solvent and a pressure of between atmospheric pressure and 150 atm, and preferably a temperature from room temperature to 60° C. and a pressure from atmospheric pressure to 5 atm. The reaction may be carried out in the copresence of an acid for more favorable results, such as increased yield. There are no particular restrictions on such an acid, and mineral acids such as hydrochloric acid and organic acids such as acetic acid are preferred.

[Step C-5]

Step C-5 is a step in which compound (Ic-5) is fluorinated to obtain compound (Ic-6).

The reaction in this step may be carried out under the same conditions as [Step B-1] described for [Production Process B] above.

[Step C-6]

Step C-6 is a step in which compound (Ic-7) is fluorinated to obtain compound (Ic-8).

The reaction in this step may be carried out under the same conditions as [Step B-1] described for [Production Process B] above.

Typical processes for production of compounds used in [Production Process A], [Production Process B] and [Production Process C] will now be described.

[Production Process D]

The starting materials used for [Production Process D] may be commercially available materials, or they may be produced by methods known to those skilled in the art from commercially available materials.

[Chemical Formula 37]

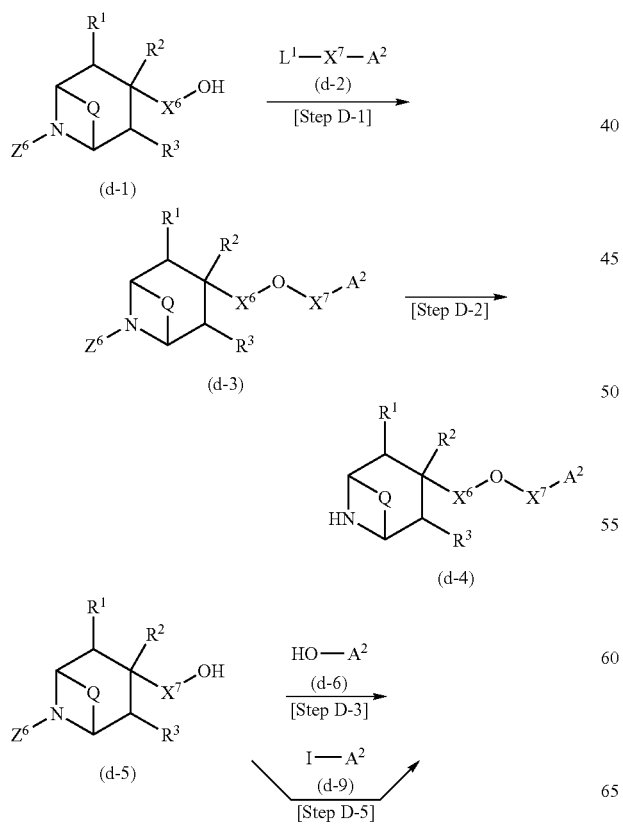

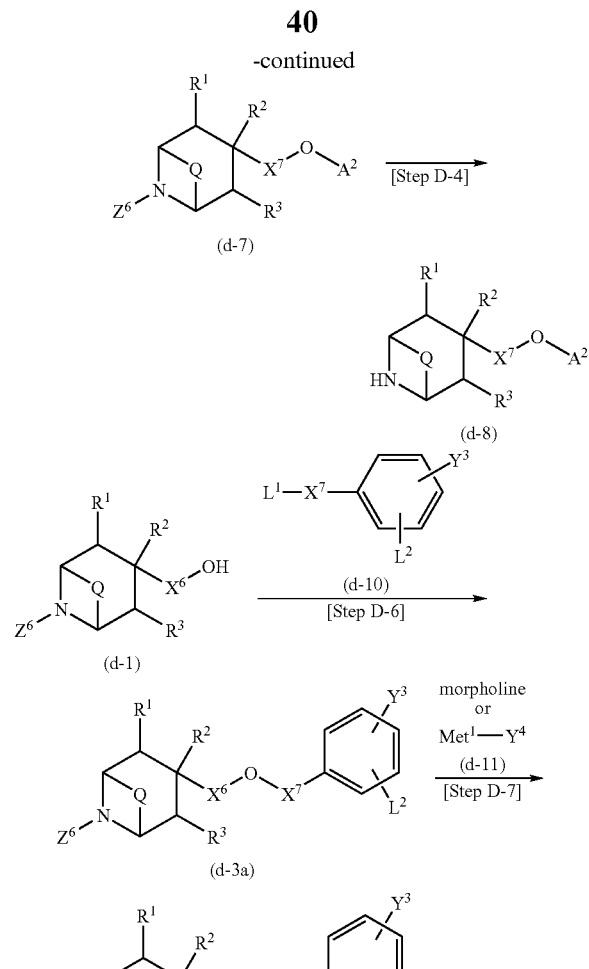

[Step D-1]

Step D-1 is a step in which compound (d-1) and compound (d-2) are subjected to nucleophilic substitution reaction to obtain compound (d-3).

Specifically, for example, compound (d-1) may be reacted with a base to form an anion, which is then reacted with compound (d-2) to obtain compound (d-3).

Compound (d-2) is usually used at 1-5 equivalents with respect to compound (d-1).

The solvent for the reaction is not particularly restricted so long as it does not inhibit the reaction, and a suitable base may be reacted at 1 equivalent to an excess, in an organic solvent such as diethyl ether, tetrahydrofuran, 1,4-dioxane, N,N-dimethylformamide, dimethyl sulfoxide or the like. As suitable bases there may be mentioned sodium hydroxide, potassium hydroxide, sodium hydride, potassium hydride, sodium methoxide, sodium ethoxide, potassium tert-butoxide and the like.

The reaction temperature is not particularly restricted but will normally be from −78° C. to the reflux temperature of the solvent, and is preferably from ice-cold to 100° C.

Favorable results such as increased yield may also be achieved by addition of sodium iodide, benzyltri-n-butylammonium iodide, tetra-n-butylammonium iodide or the like.

[Step D-2]

Step D-2 is a step in which $Z^6$ in compound (d-3) is eliminated to obtain compound (d-4).

When $Z^6$ is tert-butoxycarbonyl, the reaction may be carried out under the same conditions as commonly employed for deprotecting reaction (for example, the conditions described in T. W. Green and P. G. M. Wuts, "Protective Groups in Organic Synthesis, Third Edition", John Wiley & Sons (1999), p. 518-525). The solvent for the reaction is not particularly restricted so long as it does not inhibit the reaction, and the reaction may be conducted with a suitable acid such as hydrogen chloride, hydrochloric acid, sulfuric acid, trifluoroacetic acid, p-toluenesulfonic acid or the like in an organic solvent such as diethyl ether, tetrahydrofuran, 1,4-dioxane, acetone, ethyl acetate or the like, or in a mixture of water and an organic solvent. The reaction temperature is not particularly restricted but will normally be from ice-cold to the reflux temperature of the solvent, and is preferably from ice-cold to room temperature.

When $Z^6$ is methyl, the reaction may be carried out under the same conditions as commonly employed for deprotecting reaction (for example, the conditions described in J. H. Cooley and E. J. Evain, Synthesis, 1 (1989)). For example, 1-chloroethyl chloroformate and methanol may be reacted therewith in that order in a solvent such as 1,2-dichloroethane, toluene or the like. The reaction temperature is not particularly restricted but will normally be from −78° C. to the reflux temperature of the solvent, and is preferably from ice-cold to the reflux temperature of the solvent.

[Step D-3]

Step D-3 is a step in which compound (d-5) and compound (d-6) are subjected to Mitsunobu reaction to obtain compound (d-7).

The reaction in this step may be carried out under the same conditions as [Step A-1] described for [Production Process A] above.

[Step D-4]

Step D-4 is a step in which $Z^6$ in compound (d-7) is eliminated to obtain compound (d-8).

The reaction in this step may be carried out under the same conditions as [Step D-2] described above.

[Step D-5]

Step D-5 is a step in which compound (d-5) and compound (d-9) are reacted to obtain compound (d-7).

The reaction may be carried out under the same conditions as described in Martina Wolter, Gero Nordmann, Gabriel E. Job, and Stephen L., Buchwald, Organic Letters, 4, 973 (2002), for example.

Specifically, compound (d-5) may be reacted with compound (d-9) in the presence of a copper salt, 1,10-phenanthroline and a base, to obtain compound (d-7).

The copper salt used for the reaction is preferably copper(I) iodide.

The base is preferably cesium carbonate.

The reaction may be carried out without a solvent, or toluene, xylene or the like may be used.

The reaction temperature is not particularly restricted but will normally be from room temperature to the reflux temperature of the solvent.

[Step D-6]

Step D-6 is a step in which compound (d-1) and compound (d-10) are reacted to obtain compound (d-3a).

The reaction in this step may be carried out under the same conditions as [Step D-1] described above.

[Step D-7]

Step D-7 is a step in which compound (d-3a) is reacted with an organometallic compound (d-11) or morpholine in the presence of a transition metal catalyst to obtain compound (d-3b). This reaction may be carried out under conditions commonly employed for coupling reaction using transition metals (for example, Suzuki coupling reaction, Stille coupling reaction or the like).

Examples of reaction using an organic boron reagent as the organometallic compound are described in Tetrahedron: Asymmetry, 16, 529 (2005) and Organic Letters, 6, 277 (2004), and an example of reaction using an organic tin reagent is described in Tetrahedron, 61, 4129 (2005).

There are no particular restrictions on the organometallic catalyst used for the reaction, and as preferred examples there may be mentioned tetrakis(triphenylphosphine)palladium (0), dichlorobis(triphenylphosphine)palladium(II), [1,1'-bis(diphenylphosphino)ferrocene]palladium(II) dichloride, bis(tert-butylphosphine)palladium(0), palladium(II) acetate and the like. There are also no particular restrictions on organometallic compounds, and as preferred examples there may be mentioned organic tin reagents such as aryl tri-n-butyltins, and organic boron reagents such as arylboric acids. The solvent used for the reaction is not particularly restricted so long as it does not inhibit the reaction, and as preferred examples there may be mentioned benzene, toluene, xylene, N,N-dimethylformamide, 1-methyl-2-pyrrolidone, tetrahydrofuran, 1,4-dioxane, acetonitrile, propionitrile and the like. The reaction temperature is not particularly restricted but will normally be from ice-cold to the reflux temperature of the solvent, and is preferably, for example, from room temperature to the reflux temperature of the solvent. The reaction may be carried out in the copresence of a base for more favorable results, such as increased yield. There are no particular restrictions on the base used for the reaction, and there may be mentioned as preferable bases such as sodium carbonate, potassium carbonate, cesium carbonate and potassium phosphate, or their aqueous solutions, and triethylamine.

An example of coupling reaction with an amine such as morpholine is described in the literature, such as J. P. Wolfe, H. Tomori, J. P. Sadighi, J. Yin, and S. L. Buchwald, Journal of Organic Chemistry, 65, 1158 (2000), for example.

There are no particular restrictions on the organometallic catalyst used for the reaction, and as preferred examples there may be mentioned dichlorobis(tri-o-tolylphosphine)palladium(II), [1,1'-bis(diphenylphosphino)ferrocene]palladium (II) dichloride, bis(tert-butylphosphine)palladium(0), palladium(II) acetate and tris(dibenzylideneacetone)palladium (0). Addition of a ligand such as BINAP (2,2'-bis(diphenylphosphino)-1,1'-binaphthyl) or DPPF (1,1'-bis(diphenylphosphino)ferrocene) can smooth progress of the reaction. The reaction is preferably carried out in the copresence of a base. There are no particular restrictions on the base used for the reaction, and there may be mentioned as preferable bases such as sodium tert-butoxide, potassium phosphate and lithium bis(trimethylsilyl)amide. The solvent used for the reaction is not particularly restricted so long as it does not inhibit the reaction, and as preferred examples there may be mentioned benzene, toluene, xylene, N,N-dimethylformamide, 1-methyl-2-pyrrolidone, tetrahydrofuran, 1,4-dioxane and the like. The reaction temperature is not particularly restricted but will normally be from ice-cold to the reflux temperature of the solvent, and is preferably, for example, from room temperature to the reflux temperature of the solvent.

[Step D-8]

Step D-8 is a step in which $Z^6$ in compound (d-3b) is eliminated to obtain compound (d-4-a).

The reaction in this step may be carried out under the same conditions as [Step D-2] described above.

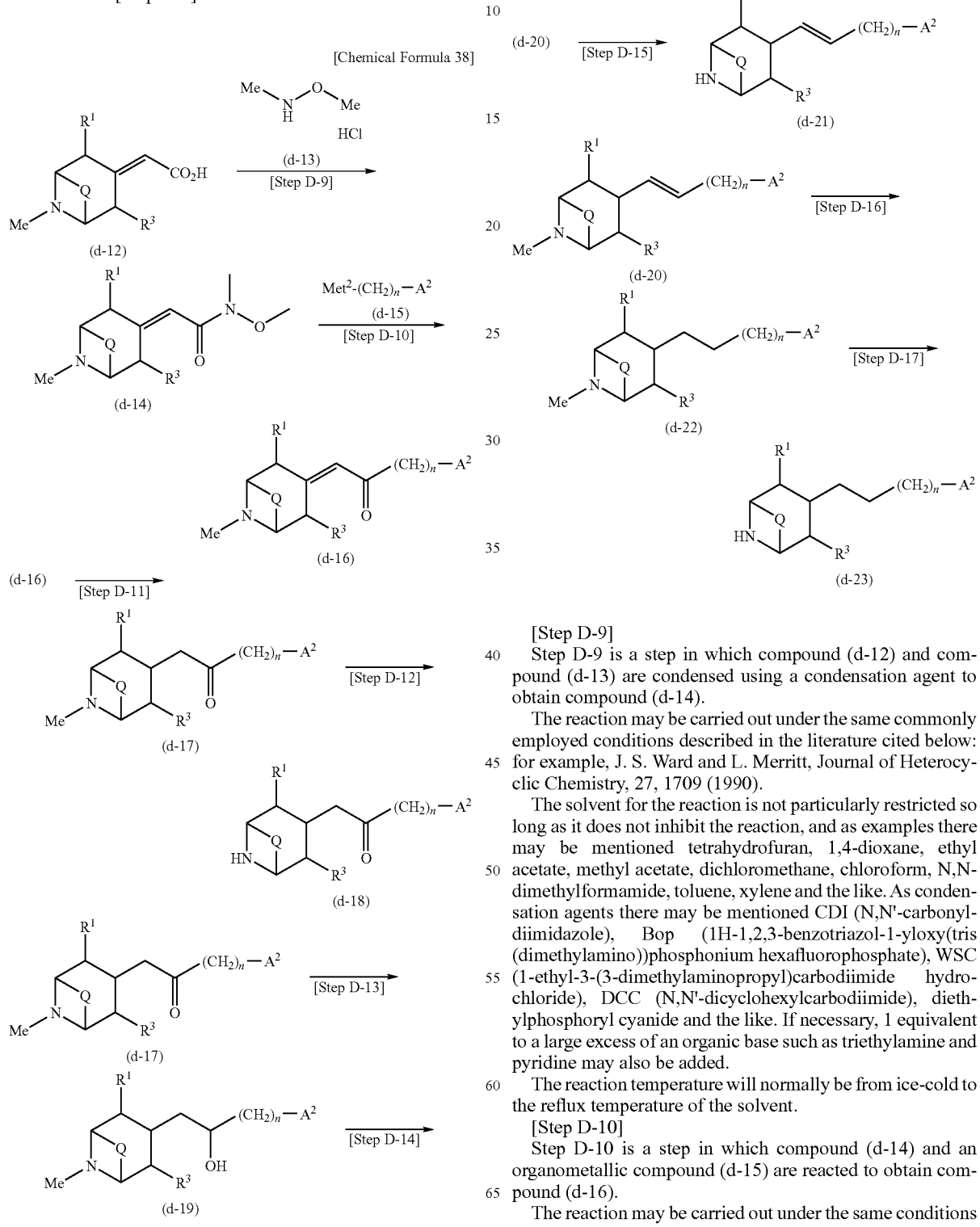

[Step D-9]

Step D-9 is a step in which compound (d-12) and compound (d-13) are condensed using a condensation agent to obtain compound (d-14).

The reaction may be carried out under the same commonly employed conditions described in the literature cited below: for example, J. S. Ward and L. Merritt, Journal of Heterocyclic Chemistry, 27, 1709 (1990).

The solvent for the reaction is not particularly restricted so long as it does not inhibit the reaction, and as examples there may be mentioned tetrahydrofuran, 1,4-dioxane, ethyl acetate, methyl acetate, dichloromethane, chloroform, N,N-dimethylformamide, toluene, xylene and the like. As condensation agents there may be mentioned CDI (N,N'-carbonyldiimidazole), Bop (1H-1,2,3-benzotriazol-1-yloxy(tris (dimethylamino))phosphonium hexafluorophosphate), WSC (1-ethyl-3-(3-dimethylaminopropyl)carbodiimide hydrochloride), DCC (N,N'-dicyclohexylcarbodiimide), diethylphosphoryl cyanide and the like. If necessary, 1 equivalent to a large excess of an organic base such as triethylamine and pyridine may also be added.

The reaction temperature will normally be from ice-cold to the reflux temperature of the solvent.

[Step D-10]

Step D-10 is a step in which compound (d-14) and an organometallic compound (d-15) are reacted to obtain compound (d-16).

The reaction may be carried out under the same conditions as commonly employed for reaction between amide compounds and organometallic reagents to obtain ketone compounds (for example, the conditions described in S. Nahm and S. M. Weinreb, Tetrahedron Letters, 22, 3825 (1981)).

The solvent used for the reaction is not particularly restricted so long as it dissolves the starting materials to some extent without inhibiting the reaction, and as examples there may be mentioned diethyl ether, tetrahydrofuran, 1,4-dioxane and the like. The reaction temperature is not particularly restricted and the reaction may normally be conducted at a temperature between −78° C. and room temperature.

Compound (d-15) used in this step may be a commercially available material, or it may be produced by a known process from commercially available materials.

For example, when $Met^2$ is lithium, the compound may be produced under the same conditions as commonly employed for reacting commercially available starting materials with alkyllithium reagents such as n-butyllithium or sec-butyllithium to obtain organic lithium reagents (for example, the conditions described in J. C. H. Hwa and H. Sims, Organic Synthesis, V, 608 (1973)).

When $Met^2$ is the formula —Mg—Br, the compound may be produced under the same conditions as commonly employed for reaction of commercially available starting materials with magnesium to obtain Grignard reagents (for example, the conditions described in N. A. Nelson and J. C. Wollensak, Journal of American Chemical Society, 80, 662 (1958)).

[Step D-11]

Step D-11 is a step in which the double bond of compound (d-16) is reduced to obtain compound (d-17).

The reaction may be carried out under the same conditions as commonly employed for catalytic reduction reaction of unsaturated ketone compounds to saturated ketone compounds under a hydrogen atmosphere (for example, the conditions described in R. L. Augustine, Journal of Organic Chemistry, 23, 1853 (1958)).

The catalyst used for the reaction is preferably palladium on carbon, palladium hydroxide on carbon or platinum oxide. The solvent used for the reaction is not particularly restricted so long as it dissolves the starting materials to some extent without inhibiting the reaction, and as examples there may be mentioned methanol, ethanol, 2-propanol and ethyl acetate. The reaction temperature is not particularly restricted but will normally be from ice-cold to 100° C. The hydrogen pressure will normally be from atmospheric pressure to 5 atm.

[Step D-12]

Step D-12 is a step in which methyl of compound (d-17) is eliminated to obtain compound (d-18). The reaction may be carried out under the same conditions as commonly employed for deprotection of methyl (for example, the conditions described in J. H. Cooley and E. J. Evain, Synthesis, 1 (1989)). For example, 1-chloroethyl chloroformate and methanol may be reacted therewith in that order in a solvent such as 1,2-dichloroethane or toluene. The reaction temperature is not particularly restricted but will normally be from −78° C. to the reflux temperature of the solvent, and is preferably from ice-cold to the reflux temperature of the solvent.

[Step D-13]

Step D-13 is a step in which carbonyl of compound (d-17) is reduced to obtain compound (d-19).

The reaction may be carried out under conditions known to those skilled in the art and commonly employed for reduction of ketones to alcohols. For example, it may be conducted under the same conditions as described in H. C. Brown, S. Krishnamurthy, Tetrahedron, 35, 567 (1979).

The reducing agent used for the reaction is preferably sodium borohydride or potassium borohydride. The solvent used for the reaction is not particularly restricted so long as it dissolves the starting materials to some extent without inhibiting the reaction, and as examples there may be mentioned methanol, ethanol and 2-propanol. The reaction temperature is not particularly restricted but will normally be from ice-cold to the reflux temperature of the solvent.

[Step D-14]

Step D-14 is a step in which compound (d-19) is dehydrated to obtain compound (d-20).

The reaction may be carried out under acidic conditions or under the same conditions as employed for dehydration reaction of alcohols (for example, the conditions described in A. Luxenburger, Tetrahedron, 59, 6045 (2003)). The solvent used in the reaction is not particularly restricted so long as it does not inhibit the reaction, and acetone, toluene, xylene or the like may be used. The acid used for the reaction may be, for example, hydrochloric acid, hydrobromic acid, sulfuric acid, oxalic acid, p-toluenesulfonic acid or the like. The acid may be used at normally 1 equivalent to a large excess, and preferably 1-3 equivalents, with respect to compound (d-19). The reaction temperature is not particularly restricted but will normally be from room temperature to the reflux temperature of the solvent. Using a Dean-Stark trap can often produce favorable results such as increased yield.

[Step D-15]

Step D-15 is a step in which methyl of compound (d-20) is eliminated to obtain compound (d-21).

The reaction in this step may be carried out under the same conditions as [Step D-12] described above.

[Step D-16]

Step D-16 is a step in which the double bond of compound (d-20) is reduced to obtain compound (d-22).

The reaction in this step may be carried out under the same conditions as [Step D-11] described above.

[Step D-17]

Step D-17 is a step in which methyl of compound (d-22) is eliminated to obtain compound (d-23).

The reaction in this step may be carried out under the same conditions as [Step D-12] described above.

[Chemical Formula 39]

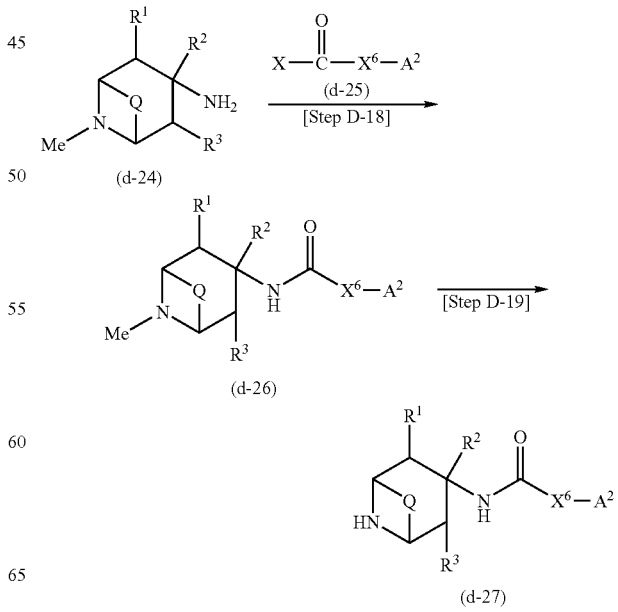

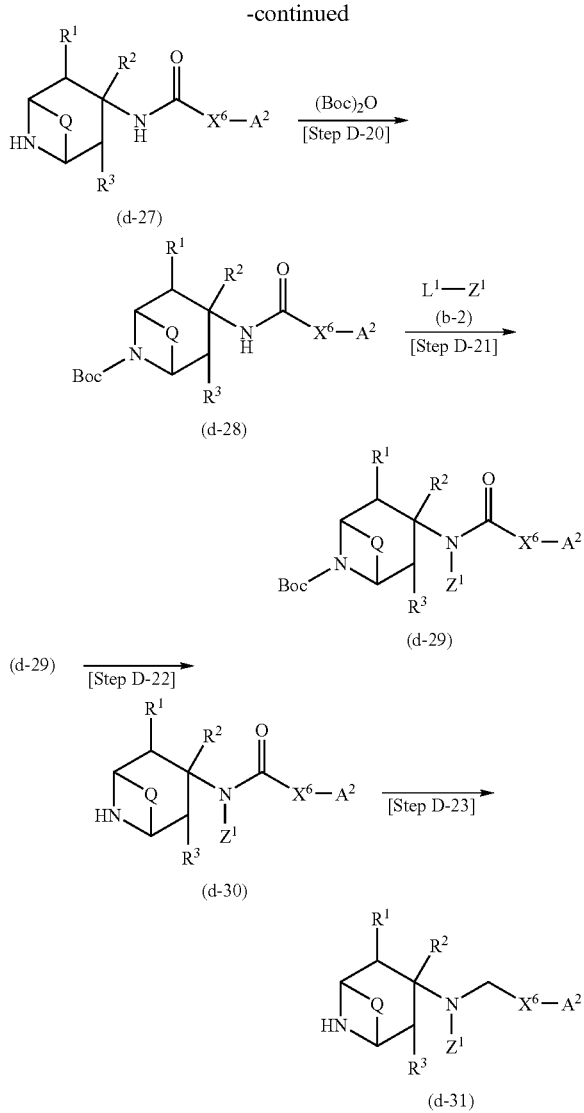

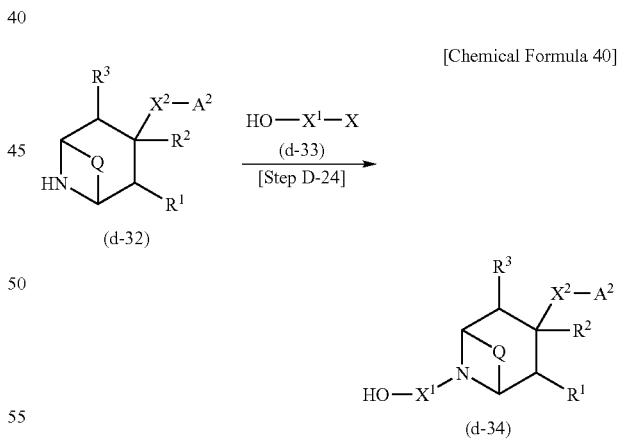

[Step D-18]

Step D-18 is a step in which compound (d-24) and compound (d-25) are reacted in the presence of a base to obtain compound (d-26).

The reaction in this step may be carried out under the same conditions as [Step B-7] described for [Production Process B] above.

[Step D-19]

Step D-19 is a step in which methyl of compound (d-26) is eliminated to obtain compound (d-27).

The reaction in this step may be carried out under the same conditions as [Step D-12] described above.

[Step D-20]

Step D-20 is a step in which amino of compound (d-27) is protected with tert-butoxycarbonyl to obtain compound (d-28).

The reaction may be carried out under the same conditions as commonly employed for tert-butoxycarbonylation of amino compounds (for example, the conditions described in T. W. Green and P. G. M. Wuts, "Protective Groups in Organic Synthesis, Third Edition", John Wiley & Sons (1999), p. 518-525).

The reaction may be conducted by reaction with di-tert-butyl carbonate in an organic solvent, or in a mixture of water and an organic solvent, in the presence of a base. The solvent used for the reaction may be diethyl ether, tetrahydrofuran, 1,4-dioxane, acetone, dichloromethane, chloroform, acetonitrile or the like, and the base used may be triethylamine or diisopropylethylamine. A sodium hydroxide aqueous solution may also be used as the base.

[Step D-21]

Step D-21 is a step in which compound (d-28) and compound (b-2) are reacted to obtain compound (d-29).

The reaction in this step may be carried out under the same conditions as [Step B-2] described for [Production Process B] above.

[Step D-22]

Step D-22 is a step in which tert-butoxycarbonyl of compound (d-29) is eliminated to obtain compound (d-30).

The reaction of this step may be carried out under the same conditions as in [Step D-2] described above, where $Z^6$ is tert-butoxycarbonyl.

[Step D-23]

Step D-23 is a step in which carbonyl of compound (d-30) is reduced to obtain compound (d-31).

The reduction reaction in this step is not particularly restricted, and it may be carried out under the same conditions as commonly employed for reduction of amide compounds to amines (for example, the conditions described in J. K. Thottathil, J. L. Moniot, R. H. Mueller, M. K. Y. Wong, and T. P. Kissick, J. Org. Chem., 51, 3140 (1986)).

The reducing agent used for the reaction in this step may be a metal hydride, and for example, lithium aluminum hydride or sodium bis(2-methoxyethoxy)aluminum hydride may be used. The solvent used for the reaction in this step is not particularly restricted so long as it dissolves the starting materials to some extent without inhibiting the reaction, and as examples there may be mentioned diethyl ether, tetrahydrofuran, 1,4-dioxane, toluene and the like.

The reaction temperature for this step will normally be from ice-cold to the reflux temperature of the solvent.

[Chemical Formula 40]

[Step D-24]

Step D-24 is a step in which compound (d-32) and compound (d-33) are subjected to nucleophilic substitution reaction to obtain compound (d-34).

The reaction in this step may be carried out under the same conditions as [Step A-5] described for [Production Process A] above.

Compound (d-1) used in [Step D-1] and [Step D-6] for [Production Process D] described above may be synthesized in the following manner, for example.

[Chemical Formula 41]

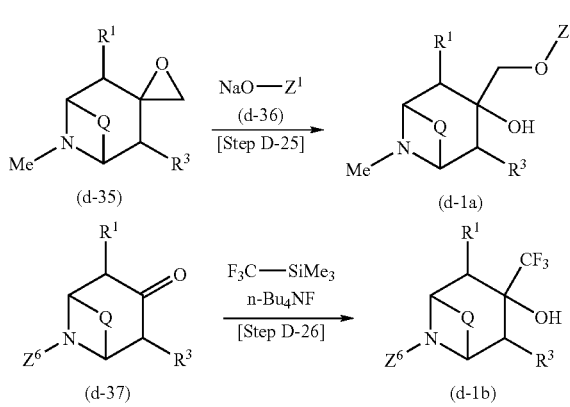

[Step D-25]

Step D-25 is a step in which compound (d-35) and compound (d-36) are reacted to obtain compound (d-1a).

This step may be carried out under the same conditions as described in, for example, T. Mall and H. Stamm, Journal of Organic Chemistry, 52, 4812 (1987).

The solvent used for the reaction is not particularly restricted so long as it dissolves the starting materials to some extent without inhibiting the reaction, and when $Z^1$ is methyl, for example, methanol or N,N-dimethylformamide may be used. The reaction temperature is not particularly restricted but will normally be from room temperature to the reflux temperature of the solvent.

[Step D-26]

Step D-26 is a step in which compound (d-37) and trifluoromethyltrimethylsilane are reacted in the presence of tetra-n-butylammonium fluoride to obtain compound (d-1b).

This step may be carried out under the same conditions as described in, for example, R. Krishnamurti, D. R. Bellew, and G. K. Surya Prakash, Journal of Organic Chemistry, 56, 984 (1991).

The solvent used for the reaction is not particularly restricted so long as it dissolves the starting materials to some extent without inhibiting the reaction, and tetrahydrofuran or the like may be used. The reaction may also be carried out with a catalytic amount of tetra-n-butylammonium fluoride. The reaction temperature is not particularly restricted but will normally be from ice-cold to room temperature.

Compound (d-2) or compound (d-10) used for alkylation in step D-1 or step D-6 described above may also be obtained by the following reaction scheme.

[Chemical Formula 42]

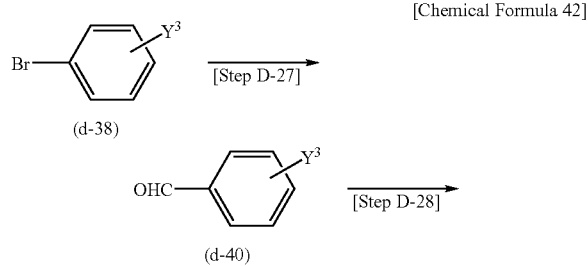

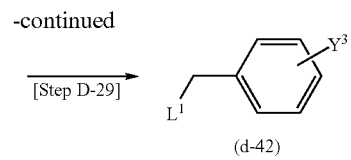

[Step D-27]

Step D-27 is a step in which compound (d-40) is obtained from compound (d-38).

Specifically, compound (d-40) may be produced by reacting compound (d-38) with an organometallic reagent to form an anion, which is then reacted with a formic acid derivative.

It may be produced under the same conditions as described in H. Cristensen, Synthetic Communications, 5, 65 (1975), for example.

There are no particular restrictions on the organometallic reagent used for the reaction, but lithium reagents such as n-butyllithium, sec-butyllithium, tert-butyllithium and phenyllithium are preferred.

There are also no particular restrictions on the formic acid derivative, but N,N-dimethylformamide, N-formylpiperidine, N-formylmorpholine and N-methyl-N-phenylformamide are preferred.

The reaction temperature is not particularly restricted but is normally from −78° C. to the reflux temperature of the solvent, and is preferably from −78° C. to room temperature. The solvent used for the reaction is not particularly restricted so long as it does not inhibit the reaction, and may be diethyl ether, tetrahydrofuran or the like.

[Step D-28]

Step D-28 is a step in which carbonyl of compound (d-40) is reduced to obtain compound (d-41).

The reaction in this step may be carried out under the same conditions as [Step D-13] described above.

[Step D-29]

Step D-29 is a step in which hydroxyl of compound (d-41) is converted to a leaving group such as chlorine to obtain compound (d-42).

As leaving groups there may be mentioned halogen (chlorine, bromine, iodine) and sulfonyloxy such as methanesulfonyloxy, p-toluenesulfonyloxy and trifluoromethanesulfonyloxy.

The reaction may be carried out under the same conditions as commonly employed for reaction to convert hydroxyl to leaving groups (for example, the conditions described in R. K. Crossland and K. L. Servis, Journal of Organic Chemistry, 35, 3195 (1970)).

For example, when the leaving group is halogen, compound (d-41) may be produced by reaction with thionyl chloride, thionyl bromide, phosphorus tribromide or a tetrahalogenomethane-triphenylphosphine. The solvent used for the reaction is not particularly restricted so long as it dissolves the starting materials to some extent without inhibiting the reaction, but benzene, toluene, xylene, dichloromethane and chloroform are preferred. Favorable results in the reaction, such as increased yield, can be obtained by addition of a base. The base used is not particularly restricted so long as it does not inhibit the reaction, but sodium carbonate, potassium carbonate, triethylamine, pyridine and diisopropylethylamine are preferred. The reaction temperature will normally be from −78° C. to the reflux temperature of the solvent, and is preferably from ice-cold to the reflux temperature of the solvent.

When the leaving group is sulfonyloxy, compound (d-41) may be produced by reaction with methanesulfonyl chloride, p-toluenesulfonyl chloride, trifluoromethanesulfonic anhydride or the like. The solvent used for the reaction is not particularly restricted so long as it dissolves the starting materials to some extent without inhibiting the reaction, and there may be mentioned as preferable tetrahydrofuran, toluene, xylene, dichloromethane, chloroform and N,N-dimethylformamide. The reaction temperature will normally be from −78° C. to the reflux temperature of the solvent, and is preferably from ice-cold to room temperature. Favorable results in the reaction, such as increased yield, can be obtained by addition of a base. The base used is not particularly restricted so long as it does not inhibit the reaction, but sodium carbonate, potassium carbonate, triethylamine, pyridine and diisopropylethylamine are preferred.

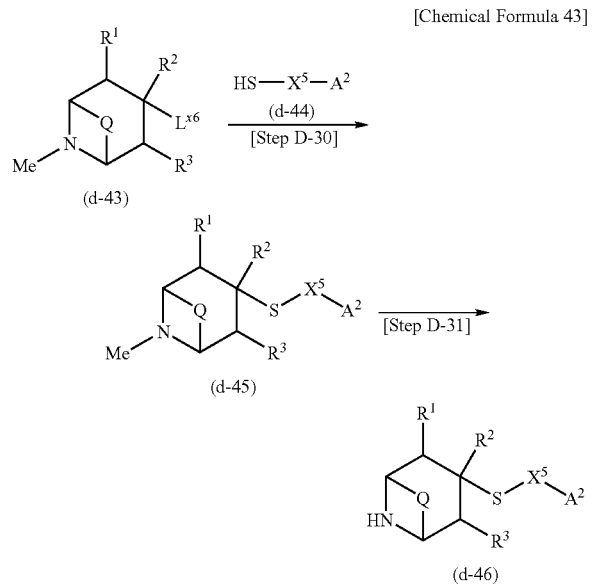

wherein $L^{x6}$ represents a chlorine or methanesulfonyloxy group.

[Step D-30]

Step D-30 is a step in which compound (d-43) and compound (d-44) are subjected to nucleophilic substitution reaction to obtain compound (d-45).

Specifically, for example, compound (d-44) may be reacted with a base to form an anion, which is then reacted with compound (d-43) to obtain compound (d-45).

Compound (d-44) will normally be used at 1-5 equivalents with respect to compound (d-43).

The solvent for the reaction is not particularly restricted so long as it does not inhibit the reaction, and a suitable base may be reacted at 1 equivalent to an excess, in an organic solvent such as diethyl ether, tetrahydrofuran, 1,4-dioxane, N,N-dimethylformamide, dimethyl sulfoxide, methanol or ethanol. As suitable bases there may be mentioned sodium hydroxide, potassium hydroxide, sodium hydride, potassium hydride, sodium methoxide, sodium ethoxide, potassium tert-butoxide, sodium carbonate, potassium carbonate, cesium carbonate and the like.

The reaction temperature is not particularly restricted but will normally be from −78° C. to the reflux temperature of the solvent, and is preferably from ice-cold to 100° C.

[Step D-31]

Step D-31 is a step in which methyl in compound (d-45) is eliminated to obtain compound (d-46).

The reaction in this step may be carried out under the same conditions as [Step D-12] described above.

[Production Process E]

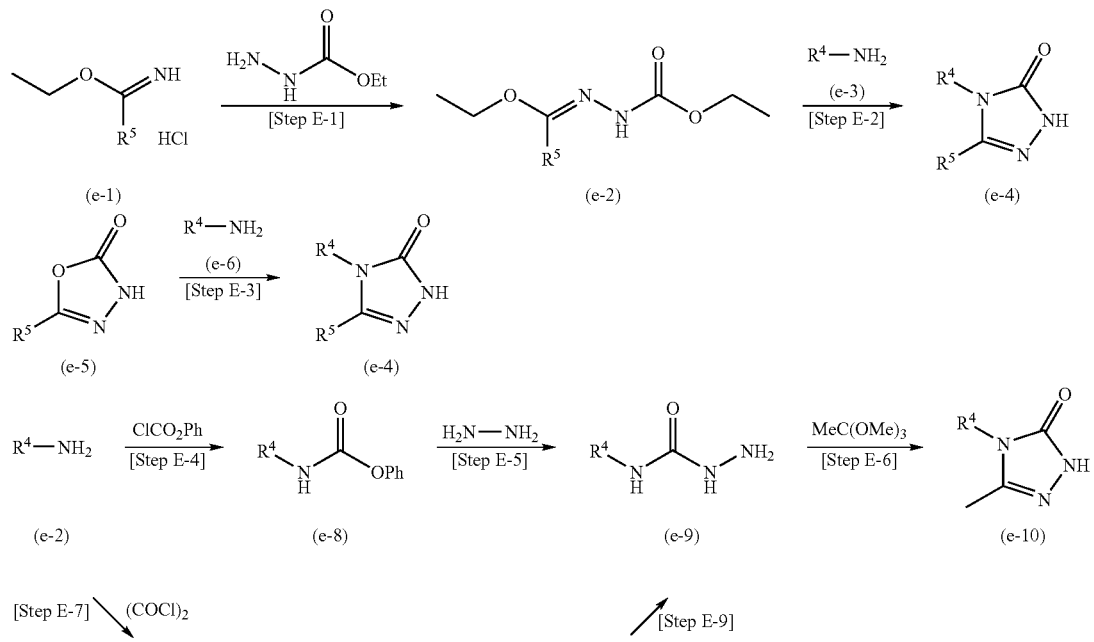

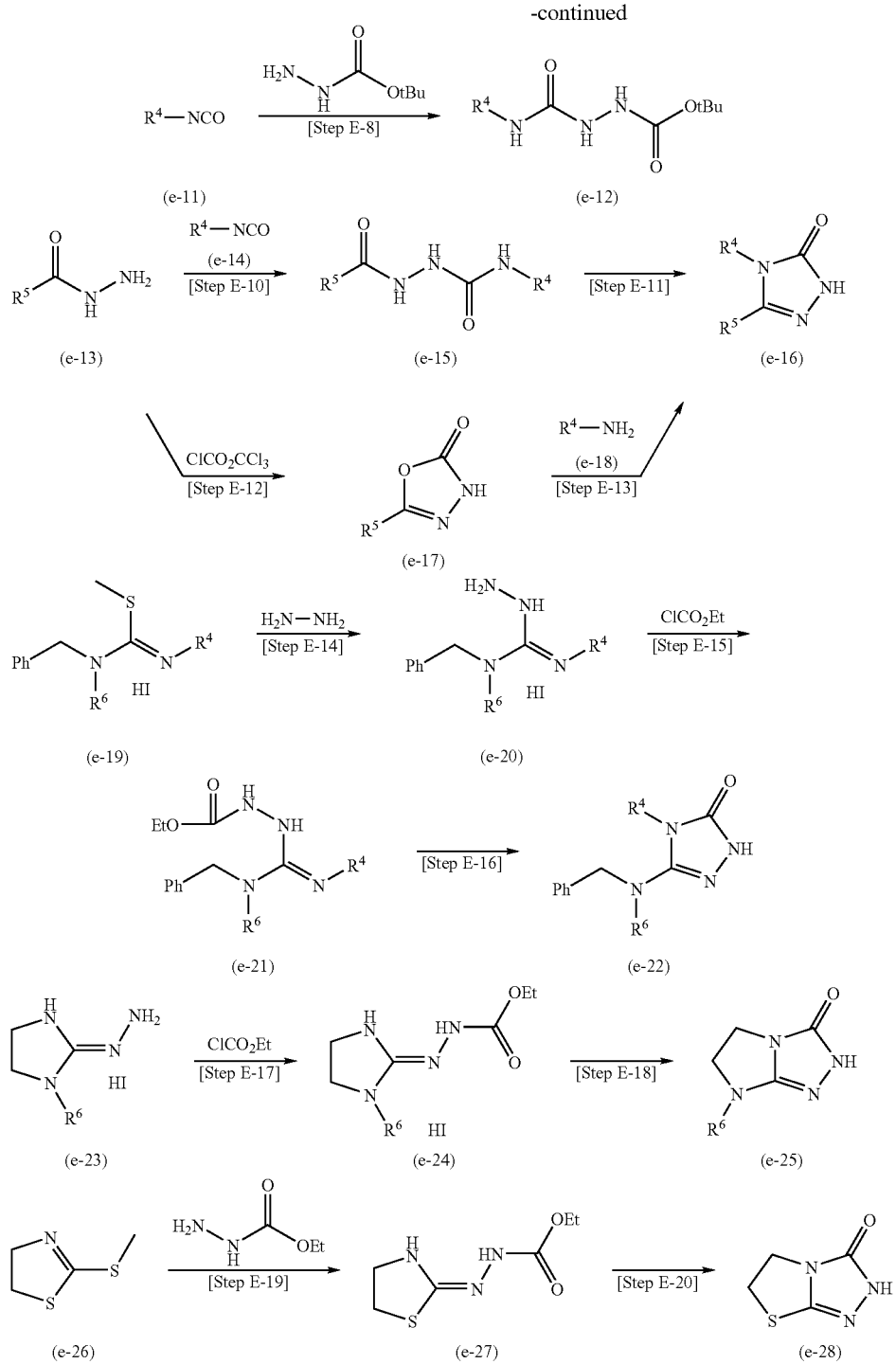

The starting materials used for [Production Process E] may be commercially available materials, or they may be produced by methods known to those skilled in the art from commercially available materials.

[Step E-1]

Step E-1 is a step in which compound (e-1) is reacted with ethyl carbazate to obtain compound (e-2).

The reaction may be carried out under the same conditions as described in, for example, M. Pesson, S. Dupin, et M. Antoine, Bulletin de la Societe Chimic de France, 1364 (1962) and Resat UN and Aysun IKIZLER, Chimica Acta Turcica, 3, 113 (1975).

The solvent used for the reaction is not particularly restricted so long as it dissolves the starting materials to some extent without inhibiting the reaction, but methanol and ethanol are preferred. Favorable results in the reaction, such as increased yield, can be obtained by addition of a base. The base is not particularly restricted so long as it does not inhibit the reaction, and sodium methoxide or sodium ethoxide may be mentioned. The reaction temperature will normally be from −78° C. to the reflux temperature of the solvent, and is preferably from ice-cold to the reflux temperature of the solvent.

[Step E-2]

Step E-2 is a step in which compound (e-2) and compound (e-3) are reacted to obtain compound (e-4).

The reaction may be carried out under the same conditions as described in, for example, M. Pesson, S. Dupin, et M. Antoine, Bulletin de la Societe Chimic de France, 1364 (1962) and Resat UN and Aysun IKIZLER, Chimica Acta Turcica, 3, 113 (1975).

The solvent used for the reaction is not particularly restricted so long as it dissolves the starting materials to some extent without inhibiting the reaction, but methanol, ethanol, propanol, acetonitrile and N,N-dimethylformamide are preferred. Favorable results in the reaction, such as increased yield, can be obtained by addition of a base. The base is not particularly restricted so long as it does not inhibit the reaction, and sodium methoxide or sodium ethoxide may be mentioned. The reaction temperature will normally be from −78° C. to the reflux temperature of the solvent, and is preferably from room temperature to the reflux temperature of the solvent.

[Step E-3]

Step E-3 is a step in which compound (e-5) and compound (e-6) are reacted to obtain compound (e-4).

The reaction may be carried out under the same conditions as described in, for example, M. Pesson, S. Dupin, et M. Antoine, Bulletin de la Societe Chimic de France, 1364 (1962) and Resat UN and Aysun IKIZLER, Chimica Acta Turcica, 3, 113 (1975).

Specifically, compound (e-5) and compound (e-6) are reacted, and the obtained compound is subjected to ring closure reaction in the presence of a base to obtain compound (e-4).

The solvent used for the reaction between compound (e-5) and compound (e-6) is not particularly restricted so long as it dissolves the starting materials to some extent without inhibiting the reaction, but methanol, ethanol and N,N-dimethylformamide are preferred. The reaction temperature will normally be from −78° C. to the reflux temperature of the solvent, and is preferably from room temperature to the reflux temperature of the solvent.

The solvent used for the ring closure reaction is not particularly restricted so long as it dissolves the starting materials to some extent without inhibiting the reaction, but aqueous sodium hydroxide and aqueous potassium hydroxide are preferred. The reaction temperature will normally be from room temperature to the reflux temperature of the solvent.

[Step E-4]

Step E-4 is a step in which amino of compound (e-2) is carbamoylated to obtain compound (e-8).

The reaction may be carried out under the same conditions as described in H. R. Kricheidorf, Justus Liebig's Annalen der Chemie, 1816 (1973), for example.

The solvent used for the reaction is not particularly restricted so long as it dissolves the starting materials to some extent without inhibiting the reaction, and there may be mentioned as preferable acetonitrile, tetrahydrofuran, toluene, xylene, dichloromethane, chloroform, N,N-dimethylformamide and pyridine. The reaction temperature will normally be from −78° C. to the reflux temperature of the solvent, and is preferably from ice-cold to room temperature. The reaction is preferably carried out in the presence of a base. The base used is not particularly restricted so long as it does not inhibit the reaction, but sodium carbonate, potassium carbonate, triethylamine, pyridine and diisopropylethylamine are preferred.

[Step E-5]

Step E-5 is a step in which compound (e-8) and hydrazine are reacted to obtain compound (e-9).

The reaction may be carried out under the same conditions as described in, for example, Q. Sun, L. Tafesse, K. Islam, X. Zhou, S. F. Victory, C. Zhongwu, M. Hachicha, L. A. Schmid, A. Patel, Y. Rotshteyn, K. J. Valenzano and D. J. Kyle, Bioorganic & Medicinal Chemistry Letters, 13, 3611 (2003).

The hydrazine used for the reaction may be a hydrate or anhydrous.

The solvent used for the reaction is not particularly restricted so long as it dissolves the starting materials to some extent without inhibiting the reaction, but methanol, ethanol and propanol are preferred. The reaction temperature will normally be from ice-cold to the reflux temperature of the solvent.

[Step E-6]

Step E-6 is a step in which compound (e-9) and methyl orthoacetate are reacted to obtain compound (e-10).

The solvent used for the reaction is not particularly restricted so long as it dissolves the starting materials to some extent without inhibiting the reaction, but methanol, ethanol and propanol are preferred. The reaction temperature will normally be from ice-cold to the reflux temperature of the solvent.

[Step E-7]

Step E-7 is a step in which compound (e-2) and oxalyl chloride are reacted to obtain compound (e-11).

The reaction may be carried out under the same conditions commonly employed for production of isocyanates from amines (for example, the conditions described in A. J. Speziale, L. R. Smith, Organic Synthesis, 46, 16 (1966)).

The solvent used for the reaction is not particularly restricted so long as it dissolves the starting materials to some extent without inhibiting the reaction, but dichloromethane, chloroform and 1,2-dichloroethane are preferred. The reaction temperature will normally be from ice-cold to the reflux temperature of the solvent.

[Step E-8]

Step. E-8 is a step in which compound (e-11) is reacted with tert-butyl carbazate to obtain compound (e-12).

The reaction may be conducted under the same conditions as commonly employed for production of ureas from isocyanates (for example, the conditions described in J. K. Snyder and L. M. Stock, Journal of Organic Chemistry, 45, 886 (1980)).

The solvent used for the reaction is not particularly restricted so long as it dissolves the starting materials to some extent without inhibiting the reaction, but dichloromethane, chloroform, 1,2-dichloroethane, tetrahydrofuran, toluene, xylene and ethyl acetate are preferred. The reaction temperature will normally be from ice-cold to the reflux temperature of the solvent.

[Step E-9]

Step E-9 is a step in which tert-butoxycarbonyl of compound (e-12) is deprotected to obtain compound (e-9).

The reaction may be carried out under the same conditions as commonly employed for deprotection of tert-butoxycarbonyl (for example, the conditions described in T. W. Green and P. G. M. Wuts, "Protective Groups in Organic Synthesis, Third Edition", John Wiley & Sons (1999), p. 518-525). The solvent for the reaction is not particularly restricted so long as it does not inhibit the reaction, and the reaction may be conducted with a suitable acid such as hydrogen chloride, hydrochloric acid, sulfuric acid, trifluoroacetic acid or p-toluenesulfonic acid in an organic solvent such as diethyl ether, tetrahydrofuran, 1,4-dioxane, acetone or ethyl acetate, or in a mixture of water and an organic solvent. The reaction temperature is not particularly restricted but will normally be from ice-cold to the reflux temperature of the solvent, and is preferably from ice-cold to room temperature.

[Step E-10]

Step E-10 is a step in which compound (e-13) and compound (e-14) are reacted to obtain compound (e-15).

The reaction in this step may be carried out under the same conditions as [Step E-8] described above.

[Step E-11]

Step E-11 is a step in which compound (e-15) is subjected to ring closure reaction under basic conditions to obtain compound (e-16).

The solvent used for the ring closure reaction is not particularly restricted so long as it dissolves the starting materials to some extent without inhibiting the reaction, but aqueous sodium hydroxide and aqueous potassium hydroxide are preferred. The reaction temperature will normally be from room temperature to the reflux temperature of the solvent.

[Step E-12]

Step E-12 is a step in which compound (e-13) and trichloromethyl chloroformate are reacted to obtain compound (e-17).

The reaction may be carried out under the same conditions as described in the literature, such as F. Chau, J-C. Malandea and R. Milcent, Journal of Heterocyclic Chemistry, 34, 1603 (1997), EP321833, for example.

The solvent used for the reaction is not particularly restricted so long as it dissolves the starting materials to some extent without inhibiting the reaction, but dichloromethane, chloroform, 1,2-dichloroethane, tetrahydrofuran, toluene, xylene and ethyl acetate are preferred. The reaction temperature will normally be from ice-cold to the reflux temperature of the solvent.

[Step E-13]

Step E-13 is a step in which compound (e-17) and compound (e-18) are reacted to obtain compound (e-16).

The reaction in this step may be carried out under the same conditions as [Step E-3] described above.

[Step E-14]

Step E-14 is a step in which compound (e-19) and hydrazine are reacted to obtain compound (e-20).

The reaction in this step may be carried out under the same conditions as [Step E-5] described above. The product may be used directly for the following step without purification.

[Step E-15]

Step E-15 is a step in which the amino group of compound (e-20) is carbamoylated to obtain compound (e-21).

The reaction in this step may be carried out under the same conditions as [Step E-4] described above. The product may be used directly for the following step without purification.

[Step E-16]

Step E-16 is a step in which compound (e-21) is subjected to ring closure reaction to obtain compound (e-22).

Specifically, compound (e-21) may be dissolved in a solvent and heated to obtain compound (e-22). The solvent used for the reaction is not particularly restricted so long as it dissolves the starting materials to some extent without inhibiting the reaction, but toluene, xylene and N,N-dimethylformamide are preferred. The reaction temperature will normally be from room temperature to the reflux temperature of the solvent.

[Step E-17]

Step E-17 is a step in which the amino group of compound (e-23) is carbamoylated to obtain compound (e-24).

The reaction in this step may be carried out under the same conditions as [Step E-4] described above.

[Step E-18]

Step E-18 is a step in which compound (e-24) is subjected to ring closure reaction to obtain compound (e-25).

The reaction in this step may be carried out under the same conditions as [Step E-16] described above.

[Step E-19]

Step E-19 is a step in which compound (e-26) is reacted with ethyl carbazate to obtain compound (e-27).

The reaction in this step may be carried out under the same conditions as [Step E-14] described above.

[Step E-20]

Step E-20 is a step in which compound (e-27) is subjected to ring closure reaction to obtain compound (e-28).

The reaction in this step may be carried out under the same conditions as [Step E-16] described above.

[Production process F]

[Chemical Formula 45]

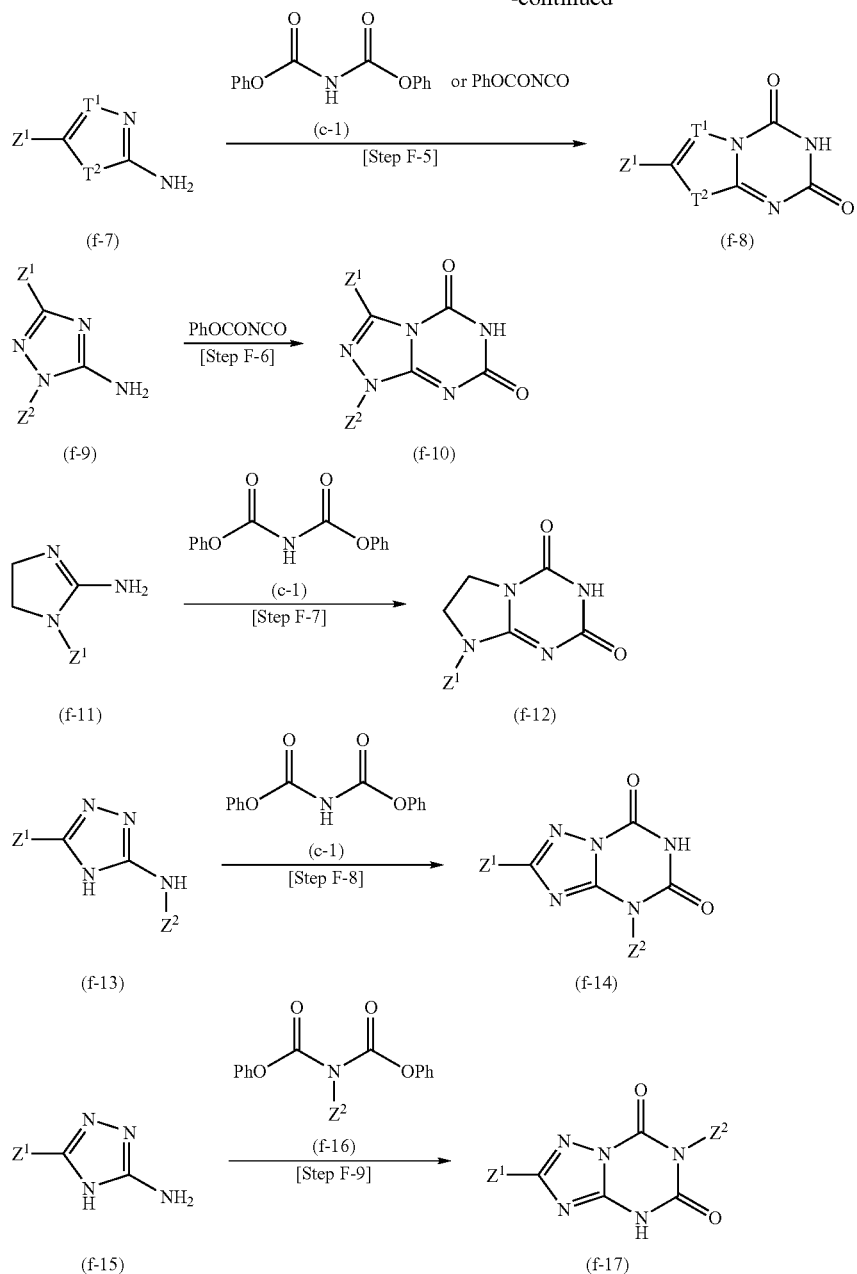

The starting materials used for [Production Process F] may be commercially available materials, or they may be produced by methods known to those skilled in the art from commercially available materials.

[Step F-1]

Step F-1 is a step in which the carbonyl group of compound (f-1) is thiocarbonylated to obtain compound (f-2).

The reaction may be carried out under the same conditions as commonly employed for thiocarbonylation of carbonyl (for example the conditions described in M. P. Cava and M. I. Levinson, Tetrahedron, 41, 5061 (1985)).

The solvent used for the reaction is not particularly restricted so long as it dissolves the starting materials to some extent without inhibiting the reaction, but dichloromethane, chloroform, 1,2-dichloroethane, tetrahydrofuran, toluene, xylene and pyridine are preferred. The reaction temperature will normally be from room temperature to the reflux temperature of the solvent.

[Step F-2]

Step F-2 is a step in which compound (f-2) is reacted with silver cyanate to obtain compound (f-3).

The reaction may be carried out under the same conditions as described in the literature, such as I. Shibuya, K. Honda, Y. Gama, M. Shimizu, Heterocycles, 53, 929 (2000), for example.

The solvent used for the reaction is not particularly restricted so long as it dissolves the starting materials to some extent without inhibiting the reaction, but acetonitrile and propionitrile are preferred. The reaction is preferably carried out in the presence of a base. The base used is not particularly restricted so long as it does not inhibit the reaction, and there may be mentioned triethylamine and diisopropylethylamine. The reaction temperature will normally be from room temperature to the reflux temperature of the solvent.

[Step F-3]

Step F-3 is a step in which compound (f-4) and compound (f-5) are reacted to obtain compound (f-6).

The reaction may be carried out under the same conditions as commonly employed for production of amidines from imidates (for example, the conditions described in A. W. Dox, Organic Synthesis, I, 5 (1941)).

Compound (f-5) used for the reaction may be a salt or in free form. Preferable salt is hydrochloride. The solvent used for the reaction is not particularly restricted so long as it dissolves the starting materials to some extent without inhibiting the reaction, but methanol, ethanol and propanol are preferred. Favorable results in the reaction, such as increased yield, can be obtained by addition of a base. The base used is not particularly restricted so long as it does not inhibit the reaction, and triethylamine and diisopropylethylamine may be mentioned. The reaction temperature will normally be from ice-cold to the reflux temperature of the solvent.

[Step F-4]

Step F-4 is a step in which compound (f-6) and compound (c-1) or phenoxycarbonyl isocyanate are reacted to obtain compound (f-3).

The reaction in this step may be carried out under the same conditions as [Step C-1] described for [Production Process C] above in the case of reacting compound (f-6) with compound (c-1).

The reaction in this step may be carried out under the same conditions as described in the literatures such as P. Rao and S. A. Benner, Journal of Organic Chemistry, 66, 5012 (2001), Y. Watanabe, H. Usui, S. Kobayashi, H. Yoshizawa, T. Shibano, T. Tanaka, Y. Morishita, M. Yasuoka and M. Kanao, Journal of Medicinal Chemistry, 35, 189 (1992) in the case of reacting compound (f-6) with phenoxycarbonyl isocyanate.

The solvent used for the reaction is not particularly restricted so long as it dissolves the starting materials to some extent without inhibiting the reaction, and there may be mentioned tetrahydrofuran, benzene, toluene, xylene, acetonitrile, dichloromethane, chloroform, N,N-dimethylformamide and dimethylsulfoxide.

The reaction temperature will normally be from ice-cold to the reflux temperature of the solvent, and preferably from room temperature to the reflux temperature of the solvent.

[Step F-5]

Step F-5 is a step in which compound (f-7) and compound (c-1) or phenoxycarbonyl isocyanate are reacted to obtain compound (f-8).

The reaction in this step may be carried out under the same conditions as [Step F-4].

[Step F-6]

Step F-6 is a step in which compound (f-9) and phenoxycarbonyl isocyanate are reacted to obtain compound (f-10).

The reaction in this step may be carried out under the same conditions as described in the literatures such as P. Rao and S. A. Benner, Journal of Organic Chemistry, 66, 5012 (2001), Y. Watanabe, H. Usui, S. Kobayashi, H. Yoshizawa, T. Shibano, T. Tanaka, Y. Morishita, M. Yasuoka and M. Kanao, Journal of Medicinal Chemistry, 35, 189 (1992).

The solvent used for the reaction is not particularly restricted so long as it dissolves the starting materials to some extent without inhibiting the reaction, and there may be mentioned tetrahydrofuran, benzene, toluene, xylene, acetonitrile, dichloromethane, chloroform, N,N-dimethylformamide and dimethylsulfoxide.

The reaction temperature will normally be from ice-cold to the reflux temperature of the solvent, and preferably from room temperature to the reflux temperature of the solvent.

[Step F-7]

Step F-7 is a step in which compound (f-11) and compound (c-1) are reacted to obtain compound (f-12).

The reaction in this step may be carried out under the same conditions as [Step C-2] described for [Production Process C] above.

[Step F-8]

Step F-8 is a step in which compound (f-13) and compound (c-1) are reacted to obtain compound (f-14).

The reaction in this step may be carried out under the same conditions as [Step C-2] described for [Production Process C] above.

[Step F-9]

Step F-9 is a step in which compound (f-15) and compound (f-16) are reacted to obtain compound (f-17).

The reaction in this step may be carried out under the same conditions as [Step C-2] described for [Production Process C] above.

[Production process G]

[Chemical Formula 46]

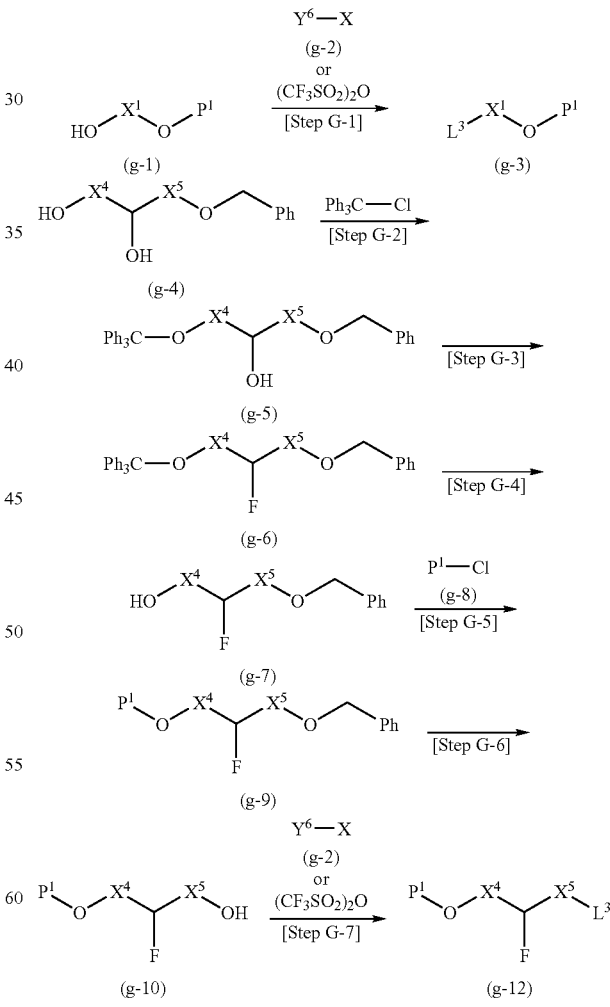

The starting materials used for [Production Process G] may be commercially available materials, or they may be produced by methods known to those skilled in the art from commercially available materials.

[Step G-1]

Step G-1 is a step in which compound (g-1) is reacted with compound (g-2) or trifluoromethanesulfonic anhydride to convert hydroxyl to a leaving group and obtain compound (g-3).

The reaction may be carried out under the same conditions as commonly employed for conversion of hydroxyl to leaving groups such as p-toluenesulfonyloxy (for example, the conditions described in Y. Yoshida, Y. Sakakura, N. Aso, S. Okada, and Y. Tanabe, Tetrahedron, 55, 2183 (1999)).

Specifically, for example, compound (g-1) may be reacted with methanesulfonyl chloride, p-toluenesulfonyl chloride, p-nitrobenzenesulfonyl chloride or the like to produce compound (g-3).

The solvent used for the reaction is not particularly restricted so long as it dissolves the starting materials to some extent without inhibiting the reaction, and as specific examples there may be mentioned dichloromethane, chloroform, tetrahydrofuran, toluene, xylene, acetonitrile and N,N-dimethylformamide.

The reaction temperature will normally be from −78° C. to the reflux temperature of the solvent, and is preferably from −78° C. to room temperature. The reaction is preferably carried out in the presence of a base. The base used is not particularly restricted so long as it does not inhibit the reaction, and as preferred examples there may be mentioned sodium carbonate, potassium carbonate, triethylamine, diisopropylethylamine and pyridine. Preferred results such as increased yield may be obtained if the reaction is conducted in the presence of trimethylammonium chloride.

The reaction may also be carried out under the same conditions as commonly employed for conversion of hydroxyl to leaving groups such as trifluoromethanesulfonyloxy (for example, P. J. Stang, M. Hanack, L. R. Subramanian, Synthesis, 85 (1982)).

The solvent used for the reaction is not particularly restricted so long as it dissolves the starting materials to some extent without inhibiting the reaction, and as preferred examples there may be mentioned dichloromethane, chloroform, tetrahydrofuran and pyridine.

The reaction temperature will normally be from −78° C. to the reflux temperature of the solvent, and is preferably from ice-cold to room temperature. The reaction is preferably carried out in the presence of a base. The base used is not particularly restricted so long as it does not inhibit the reaction, but pyridine and 2,6-lutidine are preferred.

[Step G-2]

Step G-2 is a step in which the hydroxyl of compound (g-4) is protected with trityl to obtain compound (g-5).

The reaction may be carried out under the same conditions as commonly employed for protection of hydroxyl with trityl groups (for example, the conditions described in T. W. Green and P. G. M. Wuts, "Protective Groups in Organic Synthesis, Third Edition", John Wiley & Sons (1999), p. 102-104).

The solvent used for the reaction is not particularly restricted so long as it dissolves the starting materials to some extent without inhibiting the reaction, and as preferred examples there may be mentioned dichloromethane, chloroform, tetrahydrofuran, pyridine, toluene, xylene, N,N-dimethylformamide and pyridine.

The reaction is preferably carried out in the presence of a base. The base used is not particularly restricted so long as it does not inhibit the reaction, but triethylamine, diisopropylethylamine, pyridine and 2,6-lutidine are preferred.

Addition of 4-dimethylaminopyridine (DMAP) can produce favorable results, such as shortened reaction time and increased yield.

The reaction temperature is not particularly restricted but will normally be from ice-cold to the reflux temperature of the solvent.

[Step G-3]

Step G-3 is a step in which the hydroxyl of compound (g-5) is fluorinated to obtain compound (g-6).

As an example of a method for conversion of hydroxyl to fluorine there may be mentioned the method described in P. M. Savu, D. Snustad, WO00/31003.

The fluorinating agent is preferably perfluoro-1-butanesulfonyl fluoride. The solvent used for the reaction is not particularly restricted so long as it dissolves the starting materials to some extent without inhibiting the reaction, but toluene and xylene are preferred.

The reaction is preferably carried out in the presence of a base. The base used is not particularly restricted so long as it does not inhibit the reaction, but 1,8-diazabicyclo[5.4.0]-7-undecene is preferred.

[Step G-4]

Step G-4 is a step in which trityl of compound (g-6) is deprotected to obtain compound (g-7).

The reaction may be carried out under the same conditions as commonly employed for deprotection of trityl (for example, the conditions described in T. W. Green and P. G. M. Wuts, "Protective Groups in Organic Synthesis, Third Edition", John Wiley & Sons (1999), p. 102-104).

The solvent used for the reaction is not particularly restricted so long as it does not inhibit the reaction, and an appropriate acid such as acetic acid, hydrogen chloride, hydrochloric acid, sulfuric acid, trifluoroacetic acid or p-toluenesulfonic acid may be reacted in an organic solvent such as diethyl ether, tetrahydrofuran, 1,4-dioxane, acetone or ethyl acetate, or in a mixture of water and an organic solvent. Hydrous acetic acid may also be used as the solvent. The reaction temperature is not particularly restricted but will normally be from ice-cold to the reflux temperature of the solvent.

[Step G-5]

Step G-5 is a step in which compound (g-7) is reacted with compound (g-8) to protect hydroxyl and obtain compound (g-9).

The reaction may be carried out under the same conditions as commonly employed for protection of hydroxyl with silyl (for example, the conditions described in T. W. Green and P. G. M. Wuts, "Protective Groups in Organic Synthesis, Third Edition", John Wiley & Sons (1999), p. 113-148).

The solvent used for the reaction is not particularly restricted so long as it dissolves the starting materials to some extent without inhibiting the reaction, and as preferred examples there may be mentioned dichloromethane, chloroform, tetrahydrofuran, pyridine, toluene, xylene, N,N-dimethylformamide and pyridine.

The reaction is preferably carried out in the presence of a base. The base used is not particularly restricted so long as it does not inhibit the reaction, but imidazole and pyridine are preferred.

The reaction temperature is not particularly restricted but will normally be from ice-cold to room temperature.

[Step G-6]

Step G-6 is a step in which the benzyl group of compound (g-9) is deprotected to obtain compound (g-10).

The reaction in this step may be carried out under the same conditions as [Step C-4] described for [Production Process C] above.

[Step G-7]

Step G-7 is a step in which compound (g-10) is reacted with compound (g-2) or trifluoromethanesulfonic anhydride to convert the hydroxyl to a leaving group and obtain compound (g-12).

The reaction in this step may be carried out under the same conditions as [Step G-1] described above.

Representative examples of production processes for compounds represented by general formula (I) according to the invention are described above, but the starting compounds and reagents for production of the invention compounds may also form salts or hydrates, depending on the starting materials and solvents used, and these are not particularly restricted so long as they do not inhibit the reaction. The solvent used will also differ depending on the starting materials and reagents, and of course is not particularly restricted so long as it can dissolve the starting materials to some degree and does not inhibit the reaction. When compound (I) of the invention is obtained in free form, it may be converted to an acceptable salt of compound (I) by an ordinary method. Conversely, when compound (I) of the invention is obtained as a salt of compound (I), it may be converted to the free form of compound (I) by an ordinary method. Various isomers (for example, geometric isomers, or optical isomers based on asymmetric carbons, rotational isomers, stereoisomers and the like) obtained for compound (I) of the invention may be purified and isolated using ordinary separation means such as, for example, recrystallization, a diastereomer salt method, enzymatic resolution or chromatography methods (for example, thin-layer chromatography, column chromatography, gas chromatography, etc.).

The compounds represented by formula (I) or salts thereof, as well as hydrates of the foregoing, exhibit excellent sodium channel inhibitory action and are very safe (in terms of effects on cardiovascular system, inhibitory effects on drug-metabolizing enzymes, and enzyme induction), and are therefore highly useful as drugs.

The compounds of the invention and salts thereof, as well as hydrates of the foregoing, can therefore be used to obtain pharmaceutical compositions as therapeutic agents and analgesics for diseases for which sodium channel inhibition is effective, such as various kinds of neuralgia (for example, diabetic neuralgia, HIV-induced neuralgia, postherpetic neuralgia, trigeminal neuralgia, stump pain, post-spinal cord injury pain, thalamic pain and post-apoplectic pain), epilepsy, insomnia, premature ejaculation and the like.

Also, administration of pharmacologically effective doses of compounds of the invention and salts thereof, or hydrates of the foregoing, to patients with disease for which sodium channel inhibition is effective or with neuralgia, can serve as treatment for diseases for which sodium channel inhibition is effective or with neuralgia.

The compounds of the invention and salts thereof, or hydrates of the foregoing, may be formulated into tablets, powders, fine granules, granules, coated tablets, capsules, syrups, lozenges, inhalants, suppositories, injections, ointments, eye salves, eye drops, nose drops, ear drops, poultices, lotions and the like by ordinary methods. There may also be used excipients, binders, lubricants, coloring agents, taste correctives and the like ordinarily used for formulation, as well as stabilizers, emulsifiers, absorption accelerators, surfactants, pH regulators, antiseptic agents and antioxidants as necessary, for formulation by ordinary methods using components commonly used as starting materials for drugs.

As examples of such components there may be mentioned animal and vegetable oils such as soybean oil, beef tallow and synthetic glycerides; hydrocarbons such as liquid paraffins, squalane and solid paraffins; ester oils such as octyldodecyl myristate and isopropyl myristate; higher alcohols such as cetostearyl alcohol and behenyl alcohol; silicon resins; silicon oils; surfactants such as polyoxyethylene fatty acid esters, sorbitan fatty acid esters, glycerin fatty acid esters, polyoxyethylenesorbitan fatty acid esters, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic anhydride, magnesium aluminum silicate and aluminum silicate; and purified water.

Examples of excipients include lactose, corn starch, white soft sugar, glucose, mannitol, sorbitol, crystalline cellulose, silicon dioxide and the like, examples of binders include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol-polyoxyethylene block copolymer, meglumine and the like, examples of disintegrators include starch, agar, gelatin powder, crystalline cellulose, calcium carbonate, sodium hydrogencarbonate, calcium citrate, dextrin, pectin, carboxymethylcellulose calcium and the like, examples of lubricants include magnesium stearate, talc, polyethylene glycol, silica, hydrogenated vegetable oils and the like, examples of coloring agents include those approved for addition to drugs, and examples of taste correctives include cocoa powder, menthol, aromatic powder, peppermint oil, camphor, cinnamon powder and the like.

For production of an oral formulation, a compound of the invention or its pharmacologically acceptable salt may be combined with an excipient, and with a binder, disintegrator, lubricant, coloring agent or taste corrective as necessary, to form a powder, fine granules, granules, tablets, coated tablets, capsules or the like.

Such tablets or granules may of course be provided with a sugar coating or other appropriate coating as necessary.

For production of a liquid drug such as a syrup or formulation for injection, a pH regulator, solubilizer, isotonizing agent or the like, and if necessary also a dissolving aid or stabilizer, may be added to the compound of the invention or its pharmacologically acceptable salt, for formulation by an ordinary method.

There are no restrictions on the method of producing an external preparation, and any ordinary procedure may be used.

Specifically, the starting materials used for formulation may be any of various commonly employed starting materials for drugs, quasi drugs, cosmetics and the like. As examples of specific starting materials to be used, there may be mentioned animal and vegetable oils, mineral oils, ester oils, waxes, higher alcohols, fatty acids, silicon oils, surfactants, phospholipids, alcohols, polyhydric alcohols, water-soluble polymers, clay minerals, purified water and the like, while pH regulators, antioxidants, chelating agents, antiseptic and fungicides, coloring agents, aromatics and the like may also be added; however, the base starting materials for an external preparation of the invention are not limited to these. If necessary, additional components such as blood flow accelerators, microbicides, antiphlogistics, cellular stimulants, vitamins, amino acids, humectants, keratolytic drugs and the like may also be added. The amounts of such base starting materials added may be such as to give concentrations ordinarily established for production of external preparations.

When a compound of the invention or salt thereof, or a solvate of the foregoing, is administered, it may be in any desired form without restrictions, such as an oral administration or parenteral administration, according to a commonly employed procedure. For example, it may be formulated for administration in the form of tablets, powders, granules, capsules, syrups, lozenges, inhalants, suppositories, injections, ointments, eye salves, eye drops, nose drops, ear drops, poultices, lotions or the like. The dosage for administration of a drug according to the invention may be appropriately selected according to the age, gender, body weight and degree of symptoms of the patient, and the specific type of condition and the form of administration, type of salt, etc.

The dosage for administration of a drug according to the invention will differ depending on the patient's condition, severity of symptoms, age, gender and sensitivity to drugs, but for adults it will normally be about 0.03-1000 mg and preferably 0.1-500 mg per day for oral administration, and about 1-3000 µg/kg body weight and preferably about 3-1000 µg/kg body weight for injection, administered either at once or in divided doses.

EXAMPLES

The compounds according to the invention may be produced by the methods described by the following production examples and examples. However, these specific examples are merely illustrative and the compounds of the invention are in no way restricted by these concrete examples.

Production Example 1

(Endo)-3-(4-fluorobenzyloxy)-8-azabicyclo[3.2.1]octane hydrochloride

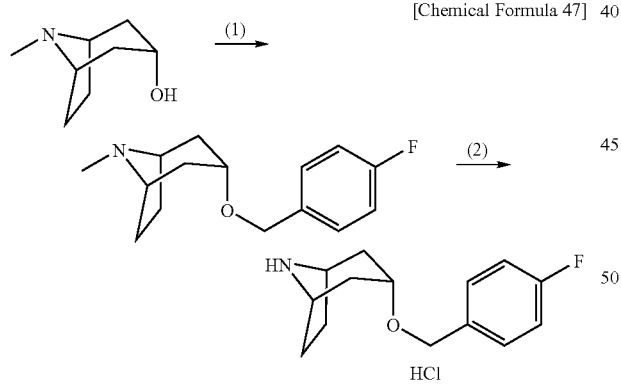

[Chemical Formula 47]

(1) (Endo)-3-(4-fluorobenzyloxy)-8-methyl-8-azabicyclo[3.2.1]octane

Tropine (25.0 g) was dissolved in 1-methyl-2-pyrrolidinone (350 ml), and then sodium hydride (60% in oil) (9.2 g) was added and the mixture was stirred at 75° C. for 2 hours. The reaction mixture was cooled on ice, 4-fluorobenzyl bromide (26.5 ml) was added and the mixture was stirred at room temperature for 69 hours. Ice water was added to the reaction mixture and extraction was performed with n-heptane. The organic layer was washed with water and brine in that order and then dried over anhydrous magnesium sulfate. The solvent was distilled off under reduced pressure to obtain the title compound (36.76 g).

(2) (Endo)-3-(4-fluorobenzyloxy)-8-azabicyclo[3.2.1]octane hydrochloride

The compound obtained in Production Example 1-(1) (36.76 g) was dissolved in 1,2-dichloroethane (150 ml), and 1-chloroethyl chloroformate (31.9 ml) was added while stirring at room temperature. After further stirring at room temperature for 15 minutes, it was heated to reflux for 5 hours. The reaction mixture was concentrated under reduced pressure and methanol (250 ml) was added to the residue. After heating to reflux for 30 minutes, the reaction mixture was concentrated under reduced pressure. Acetone-diethyl ether was added to the residue, and the solid was collected by filtration and washed with diethyl ether. The title compound (25.39 g) was thus obtained.

$^1$H-NMR (400 MHz, DMSO-$d_6$); δ 1.89-2.19 (m, 8H), 3.67-3.72 (m, 1H), 3.89-3.94 (m, 2H), 4.45 (s, 2H), 7.15-7.22 (m, 2H), 7.34-7.40 (m, 2H), 9.04 (br s, 2H).

Production Example 2

(Endo)-3-(3-fluorobenzyloxy)-8-azabicyclo[3.2.1]octane hydrochloride

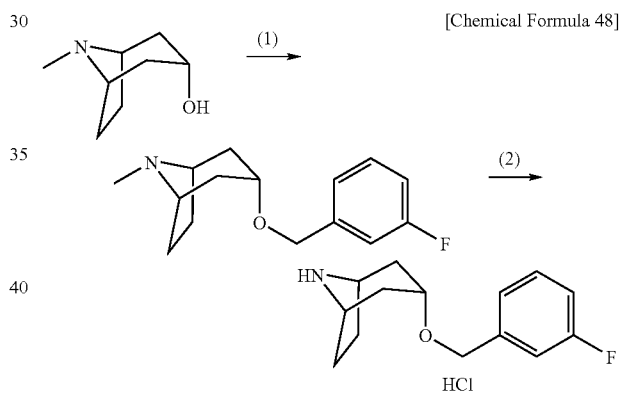

[Chemical Formula 48]

(1) (Endo)-3-(3-fluorobenzyloxy)-8-methyl-8-azabicyclo[3.2.1]octane

The title compound (21.34 g) was obtained from tropine (15.0 g) and 3-fluorobenzyl bromide by the method similar to Production Example 1-(1).

(2) (Endo)-3-(3-fluorobenzyloxy)-8-azabicyclo[3.2.1]octane hydrochloride

The compound obtained in Production Example 2-(1) (21.34 g) was dissolved in 1,2-dichloroethane (197 ml), and 1-chloroethyl chloroformate (18.4 ml) was added. Stirring was then carried out at room temperature for 30 minutes and at 110° C. for 3 hours. The reaction mixture was concentrated under reduced pressure and methanol (304 ml) was added to the residue, prior to heating to reflux for 3 hours. The reaction mixture was concentrated under reduced pressure. Acetone-diethyl ether (10:1) was added to the residue, and the solid was collected by filtration to obtain the title compound (12.94 g).

$^1$H-NMR (400 M-Hi, DMSO-$d_6$); δ 1.87-2.20 (m, 8H), 3.68-3.72 (m, 1H), 3.89-3.94 (m, 2H), 4.49 (s, 2H), 7.07-7.18 (m, 3H), 7.36-7.43 (m, 1H), 8.98 (br s, 2H).

Production Example 3

(Endo)-3-(2-methylbenzyloxy)-8-azabicyclo[3.2.1]octane hydrochloride

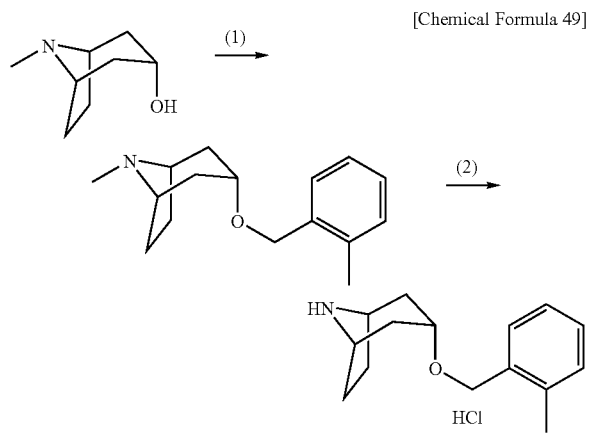

(1) (Endo)-8-methyl-3-(2-methylbenzyloxy)-8-azabicyclo[3.2.1]octane

The title compound (12.74 g) was obtained from tropine (10.0 g) and 2-methylbenzyl bromide by the method similar to Production Example 1-(1).

(2) (Endo)-3-(2-methylbenzyloxy)-8-azabicyclo[3.2.1]octane hydrochloride

The title compound (8.4 g) was obtained from the compound obtained in Production Example 3-(1) (12.74 g) by the method similar to Production Example 1-(2).

$^1$H-NMR (400 MHz, DMSO-$d_6$); δ 1.88-1.94 (m, 2H), 2.02-2.19 (m, 6H), 2.26 (s, 3H), 3.70-3.74 (m, 1H), 3.89-3.95 (m, 2H), 4.45 (s, 2H), 7.12-7.22 (m, 3H), 7.27-7.32 (m, 1H), 8.91 (br s, 1H).

Production Example 4

(Endo)-3-benzyloxy-8-azabicyclo[3.2.1]octane hydrochloride

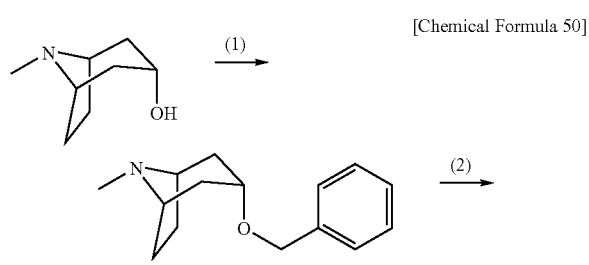

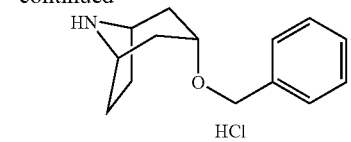

(1) (Endo)-3-benzyloxy-8-methyl-8-azabicyclo[3.2.1]octane

The title compound (4.68 g) was obtained from tropine (5.0 g) and benzyl bromide by the method similar to Production Example 1-(1).

(2) (Endo)-3-benzyloxy-8-azabicyclo[3.2.1]octane hydrochloride

The title compound (2.98 g) was obtained from the compound obtained in Production Example 4-(1) (4.68 g) by the method similar to Production Example 1-(2).

$^1$H-NMR (400 MHz, DMSO-$d_6$); δ 1.87-2.21 (m, 8H), 3.69 (t, J=4.4 Hz, 1H), 3.89-3.94 (m, 2H), 4.47 (s, 2H), 7.24-7.37 (m, 5H), 8.99 (br s, 2H).

Production Example 5

(Endo)-3-(2-fluorobenzyloxy)-8-azabicyclo[3.2.1]octane hydrochloride

[Chemical Formula 51]

(1) (Endo)-3-(2-fluorobenzyloxy)-8-methyl-8-azabicyclo[3.2.1]octane

The title compound (17.29 g) was obtained from tropine (15.0 g) and 2-fluorobenzyl bromide by the method similar to Production Example 1-(1).

(2) (Endo)-3-(2-fluorobenzyloxy)-8-azabicyclo[3.2.1]octane hydrochloride

The compound obtained in Production Example 5-(1) (17.29 g) was dissolved in 1,2-dichloroethane (70 ml), and 1-chloroethyl chloroformate (15.0 ml) was added while stirring at room temperature. After further stirring at room temperature for 15 minutes, the mixture was heated to reflux for 5 hours. It was then filtered and the filtrate was concentrated under reduced pressure. Methanol (90 ml) was added to the residue, and the mixture was heated to reflux for 30 minutes. The reaction mixture was concentrated under reduced pressure, acetone was added to the residue, and the solid was collected by filtration. It was then washed with diethyl ether to obtain the title compound (13.55 g).

$^1$H-NMR (400 MHz, DMSO-$d_6$); δ 1.86-1.94 (m, 2H), 2.00-2.19 (m, 6H), 3.73 (t, J=4.0 Hz, 1H), 3.88-3.94 (m, 2H), 4.51 (s, 2H), 7.16-7.24 (m, 2H), 7.32-7.39 (m, 1H), 7.41-7.46 (m, 1H), 8.84-9.14 (m, 2H).

Production Example 6

(Endo)-3-(benzo[b]thiophen-2-ylmethoxy)-8-azabicyclo[3.2.1]octane hydrochloride

[Chemical Formula 52]

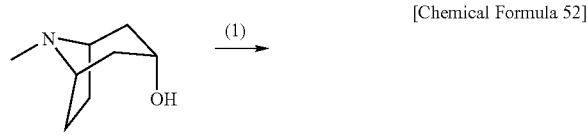

(1) (Endo)-3-(benzo[b]thiophen-2-ylmethoxy)-8-methyl-8-azabicyclo[3.2.1]octane

The title compound (1.7 g) was obtained from tropine (4.0 g) and 2-chloromethyl-benzo[b]thiophene (CAS 2076-88-2) by the method similar to Production Example 1-(1).

(2) (Endo)-3-(benzo[b]thiophen-2-ylmethoxy)-8-azabicyclo[3.2.1]octane hydrochloride The title compound (475 mg) was obtained from the compound obtained in Production Example 6-(1) (1.7 g) by the method similar to Production Example 5-(2).

$^1$H-NMR (400 MHz, CD$_3$OD); δ 2.03-2.24 (m, 6H), 2.46-2.52 (m, 2H), 3.83-3.85 (m, 1H), 3.99-4.01 (m, 2H), 4.81 (m, 2H), 7.27-7.36 (m, 3H), 7.73-7.75 (m, 1H), 7.81-7.83 (m, 1H).

Production Example 7

(Endo)-3-(benzo[b]thiophen-3-ylmethoxy)-8-azabicyclo[3.2.1]octane hydrochloride

[Chemical Formula 53]

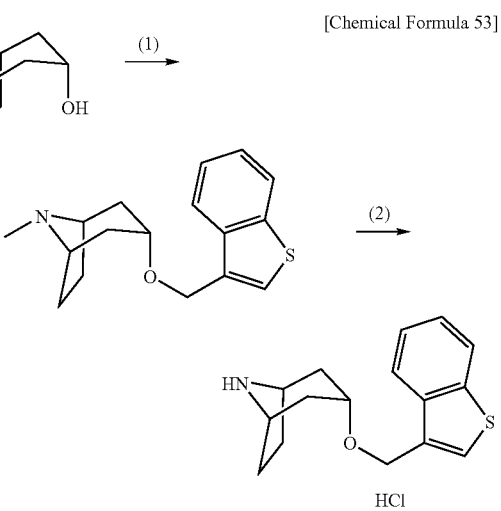

(1) (Endo)-3-(benzo[b]thiophen-3-ylmethoxy)-8-methyl-8-azabicyclo[3.2.1]octane

The title compound (4.2 g) was obtained from tropine (3.5 g) and 3-chloromethyl-benzo[b]thiophene (CAS 3216-47-5) by the method similar to Production Example 1-(1).

(2) (Endo)-3-(benzo[b]thiophen-3-ylmethoxy)-8-azabicyclo[3.2.1]octane hydrochloride The title compound (360 mg) was obtained from the compound obtained in Production Example 7-(1) (4.2 g) by the method similar to Production Example 5-(2).

$^1$H-NMR (400 MHz, CD$_3$OD); 2.01-2.44 (m, 8H), 3.81-3.82 (m, 1H), 3.98 (br, 2H), 4.79 (s, 2H), 7.33-7.42 (m, 2H), 7.53 (s, 1H), 7.87-7.89 (m, 2H).

Production Example 8

(Endo)-3-(thiophen-2-ylmethoxy)-8-azabicyclo[3.2.1]octane hydrochloride

[Chemical Formula 54]

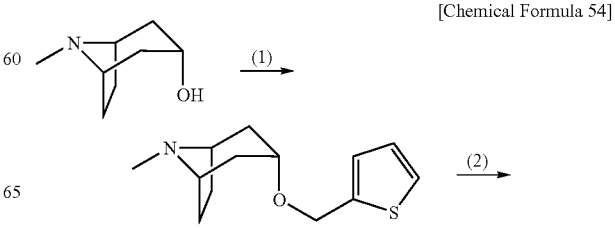

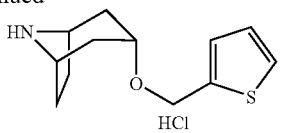

(1) (Endo)-8-methyl-3-(thiophen-2-ylmethoxy)-8-azabicyclo[3.2.1]octane

The title compound (7.06 g) was obtained from tropine (5.0 g) and 2-chloromethyl-thiophene (CAS 765-50-4) by the method similar to Production Example 1-(1).

(2) (Endo)-3-(thiophen-2-ylmethoxy)-8-azabicyclo[3.2.1]octane hydrochloride

The title compound (880 mg) was obtained from the compound obtained in Production Example 8-(1) (7.06 g) by the method similar to Production Example 5-(2).

$^1$H-NMR (400 MHz, CD$_3$OD); δ 2.01-2.19 (m, 6H), 2.40-2.45 (m, 2H), 3.78 (br, 1H), 3.97-3.98 (m, 2H), 4.70 (s, 2H), 6.96-6.98 (m, 1H), 7.01-7.02 (m, 1H), 7.36-7.37 (m, 1H).

Production Example 9

(Endo)-3-(2-methoxymethylbenzyloxy)-8-azabicyclo[3.2.1]octane hydrochloride

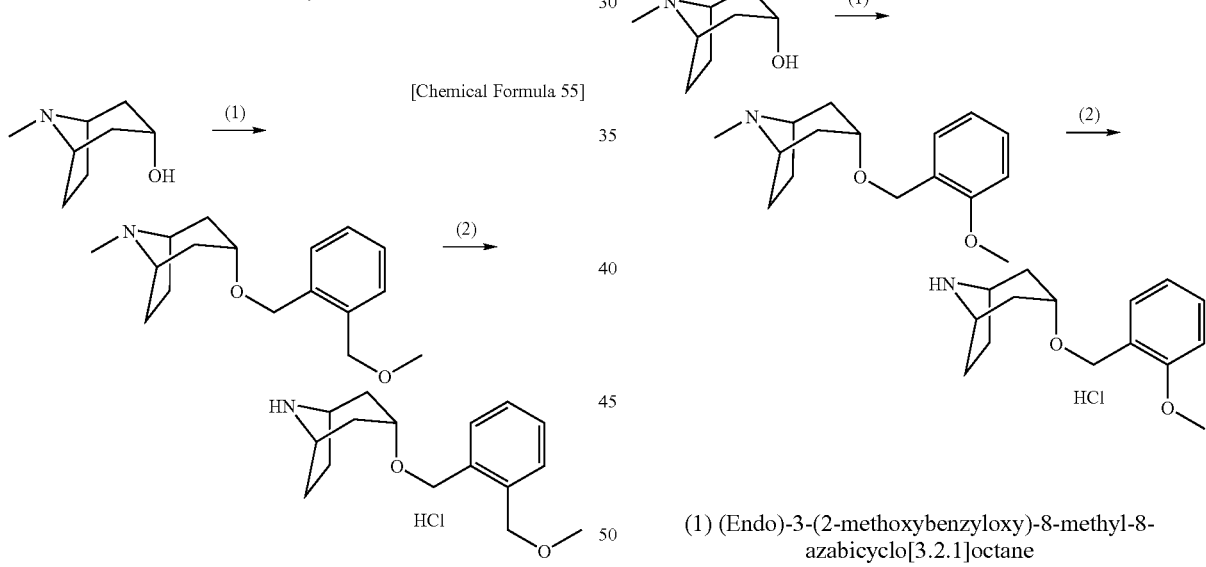

(1) (Endo)-3-(2-methoxymethylbenzyloxy)-8-methyl-8-azabicyclo[3.2.1]octane

Tropine (3.0 g) was dissolved in 1-methyl-2-pyrrolidinone (40 ml), and then sodium hydride (60% in oil) (1.19 g) was added and the mixture was stirred at 75° C. for 2 hours. The reaction mixture was cooled on ice, and then a solution of benzyltri-n-butylammonium bromide (377 mg) and 2-methoxymethylbenzyl chloride (CAS 68718-99-0) (4.64 g) in 1-methyl-2-pyrrolidinone (5 ml) was added dropwise and the mixture was stirred at room temperature for 22 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (3.95 g).

$^1$H-NMR (400 MHz, CDCl$_3$); δ 1.83-2.09 (m, 8H), 2.27 (s, 3H), 3.05-3.13 (m, 2H), 3.37 (s, 3H), 3.62 (t, J=4.8 Hz, 1H), 4.50 (s, 2H), 7.23-7.45 (m, 4H).

(2) (Endo)-3-(2-methoxymethylbenzyloxy)-8-azabicyclo[3.2.1]octane hydrochloride The title compound (2.01 g) was obtained from the compound obtained in Production Example 9-(1) (3.95 g) by the method similar to Production Example 5-(2).

$^1$H-NMR (400 MHz, DMSO-d$_6$); δ 1.87-1.97 (m, 2H), 2.01-2.08 (m, 2H), 2.10-2.19 (m, 4H), 3.29 (s, 3H), 3.70 (t, J=4.4 Hz, 1H), 3.88-3.94 (m, 2H), 4.45 (s, 2H), 4.50 (s, 2H), 7.25-7.42 (m, 4H), 8.88-9.18 (m, 2H).

Production Example 10

(Endo)-3-(2-methoxybenzyloxy)-8-azabicyclo[3.2.1]octane hydrochloride

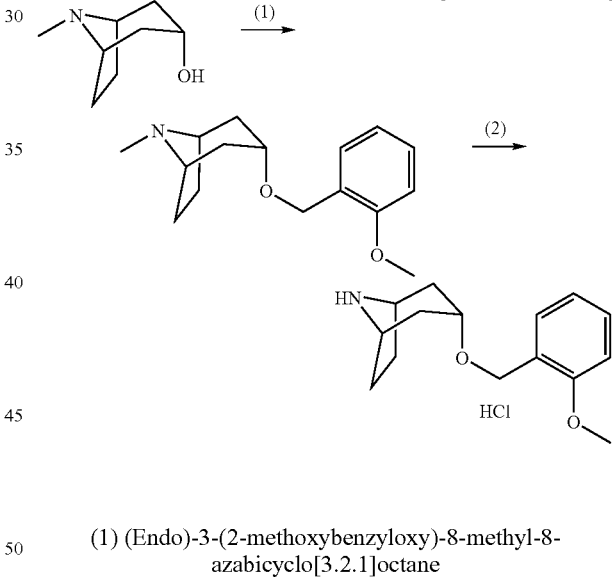

(1) (Endo)-3-(2-methoxybenzyloxy)-8-methyl-8-azabicyclo[3.2.1]octane

The title compound (3.95 g) was obtained from tropine (3.0 g) and 2-methoxybenzyl chloride by the method similar to Production Example 9-(1).

$^1$H-NMR (400 MHz, CDCl$_3$); δ 1.90-2.13 (m, 8H), 2.27 (s, 3H), 3.05-3.11 (m, 2H), 3.60-3.65 (m, 1H), 3.81 (s, 3H), 4.47 (s, 2H), 6.83 (dd, J=8.0, 0.8 Hz, 1H), 6.96 (td, J=7.2, 0.8 Hz, 1H), 7.20-7.26 (m, 1H), 7.39-7.43 (m, 1H).

(2) (Endo)-3-(2-methoxybenzyloxy)-8-azabicyclo[3.2.1]octane hydrochloride

The title compound (2.71 g) was obtained from the compound obtained in Production Example 10-(1) (3.95 g) by the method similar to Production Example 5-(2).

¹H-NMR (400 MHz, DMSO-d₆); δ 1.87-1.96 (m, 2H), 2.01-2.23 (m, 6H), 3.69-3.73 (m, 1H), 3.79 (s, 3H), 3.88-3.93 (m, 2H), 4.43 (s, 2H), 6.92-7.02 (m, 2H), 7.25-7.33 (m, 2H), 8.90-9.25 (m, 2H).

Production Example 11

(Endo)-3-cyclohexylmethoxy-8-azabicyclo[3.2.1]octane hydrochloride

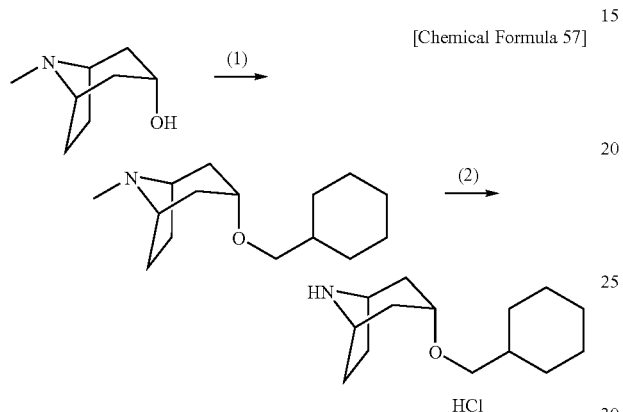

(1) (Endo)-3-cyclohexylmethoxy-8-methyl-8-azabicyclo[3.2.1]octane

Tropine (5.0 g) was dissolved in 1-methyl-2-pyrrolidinone (70 ml), and then sodium hydride (60% in oil) (1.98 g) was added and the mixture was stirred at 75° C. for 45 minutes. The reaction mixture was allowed to cool, and bromomethylcyclohexane (5.93 ml) was added dropwise. After stirring at room temperature for 13 hours, water was added to the reaction mixture and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (528 mg).

¹H-NMR (400 MHz, CDCl₃); δ 0.88-1.00 (m, 2H), 1.09-1.31 (m, 4H), 1.46-1.57 (m, 1H), 1.63-1.83 (m, 6H), 1.86-2.01 (m, 6H), 2.25 (s, 3H), 3.01-3.06 (m, 2H), 3.11 (d, J=6.4 Hz, 2H), 3.41 (t, J=4.8 Hz, 1H).

(2) (Endo)-3-cyclohexylmethoxy-8-azabicyclo[3.2.1]octane hydrochloride

The title compound (297 mg) was obtained from the compound obtained in Production Example 11-(1) (528 mg) by the method similar to Production Example 5-(2).

¹H-NMR (400 MHz, DMSO-d₆); δ 0.88-1.00 (m, 2H), 1.06-1.25 (m, 3H), 1.43-1.54 (m, 1H), 1.59-1.72 (m, 5H), 1.85-1.97 (m, 4H), 2.02-2.15 (m, 4H), 3.15 (d, J=6.0 Hz, 2H), 3.49-3.54 (m, 1H), 3.85-3.91 (m, 2H), 8.86-9.04 (m, 2H).

Production Example 12

(Endo)-3-(2-trifluoromethoxybenzyloxy)-8-azabicyclo[3.2.1]octane hydrochloride

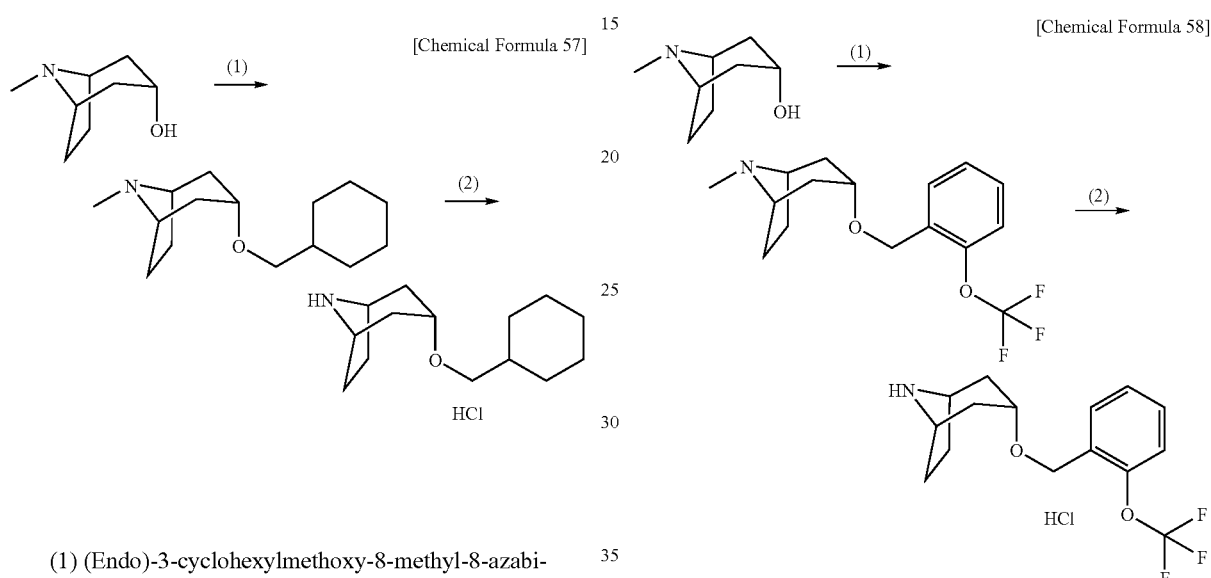

(1) (Endo)-8-methyl-3-(2-trifluoromethoxybenzyloxy)-8-azabicyclo[3.2.1]octane

The title compound (1.5 g) was obtained from tropine (3.0 g) and 2-trifluoromethoxybenzyl bromide by the method similar to Production Example 11-(1).

¹H-NMR (400 MHz, CDCl₃); δ 1.70-2.10 (m, 8H), 2.29 (s, 3H), 3.08-3.16 (m, 2H), 3.64 (t, J=4.8 Hz, 1H), 4.51 (s, 2H), 7.17-7.24 (m, 1H), 7.26-7.33 (m, 2H), 7.50-7.56 (m, 1H).

(2) (Endo)-3-(2-trifluoromethoxybenzyloxy)-8-azabicyclo[3.2.1]octane hydrochloride The title compound (425 mg) was obtained from the compound obtained in Production Example 12-(1) (1.5 g) by the method similar to Production Example 5-(2).

¹H-NMR (400 MHz, CD₃OD); δ 1.95-2.08 (m, 2H), 2.10-2.28 (m, 4H), 2.38-2.46 (m, 2H), 3.81 (t, J=4.8 Hz, 1H), 3.96-4.04 (m, 2H), 4.57 (s, 2H), 6.86 (t, J=74.0 Hz, 1H), 7.15-7.20 (m, 2H), 7.24 (dt, J=1.2 Hz, 7.6 Hz, 1H), 7.36 (dt, J=2.0 Hz, 7.6 Hz, 1H), 7.46-7.53 (m, 1H).

Production Example 13

(Endo)-3-(2-trifluoromethylbenzyloxy)-8-azabicyclo[3.2.1]octane hydrochloride

(1) (Endo)-8-methyl-3-(2-trifluoromethylbenzyloxy)-8-azabicyclo[3.2.1]octane The title compound (2.65 g) was obtained from tropine (3.0 g) and 2-trifluoromethylbenzyl bromide by the method similar to Production Example 11-(1).

$^1$H-NMR (400 MHz, CDCl$_3$); δ 1.89-2.08 (m, 8H), 2.28 (s, 3H), 3.06-3.12 (m, 2H), 3.64 (t, J=5.2 Hz, 1H), 4.62 (s, 2H), 7.31-7.37 (m, 1H), 7.51-7.57 (m, 1H), 7.60 (d, J=7.6 Hz, 1H), 7.71 (d, J=8.0 Hz, 1H).

(2) (Endo)-3-(2-trifluoromethylbenzyloxy)-8-azabicyclo[3.2.1]octane hydrochloride The compound obtained in Production Example 13-(1) (2.65 g) was dissolved in 1,2-dichloroethane (30 ml), and 1-chloroethyl chloroformate (1.91 ml) was added while stirring at room temperature. After further stirring at room temperature for 15 minutes, it was heated to reflux for 7 hours. The reaction mixture was concentrated under reduced pressure and methanol (30 ml) was added to the residue, prior to heating to reflux for 30 minutes. The reaction mixture was concentrated under reduced pressure, diethyl ether was added to the residue and the solid was collected by filtration. The title compound (1.86 g) was thus obtained.

$^1$H-NMR (400 MHz, DMSO-d$_6$); δ 2.10-2.40 (m, 6H), 2.47-2.56 (m, 2H), 3.77-3.85 (m, 1H), 4.02-4.10 (m, 2H), 4.65 (s, 2H), 7.40 (t, J=7.2 Hz, 1H), 7.54-7.68 (m, 3H), 9.46-9.75 (m, 2H).

Production Example 14

(Endo)-3-(3,4-difluorobenzyloxy)-8-azabicyclo[3.2.1]octane hydrochloride

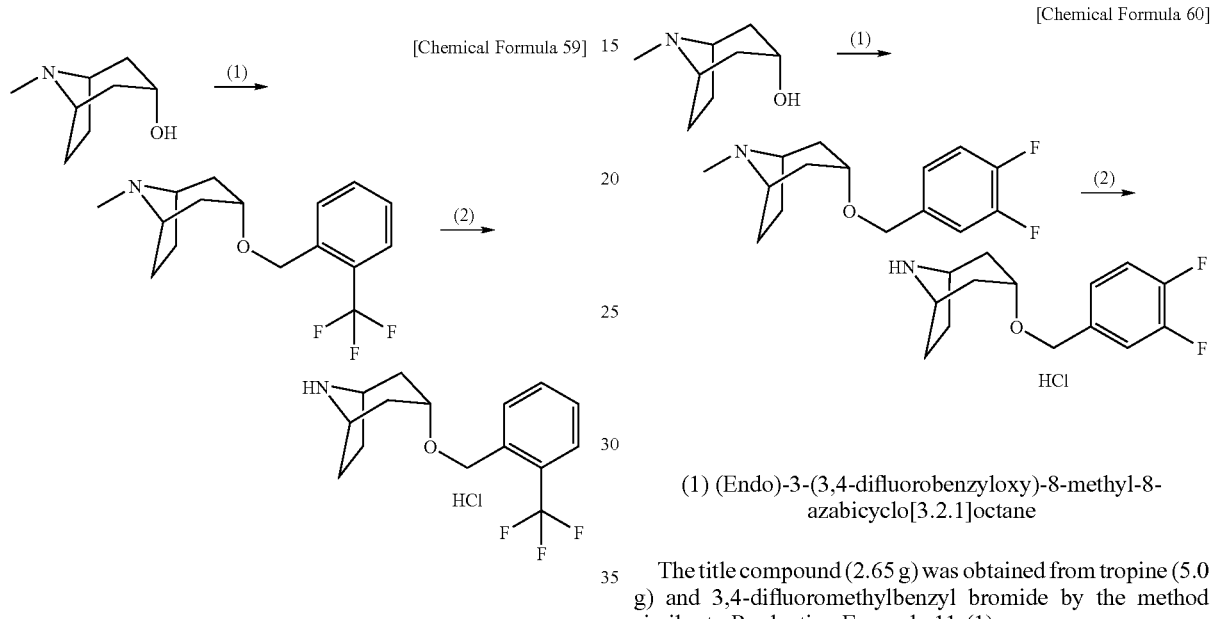

(1) (Endo)-3-(3,4-difluorobenzyloxy)-8-methyl-8-azabicyclo[3.2.1]octane

The title compound (2.65 g) was obtained from tropine (5.0 g) and 3,4-difluoromethylbenzyl bromide by the method similar to Production Example 11-(1).

(2) (Endo)-3-(3,4-difluorobenzyloxy)-8-azabicyclo[3.2.1]octane hydrochloride The title compound (2.69 g) was obtained from the compound obtained in Production Example 14-(1) (3.43 g) by the method similar to Production Example 5-(2).

$^1$H-NMR (400 MHz, CD$_3$OD); δ 2.00-2.46 (m, 8H), 3.76-3.80 (m, 1H), 3.98-4.04 (m, 2H), 4.50 (s, 2H), 7.12-7.30 (m, 3H).

Production Example 15

(Endo)-3-(3-methoxybenzyloxy)-8-azabicyclo[3.2.1]octane hydrochloride

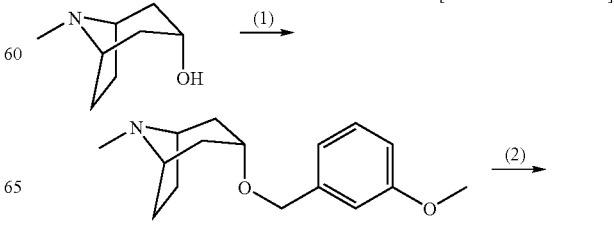

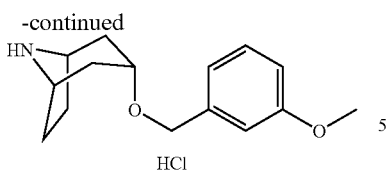

(1) (Endo)-3-(3-methoxybenzyloxy)-8-methyl-8-azabicyclo[3.2.1]octane

The title compound was obtained from tropine (5.0 g) and 3-methoxybenzyl chloride by the method similar to Production Example 11-(1).

(2) (Endo)-3-(3-methoxybenzyloxy)-8-azabicyclo[3.2.1]octane hydrochloride

The title compound (3.38 g) was obtained from the compound obtained in Production Example 15-(1) by the method similar to Production Example 5-(2).
$^1$H-NMR (400 MHz, CD$_3$OD); δ 2.01-2.48 (m, 8H), 3.74-3.81 (m, 1H), 3.78 (s, 3H), 3.97-4.03 (m, 2H), 4.50 (s, 2H), 6.81-6.93 (m, 3H), 7.25 (t, J=8.0 Hz, 1H).

Production Example 16

(Endo)-3-(2-fluorobenzyloxymethyl)-8-azabicyclo[3.2.1]octane

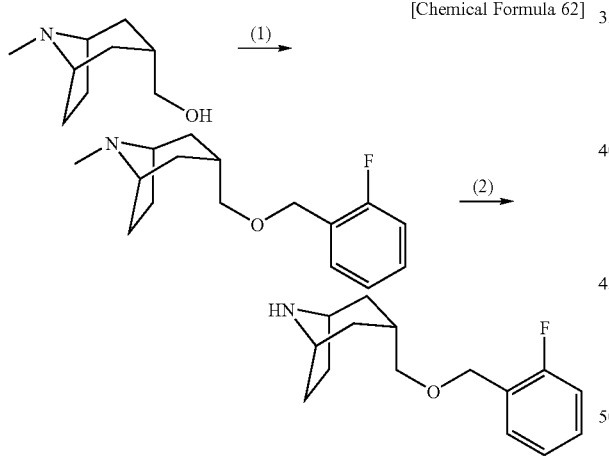

[Chemical Formula 62]

(1) (Endo)-3-(2-fluorobenzyloxymethyl)-8-methyl-8-azabicyclo[3.2.1]octane (Endo)-(8-methyl-8-azabicyclo[3.2.1]oct-3-yl)-methanol (CAS 142892-37-3) (2.0 g) was dissolved in N,N-dimethylformamide (15 ml), and then sodium hydride (60% in oil) (722 mg) was added and the mixture was stirred at room temperature for 30 minutes. The reaction mixture was cooled on ice, and 2-fluorobenzyl bromide (1.91 ml) was added. After stirring at room temperature for 15 hours and 30 minutes, water and n-heptane were added to the reaction mixture and the organic layer was separated. The organic layer was washed with water and brine in that order and then dried over anhydrous magnesium sulfate. After filtration, the solvent was distilled off under reduced pressure to obtain the title compound (3.13 g).

(2) (Endo)-3-(2-fluorobenzyloxymethyl-8-azabicyclo[3.2.1]octane

The compound obtained in Production Example 16-(1) (3.13 g) was dissolved in 1,2-dichloroethane (30 ml), and 1-chloroethyl chloroformate (2.62 ml) was added while stirring at room temperature. Stirring was then carried out at room temperature for 20 minutes and at 100° C. for 3 hours. The reaction mixture was concentrated under reduced pressure and methanol was added to the residue, prior to heating to reflux for 1 hours. The reaction mixture was concentrated under reduced pressure, the residue was dissolved in ethyl acetate, a 1N aqueous solution of sodium hydroxide was added and the organic layer was separated. The aqueous layer was extracted with ethyl acetate. The extracts were combined and dried over anhydrous potassium carbonate. After filtration, the solvent was distilled off under reduced pressure and the residue was purified by NH silica gel column chromatography. The title compound (1.61 g) was thus obtained.
$^1$H-NMR (400 MHz, CDCl$_3$); δ 1.44-1.66 (m, 4H), 1.76-1.79 (m, 2H), 1.92-1.98 (m, 2H), 2.06-2.14 (m, 1H), 3.45-3.49 (m, 4H), 4.57 (s, 2H), 7.02-7.06 (m, 1H), 7.12-7.16 (m, 1H), 7.24-7.30 (m, 1H), 7.40-7.44 (m, 1H).

Production Example 17

(Endo)-3-(2-fluoro-phenoxymethyl)-8-azabicyclo[3.2.1]octane hydrochloride

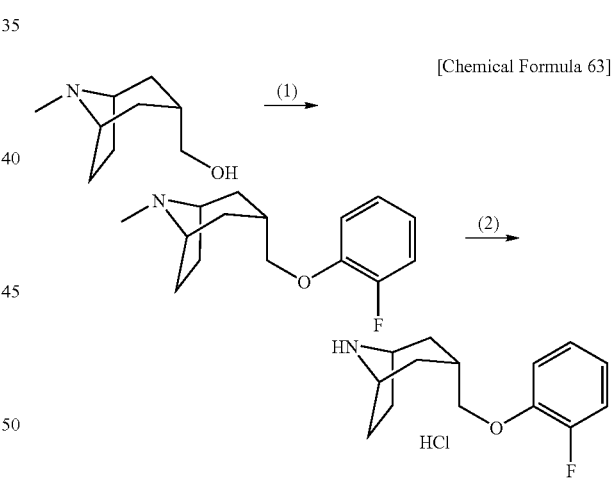

[Chemical Formula 63]

(1) (Endo)-3-(2-fluoro-phenoxymethyl)-8-methyl-8-azabicyclo[3.2.1]octane (Endo)-(8-methyl-8-azabicyclo[3.2.1]oct-3-yl)-methanol (CAS 142892-37-3) (1.4 g) was dissolved in xylene (20 ml), and then 1-fluoro-2-iodobenzene (2.1 ml), cesium carbonate (5.86 g), copper (I) iodide (172 mg) and 1,10-phenanthroline (326 mg) were added in that order and the mixture was heated to reflux for 94 hours. Ethyl acetate and concentrated aqueous ammonia were added to the reaction mixture, and the organic layer was separated. The aqueous layer was extracted with ethyl acetate. The extraction layers were combined and washed with water and brine in that order and then dried over anhydrous magnesium sulfate. After filtration, the solvent was distilled off under reduced pressure. The residue was purified by NH silica gel column chromatography to obtain the title compound (1.48 g).

$^1$H-NMR (400 MHz, CDCl$_3$); δ 1.52-1.62 (m, 4H), 2.02-2.32 (m, 5H), 2.28 (s, 3H), 3.10-3.16 (m, 2H), 3.98 (d, J=8.0 Hz, 2H), 6.85-6.98 (m, 2H), 7.00-7.10 (m, 2H).

(2) (Endo)-3-(2-fluoro-phenoxymethyl)-8-azabicyclo[3.2.1]octane hydrochloride

The compound obtained in Production Example 17-(1) (1.48 g) was dissolved in 1,2-dichloroethane (10 ml), and 1-chloroethyl chloroformate (1.28 ml) was added while stirring at room temperature. After further stirring at room temperature for 15 minutes, it was heated to reflux for 3 hours. The reaction mixture was concentrated under reduced pressure and methanol (20 ml) was added to the residue, prior to heating to reflux for 1 hour. The reaction mixture was concentrated under reduced pressure, and the residue was purified by NH silica gel column chromatography. The obtained oil was dissolved in ethyl acetate (5 ml), and 4N HCl in ethyl acetate (2.23 ml) was added. Diethyl ether was then added, and the solid was collected by filtration to obtain the title compound (1.22 g).

$^1$H-NMR (400 MHz, CD$_3$OD); δ 1.58-1.70 (m, 4H), 1.82-1.90 (m, 2H), 2.02-2.12 (m, 2H), 2.25-2.36 (m, 1H), 3.50-3.56 (m, 2H), 3.99 (d, J=8.0 Hz, 2H), 6.86-6.98 (m, 2H), 7.01-7.10 (m, 2H).

Production Example 18

(Endo)-3-(2-methyl-phenoxymethyl)-8-azabicyclo[3.2.1]octane hydrochloride

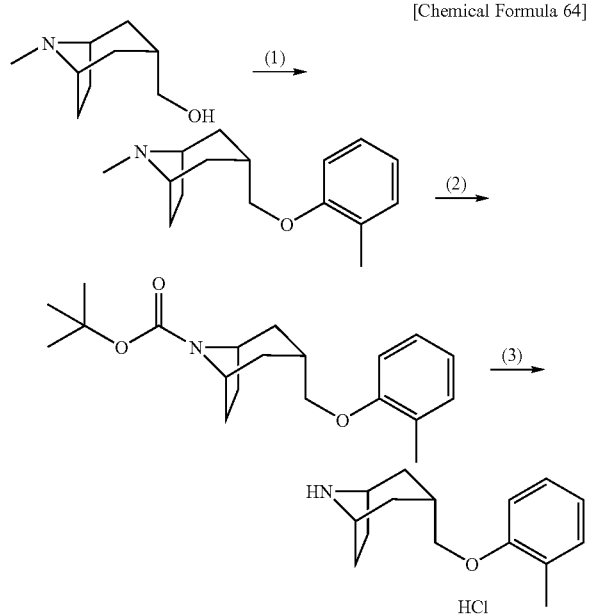

[Chemical Formula 64]

(1) (Endo)-8-methyl-3-(2-methyl-phenoxymethyl)-8-azabicyclo[3.2.1]octane

The title compound (1.67 g) was obtained from (endo)-(8-methyl-8-azabicyclo[3.2.1]oct-3-yl)-methanol (CAS 142892-37-3) (1.4 g) and 1-iodo-2-methylbenzene by the method similar to Production Example 17-(1).

$^1$H-NMR (400 MHz, CDCl$_3$); δ 1.54-1.64 (m, 4H), 2.03-2.12 (m, 2H), 2.15-2.32 (m, 3H), 2.23 (s, 3H), 2.30 (s, 3H), 3.13-3.18 (m, 2H), 3.91 (d, J=8.0 Hz, 2H), 6.79 (d, J=8.4 Hz, 1H), 6.85 (td, J=7.2, 0.8 Hz, 1H), 7.12-7.17 (m, 2H).

(2) (Endo)-3-(2-methyl-phenoxymethyl)-8-azabicyclo[3.2.1]octane-8-carboxylic acid tert-butyl ester The compound obtained in Production Example 18-(1) (1.67 g) was dissolved in 1,2-dichloroethane (15 ml), and 1-chloroethyl chloroformate (1.47 ml) was added while stirring at room temperature. Stirring was then continued at room temperature for 15 minutes and at 100° C. for 4 hours. The reaction mixture was concentrated under reduced pressure and methanol (41 ml) was added to the residue, prior to heating to reflux for 1 hour. The reaction mixture was concentrated under reduced pressure, a 2N aqueous solution of sodium hydroxide (15 ml) and a solution of di-tert-butyl dicarbonate (1.9 g) in tetrahydrofuran (15 ml) were added to the residue, and the mixture was stirred at room temperature for 40 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (1.53 g).

$^1$H-NMR (400 MHz, CDCl$_3$); δ 1.47 (s, 9H), 1.54-1.66 (m, 5H), 1.97-2.07 (m, 2H), 2.20-2.28 (m, 3H), 2.22 (s, 3H), 3.96 (d, J=6.8 Hz, 2H), 4.18-4.25 (m, 2H), 6.77-6.80 (m, 1H), 6.85 (td, J=7.2, 0.8 Hz, 1H), 7.12-7.17 (m, 2H).

(3) (Endo)-3-(2-methyl-phenoxymethyl)-8-azabicyclo[3.2.1]octane hydrochloride

The compound obtained in Production Example 18-(2) (1.53 g) was dissolved in ethyl acetate (12 ml), and then 4N HCl in ethyl acetate (11.6 ml) was added and the mixture was stirred at room temperature for 2 hours. The reaction mixture was then concentrated under reduced pressure, diethyl ether was added to the residue and the solid was collected by filtration to obtain the title compound (1.15 g).

$^1$H-NMR (400 MHz, CD$_3$OD); δ 1.99-2.06 (m, 4H), 2.14-2.22 (m, 2H), 2.20 (s, 3H), 2.26-2.45 (m, 3H), 4.00-4.06 (m, 2H), 4.04 (d, J=8.0 Hz, 2H), 6.83 (td, J=7.6, 1.2 Hz, 1H), 6.90 (d, J=7.6 Hz, 1H), 7.10-7.15 (m, 2H).

Production Example 19

(Endo)-3-(2-fluoro-6-methylbenzyloxy)-8-azabicyclo[3.2.1]octane hydrochloride

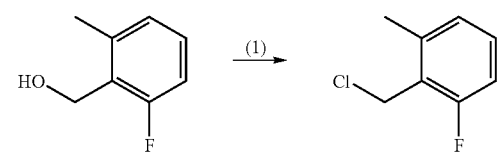

[Chemical Formula 65]

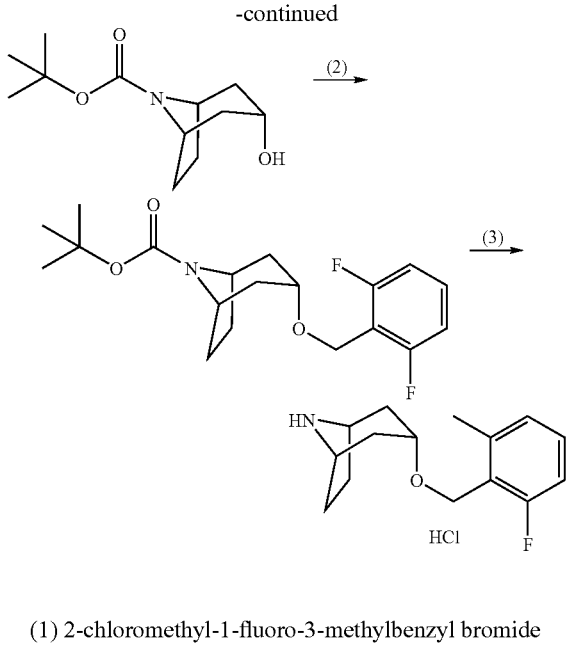

(1) 2-chloromethyl-1-fluoro-3-methylbenzyl bromide

After dissolving (2-fluoro-6-methylphenyl)methanol (CAS 478163-35-8) (2.35 g) in toluene (20 ml), thionyl chloride (3.68 ml) was added dropwise while stirring on ice. A catalytic amount of N,N-dimethylformamide was added, and the mixture was stirred at room temperature for 25 hours and 30 minutes. The reaction mixture was concentrated under reduced pressure, a saturated aqueous solution of sodium hydrogencarbonate was added to the residue, and extraction was performed with n-heptane. The organic layer was washed with water and brine in that order and then dried over anhydrous magnesium sulfate. After filtration with NH silica gel, the filtrate was concentrated under reduced pressure. The title compound (2.04 g) was thus obtained.

$^1$H-NMR (400 MHz, CDCl$_3$); δ 2.45 (s, 3H), 4.68 (d, J=1.6 Hz, 2H), 6.89-7.01 (m, 2H), 7.17-7.24 (m, 1H).

(2) (Endo)-3-(2-fluoro-6-methylbenzyloxy)-8-azabicyclo[3.2.1]octane-8-carboxylic acid tert-butyl ester After dissolving (endo)-3-hydroxy-8-azabicyclo[3.2.1]octane-8-carboxylic acid tert-butyl ester (CAS 143557-91-9) (2.00 g) and the compound obtained in Production Example 19-(1) (1.67 g) in N,N-dimethylformamide (20 ml), benzyltriethylammonium bromide (20 mg) was added. Sodium hydride (60% in oil) (459 mg) was added and the mixture was stirred at room temperature for 18 hours. Ice water was added to the reaction mixture, and extraction was performed with ethyl acetate. The organic layer was washed with water, 1N hydrochloric acid, a saturated aqueous solution of sodium hydrogencarbonate and brine in that order, and dried over anhydrous magnesium sulfate. After filtration, the solvent was distilled off under reduced pressure. The residue was purified by silica gel column chromatography to obtain the title compound (2.70 g).

$^1$H-NMR (400 MHz, CDCl$_3$); δ 1.04 (s, 9H), 3.67-3.92 (m, 4H), 4.55 (d, J=12.0 Hz, 1H), 4.59 (d, J=12.0 Hz, 1H), 4.63-4.81 (m, 1H), 7.24-7.45 (m, 11H), 7.63-7.80 (m, 4H).

(3) (Endo)-3-(2-fluoro-6-methylbenzyloxy)-8-azabicyclo[3.2.1]octane hydrochloride The compound obtained in Production Example 19-(2) (2.70 g) was dissolved in ethyl acetate (7 ml), and then 4N HCl in ethyl acetate (7.73 ml) was added and the mixture was stirred at room temperature for 2 hours. Diethyl ether was added to the reaction mixture, and the solid was collected by filtration to obtain the title compound (1.99 g).

$^1$H-NMR (400 MHz, CD$_3$OD); δ 1.93-2.22 (m, 6H), 2.31-2.38 (m, 2H), 2.42 (s, 3H), 3.75-3.79 (m, 1H), 3.95-4.00 (m, 2H), 4.59 (d, J=2.0 Hz, 2H), 6.92 (t, J=8.8 Hz, 1H), 7.03 (d, J=7.6 Hz, 1H), 7.19-7.26 (m, 1H).

Production Example 20

(Endo)-3-(2,6-dimethylbenzyloxy)-8-azabicyclo[3.2.1]octane hydrochloride

[Chemical Formula 66]

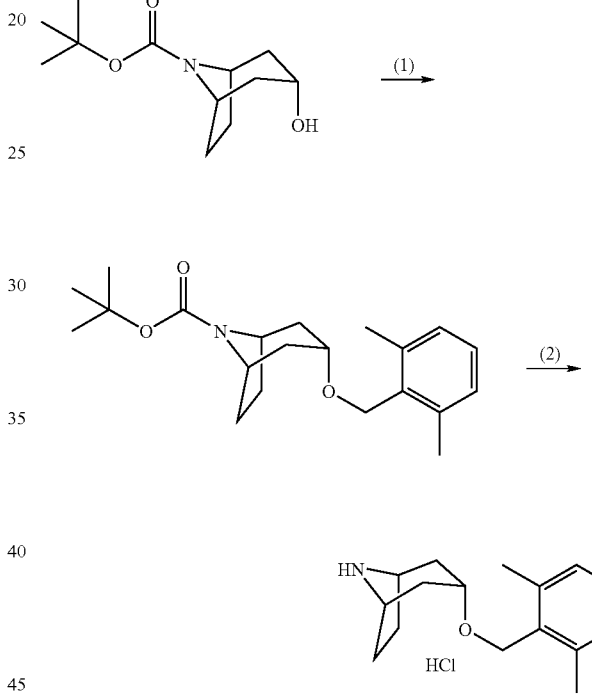

(1) (Endo)-3-(2,6-dimethylbenzyloxy)-8-azabicyclo[3.2.1]octane-8-carboxylic acid tert-butyl ester The title compound (3.32 g) was obtained from (endo)-3-hydroxy-8-azabicyclo[3.2.1]octane-8-carboxylic acid tert-butyl ester (CAS 143557-91-9) (2.00 g) and 2,6-dimethylbenzyl chloride (CAS 5402-60-8) by the method similar to Production Example 19-(2).

$^1$H-NMR (400 MHz, CDCl$_3$); δ 1.46 (s, 9H), 1.83-1.93 (m, 4H), 1.96-2.09 (m, 4H), 2.38 (s, 6H), 3.72 (t, J=4.8 Hz, 1H), 4.12-4.18 (m, 2H), 4.45 (s, 2H), 6.99-7.13 (m, 4H).

(2) (Endo)-3-(2,6-dimethylbenzyloxy)-8-azabicyclo[3.2.1]octane hydrochloride

The title compound (2.15 g) was obtained from the compound obtained in Production Example 20-(1) (3.32 g) by the method similar to Production Example 19-(3).

¹H-NMR (400 MHz, CD₃OD); δ 1.97-2.05 (m, 2H), 2.12-2.24 (m, 4H), 2.31-2.38 (m, 2H), 2.38 (s, 6H), 3.77-3.81 (m, 1H), 3.96-4.01 (m, 2H), 4.56 (s, 2H), 6.99-7.10 (m, 4H).

Production Example 21

(Endo)-3-(3-methylbenzyloxy)-8-azabicyclo[3.2.1]octane hydrochloride

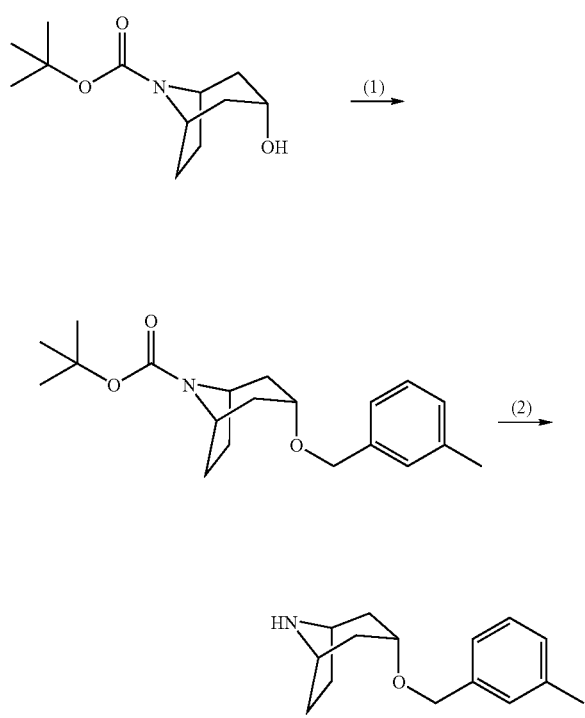

[Chemical Formula 67]

(1) (Endo)-3-(3-methylbenzyloxy)-8-azabicyclo[3.2.1]octane-8-carboxylic acid tert-butyl ester The title compound (2.28 g) was obtained from (endo)-3-hydroxy-8-azabicyclo[3.2.1]octane-8-carboxylic acid tert-butyl ester (CAS 143557-91-9) (2.00 g) and 3-methylbenzyl bromide by the method similar to Production Example 19-(2).

¹H-NMR (400 MHz, CDCl₃); δ 1.46 (s, 9H), 1.86-2.02 (m, 6H), 2.11-2.17 (m, 2H), 2.35 (s, 3H), 3.68-3.72 (m, 1H), 4.14-4.19 (m, 2H), 4.45 (s, 2H), 7.06-7.14 (m, 3H), 7.21-7.26 (m, 1H).

(2) (Endo)-3-(3-methylbenzyloxy)-8-azabicyclo[3.2.1]octane hydrochloride

The title compound (1.65 g) was obtained from the compound obtained in Production Example 21-(1) (2.28 g) by the method similar to Production Example 19-(3).

¹H-NMR (400 MHz, CD₃OD); δ 1.99-2.15 (m, 4H), 2.18-2.25 (m, 2H), 2.33 (s, 3H), 2.39-2.47 (m, 2H), 3.75 (t, J=4.8 Hz, 1H), 3.97-4.02 (m, 2H), 4.48 (s, 2H), 7.07-7.16 (m, 3H), 7.21 (t, J=7.6 Hz, 1H).

Production Example 22

(Endo)-3-(2-ethylbenzyloxy)-8-azabicyclo[3.2.1]octane hydrochloride

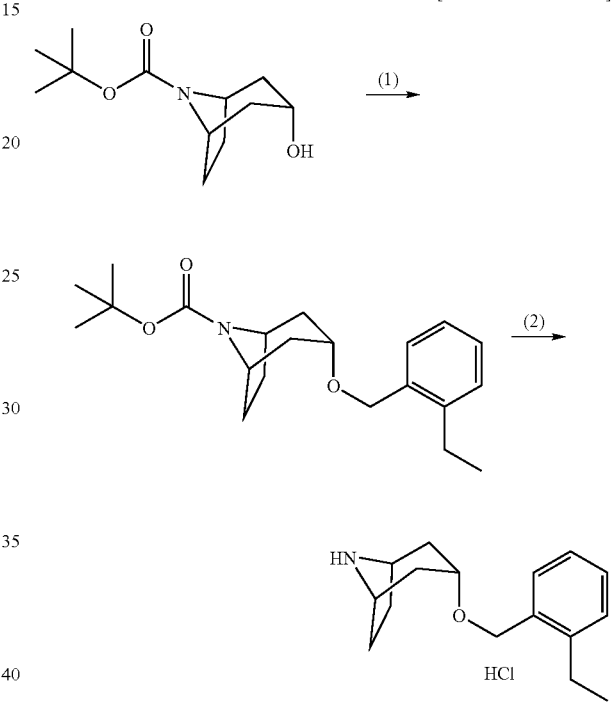

[Chemical Formula 68]

(1) (Endo)-3-(2-ethylbenzyloxy)-8-azabicyclo[3.2.1]octane-8-carboxylic acid tert-butyl ester The title compound (2.05 g) was obtained from (endo)-3-hydroxy-8-azabicyclo[3.2.1]octane-8-carboxylic acid tert-butyl ester (CAS 143557-91-9) (2.00 g) and 2-ethylbenzyl chloride (CAS 1467-06-7) by the method similar to Production Example 19-(2).

¹H-NMR (400 MHz, CDCl₃); δ 1.23 (t, J=7.6 Hz, 3H), 1.46 (s, 9H), 1.85-2.04 (m, 6H), 2.09-2.16 (m, 2H), 2.66 (q, J=7.6 Hz, 2H), 3.73 (t, J=4.4 Hz, 1H), 4.14-4.20 (m, 2H), 4.49 (s, 2H), 7.16-7.27 (m, 3H), 7.34-7.38 (m, 1H).

(2) (Endo)-3-(2-ethylbenzyloxy)-8-azabicyclo[3.2.1]octane hydrochloride

The title compound (1.40 g) was obtained from the compound obtained in Production Example 22-(1) (2.05 g) by the method similar to Production Example 19-(3).

¹H-NMR (400 MHz, CD₃OD); δ 1.22 (t, J=7.6 Hz, 3H), 1.98-2.16 (m, 4H), 2.19-2.26 (m, 2H), 2.36-2.44 (m, 2H), 2.70 (q, J=7.6 Hz, 2H), 3.79 (t, J=4.8 Hz, 1H), 3.97-4.02 (m, 2H), 4.55 (s, 2H), 7.13-7.18 (m, 1H), 7.19-7.26 (m, 2H), 7.29-7.33 (m, 1H).

$^1$H-NMR (400 MHz, CD$_3$OD); δ 1.32 (s, 3H), 1.89-2.00 (m, 4H), 2.26-2.37 (m, 4H), 2.33 (s, 3H), 3.96-4.02 (m, 2H), 4.48 (s, 2H), 7.12-7.20 (m, 3H), 7.32-7.36 (m, 1H).

Production Example 23

3β-methyl-3α-(2-methylbenzyloxy)-8-azabicyclo[3.2.1]octane hydrochloride

Production Example 24

3α-(2-fluorobenzyloxy)-3β-methyl-8-azabicyclo[3.2.1]octane hydrochloride

[Chemical Formula 69]

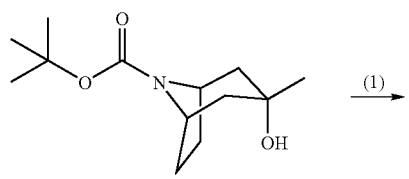

[Chemical Formula 70]

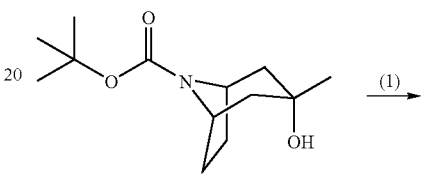

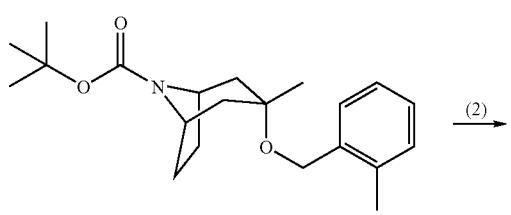

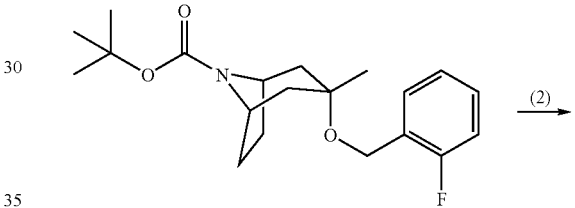

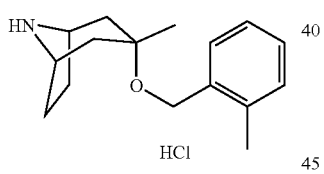

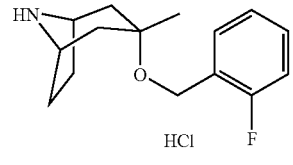

(1) 3β-methyl-3α-(2-methylbenzyloxy)-8-azabicyclo[3.2.1]octane-8-carboxylic acid tert-butyl ester The title compound (511 mg) was obtained from 3α-hydroxy-3β-methyl-3-(2-methylbenzyloxy)-8-azabicyclo[3.2.1]octane-8-carboxylic acid tert-butyl ester (CAS 870889-86-4) (770 mg) and 2-methylbenzyl bromide by the method similar to Production Example 19-(2).

$^1$H-NMR (400 MHz, CDCl$_3$); δ 1.21 (s, 3H), 1.47 (s, 9H), 1.75-1.86 (m, 4H), 2.00-2.08 (m, 4H), 2.30 (s, 3H), 4.10-4.22 (m, 2H), 4.40 (s, 2H), 7.12-7.23 (m, 3H), 7.37-7.42 (m, 1H).

(2) 3β-methyl-3α-(2-methylbenzyloxy)-8-azabicyclo[3.2.1]octane hydrochloride

The title compound (344 mg) was obtained from the compound obtained in Production Example 23-(1) (511 mg) by the method similar to Production Example 19-(3).

(1) 3α-(2-fluorobenzyloxy)-3β-methyl-8-azabicyclo[3.2.1]octane-8-carboxylic acid tert-butyl ester The title compound (235 mg) was obtained from 3α-hydroxy-3β-methyl-3-(2-methylbenzyloxy)-8-azabicyclo[3.2.1]octane-8-carboxylic acid tert-butyl ester (CAS 870889-86-4) (544 mg) and 2-fluorobenzyl bromide by the method similar to Production Example 19-(2).

$^1$H-NMR (400 MHz, CDCl$_3$); δ 1.20 (s, 3H), 1.47 (s, 9H), 1.68-1.90 (m, 4H), 1.98-2.08 (m, 4H), 4.08-4.26 (m, 2H), 4.49 (s, 2H), 6.99-7.05 (m, 1H), 7.11-7.16 (m, 1H), 7.21-7.28 (m, 1H), 7.42-7.48 (m, 1H).

(2) 3α-(2-fluorobenzyloxy)-3β-methyl-8-azabicyclo[3.2.1]octane hydrochloride

The title compound (184 mg) was obtained from the compound obtained in Production Example 24-(1) (235 mg) by the method similar to Production Example 19-(3).

¹H-NMR (400 MHz, CD₃OD); δ 1.32 (s, 3H), 1.88-2.04 (m, 4H), 2.25-2.36 (m, 4H), 3.96-4.02 (m, 2H), 4.53 (s, 2H), 7.05-7.11 (m, 1H), 7.14-7.19 (m, 1H), 7.29-7.36 (m, 1H), 7.42-7.47 (m, 1H).

Production Example 25

(Endo)-3-(4-fluoromethylbenzyloxy)-8-azabicyclo[3.2.1]octane hydrochloride

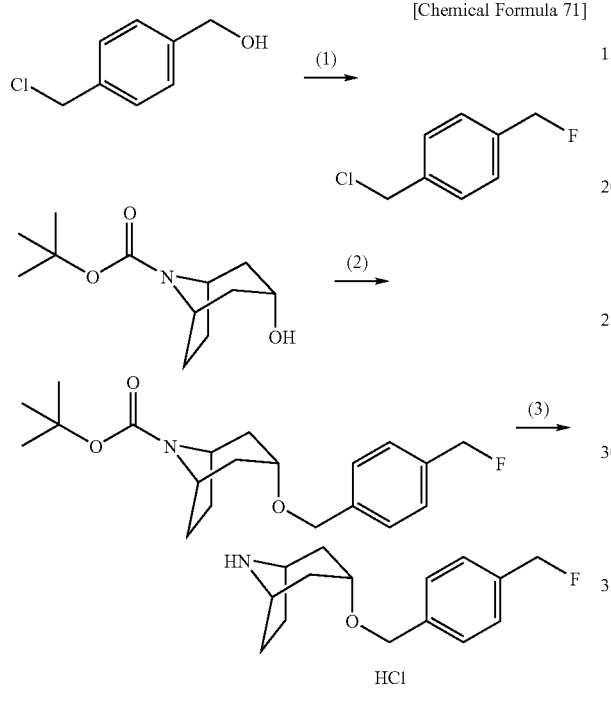

[Chemical Formula 71]

(1) 1-Chloromethyl-4-fluoromethylbenzene

After dissolving 4-(chloromethyl)benzyl alcohol (5.00 g) in dichloromethane (90 ml), dimethylaminosulfur trifluoride (8.28 ml) was added at room temperature and the mixture was stirred for one day. Water was added to the reaction mixture, and then a saturated aqueous solution of sodium hydrogencarbonate was added and extraction was performed with ethyl acetate. The organic layer was washed with brine and dried over anhydrous magnesium sulfate. After filtration, the solvent was distilled off under reduced pressure. The residue was purified by silica gel column chromatography to obtain the title compound (2.94 g).

¹H-NMR (400 MHz, CDCl₃); δ 4.60 (s, 2H), 5.38 (d, J=47.6 Hz, 2H), 7.37 (d, J=8.0 Hz, 2H), 7.42 (d, J=8.0 Hz, 2H).

(2) (Endo)-3-(4-fluoromethylbenzyloxy)-8-azabicyclo[3.2.1]octane-8-carboxylic acid tert-butyl ester The title compound (2.52 g) was obtained from (endo)-3-hydroxy-8-azabicyclo[3.2.1]octane-8-carboxylic acid tert-butyl ester (CAS 143557-91-9) (4.21 g) and the compound obtained in Production Example 25-(1), by the method similar to Production Example 19-(2).

¹H-NMR (400 MHz, CDCl₃); δ 1.47 (s, 9H), 1.88-2.18 (m, 8H), 3.69-3.73 (m, 1H), 4.09-4.25 (m, 2H), 4.47-4.55 (m, 2H), 5.37 (d, J=47.6 Hz, 2H), 7.35 (s, 4H).

(3) (Endo)-3-(4-fluoromethylbenzyloxy)-8-azabicyclo[3.2.1]octane hydrochloride

The title compound (1.80 g) was obtained from the compound obtained in Production Example 25-(2) (2.52 g) by the method similar to Production Example 19-(3).

¹H-NMR (400 MHz, CD₃OD); δ 2.00-2.48 (m, 8H), 3.76-3.81 (m, 1H, 3.95-4.05 (m, 2Hy, 4.55 (s, 2H), 5.35 (d, J=48.0 Hz, 2H), 7.38 (s, 4H).

Production Example 26

(Endo)-3-(thiophen-3-ylmethoxy)-8-azabicyclo[3.2.1]octane hydrochloride

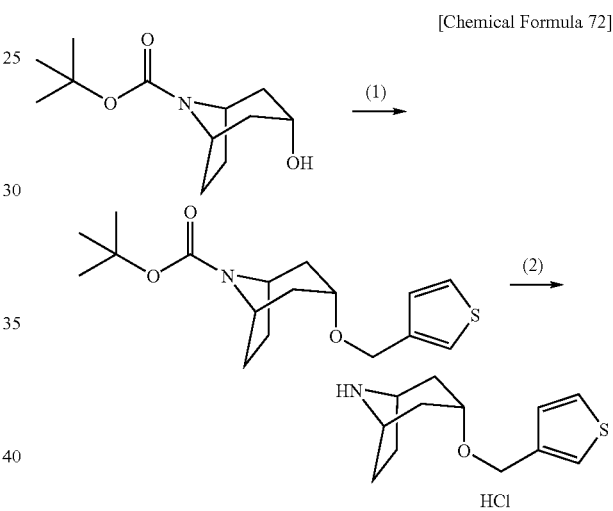

[Chemical Formula 72]

(1) (Endo)-3-(thiophen-3-ylmethoxy)-8-azabicyclo[3.2.1]octane-8-carboxylic acid tert-butyl ester The title compound (6.38 g) was obtained from (endo)-3-hydroxy-8-azabicyclo[3.2.1]octane-8-carboxylic acid tert-butyl ester (CAS 143557-91-9) (5.50 g) and 3-chloromethylthiophene (CAS 2746-23-8) by the method similar to Production Example 19-(2).

¹H-NMR (400 MHz, CDCl₃); δ 1.46 (s, 9H), 1.88-2.17 (m, 8H), 3.71 (m, 1H), 4.13 (m, 2H), 4.50 (s, 2H), 7.05 (m, 1H), 7.24 (m, 1H), 7.35 (m, 1H)

(2) (Endo)-3-(thiophen-3-ylmethoxy)-8-azabicyclo[3.2.1]octane hydrochloride

The compound obtained in Production Example 26-(1) (6.38 g) was dissolved in ethyl acetate (10 ml), and then 4N HCl in ethyl acetate (19.7 ml) was added dropwise while stirring on ice. The mixture was stirred at room temperature for 1 hour and 30 minutes. The precipitate was collected by filtration to obtain the title compound (4.51 g).

$^1$H-NMR (400 MHz, CD$_3$OD); δ 2.02-2.45 (m, 8H), 3.74 (m, 1H), 3.98 (m, 2H), 4.53 (s, 2H), 7.07 (d, J=4.8 Hz, 1H), 7.29 (m, 1H), 7.37-7.40 (m, 1H).

Production Example 27

(Endo)-3-[3-(2-fluorophenyl)propoxy]-8-azabicyclo[3.2.1]octane hydrochloride

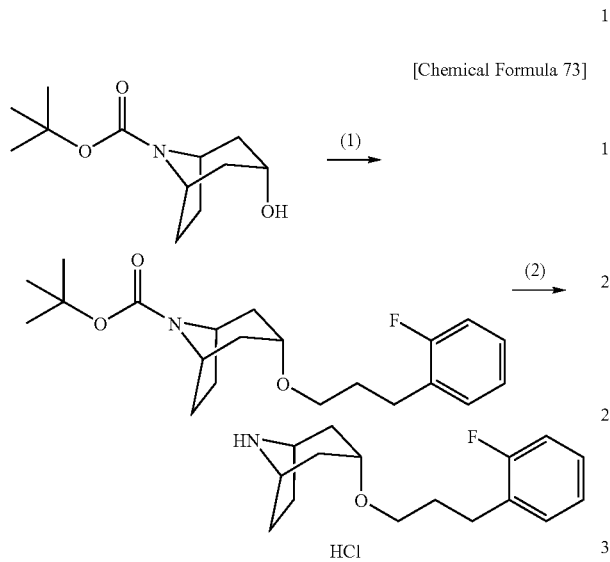

(1) (Endo)-3-[3-(2-fluorophenyl)propoxy]-8-azabicyclo[3.2.1]octane-8-carboxylic acid tert-butyl ester After dissolving (endo)-3-hydroxy-8-azabicyclo[3.2.1]octane-8-carboxylic acid tert-butyl ester (CAS 143557-91-9) (2.00 g) and 1-(3-chloropropyl)-2-fluorobenzene (CAS 110406-96-7) (1.67 g) in N,N-dimethylformamide (10 ml), tetra-n-butylammonium iodide (325 mg) was added to the solution. Sodium hydride (60% in oil) (422 mg) was added and the mixture was stirred at room temperature for 17 hours and 30 minutes. Sodium hydride (60% in oil) (352 mg) was added to the reaction mixture, and stirring was continued for 2 hours at room temperature. Water was added to the reaction mixture, and extraction was performed with ethyl acetate. The organic layer was washed with a saturated aqueous solution of ammonium chloride, water and brine in that order and then dried over anhydrous magnesium sulfate. After filtration, the solvent was distilled off under reduced pressure. The residue was purified by silica gel column chromatography to obtain the title compound (1.20 g).
$^1$H-NMR (400 MHz, CDCl$_3$); δ 1.46 (s, 9H), 1.81-1.95 (m, 8H), 2.06-2.11 (m, 2H), 2.71-2.75 (m, 2H), 3.37-3.38 (m, 2H), 3.54-3.56 (m, 1H), 4.10-4.18 (m, 2H), 6.98-7.07 (m, 2H), 7.14-7.21 (m, 2H).

(2) (Endo)-3-[3-(2-fluorophenyl)propoxy]-8-azabicyclo[3.2.1]octane hydrochloride The title compound (874 mg) was obtained from the compound obtained in Production Example 27-(1) (1.20 g) by the method similar to Production Example 19-(3).
$^1$H-NMR (400 MHz, DMSO-d$_6$); δ 1.73-1.80 (m, 2H), 1.86-1.93 (m, 4H), 2.02-2.14 (m, 4H), 2.63-2.67 (m, 2H), 3.33-3.37 (m, 2H), 3.51-3.53 (m, 1H), 3.8.5-3.86 (m, 2H), 7.09-7.13 (m, 2H), 7.19-7.29 (m, 2H), 8.88 (bs, 2H).

Production Example 28

(Endo)-3-(4-methylbenzyloxy)-8-azabicyclo[3.2.1]octane hydrochloride

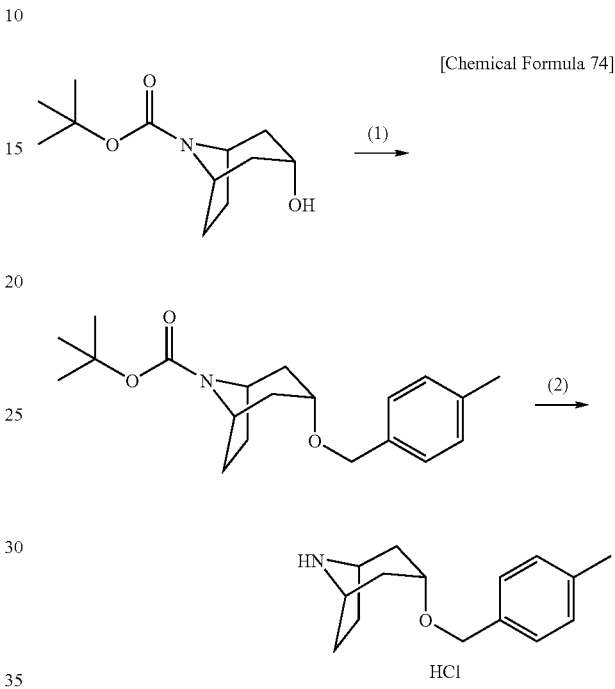

(1) (Endo)-3-(4-methylbenzyloxy)-8-azabicyclo[3.2.1]octane-8-carboxylic acid tert-butyl ester (Endo)-3-hydroxy-8-azabicyclo[3.2.1]octane-8-carboxylic acid tert-butyl ester (CAS 143557-91-9) (2.00 g) and 4-methylbenzyl bromide (1.95 g) were dissolved in N,N-dimethylformamide (20 ml). Sodium hydride (60% in oil) (459 mg) was added and the mixture was stirred at room temperature for 92 hours. Ice water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (2.16 g).
$^1$H-NMR (400 MHz, CDCl$_3$); δ 1.46 (s, 9H), 1.86-2.06 (m, 6H), 2.10-2.17 (m, 2H), 2.34 (s, 3H), 3.67-3.72 (m, 1H), 4.06-4.26 (m, 2H), 4.39-4.50 (m, 2H), 7.13-7.17 (m, 2H), 7.19-7.23 (m, 2H).

(2) (Endo)-3-(4-methylbenzyloxy)-8-azabicyclo[3.2.1]octane hydrochloride

The compound obtained in Production Example 28-(1) (2.16 g) was dissolved in ethyl acetate (8 ml), and then 4N HCl in ethyl acetate (8.15 ml) was added and the mixture was stirred at room temperature for 2 hours. The precipitate was collected by filtration to obtain the title compound (1.63 g).

¹H-NMR (400 MHz, (CD₃OD); δ 1.98-2.24 (m, 6H), 2.32 (s, 3H), 2.39-2.45 (m, 2H), 3.72-3.77 (m, 1H), 3.96-4.02 (m, 2H), 4.47 (s, 2H), 7.13-7.17 (m, 2H), 7.19-7.76 (m, 2H).

¹H-NMR (400 MHz, CD₃OD); δ 1.98-2.22 (m, 6H), 2.35-2.41 (m, 2H), 2.42 (d, J=1.2 Hz, 3H), 3.75-3.79 (m, 1H), 3.96-4.01 (m, 2H), 4.53 (s, 2H), 6.16-6.18 (m, 1H).

Production Example 29

(Endo)-3-(5-methyl-isoxazol-3-ylmethoxy)-8-azabicyclo[3.2.1]octane hydrochloride Production Example 30

(Endo)-3-(2-fluoropyridin-3-ylmethoxy-8-azabicyclo[3.2.1]octane hydrochloride

[Chemical Formula 75]

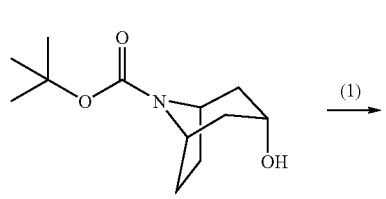

[Chemical Formula 76]

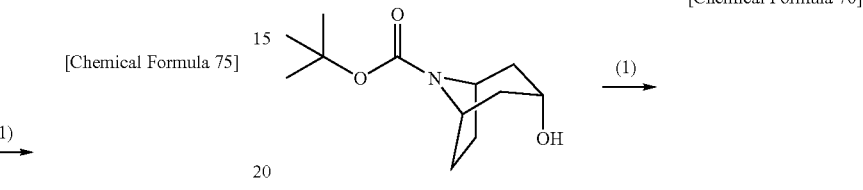

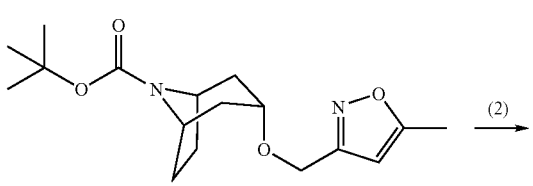

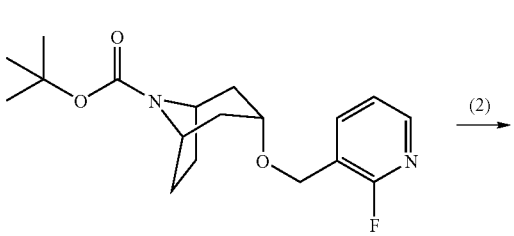

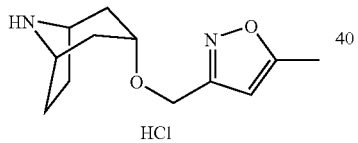

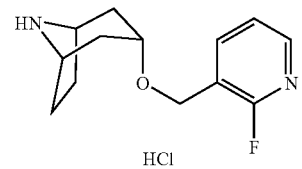

(1) (Endo)-3-(5-methyl-isoxazol-3-ylmethoxy)-8-azabicyclo[3.2.1]octane-8-carboxylic acid tert-butyl ester The title compound (1.46 g) was obtained from (endo)-3-hydroxy-8-azabicyclo[3.2.1]octane-8-carboxylic acid tert-butyl ester (CAS 143557-91-9) (2.21 g) and 3-chloromethyl-5-methylisoxazole by the method similar to Production Example 28-(1).

¹H-NMR (400 MHz, CDCl₃); δ 1.45 (s, 9H), 1.83-2.09 (m, 8H), 2.42 (d, J=0.8 Hz, 3H), 3.66-3.72 (m, 1H), 4.05-4.26 (m, 2H), 4.49 (s, 2H), 5.98-6.02 (m, 1H).

(2) (Endo)-3-(5-methyl-isoxazol-3-ylmethoxy)-8-azabicyclo[3.2.1]octane hydrochloride The title compound (1.03 g) was obtained from the compound obtained in Production Example 29-(1) (1.46 g) by the method similar to Production Example 28-(2).

(1) (Endo)-3-(2-fluoropyridin-3-ylmethoxy)-8-azabicyclo[3.2.1]octane-8-carboxylic acid tert-butyl ester The title compound (803 mg) was obtained from (endo)-3-hydroxy-8-azabicyclo[3.2.1]octane-8-carboxylic acid tert-butyl ester (CAS 143557-91-9) (1.12 g) and 3-chloromethyl-2-fluoropyridine (CAS 315180-14-4) by the method similar to Production Example 28-(1).

¹H-NMR (400 MHz, CDCl₃); δ 1.47 (s, 9H), 1.89-2.12 (m, 8H), 3.74-3.78 (m, 1H), 4.08-4.28 (m, 2H), 4.52 (s, 2H), 7.18-7.23 (m, 1H), 7.83-7.89 (m, 1H), 8.12-8.15 (m, 1H).

(2) (Endo)-3-(2-fluoropyridin-3-ylmethoxy)-8-azabicyclo[3.2.1]octane hydrochloride The title compound (611 mg) was obtained from the compound obtained in Production Example 30-(1) (803 mg) by the method similar to Production Example 28-(2).

$^1$H-NMR (400 MHz, CD$_3$OD); δ 2.00-2.28 (m, 6H), 2.36-2.42 (m, 2H), 3.82-3.86 (m, 1H), 3.99-4.04 (m, 2H), 4.58 (s, 2H), 7.31-7.36 (m, 1H), 7.96-8.02 (m, 1H), 8.12-8.16 (m, 1H).

Production Example 31

(Endo)-3-(2-difluoromethoxybenzyloxy)-8-azabicyclo[3.2.1]octane hydrochloride

[Chemical Formula 77]

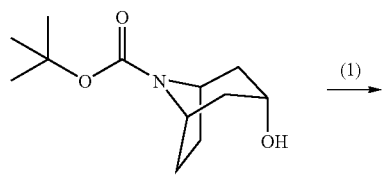

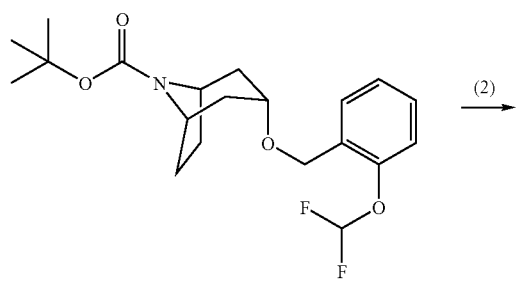

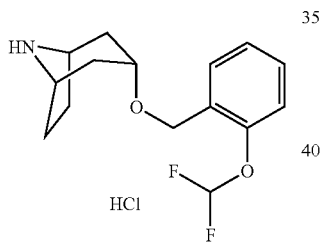

(1) (Endo)-3-(2-difluoromethoxybenzyloxy)-8-azabicyclo[3.2.1]octane-8-carboxylic acid tert-butyl ester The title compound (2.90 g) was obtained from (endo)-3-hydroxy-8-azabicyclo[3.2.1]octane-8-carboxylic acid tert-butyl ester (CAS 143557-91-9) (2.00 g) and 2-difluoromethoxybenzyl bromide by the method similar to Production Example 28-(1).

(2) (Endo)-3-(2-difluoromethoxybenzyloxy)-8-azabicyclo[3.2.1]octane hydrochloride The compound obtained in Production Example 31-(1) (2.90 g) was dissolved in ethyl acetate (30 ml), and then 4N HCl in ethyl acetate (30 ml) was added and the mixture was stirred at room temperature for 70 minutes. The reaction mixture was concentrated under reduced pressure and diethyl ether was added to the residue. The solid was collected by filtration to obtain the title compound (1.97 g).

$^1$H-NMR (400 MHz, DMSO-d$_6$); δ 1.90-2.20 (m, 8H), 3.74 (bs, 1H), 3.92 (bs, 2H), 4.49 (s, 2H), 7.04-7.41 (m, 4H), 7.46-7.49 (m, 1H), 8.93 (bs, 1H).

Production Example 32

(Endo)-3-cyclopropylmethoxy-8-azabicyclo[3.2.1]octane hydrochloride

[Chemical Formula 78]

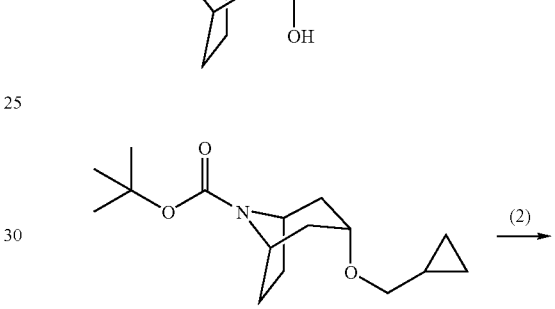

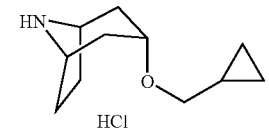

(1) (Endo)-3-cyclopropylmethoxy-8-azabicyclo[3.2.1]octane-8-carboxylic acid tert-butyl ester The title compound (734 mg) was obtained from (endo)-3-hydroxy-8-azabicyclo[3.2.1]octane-8-carboxylic acid tert-butyl ester (CAS 143557-91-9) (1.00 g) and bromomethylcyclopropane by the method similar to Production Example 28-(1).

$^1$H-NMR (400 MHz, CDCl$_3$); δ 0.17-0.21 (m, 2H), 0.47-0.52 (m, 2H), 0.98-1.04 (m, 1H), 1.46 (s, 9H), 1.80-1.92 (m, 6H), 2.05-2.09 (m, 2H), 3.21-3.23 (m, 2H), 3.60 (bs, 1H), 4.10-4.17 (m, 2H).

(2) (Endo)-3-cyclopropylmethoxy-8-azabicyclo[3.2.1]octane hydrochloride

The title compound (500 mg) was obtained from the compound of Production Example 32-(1) (734 mg) by the method similar to Production Example 31-(2).

¹H-NMR (400 MHz, CD₃OD); δ 0.20-0.24 (m, 2H), 0.50-0.55 (m, 2H), 1.01-1.07 (m, 1H), 2.01-2.16 (m, 6H), 2.40-2.45 (m, 2H), 3.28-3.29 (m, 2H), 3.66 (bs, 1H), 3.97 (bs, 2H).

Production Example 33

(Endo)-3-(2-fluoromethylbenzyloxy)-8-azabicyclo[3.2.1]octane hydrochloride

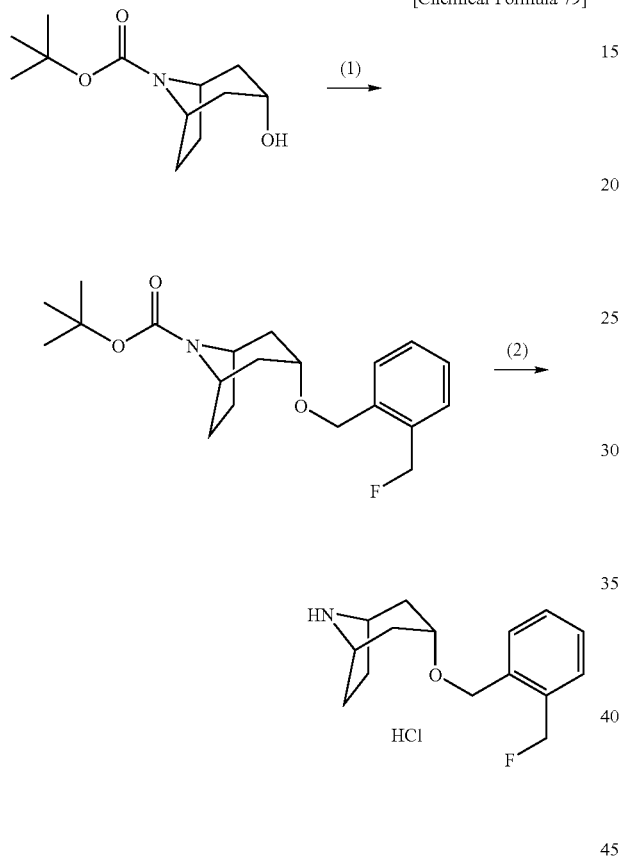

[Chemical Formula 79]

(1) (Endo)-3-(2-fluoromethylbenzyloxy)-8-azabicyclo[3.2.1]octane-8-carboxylic acid tert-butyl ester The title compound (1.76 g) was obtained from (endo)-3-hydroxy-8-azabicyclo[3.2.1]octane-8-carboxylic acid tert-butyl ester (CAS 143557-91-9) (1.91 g) and 2-fluoromethylbenzyl bromide (CAS 158884-44-7) by the method similar to Production Example 28-(1).

¹H-NMR (400 MHz, CDCl₃); δ 1.46 (s, 9H), 1.86-2.12 (m, 8H), 3.70-3.75 (m, 1H), 4.07-4.26 (m, 2H), 4.55 (s, 2H), 4.58 (d, J=48.0 Hz, 2H), 7.30-7.44 (m, 4H).

(2) (Endo)-3-(2-fluoromethylbenzyloxy)-8-azabicyclo[3.2.1]octane hydrochloride

The title compound (1.26 g) was obtained from the compound obtained in Production Example 33-(1) (1.76 g) by the method similar to Production Example 19-(3).

¹H-NMR (400 MHz, CD₃OD); δ 1.98-2.26 (m, 6H), 2.35-2.43 (m, 2H), 3.76-3.81 (m, 1H), 3.96-4.02 (m, 2H), 4.62 (s, 2H), 4.50 (d, J=47.6 Hz, 2H), 7.32-7.46 (m, 4H).

Production Example 34

(Endo)-3-(2-difluororiethylbenzyloxy)-8-azabicyclo[3.2.1]octane hydrochloride

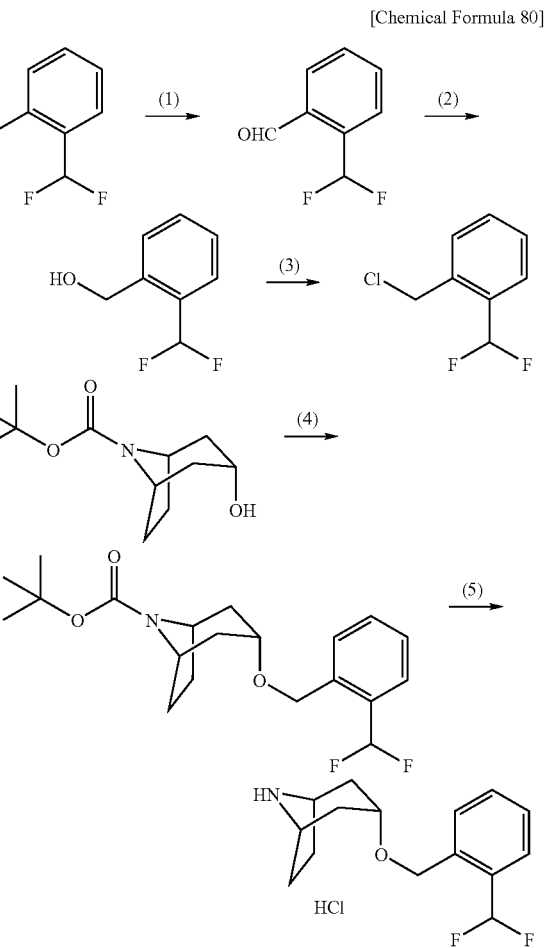

[Chemical Formula 80]

(1) 2-Difluoromethylbenzaldehyde

After dissolving 1-bromo-2-difluoromethylbenzene (3.23 g) in tetrahydrofuran (65 ml), the mixture was cooled to −78° C. After then adding n-butyllithium (2.64 M solution in hexane, 6.5 ml) and stirring for 30 minutes, N,N-dimethylformamide (2.4 ml) was added and stirring was continued for 3 hours. A saturated aqueous solution of ammonium chloride was added to the reaction mixture, and then the mixture was diluted with water and extracted with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (991 mg).

¹H-NMR (400 MHz, CDCl₃); δ 7.30-7.57 (m, 1H), 7.68-7.75 (m, 2H), 7.82-7.83 (m, 1H), 7.94-7.96 (m, 1H), 10.19 (s, 1H).

(2) (2-Difluoromethylphenyl)methanol

Sodium borohydride (485 mg) was suspended in ethanol (10 ml), and the compound obtained in Production Example 34-(1) (991 mg) was added while stirring on ice. After stirring for 2 hours, the reaction mixture was concentrated under reduced pressure. Water and ethyl acetate were added to the residue, and the organic layer was separated. The organic layer was washed with water and brine in that order and then dried over anhydrous magnesium sulfate. After filtration, the solvent was distilled off under reduced pressure. The residue was purified by silica gel column chromatography to obtain the title compound (771 mg).

$^1$H-NMR (400 MHz, CDCl$_3$); δ 1.85 (t, J=6.0 Hz, 1H), 4.85 (d, J=6.0 Hz, 2H), 6.80-7.08 (m, 1H), 7.39-7.43 (m, 1H), 7.46-7.50 (m, 2H), 7.57-7.59 (m, 1H).

(3) 1-Chloromethyl-2-difluoromethylbenzene

The compound obtained in Production Example 34-(2) (711 mg) was dissolved in benzotrifluoride (10 ml), and then thionyl chloride (0.71 ml) was added and the mixture was stirred at 60° C. for 2 hours. After then adding N,N-dimethylformamide (catalytic amount) and thionyl chloride (0.71 ml), stirring was continued for 2 hours and 30 minutes at 60° C. The reaction mixture was concentrated under reduced pressure, water and ethyl acetate were added to the residue, and the organic layer was separated. The organic layer was washed with water and brine in that order and then dried over anhydrous magnesium sulfate. After filtration, the solvent was distilled off under reduced pressure to obtain the title compound (706 mg).

$^1$H-NMR (400 MHz, CDCl$_3$); δ 4.73 (s, 2H), 6.82-7.10 (m, 1H), 7.42-7.49 (m, 1H), 7.58-7.61 (m, 1H).

(4) (Endo)-3-(2-difluoromethylbenzyloxy)-8-azabicyclo[3.2.1]octane-8-carboxylic acid tert-butyl ester The title compound (1.33 g) was obtained from (endo)-3-hydroxy-8-azabicyclo[3.2.1]octane-8-carboxylic acid tert-butyl ester (CAS 143557-91-9) (1.00 g) and the compound obtained in Production Example 34-(3), by the method similar to Production Example 28-(1).

$^1$H-NMR (400 MHz, CDCl$_3$); δ 1.46 (s, 9H) 1.89-1.92 (m, 5H), 2.06-2.10 (m, 3H), 3.72-3.73 (m, 1H), 4.10-4.22 (bs, 2H), 4.62 (s, 2H), 6.76-7.04 (m, 1H), 7.37-7.41 (m, 1H), 7.45-7.56 (m, 2H), 7.58-7.59 (m, 1H).

(5) (Endo)-3-(2-difluoromethylbenzyloxy)-8-azabicyclo[3.2.1]octane hydrochloride The title compound (980 mg) was obtained from the compound obtained in Production Example 34-(4) (1.33 g) by the method similar to Production Example 31-(2).

$^1$H-NMR (400 MHz, CD$_3$OD); δ 2.01-2.04 (m, 2H), 2.11-2.25 (m, 4H), 2.37-2.39 (m, 2H), 3.79 (bs, 1H), 3.99 (bs, 2H), 4.69 (s, 2H), 6.87-7.14 (m, 1H), 7.44-7.45 (m, 1H), 7.51 (bs, 2H), 7.59-7.61 (m, 1H).

Production Example 35

(Endo)-3-(2-morpholin-4-yl-benzyloxy)-8-azabicyclo[3.2.1]octane

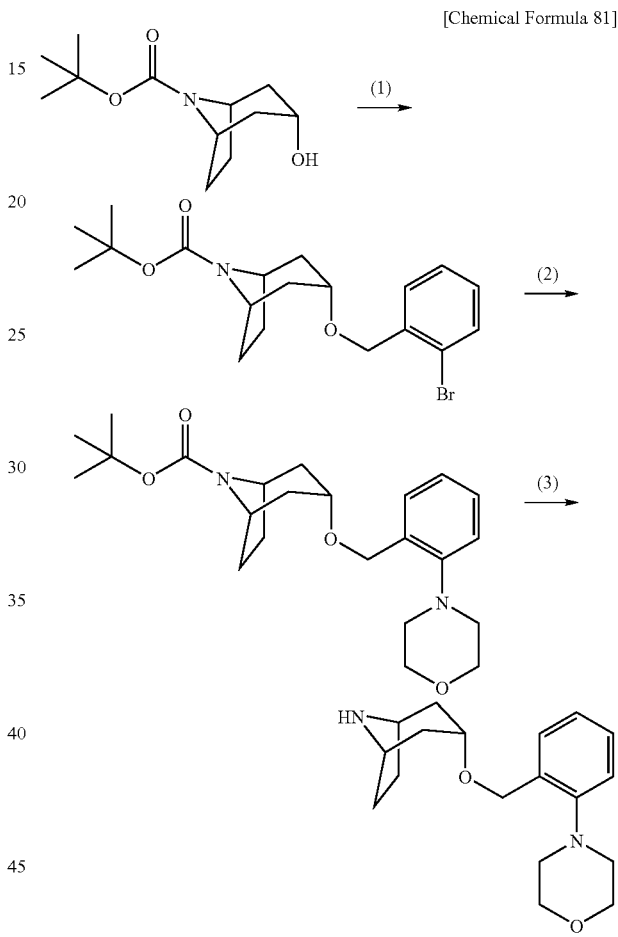

[Chemical Formula 81]

(1) (Endo)-3-(2-bromo-benzyloxy)-8-azabicyclo[3.2.1]octane-8-carboxylic acid tert-butyl ester The title compound (2.77 g) was obtained from (endo)-3-hydroxy-8-azabicyclo[3.2.1]octane-8-carboxylic acid tert-butyl ester (CAS 143557-91-9) (2.50 g) and 2-bromobenzyl bromide by the method similar to Production Example 28-(1).

$^1$H-NMR (400 MHz, CDCl$_3$); δ 1.47 (s, 9H), 1.92-2.17 (m, 8H), 3.78 (br, 1H), 4.11-4.23 (m, 2H), 4.52 (s, 2H), 7.12-7.16 (m, 1H), 7.31-7.34 (m, 1H), 7.48-7.54 (m, 2H).

(2) (Endo)-3-(2-morpholin-4-yl-benzyloxy)-8-azabicyclo[3.2.1]octane-8-carboxylic acid tert-butyl ester A mixture of the compound obtained in Production Example 35-(1) (1.00 g), morpholine (0.264 ml), tris(dibenzylideneacetone)dipalladium(0) (46.2 mg), (R)-(+)-2,2'-bis (diphenylphosphino)-1,1'-biphenyl (62.8 mg), sodium tert-butoxide (339 mg) and xylene (10 ml) was stirred at 80° C. for 16 hours and 50 minutes. The reaction mixture was filtered with Celite, and then the filtrate was concentrated under reduced pressure. The residue was purified by silica gel column chromatography to obtain the title compound (387 mg).

$^1$H-NMR (400 MHz, CDCl$_3$); δ 1.47 (s, 9H), 1.91-2.15 (m, 8H), 2.91-2.93 (m, 4H), 3.74 (br, 1H), 3.82-3.85 (m, 4H), 4.11-4.22 (m, 2H), 4.55 (s, 2H), 7.09-7.15 (m, 2H), 7.27-7.30 (m, 1H), 7.44-7.47 (m, 1H).

(3) (Endo)-3-(2-morpholin-4-yl-benzyloxy)-8-azabicyclo[3.2.1]octane

After adding 4N HCl in ethyl acetate (7.47 ml) to the compound obtained in Production Example 35-(2) (387 mg) while cooling on ice, the mixture was stirred at room temperature for 1 hour. Water and ethyl acetate were added to the reaction mixture, and the aqueous layer was separated. A 5N aqueous solution of sodium hydroxide was added to the aqueous layer to make the mixture alkaline, and then extraction was performed with ethyl acetate. The organic layer was washed with water and brine in that order and then dried over anhydrous magnesium sulfate. After filtration, the solvent was distilled off under reduced pressure to obtain the title compound (208 mg).

$^1$H-NMR (400 MHz, CDCl$_3$); δ 1.75-2.21 (m, 8H), 2.91-2.93 (m, 4H), 3.53-3.54 (m, 2H), 3.71-3.72 (m, 1H), 3.82-3.85 (m, 4H), 4.52 (s, 2H), 7.08-7.15 (m, 2H), 7.26-7.30 (m, 1H), 7.46-7.48 (m, 1H).

Production Example 36

(Endo)-3-(2-fluoro-6-pyridin-4-yl-benzyloxy)-8-azabicyclo[3.2.1]octane dihydrochloride

[Chemical Formula 82]

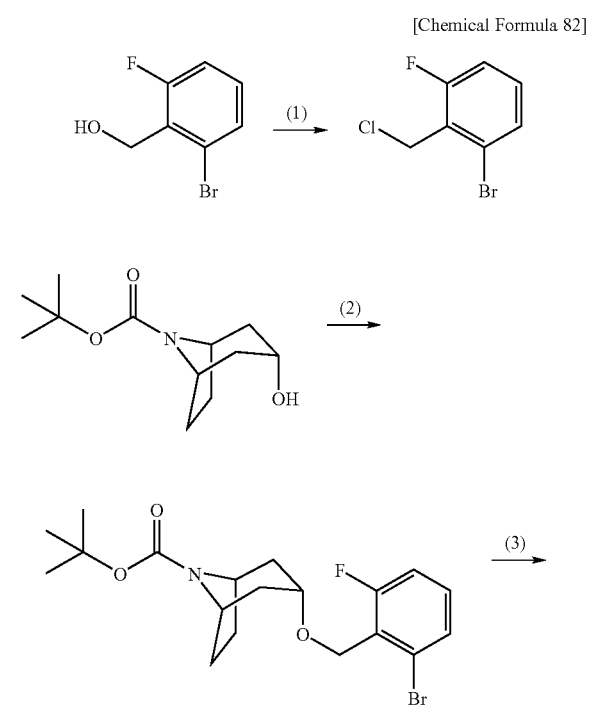

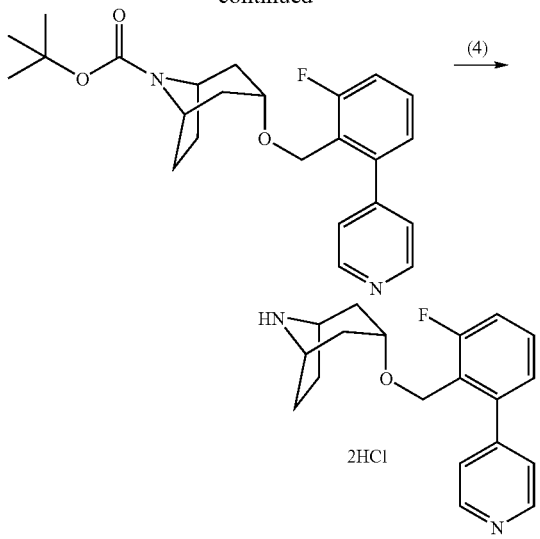

(1) 2-Bromo-6-fluorobenzyl chloride

After dissolving (2-bromo-6-fluorophenyl)methanol (CAS 261723-33-5) (4.07 g) in toluene (50 ml), thionyl chloride (2.21 ml) was added dropwise while stirring on ice. N,N-Dimethylformamide (0.1 ml) was then added and the mixture was stirred for 6 hours. The reaction mixture was diluted with water, a 1N aqueous solution of sodium hydroxide was added and extraction was performed with ethyl acetate. The organic layer was washed with brine and dried over anhydrous magnesium sulfate. After filtration, the solvent was distilled off under reduced pressure to obtain the title compound (4.45 g).

$^1$H-NMR (400 MHz, CDCl$_3$); δ 4.77 (s, 2H), 7.04-7.20 (m, 2H), 7.38-7.41 (m, 1H).

(2) (Endo)-3-(2-bromo-6-fluorobenzyloxy)-8-azabicyclo[3.2.1]octane-8-carboxylic acid tert-butyl ester After dissolving (endo)-3-hydroxy-8-azabicyclo[3.2.1]octane-8-carboxylic acid tert-butyl ester (CAS 143557-91-9) (3.00 g) and the compound obtained in Production Example 36-(1) (4.42 g) in N,N-dimethylformamide (50 ml), sodium hydride (60% in oil) (924 mg) was added. The mixture was stirred at 50° C. for 14 hours and 40 minutes. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (3.35 g).

$^1$H-NMR (400 MHz, CDCl$_3$); δ 1.46 (s, 9H), 1.84-2.12 (m, 8H), 3.76 (br, 1H), 4.09-4.18 (m, 2H), 4.58 (br, 2H), 7.01-7.06 (m, 1H), 7.14-7.19 (m, 1H), 7.38 (d, J=8.0 Hz, 1H).

(3) (Endo)-3-(2-fluoro-6-pyridin-4-yl-benzyloxy)-8-azabicyclo[3.2.1]octane-8-carboxylic acid tert-butyl ester A mixture of the compound obtained in Production Example 36-(2) (730 mg), 4-(tri-n-butylstannyl)pyridine (CAS 124252-41-1) (777 mg), tetrakis(triphenylphosphine) palladium(0) (203 mg), tetra-n-butylammonium chloride (489 mg) and xylene (20 ml) was stirred at 140° C. for 2 hours. The reaction mixture was filtered with Celite, and then the filtrate was concentrated under reduced pressure. The residue was purified by silica gel column chromatography to obtain the title compound (660 mg).

$^1$H-NMR (400 MHz, CDCl$_3$); δ 1.46 (s, 1H), 1.67-2.05 (m, 8H), 3.64-3.66 (m, 1H), 4.09-4.30 (m, 4H), 7.10-7.18 (m, 2H), 7.37-7.42 (m, 3H), 8.65-8.67 (m, 2H).

(4) (Endo)-3-(2-fluoro-6-pyridin-4-yl-benzyloxy)-8-azabicyclo[3.2.1]octane dihydrochloride After adding 4N HCl in ethyl acetate (10 ml) to the compound obtained in Production Example 36-(3) (730 mg) while cooling on ice, the mixture was stirred at room temperature for 5 hours. Diethyl ether was added to the reaction mixture, and the solid was collected by filtration to obtain the title compound (435 mg).

$^1$H-NMR (400 MHz, CD$_3$OD); δ 1.98-2.30 (m, 8H), 3.74-3.76 (m, 1H), 4.00 (br, 2H), 4.47 (m, 2H), 7.37-7.44 (m, 2H), 7.60-7.65 (m, 1H), 8.23-8.25 (m, 2H), 8.98-9.00 (m, 2H).

Production Example 37

(Endo)-3-(3-fluorobiphenyl-2-ylmethoxy)-8-azabicyclo[3.2.1]octane hydrochloride

[Chemical Formula 83]

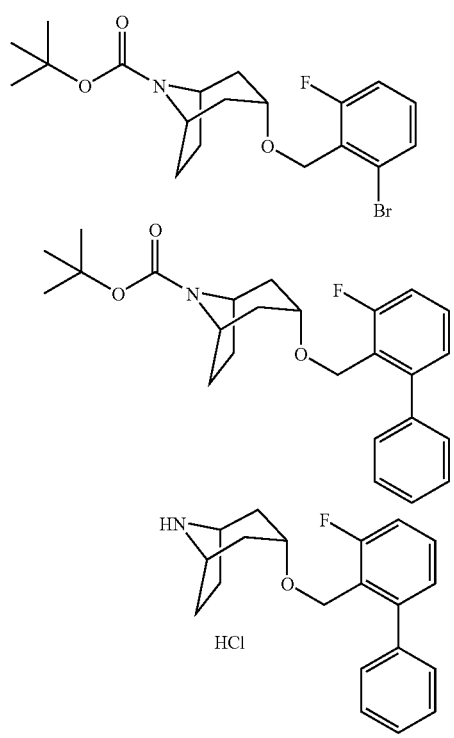

(1) (Endo)-3-(3-fluorobiphenyl-2-ylmethoxy)-8-azabicyclo[3.2.1]octane-8-carboxylic acid tert-butyl ester The title compound (740 mg) was obtained from the compound obtained in Production Example 36-(2) (730 mg) and phenyl-tri-n-butyltin by the method similar to Production Example 36-(3).

(2) (Endo)-3-(3-fluorobiphenyl-2-ylmethoxy)-8-azabicyclo[3.2.1]octane hydrochloride The title compound (383 mg) was obtained from the compound obtained in Production Example 37-(1) (740 mg) by the method similar to Production Example 19-(3).

$^1$H-NMR (400 MHz, CD$_3$OD); δ 1.95-2.08 (m, 6H), 2.26-2.31 (m, 2H), 3.62-3.63 (m, 1H), 3.93 (br, 2H), 4.39 (m, 2H), 7.12-7.16 (m, 2H), 7.38-7.46 (m, 6H).

Production Example 38

(Endo)-3-(2-fluoro-6-pyrazin-2-yl-benzyloxy)-8-azabicyclo[3.2.1]octane hydrochloride

[Chemical Formula 84]

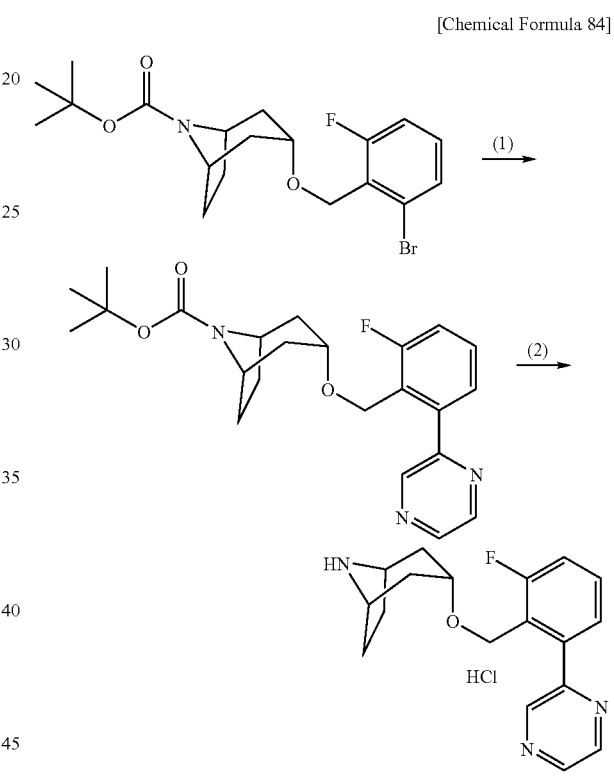

(1) (Endo)-3-(2-fluoro-6-pyrazin-2-ylbenzyloxy)-8-azabicyclo[3.2.1]octane-8-carboxylic acid tert-butyl ester The title compound (509 mg) was obtained from the compound obtained in Production Example 36-(2) (510 mg) and 2-(tri-n-butylstannyl)pyrazine, by the method similar to Production Example 36-(3).

$^1$H-NMR (400 MHz, CDCl$_3$); δ 1.44 (s, 9H), 1.57-1.90 (m, 8H), 3.59-3.62 (m, 1H), 4.05-4.15 (m, 2H), 4.51-4.53 (m, 2H), 7.19-7.22 (m, 1H), 7.34-7.36 (m, 1H), 7.42-7.47 (m, 1H), 8.58-8.59 (m, 1H), 8.66-8.67 (m, 1H), 8.89 (m, 1H).

(2) (Endo)-3-(2-fluoro-6-pyrazin-2-ylbenzyloxy)-8-azabicyclo[3.2.1]octane hydrochloride The title compound (314 mg) was obtained from the compound obtained in Production Example 38-(i) (518 mg) by the method similar to Production Example 19-(3).

$^1$H-NMR (400 MHz, CD$_3$OD); δ 1.91-2.20 (m, 8H), 3.63-3.65 (m, 1H), 3.91-3.93 (m, 2H), 4.62 (m, 2H), 7.28-7.33 (m, 1H), 7.39-7.41 (m, 1H), 7.52-7.57 (m, 1H), 8.66-8.67 (m, 1H), 8.72-8.77 (m, 1H), 8.88 (m, 1H).

Production Example 39

(Endo)-3-(2-furan-3-ylbenzyloxy)-8-azabicyclo[3.2.1]octane hydrochloride

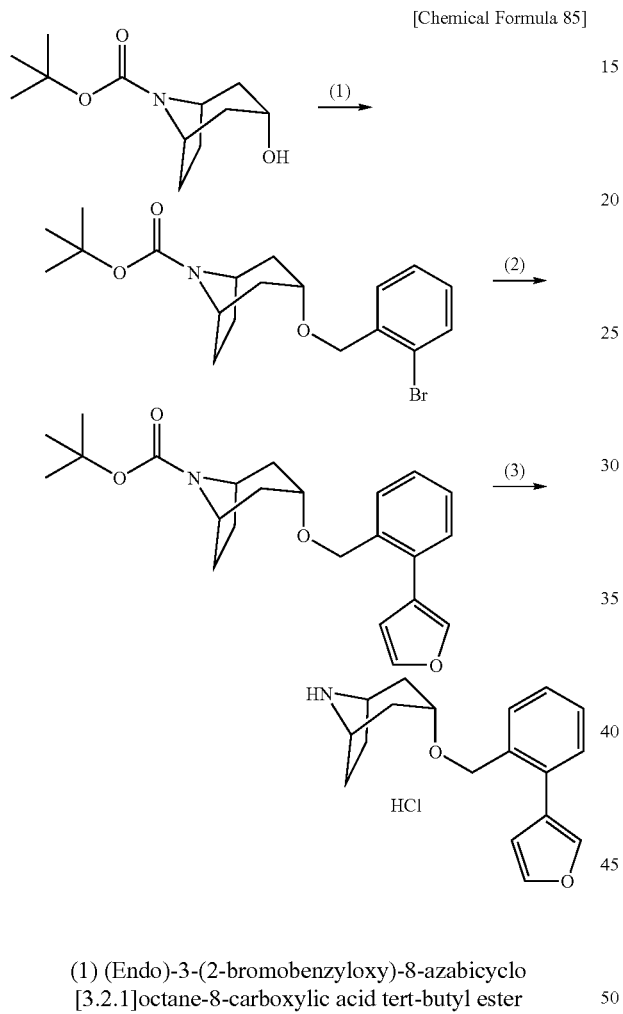

[Chemical Formula 85]

(1) (Endo)-3-(2-bromobenzyloxy)-8-azabicyclo[3.2.1]octane-8-carboxylic acid tert-butyl ester The title compound (2.77 g) was obtained from (endo)-3-hydroxy-8-azabicyclo[3.2.1]octane-8-carboxylic acid tert-butyl ester (CAS 143557-91-9) (2.50 g) and 2-bromobenzyl bromide by the method similar to Production Example 28-(1).
$^1$H-NMR (400 MHz, CDCl$_3$); δ 1.47 (s, 9H), 1.92-2.17 (m, 8H), 3.79 (br, 1H), 4.11-4.23 (m, 2H), 4.52 (s, 2H), 7.12-7.16 (m, 1H), 7.31-7.34 (m, 1H), 7.48-7.54 (m, 2H).

(2) (Endo)-3-(2-furan-3-ylbenzyloxy)-8-azabicyclo[3.2.1]octane-8-carboxylic acid tert-butyl ester The compound obtained in Production Example 39-(1) (450 mg) was dissolved in N,N-dimethylformamide (11 ml), and then furan-3-boronic acid (153 mg) and cesium carbonate (380 mg) were added and the mixture was stirred for 1 minute. Tetrakis(triphenylphosphine)palladium(0) (132 mg) was then added, and the mixture was stirred overnight at 100° C. Water was added to the reaction mixture, and extraction was performed with ethyl acetate. The extract was dried over anhydrous magnesium sulfate. After filtration, the solvent was distilled off under reduced pressure. The residue was purified by silica gel column chromatography to obtain the title compound (418 mg).
$^1$H-NMR (400 MHz, CDCl$_3$); δ 1.46 (s, 9H), 1.87-2.17 (m, 8H), 3.68-3.74 (m, 1H), 4.05-4.25 (m, 2H), 4.46 (s, 2H), 6.57-6.58 (m, 1H), 7.28-7.38 (m, 3H), 7.42-7.53 (m, 2H), 7.57-7.59 (m, 1H).

(3) (Endo)-3-(2-furan-3-ylbenzyloxy)-8-azabicyclo[3.2.1]octane hydrochloride

The compound obtained in Production Example 39-(2) (122 mg) was dissolved in ethyl acetate (3 ml), and then 4N HCl in ethyl acetate (3 ml) was added and the mixture was stirred at room temperature for 2 hours. The reaction mixture was concentrated under reduced pressure to obtain the title compound (113 mg).

Production Example 40

(Endo)-2-(8-azabicyclo[3.2.1]octan-3-yl)-1-(2-fluorophenyl)ethanone hydrochloride

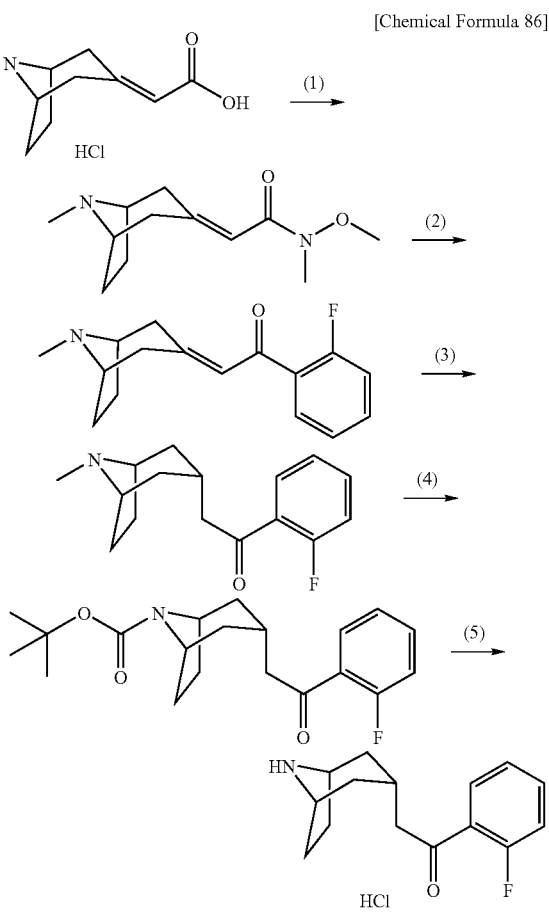

[Chemical Formula 86]

(1) N-Methoxy-N-methyl-2-(8-methyl-8-azabicyclo[3.2.1]octane-3-ylidene)acetamide Thionyl chloride (20 ml) was added to 2-(8-methyl-8-azabicyclo[3.2.1]octan-3-ylidene)-acetic acid (CAS 123368-82-1) (5.0 g), and the mixture was heated to reflux for 2 hours. The reaction mixture was concentrated under reduced pressure, and then dichloromethane was added to the residue and the mixture was concentrated under reduced pressure. The residue was suspended in dichloromethane (70 ml), and N,O-dimethylhydroxylamine hydrochloride (2.69 g) was added. Pyridine (6.51 ml) was then added dropwise while stirring on ice. After stirring for 2 hours at room temperature, the reaction mixture was concentrated under reduced pressure. A 2N aqueous solution of sodium hydroxide was added to the residue, and the mixture was extracted with ethyl acetate and dried over anhydrous magnesium sulfate. After filtration, the solvent was distilled off under reduced pressure. The residue was purified by NH silica gel column chromatography to obtain the title compound (4.36 g).

$^1$H-NMR (400 MHz, CDCl$_3$); δ 1.50-1.57 (m, 2H), 1.90-2.05 (m, 3H), 2.36-2.44 (m, 1H), 2.38 (s, 3H), 2.69-2.76 (m, 1H), 3.20 (s, 3H), 3.22-3.29 (m, 2H), 3.37-3.44 (m, 1H), 3.67 (s, 3H), 6.14 (s, 1H).

(2) 1-(2-Fluorophenyl)-2-(8-methyl-8-azabicyclo[3.2.1]octane-3-ylidene)ethanone After dissolving 1-bromo-2-fluorobenzene (3.05 g) in tetrahydrofuran (40 ml), the mixture was cooled to −78° C. Next, n-butyllithium (2.6 M solution in hexane, 6.18 ml) was added dropwise while stirring. After further stirring for 30 minutes, a solution of the compound obtained in Production Example 40-(1) (3.00 g) in tetrahydrofuran (10 ml) was added dropwise. Then mixture was stirred for 1 hour, and then a saturated aqueous solution of ammonium chloride was added, and then the mixture was diluted with water and extracted with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (2.70 g).

(3) (Endo)-1-(2-fluorophenyl)-2-(8-methyl-8-azabicyclo[3.2.1]octan-3-yl)ethanone The compound obtained in Production Example 40-(2) (3.94 g) was dissolved in ethanol (80 ml), and then 20% palladium hydroxide on carbon (50% wet) (394 mg) was added and the mixture was stirred at room temperature for 36 hours under a hydrogen atmosphere (1 atm). The reaction mixture was filtered, and then the solvent was distilled off under reduced pressure. The residue was purified by NH silica gel column chromatography to obtain the title compound (3.32 g).

$^1$H-NMR (400 MHz, CDCl$_3$); δ 1.28-1.36 (m, 2H), 1.64-1.73 (m, 2H), 2.01-2.12 (m, 2H), 2.16-2.25 (m, 2H), 2.26 (s, 3H), 2.40-2.51 (m, 1H), 3.08-3.14 (m, 2H), 3.17 (dd, J=8.0, 2.4 Hz, 2H), 7.09-7.16 (m, 1H), 7.20-7.26 (m, 1H), 7.47-7.54 (m, 1H), 7.81 (td, J=7.6, 2.0 Hz, 1H).

(4) (Endo)-3-[2-(2-fluorophenyl)-2-oxo-ethyl]-8-azabicyclo[3.2.1]octane-8-carboxylic acid tert-butyl ester The compound obtained in Production Example 40-(3) (700 mg) was dissolved in 1,2-dichloroethane (5 ml), and then potassium carbonate (185 ml) and 1-chloroethyl chloroformate (0.58 ml) were added. After further stirring at room temperature for 15 minutes, it was heated to reflux for 4 hours. The reaction mixture was filtered and the filtrate was concentrated under reduced pressure. Methanol (20 ml) was added to the residue, and the mixture was heated to reflux for 30 minutes. The reaction mixture was concentrated under reduced pressure, the residue was dissolved in chloroform (20 ml), and triethylamine (0.83 ml) was added. After then adding di-tert-butyl dicarbonate (646 mg) while stirring on ice, the mixture was stirred at room temperature for 2 hours. The reaction mixture was concentrated under reduced pressure, and the residue was purified by silica gel column chromatography. The title compound (382 mg) was thus obtained.

$^1$H-NMR (400 MHz, CDCl$_3$); δ 1.20-1.34 (m, 2H), 1.45 (s, 9H), 1.67-1.76 (m, 2H), 1.97-2.05 (m, 2H), 2.18-2.43 (m, 3H), 3.15 (dd, J=7.6, 2.4 Hz, 2H), 4.08-4.28 (m, 2H), 7.09-7.16 (m, 1H), 7.20-7.26 (m, 1H), 7.48-7.54 (m, 1H), 7.82 (td, J=7.6, 1.6 Hz, 1H).

(5) (Endo)-2-(8-azabicyclo[3.2.1]octan-3-yl)-1-(2-fluorophenyl)ethanone hydrochloride The title compound (263 mg) was obtained from the compound obtained in Production Example 40-(4) (382 mg) by the method similar to Production Example 26-(2).

$^1$H-NMR (400 MHz, DMSO-d$_6$); δ 1.53-1.61 (m, 2H), 1.93-2.05 (m, 4H), 2.20-2.29 (m, 2H), 2.40-2.50 (m, 1H), 3.26 (dd, J=7.2, 2.0 Hz, 2H), 3.87-3.94 (m, 2H), 7.32-7.39 (m, 2H), 7.64-7.70 (m, 1H), 7.82-7.87 (m, 1H), 8.60-8.76 (m, 1H), 8.82-9.00 (m, 1H).

Production Example 41

(Endo)-1-(8-azabicyclo[3.2.1]octan-3-yl)-3-(2-fluorophenyl)propan-2-one hydrochloride

[Chemical Formula 87]

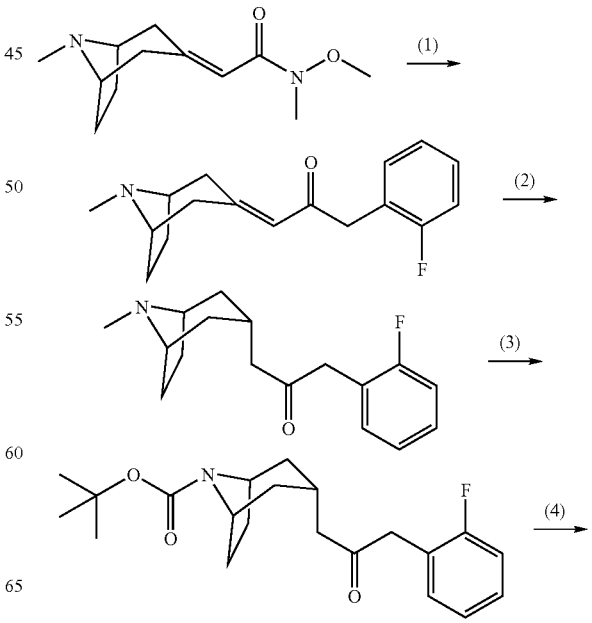

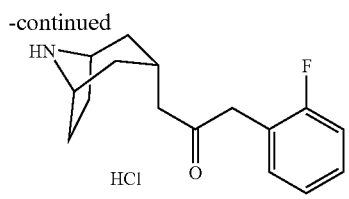

(1) 1-(2-Fluorophenyl)-3-(8-methyl-8-azabicyclo[3.2.1]octane-3-ylidene)propan-2-one Magnesium (1.36 g) was suspended in diethyl ether (5 ml), and a small amount of iodine was added. A small amount of 2-fluorobenzyl bromide was added, and the mixture was heated to start the reaction. Diethyl ether (45 ml) was added, and 2-fluorobenzyl bromide (10.1 g) was added dropwise to continue reflux. After the dropwise addition, the mixture was further stirred for 1 hour at room temperature. The obtained Grignard reagent was cooled on ice, and a solution of the compound obtained in Production Example 40-(1) (5.97 g) in tetrahydrofuran (10 ml) was added dropwise. After the dropwise addition, the mixture was further stirred for 1 hour at room temperature. A saturated aqueous solution of ammonium chloride was added to the reaction mixture and stirring was continued for a while. An aqueous solution of sodium carbonate was then added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (1.14 g).

(2) (Endo)-1-(2-fluorophenyl)-3-(8-methyl-8-azabicyclo[3.2.1]octan-3-yl)propan-2-one The title compound (1.04 g) was obtained from the compound obtained in Production Example 41-(1) (1.14 g) by the method similar to Production Example 40-(3).

$^1$H-NMR (400 MHz, CDCl$_3$); δ 1.17-1.24 (m, 2H), 1.50-1.56 (m, 2H), 1.97-2.06 (m, 2H), 2.14-2.22 (m, 2H), 2.26 (s, 3H), 2.32-2.42 (m, 1H), 2.67 (d, J=7.6 Hz, 2H), 3.06-3.12 (m, 1H), 3.70 (d, J=1.2 Hz, 2H), 7.04-7.13 (m, 2H), 7.15-7.20 (m, 1H), 7.23-7.29 (m, 1H).

(3) (Endo)-3-[3-(2-fluorophenyl)-2-oxopropyl]-8-azabicyclo[3.2.1]octane-8-carboxylic acid tert-butyl ester The compound obtained in Production Example 41-(2) (1.04 g) was dissolved in toluene (10 ml), and 1-chloroethyl chloroformate (1.22 ml) was added dropwise while stirring at room temperature. The reaction mixture was stirred at 100° C. for 3 hours and then concentrated under reduced pressure. Methanol (20 ml) was added to the residue, prior to heating to reflux for 1 hour. The reaction mixture was concentrated under reduced pressure, a 1N aqueous solution of sodium hydroxide (10 ml) was added to the residue, and a solution of di-tert-butyl dicarbonate (1.24 g) in tetrahydrofuran (10 ml) was added while stirring at room temperature, after which the mixture was stirred overnight at room temperature. Water was added to the reaction mixture, and extraction was performed with ethyl acetate. The extract was washed with water and brine in that order and then dried over anhydrous magnesium sulfate. After filtration, the solvent was distilled off under reduced pressure and the residue was purified by silica gel column chromatography. The title compound (697 mg) was thus obtained.

$^1$H-NMR (400 MHz, CDCl$_3$); δ 1.12-1.18 (m, 2H), 1.45 (s, 9H), 1.53-1.60 (m, 2H), 1.92-1.98 (m, 2H), 2.16-2.31 (m, 3H), 2.66 (d, J=7.2 Hz, 2H), 3.69 (d, J=0.8 Hz, 2H), 4.10-4.18 (m, 2H), 7.04-7.13 (m, 2H), 7.15-7.20 (m, 1H), 7.23-7.30 (m, 1H).

(4) (Endo)-1-(8-azabicyclo[3.2.1]octan-3-yl)-3-(2-fluorophenyl)propan-2-one hydrochloride The compound obtained in Production Example 41-(3) (697 mg) was dissolved in ethyl acetate (4 ml), and then 4N HCl in ethyl acetate (4 ml) was added and the mixture was stirred at room temperature for 90 minutes. Diethyl ether was added to the reaction mixture, and the obtained mixture was concentrated under reduced pressure. Ethyl acetate was added to the residue, and the solid was collected by filtration to obtain the title compound (477 mg).

$^1$H-NMR (400 MHz, CD$_3$OD); δ 1.57-1.65 (m, 2H), 1.96-2.14 (m, 4H), 2.21-2.29 (m, 2H), 2.42-2.52 (m, 1H), 2.90 (d, J=7.6 Hz, 2H), 3.82 (s, 2H), 3.92-3.98 (m, 2H), 7.05-7.16 (m, 2H), 7.22-7.34 (m, 2H).

Production Example 42

(Endo)-3-[2-(2-fluorophenyl)-ethyl]-8-azabicyclo[3.2.1]octane hydrochloride

[Chemical Formula 88]

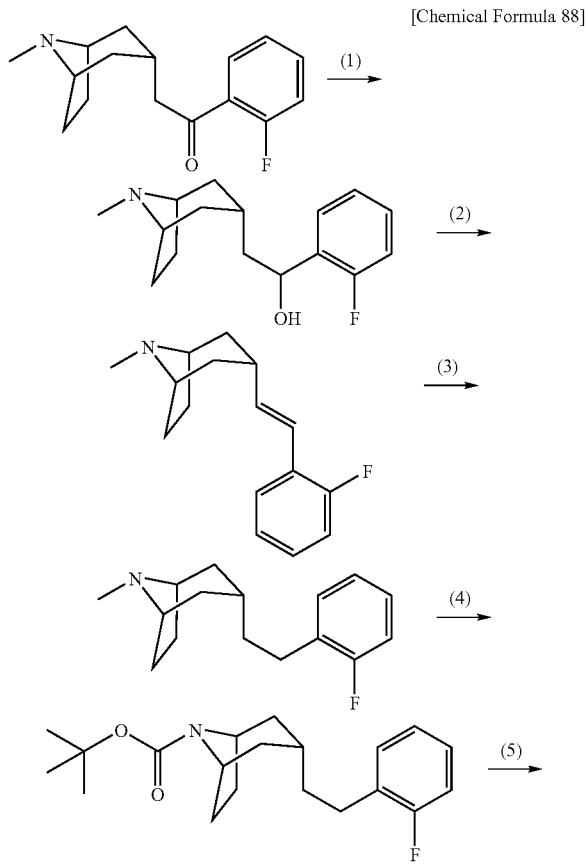

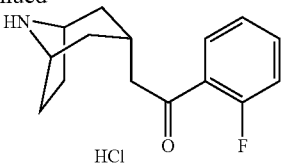

(1) (Endo)-1-(2-fluorophenyl)-2-(8-methyl-8-azabicyclo[3.2.1]oct-3-yl)ethanol The compound obtained in Production Example 40-(3) (3.03 g) was dissolved in methanol (30 ml), and sodium borohydride (527 mg) was added while stirring on ice. After stirring for 1 hour, the reaction mixture was concentrated under reduced pressure. Brine was added to the residue, and the mixture was extracted with ethyl acetate and dried over anhydrous magnesium sulfate. After filtration, the solvent was distilled off under reduced pressure to obtain the title compound (3.05 g).

$^1$H-NMR (400 MHz, CDCl$_3$); δ 1.33-1.40 (m, 1H), 1.43-1.50 (m, 1H), 1.59-1.72 (m, 2H), 1.78-1.88 (m, 1H), 1.92-2.28 (m, 12H), 2.25 (s, 3H), 3.08-3.15 (m, 2H), 5.03-5.09 (m, 1H), 6.98-7.14 (m, 1H), 7.15 (td, J=7.6, 1.2 Hz, 1H), 7.21-7.28 (m, 1H), 7.48 (td, J=7.6, 2.0 Hz, 1H).

(2) (Endo)-3-[(E)-2-(2-fluorophenyl)-vinyl]-8-methyl-8-azabicyclo[3.2.1]octane The compound obtained in Production Example 42-(1) (3.05 g) was dissolved in toluene (70 ml), and then para-toluenesulfonic acid monohydrate (3.31 g) was added and a Dean-Stark trap was used for heating to reflux for 3 hours and 30 minutes. An aqueous solution of potassium carbonate was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (2.40 g).

$^1$H-NMR (400 MHz, CDCl$_3$); δ 1.68-1.80 (m, 4H), 1.93-2.06 (m, 2H), 2.19-2.30 (m, 2H), 2.28 (s, 3H), 2.64 (t, J=8.0 Hz, 1H), 3.10-3.16 (m, 2H), 6.51-6.60 (m, 2H), 6.98-7.10 (m, 2H), 7.13-7.20 (m, 1H), 7.41 (td, J=7.6, 1.6 Hz, 1H).

(3) (Endo)-3-[2-(2-fluorophenyl)-ethyl]-8-methyl-8-azabicyclo[3.2.1]octane

The compound obtained in Production Example 42-(2) (1.84 g) was dissolved in ethanol (45 ml), and then 20% palladium hydroxide on carbon (50% wet) (130 mg) was added and the mixture was stirred at room temperature for 3 hours and 30 minutes under a hydrogen atmosphere (0.3 MPa). After filtering the reaction mixture, the solvent was distilled off under reduced pressure to obtain the title compound (1.84 g).

$^1$H-NMR (400 MHz, CDCl$_3$); δ 1.37-1.45 (m, 2H), 1.62-1.79 (m, 5H), 1.96-2.08 (m, 2H), 2.14-2.22 (m, 2H), 2.28 (s, 3H), 2.59-2.66 (m, 2H), 3.10-3.18 (m, 2H), 6.97-7.07 (m, 2H), 7.12-7.19 (m, 2H).

(4) (Endo)-3-[2-(2-fluorophenyl)-ethyl]-8-azabicyclo[3.2.1]octane-8-carboxylic acid tert-butyl ester The title compound (3.89 g) was obtained from the compound obtained in Production Example 42-(3) (3.53 g) by the method similar to Production Example 18-(2).

$^1$H-NMR (400 MHz, CDCl$_3$); δ 1.25-1.31 (m, 2H), 1.45 (s, 9H), 1.55-1.78 (m, 5H), 1.90-2.02 (m, 2H), 2.19-2.28 (m, 2H), 2.60-2.67 (m, 2H), 4.14-4.22 (m, 2H), 6.96-7.07 (m, 2H), 7.12-7.19 (m, 2H).

(5) (Endo)-3-[2-(2-fluorophenyl)-ethyl]-8-azabicyclo[3.2.1]octane hydrochloride The compound obtained in Production Example 42-(4) (3.89 g) was dissolved in ethyl acetate (10 ml), and then 4N HCl in ethyl acetate (29.3 ml) was added and the mixture was stirred at room temperature for 3 hours and 30 minutes. The reaction mixture was concentrated under reduced pressure and diethyl ether was added to the residue to produce a solid. The solid was collected by filtration to obtain the title compound (3.16 g).

$^1$H-NMR (400 MHz, DMSO-d$_6$); δ 1.59-1.80 (m, 5H), 1.85-2.03 (m, 4H), 2.12-2.21 (m, 2H), 2.59-2.65 (m, 2H), 3.88 (br s, 2H), 7.08-7.16 (m, 2H), 7.20-7.33 (m, 2H), 8.80 (br s, 2H).

Production Example 43

(Endo)-3-[(E)-2-(2-fluorophenyl)-vinyl]-8-azabicyclo[3.2.1]octane hydrochloride

[Chemical Formula 89]

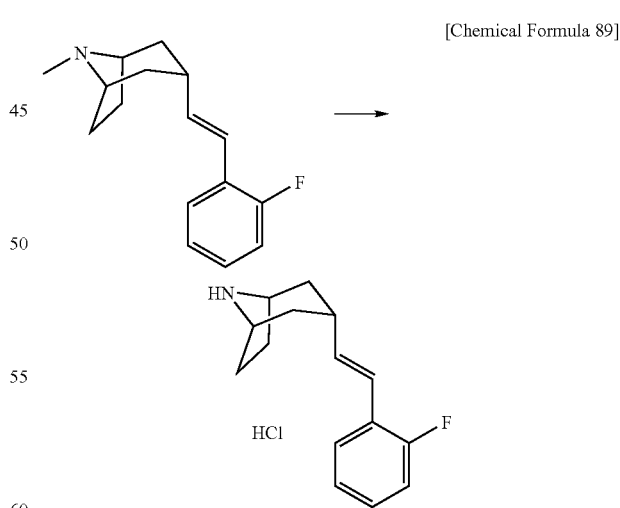

The title compound (1.53 g) was obtained from the compound obtained in Production Example 42-(2) (2.40 g) by the method similar to Production Example 5-(2).

$^1$H-NMR (400 MHz, DMSO-d$_6$); δ 1.89-2.03 (m, 6H), 2.24-2.54 (m, 2H), 2.76 (t, J=7.6 Hz, 1H), 3.91-3.98 (m, 2H), 6.60-6.70 (m, 2H), 7.14-7.22 (m, 2H), 7.25-7.32 (m, 1H), 7.63 (t, J=7.6, 1H), 8.70-9.15 (m, 2H).

Production Example 44

(Endo)-3-[2-(2-methylphenyl)ethyl]-8-azabicyclo[3.2.1]octane hydrochloride

[Chemical Formula 90]

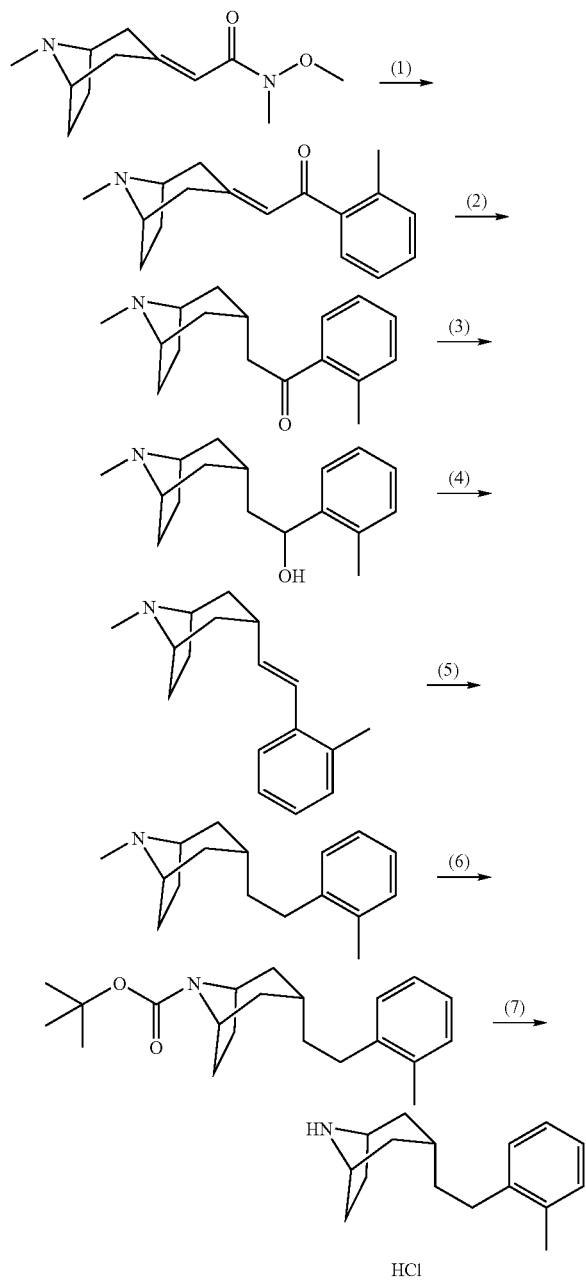

(1) 2-(8-Methyl-8-azabicyclo[3.2.1]oct-3-ylidene)-1-(2-methylphenyl)ethanone

The compound obtained in Production Example 40-(1) (5.00 g) was dissolved in tetrahydrofuran (60 ml), and then 2-methyl-phenylmagnesium bromide (1M solution in tetrahydrofuran, 33.6 ml) was added dropwise while stirring on ice. The dropwise addition was followed by stirring for 2 hours. A saturated aqueous solution of ammonium chloride was added to the reaction mixture and stirring was continued for a while. An aqueous solution of potassium carbonate was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (3.54 g).

(2) (Endo)-2-(8-methyl-8-azabicyclo[3.2.1]oct-3-yl)-1-(2-methylphenyl)ethanone

The title compound (3.56 g) was obtained from the compound obtained in Production Example 44-(1) (3.54 g) by the method similar to Production Example 40-(3).

(3) (Endo)-2-(8-methyl-8-azabicyclo[3.2.1]oct-3-yl)-1-(2-methylphenyl)ethanol

The title compound (3.56 g) was obtained from the compound obtained in Production Example 44-(2) by the method similar to Production Example 42-(1).

(4) (Endo)-3-[(E)-2-(2-methylphenyl)vinyl]-8-methyl-8-azabicyclo[3.2.1]octane

The title compound (2.44 g) was obtained from the compound obtained in Production Example 44-(3) by the method similar to Production Example 42-(2).
$^1$H-NMR (400 MHz, CDCl$_3$); δ 1.68-1.80 (m, 4H), 1.96-2.08 (m, 2H), 2.22-2.36 (m, 2H), 2.3.0 (s, 3H), 2.33 (s, 3H), 2.62-2.70 (m, 1H), 3.14-3.19 (m, 2H), 6.33 (dd, J=16.0, 6.4 Hz, 1H), 6.59 (dd, J=16.0, 2.0 Hz, 1H), 7.09-7.19 (m, 3H), 7.38 (d, J=7.2 Hz, 1H).

(5) (Endo)-8-methyl-3-[2-(2-methylphenyl)ethyl]-8-azabicyclo[3.2.1]octane

The title compound (2.44 g) was obtained from the compound obtained in Production Example 44-(4) (2.44 g) by the method similar to Production Example 42-(3).
$^1$H-NMR (400 MHz, CDCl$_3$); δ 1.39-1.45 (m, 2H), 1.61-1.80 (m, 5H), 1.99-2.06 (m, 2H), 2.16-2.24 (m, 2H), 2.28 (s, 3H), 2.31 (s, 3H), 2.55-2.61 (m, 2H), 3.11-3.16 (m, 2H), 7.05-7.16 (m, 4H).

(6) (Endo)-3-[2-(2-methylphenyl)ethyl]-8-azabicyclo[3.2.1]octane-8-carboxylic acid tert-butyl ester The title compound (1.99 g) was obtained from the compound obtained in Production Example 44-(5) (2.44 g) by the method similar to Production Example 18-(2).
$^1$H-NMR (400 MHz, CDCl$_3$); δ 1.26-1.32 (m, 2H), 1.46 (s, 9H), 1.61-1.73 (m, 5H), 1.93-2.02 (m, 2H), 2.22-2.30 (m, 2H), 2.30 (s, 3H), 4.16-4.22 (m, 2H), 7.07-7.15 (m, 4H).

(7) (Endo)-3-[2-(2-methylphenyl)ethyl]-8-azabicyclo[3.2.1]octane hydrochloride

The title compound (1.45 g) was obtained from the compound obtained in Production Example 44-(6) (1.99 g) by the method similar to Production Example 42-(5).

¹H-NMR (400 MHz, CD₃OD); δ 1.76-1.92 (m, 5H), 2.04-2.16 (m, 4H), 2.22-2.32 (m, 2H), 2.31 (s, 3H), 2.64-2.69 (m, 2H), 3.96-4.03 (m, 2H), 7.03-7.13 (m, 4H).

Production Example 45

(Endo)-3-[2-(2-methoxyphenyl)ethyl]-8-azabicyclo[3.2.1]octane hydrochloride

[Chemical Formula 91]

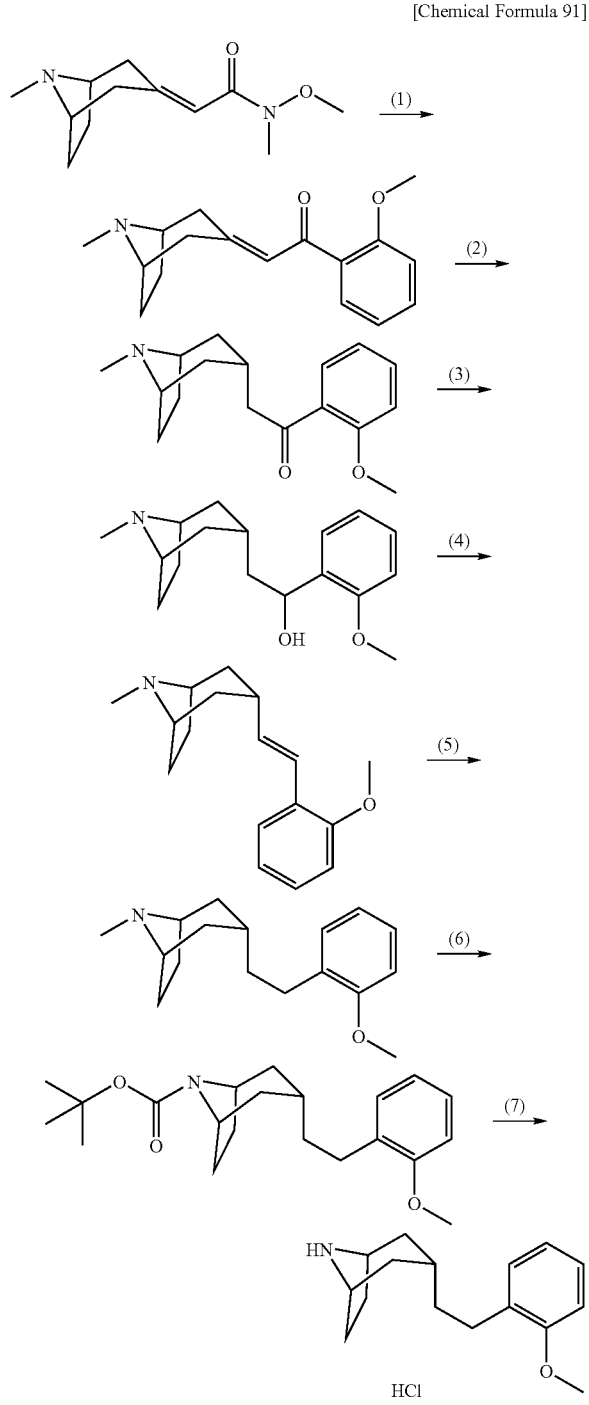

(1) 1-(2-Methoxyphenyl)-2-(8-methyl-8-azabicyclo[3.2.1]oct-3-ylidene)ethanone

The title compound (5.55 g) was obtained from the compound obtained in Production Example 40-(1) (5.00 g) and 2-methoxy-phenylmagnesium bromide, by the method similar to Production Example 44-(1).

(2) (Endo)-1-(2-methoxyphenyl)-2-(8-methyl-8-azabicyclo[3.2.1]oct-3-yl)ethanone

The title compound (4.94 g) was obtained from the compound obtained in Production Example 45-(1) (5.55 g) by the method similar to Production Example 40-(3).

(3) (Endo)-1-(2-methoxyphenyl)-2-(8-methyl-8-azabicyclo[3.2.1]oct-3-yl)ethanol

The title compound (4.94 g) was obtained from the compound obtained in Production Example 45-(2) by the method similar to Production Example 42-(1).

(4) (Endo)-3-[(E)-2-(2-methoxyphenyl)vinyl]-8-methyl-8-azabicyclo[3.2.1]octane

The title compound (2.04 g) was obtained from the compound obtained in Production Example 45-(3) by the method similar to Production Example 42-(2).
¹H-NMR (400 MHz, CDCl₃); δ 1.68-1.80 (m, 4H), 1.93-2.06 (m, 2H), 2.20-2.28 (m, 2H), 2.29 (s, 3H), 2.61-2.69 (m, 1H), 3.12-3.17 (m, 2H), 3.84 (s, 3H), 6.51-6.60 (m, 2H), 6.46 (dd, J=16.0, 6.8 Hz, 1H), 6.72 (dd, J=16.0, 2.0 Hz, 1H), 6.84-6.95 (m, 2H), 7.16-7.22 (m, 1H), 7.40 (dd, J=7.6, 2.0 Hz, 1H).

(5) (Endo)-3-[2-(2-methoxyphenyl)ethyl]-8-methyl-8-azabicyclo[3.2.1]octane

The title compound (2.04 g) was obtained from the compound obtained in Production Example 45-(4) (2.04 g) by the method similar to Production Example 42-(3).
¹H-NMR (400 MHz, CDCl₃); δ 1.42-1.48 (m, 2H), 1.65-1.76 (m, 5H), 1.96-2.06 (m, 2H), 2.12-2.20 (m, 2H), 2.29 (s, 3H), 2.56-2.62 (m, 2H), 3.10-3.16 (m, 2H), 3.83 (s, 3H), 6.82-6.90 (m, 2H), 7.11 (dd, J=7.6, 1.6 Hz, 1H), 7.17 (td, J=7.6, 1.6 Hz, 1H).

(6) (Endo)-3-[2-(2-methoxyphenyl)ethyl]-8-azabicyclo[3.2.1]octane-8-carboxylic acid tert-butyl ester The title compound (1.80 g) was obtained from the compound obtained in Production Example 45-(5) (2.04 g) by the method similar to Production Example 18-(2).
¹H-NMR (400 MHz, CDCl₃); δ 1.29-1.36 (m, 2H), 1.45 (s, 9H), 1.58-1.76 (m, 3H), 1.92-1.99 (m, 2H), 2.2.12-2.30 (m, 2H), 2.60 (t, J=8.0 Hz, 2H), 3.82 (s, 3H), 4.07-4.27 (m, 2H), 6.82-6.90 (m, 2H), 7.10 (dd, J=7.6, 1.6 Hz, 1H), 7.17 (td, J=7.6, 2.0 Hz, 1H).

(7) (Endo)-3-[2-(2-methoxyphenyl)ethyl]-8-azabicyclo[3.2.1]octane hydrochloride

The title compound (1.39 g) was obtained from the compound obtained in Production Example 45-(6) (1.80 g) by the method similar to Production Example 42-(5).
¹H-NMR (400 MHz, CD₃OD); δ 1.77-1.87 (m, 5H), 2.07-2.15 (m, 4H), 2.18-2.26 (m, 2H), 2.61-2.67 (m, 2H), 3.82 (s, 3H), 3.95-4.02 (m, 2H), 6.84 (td, J=7.6, 0.8 Hz, 1H), 6.91 (dd, J=7.6, 0.8 Hz, 1H), 7.10 (dd, J=7.6, 1.6 Hz, 1H), 7.13-7.18 (m, 1H).

Production Example 46

(Endo)-N-(8-azabicyclo[3.2.1]oct-3-yl)-2-fluorobenzamide hydrochloride

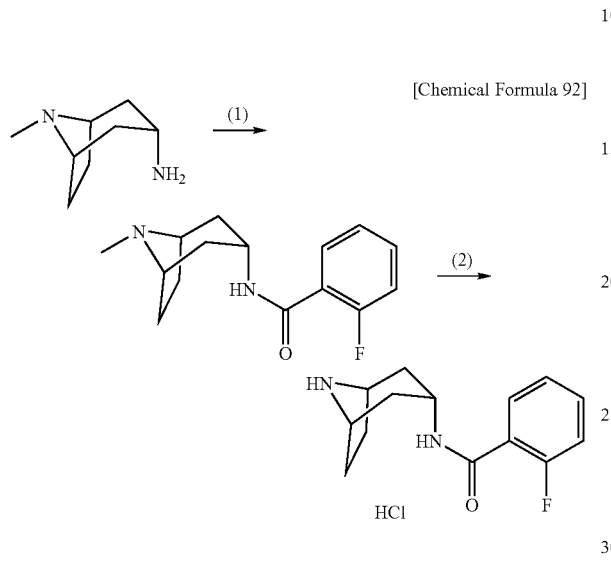

[Chemical Formula 92]

(1) (Endo)-2-fluoro-N-(8-methyl-8-azabicyclo[3.2.1]oct-3-yl)benzamide

After dissolving 8-methyl-8-azabicyclo[3.2.1]oct-3-ylamine (CAS87571-88-8) (2.00 g) and pyridine (1.62 ml) in tetrahydrofuran (30 ml), 2-fluorobenzoyl chloride (2.24 ml) was added dropwise while stirring on ice. The mixture was stirred at room temperature for 9 hours, and then an aqueous solution of potassium carbonate was added to the reaction mixture and extraction was performed with ethyl acetate. The organic layer was washed with brine and dried over anhydrous magnesium sulfate. After filtration, the solvent was distilled off under reduced pressure. The residue was purified by NH silica gel column chromatography to obtain the title compound (2.77 g).

$^1$H-NMR (400 MHz, CDCl$_3$); δ 1.72-1.92 (m, 4H), 2.12-2.21 (m, 2H), 2.26-2.34 (m, 2H), 2.31 (s, 3H), 3.14-3.25 (m, 2H), 4.29-4.36 (m, 1H), 7.09-7.16 (m, 1H), 7.24-7.35 (m, 2H), 7.44-7.51 (m, 1H), 8.09-8.15 (m, 1H).

(2) (Endo)-N-(8-azabicyclo[3.2.1]oct-3-yl)-2-fluorobenzamide hydrochloride

The compound obtained in Production Example 46-(1) (1.50 g) was dissolved in 1,2-dichloroethane (15 ml), and 1-chloroethyl chloroformate (1.23 ml) was added. After further stirring at room temperature for 45 minutes, it was heated to reflux for 3 hours. The reaction mixture was concentrated under reduced pressure, and the residue was dissolved in methanol (20 ml) and then heated to reflux for 30 minutes. The reaction mixture was concentrated under reduced pressure. Acetone was added to the residue to produce a solid, which was collected by filtration to obtain the title compound (1.52 g).

$^1$H-NMR (400 MHz, DMSO-d$_6$); δ 1.93-2.37 (m, 6H), 2.40-2.55 (m, 2H), 3.70-3.86 (m, 1H), 3.91-3.99 (m, 2H), 7.24-7.35 (m, 2H), 7.48-7.62 (m, 2H), 8.42-8.52 (m, 1H).

Production Example 47

(Endo)-(8-azabicyclo[3.2.1]oct-3-yl)-(2-fluoro-benzyl)-methylamine

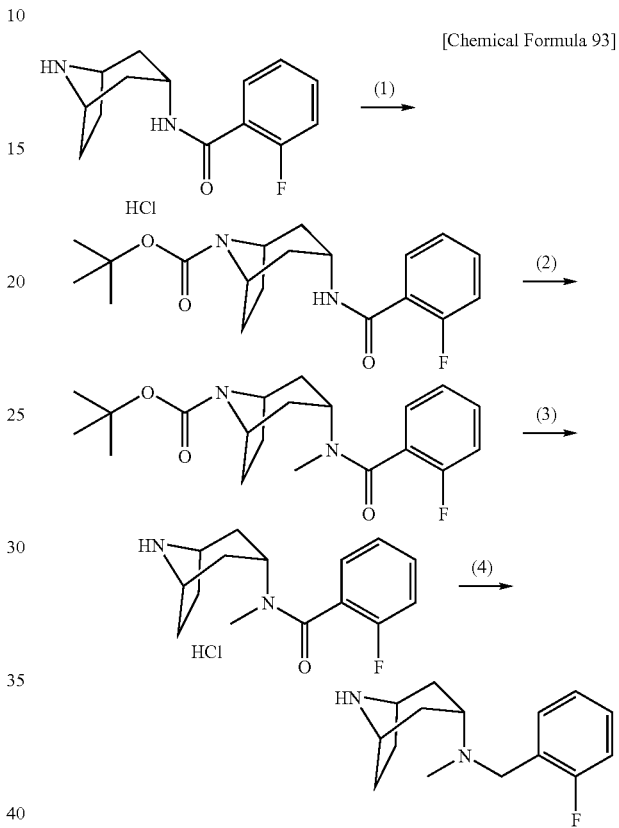

[Chemical Formula 93]

(1) (Endo)-3-(2-fluorobenzoylamino)-8-azabicyclo[3.2.1]octane-8-carboxylic acid tert-butyl ester The compound obtained in Production Example 46 (1.00 g) was suspended in tetrahydrofuran (20 ml), and then a 2N aqueous solution of sodium hydroxide (5.27 ml) and di-tert-butyl dicarbonate (919 mg) were added while stirring at room temperature. After stirring at room temperature for 21 hours, water was added to the reaction mixture and extraction was performed with ethyl acetate. The organic layer was washed with water and brine in that order and then dried over anhydrous magnesium sulfate. After filtration, the solvent was distilled off under reduced pressure and the residue was purified by silica gel column chromatography to obtain the title compound (637 mg).

$^1$H-NMR (400 MHz, CDCl$_3$); δ 1.48 (s, 9H), 1.73-1.86 (m, 2H), 1.89-1.98 (m, 2H), 2.08-2.15 (m, 2H), 2.18-2.42 (m, 2H), 4.16-4.44 (m, 3H), 7.08-7.15 (m, 1H), 7.24-7.38 (m, 2H), 7.43-7.51 (m, 1H), 8.08-8.14 (m, 1H).

(2) (Endo)-3-[(2-fluorobenzoyl)methylamino]-8-azabicyclo[3.2.1]octane-8-carboxylic acid tert-butyl ester The compound obtained in Production Example 47-(1) (508 mg) was dissolved in N,N-dimethylformamide (5 ml), and then methyl iodide (0.34 ml) and sodium hydride (60% in oil) (110 mg) were added and the mixture was stirred at room temperature for 45 minutes. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (508 mg).

$^1$H-NMR (400 MHz, CDCl$_3$); δ 1.16-2.51 (m, 17H), 2.73-2.98 (m, 3H), 3.47-4.58 (m, 3H), 7.03-7.10 (m, 1H), 7.13-7.19 (m, 1H), 7.23-7.39 (m, 2H).

(3) (Endo)-N-(8-azabicyclo[3.2.1]oct-3-yl)-2-fluoro-N-methylbenzamide hydrochloride The title compound (418 mg) was obtained from the compound obtained in Production Example 47-(2) (508 mg) by the method similar to Production Example 19-(3).

$^1$H-NMR (400 MHz, DMSO-d$_6$); δ 1.62-2.40 (m, 8H), 2.68-2.92 (m, 3H), 3.80-4.94 (m, 3H), 7.20-7.52 (m, 4H), 8.62-9.24 (m, 2H).

(4) (Endo)-(8-azabicyclo[3.2.1]oct-3-yl)-(2-fluorobenzyl)methyl]amine

Tetrahydrofuran (3 ml) was cooled on ice, and then lithium aluminum hydride (109 mg) was added in gradual small portions. A suspension of the compound obtained in Production Example 47-(3) (285 mg) in tetrahydrofuran was then gradually added. After stirring for 3 hours on ice, water (0.1 ml), a 5N aqueous solution of sodium hydroxide (0.1 ml) and water (0.3 ml) were added to the reaction mixture in that order, and stirring was continued for 30 minutes on ice. The reaction mixture was filtered with Celite, and the filtrate was concentrated under reduced pressure. The residue was purified by NH silica gel column chromatography to obtain the title compound (123 mg).

$^1$H-NMR (400 MHz, CDCl$_3$); δ 1.58-2.12 (m, 8H), 2.16 (s, 3H), 2.62-2.68 (m, 1H), 3.46-3.59 (m, 2H), 3.54 (s, 2H), 3.64-3.84 (m, 1H), 7.00 (t, J=9.2 Hz, 1H), 7.10 (t, J=7.2 Hz, 1H), 7.16-7.24 (m, 1H), 7.35-7.45 (m, 1H).

Production Example 48

(Exo)-3-(2-fluorophenoxymethyl)-8-azabicyclo[3.2.1]octane hydrochloride

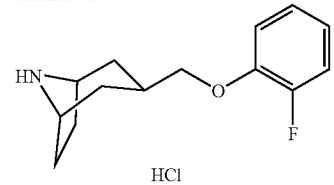

(1) (Exo)-3-(2-fluorophenoxymethyl)-8-azabicyclo[3.2.1]octane-8-carboxylic acid tert-butyl ester After dissolving (exo)-3-hydroxymethyl-8-azabicyclo[3.2.1]octane-8-carboxylic acid tert-butyl ester (CAS 273207-58-2) (974 mg), triphenylphosphine (1.17 g) and 2-fluorophenol (0.399 ml) in tetrahydrofuran (30 ml), diisopropyl azocarboxylate (1.1 ml) was slowly added while stirring on ice. The mixture was stirred overnight at room temperature. The reaction mixture was concentrated under reduced pressure, and the residue was purified by NH silica gel column chromatography.

The title compound (1.19 g) was thus obtained.

$^1$H-NMR (400 MHz, CDCl$_3$); δ 1.47 (s, 9H), 1.49-1.73 (m, 6H), 1.98-2.00 (m, 2H), 2.36-2.45 (m, 1H), 3.79-3.81 (m, 2H), 4.21-4.30 (m, 2H), 6.85-6.95 (m, 2H), 7.01-7.09 (m, 2H).

(2) (Exo)-3-(2-fluorophenoxymethyl)-8-azabicyclo[3.2.1]octane hydrochloride

The compound obtained in Production Example 48-(1) (1.19 g) was dissolved in ethyl acetate (5 ml), and then 4N HCl in ethyl acetate (10 ml) was added. The mixture was stirred at room temperature for 1 hour and then at 45° C. for 30 minutes. The reaction mixture was then concentrated under reduced pressure, diethyl ether was added to the residue, and the solid was collected by filtration to obtain the title compound (930 mg).

$^1$H-NMR (400 MHz, CD$_3$OD); δ 1.77-1.84 (m, 2H), 1.95-2.01 (m, 2H), 2.03-2.18 (m, 4H), 2.39-2.48 (m, 1H), 3.93-3.94 (m, 2H), 4.07-4.09 (m, 2H), 6.89-6.95 (m, 1H), 7.05-7.10 (m, 3H).

Production Example 49

(Exo)-3-(2-methylphenoxymethyl)-8-azabicyclo[3.2.1]octane hydrochloride

[Chemical Formula 94]

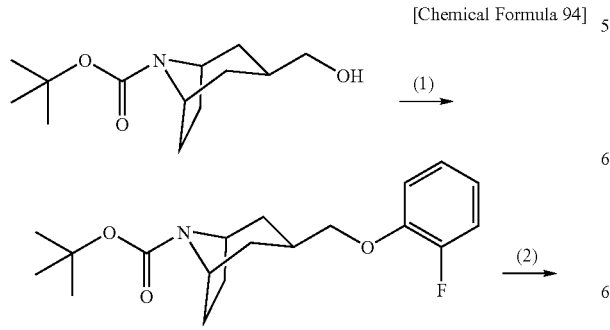

[Chemical Formula 95]

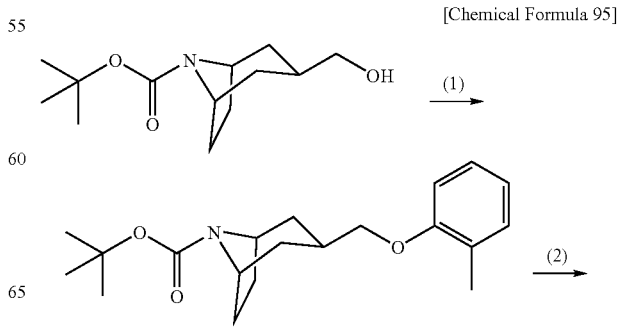

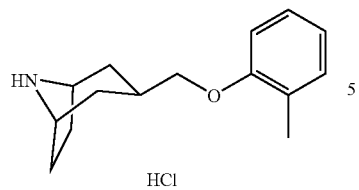

(1) (Exo)-3-(2-methylphenoxymethyl)-8-azabicyclo[3.2.1]octane-8-carboxylic acid tert-butyl ester The title compound (574 mg) was obtained from (exo)-3-hydroxymethyl-8-azabicyclo[3.2.1]octane-8-carboxylic acid tert-butyl ester (CAS 273207-58-2) (800 mg) and 2-methylphenol by the method similar to Production Example 48-(1).

$^1$H-NMR (400 MHz, CDCl$_3$); δ 1.47 (s, 9H), 1.62-1.73 (m, 6H), 1.97-2.00 (s, 2H), 2.20 (s, 3H), 2.33-2.42 (m, 1H), 3.75 (bs, 2H), 4.20-4.30 (m, 2H), 6.74-6.77 (m, 1H), 6.81-6.85 (m, 1H), 7.10-7.14 (m, 2H).

(2) (Exo)-3-(2-methylphenoxymethyl)-8-azabicyclo[3.2.1]octane hydrochloride

The title compound (422 mg) was obtained from the compound obtained in Production Example 49-(1) (574 mg) by the method similar to Production Example 48-(2).

$^1$H-NMR (400 MHz, CD$_3$OD); δ 1.75-1.82 (m, 2H), 1.96-2.16 (m, 6H), 2.20 (s, 3H), 2.40-2.48 (m, 1H), 3.85-3.87 (m, 2H), 4.08 (s, 2H), 6.80-6.86 (m, 2H), 7.09-7.13 (m, 2H).

Production Example 50

3β-methoxymethyl-3α-(2-methylbenzyloxy)-8-azabicyclo[3.2.1]octane hydrochloride

[Chemical Formula 96]

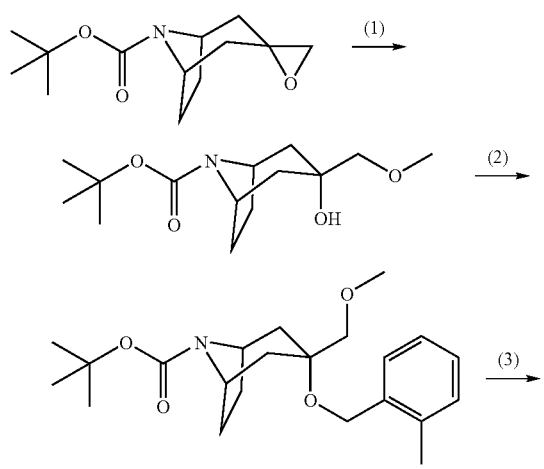

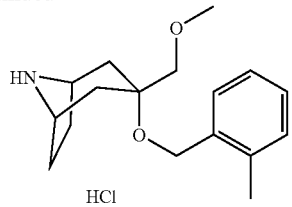

(1) 3α-hydroxy-3β-methoxymethyl-8-azabicyclo[3.2.1]octane-8-carboxylic acid tert-butyl ester After dissolving spiro[nortropane-3,2'-oxirane]-8-carboxylic acid tert-butyl ester (CAS 918441-60-8) (4.21 g) in methanol (50 ml), sodium methoxide (28% solution in methanol, 3.72 ml) was added and the mixture was heated to reflux for 4 hours and 30 minutes and then stirred at 70° C. for 11 hours. The reaction mixture was concentrated under reduced pressure, water was added to the residue, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (3.33 g).

$^1$H-NMR (400 MHz, CDCl$_3$); δ 1.46 (s, 9H), 1.61-1.68 (m, 2H), 1.78-1.94 (m, 4H), 2.12-2.18 (m, 2H), 2.31-2.35 (m, 1H), 3.03 (s, 2H), 3.36 (s, 3H), 4.17-4.23 (m, 2H).

(2) 3β-methoxymethyl-3α-(2-methylbenzyloxy)-8-azabicyclo[3.2.1]octane-8-carboxylic acid tert-butyl ester The compound obtained in Production Example 50-(1) (1.50 g) was dissolved in 1-methyl-2-pyrrolidinone (15 ml), and then 2-methylbenzyl bromide (0.89 ml), benzyltriethylammonium iodide (88 mg) and sodium hydride (60% in oil) (288 mg) were added and the mixture was stirred at room temperature for 17 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (860 mg).

$^1$H-NMR (400 MHz, CDCl$_3$); δ 1.47 (s, 9H), 1.83-2.07 (m, 8H), 2.31 (s, 3H), 3.18-3.32 (m, 2H), 3.31 (s, 3H), 4.10-4.27 (m, 2H), 4.48 (s, 2H), 7.12-7.22 (m, 3H), 7.38-7.44 (m, 1H).

(3) 3β-methoxymethyl-3α-(2-methylbenzyloxy)-8-azabicyclo[3.2.1]octane hydrochloride The title compound (734 mg) was obtained from the compound obtained in Production Example 50-(2) (860 mg) by the method similar to Production Example 42-(5).

¹H-NMR (400 MHz, CD₃OD); δ 1.93-2.08 (m, 4H), 2.23-2.30 (m, 4H), 2.34 (s, 3H), 3.35 (s, 3H), 3.39 (s, 2H), 4.00-4.05 (m, 2H), 4.53 (s, 2H), 7.12-7.20 (m, 3H), 7.32-7.36 (m, 1H).

Production Example 51

(Endo)-3-(2-fluorobenzyloxy)-3-methoxymethyl-8-azabicyclo[3.2.1]octane hydrochloride

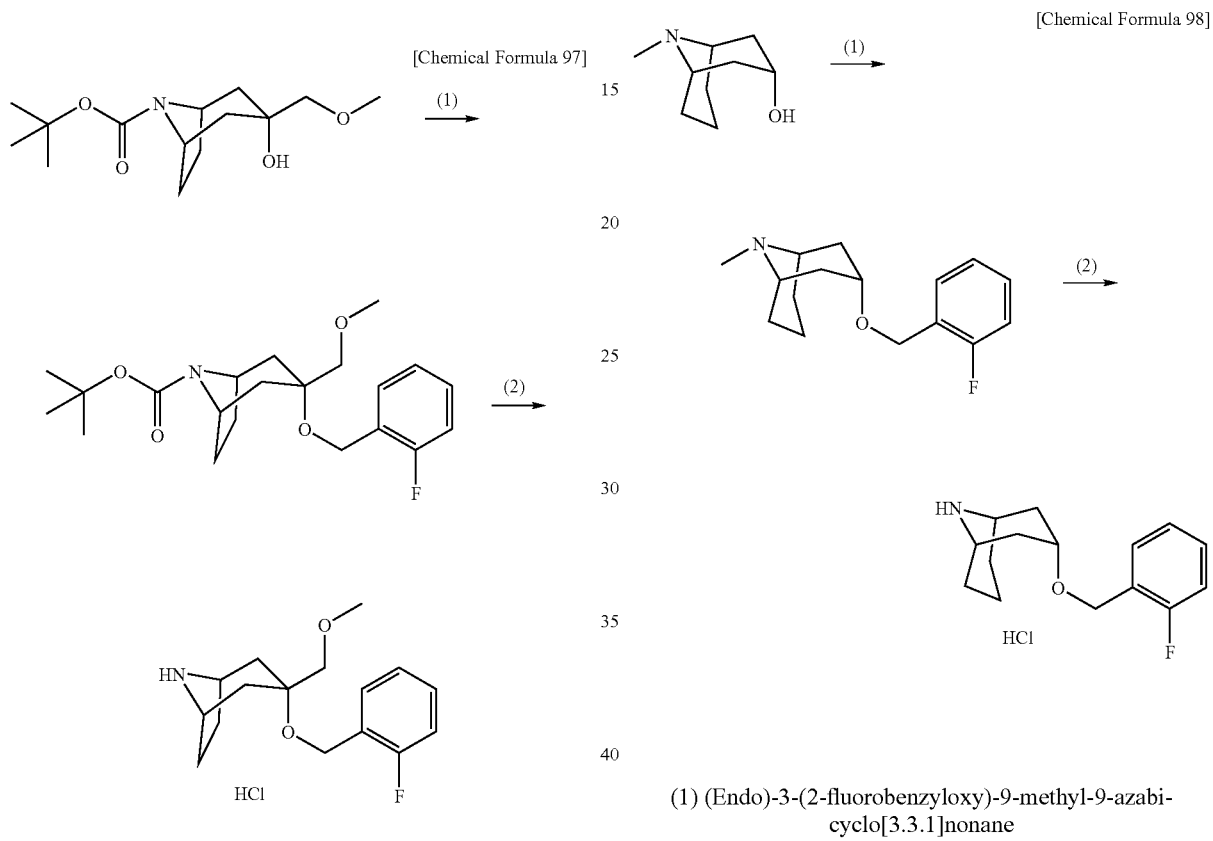

(1) 3α-(2-fluorobenzyloxy)-3β-methoxymethyl-8-azabicyclo[3.2.1]octane-8-carboxylic acid tert-butyl ester The title compound (1.34 g) was obtained from the compound obtained in Production Example 50-(1) (1.50 g) and 2-fluorobenzyl bromide by the method similar to Production Example 50-(2).

¹H-NMR (400 MHz, CDCl₃); δ 1.47 (s, 9H), 1.83-2.05 (m, 8H), 3.24 (s, 2H), 3.32 (s, 3H), 4.15-4.23 (m, 2H), 4.56 (s, 2H), 6.98-7.04 (m, 1H), 7.11-7.16 (m, 1H), 7.21-7.27 (m, 1H), 7.46-7.51 (m, 1H).

(2) 3α-(2-fluorobenzyloxy)-3β-methoxymethyl-8-azabicyclo[3.2.1]octane hydrochloride The title compound (1.02 g) was obtained from the compound obtained in Production Example 51-(1) (1.34 g) by the method similar to Production Example 42-(5).

¹H-NMR (400 MHz, CD₃OD); δ 1.93-2.08 (m, 4H), 2.20-2.34 (m, 4H), 3.36 (s, 3H), 3.39 (s, 2H), 4.00-4.05 (m, 2H), 4.59 (s, 2H), 7.05-7.11 (m, 1H), 7.17 (td, J=7.6, 1.2 Hz, 1H), 7.29-7.36 (m, 1H), 7.46 (td, J=7.6, 1.6 Hz, 1H).

Production Example 52

(Endo)-3-(2-fluorobenzyloxy)-9-azabicyclo[3.3.1]nonane hydrochloride (1) (Endo)-3-(2-fluorobenzyloxy)-9-methyl-9-azabicyclo[3.3.1]nonane The title compound (2.96 g) was obtained from (endo)-9-methyl-9-azabicyclo[3.3.1]nonan-3-ol (CAS 2038-40-6) (3.00 g) and 2-fluorobenzyl bromide by the method similar to Production Example 9-(1).

¹H-NMR (400 MHz, CDCl₃); δ 1.15-1.22 (m, 2H), 1.37-1.46 (m, 1H), 1.49-1.57 (m, 2H), 1.89-2.00 (m, 2H), 2.25-2.47 (m, 3H), 2.45 (s, 3H), 2.93-3.00 (m, 2H), 3.81-3.88 (m, 1H), 4.59 (s, 2H), 6.98-7.04 (m, 1H), 7.09-7.14 (m, 1H), 7.20-7.27 (m, 1H), 7.41-7.47 (m, 1H).

(2) (Endo)-3-(2-fluorobenzyloxy)-9-azabicyclo[3.3.1]nonane hydrochloride

The title compound (1.70 g) was obtained from the compound obtained in Production Example 52-(1) (2.96 g) by the method similar to Production Example 5-(2).

¹H-NMR (400 MHz, DMSO-d₆); δ 1.30-1.39 (m, 1H), 1.55-1.64 (m, 2H), 1.77-1.95 (m, 4H), 2.29-2.39 (m, 2H), 2.41-2.55 (m, 1H), 3.55-3.62 (m, 2H), 3.78-3.84 (m, 1H), 4.55 (s, 2H), 7.15-7.24 (m, 2H), 7.33-7.40 (m, 1H), 7.42-7.48 (m, 1H), 8.85-9.10 (m, 2H).

Production Example 53

(Endo)-3-[3-(2-fluorobenzyloxy)-8-azabicyclo[3.2.1]oct-8-yl]propan-1-ol

[Chemical Formula 99]

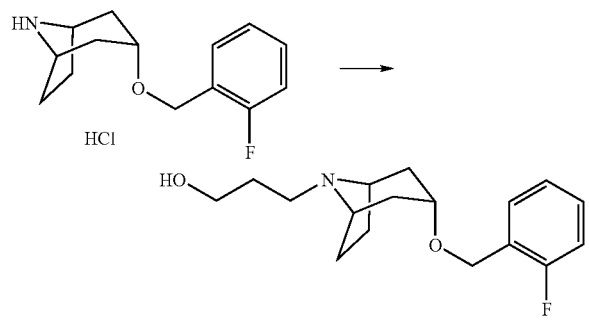

A mixture of the compound obtained in Production Example 5 (1.0 g), 3-bromo-1-propanol (0.40 ml), anhydrous potassium carbonate (1.12 g) and N,N-dimethylformamide (10 ml) was stirred at room temperature for 6 days. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (527 mg).

$^1$H-NMR (400 MHz, CDCl$_3$); δ 1.64-1.70 (m, 2H), 1.83-2.11 (m, 8H), 2.64 (t, J=6.0 Hz, 2H), 3.24-3.32 (m, 2H), 3.60-3.65 (m, 1H), 3.87 (t, J=5.2 Hz, 2H), 4.50 (s, 2H), 6.99-7.05 (m, 1H), 7.11-7.16 (m, 1H), 7.22-7.28 (m, 1H), 7.39-7.45 (m, 1H)

Production Example 54

(Endo)-3-(3-fluoromethylbenzyloxy)-8-azabicyclo[3.2.1]octane hydrochloride

[Chemical Formula 100]

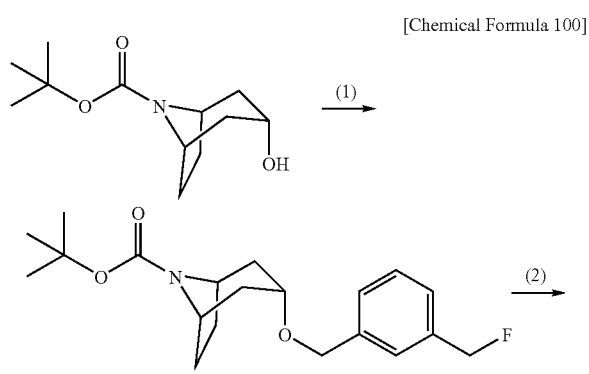

-continued

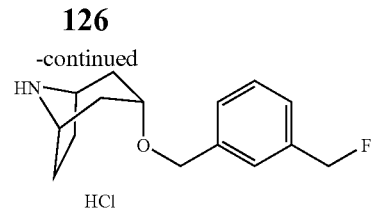

(1) (Endo)-3-(3-fluoromethylbenzyloxy)-8-azabicyclo[3.2.1]octane-8'-carboxylic acid tert-butyl ester The title compound (2.45 g) was obtained from (endo)-3-hydroxy-8-azabicyclo[3.2.1]octane-8-carboxylic acid tert-butyl ester (CAS 143557-91-9) (3.18 g) and 3-fluoromethylbenzyl bromide (CAS 612057-33-7) by the method similar to Production Example 28-(1).

$^1$H-NMR (400 MHz, CDCl$_3$); δ 1.47 (s, 9H), 1.87-2.18 (m, 8H), 3.70-3.74 (m, 1H), 4.09-4.26 (m, 2H), 4.47-4.55 (m, 2H), 5.38 (d, J=48.0 Hz, 2H), 7.25-7.40 (m, 4H).

(2) (Endo)-3-(3-fluoromethylbenzyloxy)-8-azabicyclo[3.2.1]octane hydrochloride

The title compound (1.80 g) was obtained from the compound obtained in Production Example 54-(1) (2.45 g) by the method similar to Production Example 19-(3).

$^1$H-NMR (400 MHz, CD$_3$OD); δ 2.01-2.48 (m, 8H), 3.76-3.81 (m, 1H), 3.98-4.03 (m, 2H), 4.55 (s, 2H), 5.36 (d, J=48.0 Hz, 2H), 7.29-7.40 (m, 4H).

Production Example 55

(Exo)-3-(2-methylbenzyloxy)-8-azabicyclo[3.2.1]octane hydrochloride

[Chemical Formula 101]

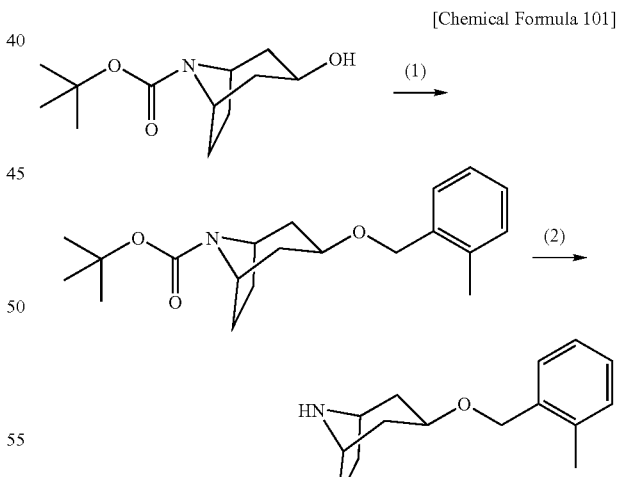

(1) (Exo)-3-(2-methylbenzyloxy)-8-azabicyclo[3.2.1]octane-8-carboxylic acid tert-butyl ester The title compound (1.74 g) was obtained from (exo)-3-hydroxy-8-azabicyclo[3.2.1]octane-8-carboxylic acid tert-butyl ester (CAS 194222-05-4) (1.20 g) and 2-methylbenzyl bromide by the method similar to Production Example 28-(1).

$^1$H-NMR (400 MHz, CDCl$_3$); δ 1.46 (s, 9H), 1.54-1.76 (m, 4H), 1.91-2.06 (m, 4H), 2.32 (s, 3H), 3.80-3.90 (m, 1H), 4.04-4.35 (m, 2H), 4.44-4.56 (m, 2H), 7.14-7.22 (m, 3H), 7.28-7.32 (m, 1H).

(2) (Exo)-3-(2-methylbenzyloxy)-8-azabicyclo[3.2.1]octane hydrochloride

The title compound (1.26 g) was obtained from the compound obtained in Production Example 55-(1) (1.74 g) by the method similar to Production Example 19-(3).

$^1$H-NMR (400 MHz, CD$_3$OD); δ 1.69-1.78 (m, 2H), 1.96-2.14 (m, 4H), 2.23-2.31 (m, 2H), 2.32 (s, 3H), 3.88-3.98 (m, 1H), 4.04-4.09 (m, 2H), 4.56 (s, 2H), 7.11-7.21 (m, 3H), 7.27 (d, J=7.2 Hz, 1H).

Production Example 56

(Exo)-3-(2-fluorobenzyloxy)-8-azabicyclo[3.2.1]octane hydrochloride

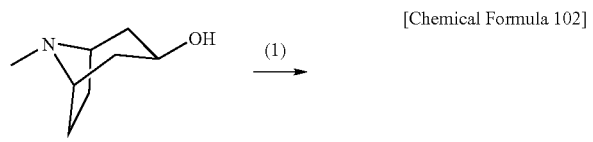

[Chemical Formula 102]

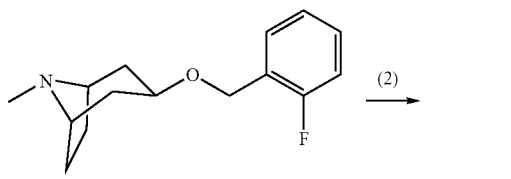

(1) (Exo)-3-(2-fluorobenzyloxy)-8-methyl-8-azabicyclo[3.2.1]octane

After dissolving (exo)-3-hydroxy-8-methyl-8-azabicyclo[3.2.1]octane (CAS 135-97-7) (1.50 g) in N,N-dimethylformamide (20 ml), sodium hydride (60% in oil) (551 mg) was added and the mixture was stirred at 70° C. for 1 hour. The reaction mixture was allowed to cool, and 2-fluorobenzyl bromide (1.53 ml) was added. Stirring was then carried out at 70° C. for 1 hour and then at room temperature overnight. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (722 mg).

$^1$H-NMR (400 MHz, CDCl$_3$); δ 1.48-1.55 (m, 2H), 1.68-1.76 (m, 2H), 1.83-1.89 (m, 2H), 1.95-2.04 (m, 2H), 2.32 (s, 3H), 3.16-3.23 (m, 2H), 3.63-3.72 (m, 1H), 4.56 (s, 2H), 6.97-7.03 (m, 1H), 7.08-7.13 (m, 1H), 7.20-7.27 (m, 1H), 7.39-7.43 (m, 1H).

(2) (Exo)-3-(2-fluorobenzyloxy)-8-azabicyclo[3.2.1]octane hydrochloride

The compound obtained in Production Example 56-(1) (722 mg) was dissolved in 1,2-dichloroethane (5 ml), and 1-chloroethyl chloroformate (0.62 ml) was added while stirring at room temperature. After further stirring at room temperature for 15 minutes, the mixture was heated to reflux for 2 hours. The reaction mixture was concentrated under reduced pressure, and the residue was dissolved in methanol and then heated to reflux for 30 minutes. The reaction mixture was concentrated under reduced pressure, and the residue was purified by silica gel column chromatography. Acetone-diethyl ether was added to the obtained oil, and the resulting solid was collected by filtration to obtain the title compound (229 mg).

$^1$H-NMR (400 MHz, DMSO-d$_6$); δ 1.67-1.76 (m, 2H), 1.81-1.99 (m, 4H), 2.08-2.16 (m, 2H), 3.81-3.91 (m, 1H), 3.96-4.01 (m, 2H), 4.53 (s, 2H), 7.14-7.22 (m, 2H), 7.32-7.45 (m, 2H), 9.08 (br s, 2H).

Production Example 57

(Endo)-3-(2-fluorobenzyloxy)-8-azabicyclo[3.2.1]octane

[Chemical Formula 103]

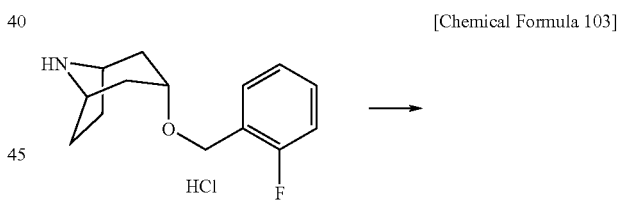

Concentrated aqueous ammonia was added to the compound obtained in Production Example 5 (2.94 g), and extraction was performed with diethyl ether. The organic layer was washed with water and brine in that order and dried over anhydrous potassium carbonate. After filtration, the solvent was distilled off under reduced pressure to obtain the title compound (2.51 g).

$^1$H-NMR (400 MHz, CDCl$_3$); δ 1.67-1.80 (m, 2H), 1.84-1.92 (m, 2H), 1.94-2.01 (m, 2H), 2.12-2.19 (m, 2H), 3.45-

3.51 (m, 2H), 3.69 (t, J=4.8 Hz, 1H), 4.51 (s, 2H), 6.99-7.05 (m, 1H), 7.11-7.16 (m, 1H), 7.22-7.28 (m, 1H), 7.42-7.47 (m, 1H).

Production Example 58

(Endo)-3-(3-fluorobenzyloxy)-8-azabicyclo[3.2.1]octane

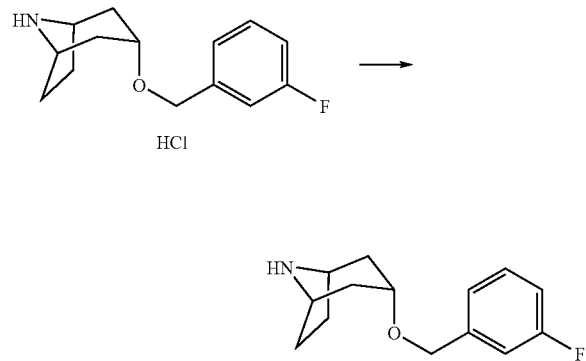

[Chemical Formula 104]

The title compound (336 mg) was obtained from the compound obtained in Production Example 2 (400 mg) by the method similar to Production Example 57.

$^1$H-NMR (400 MHz, CDCl$_3$); δ 1.67-1.80 (m, 2H), 1.84-1.99 (m, 4H), 2.13-2.20 (m, 2H), 3.46-3.52 (m, 2H), 3.65-3.69 (m, 1H), 4.46 (s, 2H), 6.92-6.98 (m, 1H), 7.03-7.10 (m, 2H), 7.26-7.32 (m, 1H).

Production Example 59

(Endo)-3-(4-fluorobenzyloxy)-8-azabicyclo[3.2.1]octane

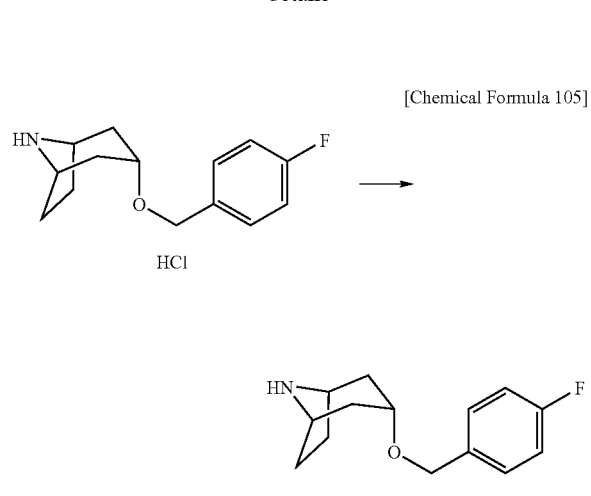

[Chemical Formula 105]

Diluted aqueous ammonia was added to the compound obtained in Production Example 1 (1.09 g), and extraction was performed with diethyl ether. The extract was dried over anhydrous magnesium sulfate. After filtration, the solvent was distilled off under reduced pressure to obtain the title compound (942 mg).

$^1$H-NMR (400 MHz, CDCl$_3$); δ 1.67-1.80 (m, 2H), 1.83-1.98 (m, 4H), 2.11-2.19 (m, 2H), 3.45-3.51 (m, 2H), 3.64-3.68 (m, 1H), 4.42 (s, 2H), 6.99-7.05 (m, 2H), 7.26-7.31 (m, 2H).

Production Example 60

(Endo)-3-(4-methylbenzyloxy)-8-azabicyclo[3.2.1]octane

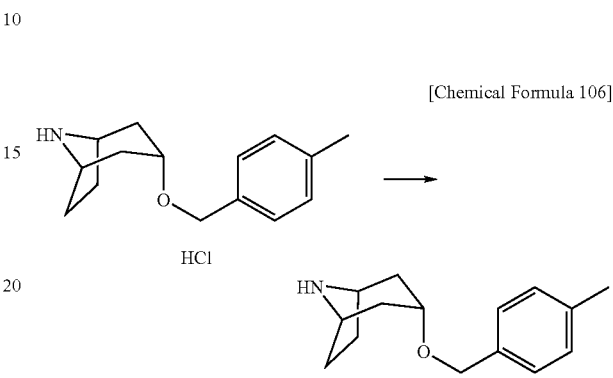

[Chemical Formula 106]

The title compound (919 mg) was obtained from the compound obtained in Production Example 28 (1.1 g) by the method similar to Production Example 59.

$^1$H-NMR (400 MHz, CDCl$_3$); δ 1.69-1.75 (m 2H), 1.82-1.88 (m, 2H), 1.93-1.98 (m, 2H), 2.15-2.20 (m, 2H), 2.34 (m, 3H), 3.47-3.48 (m, 2H), 3.64-3.67 (m, 1H), 4.42 (s, 2H), 7.14-7.16 (m, 2H), 7.21-7.23 (m, 2H).

Production Example 61

(Endo)-N-{3-[3-(2-fluorobenzyloxy)-8-azabicyclo[3.2.1]oct-8-yl]-propan-1-yl}diphenyl imidodicarbonate

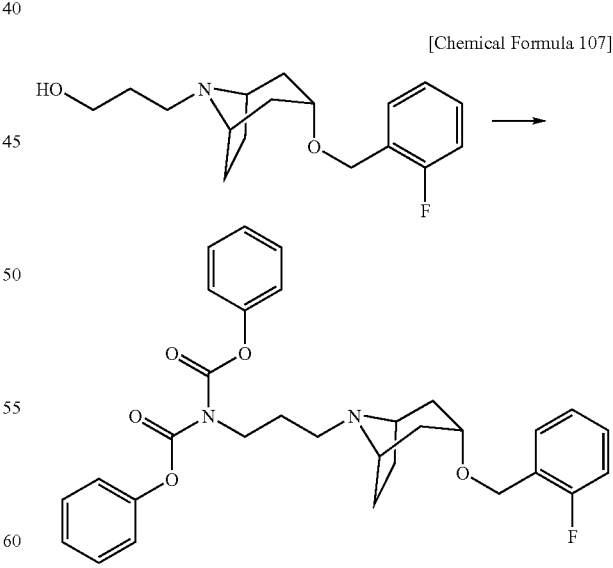

[Chemical Formula 107]

After dissolving the compound obtained in Production Example 53 (344 mg), diphenyl imidodicarbonate (CAS 99911-94-1) (361 mg) and triphenylphosphine (368 mg) in tetrahydrofuran (5 ml), diethyl azodicarboxylate (2.2 M solution in toluene, 0.70 ml) was added dropwise while stirring on ice. The mixture was stirred on ice for 30 minutes and then at room temperature for 15 hours. The reaction mixture was concentrated under reduced pressure, and the residue was purified by silica gel column chromatography to obtain the title compound (76 mg).

$^1$H-NMR (400 MHz, CDCl$_3$); δ 1.82-2.08 (m, 10H), 2.49 (t, J=7.2 Hz, 2H), 3.16-3.23 (m, 2H), 3.60-3.65 (m, 1H), 4.05 (t, J=7.2 Hz, 2H), 4.49 (s, 2H), 6.98-7.06 (m, 1H), 7.10-7.15 (m, 1H), 7.18-7.29 (m, 7H), 7.37-7.45 (m, 5H).

Production Example 62

Trifluoromethanesulfonic acid (R)-3-benzyloxy-2-fluoropropyl ester

[Chemical Formula 108]

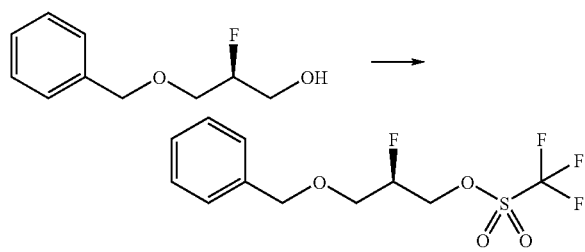

After dissolving (S)-3-benzyloxy-2-fluoropropan-1-ol (CAS 197389-28-9) (2.62 g) in dichloromethane (40 ml), pyridine (1.26 ml) was added. Trifluoromethanesulfonic anhydride (2.63 ml) was added dropwise while stirring on ice, and the mixture was stirred for 1 hour. Ice water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (4.38 g).

$^1$H-NMR (400 MHz, CDCl$_3$); δ 3.69-3.72 (m, 1H), 3.75 (d, J=5.2 Hz, 1H), 4.55 (d, J=12.0 Hz, 1H), 4.60 (d, J=12.0 Hz, 1H), 4.65-4.79 (m, 2H), 4.81-4.97 (m, 1H), 7.29-7.40 (m, 5H).

Production Example 63

Trifluoromethanesulfonic acid (S)-3-benzyloxy-2-fluoropropyl ester

[Chemical Formula 109]

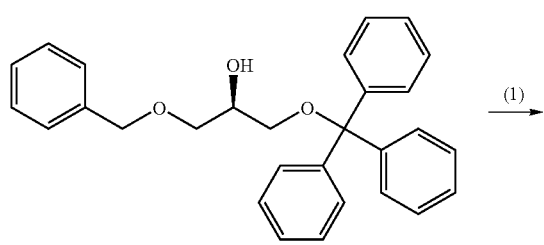

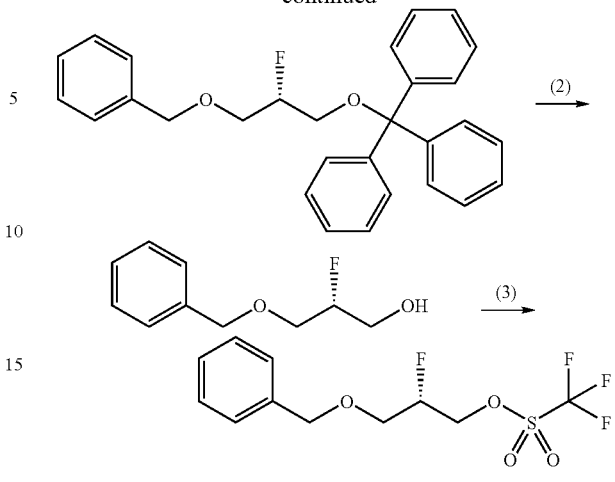

(1) (S)-1-Benzyloxy-2-fluoro-3-trityloxypropane

After dissolving (R)-1-benzyloxy-3-trityloxypropan-2-ol (CAS 83526-68-5) (10.45 g) in toluene (50 ml), nonafluoro-1-butanesulfonyl fluoride (7.95 ml) was added and the mixture was cooled on ice. Next, 1,8-diazabicyclo[5.4.0]undeca-7-ene (6.63 ml) was added dropwise while stirring. The mixture was stirred for 30 minutes on ice, and then for 3 hours and 30 minutes at room temperature. The reaction mixture was directly purified by silica gel column chromatography to obtain the title compound (7.52 g).

$^1$H-NMR (400 MHz, CDCl$_3$); δ 3.33 (dd, J=22.0, 4.8 Hz, 2H), 3.63-3.80 (m, 2H), 4.53 (d, J=12.4 Hz, 1H), 4.56 (d, J=12.4 Hz, 1H), 4.70-4.87 (m, 1H), 7.21-7.34 (m, 14H), 7.41-7.48 (m, 6H).

(2) (R)-3-Benzyloxy-2-fluoropropan-1-ol

The compound obtained in Production Example 63-(1) (7.42 g) was dissolved in 80% aqueous acetic acid, and the solution was stirred at 90° C. for 1 hour. The reaction mixture was concentrated under reduced pressure, water was added to the residue, and extraction was performed with ethyl acetate. The organic layer was washed with water, a 2N aqueous solution of sodium hydroxide, water and brine in that order and dried over anhydrous magnesium sulfate. After filtration, the solvent was distilled off under reduced pressure and the residue was purified by silica gel column chromatography. The title compound (2.62 g) was thus obtained.

$^1$H-NMR (400 MHz, CDCl$_3$); δ 1.94 (t, J=6.0 Hz, 1H), 3.68-3.71 (m, 1H), 3.74-3.76 (m, 1H), 3.81-3.84 (m, 1H), 3.86-3.90 (m, 1H), 4.57 (d, J=12.4 Hz, 1H), 4.60 (d, J=12.4 Hz, 1H), 4.64-4.82 (m, 1H), 7.28-7.39 (m, 5H).

(3) Trifluoromethanesulfonic acid (S)-3-benzyloxy-2-fluoropropyl ester

The title compound (4.38 g) was obtained from the compound obtained in Production Example 63-(2) (2.62 g) and trifluoromethanesulfonic anhydride, by the method similar to Production Example 62.

¹H-NMR (400 MHz, CDCl₃); δ 3.69-3.72 (m, 1H), 3.75 (d, J=5.2 Hz, 1H), 4.55 (d, J=12.0 Hz, 1H), 4.60 (d, J=12.0 Hz, 1H), 4.65-4.79 (m, 2H), 4.81-4.97 (m, 1H), 7.29-7.40 (m, 5H).

Production Example 64

Trifluoromethanesulfonic acid (S)-3-(tert-butyl-dimethyl-silanyloxy)-2-fluoropropyl ester

[Chemical Formula 110]

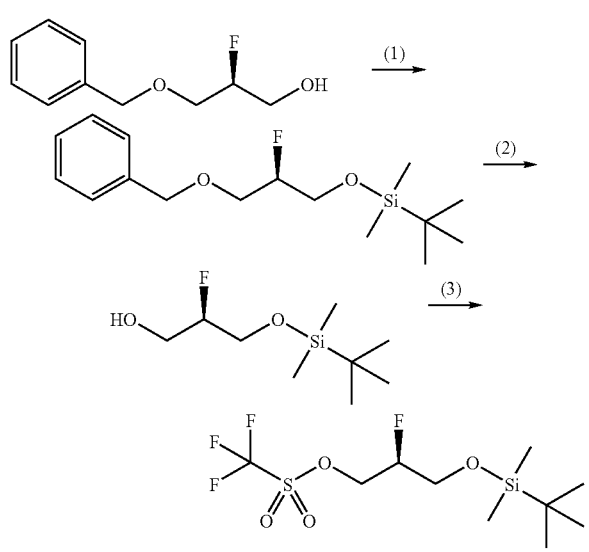

(1) (R)-(3-Benzyloxy-2-fluoropropoxy)-tert-butyldimethylsilane

After dissolving (S)-3-benzyloxy-2-fluoropropan-1-ol (CAS 197389-28-9) (6.00 g) and imidazole (2.44 g) in N,N-dimethylformamide (60 ml), the mixture was cooled on ice. Next, tert-butyldimethylchlorosilane (5.57 g) was added and the mixture was stirred at room temperature for 16 hours. Water was added to the reaction mixture, and extraction was performed with ethyl acetate. The organic layer was washed with water, a saturated aqueous solution of ammonium chloride, water and brine in that order and then dried over anhydrous magnesium sulfate. After filtration, the solvent was distilled off under reduced pressure and the residue was purified by silica gel column chromatography. The title compound (9.48 g) was thus obtained.

¹H-NMR (400 MHz, CDCl₃); δ 0.06 (s, 6H), 0.89 (s, 9H), 3.65-3.73 (m, 2H), 3.78-3.85 (m, 2H), 4.57 (d, J=12.4 Hz, 1H), 4.60 (d, J=12.4 Hz, 1H), 4.57-4.75 (m, 1H), 7.27-7.36 (m, 5H).

(2) (R)-3-(tert-Butyldimethylsilanyloxy)-2-fluoropropan-1-ol

The compound obtained in Production Example 64-(1) (9.48 g) was dissolved in methanol (220 ml), and then 20% palladium hydroxide on carbon (50% wet) (4.82 g) was added and the mixture was stirred at room temperature for 14 hours and 30 minutes under a hydrogen atmosphere (1 atm). The reaction mixture was filtered with Celite, and the filtrate was concentrated under reduced pressure. The residue was purified by NH silica gel column chromatography to obtain the title compound (6.26 g).

¹H-NMR (400 MHz, CDCl₃); δ 0.09 (s, 6H), 0.90 (s, 9H), 2.00 (t, J=6.4 Hz, 1H), 3.80-3.91 (m, 4H), 4.49-4.66 (m, 1H).

(3) Trifluoromethanesulfonic acid (S)-3-(tert-butyldimethylsilanyloxy)-2-fluoropropyl ester The compound obtained in Production Example 64-(2) (6.26 g) was dissolved in dichloromethane (80 ml), and pyridine (2.92 ml) was added. A solution of trifluoromethanesulfonic anhydride (6.08 ml) in dichloromethane (10 ml) was slowly added dropwise while stirring on ice, and the mixture was stirred for 1 hour. Ice water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (7.14 g).

¹H-NMR (400 MHz, CDCl₃); δ 0.09 (s, 3H), 0.09 (s, 3H), 0.90 (s, 9H), 3.83-3.90 (m, 4H), 4.67-4.85 (m, 3H).

Production Example 65

Trifluoromethanesulfonic acid (R)-3-(tert-butyldimethylsilanyloxy)-2-fluoropropyl ester

[Chemical Formula 111]

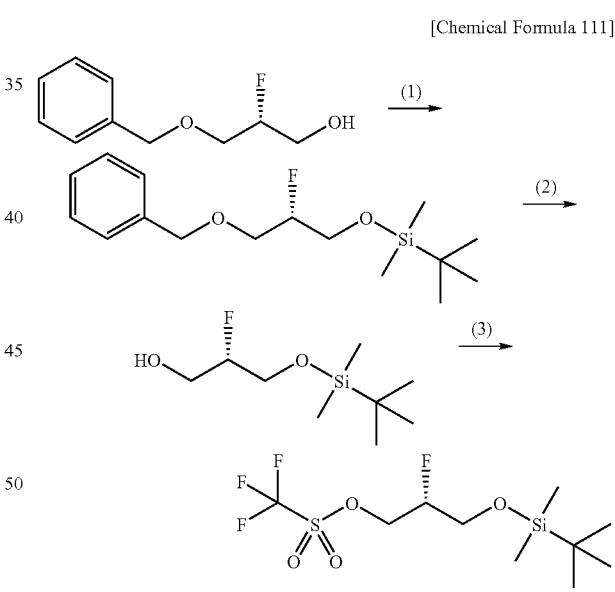

(1) (S)-(3-Benzyloxy-2-fluoropropoxy)-tert-butyldimethylsilane

The compound obtained in Production Example 63-(2) (6.75 g) and imidazole (2.75 g) were dissolved in N,N-dimethylformamide (75 ml), and the mixture was cooled on ice. Next, tert-butyldimethylchlorosilane (6.09 g) was added and the mixture was stirred at room temperature for 15 hours. Water was added to the reaction mixture, and extraction was performed with ethyl acetate. The organic layer was washed with water and brine in that order and then dried over anhydrous magnesium sulfate. After filtration, the solvent was distilled off under reduced pressure to obtain the title compound (11.16 g).

(2) (S)-3-(tert-Butyldimethylsilanyloxy)-2-fluoropropan-1-ol The compound obtained in Production Example 65-(1) (11.16 g) was dissolved in methanol (225 ml), and then 20% palladium hydroxide on carbon (50% wet) (1.31 g) was added and the mixture was stirred at room temperature for 14 hours under a hydrogen atmosphere (1 atm). Ethyl acetate was added to the reaction mixture and the resulting mixture was filtered. The filtrate was concentrated under reduced pressure to obtain the title compound (7.68 g).

(3) Trifluoromethanesulfonic acid (R)-3-(tert-butyldimethylsilanyloxy)-2-fluoropropyl ester The title compound (10.62 g) was obtained from the compound obtained in Production Example 65-(2) (7.68 g) and trifluoromethanesulfonic anhydride, by the method similar to Production Example 62.

$^1$H-NMR (400 MHz, CDCl$_3$); δ 0.09 (s, 3H), 0.09 (s, 3H), 0.90 (s, 9H), 3.83-3.90 (m, 4H), 4.67-4.85 (m, 3H).

Production Example 66

Trifluoromethanesulfonic acid 3-(tert-butyldimethylsilanyloxy)-2-fluoropropyl ester

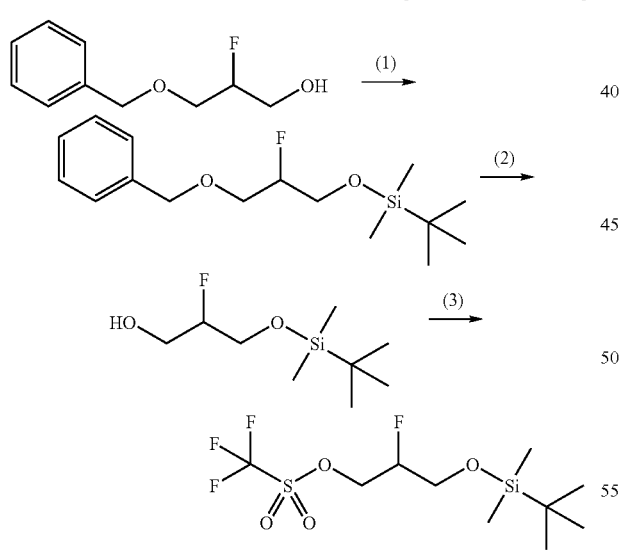

[Chemical Formula 112]

(1) (3-Benzyloxy-2-fluoropropoxy)-tert-butyldimethylsilane

The title compound (21.29 g) was obtained from 3-benzyloxy-2-fluoro-propan-1-ol (CAS 112482-37-8) (13.3 g) and tert-butyldimethylchlorosilane by the method similar to Production Example 64-(1).

(2) 3-(tert-Butyldimethylsilanyloxy)-2-fluoropropan-1-ol

The compound obtained in Production Example 66-(1) (21.29 g) was dissolved in methanol (450 ml), and then 20% palladium hydroxide on carbon (50% wet) (10.8 g) was added. The mixture was stirred at room temperature for 25 hours under a hydrogen atmosphere (1 atm). The reaction mixture was diluted with ethyl acetate, and the resulting mixture was filtered. The filtrate was concentrated under reduced pressure. The residue was then dissolved in ethyl acetate and filtered with NH silica gel. The filtrate was concentrated under reduced pressure to obtain the title compound (14.65 g).

(3) Trifluoromethanesulfonic acid 3-(tert-butyldimethylsilanyloxy)-2-fluoropropyl ester The title compound (10.62 g) was obtained from the compound obtained in Production Example 66-(2) (7.68 g) and trifluoromethanesulfonic anhydride, by the method similar to Production Example 62.

$^1$H-NMR (400 MHz, CDCl$_3$); δ 0.09 (s, 3H), 0.09 (s, 3H), 0.90 (s, 9H), 3.83-3.90 (m, 4H), 4.67-4.85 (m, 3H).

Production Example 67

Trifluoromethanesulfonic acid 3-(tert-butyldimethylsilanyloxy)-2-methoxypropyl ester

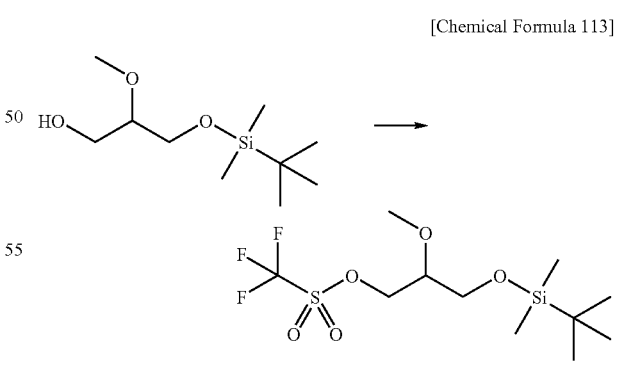

[Chemical Formula 113]

The title compound (4.76 g) was obtained from 3-(tert-butyldimethyl-silanyloxy)-2-methoxypropan-1-ol (CAS 160052-21-1) (3.94 g) and trifluoromethanesulfonic anhydride by the method similar to Production Example 62.

$^1$H-NMR (400 MHz, CDCl$_3$); δ 0.07 (s, 6H), 0.89 (s, 9H), 3.46 (s, 3H), 3.51-3.56 (m, 1H), 3.61 (dd, J=7.6, 10.0 Hz, 1H), 3.75 (dd, J=4.4, 10.0 Hz, 1H), 4.53 (dd, J=5.6, 10.4 Hz, 1H), 4.68 (dd, J=3.2, 10.4 Hz, 1H).

Production Example 68

Trifluoromethanesulfonic acid 3-(tert-butyldimethyl-silanyloxy)-2,2-difluoropropyl ester

[Chemical Formula 114]

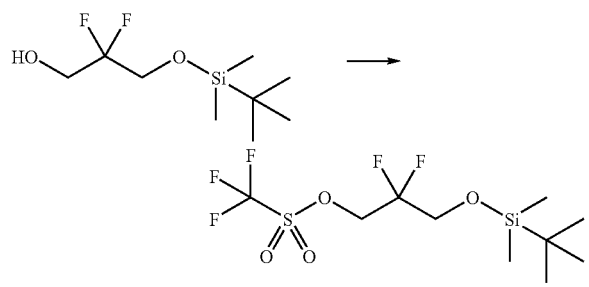

The title compound (1.85 g) was obtained from 3-(tert-butyl-dimethyl-silanyloxy)-2,2-difluoro-propan-1-ol (CAS 160052-20-0) (1.5 g) and trifluoromethanesulfonic anhydride by the method similar to Production Example 62.

$^1$H-NMR (400 MHz, CDCl$_3$); δ 0.07 (s, 6H), 0.89 (s, 9H), 3.46 (s, 3H), 3.51-3.56 (m, 1H), 3.61 (dd, J=7.6, 10.0 Hz, 1H), 3.75 (dd, J=4.4, 10.0 Hz, 1H), 4.53 (dd, J=5.6, 10.4 Hz, 1H), 4.68 (dd, J=3.2, 10.4 Hz, 1H).

Production Example 69

Trifluoromethanesulfonic acid (endo)-trans-2-[3-(2-fluoro-6-methylbenzyloxy)-8-azabicyclo[3.2.1]octan-8-ylmethyl]cyclopropylmethyl ester

[Chemical Formula 115]

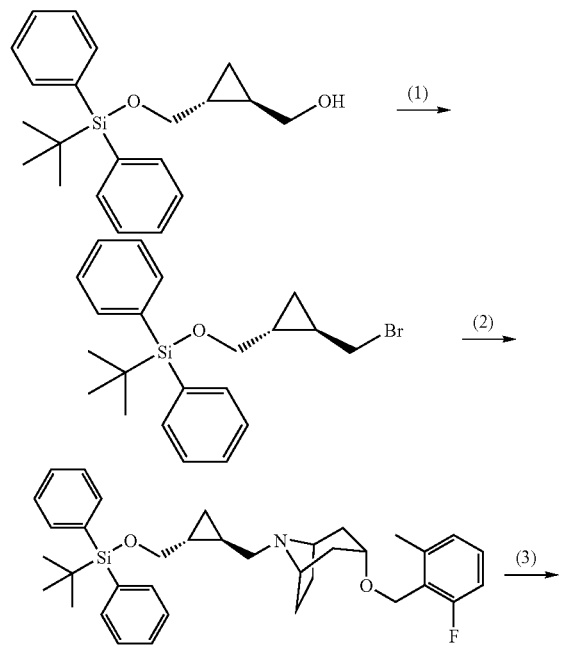

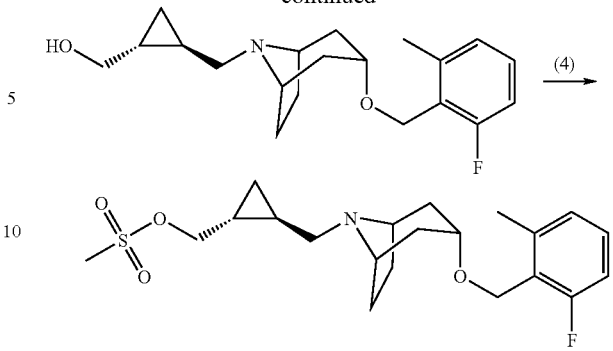

(1) Trans-(2-bromomethylcyclopropylmethoxy)-tert-butyldiphenylsilane

After dissolving trans-(2-tert-butyldiphenylsilanyloxymethyl)cyclopropyl)methanol (CAS 197432-76-1) (5.0 g), triphenylphosphine (5.8 g) and pyridine (1.79 ml) in tetrahydrofuran (50 ml), bromine (1.13 ml) was added dropwise while stirring on ice, and the mixture was stirred for 40 minutes while cooling on ice. A saturated aqueous solution of sodium hydrogencarbonate was added to the reaction mixture, and extraction was performed with ethyl acetate. The organic layer was washed with an aqueous solution of sodium hypochlorite and brine in that order and then dried over anhydrous magnesium sulfate. After filtration, the solvent was distilled off under reduced pressure. The residue was dissolved in ethyl acetate (50 ml), n-heptane (200 ml) was added, and the mixture was filtered with silica gel. The filtrate was concentrated under reduced pressure, n-heptane was added to the residue, and the mixture was filtered with silica gel. The filtrate was concentrated under reduced pressure to obtain the title compound (3.98 g).

$^1$H-NMR (400 MHz, CDCl$_3$); δ 0.51 (m, 1H), 0.68 (m, 1H), 1.05 (s, 9H), 1.07 (m, 1H), 1.18 (m, 1H), 3.27-3.36 (m, 2H), 3.52 (m, 1H), 3.65 (m, 1H), 7.36-7.45 (m, 6H), 7.65-7.67 (m, 4H).

(2) (Endo)-8-[trans-2-(tert-butyldiphenylsilanyloxymethyl)cyclopropylmethyl]-3-(2-fluoro-6-methylbenzyloxy)-8-azabicyclo[3.2.1]octane The compound obtained in Production Example 69-(1) (700 mg) was dissolved in N,N-dimethylformamide (8 ml), and then the compound obtained in Production Example 19 (597 mg) and anhydrous potassium carbonate (721 mg) were added and the mixture was stirred at room temperature for 2 days. Ethyl acetate was added to the reaction mixture and the resulting mixture was filtered. The filtrate was concentrated under reduced pressure, and the residue was purified by silica gel column chromatography to obtain the title compound (767 mg).

$^1$H-NMR (400 MHz, CDCl$_3$); δ 0.27 (m, 1H), 0.35 (m, 1H), 0.89 (m, 2H), 1.04 (s, 9H), 1.78-2.17 (m, 9H), 2.41 (s, 3H), 2.49 (m, 1H), 3.30 (m, 1H), 3.38 (dd, J=6.8, 10.4 Hz, 1H), 3.56 (m, 1H), 3.63 (m, 1H), 3.69 (m, 1H), 4.46 (d, J=2.0 Hz, 2H), 6.88 (m, 1H), 6.82 (d, J=7.2 Hz, 1H), 7.16 (m, 1H), 7.36-7.44 (m, 6H), 7.65-7.68 (m, 4H).

(3) (Endo)-{trans-2-[3-(2-fluoro-6-methylbenzyloxy)-8-azabicyclo[3.2.1]octan-8-ylmethyl]cyclopropylmethyl}methanol The compound obtained in Production Example 69-(2) (767 mg) was dissolved in tetrahydrofuran (10 ml), and then tetra-n-butylammonium fluoride (1 M solution in tetrahydrofuran, 1.61 ml) was added and the mixture was stirred at room temperature for 2 hours. The reaction mixture was concentrated under reduced pressure, and the residue was purified by silica gel column chromatography to obtain the title compound (322 mg).

$^1$H-NMR (400 MHz, CDCl$_3$); δ 0.38 (m, 1H), 0.47 (m, 1H), 0.90 (m, 1H), 1.02 (m, 1H), 1.81-2.13 (m, 9H), 2.40 (s, 3H), 2.56 (m, 1H), 3.22 (m, 1H), 3.37 (m, 1H), 3.65 (m, 1H), 3.68 (m, 1H), 4.47 (d, J=2.0 Hz, 2H), 6.88 (m, 1H), 6.97 (d, J=7.2 Hz, 1H), 7.16 (m, 1H).

(4) Trifluoromethanesulfonic acid (endo)-trans-2-[3-(2-fluoro-6-methylbenzyloxy)-8-azabicyclo[3.2.1]octan-8-ylmethyl]cyclopropylmethyl ester The compound obtained in Example 69-(3) (100 mg) was dissolved in dichloromethane (2 ml), and then triethylamine (63 μl) was added and methanesulfonyl chloride (28 μl) was slowly added while stirring on ice. After stirring overnight at room temperature, triethylamine (63 μl) and methanesulfonyl chloride (28 μl) were further added and stirring was continued for 1 hour and 30 minutes. A saturated aqueous solution of sodium hydrogencarbonate was added to the reaction mixture, and extraction was performed with chloroform. The organic layer was washed with brine and dried over anhydrous magnesium sulfate. After filtration, the solvent was distilled off under reduced pressure. The residue was purified by NH silica gel column chromatography to obtain the title compound (83 mg).

$^1$H-NMR (400 MHz, CDCl$_3$); δ 0.53-0.64 (m, 2H), 0.95-1.12 (m, 2H), 1.76-2.01 (m, 8H), 2.26-2.36 (m, 2H), 2.41 (s, 3H), 3.02 (s, 3H), 3.26 (m, 2H), 3.61 (m, 1H), 4.07-4.15 (m, 2H), 4.46 (d, J=2.0 Hz, 2H), 6.88 (t, J=8.8 Hz, 1H), 6.96 (d, J=7.2 Hz, 1H), 7.16 (m, 1H).

Production Example 70

(Endo)-3-(naphthalen-2-ylmethoxy)-8-azabicyclo[3.2.1]octane hydrochloride

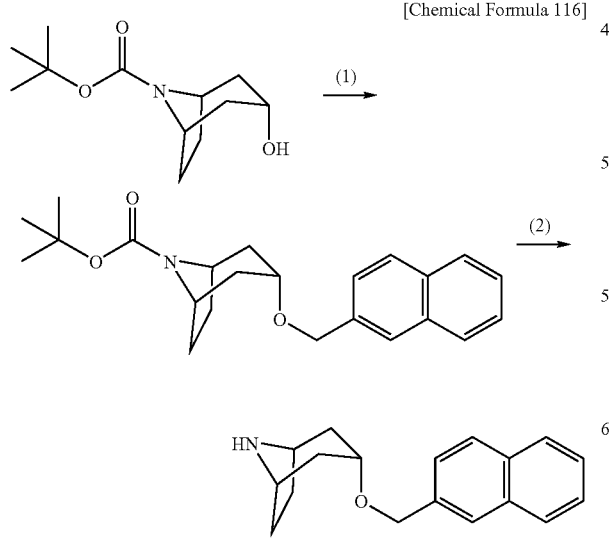

[Chemical Formula 116]

(1) (Endo)-3-(naphthalen-2-ylmethoxy)-8-azabicyclo[3.2.1]octane-8-carboxylic acid tert-butyl ester The title compound (1.28 g) was obtained from (endo)-3-hydroxy-8-aza-bicyclo[3.2.1]octane-8-carboxylic acid tert-butyl ester (CAS 143557-91-9) (1.00 g) and 2-(bromomethyl)naphthalene, by the method similar to Production Example 28-(1).

$^1$H-NMR (400 MHz, CDCl$_3$); δ 1.46 (s, 9H), 1.86-2.10 (m, 6H), 2.15-2.22 (m, 2H), 3.74-3.79 (m, 1H), 4.09-4.28 (m, 2H), 4.59-4.70 (m, 2H), 7.42-7.31 (m, 3H), 7.76 (s, 1H), 7.79-7.85 (m, 3H).

(2) (Endo)-3-(naphthalen-2-ylmethoxy)-8-azabicyclo[3.2.1]octane hydrochloride

The title compound (1.00 g) was obtained from the compound obtained in Production Example 70-(1) (1.28 g) by the method similar to Production Example 19-(3).

$^1$H-NMR (400 MHz, CD$_3$OD); δ 2.00-2.18 (m, 4H), 2.24-2.30 (m, 2H), 2.45-2.51 (m, 2H), 3.81-3.85 (m, 1H), 3.99-4.03 (m, 2H), 4.69 (s, 2H), 7.44-7.50 (m, 3H), 7.79-7.87 (m, 4H).

Production Example 71

3α-(2-methylbenzyloxy)-3β-trifluoromethyl-8-azabicyclo[3.2.1]octane hydrochloride

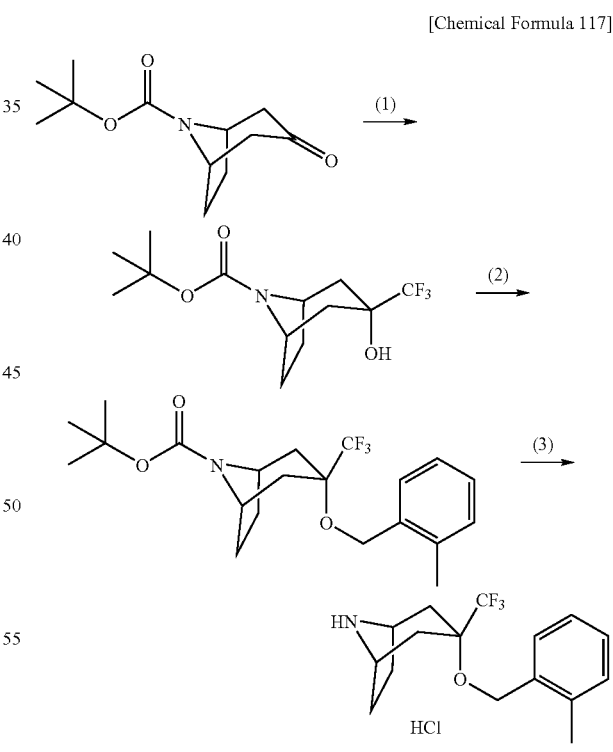

[Chemical Formula 117]

(1) 3α-hydroxy-3β-trifluoromethyl-8-azabicyclo[3.2.1]octane-8-carboxylic acid tert-butyl ester A mixture of 3-oxo-8-azabicyclo[3.2.1]octane-8-carboxylic acid tert-butyl ester (CAS 185099-67-6) (1.00 g), (trifluoromethyl)trimethylsilane (1.18 ml) and tetrahydrofuran (15 ml) was cooled on ice, and then tetra-n-butylammonium fluoride (1 M solution in tetrahydrofuran, 0.33 ml) was added and the mixture was stirred at room temperature for 3 hours. After then adding tetra-n-butylammonium fluoride (1 M solution in tetrahydrofuran, 0.33 ml), the mixture was further stirred at room temperature for 19 hours. Aqueous ammonia chloride was added to the reaction mixture and extraction was performed with ethyl acetate. The organic layer was washed with water and brine in that order and then dried over anhydrous magnesium sulfate. After filtration, the solvent was distilled off under reduced pressure.

The residue was dissolved in methanol (15 ml), and sodium borohydride (252 mg) was added while stirring on ice. After stirring for 1 hour, the reaction mixture was concentrated under reduced pressure. Water was added to the residue and extraction was performed with ethyl acetate. The organic layer was washed with water and brine in that order and then dried over anhydrous magnesium sulfate. After filtration, the solvent was distilled off under reduced pressure.

The residue was purified by silica gel column chromatography to obtain the title compound (940 mg).
$^1$H-NMR (400 MHz, CDCl$_3$); δ 1.46 (s, 9H), 1.58-2.37 (m, 8H), 4.19-4.37 (m, 1H).

(2) 3α-hydroxy-3β-(2-methylbenzyloxy)-8-azabicyclo[3.2.1]octane-8-carboxylic acid tert-butyl ester The title compound (577 mg) was obtained from the compound obtained in Production Example 71-(1) (705 mg) and 2-methylbenzyl bromide by the method similar to Production Example 19-(2).
$^1$H-NMR (400 MHz, CDCl$_3$); δ 1.47 (s, 9H), 1.85-2.26 (m, 8H), 2.33 (s, 3H), 4.16-4.22 (m, 1H), 4.27-4.33 (m, 1H), 4.67 (s, 2H), 7.16-7.25 (m, 3H), 7.34-7.37 (m, 1H).

(3) 3α-(2-methylbenzyloxy)-3β-trifluoromethyl-8-azabicyclo[3.2.1]octane hydrochloride The title compound (414 mg) was obtained from the compound obtained in Production Example 71-(2) (577 mg) by the method similar to Production Example 19-(3).
$^1$H-NMR (400 MHz, CD$_3$OD); δ 1.93-2.03 (m, 2-H), 2.16-2.23 (m, 2H), 2.25-2.31 (m, 2H), 2.36 (s, 3H), 2.42-2.48 (m, 2H), 4.17-4.16 (m, 2H), 4.73 (s, 2H), 7.15-7.26 (m, 3H), 7.34-7.38 (m, 1H).

Production Example 72

(Exo)-3-(4-methoxybenzylsulfanyl)-8-azabicyclo[3.2.1]octane hydrochloride

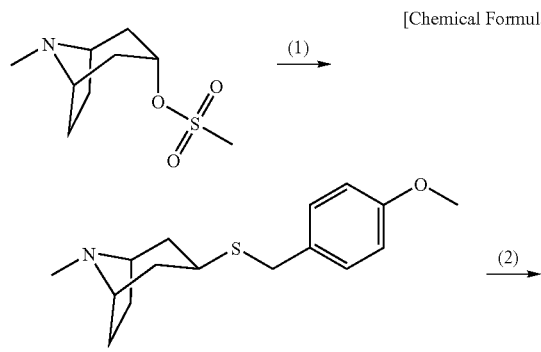

[Chemical Formula 118]

-continued

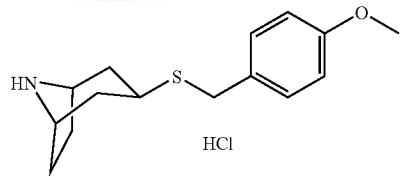

(1) (Exo)-3-(4-methoxybenzylsulfanyl)-8-methyl-8-azabicyclo[3.2.1]octane

After dissolving 4-methoxy-α-toluenethiol (2.29 ml) in tetrahydrofuran (60 ml), the mixture was cooled on ice. Potassium tert-butoxide (1.85 g) was then added and the mixture was stirred at room temperature for 10 minutes. Methanesulfonic acid (endo)-8-methyl-8-azabicyclo[3.2.1]oct-3-yl ester (CAS 35130-97-3) (3.00 g) was added, and stirring was continued at 60° C. for 5 hours. Water was further added to the reaction mixture and extraction was performed with n-heptane. The organic layer was washed with a 5N aqueous solution of sodium hydroxide and brine in that order and dried over anhydrous magnesium sulfate. After filtration, the solvent was distilled off under reduced pressure. The residue was purified by NH silica gel column chromatography to obtain the title compound (2.09 g).
$^1$H-NMR (400 MHz, CDCl$_3$); δ 1.41-1.47 (m, 2H), 1.64-1.80 (m, 4H), 1.93-2.01 (m, 2H), 2.27 (s, 3H), 2.73-2.83 (m, 1H), 3.11-3.16 (m, 2H), 3.68 (s, 2H), 3.80 (s, 3H), 6.82-6.86 (m, 2H), 7.21-7.25 (m, 2H).

(2) (Exo)-3-(4-methoxybenzylsulfanyl)-8-azabicyclo[3.2.1]octane hydrochloride

The title compound (1.66 g) was obtained from the compound obtained in Production Example 72-(1) (2.09 g) by the method similar to Production Example 5-(2).
$^1$H-NMR (400 MHz, CD$_3$OD); δ 1.74-1.94 (m, 4H), 1.96-2.10 (m, 4H), 2.91-3.02 (m, 1H), 3.76 (s, 2H), 3.77 (s, 3H), 3.96-4.00 (m, 2H), 6.85-6.89 (m, 2H), 7.24-7.28 (m, 2H).

Production Example 73

(Endo)-3-(4-methoxybenzylsulfanyl)-8-azabicyclo[3.2.1]octane hydrochloride

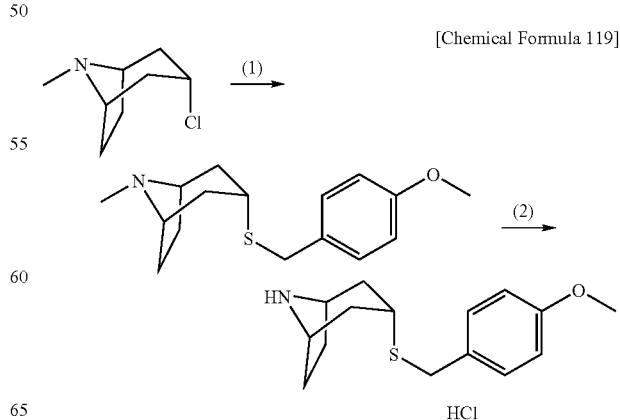

[Chemical Formula 119]

143

(1) (Endo)-3-(4-methoxybenzylsulfanyl)-8-methyl-8-azabicyclo[3.2.1]octane

After dissolving 4-methoxy-α-toluenethiol (3.88 ml) in ethanol (50 ml), the mixture was cooled on ice. Potassium tert-butoxide (3.12 g) was then added and the mixture was stirred at room temperature for 10 minutes. An ethanol solution (20 ml) containing (Endo)-3-chloro-8-methyl-8-azabicyclo[3.2.1]octane (CAS 13514-03-9) (3.7 g) was added, and the mixture was heated to reflux for 16 hours. The reaction mixture was concentrated under reduced pressure, water was added to the residue, and extraction was performed with n-heptane. The organic layer was washed with a 5N aqueous solution of sodium hydroxide and brine in that order and dried over anhydrous magnesium sulfate. After filtration, the solvent was distilled off under reduced pressure. The residue was purified by silica gel column chromatography to obtain the title compound (1.33 g).

$^1$H-NMR (400 MHz, CDCl$_3$); δ 1.69-1.75 (m, 2H), 1.96-2.11 (m, 4H), 2.19-2.27 (m, 2H), 2.25 (s, 3H), 2.93 (t, J=7.6 Hz, 1H), 3.08-3.12 (m, 2H), 3.68 (s, 2H), 3.79 (s, 3H), 6.81-6.86 (m, 2H), 7.19-7.23 (m, 2H).

(2) (Endo)-3-(4-methoxybenzylsulfanyl)-8-azabicyclo[3.2.1]octane hydrochloride The title compound (0.93 g) was obtained from the compound obtained in Production Example 73-(1) (1.33 g) by the method similar to Production Example 5-(2).

1H-NMR (400 MHz, CD$_3$OD); 62.00-2.14 (m, 4H), 2.29-2.37 (m, 2H), 2.47-2.53 (m, 2H), 3.02 (t, J=7.6 Hz, 1H), 3.77 (s, 3H), 3.78 (s, 2H) 3.97-4.02 (m, 2H), 6.84-6.88 (m, 2H), 7.21-7.26 (m, 2H).

Example 1

(Endo)-2-{(R)-2-fluoro-3-[3-(3-fluorobenzyloxy)-8-azabicyclo[3.2.1]oct-8-yl]propyl}-4,5-dimethyl-2,4-dihydro[1,2,4]triazol-3-one

[Chemical Formula 120]

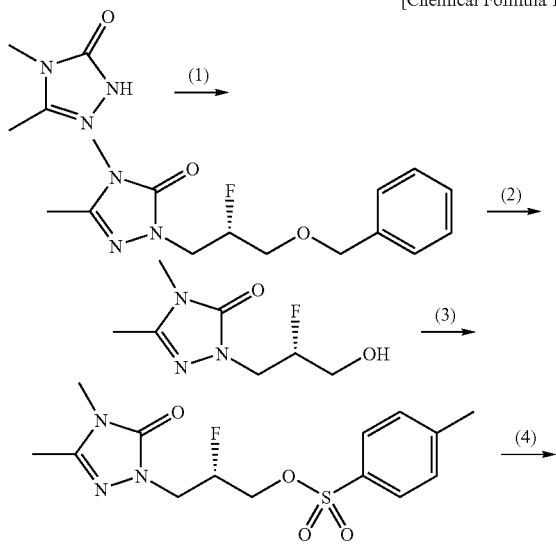

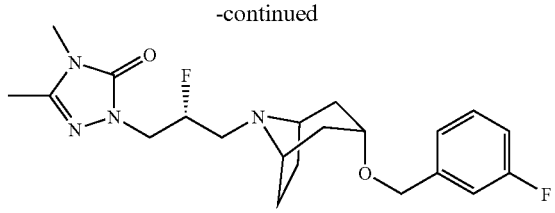

(1) 2-((S)-3-Benzyloxy-2-fluoropropyl)-4,5-dimethyl-2,4-dihydro[1,2,4]triazol-3-one After dissolving 4,5-dimethyl-2,4-dihydro[1,2,4]triazol-3-one (CAS 54770-19-3) (600 mg) and the compound obtained in Production Example 62 (1.84 g) in N,N-dimethylformamide (18 ml), sodium hydride (60% in oil) (233 mg) was added while cooling on ice and the mixture was stirred at room temperature for one day. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography to obtain the title compound (860 mg).

(2) 2-((S)-2-Fluoro-3-hydroxypropyl)-4,5-dimethyl-2,4-dihydro[1,2,4]triazol-3-one The compound obtained in Example 1-(1) (860 mg) was dissolved in methanol (20 ml), and then 20% palladium hydroxide on carbon (50% wet) (500 mg) was added and the mixture was stirred at room temperature for one day under a hydrogen atmosphere (1 atm). After further addition of 20% palladium hydroxide on carbon (50% wet) (120 mg), stirring was continued at room temperature for one day. The reaction mixture was filtered with Celite, and the filtrate was concentrated under reduced pressure. The residue was purified by silica gel column chromatography to obtain the title compound (585 mg).

$^1$H-NMR (400 MHz, CDCl$_3$); δ 2.23 (s, 3H), 3.25 (s, 3H), 3.38-3.45 (m, 1H), 3.66-3.78 (m, 2H), 4.04-4.24 (m, 2H), 4.70-4.88 (m, 1H).

(3) Toluene-4-sulfonic acid (S)-3-(3,4-dimethyl-5-oxo-4,5-dihydro[1.24]triazol-1-yl)-2-fluoropropyl ester After adding p-toluenesulfonyl chloride (615 mg) to a mixture of the compound obtained in Example 1-(2) (580 mg), triethylamine (0.51 ml), trimethylamine hydrochloride (29 mg) and acetonitrile (9 ml), the resulting mixture was stirred at room temperature for one day. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography to obtain the title compound (950 mg).

$^1$H-NMR (400 MHz, CDCl$_3$); δ 2.20 (s, 3H), 2.46 (s, 3H), 3.21 (s, 3H), 3.84-3.96 (m, 1H), 4.02-4.36 (m, 3H), 4.87-5.05 (m, 1H), 7.35 (d, J=8.0 Hz, 2H), 7.80 (d, J=8.0 Hz, 2H).

(4) (Endo-2-{(R)-2-fluoro-3-[3-(3-fluorobenzyloxy-8-azabicyclo[3.2.1]oct-8-yl]propyl}-4,5-dimethyl-2,4-dihydro[1,2,4]triazol-3-one The compound obtained in Example 1-(3) (50 mg) was dissolved in N,N-dimethylformamide (1 ml), and then the compound obtained in Production Example 2 (38 mg) and anhydrous potassium carbonate (44 mg) were added and the mixture was stirred at 50° C. for 2 days. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by preparative thin-layer chromatography to obtain the title compound (34 mg).

$^1$H-NMR (400 MHz, CD$_3$OD); δ 1.83-2.15 (m, 8H), 2.24 (s, 3H), 2.60-2.73 (m, 2H), 3.20-3.29 (m, 2H), 3.23 (s, 3H), 3.61 (t, J=4.8 Hz, 1H), 3.88-4.11 (m, 2H), 4.46 (s, 2H), 4.80-4.98 (m, 1H), 6.96 (td, J=8.4, 2.4 Hz, 1H), 7.03-7.09 (m, 1H), 7.12 (d, J=8.0 Hz, 1H), 7.32 (td, J=8.0, 6.0 Hz, 1H).

Example 2

(Endo)-2-[(R)-3-(3-benzyloxy-8-azabicyclo[3.2.1]oct-8-yl)-2-fluoropropyl]-4,5-dimethyl-2,4-dihydro[1,2,4]triazol-3-one

[Chemical Formula 121]

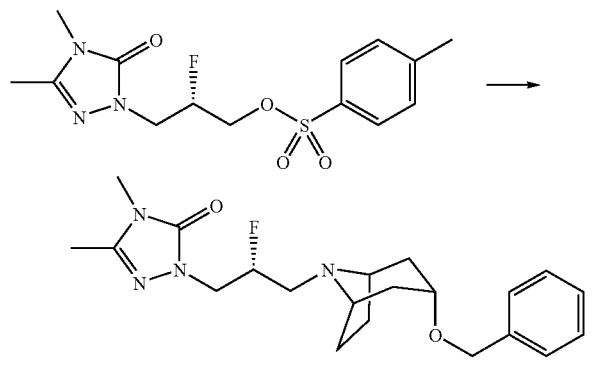

The title compound (52 mg) was obtained from the compound obtained in Example 1-(3) (80 mg) and the compound obtained in Production Example 4 (56 mg), by the method similar to Example 1-(4).

$^1$H-NMR (400 MHz, CD$_3$OD); δ 1.84-2.14 (m, 8H), 2.24 (s, 3H), 2.49-2.75 (m, 2H), 3.18-3.27 (m, 2H), 3.23 (s, 3H), 3.61 (t, J=4.8 Hz, 1H), 3.87-4.10 (m, 2-H), 4.45 (s, 2H), 4.79-4.98 (m, 1H), 7.20-7.34 (m, 5H).

Example 3

(Endo)-2-{(R)-2-fluoro-3-[3-(3-methoxybenzyloxy)-8-azabicyclo[3.2.1]oct-8-yl]propyl}-4,5-dimethyl-2,4-dihydro[1,2,4]triazol-3-one

[Chemical Formula 122]

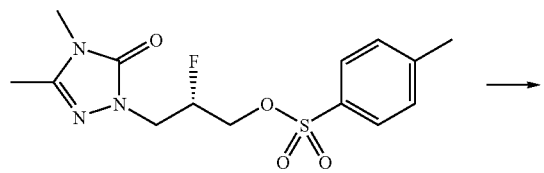

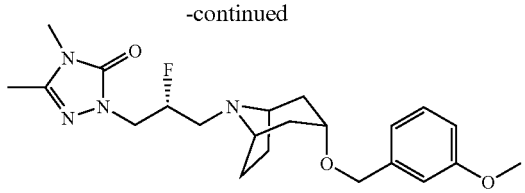

The title compound (59 mg) was obtained from the compound obtained in Example 1-(3) (80 mg) and the compound obtained in Production Example 15 (63 mg), by the method similar to Example 1-(4).

$^1$H-NMR (400 MHz, CD$_3$OD); δ 1.85-2.15 (m, 8H), 2.24 (s, 3H), 2.49-2.76 (m, 2H), 3.19-3.28 (m, 2H), 3.23 (s, 3H), 3.60 (t, J=4.8 Hz, 1H), 3.78 (s, 3H), 3.87-4.10 (m, 2H), 4.43 (s, 2H), 4.79-4.98 (m, 1H), 6.78-6.82 (m, 1H), 6.86-6.91 (m, 2H), 7.19-7.24 (m, 1H).

Example 4

(Endo)-2-{(R)-2-fluoro-3-[3-(2-fluorobenzyloxy)-8-azabicyclo[3.2.1]oct-8-yl]propyl}-4,5-dimethyl-2,4-dihydro[1,2,4]triazol-3-one

[Chemical Formula 123]

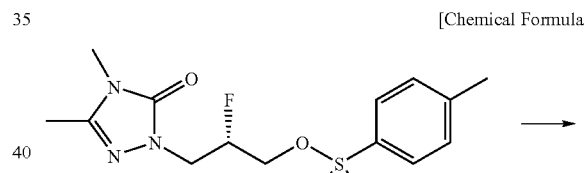

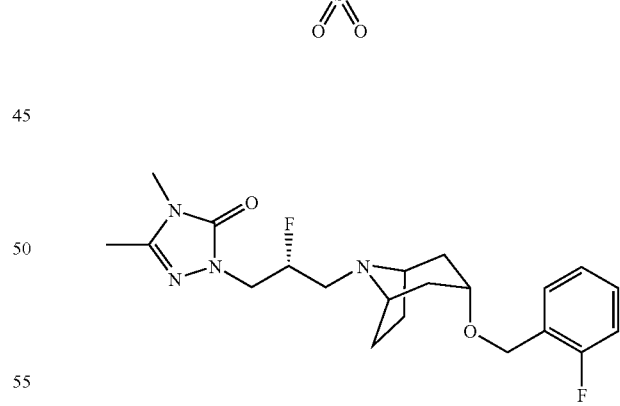

The title compound (38 mg) was obtained from the compound obtained in Example 1-(3) (50 mg) and the compound obtained in Production Example 5 (38 mg), by the method similar to Example 1-(4).

$^1$H-NMR (400 MHz, CD$_3$OD); δ 1.83-2.13 (m, 8H), 2.24 (s, 3H), 2.49-2.72 (m, 2H), 3.18-3.27 (m, 2H), 3.23 (s, 3H), 3.65 (t, J=4.8 Hz, 1H), 3.81-4.10 (m, 2H), 4.50 (s, 2H), 4.79-4.98 (m, 1H), 7.02-7.08 (m, 1H), 7.14 (td, J=7.6, 1.2 Hz, 1H), 7.25-7.32 (m, 1H), 7.42 (td, J=7.6, 1.6 Hz, 1H).

Example 5

(Endo)-2-{(R)-2-fluoro-3-[3-(4-fluorobenzyloxy)-8-azabicyclo[3.2.1]oct-8-yl]propyl}-4,5-dimethyl-2,4-dihydro[1,2,4]triazol-3-one

[Chemical Formula 124]

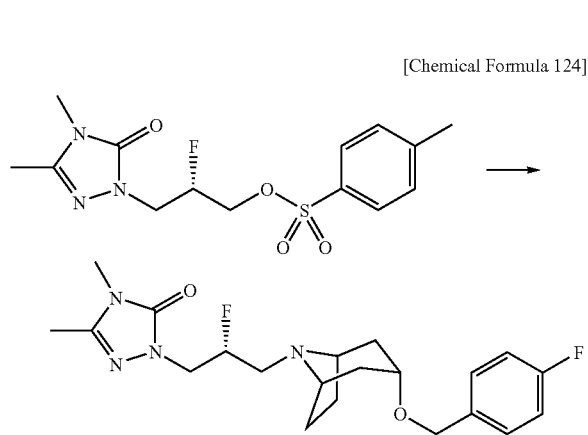

The title compound (42 mg) was obtained from the compound obtained in Example 1-(3) (50 mg) and the compound obtained in Production Example 1 (38 mg), by the method similar to Example 1-(4).

$^1$H-NMR (400 MHz, CD$_3$OD); δ 1.83-2.13 (m, 8H), 2.24 (s, 3H), 2.60-2.73 (m, 2H), 3.19-3.29 (m, 2H), 3.23 (s, 3H), 3.61 (t, J=5.2 Hz, 1H), 3.87-4.10 (m, 2H), 4.42 (s, 2H), 4.80-4.98 (m, 1H), 7.01-7.07 (m, 2H), 7.30-7.36 (m, 2H).

Example 6

(Endo)-2-{(R)-2-fluoro-3-[3-(2-fluoromethylbenzyloxy)-8-azabicyclo[3.2.1]oct-8-yl]propyl}-4,5-dimethyl-2,4-dihydro[1,2,4]triazol-3-one

[Chemical Formula 125]

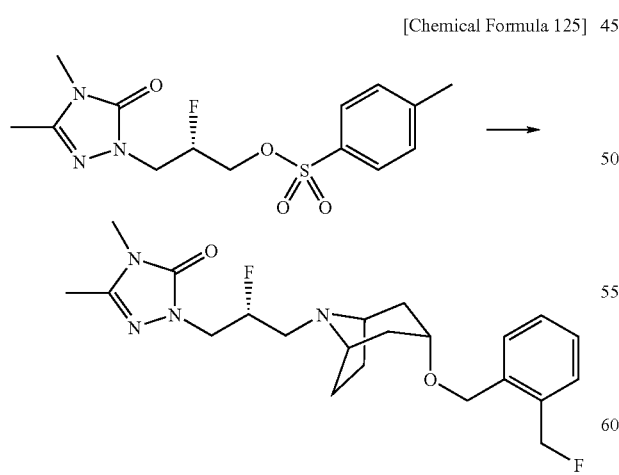

The title compound (41 mg) was obtained from the compound obtained in Example 1-(3) (50 mg) and the compound obtained in Production Example 33 (40 mg), by the method similar to Example 1-(4).

$^1$H-NMR (400 MHz, CD$_3$OD); δ 1.82-2.13 (m, 8H), 2.24 (s, 3H), 2.58-2.75 (m, 2H), 3.18-3.28 (m, 2H), 3.23 (s, 3H), 3.62 (t, J=4.8 Hz, 1H), 3.87-4.10 (m, 2H), 4.53 (s, 2H), 4.79-4.98 (m, 1H), 5.48 (d, J=47.6 Hz, 2H), 7.27-7.44 (m, 4H).

Example 7

(Endo)-2-{(R)-2-fluoro-3-[3-(thiophen-2-yl-methoxy)-8-azabicyclo[3.2.1]oct-8-yl]propyl}-4,5-dimethyl-2,4-dihydro[1,2,4]triazol-3-one

[Chemical Formula 126]

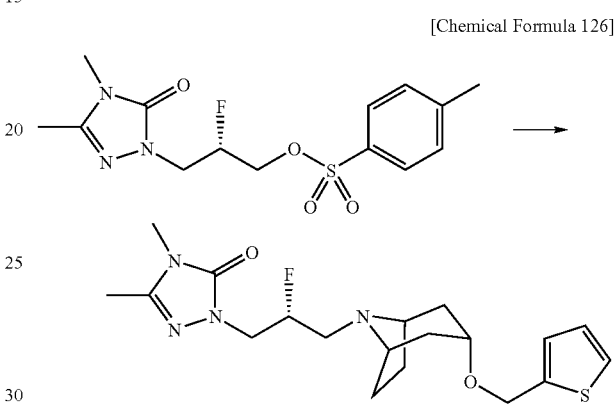

The title compound (26 mg) was obtained from the compound obtained in Example 1-(3) (80 mg) and the compound obtained in Production Example 8 (58 mg), by the method similar to Example 1-(4).

$^1$H-NMR (400 MHz, CD$_3$OD); δ 1.82-2.15 (m, 8H), 2.24 (s, 3H), 2.49-2.76 (m, 2H), 3.18-3.26 (m, 2H), 3.23 (s, 3H), 3.62 (t, J=4.8 Hz, 1H), 3.87-4.10 (m, 2H), 4.61 (s, 2H), 4.78-4.97 (m, 1H), 6.92-6.97 (m, 2H), 7.31 (dd, J=4.8, 1.2 Hz, 1H).

Example 8

(Endo)-2-{(S)-2-fluoro-3-[3-(2-fluorobenzyloxy)-8-azabicyclo[3.2.1]oct-8-yl]propyl}-4,5-dimethyl-2,4-dihydro[1,2,4]triazol-3-one

[Chemical Formula 127]

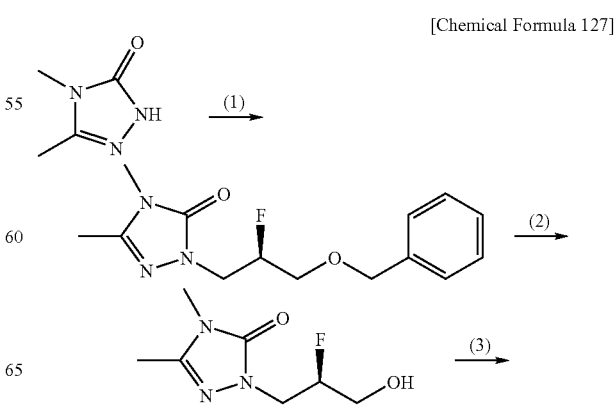

-continued

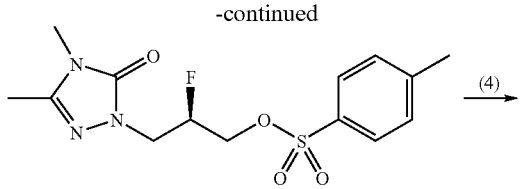

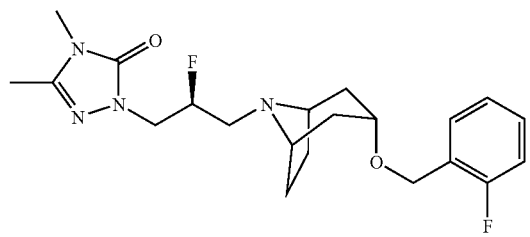

(1) 2-((R)-3-Benzyloxy-2-fluoropropyl)-4,5-dimethyl-2,4-dihydro[1,2,4]triazol-3-one The title compound (900 mg) was obtained from 4,5-dimethyl-2,4-dihydro[1,2,4]triazol-3-one (CAS 54770-19-3) (600 mg) and the compound obtained in Production Example 63 (1.84 g), by the method similar to Example 1-(1).

(2) 2-((R)-2-Fluoro-3-hydroxypropyl)-4,5-dimethyl-2,4-dihydro[1,2,4]triazol-3-one The title compound (570 mg) was obtained from the compound obtained in Example 8-(1) (900 mg), by the method similar to Example 1-(2).

$^1$H-NMR (400 MHz, CDCl$_3$); δ 2.23 (s, 3H), 3.25 (s, 3H), 3.38-3.45 (m, 1H), 3.66-3.78 (m, 2H), 4.04-4.24 (m, 2H), 4.70-4.88 (m, 1H).

(3) Toluene-4-sulfonic acid (R)-3-(3,4-dimethyl-5-oxo-4,5-dihydro[1,2,4]triazol-1-yl)-2-fluoropropyl ester The title compound (880 mg) was obtained from the compound obtained in Example 8-(2) (565 mg) and p-toluenesulfonyl chloride, by the method similar to Example 1-(3).

$^1$H-NMR (400 MHz, CDCl$_3$); δ 2.20 (s, 3H), 2.46 (s, 3H), 3.21 (s, 3H), 3.84-3.96 (m, 1H), 4.02-4.36 (m, 3H), 4.87-5.05 (m, 1H), 7.35 (d, J=8.0 Hz, 2H), 7.80 (d, J=8.0 Hz, 2H).

(4) (Endo)-2-{(S)-2-fluoro-3-[3-(2-fluorobenzyloxy)-8-azabicyclo[3.2.1]oct-8-yl]propyl}-4,5-dimethyl-2,4-dihydro[1,2,4]triazol-3-one The title compound (44 mg) was obtained from the compound obtained in Example 8-(3) (50 mg) and the compound obtained in Production Example 5 (38 mg), by the method similar to Example 1-(4).

$^1$H-NMR (400 MHz, CD$_3$OD); δ 1.83-2.13 (m, 8H), 2.24 (s, 3H), 2.49-2.72 (m, 2H), 3.18-3.27 (m, 2H), 3.23 (s, 3H), 3.65 (t, J=4.8 Hz, 1H), 3.81-4.10 (m, 2H), 4.50 (s, 2H), 4.79-4.98 (m, 1H), 7.02-7.08 (m, 1H), 7.14 (td, J=7.6, 1.2 Hz, 1H), 7.25-7.32 (m, 1H), 7.42 (td, J=7.6, 1.6 Hz, 1H).

Example 9

(Endo)-2-{(S)-2-fluoro-3-[3-(3-fluorobenzyloxy)-8-azabicyclo[3.2.1]oct-8-yl]propyl}-4,5-dimethyl-2,4-dihydro[1,2,4]triazol-3-one

[Chemical Formula 128]

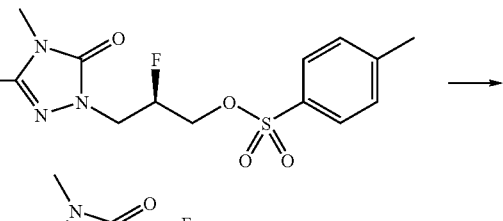

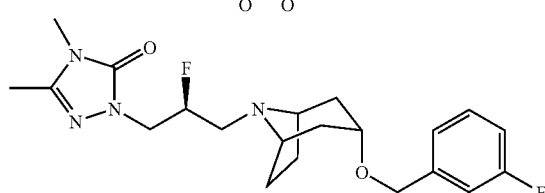

The title compound (30 mg) was obtained from the compound obtained in Example 8-(3) (50 mg) and the compound obtained in Production Example 2 (38 mg), by the method similar to Example 1-(4).

$^1$H-NMR (400 MHz, CD$_3$OD); δ 1.83-2.15 (m, 8H), 2.24 (s, 3H), 2.60-2.73 (m, 2H), 3.20-3.29 (m, 2H), 3.23 (s, 3H), 3.61 (t, J=4.8 Hz, 1H), 3.88-4.11 (m, 2H), 4.46 (s, 2H), 4.80-4.98 (m, 1H), 6.96 (td, J=8.4, 2.4 Hz, 1H), 7.03-7.09 (m, 1H), 7.11 (d, J=8.0 Hz, 1H), 7.32 (td, J=8.0, 6.0 Hz, 1H).

Example 10

(Endo)-2-{(S)-2-fluoro-3-[3-(4-fluorobenzyloxy)-8-azabicyclo[3.2.1]oct-8-yl]propyl}-4,5-dimethyl-2,4-dihydro[1,2,4]triazol-3-one

[Chemical Formula 129]

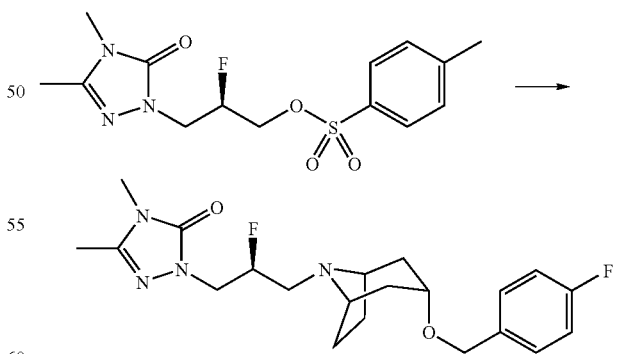

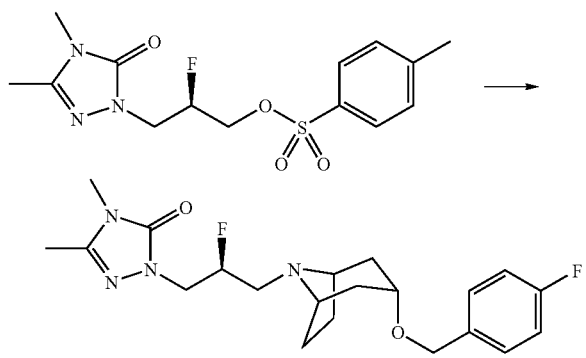

The title compound (39 mg) was obtained from the compound obtained in Example 8-(3) (50 mg) and the compound obtained in Production Example 1 (38 mg), by the method similar to Example 1-(4).

$^1$H-NMR (400 MHz, CD$_3$OD); δ 1.83-2.13 (m, 8H), 2.24 (s, 3H), 2.60-2.73 (m, 2H), 3.19-3.29 (m, 2H), 3.23 (s, 3H), 3.61 (t, J=5.2 Hz, 1H), 3.87-4.10 (m, 2H), 4.42 (s, 2H), 4.80-4.98 (m, 1H), 7.01-7.07 (m, 2H), 7.30-7.36 (m, 2H).

Example 11

(Endo)-2-{(S)-2-fluoro-3-[3-(2-fluoromethylbenzyloxy)-8-azabicyclo[3.2.1]oct-8-yl]propyl}-4,5-dimethyl-2,4-dihydro[1,2,4]triazol-3-one

[Chemical Formula 130]

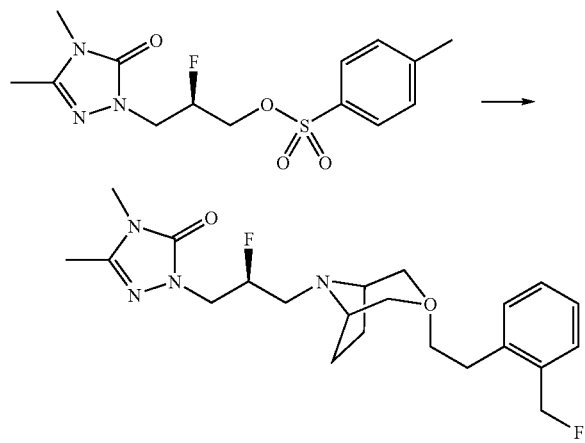

The title compound (40 mg) was obtained from the compound obtained in Example 8-(3) (50 mg) and the compound obtained in Production Example 33 (40 mg), by the method similar to Example 1-(4).

$^1$H-NMR (400 MHz, CD$_3$OD); δ 1.82-2.13 (m, 8H), 2.24 (s, 3H), 2.58-2.75 (m, 2H), 3.18-3.28 (m, 2H), 3.23 (s, 3H), 3.62 (t, J=4.8 Hz, 1H), 3.87-4.10 (m, 2H), 4.53 (s, 2H), 4.79-4.98 (m, 1H), 5.48 (d, J=47.6 Hz, 2H), 7.27-7.44 (m, 4H).

Example 12

(Endo)-3-{(S)-2-fluoro-3-[3-(4-fluorobenzyloxy)-8-azabicyclo[3.2.1]oct-8-yl]propyl}-1,6-dimethyl-1H-[1,3,5]triazine-2,4-dione oxalate

[Chemical Formula 131]

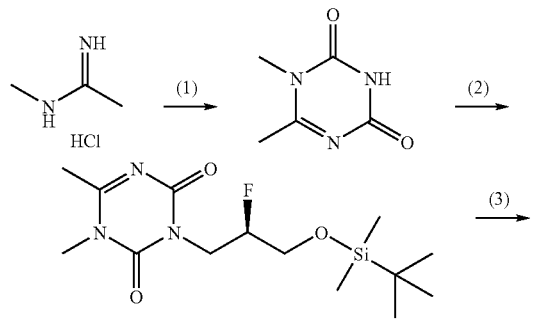

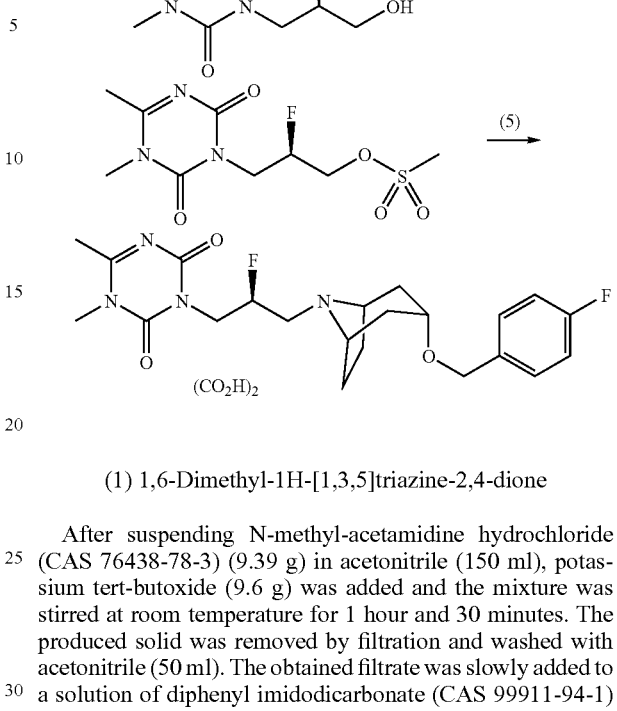

(1) 1,6-Dimethyl-1H-[1,3,5]triazine-2,4-dione

After suspending N-methyl-acetamidine hydrochloride (CAS 76438-78-3) (9.39 g) in acetonitrile (150 ml), potassium tert-butoxide (9.6 g) was added and the mixture was stirred at room temperature for 1 hour and 30 minutes. The produced solid was removed by filtration and washed with acetonitrile (50 ml). The obtained filtrate was slowly added to a solution of diphenyl imidodicarbonate (CAS 99911-94-1) (20 g) in acetonitrile (200 ml) that had been heated to reflux. After heating to reflux for 2 hours, the reaction mixture was concentrated under reduced pressure. The residue was purified by silica gel column chromatography. The obtained solid was suspended in a small amount of acetone and collected by filtration to obtain the title compound (6.07 g).

$^1$H-NMR (400 MHz, CD$_3$OD); δ 2.44 (s, 3H), 3.40 (s, 3H).

(2) 3-[(R)-3-(tert-Butyl-dimethyl-silanyloxy)-2-fluoro-propyl]-1,6-dimethyl-1H-[1,3,5]triazine-2,4-dione The compound obtained in Example 12-(1) (745 mg) and the compound obtained in Production Example 64 (1.5 g) were dissolved in N,N-dimethylformamide (23 ml), and then potassium tert-butoxide (544 mg) was added while cooling on ice and the mixture was stirred for 3 hours and 30 minutes. Ethyl acetate and a saturated aqueous solution of ammonium chloride were added to the reaction mixture, and then the organic layer was separated. The organic layer was washed with brine and dried over anhydrous magnesium sulfate. After filtration, the solvent was distilled off under reduced pressure. The residue was purified by silica gel column chromatography to obtain the title compound (373 mg).

$^1$H-NMR (400 MHz, CDCl$_3$); δ 0.07-0.09 (m, 6H), 0.91 (s, 9H), 2.47 (s, 3H), 3.47 (s, 3H), 3.79-4.00 (m, 3H), 4.48-4.57 (m, 1H), 4.77-4.95 (m, 1H)

(3) 3-((R)-2-Fluoro-3-hydroxypropyl)-1,6-dimethyl-1H-[1,3,5]triazine-2,4-dione

The compound obtained in Example 12-(2) (373 mg) was dissolved in tetrahydrofuran (1.7 ml), and then acetic acid (0.1 ml) and tetra-n-butylammonium fluoride (1 M solution in tetrahydrofuran, 1.32 ml) was added and the mixture was stirred at room temperature for 16 hours. The reaction mixture was concentrated under reduced pressure, and the residue was purified by silica gel column chromatography. The title compound (162 mg) was thus obtained.

$^1$H-NMR (400 MHz, CD$_3$OD); δ 2.46 (s, 3H), 3.45 (s, 3H), 3.63-3.82 (m, 2H), 3.90-4.01 (m, 1H), 4.34-4.43 (m, 1H), 4.69-4.86 (m, 1H).

(4) Methanesulfonic acid (R)-3-(3,4-dimethyl-2,6-dioxo-3,6-dihydro-2H-[1,3,5]triazin-1-yl)-2-fluoro-propyl ester A mixture of the compound obtained in Example 12-(3) (162 mg), triethylamine (0.16 ml), trimethylamine hydrochloride (7 mg) and acetonitrile (1 ml) was cooled on ice, and then methanesulfonyl chloride (0.09 ml) was slowly added while stirring. After stirring for 1 hour, triethylamine (0.05 ml) and methanesulfonyl chloride (0.03 ml) were further added and stirring was continued for 4 hours and 30 minutes. The reaction mixture was concentrated under reduced pressure, and the residue was purified by silica gel column chromatography. The title compound (208 mg) was thus obtained.

$^1$H-NMR (400 MHz, CD$_3$OD); δ 2.46 (s, 3H), 3.13 (s, 3H), 3.46 (s, 3H), 4.04-4.14 (m, 1H), 4.33-4.56 (m, 3H), 4.95-5.11 (m, 1H).

(5) (Endo)-3-{(S)-2-fluoro-3-[3-(4-fluorobenzyloxy)-8-azabicyclo[3.2.1]oct-8-yl]propyl}-1,6-dimethyl-1H-[1,3,5]triazine-2,4-dione oxalate A mixture of the compound obtained in Example 12-(4) (1.04 mg), the compound obtained in Production Example 59 (94 mg), anhydrous potassium carbonate (49 mg), sodium iodide (26 mg) and N,N-dimethylformamide (2 ml) was stirred at 50° C. for 37 hours and 30 minutes. Water and ethyl acetate were added to the reaction mixture, and the organic layer was separated. The organic layer was washed with water and brine in that order and then dried over anhydrous magnesium sulfate. After filtration, the solvent was distilled off under reduced pressure. The residue was purified by preparative thin-layer chromatography to obtain the free form of the title compound (13 mg).

This was dissolved in ethanol, and then a solution of oxalic acid (2.7 mg) in ethanol was added and the solvent was distilled off under a nitrogen stream. Diethyl ether was added to the residue to form a solid, and the solvent was distilled off under a nitrogen stream. The residue was dried under reduced pressure to obtain the title compound (18 mg).

$^1$H-NMR (400 MHz, CD$_3$OD); δ2.13-2.19 (m, 6H), 2.35-2.37 (m, 2H), 2.45-2.47 (m, 3H), 3.17-3.32 (m, 2H), 3.46 (s, 3H), 3.71 (bs, 1H), 3.78-3.84 (m, 2H), 4.03-4.12 (m, 1H), 4.31-4.39 (m, 1H), 4.48 (s, 2H), 5.15-5.28 (m, 1H), 7.04-7.08 (m, 2H), 7.34-7.37 (m, 2H).

Example 13

(Endo)-3-{(S)-2-fluoro-3-[3-(3-fluorobenzyloxy)-8-azabicyclo[3.2.1]oct-8-yl]propyl}-1,6-dimethyl-1H-[1,3,5]triazine-2,4-dione oxalate

[Chemical Formula 132]

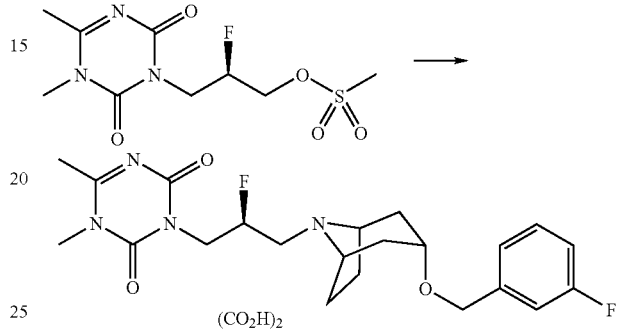

The title compound (18 mg) was obtained from the compound obtained in Example 12-(4) (104 mg) and the compound obtained in Production Example 58 (92 mg), by the method similar to Example 12-(5).

$^1$H-NMR (400 MHz, CD$_3$OD); δ 2.14-2.27 (m, 6H), 2.35-2.41 (m, 2H), 2.45-2.47 (m, 3H), 3.19-3.34 (m, 2H), 3.46 (s, 3H), 3.71-3.72 (m, 1H), 3.80-3.86 (m, 2H), 4.02-4.13 (m, 1H), 4.29-4.38 (m, 1H), 4.52 (s, 2H), 5.16-5.30 (m, 1H), 6.97-7.02 (m, 1H), 7.07-7.10 (m, 1H), 7.13-7.15 (m, 1H), 7.32-7.37 (m, 1H).

Example 14

(Endo)-3-{(S)-2-fluoro-3-[3-(2-fluoromethylbenzyloxy)-8-azabicyclo[3.2.1]oct-8-yl]propyl}-1,6-dimethyl-1H-[1,3,5]triazine-2,4-dione oxalate

[Chemical Formula 133]

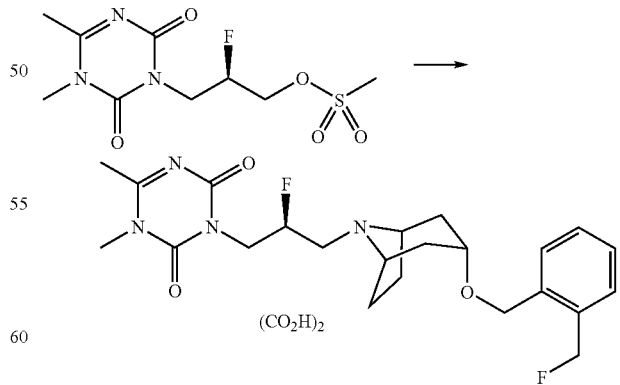

The title compound (57 mg) was obtained from the compound obtained in Example 12-(4) (175 mg) and the compound obtained in Production Example 33 (167 mg), by the method similar to Example 12-(5).

¹H-NMR (400 MHz, CD₃OD); δ 2.18-2.31 (m, 6H), 2.38-2.46 (m, 2H), 2.47 (s, 3H), 3.34-3.46 (m, 2H), 3.46 (s, 3H), 3.76 (bs, 1H), 3.93-3.99 (m, 2H), 4.03-4.13 (m, 1H), 4.31-4.39 (m, 1H), 4.62 (s, 2H), 5.21-5.35 (m, 1H), 5.44-5.56 (m, 2H), 7.33-7.39 (m, 2H), 7.41-7.44 (m, 2H).

Example 15

(Endo)-3-{(R)-2-fluoro-3-[3-(3-fluorobenzyloxy)-8-azabicyclo[3.2.1]oct-8-yl]propyl}-1,6-dimethyl-1H-[1,3,5]triazine-2,4-dione oxalate

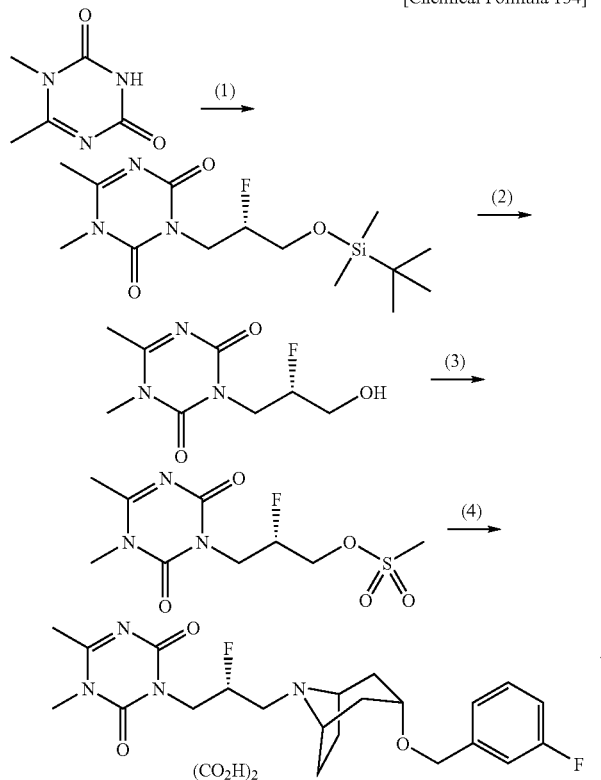

[Chemical Formula 134]

(1) 3-[(S)-3-(tert-Butyl-dimethyl-silanyloxy)-2-fluoropropyl]-1,6-dimethyl-1H-[1,3,5]triazine-2,4-dione The title compound (332 mg) was obtained from the compound obtained in Example 12-(1) (745 mg) and the compound obtained in Production Example 65 (1.5 g), by the method similar to Example 12-(2).
¹H-NMR (400 MHz, CDCl₃); δ 0.07-0.09 (m, 6H), 0.91 (s, 9H), 2.47 (s, 3H), 3.47 (s, 3H), 3.79-4.00 (m, 3H), 4.48-4.57 (m, 1H), 4.77-4.92 (s, 1H).

(2) 3-((S)-2-Fluoro-3-hydroxypropyl)-1,6-dimethyl-1H-[1,3,5]triazine-2,4-dione

The title compound (138 mg) was obtained from the compound obtained in Example 15-(1) (332 mg), by the method similar to Example 12-(3).
¹H-NMR (400 MHz, CDCl₃); δ 2.46 (s, 3H), 3.45 (s, 3H), 3.63-3.82 (m, 2H), 3.90-4.01 (m, 1H), 4.34-4.43 (m, 1H), 4.69-4.86 (m, 1H).

(3) Methanesulfonic acid (S)-3-(3,4-dimethyl-2,6-dioxo-3,6-dihydro-2H-[1,3,5]triazin-1-yl)-2-fluoropropyl ester The title compound (177 mg) was obtained from the compound obtained in Example 15-(2) (138 mg) and methanesulfonyl chloride, by the method similar to Example 12-(4).
¹H-NMR (400 MHz, CD₃OD); δ 2.46 (s, 3H), 3.13 (s, 3H), 3.46 (s, 3H), 4.04-4.14 (m, 1H), 4.33-4.55 (m, 3H), 4.96-5.12 (m, 1H).

(4) (Endo)-3-{(R)-2-fluoro-3-[3-(3-fluorobenzyloxy)-8-azabicyclo[3.2.1]oct-8-yl]propyl}-1,6-dimethyl-1H-[1,3,5]triazine-2,4-dione oxalate The title compound (1.5 mg) was obtained from the compound obtained in Example 15-(3) (88 mg) and the compound obtained in Production Example 58 (78 mg), by the method similar to Example 12-(5).
¹H-NMR (400 MHz, CD₃OD); δ 2.21-2.29 (m, 6H), 2.44-2.48 (m, 5H), 3.34-3.52 (m, 5H), 3.75 (bs, 1H), 3.97-4.14 (m, 3H), 4.31-4.40 (m, 1H), 4.54 (s, 2H), 5.23-5.37 (m, 1H), 6.98-7.03 (m, 1H), 7.08-7.11 (m, 1H), 7.14-7.16 (m, 1H), 7.32-7.38 (m, 1H).

Example 16

(Endo)-3-{(R)-2-fluoro-3-[3-(4-fluorobenzyloxy)-8-azabicyclo[3.2.1]oct-8-yl]propyl}-1,6-dimethyl-1H-[1,3,5]triazine-2,4-dione oxalate

[Chemical Formula 135]

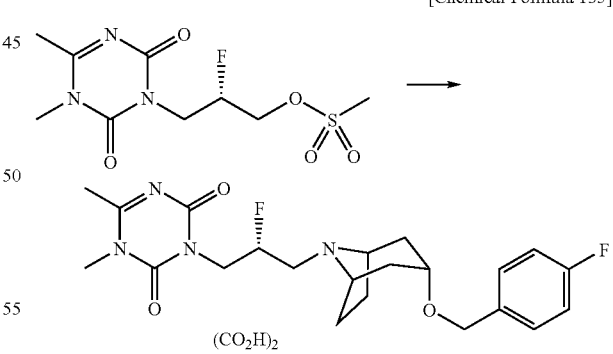

The title compound (16 mg) was obtained from the compound obtained in Example 15-(3) (88 mg) and the compound obtained in Production Example 59 (80 mg), by the method similar to Example 12-(5).
¹H-NMR (400 MHz, CD₃OD); δ 2.14-2.27 (m, 6H), 2.35-2.41 (m, 2H), 2.45-2.47 (m, 3H), 3.19-3.34 (m, 2H), 3.46 (s, 3H), 3.71-3.72 (m, 1H), 3.80-3.86 (m, 2H), 4.02-4.13 (m, 1H), 4.29-4.38 (m, 1H), 4.52 (s, 2H), 5.16-5.30 (m, 1H), 6.97-7.02 (m, 1H), 7.07-7.10 (m, 1H), 7.13-7.15 (m, 1H), 7.32-7.37 (m, 1H).

Example 17

(Endo)-3-{(R)-2-fluoro-3-[3-(2-fluoromethylbenzyloxy)-8-azabicyclo[3.2.1]oct-8-yl]propyl}-1,6-dimethyl-1H-[1,3,5]triazine-2,4-dione oxalate

[Chemical Formula 136]

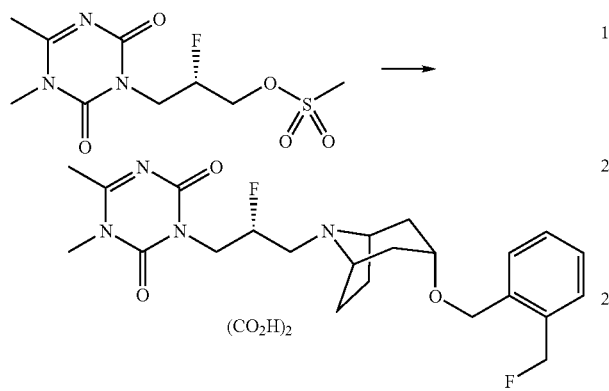

The title compound (48 mg) was obtained from the compound obtained in Example 15-(3) (177 mg) and the compound obtained in Production Example 33 (185 mg), by the method similar to Example 12-(5).

$^1$H-NMR (400 MHz, CD$_3$OD); δ 2.12-2.31 (m, 6H), 2.38-2.44 (m, 2H), 2.47 (s, 3H), 3.36-3.44 (m, 2H), 3.46 (s, 3H), 3.76 (bs, 1H), 3.92-3.99 (m, 2H), 4.03-4.14 (m, 1H), 4.29-4.38 (m, 1H), 4.62 (s, 2H), 5.21-5.35 (m, 1H), 5.44-5.56 (m, 2H), 7.32-7.39 (m, 2H), 7.41-7.44 (m, 2H).

Example 18

(Endo)-3-{(R)-2-fluoro-3-[3-(4-fluoromethylbenzyloxy)-8-azabicyclo[3.2.1]oct-8-yl]propyl}-1,6-dimethyl-1H-[1,3,5]triazine-2,4-dione oxalate

[Chemical Formula 137]

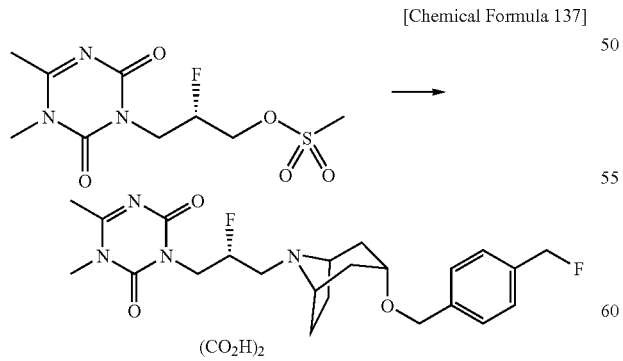

The title compound (29 mg) was obtained from the compound obtained in Example 15-(3) (177 mg) and the compound obtained in Production Example 25 (91 mg), by the method similar to Example 12-(5).

$^1$H-NMR (400 MHz, CD$_3$OD); δ 2.18-2.31 (m, 6H), 2.40-2.44 (m, 2H), 2.46-2.47 (m, 3H), 3.32-3.41 (m, 2H), 3.46 (s, 3H), 3.74 (bs, 1H), 3.88-3.94 (m, 2H), 4.03-4.13 (m, 1H), 4.31-4.39 (m, 1H), 4.54 (s, 2H), 5.19-5.33 (m, 1H), 5.29-5.41 (m, 2H), 7.38 (bs, 4H).

Example 19

(Endo)-3-{2-fluoro-3-[3-(2-fluorobenzyloxy)-8-azabicyclo[3.2.1]oct-8-yl]propyl}-1,6-dimethyl-1H-[1,3,5]triazine-2,4-dione oxalate

[Chemical Formula 138]

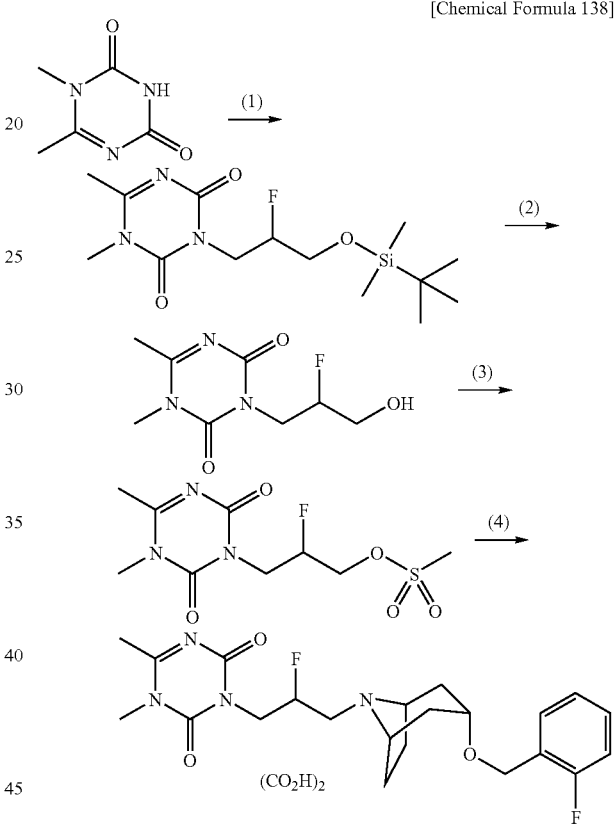

(1) 3-[3-(tert-Butyl-dimethyl-silanyloxy)-2-fluoropropyl]-1,6-dimethyl-1H-[1,3,5]triazine-2,4-dione The title compound (1.54 g) was obtained from the compound obtained in Example 12-(1) (1.83 g) and the compound obtained in Production Example 66 (4.0 g), by the method similar to Example 12-(2).

$^1$H-NMR (400 MHz, CDCl$_3$); δ 0.07-0.09 (m, 6H), 0.91 (s, 9H), 2.47 (s, 3H), 3.47 (s, 3H), 3.79-4.00 (m, 3H), 4.48-4.57 (s, 1H), 4.77-4.95 (s, 1H).

(2) 3-(2-Fluoro-3-hydroxypropyl)-1,6-dimethyl-1H-[1,3,5]triazine-2,4-dione

The title compound (640 mg) was obtained from the compound obtained in Example 19-(1) (1.54 g), by the method similar to Example 12-(3).

$^1$H-NMR (400 MHz, CD$_3$OD); δ 2.45 (s, 3H), 3.45 (s, 3H), 3.63-3.81 (m, 2H), 3.89-4.01 (m, 1H), 4.34-4.42 (m, 1H), 4.69-4.85 (m, 1H).

(3) Methanesulfonic acid-3-(3,4-dimethyl-2,6-dioxo-3,6-dihydro-2H-[1,3,5]triazin-1-yl)-2-fluoropropyl ester The title compound (937 mg) was obtained from the compound obtained in Example 19-(2) (640 mg) and methanesulfonyl chloride, by the method similar to Example 12-(4).

$^1$H-NMR (400 MHz, CD$_3$OD); δ 2.46 (s, 3H), 3.13 (s, 3H), 3.46 (s, 3H), 4.04-4.14 (m, 1H), 4.33-4.56 (m, 3H), 4.95-5.11 (m, 1H).

(4) (Endo)-3-{2-fluoro-3-[3-(2-fluorobenzyloxy)-8-azabicyclo[3.2.1]oct-8-yl]-propyl}-1,6-dimethyl-1H-[1,3,5]triazine-2,4-dione oxalate The title compound (32 mg) was obtained from the compound obtained in Example 19-(3) (111 mg) and the compound obtained in Production Example 57 (108 mg), by the method similar to Example 12-(5).

$^1$H-NMR (400 MHz, CD$_3$OD); δ 2.21-2.29 (m, 6H), 2.44-2.48 (m, 5H), 3.34-3.52 (m, 5H), 3.75 (bs, 1H), 3.97-4.14 (m, 3H), 4.31-4.40 (m, 1H), 4.54 (s, 2H), 5.23-5.37 (m, 1H), 6.98-7.03 (m, 1H), 7.08-7.11 (m, 1H), 7.14-7.16 (m, 1H), 7.32-7.38 (m, 1H).

Example 20

(Endo)-3-[3-(3-benzyloxy)-8-azabicyclo[3.2.1]oct-8-yl]-2-fluoropropyl]-1,6-dimethyl-1H-[1,3,5]triazine-2,4-dione oxalate

[Chemical Formula 139]

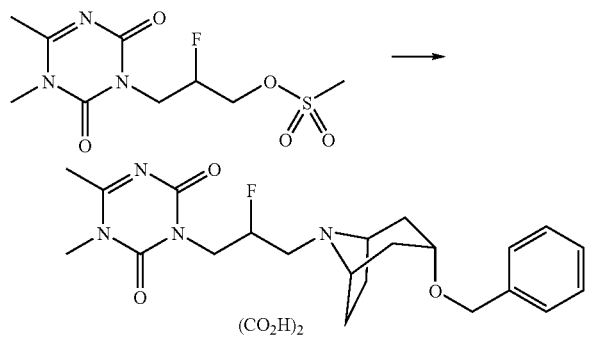

The title compound (25 mg) was obtained from the compound obtained in Example 19-(3) (156 mg) and the compound obtained in Production Example 4 (132 mg), by the method similar to Example 12-(5).

$^1$H-NMR (400 MHz, CD$_3$OD); δ 2.17-2.30 (m, 6H), 2.42-2.47 (m, 5H), 3.35-3.46 (m, 5H), 3.74 (bs, 1H), 3.92-3.98 (m, 2H), 4.03-4.14 (m, 1H), 4.29-4.38 (m, 1H), 4.52 (s, 2H), 5.20-5.37 (m, 1H), 7.25-7.31 (m, 1H), 7.33-7.34 (m, 4H).

Example 21

(Endo)-3-{2-fluoro-3-[3-(3-methylbenzyloxy)-8-azabicyclo[3.2.1]oct-8-yl]-propyl}-1,6-dimethyl-1H-[1,3,5]triazine-2,4-dione oxalate

[Chemical Formula 140]

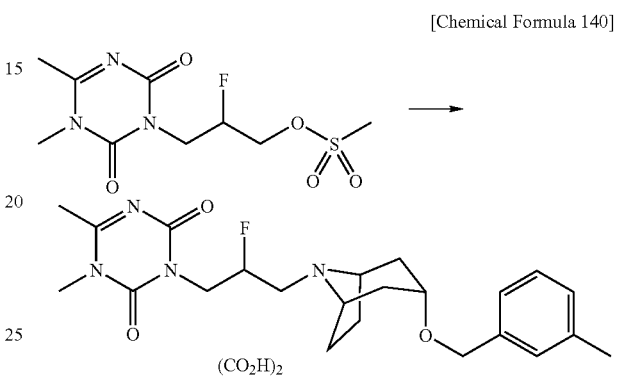

The title compound (24 mg) was obtained from the compound obtained in Example 19-(3) (156 mg) and the compound obtained in Production Example 21 (139 mg), by the method similar to Example 12-(5).

$^1$H-NMR (400 MHz, CD$_3$OD); δ 2.17-2.31 (m, 6H), 2.33 (s, 3H), 2.42-2.47 (m, 5H), 3.34-3.44 (m, 2H), 3.46 (s, 3H), 3.72 (bs, 1H), 3.91-3.97 (m, 2H), 4.04-4.14 (m, 1H), 4.29-4.38 (m, 1H), 5.22-5.35 (m, 1H), 7.08-7.15 (m, 3H), 7.19-7.23 (m, 1H).

Example 22

(Endo)-3-{2,2-difluoro-3-[3-(2-fluorobenzyloxy)-8-azabicyclo[3.2.1]oct-8-yl]-propyl}-1,6-dimethyl-1H-[1,3,5]triazine-2,4-dione

[Chemical Formula 141]

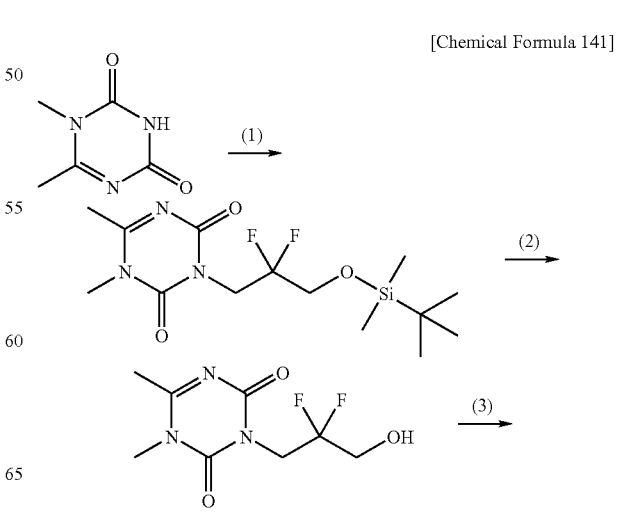

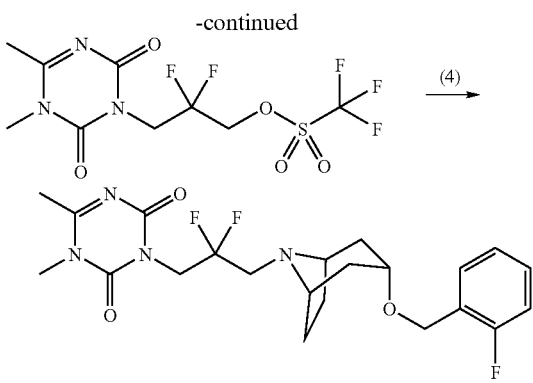

(1) 3-[3-(tert-Butyl-dimethyl-silanyloxy)-2,2-difluoro-propyl]-1,6-dimethyl-1H-[1,3,5]triazine-2,4-dione The title compound (476 mg) was obtained from the compound obtained in Example 12-(1) (265 mg) and the compound obtained in Production Example 68 (741 mg), by the method similar to Example 1-(1).

$^1$H-NMR (400 MHz, CDCl$_3$); δ 0.09 (s, 6H), 0.90 (s, 9H), 2.47 (s, 3H), 3.4.8 (s, 3-H), 3.84-3.90 (m, 2H), 4.47-4.54 (m, 2H).

(2) 3-(2,2-Difluoro-3-hydroxypropyl)-1,6-dimethyl-1H-[1,3,5]triazine-2,4-dione

The compound obtained in Example 22-(1) (476 mg) was dissolved in tetrahydrofuran (5 ml), and then tetra-n-butylammonium fluoride (1 M solution in tetrahydrofuran, 1.6 ml) was added and the mixture was stirred at room temperature for 15 hours. The reaction mixture was concentrated under reduced pressure, and the residue was purified by silica gel column chromatography to obtain the title compound (43 mg).

$^1$H-NMR (400 MHz, CD$_3$OD); δ 2.52 (s, 3H), 3.52 (s, 3H), 3.54-3.57 (m, 1H), 3.64-3.72 (m, 2H), 4.44-4.50 (m, 2H).

(3) Trifluoromethanesulfonic acid 3-(3,4-dimethyl-2,6-dioxo-3,6-dihydro-2H-[1,3,5]triazin-1-yl)-2,2-difluoropropyl ester The compound obtained in Example 22-(2) (41 mg) was dissolved in dichloromethane (1 ml), and pyridine (0.11 ml) was added. Trifluoromethanesulfonic anhydride (0.035 ml) was added while stirring on ice, and the temperature was gradually raised to room temperature. After stirring for 3 hours and 30 minutes, 1N hydrochloric acid and ethyl acetate were added to the reaction mixture and the organic layer was separated. The organic layer was washed with water and brine in that order and then dried over anhydrous magnesium sulfate. After filtration, the solvent was distilled off under reduced pressure to obtain the title compound (67 mg).

$^1$H-NMR (400 MHz, CDCl$_3$); δ 2.52 (s, 3H), 3.51 (s, 3H), 4.48-4.54 (m, 2H), 4.63-4.69 (m, 2H).

(4) (Endo)-3-{2,2-difluoro-3-[3-(2-fluorobenzyloxy)-8-azabicyclo[3.2.1]oct-8-yl]propyl}-1,6-dimethyl-1H-[1,3,5]triazine-2,4-dione A mixture of the compound obtained in Example 22-(3) (67 mg), the compound obtained in Production Example 5 (49 mg), anhydrous potassium carbonate (68 mg) and N,N-dimethylformamide (1 ml) was stirred at room temperature for 119 hours and 30 minutes. The reaction mixture was concentrated under reduced pressure, and the residue was purified by preparative thin-layer chromatography to obtain the title compound (12 mg).

$^1$H-NMR (400 MHz, CD$_3$OD); δ 1.80-2.08 (m, 8H), 2.46 (s, 3H), 2.76-2.83 (m, 2H), 3.21 (bs, 2H), 3.46 (s, 3H), 3.61-3.64 (1H), 4.49 (s, 2H), 4.52-4.59 (m, 2H), 7.02-7.07 (m, 1H), 7.12-7.17 (m, 1H), 7.26-7.31 (m, 1H), 7.41-7.45 (m, 1H).

Example 23

(Endo)-2-{(R)-2-fluoro-3-[3-(3-fluorobenzyloxy)-8-azabicyclo[3.2.1]oct-8-yl]propyl}-5-methyl-4-(1-methyl-1H-pyrazol-3-yl)-2,4-dihydro[1,2,4]triazol-3-one oxalate

[Chemical Formula 142]

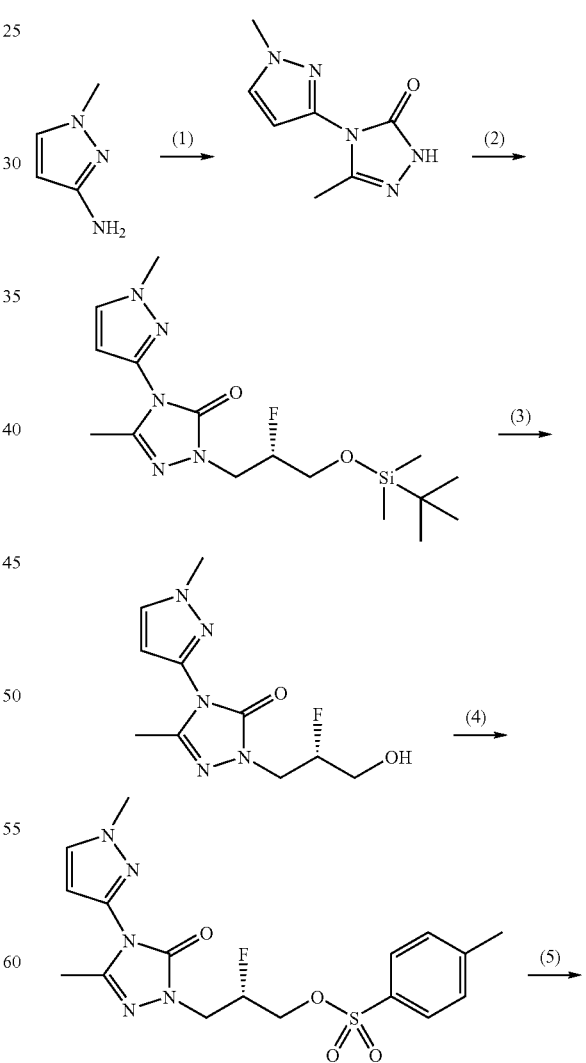

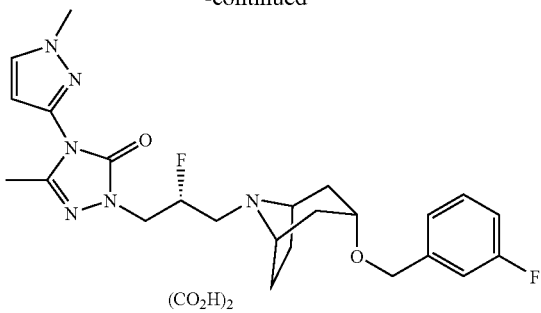

(CO₂H)₂

(1) 55-Methyl-4-(1-methyl-1H-pyrazol-3-yl)-2,4-dihydro[1,2,4]triazol-3-one

A mixture of 1-methyl-1H-pyrazol-3-yl-amine (CAS 1904-31-0) (34.8 g), N'-[1-ethoxy-ethylidene]-hydrazinecarboxylic acid ethyl ester (CAS 58910-28-4) (19.4 g) and N,N-dimethylformamide (100 ml) was stirred at 130° C. for 14 hours, and then at 150° C. for 5 hours. The reaction mixture was concentrated under reduced pressure, and the obtained solid wars washed with ethyl acetate and diethyl ether to obtain the title compound (17.1 g).
$^1$H-NMR (400 MHz, DMSO-$d_6$); δ 2.13 (s, 3H), 3.86 (s, 3H), 6.42 (m, 1H), 7.80 (m, 1H), 11.59 (br, 1H).

(2) 2-[(S)-3-(tert-Butyl-dimethyl-silanyloxy)-2-fluoropropyl]-5-methyl-4-(1-methyl-1H-pyrazol-3-yl)-2,4-dihydro[1,2,4]triazol-3-one The compound obtained in Example 23-(i) (1.0 g) was dissolved in N,N-dimethylformamide (30 ml), and then sodium hydride (60% in oil) (245 mg) was added while stirring on ice. After stirring for 15 minutes, the compound obtained in Production Example 65 (1.9 g) was added in gradual portions. Stirring was then continued for 1 hour at room temperature, the reaction mixture was diluted with ethyl acetate, and ice water was added. The organic layer was separated and washed with water and brine. The extract was dried over anhydrous magnesium sulfate and filtered, and then the solvent was distilled off under reduced pressure. The residue was purified by silica gel column chromatography to obtain the title compound (1.56 g).
$^1$H-NMR (400 MHz, CDCl₃); δ 0.08 (s, 6H), 0.91 (s, 9H), 2.31 (s, 3H), 3.78-4.20 (m, 4H), 3.91 (s, 3H), 4.81-4.96 (m, 1H), 6.49 (m, 1H), 7.40 (m, 1H).

(3) 2-((S)-2-Fluoro-3-hydroxypropyl)-5-methyl-4-(1-methyl-1H-pyrazol-3-yl)-2,4-dihydro[1,2,4]triazol-3-one The title compound (903 mg) was obtained from the compound obtained in Example 23-(2) (1.56 g), by the method similar to Example 12-(3).
$^1$H-NMR (400 MHz, CDCl₃); δ 2.31 (s, 3H), 3.71-3.85 (m, 2H), 3.92 (s, 3H), 4.10-4.27 (m, 2H), 4.75-4.91 (m, 1H), 6.46-6.47 (m, 1H), 7.41-7.42 (m, 1H).

(4) Toluene-4-sulfonic acid (S)-2-fluoro-3-[3-methyl-4-(1-methyl-1H-pyrazol-3-yl)-5-oxo-4,5-dihydro[1,2,4]triazol-1-yl]propyl ester The compound obtained in Example 23-(3) (903 mg) was dissolved in acetonitrile (10 ml), and then triethylamine (0.99 ml) and trimethylamine hydrochloride (34 mg) were added. After then adding p-toluenesulfonyl chloride (1.01 g) while cooling on ice, the mixture was stirred for 1 hour. The reaction mixture was concentrated under reduced pressure, and the residue was purified by silica gel column chromatography to obtain the title compound (1.31 g).
$^1$H-NMR (400 MHz, CDCl₃); δ 2.28 (s, 3H), 2.45 (s, 3H), 3.91 (s, 3H), 3.89-4.39 (m, 4H), 4.94-5.07 (m, 1H), 6.46-6.47 (m, 1H), 7.34-7.36 (m, 2H), 7.40-7.41 (m, 1H), 7.81-7.83 (m, 2H).

(5) (Endo)-2-{(R)-2-fluoro-3-[3-(3-fluorobenzyloxy)-8-azabicyclo[3.2.1]oct-8-yl]propyl}-5-methyl-4-(1-methyl-1H-pyrazol-3-yl)-2,4-dihydro[1,2,4]triazol-3-one oxalate A mixture of the compound obtained in Example 23-(4) (226 mg), the compound obtained in Production Example 2 (150 mg), anhydrous potassium carbonate (233 mg), sodium iodide (83 mg) and N,N-dimethylformamide (7.5 ml) was stirred at 50° C. for 18 hours. The reaction mixture was filtered with Celite, and the filtrate was concentrated under reduced pressure. Water was added to the residue, and extraction was performed with chloroform. The extract was dried over anhydrous magnesium sulfate and filtered, and then the solvent was distilled off under reduced pressure. The residue was purified by preparative thin-layer chromatography to obtain the free form of the title compound (127 mg).
This was dissolved in ethanol, oxalic acid (24 mg) was added, and the mixture was concentrated under reduced pressure. The precipitate was collected by filtration and washed with diethyl ether. The title compound (133 mg) was thus obtained.
$^1$H-NMR (400 MHz, CD₃OD); δ 2.23-2.51 (m, 1H), 3.47-3.55 (m, 2H), 3.78 (br, 1H), 3.92 (s, 3H), 4.06-4.15 (m, 4H), 4.55 (s, 2H), 5.30-5.43 (m, 1H), 6.45-6.46 (m, 1H), 6.99-7.17 (m, 3H), 7.33-7.38 (m, 1H), 7.70-7.71 (m, 1H).

Example 24

(Endo)-2-{(S)-2-fluoro-3-[3-(4-fluorobenzyloxy)-8-azabicyclo[3.2.1]oct-8-yl]propyl}-5-methyl-4-(1-methyl-1H-pyrazol-3-yl)-2,4-dihydro[1,2,4]triazol-3-one oxalate

[Chemical Formula 143]

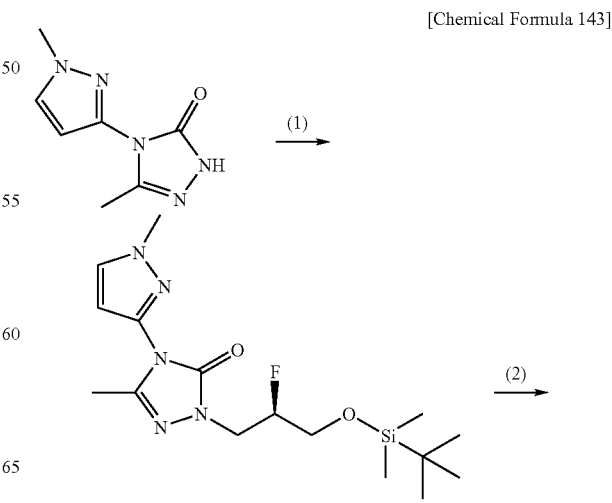

-continued

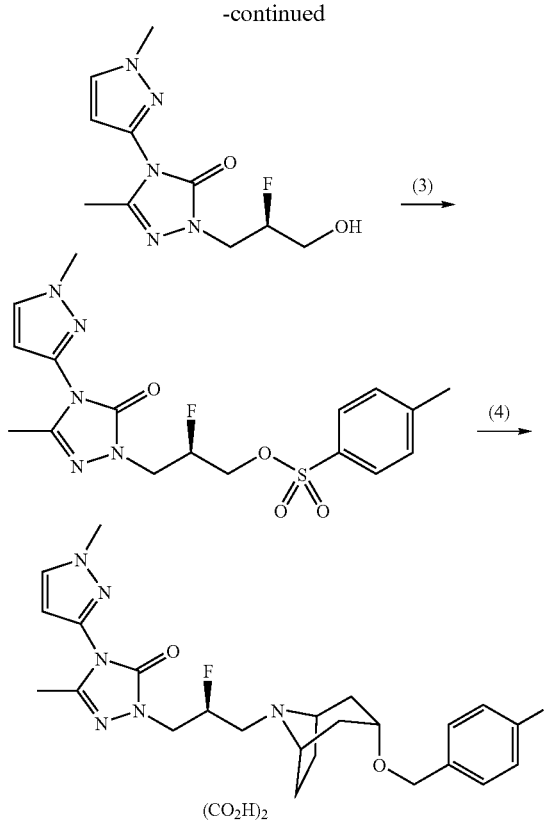

(1) 2-[(R)-3-(tert-Butyl-dimethyl-silanyloxy)-2-fluoropropyl]-5-methyl-4-(1-methyl-1H-pyrazol-3-yl)-2,4-dihydro[1,2,4]triazol-3-one The title compound (1.66 g) was obtained from the compound obtained in Example 23-(1) (1.0 g) and the compound obtained in Production Example 64 (1.9 g), by the method similar to Example 23-(2).
$^1$H-NMR (400 MHz, CDCl$_3$); δ 0.08 (s, 6H), 0.91 (s, 9H), 2.31 (s, 3H), 3.78-4.20 (m, 4H), 3.91 (s, 3H), 4.81-4.96 (m, 1H), 6.49 (m, 1H), 7.40 (m, 1H).

(2) 2-((R)-2-Fluoro-3-hydroxypropyl)-5-methyl-4-(1-methyl-1H-pyrazol-3-yl)-2,4-dihydro[1,2,4]triazol-3-one The title compound (1.05 g) was obtained from the compound obtained in Example 24-(1) (1.66 g), by the method similar to Example 12-(3).
$^1$H-NMR (400 MHz, CDCl$_3$); δ 2.31 (s, 3H), 3.71-3.83 (m, 2H), 3.92 (s, 3H), 4.10-4.27 (m, 2H), 4.75-4.91 (m, 1H), 6.47-6.48 (m, 1H), 7.43 (m, 1H).

(3) Toluene-4-sulfonic acid (R)-2-fluoro-3-[3-methyl-4-(1-methyl-1H-pyrazol-3-yl)-5-oxo-4,5-dihydro[1,2,4]triazol-1-yl]propyl ester The title compound (1.35 g) was obtained from the compound obtained in Example 24-(2) (1.05 g) and p-toluenesulfonyl chloride, by the method similar to Example 23-(4).
$^1$H-NMR (400 MHz, CDCl$_3$); δ 2.28 (s, 3H), 2.45 (s, 3H), 3.91 (s, 3H), 3.89-4.39 (m, 4H), 4.94-5.07 (m, 1H), 6.46-6.47 (m, 1H), 7.34-7.36 (m, 2H), 7.40-7.41 (m, 1H), 7.81-7.83 (m, 2H).

(4) (Endo)-2-{(S)-2-fluoro-3-[3-(4-fluorobenzyloxy)-8-azabicyclo[3.2.1]oct-8-yl]propyl}-5-methyl-4-(1-methyl-1H-pyrazol-3-yl)-2,4-dihydro[1,2,4]triazol-3-one oxalate The title compound (133 mg) was obtained from the compound obtained in Example 24-(3) (226 mg) and the compound obtained in Production Example 1 (150 mg), by the method similar to Example 23-(5).
$^1$H-NMR (400 MHz, CD$_3$OD); δ 2.23-2.51 (m, 11H), 3.47-3.55 (m, 2H), 3.78 (br, 1H), 3.92 (s, 3H), 4.06-4.15 (m, 4H), 4.55 (s, 2H), 5.30-5.43 (m, 1H), 6.45-6.46 (m, 1H), 6.99-7.17 (m, 3H), 7.33-7.38 (m, 1H), 7.70-7.71 (m, 1H).

Example 25

(Endo)-5-dimethylamino-2-{2-fluoro-3-[3-(3-methylbenzyloxy)-8-azabicyclo[3.2.1]oct-8-yl]propyl}-4-methyl-2,4-dihydro[1,2,4]triazol-3-one

[Chemical Formula 144]

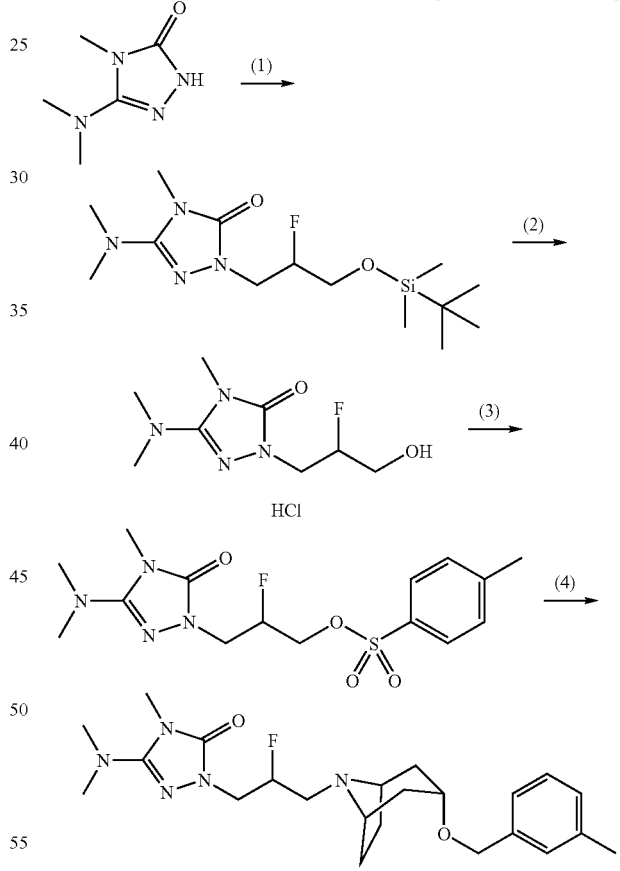

(1) 2-[3-(tert-Butyldimethylsilanyloxy)-2-fluoropropyl]-5-dimethylamino-4-methyl-2,4-dihydro[1,2,4]triazol-3-one After dissolving 5-dimethylamino-4-methyl-2,4-dihydro[1,2,4]triazol-3-one (CAS 118846-73-4) (1.5 g) in N,N-dimethylformamide (30 ml), sodium hydride (60% in oil) (469 mg) was added while stirring on ice. A solution of the compound obtained in Production Example 66 (4.15 g) in N,N- dimethylformamide was added, and the mixture was stirred at room temperature for 2 hours. Ethyl acetate and a saturated aqueous solution of ammonium chloride were added to the reaction mixture, and the organic layer was separated. The extract was dried over anhydrous magnesium sulfate and filtered, and then the solvent was distilled off under reduced pressure. The residue was purified by silica gel column chromatography to obtain the title compound (3.08 g).

$^1$H-NMR (400 MHz, CDCl$_3$); δ 0.08 (s, 3H), 0.08 (s, 3H), 0.90 (s, 9H), 2.77 (s, 6H), 3.21 (s, 3H), 3.76-3.92 (m, 3H), 4.08 (dt, J=7.6, 14.8 Hz, 1H), 4.85 (m, 1H).

(2) 5-Dimethylamino-2-(2-fluoro-3-hydroxypropyl)-4-methyl-2,4-dihydro[1,2,4]triazol-3-one hydrochloride The compound obtained in Example 25-(1) (3.00 g) was dissolved in 1% HCl in ethanol (200 ml), and the mixture was stirred at room temperature for 12 hours. The reaction mixture was concentrated under reduced pressure, and the residue was recrystallized from ethyl acetate-methanol to obtain the title compound (1.78 g).

$^1$H-NMR (400 MHz, DMSO-d$_6$); δ 2.71 (s, 6H), 3.11 (s, 3H), 3.49-3.62 (m, 2H), 3.70 (ddd, 3.6, 13.6, 28.0 Hz, 1H), 3.95 (dt, J=8.4, 15.2 Hz, 1H), 4.72 (m, 1H).

(3) Toluene-4-sulfonic acid 3-(3-dimethylamino-4-methyl-5-oxo-4,5-dihydro[1.24]triazol-1-yl)-2-fluoropropyl ester The title compound (2.5 g) was obtained from the compound obtained in Example 25-(2) (1.7 g), by the method similar to Example 23-(4).

$^1$H-NMR (400 M-Hz, CDCl$_3$); δ 2.45 (s, 3H), 2.76 (s, 6H), 3.20 (s, 3H), 3.83 (ddd, J=5.2, 14.4, 19.6 Hz, 1H), 4.04 (dt, J=6.4, 15.2 Hz, 1H), 2.20 (ddd, J=6.0, 11.6, 22.0 Hz, 1H), 4.32 (ddd, J=2.8, 12.0, 24.4 Hz, 1H), 4.97 (m, 1H), 7.35 (d, J=8.0 Hz, 2H), 7.81 (d, J=8.4 Hz, 2H).

(4) (Endo)-5-dimethylamino-2-{2-fluoro-3-[3-(3-methylbenzyloxy)-8-azabicyclo[3.2.1]oct-8-yl]propyl}-4-methyl-2,4-dihydro[1,2,4]triazol-3-one A mixture of the compound obtained in Example 25-(3) (200 mg), the compound obtained in Production Example 21 (158 mg), anhydrous potassium carbonate (225 mg) and N,N-dimethylformamide (4 ml) was stirred at 60° C. for 14 hours and 30 minutes. The reaction mixture was concentrated under reduced pressure, water was added to the residue, and extraction was performed with chloroform. The extract was concentrated under reduced pressure, and the residue was purified by preparative thin-layer chromatography to obtain the title compound (94 mg).

$^1$H-NMR (400 MHz, CDCl$_3$); δ 1.86-2.09 (m, 8H), 2.35 (s, 3H), 2.60-2.71 (m, 2H), 2.77 (s, 6H), 3.17-3.23 (m, 2H), 3.21 (s, 3H), 3.60 (m, 1H), 3.93 (ddd, J=4.4, 14.8, 24.8 Hz, 1H), 4.07 (dt, J=7.2, 14.8 Hz, 1H), 4.41 (s, 2H), 4.90 (m, 1H), 7.06-7.12 (m, 3H), 7.22 (m, 1H).

Example 26

(Endo)-2-{2-fluoro-3-[3-(2-fluorobenzyloxy)-8-azabicyclo[3.2.1]oct-8-yl]propyl}-4-methyl-5-methylamino-2,4-dihydro[1,2,4]triazol-3-one

[Chemical Formula 145]

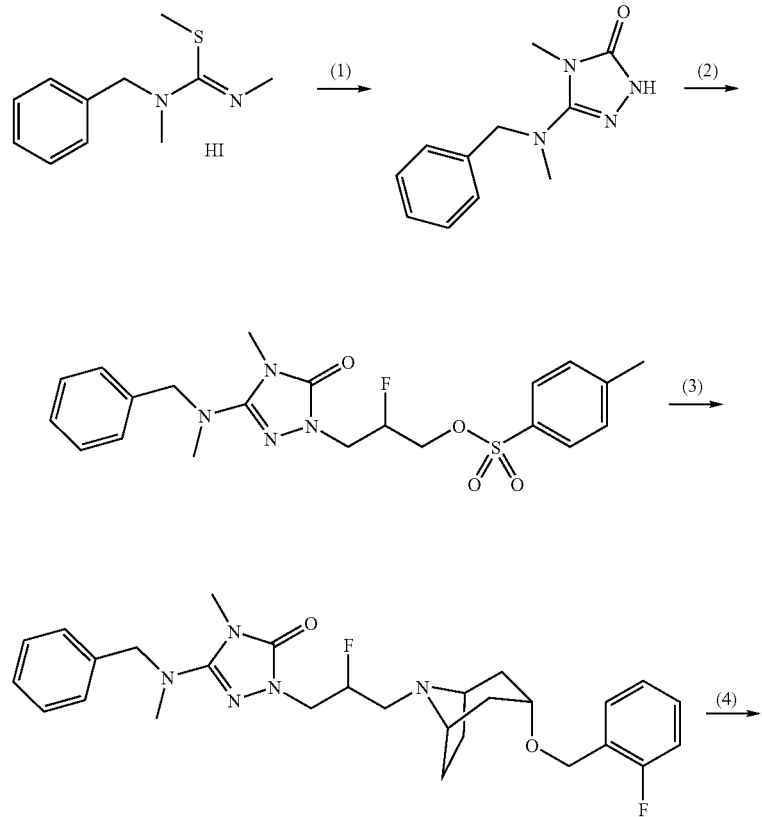

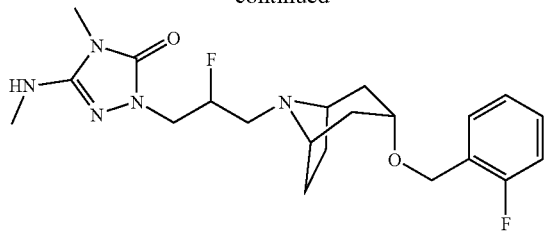

(1) 5-(Benzyl-methyl-amino)-4-methyl-2,4-dihydro[1,2,4]triazol-3-one

Hydrazine hydrate (9.41 ml) was added to a mixture of 1-benzyl-1,2,3-trimethyl-isourea hydroiodide (CAS 56043-41-5) (65.2 g) and ethanol (400 ml), and the mixture was stirred at room temperature for 4 hours. The reaction mixture was concentrated under reduced pressure, pyridine (300 ml) was added to the residue, and ethyl chloroformate (20.4 ml) was added dropwise while stirring on ice. After heating to reflux for 1 hour and 30 minutes, the reaction mixture was concentrated under reduced pressure. After then adding N,N-dimethylformamide (452 ml) to the residue, the mixture was stirred at 150° C. for 17 hours. The reaction mixture was concentrated under reduced pressure, ethyl acetate was added to the residue, and the mixture was filtered. The filtrate was concentrated under reduced pressure and the residue was purified by silica gel column chromatography. The obtained solid was recrystallized from diethyl ether-n-heptane to obtain the title compound (17.2 g).

$^1$H-NMR (400 MHz, DMSO-$d_6$); δ 2.59 (s, 3H), 3.12 (s, 3H), 4.17 (s, 2H), 7.27-7.38 (m, 5H), 10.96 (br, 1H).

(2) Toluene-4-sulfonic acid 3-[3-(benzyl-methyl-amino)-4-methyl-5-oxo-4,5-dihydro[1,2,4]triazol-1-yl-2-fluoropropyl ester The compound obtained in Example 26-(1) (1.7 g) was dissolved in N,N-dimethylformamide (60 ml), and then anhydrous cesium carbonate (5.08 g) and sodium iodide (1.17 g) were added and an solution of the compound obtained in Production Example 66 (3.0 g) in N,N-dimethylformamide was added dropwise. Stirring was then carried out at room temperature for 1 hour and 30 minutes and then at 60° C. for 17 hours. Water was added to the reaction mixture, and extraction was performed with ethyl acetate and chloroform. The organic layer was washed with water and then dried over anhydrous magnesium sulfate. After filtration, the solvent was distilled off under reduced pressure.

The residue was dissolved in 1% HCl in ethanol and the solution was stirred at room temperature for 1 hour and 30 minutes. The reaction mixture was concentrated under reduced pressure.

The residue was treated by the method similar to Example 1-(3) to obtain the title compound (1.65 g).

$^1$H-NMR (400 MHz, CDCl$_3$); δ 2.44 (s, 3H), 2.67 (s, 3H), 3.23 (s, 3H), 3.86 (ddd, J=5.6, 14.8, 19.2 Hz, 1H), 4.05 (dt, J=6.4, 14.8 Hz, 1H), 4.17 (s, 2H), 4.18 (m, 1H), 4.31 (ddd, J=2.8, 11.6, 24.4 Hz, 1H), 4.95 (m, 1H), 7.29-7.39 (m, 7H), 7.81 (m, 2H).

(3) 5-(Benzyl-methyl-amino)-2-{2-fluoro-3-[3-(2-fluorobenzyloxy)-8-azabicyclo[3.2.1]oct-8-yl]propyl}-4-methyl-2,4-dihydro[1,2,4]triazol-3-one A mixture of the compound obtained in Example 26-(2) (100 mg), the compound obtained in Production Example 57 (67 mg), anhydrous potassium carbonate (62 mg) and N,N-dimethylformamide (2 ml) was stirred at 50° C. for 11 hours and 30 minutes. A saturated aqueous solution of sodium hydrogencarbonate was added to the reaction mixture, and extraction was performed with ethyl acetate. The organic layer was washed with water and brine in that order. The extract was dried over anhydrous magnesium sulfate and filtered, and then the solvent was distilled off under reduced pressure. The residue was purified by silica gel column chromatography to obtain the title compound (26 mg).

$^1$H-NMR (400 MHz, CDCl$_3$); δ 1.79-2.60 (m, 8H), 2.60-2.65 (m, 2H), 2.68 (s, 3H), 3.19 (m, 2H), 3.24 (s, 3H), 3.62 (m, 1H), 3.95 (ddd, J=4.0, 14.8, 25.2 Hz, 1H), 4.09 (dt, J=7.2, 15.2 Hz, 1H), 4.19 (s, 2H), 4.50 (s, 2H), 4.88 (m, 1H), 7.01 (m, 1H), 7.13 (m, 1H), 7.24 (m, 1H), 7.31-7.38 (m, 5H), 7.43 (m, 1H).

(4) (Endo)-2-{2-fluoro-3-[3-(2-fluorobenzyloxy)-8-azabicyclo[3.2.1]oct-8-yl]propyl}-4-methyl-5-methylamino-2,4-dihydro[1,2,4]triazol-3-one The compound obtained in Example 26-(3) (26 mg) was dissolved in methanol (5 ml), and then acetic acid (1 ml) and 20% palladium hydroxide on carbon (50% wet) (18 mg) were added and the mixture was stirred at room temperature for 3 hours under a hydrogen atmosphere (1 atm). The reaction mixture was diluted with ethyl acetate, and the resulting mixture was filtered. The filtrate was concentrated under reduced pressure, a saturated aqueous solution of sodium hydrogencarbonate was added to the residue and the mixture was extracted with ethyl acetate. The organic layer was separated and dried over anhydrous magnesium sulfate. After filtration, the solvent was distilled off under reduced pressure to obtain the title compound (21 mg).

$^1$H-NMR (400 MHz, CDCl$_3$); δ 1.86-2.09 (m, 8H), 2.62-2.69 (m, 2H), 2.90 (d, J=5.6 Hz, 3H), 3.11 (s, 3H), 3.21-3.25 (m, 2H), 3.60 (m, 1H), 3.63 (m, 1H), 3.91 (ddd, J=4.0, 14.8, 24.4 Hz, 1H), 4.06 (dt, J=7.2, 14.8 Hz, 1H), 4.50 (s, 2H), 4.93 (m, 1H), 7.01 (m, 1H), 7.13 (m, 1H), 7.24 (m, 1H), 7.43 (m, 1H).

Example 27

(Endo)-2-{2-hydroxy-3-[3-(2-methoxymethylbenzyloxy)-8-azabicyclo[3.2.1]oct-8-yl]propyl}-4,5-dimethyl-2,4-dihydro[1,2,4]triazol-3-one

[Chemical Formula 146]

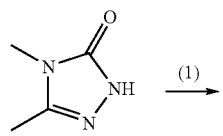

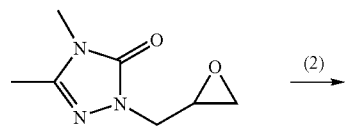

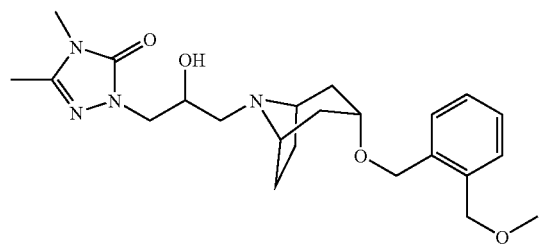

(1) 4,5-Dimethyl-2-oxiranylmethyl-2,4-dihydro[1,2,4]triazol-3-one

After dissolving 4,5-dimethyl-2,4-dihydro[1,2,4]triazol-3-one (CAS 54770-19-3) (560 mg) in N,N-dimethylformamide (5 ml), sodium hydride (60% in oil) (238 mg) and epibromohydrin (0.85 ml) were added and the mixture was stirred at room temperature for one day. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography to obtain the title compound (390 mg).

$^1$H-NMR (400 MHz, CDCl$_3$); δ 2.21 (s, 3H), 2.67 (dd, J=4.8, 2.8 Hz, 1H), 2.82 (t, J=4.8 Hz, 1H), 3.20-3.26 (m, 1H), 3.22 (s, 3H), 3.87 (dd, J=14.8, 5.6 Hz, 1H), 3.97 (dd, J=14.8, 4.8 Hz, 1H).

(2) (Endo)-2-{2-hydroxy-3-[3-(2-methoxymethylbenzyloxy)-8-azabicyclo[3.2.1]oct-8-yl]propyl}-4,5-dimethyl-2,4-dihydro[1,2,4]triazol-3-one A mixture of the compound obtained in Example 27-(1) (60 mg), the compound obtained in Production Example 9 (106 mg), anhydrous potassium carbonate (103 mg) and N,N-dimethylformamide (1.2 ml) was stirred at 100° C. for one day. The reaction mixture was diluted with dichloromethane-methanol (10:1) and filtered with NH silica gel. The filtrate was concentrated under reduced pressure, a saturated aqueous solution of sodium hydrogencarbonate was added to the residue and the mixture was extracted with ethyl acetate. The organic layer was washed with water and brine in that order. The extract was dried over anhydrous magnesium sulfate and filtered, and then the solvent was distilled off under reduced pressure. The residue was purified by preparative thin-layer chromatography to obtain the title compound (80 mg).

$^1$H-NMR (400 MHz, CD$_3$OD); δ 1.84-2.10 (m, 8H), 2.23 (s, 3H), 2.40-2.51 (m, 2H), 3.14-3.29 (m, 2H), 3.22 (s, 3H), 3.60-3.64 (m, 1H), 3.72-3.83 (m, 2H), 3.96-4.03 (m, 1H), 4.51 (s, 2H), 4.52 (s, 2H), 7.22-7.30 (m, 2H), 7.32-7.35 (m, 1H), 7.38-7.41 (m, 1H).

Example 28

(Endo)-2-{2-fluoro-3-[3-(2-methoxymethylbenzyloxy)-8-azabicyclo[3.2.1]oct-8-yl]propyl}-4,5-dimethyl-2,4-dihydro[1,2,4]triazol-3-one

[Chemical Formula 147]

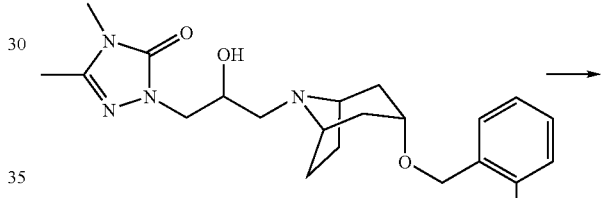

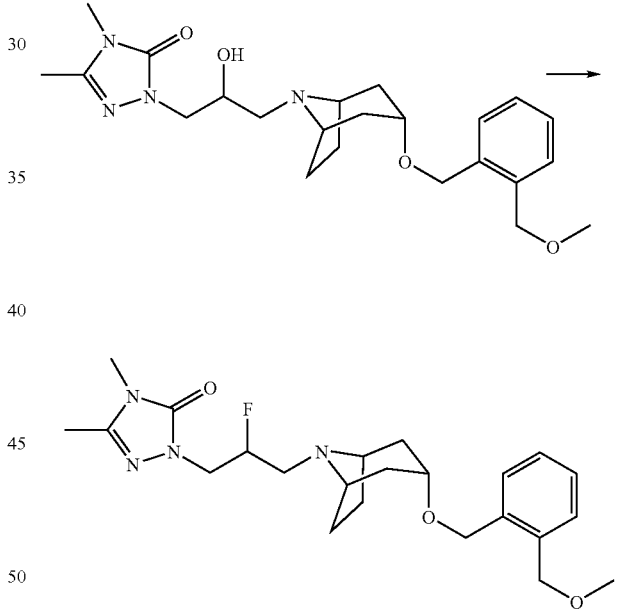

The compound obtained in Example 27 (70 mg) was dissolved in dichloromethane (1.4 ml), and then dimethylaminosulfur trifluoride (33 μl) was added and the mixture was stirred at room temperature for one day. Water was added to the reaction mixture, and the extraction was performed with ethyl acetate and dichloromethane-methanol (100:1). The organic layer was washed with water and brine in that order and then dried over anhydrous magnesium sulfate. After filtration, the solvent was distilled off under reduced pressure. The residue was purified by preparative thin-layer chromatography to obtain the title compound (24 mg).

$^1$H-NMR (400 MHz, CD$_3$OD); δ 1.84-2.12 (m, 8H), 2.24 (s, 3H), 2.32 (s, 3H), 2.60-2.73 (m, 2H), 3.19-3.29 (m, 2H), 3.23 (s, 3H), 3.37 (s, 3H), 3.62 (t, J=5.2 Hz, 1H), 3.87-4.11

(m, 2H), 4.52 (s, 2H), 4.53 (s, 2H), 4.79-4.98 (m, 1H), 7.22-7.30 (m, 2H), 7.32-7.36 (m, 1H), 7.38-7.41 (m, 1H).

Example 29

(Endo)-2-{2-hydroxy-3-[3-(2-methylbenzyloxy)-8-azabicyclo[3.2.1]oct-8-yl]propyl}-4,5-dimethyl-2,4-dihydro[1,2,4]triazol-3-one

[Chemical Formula 148]

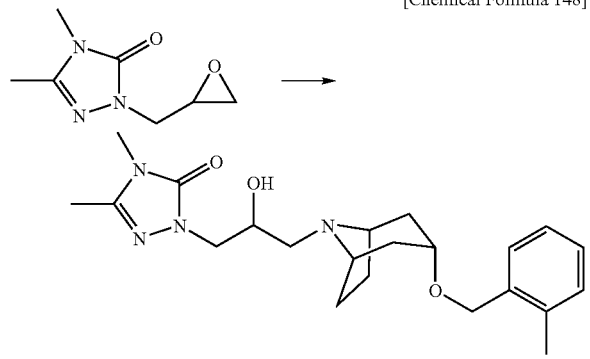

A mixture of the compound obtained in Example 27-(1) (80 mg), the compound obtained in Production Example 3 (127 mg), anhydrous potassium carbonate (137 mg) and N,N-dimethylformamide (2 ml) was stirred at 100° C. for one day. The reaction mixture was filtered and the filtrate was concentrated under reduced pressure. A saturated aqueous solution of sodium hydrogencarbonate was added to the residue and extraction was performed with ethyl acetate. The organic layer was washed with water and brine in that order and then dried over anhydrous magnesium sulfate. After filtration, the solvent was distilled off under reduced pressure. The obtained solid was washed with diethyl ether to obtain the title compound (51 mg).

$^1$H-NMR (400 MHz, CD$_3$OD); δ 1.82-2.14 (m, 8H), 2.23 (s, 3H), 2.31 (s, 3H), 2.43-2.55 (m, 2H), 3.19-3.36 (m, 2H), 3.23 (s, 3H), 3.64 (t, J=4.8 Hz, 1H), 3.75 (dd, J=14.0, 6.8 Hz, 1H), 3.80 (dd, J=14.0, 5.2 Hz, 1H), 3.98-4.05 (m, 1H), 4.44 (s, 2H), 7.10-7.18 (m, 3H), 7.27-7.31 (m, 1H).

Example 30

(Endo)-2-{(S)-2-hydroxy-3-[3-(thiophen-3-yl-methoxy)-8-azabicyclo[3.2.1]oct-8-yl]propyl}-4,5-dimethyl-2,4-dihydro[1,2,4]triazol-3-one

[Chemical Formula 149]

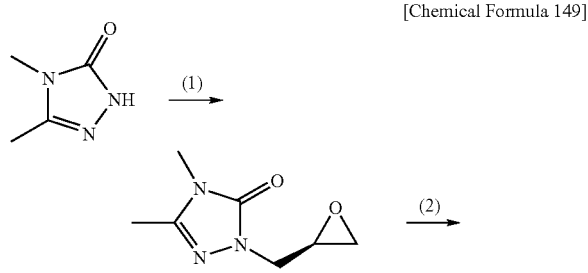

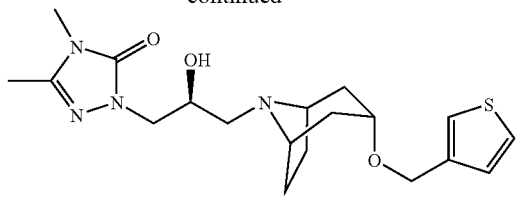

(1) 4,5-Dimethyl-2-(R)-1-oxiranylmethyl-2,4-dihydro[1,2,4]triazol-3-one

After dissolving 4,5-dimethyl-2,4-dihydro[1,2,4]triazol-3-one (CAS 54770-19-3) (4.00 g) in N,N-dimethylformamide (40 ml), sodium iodide (531 mg), sodium hydride (60% in oil) (1.7 g) and (S)-(+)-epichlorhydrin (5.65 ml) were added and the mixture was stirred at room temperature for one day. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography to obtain the title compound (3.82 g).

(2) (Endo)-2-{(S)-2-hydroxy-3-[3-(thiophen-3-yl-methoxy)-8-azabicyclo[3.2.1]oct-8-yl]propyl}-4,5-dimethyl-2,4-dihydro[1,2,4]triazol-3-one A mixture of the compound obtained in Example 30-(1) (100 mg), the compound obtained in Production Example 26 (153 mg), anhydrous potassium carbonate (171 mg) and N,N-dimethylformamide (2 ml) was stirred at 100° C. for one day. The reaction mixture was diluted with dichloromethane-methanol (10:1) and filtered with NH silica gel. The filtrate was concentrated under reduced pressure, and the obtained solid was washed with diethyl ether to obtain the title compound (139 mg).

$^1$H-NMR (400 MHz, CD$_3$OD); δ 1.81-2.12 (m, 8H), 2.23 (s, 3H), 2.39-2.52 (m, 2H), 3.13-3.28 (m, 2H), 3.22 (s, 3H), 3.59 (t, J=4.8 Hz, 1H), 3.71-3.83 (m, 2H), 3.95-4.03 (m, 1H), 4.45 (s, 2H), 7.04 (dd, J=5.2, 1.2 Hz, 1H), 7.21-7.24 (m, 1H), 7.34 (dd, J=5.2, 2.8 Hz, 1H).

Example 31

(Endo)-4-ethyl-2-{(S)-3-[3-(2-ethylbenzyloxy)-8-azabicyclo[3.2.1]oct-8-yl]-2-hydroxypropyl}-5-methyl-2,4-dihydro[1,2,4]triazol-3-one

[Chemical Formula 150]

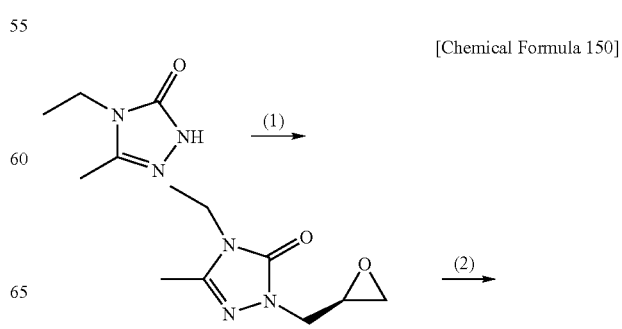

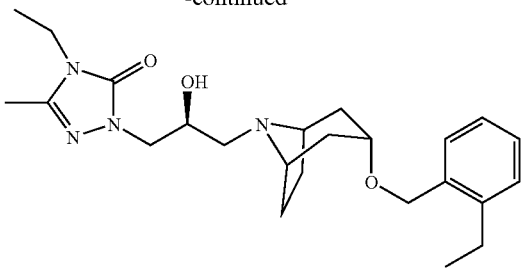

(1) 4-Ethyl-5-methyl-2-(R)-1-oxiranylmethyl-2,4-dihydro[1,2,4]triazol-3-one

After dissolving 4-ethyl-5-methyl-2,4-dihydro[1,2,4]triazol-3-one (CAS 58910-25-1) (2.00 g) in N,N-dimethylformamide (5 ml), sodium iodide (235 mg), sodium hydride (60% in oil) (238 mg) and (S)-(+)-epichlorhydrin (2.48 ml) were added and the mixture was stirred at room temperature for one day. Water was added to the reaction mixture, and extraction was performed with dichloromethane and ethyl acetate. The organic layer was washed with brine and dried over anhydrous magnesium sulfate. After filtration, the solvent was distilled off under reduced pressure. The residue was purified by silica gel column chromatography to obtain the title compound (540 mg).

$^1$H-NMR (400 MHz, CDCl$_3$); δ 1.29 (t, J=7.2 Hz, 3H), 2.24 (s, 3H), 2.67 (dd, J=4.8, 2.8 Hz, 1H), 2.84 (t, J=4.8 Hz, 1H), 3.22-3.27 (m, 1H), 3.68 (q, J=7.2 Hz, 2H), 3.86 (dd, J=14.8, 5.6 Hz, 1H), 3.96 (dd, J=14.8, 4.4 Hz, 1H).

(2) (Endo)-4-ethyl-2-{(S)-3-[3-(2-ethylbenzyloxy)-8-azabicyclo[3.2.1]oct-8-yl]-2-hydroxypropyl}-5-methyl-2,4-dihydro[1,2,4]triazol-3-one A mixture of the compound obtained in Example 31-(1) (100 mg), the compound obtained in Production Example 22 (154 mg), anhydrous potassium carbonate (158 mg) and N,N-dimethylformamide (2 ml) was stirred at 100° C. for one day. The reaction mixture was filtered and the filtrate was concentrated under reduced pressure. The residue was purified by preparative thin-layer chromatography to obtain the title compound (120 mg).

$^1$H-NMR (400 MHz, CD$_3$OD); δ 1.22 (t, J=7.6 Hz, 3H), 1.25 (t, J=7.6 Hz, 3H), 1.82-2.14 (m, 8H), 2.25 (s, 3H), 2.44-2.57 (m, 2H), 2.68 (q, J=7.6 Hz, 2H), 3.20-3.35 (m, 2H), 3.62-3.67 (m, 1H), 3.71 (q, J=7.6 Hz, 2H), 3.75-3.84 (m, 2H), 3.99-4.07 (m, 1H), 4.47 (s, 2H), 7.10-7.23 (m, 3H), 7.30 (d, J=7.6 Hz, 1H).

Example 32

(Endo)-2-{(S)-3-[3-(4-fluorobenzyloxy)-8-azabicyclo[3.2.1]oct-8-yl]-2-hydroxypropyl}-4,5-dimethyl-2,4-dihydro[1,2,4]triazol-3-one

[Chemical Formula 151]

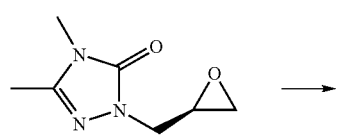

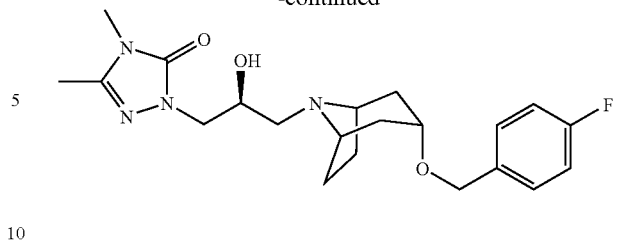

A mixture of the compound obtained in Example 30-(1) (200 mg), the compound obtained in Production Example 1 (321 mg), anhydrous potassium carbonate (343 mg) and N,N-dimethylformamide (4 ml) was stirred at 100° C. for one day. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (290 mg).

$^1$H-NMR (400 MHz, CD$_3$OD); δ 1.81-2.12 (m, 8H), 2.23 (s, 3H), 2.39-2.52 (m, 2H), 3.15-3.20 (m, 1H), 3.23 (s, 3H), 3.24-3.29 (m, 1H), 3.60 (t, J=4.8 Hz, 1H), 3.71-3.83 (m, 2H), 3.86-4.04 (m, 1H), 4.42 (s, 2H), 7.00-7.07 (m, 2H), 7.30-7.36 (m, 2H).

Example 33

(Endo)-2-{(S)-3-[3-(4-fluorobenzyloxy)-8-azabicyclo[3.2.1]oct-8-yl]-2-methoxypropyl}-4,5-dimethyl-2,4-dihydro[1,2,4]triazol-3-one

[Chemical Formula 152]

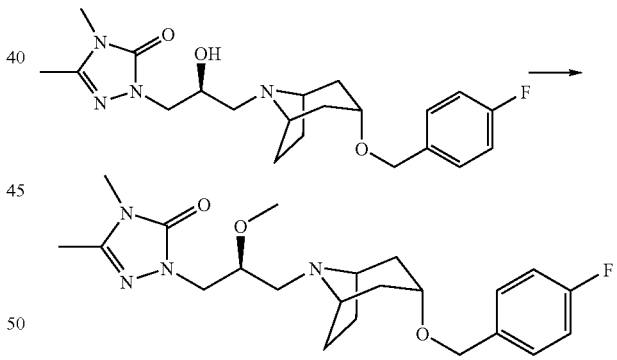

The compound obtained in Example 32 (96 mg) was dissolved in N,N-dimethylformamide (2 ml), and then sodium hydride (60% in oil) (11 mg) was added and the mixture was stirred at room temperature for 15 minutes. Methyl iodide (16 μl) was added, and stirring was continued at room temperature for one day. Water was added to the reaction mixture, and extraction was performed with ethyl acetate. The organic layer was washed with brine and dried over anhydrous magnesium sulfate. After filtration, the solvent was distilled off under reduced pressure. The residue was purified by NH silica gel column chromatography to obtain the title compound (49 mg).

$^1$H-NMR (400 MHz, CD$_3$OD); δ 1.81-2.10 (m, 8H), 2.23 (s, 3H), 2.47-2.58 (m, 2H), 3.16-3.28 (m, 2H), 3.23 (s, 3H), 3.37 (s, 3H), 3.60 (t, J=4.8 Hz, 1H), 3.62-3.68 (m, 1H), 3.80-3.91 (m, 2H), 4.42 (s, 2H), 7.00-7.07 (m, 2H), 7.30-7.35 (m, 2H).

Example 34

(Endo)-2-{(R)-3-[3-(4-fluorobenzyloxy)-8-azabicyclo[3.2.1]oct-8-yl]-2-hydroxypropyl}-5-methyl-4-(1-methyl-1H-pyrazol-4-yl)-2,4-dihydro[1,2,4]triazol-3-one

[Chemical Formula 153]

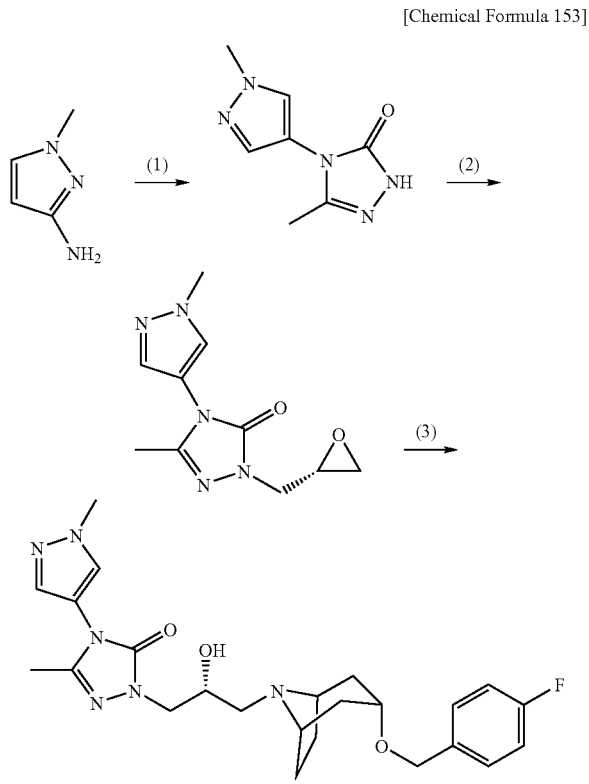

(1) 5-Methyl-4-(1-methyl-1H-pyrazol-4-yl)-2,4-dihydro[1,2,4]triazol-3-one

The title compound (18.85 g) was obtained from 1-methyl-1H-pyrazol-4-ylamine (CAS 69843-13-6) (15.5 g) and N'-[1-ethoxy-ethylidene]-hydrazinecarboxylic acid ethyl ester (CAS 58910-28-4) (33.4 g) by the method similar to Example 23-(1).

¹H-NMR (400 MHz, DMSO-d₆); δ 2.09 (s, 3H), 3.87 (s, 3H), 7.62 (s, 1H), 8.02 (s, 1H), 11.56 (br, 1H).

(2) 5-Methyl-4-(1-methyl-1H-pyrazol-4-yl)-2-(S)-1-oxiranylmethyl-2,4-dihydro[1,2,4]triazol-3-one The compound obtained in Example 34-(1) (3.5 g) and (R)-(−)-epichlorhydrin (4.6 ml) were dissolved in N,N-dimethylformamide (40 ml), and then sodium hydride (60% in oil) (936 mg) was added and the mixture was stirred at room temperature for 16 hours. The reaction mixture was concentrated under reduced pressure, a small amount of water was added to the residue, and extraction was performed with chloroform. The extract was dried over anhydrous magnesium sulfate and filtered, and then the solvent was distilled off under reduced pressure. The residue was purified by silica gel column chromatography. The obtained solid was washed with diethyl ether to obtain the title compound (3.03 g).

¹H-NMR (400 MHz, CDCl₃); δ 2.22 (s, 3H), 2.71-2.73 (m, 1H), 2.86-2.88 (m, 1H), 3.28-3.31 (m, 1H), 3.89-4.05 (m, 5H), 7.54 (s, 1H), 7.67 (s, 1H).

(3) (Endo)-2-{(R)-3-[3-(4-fluorobenzyloxy)-8-azabicyclo[3.2.1]oct-8-yl]-2-hydroxypropyl}-5-methyl-4-(1-methyl-1H-pyrazol-4-yl)-2,4-dihydro[1,2,4]triazol-3-one A mixture of the compound obtained in Example 34-(2) (200 mg), the compound obtained in Production Example 1 (173 mg), anhydrous potassium carbonate (173 mg) and N,N-dimethylformamide (10 ml) was stirred at 100° C. for 15 hours. The reaction mixture was filtered with Celite, and the filtrate was concentrated under reduced pressure. The residue was purified by silica gel column chromatography. Diethyl ether was then added to produce a solid, which was collected by filtration to obtain the title compound (105 mg).

¹H-NMR (400 MHz, CD₃OD); δ 1.87-2.08 (m, 8H), 2.17 (s, 3H), 2.44-2.54 (m, 2H), 3.19-3.29 (m, 2H), 3.59-3.62 (m, 1H), 3.76-3.87 (m, 2H), 3.94 (s, 3H), 4.02-4.08 (m, 1H), 4.42 (s, 2H), 7.02-7.06 (m, 2H), 7.32-7.35 (m, 2H), 7.63 (s, 1H), 7.90 (s, 1H).

Example 35

(Endo)-4-ethyl-2-{(S)-3-[3-(2-fluoro-6-methylbenzyloxy)-8-azabicyclo[3.2.1]oct-8-yl]-2-hydroxypropyl}-2,4-dihydro[1,2,4]triazol-3-one

[Chemical Formula 154]

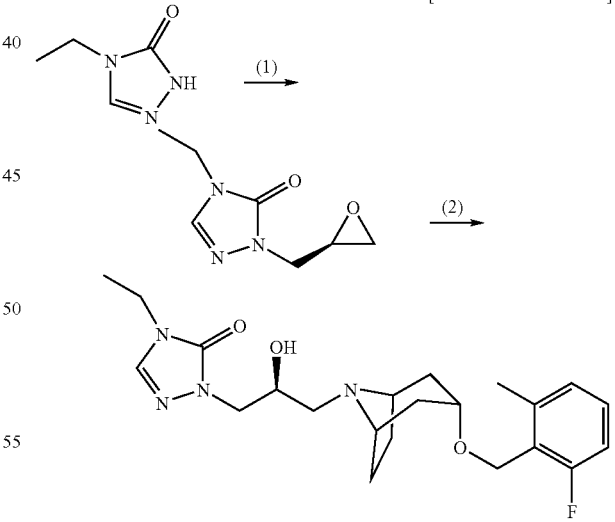

(1) 4-Ethyl-2-(R)-1-oxiranylmethyl-2,4-dihydro[1,2,4]triazol-3-one

The title compound (1.68 g) was obtained from 4-ethyl-2,4-dihydro[1,2,4]triazol-3-one (CAS 135302-04-4) (2.00 g) and (S)-(+)-epichlorhydrin by the method similar to Example 30-(1).

$^1$H-NMR (400 MHz, CDCl$_3$); δ 1.37 (t, J=7.2 Hz, 3H), 2.68 (dd, J=4.8, 2.4 Hz, 1H), 2.85 (t, J=4.8 Hz, 1H), 3.24-3.29 (m, 1H), 3.70 (q, J=7.2 Hz, 2H), 3.93 (dd, J=14.8, 5.6 Hz, 1H), 4.00 (dd, J=14.8, 4.4 Hz, 1H), 7.41 (s, 1H).

(2) (Endo)-4-ethyl-2-{(S)-3-[3-(2-fluoro-6-methyl-benzyloxy)-8-azabicyclo[3.2.1]oct-8-yl]-2-hydroxy-propyl}-2,4-dihydro[1,2,4]triazol-3-one A mixture of the compound obtained in Example 35-(1) by the method similar to Example 29 (100 mg), the compound obtained in Production Example 19 (169 mg), anhydrous potassium carbonate (172 mg) and N,N-dimethylformamide (2 ml) was stirred at 100° C. for one day. The reaction mixture was filtered and the filtrate was concentrated under reduced pressure. A saturated aqueous solution of sodium hydrogencarbonate was added to the residue and extraction was performed with ethyl acetate-dichloromethane-methanol. The organic layer was washed with water and brine in that order and then dried over anhydrous magnesium sulfate. After filtration, the solvent was distilled off under reduced pressure. The obtained solid was washed with diethyl ether to obtain the title compound (25 mg).
$^1$H-NMR (400 MHz, CD$_3$OD); δ 1.32 (t, J=7.2 Hz, 3H), 1.80-2.08 (m, 8H), 2.41 (s, 3H), 2.43-2.56 (m, 2H), 3.18-3.23 (m, 1H), 3.27-3.32 (m, 1H), 3.62 (t, J=4.8 Hz, 1H), 3.70 (q, J=7.2 Hz, 2H), 3.76-3.87 (m, 2H), 4.00-4.08 (m, 1H), 4.50 (d, J=2.0 Hz, 2H), 6.89 (t, J=8.8 Hz, 1H), 7.00 (d, J=7.2 Hz, 1H), 7.18 (td, J=8.0, 5.6 Hz, 1H), 7.82 (s, 1H).

Example 36

(Endo)-5-benzyl-4-ethyl-2-{3-[3-(2-fluorobenzyloxy)-8-azabicyclo[3.2.1]oct-8-yl]-2-hydroxypropyl}-2,4-dihydro[1,2,4]triazol-3-one

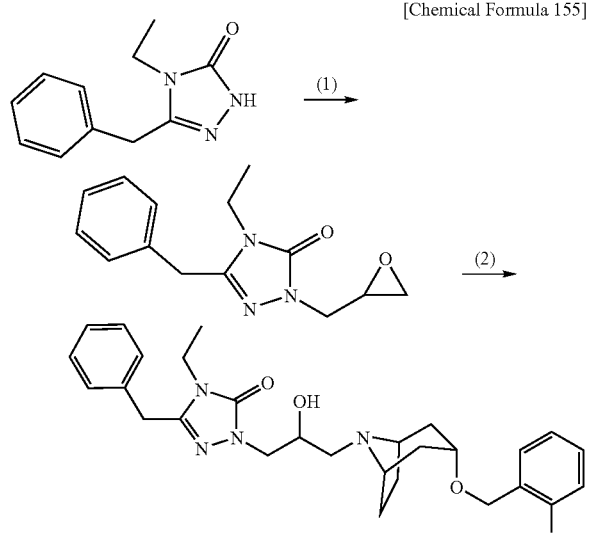

[Chemical Formula 155]

(1) 5-Benzyl-4-ethyl-2-oxiranylmethyl-2,4-dihydro[1,2,4]triazol-3-one

The title compound (2.10 g) was obtained from 5-benzyl-4-ethyl-2,4-dihydro[1,2,4]triazol-3-one (CAS 95348-09-7) (2.00 g) and epibromohydrin by the method similar to Example 27-(1).

$^1$H-NMR (400 MHz, CDCl$_3$); δ 1.01 (t, J=7.2 Hz, 3H), 2.71 (dd, J=4.4, 2.4 Hz, 1H), 2.87 (t, J=4.4 Hz, 1H), 3.27-3.32 (m, 1H), 3.50 (q, J=7.2 Hz, 2H), 3.91 (s, 2H), 3.92 (dd, J=14.8, 5.6 Hz, 1H), 4.03 (dd, J=14.8, 4.4 Hz, 1H), 7.20-7.28 (m, 5H).

(2) (Endo)-5-benzyl-4-ethyl-2-{3-[3-(2-fluorobenzyloxy)-8-azabicyclo[3.2.1]oct-8-yl]-2-hydroxypropyl}-2,4-dihydro[1,2,4]triazol-3-one A mixture of the compound obtained in Example 36-(1) (100 mg), the compound obtained in Production Example 5 (105 mg), anhydrous potassium carbonate (103 mg) and N,N-dimethylformamide (1.2 ml) was stirred at 100° C. for one day. The reaction mixture was filtered and the filtrate was concentrated under reduced-pressure. A saturated aqueous solution of sodium hydrogencarbonate was added to the residue and extraction was performed with ethyl acetate. The organic layer was washed with brine and dried over anhydrous magnesium sulfate. After filtration, the solvent was distilled off under reduced pressure. The residue was purified by preparative thin-layer chromatography to obtain the title compound (39 mg).
$^1$H-NMR (400 MHz, CD$_3$OD); δ 0.94 (t, J=7.2 Hz, 3H), 1.82-2.22 (m, 8H), 2.46-2.62 (m, 2H), 3.24-3.40 (m, 2H), 3.59 (q, J=7.2 Hz, 2H), 3.61-3.67 (m, 1H), 3.79-3.89 (m, 2H), 3.98 (s, 2H), 4.04-4.12 (m, 1H), 4.54 (s, 2H), 7.02-7.08 (m, 1H), 7.15 (td, J=7.2, 1.2 Hz, 1H), 7.24-7.36 (m, 6H), 7.42 (td, J=7.2, 1.6 Hz, 1H).

Example 37

(Endo)-2-{3-[3-(2-fluorobenzyloxy)-8-azabicyclo[3.2.1]oct-8-yl]-2-hydroxypropyl}-5-methyl-4-phenyl-2,4-dihydro[112.4]triazol-3-one

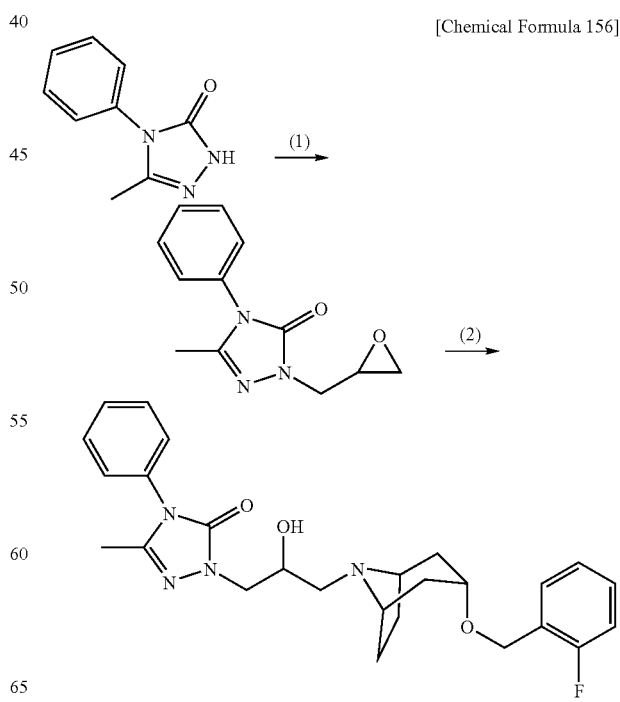

[Chemical Formula 156]

(1) 5-Methyl-2-oxiranylmethyl-4-phenyl-2,4-dihydro[1,2,4]triazol-3-one

The title compound (2.14 g) was obtained from 5-methyl-4-phenyl-2,4-dihydro[1,2,4]triazol-3-one (CAS 1010-54-4) (2.00 g) and epibromohydrin by the method similar to Example 27-(1).

¹H-NMR (400 MHz, CDCl₃); δ 2.16 (s, 3H), 2.74 (dd, J=4.4, 2.8 Hz, 1H), 2.88 (t, J=4.4 Hz, 1H), 3.30-3.35 (m, 1H), 3.93 (dd, J=14.4, 5.6 Hz, 1H), 4.05 (dd, J=14.4, 4.4 Hz, 1H), 7.28-7.32 (m, 2H), 7.41-7.53 (m, 3H).

(2) (Endo)-2-{3-[3-(2-fluorobenzyloxy)-8-azabicyclo[3.2.1]oct-8-yl]-2-hydroxypropyl}-5-methyl-4-phenyl-2,4-dihydro[1,2,4]triazol-3-one The title compound (170 mg) was obtained from the compound obtained in Example 37-(1) (100 mg) and the compound obtained in Production Example 5 (117 mg), by the method similar to Example 36-(2).

¹H-NMR (400 MHz, CD₃OD); δ 1.86-2.16 (m, 8H), 2.14 (s, 3H), 2.54 (dd, J=13.2, 7.2 Hz, 1H), 2.60 (dd, J=13.2, 4.8 Hz, 1H), 3.24-3.38 (m, 2H), 3.65 (t, J=4.8 Hz, 1H), 3.83 (dd, J=14.0, 7.2 Hz, 1H), 3.88 (dd, J=14.0, 4.8 Hz, 1H), 4.08-4.15 (m, 1H), 4.51 (s, 2H), 7.02-7.08 (m, 1H), 7.15 (td, J=7.2, 1.2 Hz, 1H), 7.26-7.32 (m, 1H), 7.36-7.40 (m, 2H), 7.44 (td, J=7.2, 2.0 Hz, 1H), 7.47-7.58 (m, 3H).

Example 38

(Endo)-2-{3-[3-(2-fluoro-6-methylbenzyloxy)-8-azabicyclo[3.2.1]oct-8-yl]-2-hydroxypropyl}-4-isopropyl-5-methyl-2,4-dihydro[1,2,4]triazol-3-one

[Chemical Formula 157]

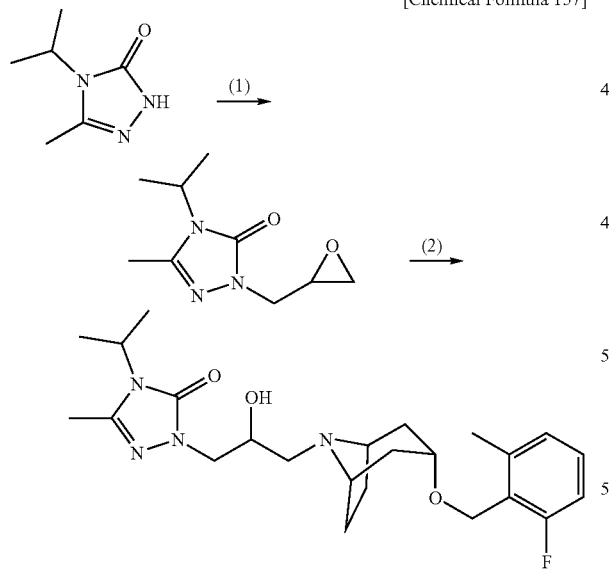

(1) 4-Isopropyl-5-methyl-2-oxiranylmethyl-2,4-dihydro[1,2,4]triazol-3-one

The title compound (1.62 g) was obtained from 4-isopropyl-5-methyl-2,4-dihydro[1,2,4]triazol-3-one (CAS 135280-76-1) (1.50 g) and epibromohydrin by the method similar to Example 27-(1).

¹H-NMR (400 MHz, CDCl₃); δ 1.47 (d, J=6.8 Hz, 6H), 2.26 (s, 3H), 2.67 (dd, J=4.4, 2.8 Hz, 1H), 2.83 (t, J=4.4 Hz, 1H), 3.21-3.26 (m, 1H), 3.83 (dd, J=14.8, 5.6 Hz, 1H), 3.93 (dd, J=14.8, 4.8 Hz, 1H), 4.20-4.31 (m, 1H).

(2) (Endo)-2-{3-[3-(2-fluoro-6-methylbenzyloxy)-8-azabicyclo[3.2.1]oct-8-yl]-2-hydroxypropyl}-4-isopropyl-5-methyl-2,4-dihydro[1,2,4]triazol-3-one The title compound (125 mg) was obtained from the compound obtained in Example 38-(1) (100 mg) and the compound obtained in Production Example 19 (145 mg), by the method similar to Example 29.

¹H-NMR (400 MHz, CD₃OD); δ 1.47 (d, J=6.8 Hz, 6H), 1.79-2.06 (m, 8H), 2.27 (s, 3H), 2.40 (s, 3H), 2.41-2.53 (m, 2H), 3.15-3.32 (m, 2H), 3.61 (t, J=4.8 Hz, 1H), 3.70 (dd, J=14.0, 7.2 Hz, 1H), 3.75 (dd, J=14.0, 5.2 Hz, 1H), 3.97-4.03 (m, 1H), 4.22-4.31 (m, 1H), 4.50 (d, J=1.6 Hz, 2H), 6.89 (t, J=8.8 Hz, 1H), 7.00 (d, J=7.6 Hz, 1H), 7.18 (td, J=7.6, 5.6 Hz, 1H).

Example 39

(Endo)-5-cyclopropyl-4-ethyl-2-{3-[3-(2-fluorobenzyloxy)-8-azabicyclo[3.2.1]oct-8-yl]-2-hydroxypropyl}-2,4-dihydro[1,2,4]triazol-3-one

[Chemical Formula 158]

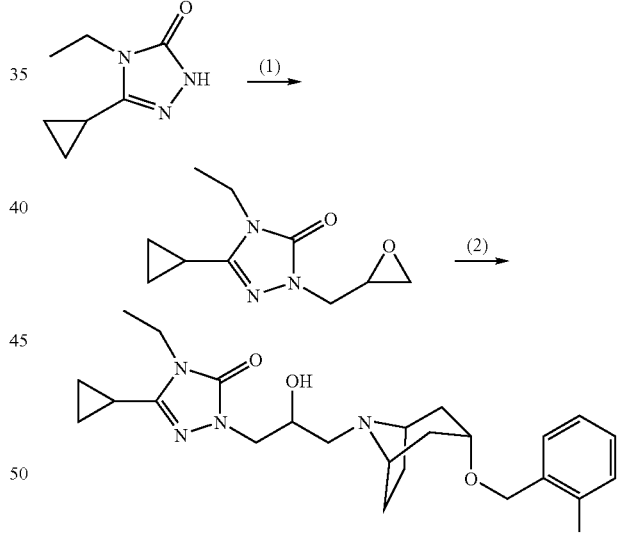

(1) 5-Cyclopropyl-4-ethyl-2-oxiranylmethyl-224-dihydro[1,2,4]triazol-3-one

The title compound (2.20 g) was obtained from 5-cyclopropyl-4-ethyl-2,4-dihydro[1,2,4]triazol-3-one (CAS 135301-78-9) (2.00 g) and epibromohydrin by the method similar to Example 27-(1).

¹H-NMR (400 MHz, CDCl₃); δ 0.94-1.00 (m, 4H), 1.34 (t, J=7.2 Hz, 3H), 1.60-1.68 (m, 1H), 2.66 (dd, J=4.8, 2.4 Hz, 1H), 2.81 (t, J=4.8 Hz, 1H), 3.20-3.25 (m, 1H), 3.80 (q, J=7.2 Hz, 2H), 3.86-3.90 (m, 2H).

(2) (Endo)-5-cyclopropyl-4-ethyl-2-{3-[3-(2-fluorobenzyloxy)-8-azabicyclo[3.2.1]oct-8-yl]-2-hydroxy-propyl}-2,4-dihydro[1,2,4]triazol-3-one The title compound (153 mg was obtained from the compound obtained in Example 39-(1) (100 mg) and the compound obtained in Production Example 5 (130 mg), by the method similar to Example 30-(2).

¹H-NMR (400 MHz, CD₃OD); δ 0.90-1.03 (m, 4H), 1.31 (t, J=7.2 Hz, 3H), 1.81-2.14 (m, 8H), 2.42-2.56 (m, 2H), 3.19-3.36 (m, 2H), 3.64 (t, J=4.8 Hz, 1H), 3.70-3.80 (m, 2H), 3.83 (q, J=7.2 Hz, 2H), 3.97-4.04 (m, 1H), 4.50 (s, 2H), 7.05 (ddd, J=9.2, 8.0, 1.2 Hz, 1H), 7.14 (td, J=7.6, 1.2 Hz, 1H), 7.26-7.33 (m, 1H), 7.42 (td, J=7.6, 2.0 Hz, 1H).

Example 40

(Endo)-4-cyclopropyl-2-{3-[3-(2-difluoromethylbenzyloxy)-8-azabicyclo[3.2.1]oct-8-yl]-2-hydroxypropyl}-5-methyl-2,4-dihydro[1,2,4]triazol-3-one

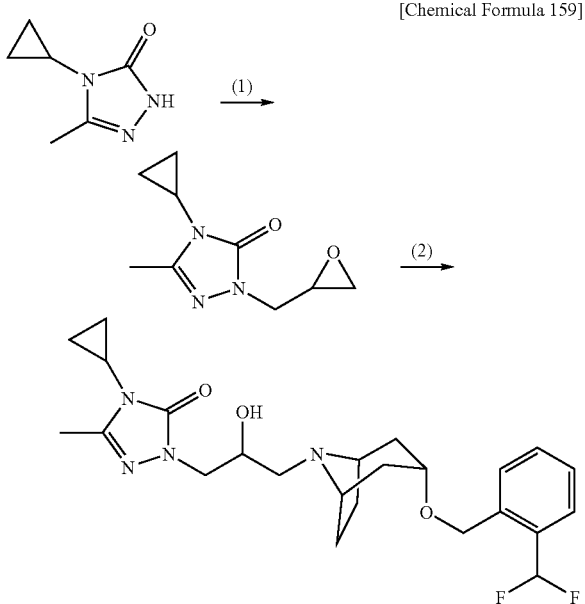

[Chemical Formula 159]

(1) 4-Cyclopropyl-5-methyl-2-oxiranylmethyl-2,4-dihydro[1,2,4]triazol-3-one The title compound (550 mg) was obtained from 4-cyclopropyl-5-methyl-2,4-dihydro[1,2,4]triazol-3-one (CAS 125835-24-7) (500 mg) and epibromohydrin by the method similar to Example 27-(1).

¹H-NMR (400 MHz, CDCl₃); δ 0.95-1.08 (m, 4H), 2.28 (s, 3H), 2.65-2.74 (m, 2H), 2.82 (t, J=4.4 Hz, 1H), 3.20-3.24 (m, 1H), 3.82 (dd, J=14.4, 5.6 Hz, 1H), 3.91 (dd, J=14.4, 4.4 Hz, 1H).

(2) (Endo)-4-cyclopropyl-2-{3-[3-(2-difluoromethylbenzyloxy)-8-azabicyclo[3.2.1]oct-8-yl]-2-hydroxypropyl}-5-methyl-2,4-dihydro[1,2,4]triazol-3-one The title compound (40 mg) was obtained from the compound obtained in Example 40-(1) (30 mg) and the compound obtained in Production Example 34 (47 mg), by the method similar to Example 36-(2).

¹H-NMR (400 MHz, CD₃OD); δ 0.92-1.07 (m, 4H), 1.90-2.22 (m, 8H), 2.30 (s, 3H), 2.60-2.84 (m, 3H), 3.31-3.61 (m, 2H), 3.67-3.71 (m, 1H), 3.72-3.79 (m, 2H), 4.05-4.13 (m, 1H), 4.63 (s, 2H), 7.00 (t, J=15.2 Hz, 1H), 7.38-7.52 (m, 3H), 7.58 (d, J=7.2 Hz, 1H).

Example 41

(Endo)-2-{3-[3-(2-fluorophenoxymethyl)-8-azabicyclo[3.2.1]oct-8-yl]-2-hydroxypropyl}-4,5-dimethyl-2,4-dihydro[1,2,4]triazol-3-one

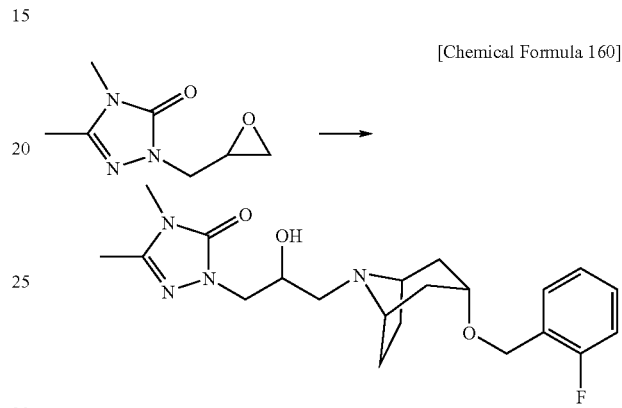

[Chemical Formula 160]

The title compound (92 mg) was obtained from the compound obtained in Example 27-(1) (60 mg) and the compound obtained in Production Example 17 (97 mg), by the method similar to Example 30-(2).

¹H-NMR (400 MHz, CD₃OD); δ 1.56-1.66 (m, 4H), 1.98-2.22 (m, 5H), 2.24 (s, 3H), 2.45 (dd, J=13.2, 7.2 Hz, 1H), 2.51 (dd, J=13.2, 4.8 Hz, 1H), 3.20-3.25 (m, 2H), 3.23 (s, 3H), 3.76 (dd, J=14.0, 7.2 Hz, 1H), 3.82 (dd, J=14.0, 5.2 Hz, 1H), 3.97-4.04 (m, 3H), 6.86-6.92 (m, 1H), 7.03-7.09 (m, 3H).

Example 42

(Endo)-4-ethyl-2-{3-[3-(2-fluoro-6-methylbenzyloxy)-8-azabicyclo[3.2.1]oct-8-yl]-2-hydroxypropyl}-5-methoxymethyl-2,4-dihydro[1,2,4]triazol-3-one

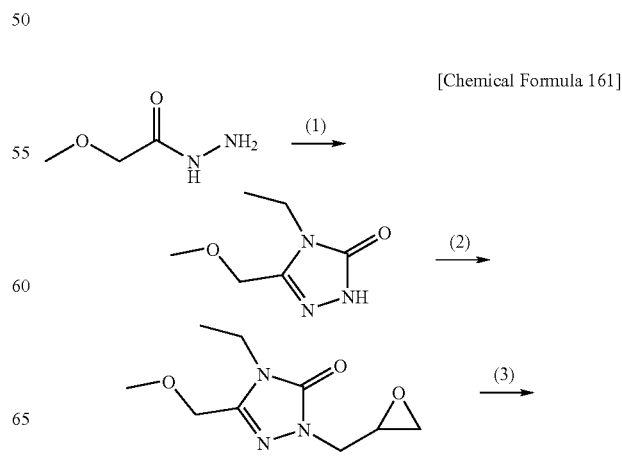

[Chemical Formula 161]

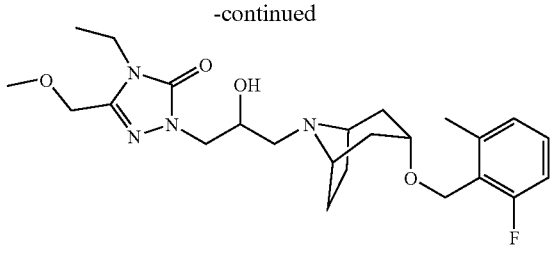

(1) 4-Ethyl-5-methoxymethyl-2,4-dihydro[1,2,4]triazol-3-one

Methoxyacetic acid hydrazide (3.0 g) was heated and dissolved in toluene (60 ml), and then ethyl isocyanate (2.56 ml) was added dropwise. After stirring for at room temperature for one day, the reaction mixture was concentrated under reduced pressure. The residue was added to a 2% aqueous solution of potassium hydroxide (100 ml) that had been heated to 95° C., and the mixture was stirred at 95° C. for 45 minutes. After cooling to room temperature, concentrated hydrochloric acid (2.9 ml) was added and the mixture was stirred at room temperature for one day. Silica gel was then added to the reaction mixture, and it was concentrated under reduced pressure and purified by silica gel column chromatography. The obtained solid was washed with diethyl ether to obtain the title compound (3.56 g).

$^1$H-NMR (400 MHz, DMSO-$d_6$); δ 1.14 (t, J=7.2 Hz, 3H), 3.24 (s, 3H), 3.58 (q, J=7.2 Hz, 2H), 4.29 (s, 2H), 11.62 (bs, 1H).

(2) 4-Ethyl-5-methoxymethyl-2-oxiranylmethyl-2,4-dihydro[1,2,4]triazol-3-one The title compound (1.16 g) was obtained from the compound obtained in Example 42-(1) (1.00 g) and epibromohydrin, by the method similar to Example 27-(1).

$^1$H-NMR (400 MHz, CDCl$_3$); δ 1.31 (t, J=7.2 Hz, 3H), 2.66-2.69 (m, 1H), 2.84 (t, J=4.4 Hz, 1H), 3.22-3.28 (m, 1H), 3.36 (s, 3H), 3.77 (q, J=7.2 Hz, 2H), 3.89 (dd, J=14.4, 5.6 Hz, 1H), 4.00 (dd, J=14.4, 4.4 Hz, 1H).

(3) (Endo)-4-ethyl-2-{3-[3-(2-fluoro-6-methylbenzyloxy)-8-azabicyclo[3.2.1]oct-8-yl]-2-hydroxypropyl}-5-methoxymethyl-2,4-dihydro[1,2,4]triazol-3-one The title compound (159 mg) was obtained from the compound obtained in Example 42-(2) (100 mg) and the compound obtained in Production Example 19 (134 mg), by the method similar to Example 30-(2).

$^1$H-NMR (400 MHz, CD$_3$OD); δ 1.28 (t, J=7.2 Hz, 3H), 1.77-2.05 (m, 8H), 2.41 (s, 3H), 2.40-2.46 (m, 1H), 2.49 (dd, J=12.8, 4.8 Hz, 1H), 3.13-3.18 (m, 1H), 3.22-3.27 (m, 1H), 3.36 (s, 3H), 3.60 (t, J=5.2 Hz, 1H), 3.77 (q, J=7.2 Hz, 2H), 3.76-3.81 (m, 1H), 3.84 (dd, J=14.0, 5.2 Hz, 1H), 3.98-4.05 (m, 1H), 4.38 (s, 2H), 4.49 (d, J=2.4 Hz, 2H), 6.88 (t, J=9.2 Hz, 1H), 6.99 (d, J=7.6 Hz, 1H), 7.18 (td, J=8.0, 2.0 Hz, 1H).

Example 43

(Endo)-2-{3-[3-(2-fluoro-6-methylbenzyloxy)-8-azabicyclo[3.2.1]oct-8-yl]-2-hydroxypropyl}-5-methyl-4-(tetrahydropyran-4-yl)-2,4-dihydro[1,2,4]triazol-3-one

[Chemical Formula 162]

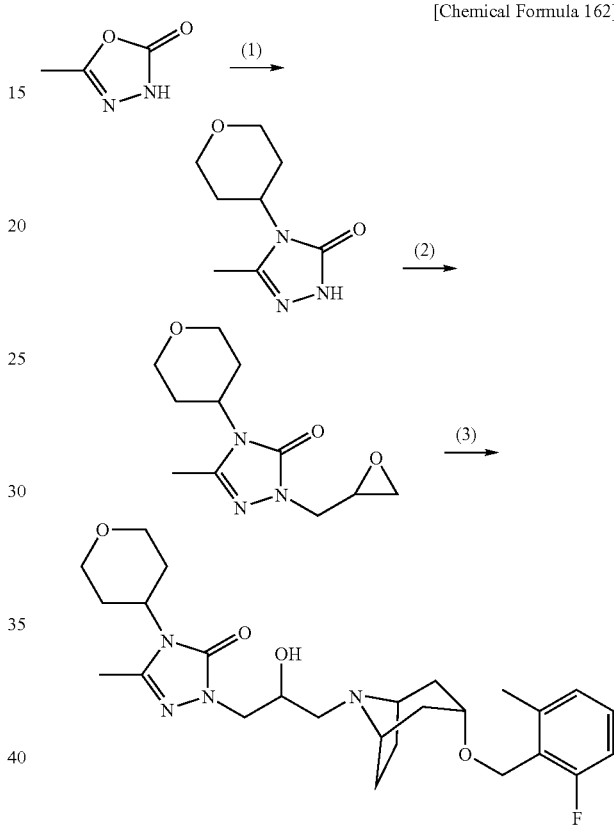

(1) 5-Methyl-4-(tetrahydropyran-4-yl)-2,4-dihydro[1,2,4]triazol-3-one

After dissolving 5-methyl-3H-[1,3,4]oxadiazol-2-one (CAS 3069-67-8) (500 mg) in methanol (5 ml), 4-aminotetrahydropyran (1.01 g) was added and the mixture was heated to reflux for 15 hours. The reaction mixture was concentrated under reduced pressure, and then a 1N aqueous solution of sodium hydroxide (5.5 ml) was added to the residue and the mixture was stirred at 100° C. for 2 hours. After then adding 5N hydrochloric acid (1.1 ml) to the reaction mixture, it was stirred at room temperature for 3 hours. The precipitate was collected by filtration and washed with water and ethyl acetate in that order to obtain the title compound (400 mg).

$^1$H-NMR (400 MHz, DMSO-$d_6$); δ 1.55-1.62 (m, 2H), 2.17 (s, 3H), 2.22-2.38 (m, 2H), 3.28-3.38 (m, 1H), 3.88-3.95 (m, 5H).

(2) 4-Ethyl-5-methoxymethyl-2-oxiranylmethyl-2,4-dihydro[1,2,4]triazol-3-one The title compound (380 mg) was obtained from the compound obtained in Example 43-(1) (400 mg) and epibromohydrin, by the method similar to Example 27-(1).

¹H-NMR (400 MHz, CDCl₃); δ 1.31 (t, J=7.2 Hz, 3H), 2.66-2.69 (m, 1H), 2.84 (t, J=4.4 Hz, 1H), 3.22-3.28 (m, 1H), 3.36 (s, 3H), 3.77 (q, J=7.2 Hz, 2H), 3.89 (dd, J=14.4, 5.6 Hz, 1H), 4.00 (dd, J=14.4, 4.4 Hz, 1H).

(3) (Endo)-2-{3-[3-(2-fluoro-6-methylbenzyloxy)-8-azabicyclo[3.2.1]oct-8-yl]-2-hydroxypropyl}-5-methyl-4-(tetrahydropyran-4-yl)-2,4-dihydro[1,2,4]triazol-3-one The title compound (101 mg) was obtained from the compound obtained in Example 43-(2) (70 mg) and the compound obtained in Production Example 19 (84 mg), by the method similar to Example 30-(2).

¹H-NMR (400 MHz, CD₃OD); δ 1.28 (t, J=7.2 Hz, 3H), 1.77-2.05 (m, 8H), 2.41 (s, 3H), 2.40-2.46 (m, 1H), 2.49 (dd, J=12.8, 4.8 Hz, 1H), 3.13-3.18 (m, 1H), 3.22-3.27 (m, 1H), 3.36 (s, 3H), 3.60 (t, J=5.2 Hz, 1H), 3.77 (q, J=7.2 Hz, 2H), 3.76-3.81 (m, 1H), 3.84 (dd, J=14.0, 5.2 Hz, 1H), 3.98-4.05 (m, 1H), 4.38 (s, 2H), 4.49 (d, J=2.4 Hz, 2H), 6.88 (t, J=9.2 Hz, 1H), 6.99 (d, J=7.6 Hz, 1H), 7.18 (td, J=8.0, 2.0 Hz, 1H).

Example 44

(Endo)-2-{3-[3-(2-fluorobenzyloxy)-8-azabicyclo[3.2.1]oct-8-yl]-2-hydroxypropyl}-5-methyl-4-pyridin-3-yl-2,4-dihydro[1,2,4]triazol-3-one

[Chemical Formula 163]

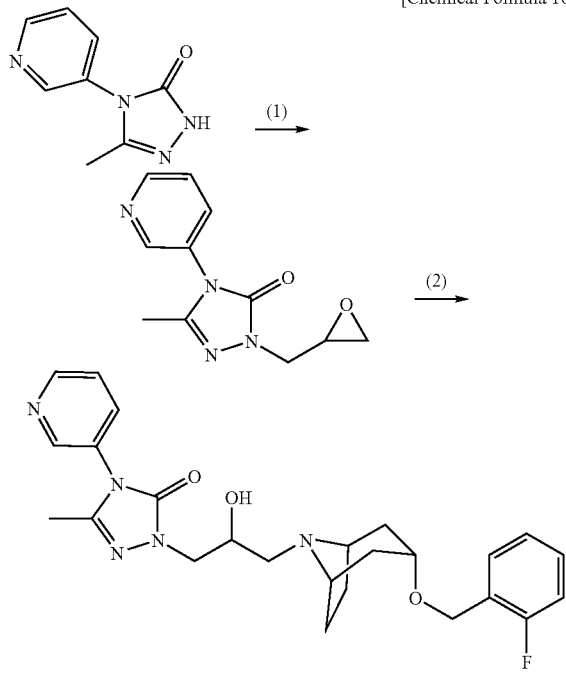

(1) 5-Methyl-2-oxiranylmethyl-4-pyridin-3-yl-2,4-dihydro[1,2,4]triazol-3-one

After dissolving 5-methyl-4-pyridin-3-yl-2,4-dihydro[1,2,4]triazol-3-one (CAS 79369-46-3) (100 mg) in N,N-dimethylformamide (2 ml), sodium hydride (60% in oil) (27 mg) was added and the mixture was stirred at room temperature. Epibromohydrin (73 μl) was then added and the mixture was stirred overnight at room temperature. A saturated aqueous solution of sodium carbonate was added to the reaction mixture, and extraction was performed with ethyl acetate and chloroform. The extract was dried over anhydrous magnesium sulfate. After filtration, the solvent was distilled off under reduced pressure. The residue was purified by silica gel column chromatography to obtain the title compound (136 mg).

¹H-NMR (400 MHz, CDCl₃); δ 2.21 (s, 3H), 2.74 (m, 1H), 2.90 (m, 1H), 3.33 (m, 1H), 3.93 (m, 1H), 4.07 (dd, J=4.4, 14.8 Hz, 1H), 7.49 (m, 1H), 7.74 (m, 1H), 8.61 (d, J=2.0 Hz, 1H), 8.70 (m, 1H).

(2) (Endo)-2-{3-[3-(2-fluorobenzyloxy)-8-azabicyclo[3.2.1]oct-8-yl]-2-hydroxypropyl}-5-methyl-4-pyridin-3-yl-2,4-dihydro[1,2,4]triazol-3-one A mixture of the compound obtained in Example 44-(1) (136 mg), the compound obtained in Production Example 5 (175 mg), anhydrous potassium carbonate (162 mg) and N,N-dimethylformamide (5 ml) was stirred at 100° C. for 16 hours and 30 minutes. The reaction mixture was concentrated under reduced pressure, and the residue was purified by NH silica gel column chromatography. The title compound (116 mg) was thus obtained.

¹H-NMR (400 MHz, CDCl₃); δ 1.85-1.98 (m, 6H), 2.09-2.28 (m, 2H), 2.22 (s, 3H), 2.25 (m, 1H), 2.59 (dd, J=4.0, 12.4 Hz, 1H), 3.13 (m, 1H), 3.19 (m, 1H), 3.64 (m, 1H), 3.88 (m, 2H), 3.98 (m, 1H), 4.50 (s, 2H), 7.02 (m, 1H), 7.13 (dt, J=1.2, 7.6 Hz, 1H), 7.25 (m, 1H), 7.42 (m, 1H), 7.47 (m, 1H), 8.61 (dd, J=0.8, 2.4 Hz, 1H), 8.69 (dd, J=1.6, 4.8 Hz, 1H).

Example 45

(Endo)-4-ethyl-2-{3-[3-(2-fluorobenzyloxy)-8-azabicyclo[3.2.1]oct-8-yl]-2-hydroxy-propyl}-5-pyridin-3-yl-2,4-dihydro[1,2,4]triazol-3-one oxalate

[Chemical Formula 164]

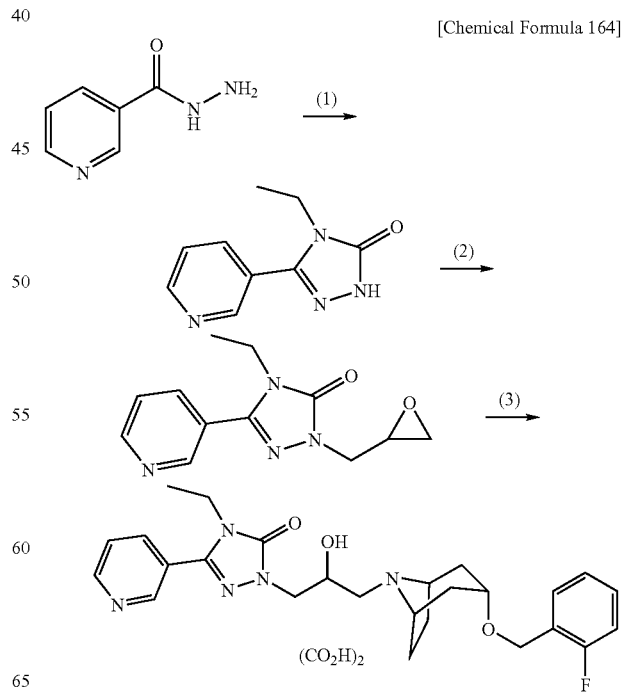

(1) 4-Ethyl-5-pyridin-3-yl-2,4-dihydro[1,2,4]triazol-3-one

The title compound (2.21 g) was obtained from nicotinic acid hydrazide (3.0 g) by the method similar to Example 42-(1).

$^1$H-NMR (400 MHz, DMSO-$d_6$); δ 1.09 (t, J=7.2 Hz, 3H), 3.72 (q, J=7.2 Hz, 2H), 7.58 (dd, J=4.8, 8.0 Hz, 1H), 8.09 (dt, J=1.6, 6.4 Hz, 1H), 8.74 (dd, J=1.6, 4.8. Hz, 1H), 8.84 (d, J=1.6 Hz, 1H), 12.06 (br, 1H).

(2) 4-Ethyl-2-oxiranylmethyl-5-pyridin-3-yl-2,4-dihydro[1,2,4]triazol-3-one

The compound obtained in Example 45-(1) (300 mg) was dissolved in N,N-dimethylformamide (14 ml), and then sodium hydride (60% in oil) (95 mg) was added and the mixture was stirred at room temperature. Epibromohydrin (0.27 ml) was then added, and the mixture was stirred at room temperature for 3 days. A saturated aqueous solution of sodium carbonate was added to the reaction mixture, and extraction was performed with chloroform. The extract was dried over anhydrous magnesium sulfate. After filtration, the solvent was distilled off under reduced pressure. The residue was purified by silica gel column chromatography to obtain the title compound (363 mg).

$^1$H-NMR (400 MHz, CDCl$_3$); δ 1.30 (t, J=7.2 Hz, 3H), 2.76 (dd, J=2.4, 4.4 Hz, 1H), 2.89 (m, 1H), 3.35 (m, 1H), 3.86 (q, J=7.2 Hz, 2H), 4.02 (dd, J=5.6, 14.8 Hz, 1H), 4.09 (dd, J=4.8, 14.8 Hz, 1H), 7.46 (dd, J=4.8, 8.0 Hz, 1H), 7.93 (dt, J=2.0, 8.0 Hz, 1H), 8.76 (dd, J=1.6, 4.8 Hz, 1H), 8.86 (d, J=1.6 Hz, 1H).

(3) (Endo)-4-ethyl-2-{3-[3-(2-fluorobenzyloxy)-8-azabicyclo[3.2.1]oct-8-yl]-2-hydroxypropyl}-5-pyridin-3-yl-2,4-dihydro[1,2,4]triazol-3-one oxalate A mixture of the compound obtained in Example 45-(2) (112 mg), the compound obtained in Production Example 5 (136 mg), anhydrous potassium carbonate (189 mg) and N,N-dimethylformamide (5 ml) was irradiated with microwaves, and was stirred at 100° C. for 3 hours and then at 120° C. for 2 hours. The reaction mixture was filtered and the filtrate was concentrated under reduced pressure. The residue was purified by silica gel column chromatography to obtain the free form of the title compound (87 mg).

This was dissolved in ethanol, and then oxalic acid (16 mg) was added and the solvent was distilled off under reduced pressure to obtain the title compound (102 mg).

$^1$H-NMR (400 MHz, CD$_3$OD); δ 1.24 (t, J=7.2 Hz, 3H), 2.19-2.45 (m, 8H), 3.13 (m, 1H), 3.26 (m, 1H), 3.78 (m, 1H), 3.86 (q, J=7.2 Hz, 2H), 3.94-3.99 (m, 3H), 4.25 (m, 1H), 4.47 (m, 1H), 4.56 (s, 2H), 7.08 (m, 1H), 7.17 (t, J=7.2 Hz, 1H), 7.33 (m, 1H), 7.43 (m, 1H), 7.62 (m, 1H), 8.14 (d, J=8.0 Hz, 1H), 8.73 (dd, J=1.2, 4.8 Hz, 1H), 8.84 (d, J=1.6 Hz, 1H).

Example 46

(Endo)-4-ethyl-2-{3-[3-(2-fluorobenzyloxy)-8-azabicyclo[3.2.1]oct-8-yl]-2-hydroxypropyl}-5-pyrazin-2-yl-2,4-dihydro[1,2,4]triazol-3-one oxalate

[Chemical Formula 165]

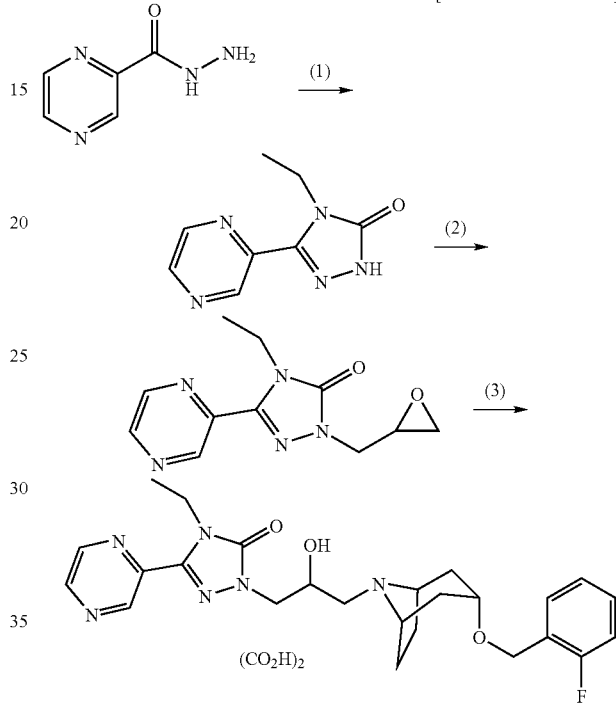

(1) 4-Ethyl-5-pyrazin-2-yl-2,4-dihydro[1,2,4]triazol-3-one

The title compound (1.2 g) was obtained from 2-pyrazinecarboxylic acid hydrazide (3.0 g) by the method similar to Example 42-(1).

$^1$H-NMR (400 MHz, DMSO-$d_6$); δ 1.20 (t, J=6.8 Hz, 3H), 4.07 (q, J=6.8 Hz, 2H), 8.74-8.76 (m, 2H), 9.17 (d, J=1.2 Hz, 1H), 12.32 (br, 1H).

(2) 4-Ethyl-2-oxiranylmethyl-5-pyrazin-2-yl-2,4-dihydro[1,2,4]triazol-3-one

The title compound (341 mg) was obtained from the compound obtained in Example 46-(1) (300 mg) and epibromohydrin, by the method similar to Example 45-(2).

$^1$H-NMR (400 MHz, CDCl$_3$); δ 1.33 (t, J=7.2 Hz, 3H), 2.75 (m, 1H), 2.89 (m, 1H), 3.36 (m, 1H), 4.05 (dd, J=5.2, 14.8 Hz, 1H), 4.12 (dd, J=4.8, 14.8 Hz, 1H), 4.29 (q, J=7.2 Hz, 2H), 8.59 (dd, J=1.6, 2.4 Hz, 1H), 8.62 (d, J=2.8 Hz, 1H), 9.28 (d, J=1.6 Hz, 1H).

(3) (Endo)-4-ethyl-2-{3-[3-(2-fluorobenzyloxy)-8-azabicyclo[3.2.1]oct-8-yl]-2-hydroxypropyl}-5-pyrazin-2-yl-2,4-dihydro[1,2,4]triazol-3-one oxalate A mixture of the compound obtained in Example 46-(2) (100 mg), the compound obtained in Production Example 5

(121 mg), anhydrous potassium carbonate (168 mg) and N,N-dimethylformamide (4.9 ml) was stirred at 100° C. for 4 hours and 30 minutes. A saturated aqueous solution of sodium hydrogencarbonate was added to the reaction mixture, and extraction was performed with chloroform. The extract was dried over anhydrous magnesium sulfate and filtered, and then the solvent was distilled off under reduced pressure. The residue was purified by silica gel column chromatography to obtain the free form of the title compound (105 mg).

This was dissolved in ethanol, and then oxalic acid (20 mg) was added and the solvent was distilled off under reduced pressure to obtain the title compound (116 mg).

$^1$H-NMR (400 MHz, CD$_3$OD); δ 1.32 (t, J=7.2 Hz, 3H), 2.21-2.46 (m, 8H), 3.14 (m, 1H), 3.26 (m, 1H), 3.78 (m, 1H), 3.98-4.07 (m, 3H), 4.25 (m, 1H), 4.26 (q, 2H), 4.50 (m, 1H), 4.57 (s, 2H), 7.08 (m, 1H), 7.17 (m, 1H), 7.33 (m, 1H), 7.43 (m, 1H), 8.66 (d, J=2.4 Hz, 1H), 8.70 (s, 1H), 9.21 (s, 1H).

Example 47

(Endo)-2-{3-[3-(2-fluorobenzyloxy)-8-azabicyclo[3.2.1]oct-8-yl]-2-hydroxypropyl}-5-methyl-4-(3-methyl-isoxazol-5-yl)-2,4-dihydro[1,2,4]triazol-3-one oxalate

[Chemical Formula 166]

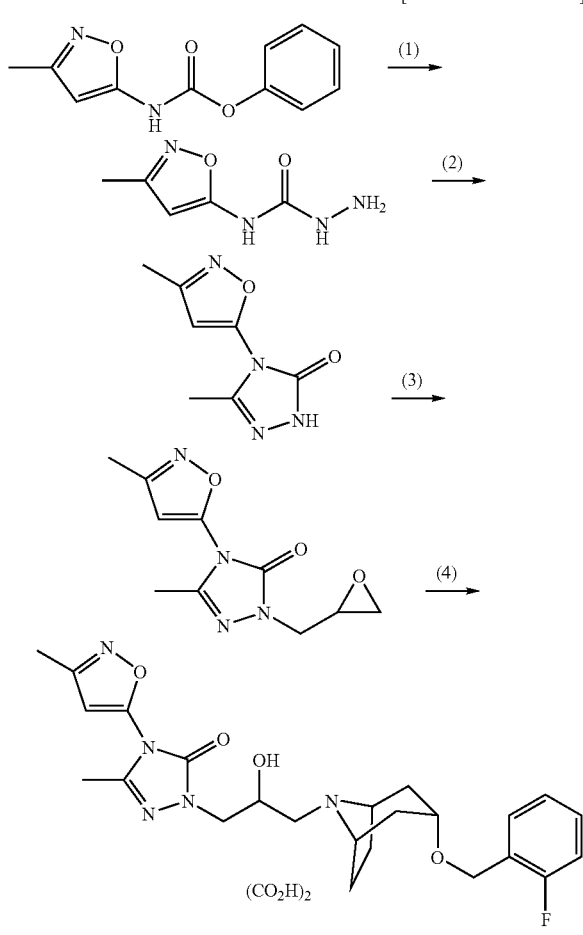

(1)

N-(3-Methyl-isoxazol-5-yl)-hydrazinecarboxamide

Hydrazine hydrate (95 μl) was added to a mixture of (3-methyl-isoxazol-5-yl)-carbamic acid phenyl ester (CA 81479-55-2) (417 mg) and ethanol (5 ml), and the resulting mixture was stirred overnight at room temperature. The precipitate was collected by filtration to obtain the title compound (100 mg).

$^1$H-NMR (400 MHz, CD$_3$OD); δ 2.20 (s, 3H), 5.99 (s, 1H).

(2) 5-Methyl-4-(3-methyl-isoxazol-5-yl)-2,4-dihydro[1,2,4]triazol-3-one

A mixture of the compound obtained in Example 47-(1) (100 mg), methyl orthoformate (0.18 ml) and methanol (3 ml) was stirred at room temperature for 3 hours, and then heated to reflux for 2 hours and 30 minutes. The reaction mixture was concentrated under reduced pressure to obtain the title compound (108 mg).

$^1$H-NMR (400 MHz, CDCl$_3$); δ 2.36 (s, 3H), 2.50 (s, 3H), 6.46 (s, 1H).

(3) 5-Methyl-4-(3-methyl-isoxazol-5-yl)-2-oxiranyl-methyl-2,4-dihydro[1,2,4]triazol-3-one The compound obtained in Example 47-(2) (100 mg) and epibromohydrin (48 μl) were dissolved in N,N-dimethylformamide (3 ml), and then sodium hydride (60% in oil) (45 mg) was added and the mixture was stirred overnight at room temperature.

Water was added to the reaction mixture, and extraction was performed with chloroform. The organic layer was washed with brine and dried over anhydrous magnesium sulfate. After filtration, the solvent was distilled off under reduced pressure. The residue was purified by silica gel column chromatography to obtain the title compound (71 mg).

$^1$H-NMR (400 MHz, CDCl$_3$); δ 2.36 (s, 3H), 2.50 (s, 3H), 2.70-2.72 (m, 1H), 2.87-2.89 (m, 1H), 3.27-3.31 (m, 1H), 3.91 (dd, J=5.6, 14.8 Hz, 1H), 4.03 (dd, J=5.2, 14.8 Hz, 1H), 6.45 (s, 1H).

(4) (Endo)-2-{3-[3-(2-fluorobenzyloxy)-8-azabicyclo[3.2.1]oct-8-yl]-2-hydroxypropyl}-5-methyl-4-(3-methyl-isoxazol-5-yl)-2,4-dihydro[1,2,4]triazol-3-one oxalate A mixture of the compound obtained in Example 47-(3) (35 mg), the compound obtained in Production Example 5 (40 mg), anhydrous potassium carbonate (41 mg) and N,N-dimethylformamide (2 ml) was stirred at 100° C. for 6 hours. Water was added to the reaction mixture, and extraction was performed with chloroform. The organic layer was washed with brine and dried over anhydrous magnesium sulfate. After filtration, the solvent was distilled off under reduced pressure. The residue was purified by silica gel column chromatography to obtain the free form of the title compound (25 mg).

This was dissolved in ethanol, and then oxalic acid (5 mg) was added and the solvent was distilled off under reduced pressure to obtain the title compound (30 mg).

$^1$H-NMR (400 MHz, CD$_3$OD); δ 2.15-2.34 (m, 6H), 2.34 (s, 3H), 2.39 (s, 3H), 2.43-2.46 (m, 2H), 3.06-3.18 (m, 1H), 3.20-3.26 (m, 1H), 3.76-3.82 (m, 1H), 3.84-3.88 (m, 2H), 3.94-4.00 (m, 1H), 4.07-4.16 (m, 1H), 4.36-4.45 (m, 1H), 4.57 (s, 2H), 6.51 (s, 1H), 7.06-7.11 (m, 1H), 7.15-7.19 (m, 1H), 7.31-7.36 (m, 1H), 7.41-7.45 (m, 1H).

Example 48

(Endo)-2-{3-[3-(2-fluorobenzyloxy)-8-azabicyclo [3.2.1]oct-8-yl]-2-hydroxypropyl}-5-methyl-4-thiazol-2-yl-2,4-dihydro[1,2,4]triazol-3-one oxalate

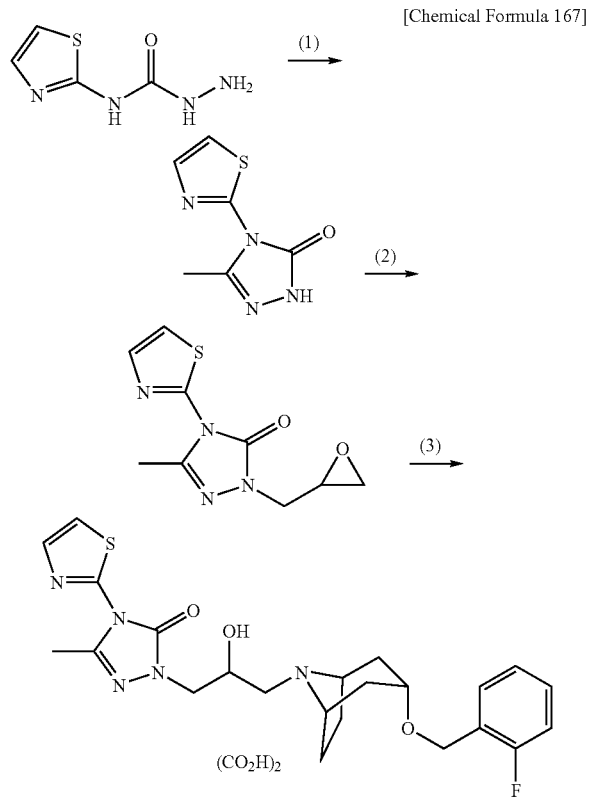

[Chemical Formula 167]

(1) 5-Methyl-4-thiazol-2-yl-2,4-dihydro[1,2,4]triazol-3-one

The title compound (480 mg) was obtained from N-(4-thiazol-2-yl)-hydrazinecarboxamide (CAS 3673-41-4) (345 mg) by the method similar to Example 47-(2).

$^1$H-NMR (400 MHz, CDCl$_3$); δ 2.71 (s, 3H), 7.25 (d, J=3.6 Hz, 1H), 7.61 (d, J=3.6 Hz, 1H), 9.22 (brs, 1H).

(2) 5-Methyl-2-oxiranylmethyl-4-thiazol-2-yl-2,4-dihydro[1,2,4]triazol-3-one

The title compound (76 mg) was obtained from the compound obtained in Example 48-(1) (397 mg) and epibromohydrin, by the method similar to Example 47-(3).

$^1$H-NMR (400 MHz, CDCl$_3$); δ 2.71 (s, 3H), 2.72-2.74 (m, 1H), 2.87-2.89 (m, 1H), 3.29-3.33 (m, 1H), 3.97 (dd, J=6.0, 14.8 Hz, 1H), 4.05 (dd, J=4.4, 14.8 Hz, 1H), 7.24 (d, J=3.2 Hz, 1H), 7.61 (d, J=3.2 Hz, 1H).

(3) (Endo)-2-{3-[3-(2-fluorobenzyloxy)-8-azabicyclo[3.2.1]oct-8-yl]-2-hydroxypropyl}-5-methyl-4-thiazol-2-yl-2,4-dihydro[1,2,4]triazol-3-one oxalate The title compound (9.5 mg) was obtained from the compound obtained in Example 48-(2) (38 mg) and the compound obtained in Production Example 5 (43 mg), by the method similar to Example 47-(4).

$^1$H-NMR (400 MHz, CD$_3$OD); δ 2.15-2.30 (m, 6H), 2.40-2.43 (m, 2H), 2.64 (s, 3H), 3.10-3.20 (m, 1H), 3.20-3.30 (m, 1H), 3.76-3.82 (m, 1H), 3.87-3.93 (m, 2H), 3.93-4.00 (m, 1H), 4.06-4.14 (m, 1H), 4.34-4.48 (m, 1H), 4.57 (s, 2H), 7.06-7.11 (m, 1H), 7.15-7.20 (m, 1H), 7.30-7.37 (m, 1H), 7.40-7.46 (m, 1H), 7.49 (d, J=3.6 Hz, 1H), 7.66 (d, J=3.6 Hz, 1H).

Example 49

(Endo)-2'-{3-[3-(2-fluorobenzyloxy)-8-azabicyclo [3.2.1]oct-8-yl]-2-hydroxypropyl}-2,5,5'-trimethyl-2H,2'H-[3,4']bi[[1,2,4]triazolyl]-3'-one oxalate

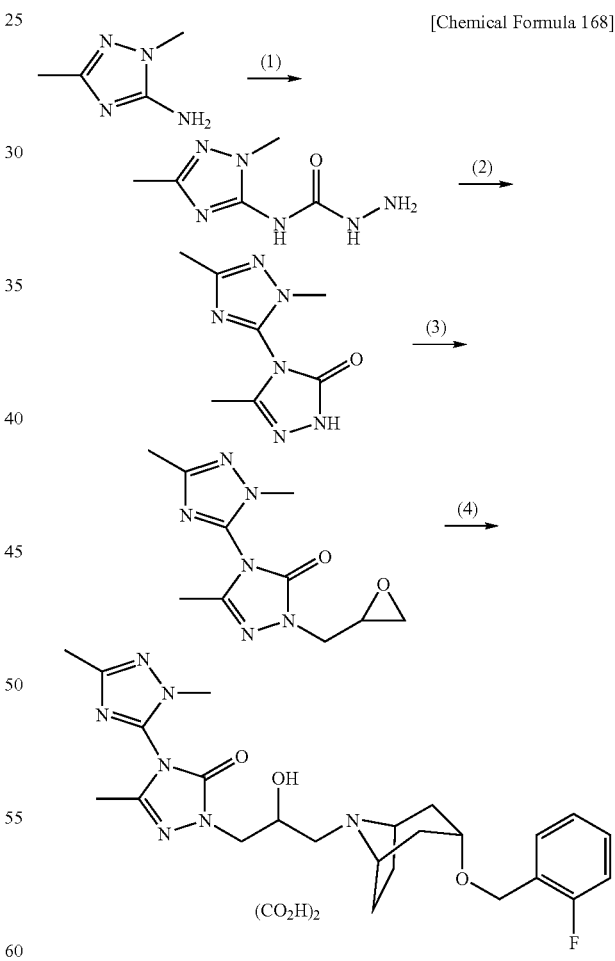

[Chemical Formula 168]

(1) N-(2,5-Dimethyl-2H-[1,2,4]triazol-3-yl)hydrazinecarboxamide

Phenyl chloroformate (1.23 ml) was added dropwise to a mixture of 2,5-dimethyl-2H-[1,2,4]triazol-3-ylamine (CAS 51108-32-8) (1.00 g) and pyridine (10 ml) while cooling on ice. The reaction mixture was stirred overnight at room temperature, and then water was added and the precipitate was collected by filtration.

Ethanol (10 ml) and hydrazine hydrate (0.47 ml) were added to the filtered product, and the mixture was stirred at room temperature for 4 hours and 10 minutes. The precipitate was collected by filtration and washed with chloroform to obtain the title compound (578 mg).

$^1$H-NMR (400 MHz, CDCl$_3$); δ 2.27 (s, 3H), 3.73 (s, 3H), 3.86 (brs, 2H), 9.23 (brs, 1H), 9.86 (brs, 1H).

(2) 2,5,5'-Trimethyl-2H,2'H-[3,4']bi[[1,2,4]triazolyl]-3'-one

A mixture of the compound obtained in Example 49-(1) (540 mg), methyl orthoformate (0.88 ml) and methanol (10 ml) was stirred overnight at room temperature. The reaction mixture was concentrated under reduced pressure, and then acetic acid was added to the residue and the mixture was stirred at 70° C. for 30 minutes. The reaction mixture was concentrated under reduced pressure, and the residue was purified by silica gel column chromatography to obtain the title compound (304 mg).

$^1$H-NMR (400 MHz, CDCl$_3$); δ 2.26 (s, 3H), 2.39 (s, 3H), 3.84 (s, 3H).

(3) 2,5,5'-Trimethyl-2'-oxiranylmethyl-2H 2'H-[3,4']bi[[1,2,4]triazolyl]-3'-one

The title compound (230 mg) was obtained from the compound obtained in Example 49-(2) (300 mg) and epibromohydrin, by the method similar to Example 27-(1).

$^1$H-NMR (400 MHz, CDCl$_3$); δ 2.27 (s, 3H), 2.39 (s, 3H), 2.71 (dd, J=2.4, 4.8 Hz, 1H), 2.87-2.89 (m, 1H), 3.27-3.31 (m, 1H), 3.83 (s, 3H), 3.90 (dd, J=5.6, 14.4 Hz, 1H), 4.02 (dd, J=4.4, 14.4 Hz, 1H).

(4) (Endo)-2'-{3-[3-(2-fluorobenzyloxy)-8-azabicyclo[3.2.1]oct-8-yl]-2-hydroxy-propyl}-2,5,5'-trimethyl-2H,2'H-[3,4']bi[[1,2,4]triazolyl]-3'-one oxalate The title compound (45 mg) was obtained from the compound obtained in Example 49-(3) (50 mg) and the compound obtained in Production Example 5 (54 mg), by the method similar to Example 47-(4).

$^1$H-NMR (400 MHz, CD$_3$OD); δ 2.14-2.34 (m, 9H), 2.35 (s, 3H), 2.4.0-2.50 (m, 2H), 3.10-3.22 (m, 2H), 3-0.80 (s, 3H), 3.78-3.91 (m, 3H), 3.96-4.05 (m, 1H), 4.08-4.20 (m, 1H), 4.36-4.44 (m, 1H), 4.58 (s, 2H), 7.07-7.11 (m, 1H), 7.16-7.19 (m, 1H), 7.30-7.37 (m, 1H), 7.41-7.45 (m, 1H).

Example 50

(Endo)-2-{3-[3-(3-fluorobenzyloxy)-8-azabicyclo[3.2.1]oct-8-yl]-2-hydroxy-propyl}-5-methyl-4-(5-methyl-[1,2,4]oxadiazol-3-yl)-2,4-dihydro[1,2,4]triazol-3-one oxalate

[Chemical Formula 169]

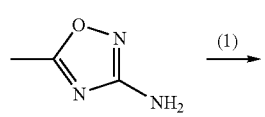

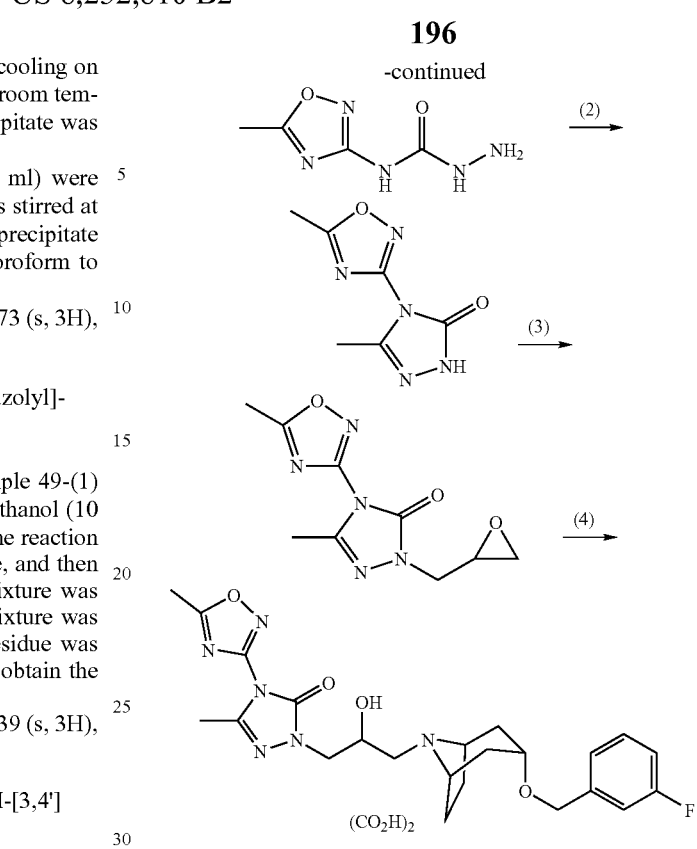

(1) N-(5-Methyl-F [1,2,4]oxadiazol-3-yl)-hydrazinecarboxamide

Phenyl chloroformate (1.27 ml) was added dropwise to a mixture of 5-methyl-[1,2,4]oxadiazol-3-ylamine (CAS 40483-47-4) (1.00 g) and pyridine (20 ml) while cooling on ice. After stirring at room temperature for 1 hour and 30 minutes, water was added to the reaction mixture and extraction was performed with ethyl acetate. The organic layer was washed with brine and dried over anhydrous magnesium sulfate. After filtration, the solvent was distilled off under reduced pressure. The residue was purified by silica gel column chromatography to obtain a solid (1.17 g).

A mixture of the obtained solid (1.17 g), ethanol (20 ml) and hydrazine hydrate (0.53 ml) was stirred overnight at room temperature. The precipitate was collected by filtration to obtain the title compound (792 mg).

$^1$H-NMR (400 MHz, DMSO-d$_6$); δ 2.50 (s, 3H), 4.23 (brs, 1H), 7.84 (brs, 1H).

(2) 5-Methyl-4-(5-methyl-[1,2,4]oxadiazol-3-yl)-2,4-dihydro[1,2,4]triazol-3-one

The title compound (436 mg) was obtained from the compound obtained in Example 50-(1) (550 mg) and methyl orthoacetate, by the method similar to Example 49-(2).

$^1$H-NMR (400 MHz, CDCl$_3$); δ 2.42 (s, 3H), 2.70 (s, 3H), 9.00 (brs, 1H).

(3) 5-Methyl-4-(5-methyl-[1,2,4]oxadiazol-3-yl)-2-oxiranylmethyl-2,4-dihydro[1,2,4]triazol-3-one The title compound (243 mg) was obtained from the compound obtained in Example 50-(2) (436 mg) and epibromohydrin, by the method similar to Example 47-(3).

$^1$H-NMR (400 MHz, CDCl$_3$); δ 2.37 (s, 3H), 2.66 (s, 3H), 2.67-2.69 (m, 1H), 2.82-2.84 (m, 1H), 3.23-3.27 (m, 1H), 3.88 (dd, J=5.6, 14.8 Hz, 1H), 3.98 (dd, J=4.4, 14.8 Hz, 1H).

(4) (Endo)-2-{3-[3-(3-fluorobenzyloxy)-8-azabicyclo[3.2.1]oct-8-yl]-2-hydroxypropyl}-5-methyl-4-(5-methyl-[1,2,4]oxadiazol-3-yl)-2,4-dihydro[1,2,4]triazol-3-one oxalate The title compound (30 mg) was obtained from the compound obtained in Example 50-(3) (42 mg) and the compound obtained in Production Example 58 (42 mg), by the method similar to Example 47-(4).

$^1$H-NMR (400 MHz, CD$_3$OD); δ 2.18-2.38 (m, 6H), 2.39 (s, 3H), 2.40-2.46 (m, 2H), 2.67 (s, 3H), 3.10-3.20 (m, 1H), 3.21-3.30 (m, 1H), 3.74-3.78 (m, 1H), 3.84-3.88 (m, 2H), 3.96-4.04 (m, 1H), 4.14-4.20 (m, 1H), 4.38-4.48 (m, 1H), 4.53 (s, 2H), 6.96-7.03 (m, 1H), 7.06-7.11 (m, 1H), 7.12-7.16 (m, 1H), 7.31-7.37 (m, 1H).

Example 51

(Endo)-2-{3-[3-(4-fluorobenzyloxy)-8-azabicyclo[3.2.1]oct-8-yl]-2-hydroxypropyl}-5-methyl-4-(3-methyl-[1,2,4]oxadiazol-5-yl)-2,4-dihydro[1,2,4]triazol-3-one oxalate

[Chemical Formula 170]

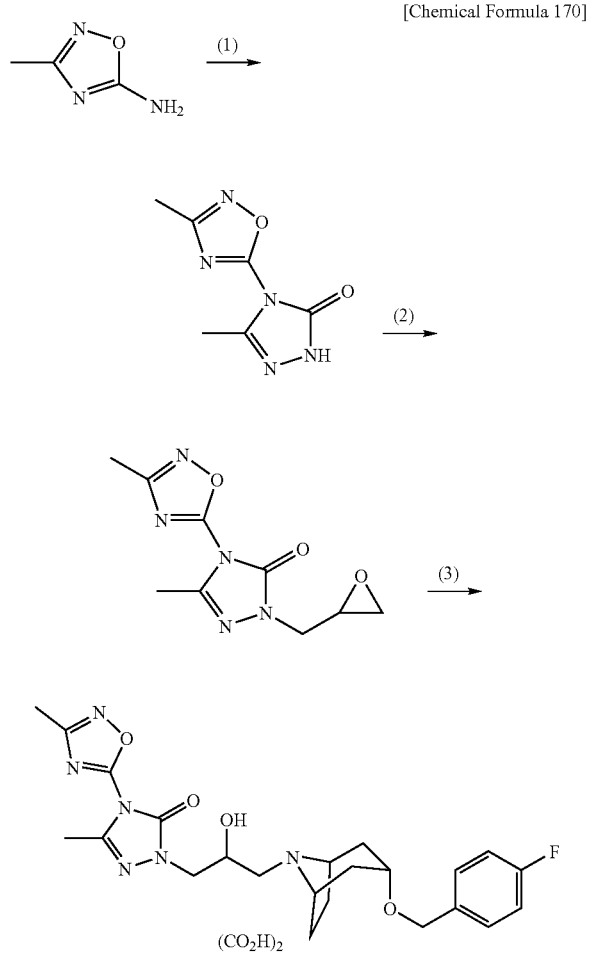

(1) 5-Methyl-4-(3-methyl-[1,2,4]oxadiazol-5-yl)-2,4-dihydro[1,2,4]triazol-3-one

After dissolving 3-methyl-[1,2,4]oxadiazol-5-ylamine (CAS 3663-39-6) (4.48 g) in 1,2-dichloroethane (150 ml), oxalyl chloride (2.64 ml) was added dropwise at room temperature and the mixture was heated to reflux for 2 hours.

The reaction mixture was concentrated under reduced pressure, tetrahydrofuran (100 ml) was added to the residue, and the mixture was cooled on ice. After adding tert-butyl carbazate (4.00 g) while stirring, the mixture was continuously stirred overnight at room temperature. Water was added to the reaction mixture, and extraction was performed with ethyl acetate. The extract was washed with brine and dried over anhydrous magnesium sulfate. After filtration, the solvent was distilled off under reduced pressure and the residue was purified by silica gel column chromatography.

The obtained compound was dissolved in dichloromethane (20 ml), and then trifluoroacetic acid (20 ml) was added and the mixture was stirred at room temperature for 1 hour and 30 minutes. The reaction mixture was concentrated under reduced pressure, diethyl ether and ethyl acetate were added to the residue, and the insoluble matter was collected by filtration.

The filtered substance was dissolved in N,N-dimethylformamide (40 ml), and then methyl orthoformate (2.77 ml) was added and the mixture was stirred overnight at room temperature. The reaction mixture was concentrated under reduced pressure, and then acetic acid was added to the residue and the mixture was stirred at 100° C. for 50 minutes. The reaction mixture was concentrated under reduced pressure, and the residue was purified by silica gel column chromatography to obtain the title compound (180 mg).

$^1$H-NMR (400 MHz, CDCl$_3$); δ 2.47 (s, 3H), 2.55 (s, 3H), 9.61 (brs, 1H).

(2) 5-Methyl-4-(3-methyl-[1,2,4]oxadiazol-5-yl)-2-oxiranylmethyl-2,4-dihydro[1,2,4]triazol-3-one The title compound (17 mg) was obtained from the compound obtained in Example 51-(1) (117 mg) and epibromohydrin, by the method similar to Example 47-(3).

$^1$H-NMR (400 MHz, CDCl$_3$); δ 2.40 (s, 3H), 2.44 (s, 3H), 2.62 (dd, J=2.4, 4.4 Hz, 1H), 2.87-2.91 (m, 1H), 3.24-3.28 (m, 1H), 3.66 (dd, J=5.6, 15.2 Hz, 1H), 4.23 (dd, J=2.4, 15.2 Hz, 1H).

(3) (Endo)-2-{3-[3-(4-fluorobenzyloxy)-8-azabicyclo[3.2.1]oct-8-yl]-2-hydroxypropyl}-5-methyl-4-(3-methyl-[1,2,4]oxadiazol-5-yl)-2,4-dihydro[1,2,4]triazol-3-one oxalate A mixture of the compound obtained in Example 51-(2) (60 mg), the compound obtained in Production Example 59 (77 mg) and N,N-dimethylformamide (2 ml) was stirred overnight at 80° C. The reaction mixture was concentrated under reduced pressure, and the residue was purified by preparative thin-layer chromatography (NH silica gel). The title compound (5 mg) was thus obtained.

$^1$H-NMR (400 MHz, CD$_3$OD); δ 1.78-1.96 (m, 6H), 2.06-2.13 (m, 2H), 2.43 (s, 3H), 2.46 (s, 3H), 2.60-2.66 (m, 1H), 3.06-3.10 (m, 1H), 3.13-3.18 (m, 1H), 3.47-3.51 (m, 2H), 3.58-3.62 (m, 1H), 3.68-3.76 (m, 1H), 3.80-3.90 (m, 2H), 4.40 (s, 2H), 6.98-7.05 (m, 2H), 7.24-7.30 (m, 2H).

Example 52

(Endo)-2-{3-[3-(2-fluorobenzyloxy)-8-azabicyclo[3.2.1]oct-8-yl]-2-hydroxypropyl}-5-methyl-4-(5-methyl-[1,3,4]thiadiazol-2-yl)-2,4-dihydro[1,2,4]triazol-3-one

[Chemical Formula 171]

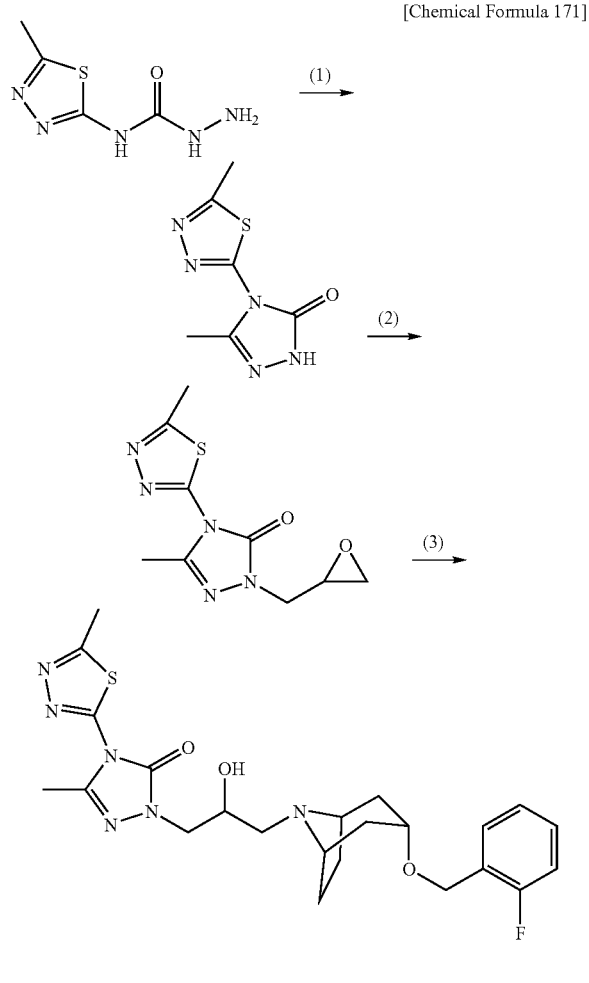

(1) 5-Methyl-4-(5-methyl-[1,3,4]thiadiazol-2-yl)-2,4-dihydro[1,2,4]triazol-3-one The title compound (223 mg) was obtained from N-(5-methyl-[1,3,4]thiadiazol-2-yl)-hydrazinecarboxamide (CAS 81091-60-3) (255 mg) by the method similar to Example 49-(2).

$^1$H-NMR (400 MHz, CD$_3$OD); δ 2.65 (s, 3H), 2.76 (s, 3H).

(2) 5-Methyl-4-(5-methyl-[1,3,4]thiadiazol-2-yl)-2-oxiranylmethyl-2,4-dihydro[1,2,4]triazol-3-one The title compound (109 mg) was obtained from the compound obtained in Example 52-(1) (223 mg) and epibromohydrin, by the method similar to Example 27-(1).

$^1$H-NMR (400 MHz, CDCl$_3$); δ 2.71-2.73 (m, 1H), 2.75 (s, 3H), 2.79 (s, 3H), 2.89 (t, J=4.0 Hz, 1H), 3.28-3.33 (m, 1H), 3.95 (dd, J=14.8 Hz, 5.6 Hz, 1H), 4.05 (dd, J=14.8 Hz, 4.0 Hz, 1H).

(3) (Endo)-2-{3-[3-(2-fluorobenzyloxy)-8-azabicyclo[3.2.1]oct-8-yl]-2-hydroxypropyl}-5-methyl-4-(5-methyl-[1,3,4]thiadiazol-2-yl)-2,4-dihydro[1,2,4]triazol-3-one A mixture of the compound obtained in Example 52-(2) (109 mg), the compound obtained in Production Example 5 (117 mg), anhydrous potassium carbonate (131 mg) and N,N-dimethylformamide (1.4 ml) was stirred overnight at 100° C. Water was added to the reaction mixture, and extraction was performed with ethyl acetate. The extract was dried over anhydrous magnesium sulfate and filtered, and then the solvent was distilled off under reduced pressure. The residue was purified by preparative thin-layer chromatography to obtain the title compound (136 mg).

$^1$H-NMR (400 MHz, CDCl$_3$); δ 1.73-2.01 (m, 6H), 2.08-2.14 (m, 2H), 2.17-2.25 (m, 1H), 2.57 (dd, J=12.6 Hz, 3.8 Hz, 1H), 2.75 (s, 3H), 2.78 (s, 3H), 3.09-3.14 (m, 1H), 3.15-3.20 (m, 1H), 3.61-3.66 (m, 1H), 3.83-3.90 (m, 2H), 3.92-4.02 (m, 1H), 4.49 (s, 2H), 7.02 (t, J=9.2 Hz, 1H), 7.13 (t, J=7.4 Hz, 1H), 7.22-7.28 (m, 1H), 7.39-7.45 (m, 1H).

Example 53

(Endo)-4-ethyl-2-{3-[3-(2-fluorobenzyloxy)-8-azabicyclo[3.2.1]oct-8-yl]-2-hydroxypropyl}-5-(1-methyl-1H-pyrrol-2-yl)-2,4-dihydro[1,2,4]triazol-3-one oxalate

[Chemical Formula 172]

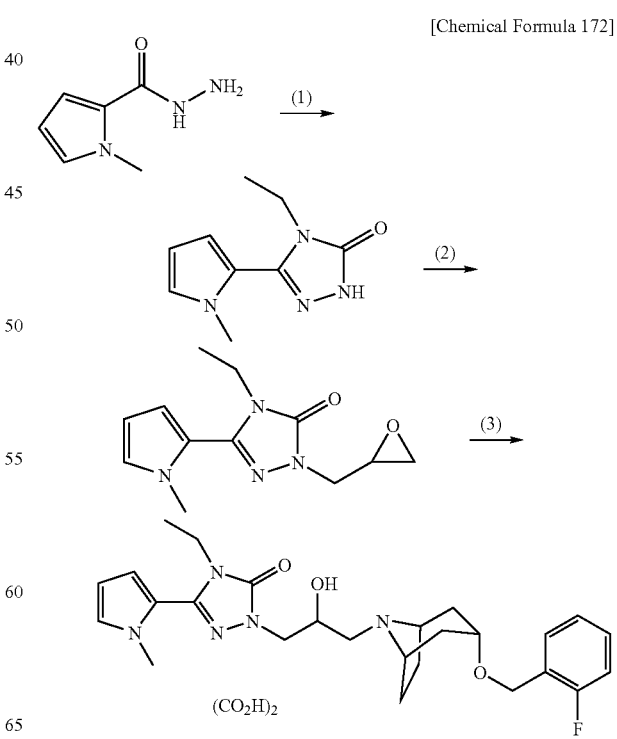

(1) 4-Ethyl-5-(1-methyl-1H-pyrrol-2-yl)-2,4-dihydro [1,2,4]triazol-3-one

After dissolving 1-methyl-1H-pyrrole-2-carboxylic acid hydrazide (CAS 113398-02-0) (967 mg) in toluene (10 ml), ethyl isocyanate (0.72 ml) was added dropwise. The mixture was stirred at room temperature for 3 days, and then the precipitate was collected by filtration and washed with diethyl ether.

Water (34 ml) and a 50% aqueous solution of sodium hydroxide (0.4 ml) were added to the filtered substance, and the mixture was heated to reflux for 2 hours. The reaction mixture was cooled on ice, 5N hydrochloric acid (1.52 ml) was added and the mixture was stirred. The precipitate was collected by filtration to obtain the title compound (795 mg).

$^1$H-NMR (400 MHz, DMSO-$d_6$); δ 1.11 (t, J=7.2 Hz, 3H), 3.65 (q, J=7.2 Hz, 2H), 3.69 (s, 3H).

(2) 4-Ethyl-5-(1-methyl-1H-pyrrol-2-yl)-2-oxiranylmethyl-2,4-dihydro[1,2,4]triazol-3-one The title compound (548 mg) was obtained from the compound obtained in Example 53-(1) (400 mg) and epibromohydrin, by the method similar to Example 45-(2).

$^1$H-NMR (400 MHz, CDCl$_3$); δ 1.30 (t, J=7.2 Hz, 3H), 2.72 (dd, J=2.4, 4.8 Hz, 1H), 2.86 (m, 1H), 3.32 (m, 1H), 3.78 (s, 3H), 3.83 (q, J=7.2 Hz, 2H), 6.22 (dd, J=2.8, 4.0 Hz, 1H), 6.46 (dd, J=1.6, 4.0 Hz, 1H), 7.78 (dd, J=1.6, 2.4 Hz, 1H).

(3) (Endo-4-ethyl-2-{3-[3-(2-fluorobenzyl oxy)-8-azabicyclo[3.2.1]oct-8-yl]-2-hydroxypropyl}-5-(1-methyl-1H-pyrrol-2-yl)-2,4-dihydro[1,2,4]triazol-3-one oxalate A mixture of the compound obtained in Example 53-(2) (128 mg), the compound obtained in Production Example 5 (168 mg), anhydrous potassium carbonate (214 mg) and N,N-dimethylformamide (5 ml) was stirred at 100° C. for 6 hours and 30 minutes. The solvent was distilled off, and the residue was purified by preparative thin-layer chromatography to obtain the free form of the title compound (147 mg).

The free form of the title compound (26 mg) was dissolved in ethanol, and then oxalic acid (5 mg) was added and the solvent was distilled off under reduced pressure to obtain the title compound (23 mg).

$^1$H-NMR (400 MHz, CD$_3$OD); δ 1.24 (m, 1H), 2.18-2.46 (m, 8H), 3.13 (br, 1H), 3.22 (br, 1H), 3.72 (s, 3H), 3.76-3.85 (m, 3H), 3.93 (m, 2H), 4.01 (br, 1H), 4.19 (br, 1H) 4.43 (br, 1H), 4.57 (s, 2H), 6.21 (m, 1H), 6.52 (m, 1H), 6.91 (dd, J=1.6, 2.8 Hz, 1H), 7.09 (m, 1H), 7.17 (m, 1H), 7.33 (m, 1H), 7.43 (m, 1H).

Example 54

(Endo)-5-(2,5-dimethyl-2H-pyrazol-3-yl)-2-{3-[3-(2-fluorobenzyloxy)-8-azabicyclo[3.2.1]oct-8-yl]-2-hydroxypropyl}-4-methyl-2,4-dihydro[1,2,4]triazol-3-one oxalate

[Chemical Formula 173]

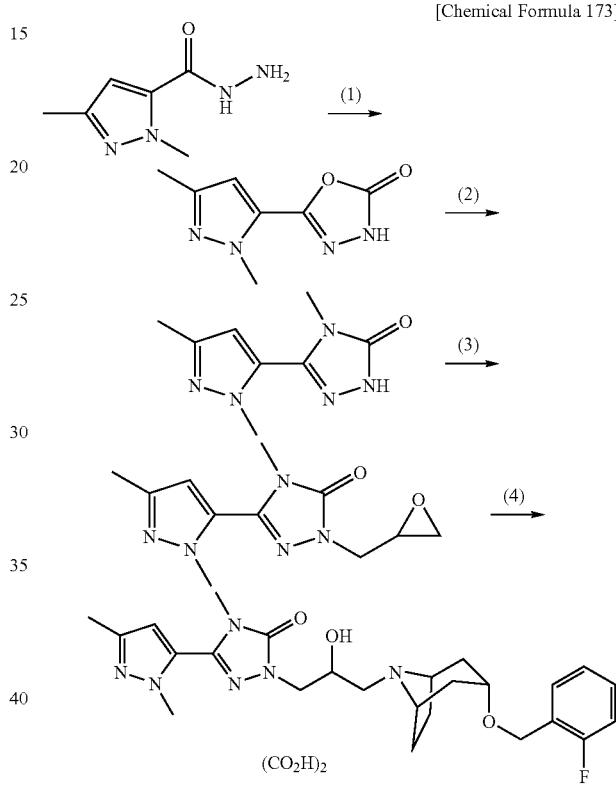

(1) 5-(2,5-Dimethyl-2H-pyrazol-3-yl)-3H-[1,3,4]oxadiazol-2-one

After suspending 2,5-dimethyl-2H-pyrazole-3-carboxylic acid hydrazide (CAS 89187-40-6) (1.15 g) in ethyl acetate (10 ml), trichloromethyl chloroformate (0.90 ml) was added dropwise while stirring on ice. Upon completion of the dropwise addition, the mixture was heated to reflux overnight. It was then allowed to cool, n-heptane (10 ml) was added to the reaction mixture, and the precipitate was collected by filtration to obtain the title compound (1.58 g).

$^1$H-NMR (400 MHz, DMSO-$d_6$); δ 2.19 (s, 3H), 3.97 (s, 3H), 6.58 (s, 1H), 12.79 (brs, 1H).

(2) 5-(2,5-Dimethyl-2H-pyrazol-3-yl)-4-methyl-2,4-dihydro[1,2,4]triazol-3-one Methylamine (40% solution in methanol, 0.22 ml) was added to a mixture of the compound obtained in Example 54-(1) (580 mg) and methanol (5 ml), and the mixture was heated to reflux for 7 hours.

The reaction mixture was concentrated under reduced pressure, and then water (5 ml) and a 1N aqueous solution of sodium hydroxide (3.6 ml) was added to the residue and the mixture was stirred overnight at 100° C. After then adding 5N hydrochloric acid (1.1 ml) to the reaction mixture, it was filtered. Silica gel was added to the filtrate, and the mixture was concentrated under reduced pressure. The residue was purified by silica gel column chromatography to obtain the title compound (104 mg).

¹H-NMR (400 MHz, CDCl₃); δ 2.32 (s, 3H), 3.37 (s, 3H), 4.00 (s, 3H), 6.34 (s, 1H), 9.93 (brs, 1H).

(3) 5-(2,5-Dimethyl-2H-pyrazol-3-yl)-4-methyl-2-oxiranylmethyl-2,4-dihydro[1,2,4]triazol-3-one The title compound (138 mg) was obtained from the compound obtained in Example 54-(2) (100 mg) and epibromohydrin, by the method similar to Example 45-(2).

¹H-NMR (400 MHz, CDCl₃); δ 2.32 (s, 3H), 2.72 (m, 1H), 2.87 (m, 1H), 3.31 (m, 1H), 3.37 (s, 3H), 4.01 (s, 3H), 4.02 (m, 1H), 4.09 (dd, J=4.4, 14.8 Hz, 1H), 6.32 (s, 1H).

(4) (Endo)-5-(2,5-dimethyl-2H-pyrazol-3-yl)-2-{3-[3-(2-fluorobenzyloxy)-8-azabicyclo[3.2.1]oct-8-yl]-2-hydroxypropyl}-4-methyl-2,4-dihydro[1,2,4]triazol-3-one oxalate The title compound (19 mg) was obtained from the compound obtained in Example 54-(3) (105 mg) and the compound obtained in Production Example 5 (126 mg), by the method similar to Example 53-(3).

¹H-NMR (400 MHz, CD₃OD); δ 2.18-2.46 (m, 8H), 2.28 (s, 3H), 3.13-3.24 (m, 2H), 3.36 (s, 3H), 3.78 (m, 1H), 3.94-4.20 (m, 3H), 3.97 (s, 3H), 4.20 (m, 1H), 4.45 (m, 1H), 4.57 (s, 2H), 6.57 (s, 1H), 7.09 (m, 1H), 7.17 (m, 1H), 7.33 (m, 1H), 7.43 (m, 1H).

Example 55

(Endo)-2-{3-[3-(2-fluoromethylbenzyloxy)-8-azabicyclo[3.2.1]oct-8-yl]-2-hydroxy-propyl}-4-methyl-5-oxazol-4-yl-2,4-dihydro[1,2,4]triazol-3-one

[Chemical Formula 174]

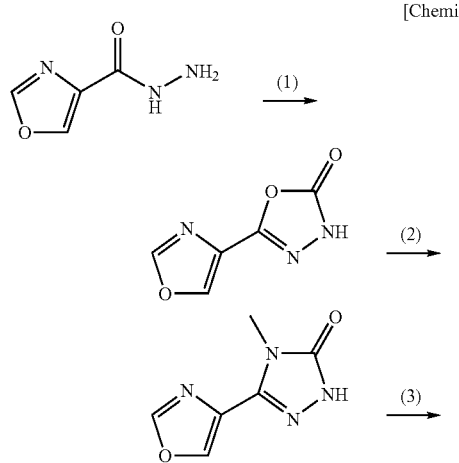

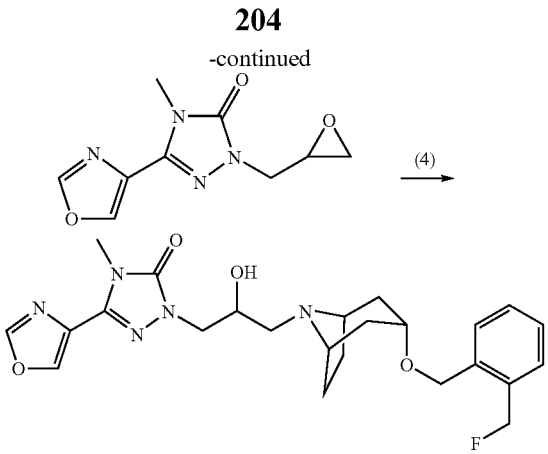

(1) 5-Oxazol-4-yl-3H-[1,3,4]oxadiazol-2-one

After suspending oxazole-4-carboxylic acid hydrazide (CAS 885274-12-4) (1.06 g) in ethyl acetate (10 ml), trichloromethyl chloroformate (1.21 ml) was added dropwise while stirring on ice. Upon completion of the dropwise addition, the mixture was heated to reflux for 2 hours and 20 minutes. It was then allowed to cool, n-heptane was added to the reaction mixture, and the precipitate was collected by filtration. The filtrate was concentrated under reduced pressure and the residue was recrystallized with toluene-ethyl acetate. This was combined with the previously filtered substance to obtain the title compound (1.38 g).

¹H-NMR (400 MHz, DMSO-d₆); δ 8.65 (d, J=0.8 Hz, 1H), 8.87 (d, J=0.8 Hz, 1H), 12.66 (brs, 1H).

(2) 4-Methyl-5-oxazol-4-yl-2,4-dihydro[1,2,4]triazol-3-one

The title compound (287 mg) was obtained from the compound obtained in Example 55-(1) (1.38 g), by the method similar to Example 54-(2).

¹H-NMR (400 MHz, DMSO-d₆); δ 3.33 (s, 3H), 8.63 (s, 1H), 8.73 (s, 1H), 11.96 (brs, 1H).

(3) 4-Methyl-5-oxazol-4-yl-2-oxiranylmethyl-2,4-dihydro[1,2,4]triazol-3-one

The title compound (399 mg) was obtained from the compound obtained in Example 55-(2) (280 mg) and epibromohydrin, by the method similar to Example 45-(2).

¹H-NMR (400 MHz, CDCl₃); δ 2.72 (m, 1H), 2.86 (m, 1H), 3.31 (m, 1H), 3.57 (s, 3H), 4.00 (dd, J=5.2, 14.8 Hz, 1H), 4.07 (m, 1H), 8.00 (d, J=0.4 Hz, 1H), 8.18 (d, J=1.2 Hz, 1H).

(4) (Endo)-2-{3-[3-(2-fluoromethylbenzyloxy)-8-azabicyclo[3.2.1]oct-8-yl]-2-hydroxypropyl}-4-methyl-5-oxazol-4-yl-2,4-dihydro[1,2,4]triazol-3-one The title compound (95 mg) was obtained from the compound obtained in Example 55-(3) (100 mg) and the compound obtained in Production Example 33 (127 mg), by the method similar to Example 44-(2).

¹H-NMR (400 MHz, CDCl₃); δ 1.83-2.10 (m, 8H), 2.28 (dd, J=9.2, 12.4 Hz, 1H), 2.56 (dd, J=4.0, 12.4 Hz, 1H), 3.18 (m, 2H), 3.56 (s, 3H), 3.63 (m, 1H), 3.91 (m, 2H), 4.00 (m,

1H), 4.51 (s, 2H), 5.47 (d, J=48.0 Hz, 2H), 7.32-7.42 (m, 4H), 7.99 (s, 1H), 8.17 (d, J=0.4 Hz, 1H).

Example 56

(Endo)-4,5-dimethyl-2-{3-[3-(2-methylbenzyloxy)-8-azabicyclo[3.2.1]oct-8-yl]-2-oxopropyl}-2,4-dihydro[1,2,4]triazol-3-one

[Chemical Formula 175]

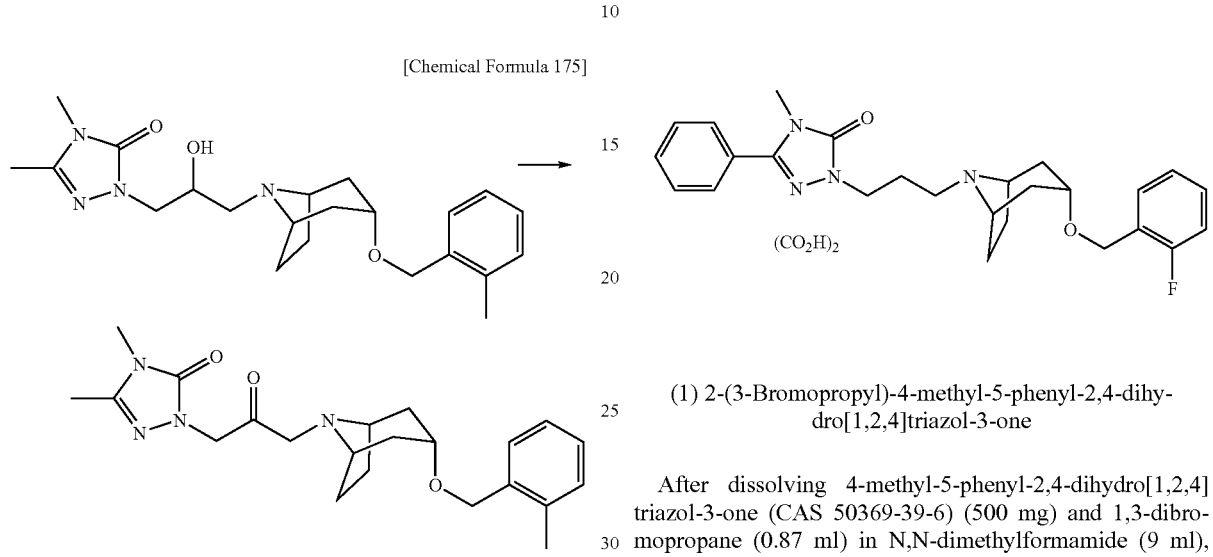

Oxalyl chloride (0.35 ml) was dissolved in dichloromethane (10 ml), and the mixture was cooled to −78° C. After then slowly adding dimethyl sulfoxide (0.57 ml) at −50 to −60° C., the mixture was stirred for 5 minutes. A solution of the compound obtained in Example 29 (800 mg) in dichloromethane (10 ml) was added dropwise, and stirring was continued for 20 minutes. Triethylamine (2.23 ml) was added, and the cooling bath was removed to allow the temperature to rise to room temperature. After stirring for 30 minutes, water was added to the reaction mixture and extraction was performed with ethyl acetate. The organic layer was washed with brine and dried over anhydrous magnesium sulfate. After filtration, the solvent was distilled off under reduced pressure. The residue was purified by silica gel column chromatography. The obtained solid was washed with diethyl ether to obtain the title compound (550 mg).

$^1$H-NMR (400 MHz, CDCl$_3$); δ 1.83-2.14 (m, 8H), 2.23 (s, 3H), 2.30 (s, 3H), 3.10-3.16 (m, 2H), 3.22 (s, 2H), 3.24 (s, 3H), 3.64 (t, J=4.8 Hz, 1H), 4.42 (s, 2H), 4.87 (s, 2H), 7.12-7.20 (m, 3H), 7.32-7.37 (m, 1H).

Example 57

(Endo)-2-{3-[3-(2-fluorobenzyloxy)-8-azabicyclo[3.2.1]oct-8-yl]propyl}-4-methyl-5-phenyl-2,4-dihydro[1,2,4]triazol-3-one oxalate

[Chemical Formula 176]

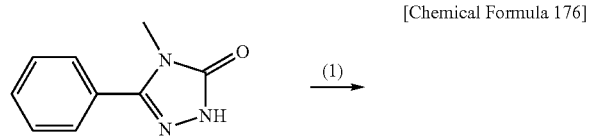

(1) 2-(3-Bromopropyl)-4-methyl-5-phenyl-2,4-dihydro[1,2,4]triazol-3-one

After dissolving 4-methyl-5-phenyl-2,4-dihydro[1,2,4]triazol-3-one (CAS 50369-39-6) (500 mg) and 1,3-dibromopropane (0.87 ml) in N,N-dimethylformamide (9 ml), sodium hydride (60% in oil) (125 mg) was added and the mixture was stirred at room temperature for 6 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (649 mg).

$^1$H-NMR (400 MHz, CDCl$_3$); δ 2.38 (quintet, J=6.8 Hz, 2H), 3.39 (s, 3H), 3.48 (t, J=6.8 Hz, 2H), 4.03 (t, J=6.8 Hz, 2H), 7.47-7.53 (m, 3H), 7.57-7.63 (m, 1H).

(2) (Endo)-2-{3-[3-(2-fluorobenzyloxy)-8-azabicyclo[3.2.1]oct-8-yl]propyl}-4-methyl-5-phenyl-2,4-dihydro[1,2,4]triazol-3-one oxalate The compound obtained in Example 57-(1) (70 mg) was dissolved in N,N-dimethylformamide (1 ml), and then the compound obtained in Production Example 5 (64 mg) and anhydrous potassium carbonate (72 mg) were added and the mixture was stirred at room temperature for 19 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the free form of the title compound (78 mg). This was dissolved in ethanol, and then oxalic acid (16 mg) was added. Diethyl ether was then added to produce a solid, which was collected by filtration to obtain the title compound (80 mg).

$^1$H-NMR (400 MHz, DMSO-d$_6$); δ2.00-2.23 (m, 10H), 2.94-3.08 (m, 2H), 3.30 (s, 3H), 3.69-3.74 (m, 1H), 3.82-3.96

(m, 4H), 4.52 (s, 2H), 7.17-7.24 (m, 2H), 7.34-7.41 (m, 1H), 7.42-7.48 (m, 1H), 7.52-7.59 (m, 3H), 7.67-7.73 (m, 2H).

Example 58

(Endo)-2-{3-[3-(2-fluorobenzyloxy)-8-azabicyclo[3.2.1]oct-8-yl]propyl}-4-phenyl-2,4-dihydro[1,2,4]triazol-3-one

[Chemical Formula 177]

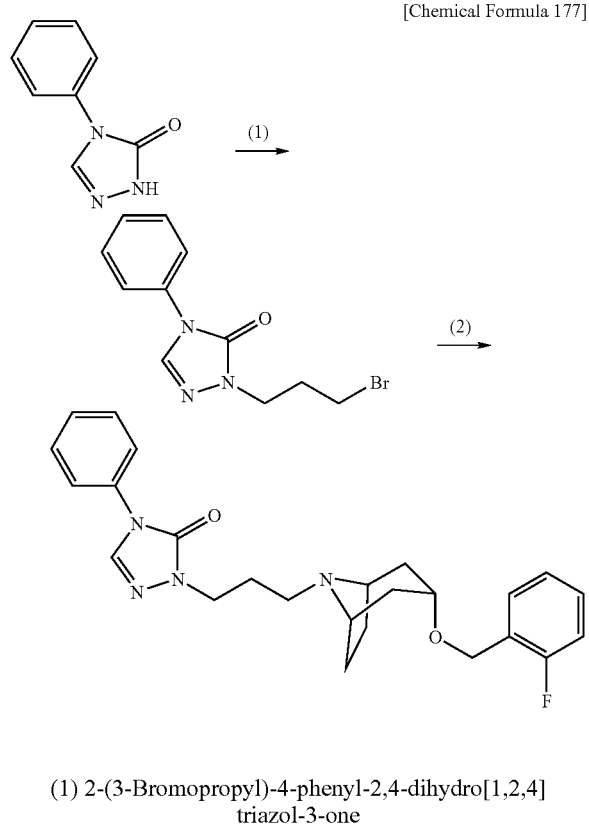

(1) 2-(3-Bromopropyl)-4-phenyl-2,4-dihydro[1,2,4]triazol-3-one

After dissolving 4-phenyl-2,4-dihydro[1,2,4]triazol-3-one (CAS 1008-30-6) (1.00 g) and 1,3-dibromopropane (1.89 ml) in N,N-dimethylformamide (15 ml), sodium hydride (60% in oil) (273 mg) was added and the mixture was stirred at room temperature for 4 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography. The obtained solid was washed with n-heptane to obtain the title compound (840 mg).

$^1$H-NMR (400 MHz, CDCl$_3$); δ 2.38 (quintet, J=6.8 Hz, 2H), 3.49 (t, J=6.8 Hz, 2H), 4.04 (t, J=6.8 Hz, 2H), 7.34-7.40 (m, 1H), 7.46-7.51 (m, 2H), 7.54-7.57 (m, 2H), 7.71 (s, 1H).

(2) (Endo)-2-{3-[3-(2-fluorobenzyloxy)-8-azabicyclo[3.2.1]oct-8-yl]propyl}-4-phenyl-2,4-dihydro[1,2,4]triazol-3-one The compound obtained in Example 58-(1) (70 mg) was dissolved in N,N-dimethylformamide (1 ml), and then the compound obtained in Production Example 5 (68 mg) and anhydrous potassium carbonate (75 mg) were added and the mixture was stirred at room temperature for 19 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography. The obtained solid was washed with n-heptane to obtain the title compound (65 mg).

$^1$H-NMR (400 MHz, CDCl$_3$); δ 1.80-2.06 (m, 10H), 2.44 (t, J=6.8 Hz, 2H), 3.14-3.22 (m, 2H), 3.63 (t, J=4.8 Hz, 1H), 3.96 (t, J=6.8 Hz, 2H), 4.50 (s, 2H), 6.98-7.04 (m, 1H), 7.10-7.16 (m, 1H), 7.21-7.28 (m, 1H), 7.33-7.39 (m, 1H), 7.41-7.58 (m, 6H), 7.69 (s, 1H).

Example 59

(Endo)-2-{4-[3-(2-fluoro-6-methylbenzyloxy)-8-azabicyclo[3.2.1]oct-8-yl]butyl}-4-isopropyl-5-methyl-2,4-dihydro[112.4]triazol-3-one

[Chemical Formula 178]

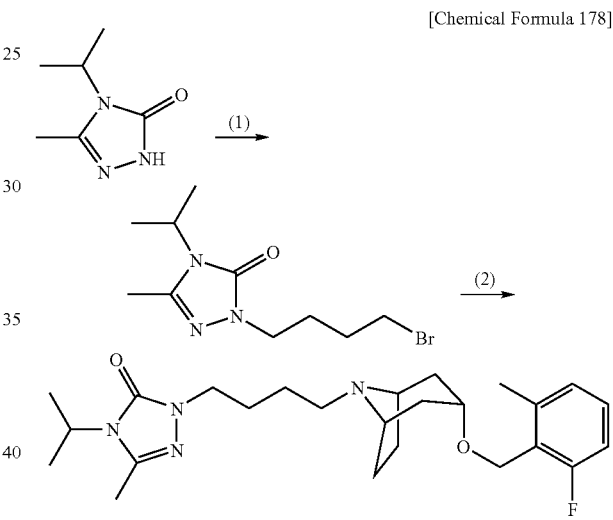

(1) 2-(4-Bromo-butyl)-4-isopropyl-5-methyl-2,4-dihydro[1,2,4]triazol-3-one

The title compound (1.90 g) was obtained from 4-isopropyl-5-methyl-2,4-dihydro[1,2,4]triazol-3-one (CAS 135280-76-1) (1.50 g) and 1,4-dibromobutane by the method similar to Example 57-(1).

$^1$H-NMR (400 MHz, CDCl$_3$); δ 1.47 (d, J=7.2 Hz, 6H), 1.83-1.94 (m, 2H), 2.25 (s, 3H), 3.41-3.47 (m, 2H), 3.71-3.77 (m, 2H), 4.20-4.31 (m, 1H).

(2) (Endo)-2-{4-[3-(2-fluoro-6-methylbenzyloxy)-8-azabicyclo[3.2.1]oct-8-yl]butyl}-4-isopropyl-5-methyl-2,4-dihydro[1,2,4]triazol-3-one The title compound (50 mg) was obtained from the compound obtained in Example 59-(1) (100 mg) and the compound obtained in Production Example 19 (103 mg), by the method similar to Example 36-(2).

$^1$H-NMR (400 MHz, CD$_3$OD); δ 1.47 (d, J=7.2 Hz, 6H), 1.58-1.68 (m, 2H), 1.72-1.81 (m, 2H), 2.00-2.28 (m, 8H), 2.26 (s, 3H), 2.42 (s, 3H), 2.77-2.85 (m, 2H), 3.61-3.76 (m,

3H), 3.74 (t, J=6.8 Hz, 2H), 4.21-4.31 (m, 1H), 4.56 (d, J=2.4 Hz, 2H), 6.91 (t, J=8.8 Hz, 1H), 7.02 (d, J=7.6 Hz, 1H), 7.21 (td, J=7.6, 6.0 Hz, 1H).

Example 60

(Endo)-4-ethyl-5-ethylsulfanyl-2-{3-[3-(2-fluorobenzyloxy)-8-azabicyclo[3.2.1]oct-8-yl]propyl}-2,4-dihydro[1,2,4]triazol-3-one oxalate

[Chemical Formula 179]

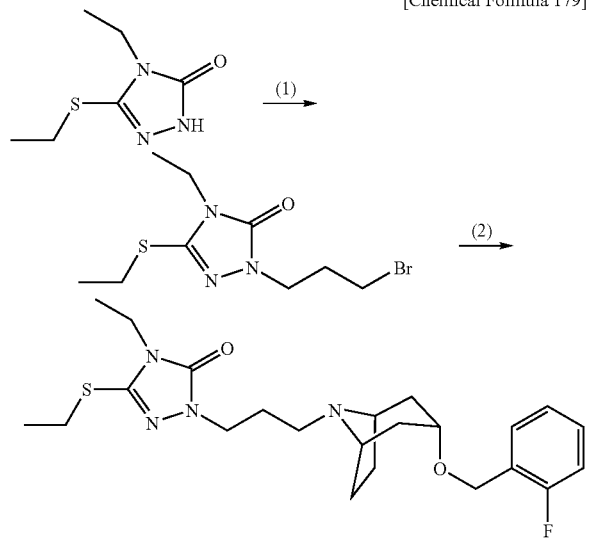

(1) 2-(3-Bromo-propyl)-4-methyl-5-methylsulfanyl-2,4-dihydro[12.41]triazol-3-one The title compound (225 mg) was obtained from 4-ethyl-5-ethylsulfanyl-2,4-dihydro[1,2,4]triazol-3-one (CAS 135838-53-8) (200 mg) and 1,3-dibromopropane by the method similar to Example 57-(1).

$^1$H-NMR (400 MHz, CDCl$_3$); δ 1.28 (t, J=7.2 Hz, 3H), 1.39 (t, J=7.2 Hz, 3H), 2.30 (quintet, J=6.8 Hz, 2H), 3.06 (q, J=7.2 Hz, 2H), 3.44 (t, J=6.8 Hz, 2 h), 3.67 (q, J=6.8 Hz, 2H), 3.92 (q, J=6.8 Hz, 2H).

(2) (Endo)-4-ethyl-5-ethylsulfanyl-2-{3-[3-(2-fluorobenzyloxy)-8-azabicyclo[3.2.1]oct-8-yl]propyl}-2,4-dihydro[1,2,4]triazol-3-one A mixture of the compound obtained in Example 60-(1) (50 mg), the compound obtained in Production Example 5 (54 mg), anhydrous potassium carbonate (102 mg), sodium iodide (55 mg) and N,N-dimethylformamide. (2 ml) was stirred at 80° C. for 4 hours, and then stirred overnight at room temperature. Water was added to the reaction mixture and extraction was performed with diethyl ether. The organic layer was washed with water and brine in that order and then dried over anhydrous magnesium sulfate. After filtration, the solvent was distilled off under reduced pressure. The residue was purified by NH silica gel column chromatography to obtain the free form of the title compound (50 mg).

This was dissolved in methanol (2 ml), and then oxalic acid (10 mg) was added and the solvent was distilled off under reduced pressure. The residue was dissolved in a small amount of dichloromethane, diethyl ether was added, and the resultant solid was collected by filtration. It was then washed with diethyl ether to obtain the title compound (59 mg).

$^1$H-NMR (400 MHz, CD$_3$OD); δ 1.26 (t, J=7.2 Hz, 3H), 1.40 (t, J=7.2 Hz, 3H), 2.10-2.36 (m, 8H), 2.40-2.48 (m, 2H), 3.08 (brs, 2H), 33.12 (q, J=7.2 Hz, 2H), 3.70 (q, J=7.2 Hz, 2H), 3.80 (brs, 1H), 3.90 (t, J=6.4 Hz, 2H), 3.99 (brs, 2H), 4.58 (s, 2H), 7.05-7.12 (m, 1H), 7.14-7.20 (m, 1H), 7.30-7.37 (m, 1H), 7.39-7.45 (m, 1H).

Example 61

(Endo)-2-{2-fluoro-3-[3-(2-methylbenzyloxy)-8-azabicyclo[3.2.1]oct-8-yl]propyl}-5-hydroxymethyl-4-methyl-2,4-dihydro[1,2,4]triazol-3-one

[Chemical Formula 180]

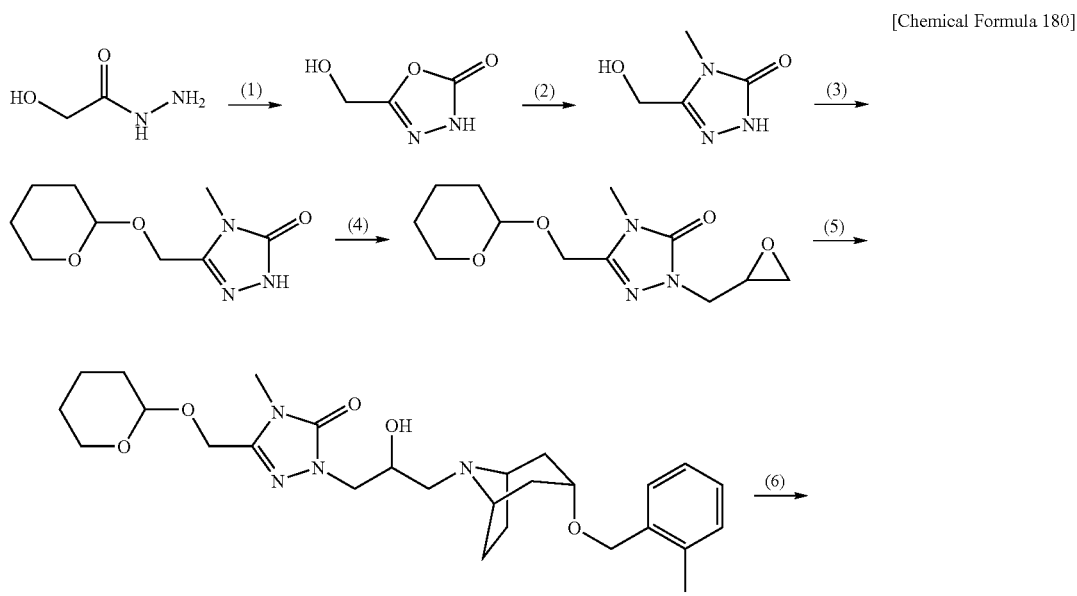

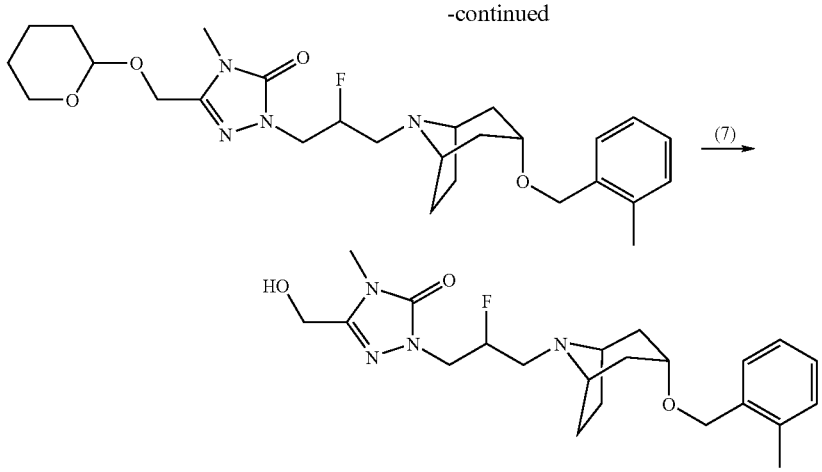

(1) 5-Hydroxymethyl-3H-[1,3,4]oxadiazol-2-one

After suspending glycolic acid hydrazide (CAS 3530-14-1) (3.0 g) in 1,4-dioxane (30 ml), trichloromethyl chloroformate (4.02 ml) was added dropwise while stirring on ice. Upon completion of the dropwise addition, the mixture was heated to reflux for 5 hours. After standing to cool, the reaction mixture was filtered and the filtrate was concentrated under reduced pressure. The residue was purified by silica gel column chromatography. Diethyl ether was then added to produce a solid, which was collected by filtration to obtain the title compound (1.5 g).

$^1$H-NMR (400 MHz, DMSO-$d_6$); δ 3.14 (s, 3H), 3.31 (s, 2H), 4.29 (d, J=6.0 Hz, 2H), 5.46 (t, J=6.0 Hz, 1H), 11.47 (bs, 1H).

(2) 5-Hydroxymethyl-4-methyl-2,4-dihydro[1,2,4]triazol-3-one

The title compound (576 mg) was obtained from the compound obtained in Example 61-(1) (1.5 g) and methylamine, by the method similar to Example 54-(2).

$^1$H-NMR (400 MHz, DMSO-$d_6$); δ 3.14 (s, 3H), 3.31 (s, 2H), 4.29 (d, J=6.0 Hz, 2H), 5.46 (t, J=6.0 Hz, 1H), 11.47 (bs, 1H).

(3) 4-Methyl-5-(tetrahydropyran-2-yloxymethyl)-2,4-dihydro[1,2,4]triazol-3-one After dissolving the compound obtained in Example 61-(2) (576 mg) and 3,4-dihydropyran (0.52 ml) in dichloromethane (10 ml), p-toluenesulfonic acid monohydrate (17 mg) was added and the mixture was stirred at room temperature for one day. A saturated aqueous solution of sodium hydrogencarbonate was added to the reaction mixture, and extraction was performed with ethyl acetate and dichloromethane. The organic layer was washed with brine and dried over anhydrous magnesium sulfate. After filtration, the solvent was distilled off under reduced pressure. The residue was purified by silica gel column chromatography to obtain the title compound (680 mg).

$^1$H-NMR (400 MHz, DMSO-$d_6$); δ 1.40-1.74 (m, 6H), 3.14 (s, 3H), 3.43-3.50 (m, 1H), 3.68-3.76 (m, 1H), 4.32 (d, J=8.4 Hz, 1H), 4.49 (d, J=8.4 Hz, 1H), 4.65-4.68 (m, 1H), 11.62 (bs, 1H).

(4) 4-Methyl-2-oxiranylmethyl-5-(tetrahydropyran-2-yloxymethyl)-2,4-dihydro[1,2,4]triazol-3-one The title compound (689 mg) was obtained from the compound obtained in Example 61-(3) (680 mg) and epibromohydrin, by the method similar to Example 27-(1).

$^1$H-NMR (400 MHz, CDCl$_3$); δ 1.50-1.95 (m, 6H), 2.67-2.71 (m, 1H), 2.84 (t, J=4.4 Hz, 1H), 3.23-3.28 (m, 1H), 3.34 (s, 3H), 3.54-3.60 (m, 1H), 3.80-4.03 (m, 3H), 4.38-4.43 (m, 1H), 4.59-4.65 (m, 1H), 4.67-4.51 (m, 1H).

(5) 2-{2-Hydroxy-3-[3-(2-methylbenzyloxy)-8-azabicyclo[3.2.1]oct-8-yl]-propyl}-4-methyl-5-(tetrahydropyran-2-yloxymethyl)-2,4-dihydro[1,2,4]triazol-3-one The title compound (282 mg) was obtained from the compound obtained in Example 61-(4) (200 mg) and the compound obtained in Production Example 3 (199 mg), by the method similar to Example 27-(2).

$^1$H-NMR (400 MHz, CD$_3$OD); δ 1.81-2.06 (m, 8H), 2.20-2.70 (m, 4H), 2.68 (t, J=6.4 Hz, 2H), 2.76-2.86 (m, 1H), 3.46-3.56 (bs, 1H), 3.61 (t, J=6.4 Hz, 2H), 3.68-3.74 (m, 1H), 3.86 (d, J=6.4 Hz, 2H), 4.26-4.38 (bs, 1H), 4.50 (s, 2H), 7.03 (ddd, J=9.6, 8.0, 1.2 Hz, 1H), 7.13 (td, J=8.0, 1.2 Hz, 1H), 7.24-7.31 (m, 1H), 7.35-7.41 (m, 1H).

(6) 2-{2-Fluoro-3-[3-(2-methylbenzyloxy)-8-azabicyclo[3.2.1]oct-8-yl]-propyl}-4-methyl-5-(tetrahydropyran-2-yloxymethyl)-2,4-dihydro[1,2,4]triazol-3-one The title compound (165 mg) was obtained from the compound obtained in Example 61-(5) (280 mg), by the method similar to Example 28.

(7) (Endo)-2-{2-fluoro-3-[3-(2-methylbenzyloxy)-8-azabicyclo[3.2.1]oct-8-yl]propyl}-5-hydroxymethyl-4-methyl-2,4-dihydro[1,2,4]triazol-3-one The compound obtained in Production Example 61-(6) (165 mg) was dissolved in ethanol (2 ml), and then 4N HCl in ethyl acetate (0.41 ml) was added and the mixture was stirred at room temperature for 2 hours. A saturated aqueous solution of sodium hydrogencarbonate was added to the reaction mixture, and extraction was performed with ethyl acetate. The organic layer was washed with brine and dried over anhydrous magnesium sulfate. After filtration, the solvent was distilled off under reduced pressure. The residue was purified by preparative thin-layer chromatography to obtain the title compound (107 mg).

¹H-NMR (400 MHz, CD₃OD); δ 1.85-2.13 (m, 8H), 2.31 (s, 3H), 2.31 (s, 3H), 2.62-2.77 (m, 2H), 3.20-3.30 (m, 2H), 3.34 (s, 3H), 3.64 (t, J=4.8 Hz, 1H), 3.82-4.14 (m, 2H), 4.44 (s, 2H), 4.49 (s, 2H), 4.80-5.00 (m, 1H), 7.10-7.17 (m, 3H), 7.27-7.31 (m, 1H).

Example 62

(Endo)-5-fluoromethyl-2-{2-fluoro-3-[3-(2-methyl-benzyloxy)-8-azabicyclo[3.2.1]oct-8-yl]propyl}-4-methyl-2,4-dihydro[1,2,4]triazol-3-one

[Chemical Formula 181]

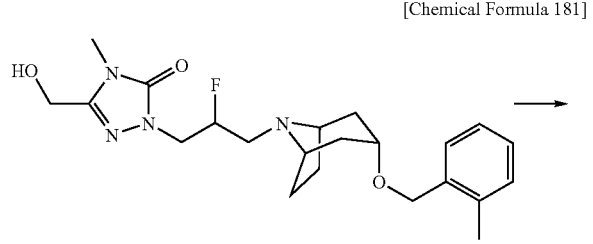

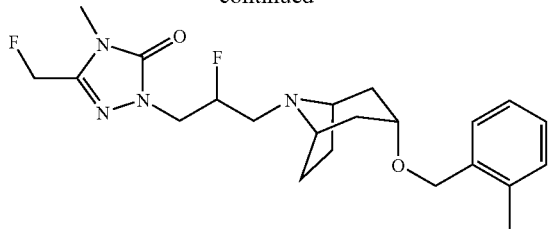

The compound obtained in Example 61 (85 mg) was dissolved in dichloromethane (1.7 ml), and then dimethylaminosulfur trifluoride (40 µl) was added and the mixture was stirred at room temperature for one day. Water was added to the reaction mixture, and extraction was performed with ethyl acetate. The organic layer was washed with brine and dried over anhydrous magnesium sulfate. After filtration, the solvent was distilled off under reduced pressure. The residue was purified by preparative thin-layer chromatography to obtain the title compound (64 mg).

¹H-NMR (400 MHz, CD₃OD); δ 1.84-2.13 (m, 8H), 2.31 (s, 3H), 2.61-2.76 (m, 2H), 3.20-3.30 (m, 2H), 3.35 (s, 3H), 3.63 (t, J=4.8 Hz, 1H), 3.96-4.19 (m, 2H), 4.44 (s, 2H), 4.80-5.01 (m, 1H), 5.33 (d, J=47.6 Hz, 2H), 7.10-7.18 (m, 3H), 7.27-7.31 (m, 1H).

Example 63

(Endo)-2-{2-fluoro-3-[3-(2-fluorobenzyloxy)-8-azabicyclo[3.2.1]oct-8-yl]propyl}-4-(2-hydroxyethyl)-5-methyl-2,4-dihydro[1,2,4]triazol-3-one

[Chemical Formula 182]

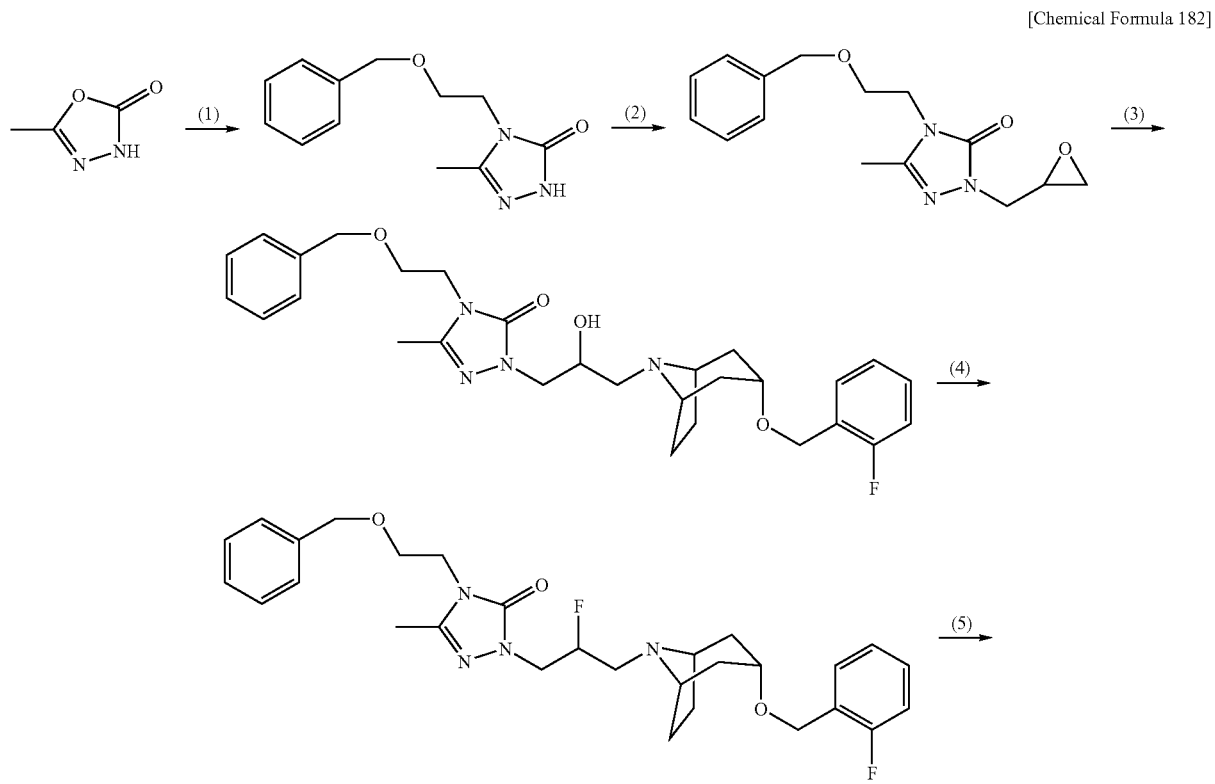

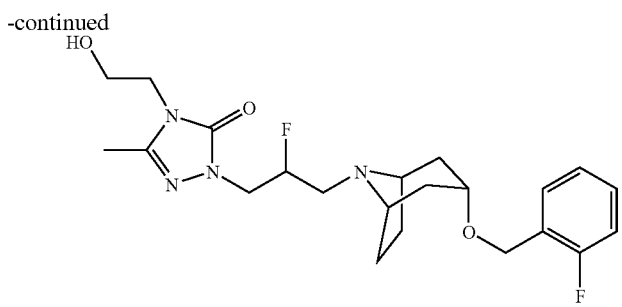

(1) 4-(2-Benzyloxyethyl)-5-methyl-2,4-dihydro[1,2,4]triazol-3-one

The title compound (6.48 g) was obtained from 5-methyl-3H-[1,3,4]oxadiazol-2-one (CAS 3069-67-8) (3.79 g) by the method similar to Example 43-(1).
$^1$H-NMR (400 MHz, DMSO-d$_6$); δ 2.12 (s, 3H), 3.56 (t, J=5.2 Hz, 2H), 3.71 (t, J=5.2 Hz, 2H), 4.45 (s, 2H), 7.20-7.35 (m, 5H), 11.30 (bs, 1H).

(2) 4-(2-Benzyloxyethyl)-5-methyl-2-oxiranylmethyl-2,4-dihydro[1,2,4]triazol-3-one The title compound (4.29 g) was obtained from the compound obtained in Example 63-(1) (4.3 g) and epibromohydrin, by the method similar to Example 44-(1).
$^1$H-NMR (400 MHz, CDCl$_3$); δ 2.25 (s, 3H), 2.68 (dd, J=4.4, 2.8 Hz, 1H), 2.84 (t, J=4.4 Hz, 1H), 3.22-3.28 (m, 1H), 3.67 (t, J=5.2 Hz, 2H), 3.81 (t, J=5.2 Hz, 2H), 3.88 (dd, J=14.4, 5.6 Hz, 1H), 3.95 (dd, J=14.4, 5.2 Hz, 1H), 4.48 (s, 2H), 7.21-7.35 (m, 5H).

(3) (Endo)-4-(2-benzyloxyethyl)-2-{3-[3-(2-fluorobenzyloxy)-8-azabicyclo[3.2.1]oct-8-yl]-2-hydroxypropyl}-5-methyl-2,4-dihydro[1,2,4]triazol-3-one The title compound (667 mg) was obtained from the compound obtained in Example 63-(2) (500 mg) and the compound obtained in Production Example 5 (470 mg), by the method similar to Example 27-(2).
$^1$H-NMR (400 MHz, CD$_3$OD); δ 1.79-2.10 (m, 8H), 2.24 (s, 3H), 2.38-2.51 (m, 2H), 3.12-3.18 (m, 1H), 3.22-3.28 (m, 1H), 3.62 (t, J=4.8 Hz, 1H), 3.66 (t, J=4.8 Hz, 2H), 3.70-3.83 (m, 2H), 3.86 (t, J=4.8 Hz, 2H), 3.97-4.04 (m, 1H), 4.48 (s, 4H), 7.01-7.08 (m, 1H), 7.11-7.17 (m, 1H), 7.21-7.33 (m, 6H), 7.39-7.44 (m, 1H).

(4) (Endo)-4-(2-benzyloxyethyl)-2-{2-fluoro-3-[3-(2-fluorobenzyloxy)-8-azabicyclo[3.2.1]oct-8-yl]propyl}-5-methyl-2,4-dihydro[1,2,4]triazol-3-one The title compound (381 mg) was obtained from the compound obtained in Example 63-(3) (660 mg), by the method similar to Example 62.
$^1$H-NMR (400 MHz, CD$_3$OD); δ 1.81-2.12 (m, 8H), 2.24 (s, 3H), 2.58-2.72 (m, 2H), 3.17-3.25 (m, 2H), 3.60-3.69 (m, 3H), 3.83-4.10 (m, 4H), 4.48 (s, 2H), 4.49 (s, 2H), 4.80-4.99 (m, 1H), 7.02-7.08 (m, 1H), 7.14 (td, J=7.6, 1.2 Hz, 1H), 7.20-7.32 (m, 6H), 7.42 (td, J=7.6, 1.6 Hz, 1H).

(5) (Endo)-2-{2-fluoro-3-[3-(2-fluorobenzyloxy)-8-azabicyclo[3.2.1]oct-8-yl]propyl}-4-(2-hydroxyethyl)-5-methyl-2,4-dihydro[1,2,4]triazol-3-one The compound obtained in Example 63-(4) (380 mg) was dissolved in methanol (10 ml), and then 20% palladium hydroxide on carbon (50% wet) (120 mg) was added and the mixture was stirred at room temperature for 2 days under a hydrogen atmosphere (1 atm). After further addition of 20% palladium hydroxide on carbon (50% wet) (60 mg) and acetic acid (2 ml), stirring was continued at room temperature for two days. The reaction mixture was filtered with Celite, and the filtrate was concentrated under reduced pressure. The residue was purified by silica gel column chromatography to obtain the title compound (170 mg).
$^1$H-NMR (400 MHz, (CD$_3$OD); δ 1.83-2.13 (m, 8H), 2.28 (s, 3H), 2.59-2.72 (m, 2H), 3.18-3.28 (m, 2H), 3.63 (t, J=5.2 Hz, 1H), 3.70-3.78 (m, 4H), 3.88-4.11 (m, 2H), 4.50 (s, 2H), 4.80-4.99 (m, 1H), 7.02-7.08 (m, 1H), 7.14 (td, J=7.6, 1.2 Hz, 1H), 7.25-7.32 (m, 1H), 7.42 (td, J=7.6, 1.6 Hz, 1H).

Example 64

(Endo)-4-(2-fluoroethyl)-2-{2-fluoro-3-[3-(2-fluorobenzyloxy)-8-azabicyclo[3.2.1]oct-8-yl]propyl}-5-methyl-2,4-dihydro[1,2,4]triazol-3-one

[Chemical Formula 183]

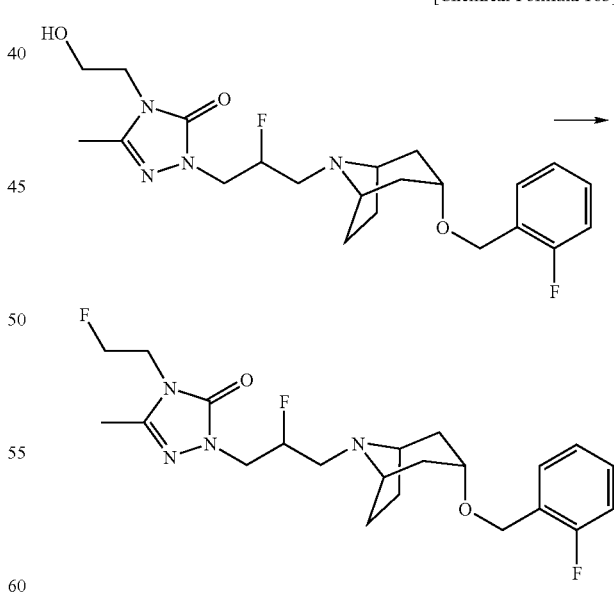

The title compound (110 mg) was obtained from the compound obtained in Example 63 (130 mg), by the method similar to Example 62.
$^1$H-NMR (400 MHz, CD$_3$OD); δ 1.83-2.13 (m, 8H), 2.25 (s, 3H), 2.60-2.73 (m, 2H), 3.18-3.28 (m, 2H), 3.63 (t, J=4.8 Hz, 1H), 3.89-4.12 (m, 4H), 4.50 (s, 2H), 4.54 (t, J=4.8 Hz, 1H), 4.66 (t, J=4.8 Hz, 1H), 4.80-5.00 (m, 1H), 7.02-7.08 (m, 1H), 7.14 (td, J=7.6, 1.2 Hz, 1H), 7.25-7.32 (m, 1H), 7.42 (td, J=7.6, 1.6 Hz, 1H).

Example 65

(Endo)-3-{3-[3-(2-fluorobenzyloxy)-8-azabicyclo[3.2.1]oct-8-yl]-2-methoxypropyl}-1,6-dimethyl-1H-[1,3,5]triazine-2,4-dione

[Chemical Formula 184]

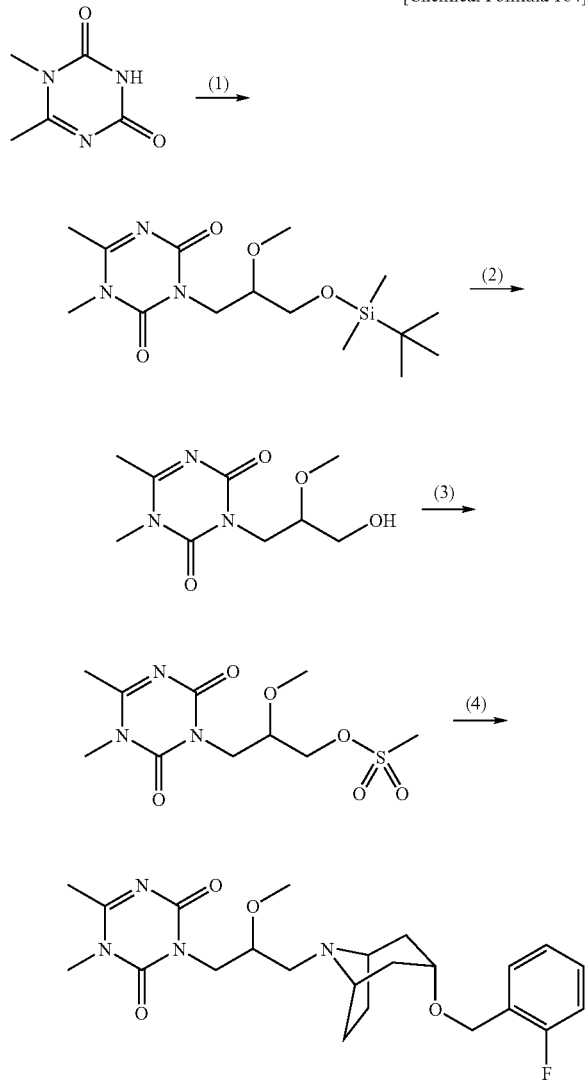

(1) 3-[3-(tert-Butyl-dimethyl-silanyloxy)-2-methoxy-propyl]-1,6-dimethyl-1H-[1,3,5]triazine-2,4-dione The compound obtained in Example 12-(1) (579 mg) and the compound obtained in Production Example 67 (1.31 g) were dissolved in N,N-dimethylformamide (10 ml), and then sodium hydride (60% in oil) (164 mg) was added while cooling on ice and the mixture was stirred for 2 hours and 30 minutes. Sodium hydride (60% in oil) (100 mg) was further added and the mixture was stirred at room temperature for 1 hour. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (520 mg).

$^1$H-NMR (400 MHz, CDCl$_3$); δ 0.06 (s, 6H), 0.89 (s, 9H), 2.46 (s, 3H), 3.40 (s, 3H), 3.46 (s, 3H), 3.66-3.73 (m, 3H), 3.89-3.95 (m, 1H), 4.15-4.21 (m, 1H).

(2) 3-(3-Hydroxy-2-methoxypropyl)-1,6-dimethyl-1H-[1,3,5]triazine-2,4-dione

The title compound (330 mg) was obtained from the compound obtained in Example 65-(1) (520 mg), by the method similar to Example 12-(3).

(3) Methanesulfonic acid 3-(3,4-dimethyl-2,6-dioxo-3,6-dihydro-2H-[1,3,5]triazin-1-yl)-2-methoxypropyl ester A mixture of the compound obtained in Example 65-(2) (330 mg), triethylamine (0.60 ml), trimethylamine hydrochloride (41 mg) and acetonitrile (6 ml) was cooled on ice, and then methanesulfonyl chloride (0.34 ml) was added dropwise while stirring. After stirring for 1 hour, the reaction mixture was concentrated under reduced pressure. Acetone was added to the residue, and the mixture was filtered. The filtrate was concentrated under reduced pressure and the residue was purified by silica gel column chromatography. The obtained oil was solidified with diethyl ether-ethyl acetate and collected by filtration to obtain the title compound (382 mg).

$^1$H-NMR (400 MHz, CDCl$_3$); δ 2.49 (s, 3H), 3.08 (s, 3H), 3.48 (s, 3H), 3.48 (s, 3H), 3.83-3.89 (m, 1H), 4.06 (dd, J=6.4, 13.6 Hz, 1H), 4.15-4.22 (m, 2H), 4.38 (dd, J=3.6, 11.2 Hz, 1H).

(4) (Endo)-3-{3-[3-(2-fluorobenzyloxy)-8-azabicyclo[3.2.1]oct-8-yl]-2-methoxypropyl}-1,6-dimethyl-1H-[1,3,5]triazine-2,4-dione A mixture of the compound obtained in Example 65-(3) (104 mg), the compound obtained in Production Example 57 (80 mg), anhydrous potassium carbonate (52 mg), sodium iodide (catalytic amount) and N,N-dimethylformamide (1 ml) was stirred at 50° C. for 20 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography. The obtained oil was solidified with diethyl ether and collected by filtration to obtain the title compound (15 mg).

$^1$H-NMR (400 MHz, CDCl$_3$); δ 1.75-2.06 (m, 8H), 2.42-2.50 (m, 1H), 2.45 (s, 3H), 2.55-2.61 (m, 1H), 3.09-3.20 (m, 2H), 3.40 (s, 3H), 3.46 (s, 3H), 3.57-3.61 (m, 1H), 3.65-3.72 (m, 1H), 4.08 (dd, J=6.0, 13.2 Hz, 1H), 4.17 (dd, J=6.8, 13.2

Hz, 1H), 4.49 (s, 2H), 6.98-7.04 (m, 1H), 7.11-7.16 (m, 1H), 7.21-7.28 (m, 1H), 7.40-7.46 (m, 1H).

Example 66

(Endo)-1-ethyl-3-{(R)-3-[3-(2-fluoromethylbenzyloxy)-8-azabicyclo[3.2.1]oct-8-yl]-2-hydroxypropyl}-6-methyl-1H-[1,3,5]triazine-2,4-dione oxalate

[Chemical Formula 185]

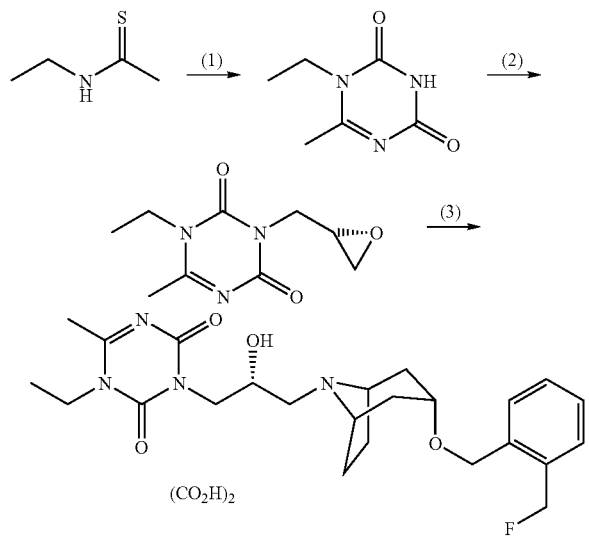

(1) 1-Ethyl-6-methyl-1H-[1,3,5]triazine-2,4-dione

After dissolving N-ethylthioacetamide (CAS 3956-29-4) (5.0 g) and triethylamine (13.4 ml) in propionitrile (150 ml), silver cyanate (14.5 g) was slowly added while stirring at room temperature. Upon completion of the addition, the mixture was heated to reflux for 2 hours and 30 minutes. The reaction mixture was filtered and the filtrate was concentrated under reduced pressure. The residue was purified by silica gel column chromatography to obtain the title compound (3.18 g).

$^1$H-NMR (400 MHz, CD$_3$OD); δ 1.28 (t, J=7.2 Hz, 3H), 2.48 (s, 3H), 3.95 (q, J=7.2 Hz, 2H).

(2) 1-Ethyl-6-methyl-3-(S)-1-oxiranylmethyl-1H-[1,3,5]triazine-2,4-dione

The compound obtained in Example 66-(1) (500 mg) and (R)-(−)-epichlorhydrin (0.76 ml) were dissolved in N,N-dimethylformamide (10 ml), and then sodium hydride (60% in oil) (155 mg) and sodium iodide (155 mg) were added and the mixture was stirred at room temperature for 3 days. Water was added to the reaction mixture, and extraction was performed with chloroform. The extract was dried over anhydrous magnesium sulfate and filtered, and then the solvent was distilled off under reduced pressure. The residue was purified by NH silica gel column chromatography to obtain the title compound (214 mg).

$^1$H-NMR (400 MHz, CDCl$_3$); δ 1.35 (t, J=7.2 Hz, 3H), 2.50 (s, 3H), 2.70-2.72 (m, 1H), 2.79-2.81 (m, 1H), 3.29-3.34 (m, 1H), 3.97 (q, J=7.2 Hz, 2H), 4.01-4.22 (m, 2H).

(3) (Endo)-1-ethyl-3-{(R)-3-[3-(2-fluoromethylbenzyloxy)-8-azabicyclo[3.2.1]oct-8-yl]-2-hydroxypropyl}-6-methyl-1H-[1,3,5]triazine-2,4-dione oxalate A mixture of the compound obtained in Example 66-(2) (100 mg), the compound obtained in Production Example 33 (77 mg), anhydrous potassium carbonate (37 mg) and N,N-dimethylformamide (2 ml) was stirred at 80° C. for 5 hours and 10 minutes. The reaction mixture was concentrated and the residue was purified by silica gel column chromatography. The obtained oil was dissolved in ethanol, and then oxalic acid (5 mg) was added and the mixture was concentrated under reduced pressure. Diethyl ether was added to the residue to produce a solid, which was collected by filtration to obtain the title compound (23 mg).

$^1$H-NMR (400 MHz, DMSO-d$_6$); δ 1.18-1.22 (m, 3H), 2.07-2.26 (m, 8H), 2.44 (s, 3H), 2.90-3.00 (m, 2H), 3.67-3.71 (m, 2H), 3.85-3.90 (m, 4H), 4.06 (bs, 1H), 4.26 (bs, 1H), 4.56 (s, 2H), 5.46-5.58 (m, 2H), 7.34-7.45 (m, 4H).

Example 67

(Endo)-3-{3-[3-(2-difluoromethoxybenzyloxy)-8-azabicyclo[3.2.1]oct-8-yl]-2-hydroxypropyl}-1,6-dimethyl-1H-[1,3,5]triazine-2,4-dione oxalate

[Chemical Formula 186]

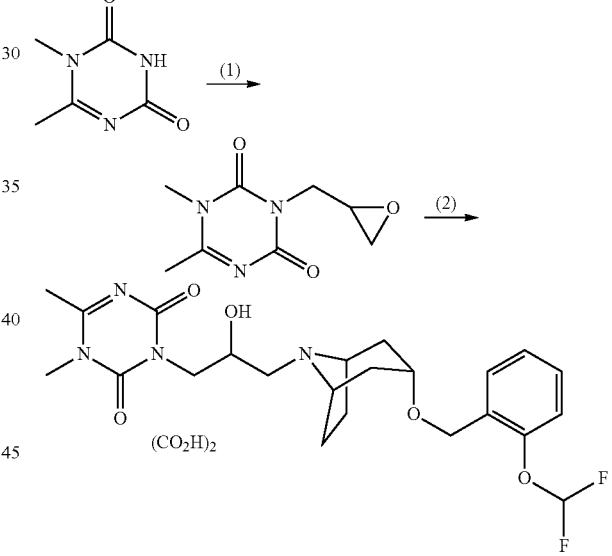

(1) 1,6-Dimethyl-3-oxiranylmethyl-1H-[1,3,5]triazine-2,4-dione

The title compound (398 mg) was obtained from the compound obtained in Example 12-(1) (400 mg) and epibromohydrin, by the method similar to Example 66-(2).

$^1$H-NMR (400 MHz, CD$_3$OD); δ 2.48 (s, 3H), 2.70-2.72 (m, 1H), 2.79-2.81 (m, 1H), 3.27-3.31 (m, 1H), 3.47 (s, 3H), 3.96-4.21 (m, 2H).

(2) (Endo)-3-{3-[3-(2-difluoromethoxybenzyloxy)-8-azabicyclo[3.2.1]oct-8-yl]-2-hydroxy-propyl}-1,6-dimethyl-1H-[1,3,5]triazine-2,4-dione oxalate The title compound (19 mg) was obtained from the compound obtained in Example 67-(1) (60 mg) and the compound obtained in Production Example 31 (107 mg), by the method similar to Example 66-(3).

$^1$H-NMR (400 MHz, CD$_3$OD); δ 2.07-2.36 (m, 6H), 2.46-2.47 (m, 5H), 3.02-3.17 (m, 2H), 3.46 (s, 3H), 3.79 (bs, 1H), 3.89-4.09 (m, 3H), 4.18 (bs, 1H), 4.37-4.39 (m, 1H), 4.57 (s, 2H), 6.67-7.04 (m, 1H), 7.16-7.18 (m, 1H), 7.22-7.26 (m, 1H), 7.34-7.38 (m, 1H), 7.46-7.49 (m, 1H).

Example 68

(Endo)-3-{3-[3-(2-fluorobenzyloxy)-8-azabicyclo[3.2.1]oct-8-yl]propyl}-6-methyl-1-(2,2,2-trifluoroethyl)-1H-[1,3,5]triazine-2,4-dione

[Chemical Formula 187]

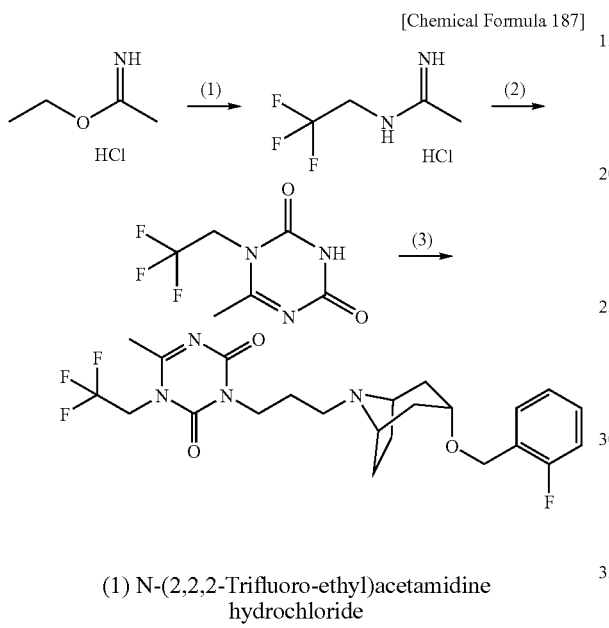

(1) N-(2,2,2-Trifluoro-ethyl)acetamidine hydrochloride

A mixture of 2,2,2-trifluoroethylamine (3 ml), ethyl acetimidate hydrochloride (4.8 g) and ethanol (12 ml) was stirred at room temperature for 90 minutes, and then stirred overnight at 80° C. The reaction mixture was concentrated under reduced pressure to obtain the title compound (6.66 g).

(2) 6-Methyl-1-(2,2,2-trifluoroethyl)-1H-[1,3,5]triazine-2,4-dione

The compound obtained in Example 68-(1) (1.0 g) was suspended in ethanol (30 ml), and then potassium tert-butoxide (635 mg) was added and the mixture was stirred at room temperature for 1 hour. The reaction mixture was filtered and the filtrate was concentrated under reduced pressure. The residue was suspended in acetonitrile (30 ml), and then diphenyl imidodicarbonate (CAS 99911-94-1) (1.6 g) was added and the mixture was stirred at room temperature for 5 hours. Toluene was added to the reaction mixture, which was then concentrated under reduced pressure until precipitation of a solid. The obtained solid was collected by filtration to obtain the title compound (625 mg).
$^1$H-NMR (400 MHz, CD$_3$OD); δ 2.54 (s, 3H), 4.61-4.67 (m, 2H).

(3) (Endo)-3-{3-[3-(2-fluorobenzyloxy)-8-azabicyclo[3.2.1]oct-8-yl]propyl}-6-methyl-1-(2,2,2-trifluoroethyl)-1H-[1,3,5]triazine-2,4-dione A mixture of the compound obtained in Example 68-(2) (100 mg), the compound obtained in Production Example 53 (168 mg), triphenylphosphine (150 mg) and tetrahydrofuran (2 ml) was cooled on ice, and then diisopropyl azodicarboxylate (0.14 ml) was added while stirring and the temperature was gradually raised to room temperature. After stirring for 4 hours, the reaction mixture was concentrated under reduced pressure. The residue was purified by silica gel column chromatography. The obtained solid was washed with diethyl ether to obtain the title compound (21 mg).
$^1$H-NMR (400 MHz, DMSO-d$_6$); δ 1.91-2.33 (m, 10H), 2.46 (s, 3H), 2.97 (bs, 2H), 3.73 (bs, 1H), 3.81-3.84 (m, 2H), 3.91 (bs, 2H), 4.52 (s, 2H), 4.84-4.91 (m, 2H), 7.18-7.23 (m, 2H), 7.35-7.40 (m, 1H), 7.43-7.47 (m, 1H).

Example 69

(Endo)-3-[3-(3-cyclopropylmethoxy-8-azabicyclo[3.2.1]oct-8-yl)propyl]-1-ethyl-6-methyl-1H-[1,3,5]triazine-2,4-dione oxalate

[Chemical Formula 188]

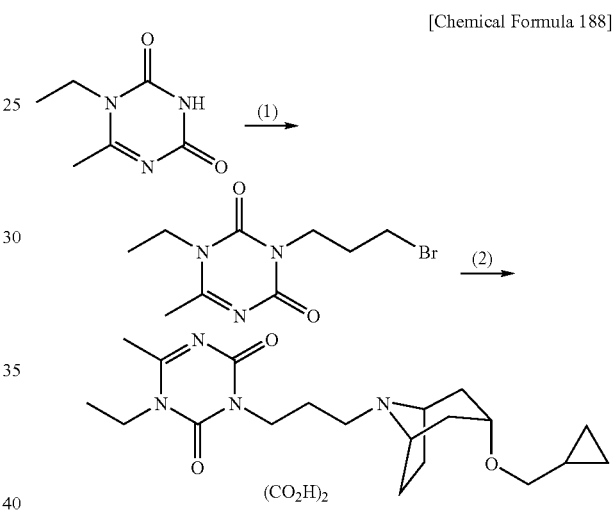

(1) 3-(3-Bromopropyl)-1-ethyl-6-methyl-1H-[1,3,5]triazine-2,4-dione

The compound obtained in Example 66-(1) (600 mg) and 1,3-dibromopropane (1.18 ml) were dissolved in N,N-dimethylformamide (25 ml), and then sodium hydride (60% in oil) (200 mg) was added and the mixture was stirred at room temperature for one day. Water was added to the reaction mixture, and extraction was performed with chloroform. The extract was dried over anhydrous magnesium sulfate and filtered, and then the solvent was distilled off under reduced pressure. The residue was purified by NH silica gel column chromatography to obtain the title compound (799 mg).
$^1$H-NMR (400 MHz, CDCl$_3$); δ 1.34 (t, J=7.2 Hz, 3H), 2.26 (quintet, J=6.8 Hz, 2H), 2.49 (s, 3H), 3.43 (t, J=6.8 Hz, 3H), 3.96 (q, J=7.2 Hz, 2H), 4.06 (t, J=6.8 Hz, 2H).

(2) (Endo)-3-[3-(3-cyclopropylmethoxy-8-azabicyclo[3.2.1]oct-8-yl)propyl]-1-ethyl-6-methyl-1H-[1,3,5]triazine-2,4-dione oxalate A mixture of the compound obtained in Example 69-(1) (100 mg), the compound obtained in Production Example 32 (87 mg), anhydrous potassium carbonate (150 mg) and N,N-dimethylformamide (1 ml) was stirred at room temperature for one day. The reaction mixture was concentrated under reduced pressure, and the residue was purified by NH silica gel column chromatography. The obtained free form of the title compound (87 mg) was dissolved in ethanol, and oxalic acid (20 mg) was added. The mixture was concentrated under reduced pressure, and diethyl ether was added to the residue to produce a solid, which was collected by filtration to obtain the title compound (48 mg).

$^1$H-NMR (400 MHz, CD$_3$OD); δ 0.20-0.24 (m, 2H), 0.50-0.54 (m, 2H), 1.01-1.06 (m, 1H), 1.29-1.32 (m, 3H), 2.07-2.25 (m, 8H), 2.43-2.50 (m, 5H), 3.07-3.11 (m, 2H), 3.28-3.29 (m, 2H), 3.66 (bs, 1H), 3.93 (bs, 2H), 3.97-4.02 (m, 4H).

Example 70

(Endo)-3-{3-[3-(2-fluorobenzyloxy)-8-azabicyclo[3.2.1]oct-8-yl]propyl}-1-(2-fluoro-ethyl)-6-methyl-1H-[1,3,5]triazine-2,4-dione oxalate

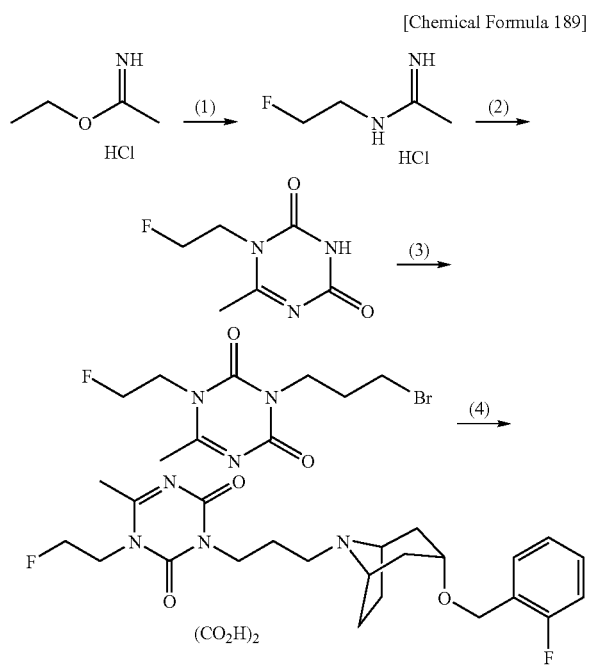

[Chemical Formula 189]

(1) N-(2-Fluoroethyl)acetamidine hydrochloride

After suspending ethyl acetamidate hydrochloride (2.31 g) in ethanol (50 ml), potassium tert-butoxide (2.03 g) was added and the mixture was stirred at room temperature for 30 minutes. The reaction mixture was filtered, 2-fluoroethylamine hydrochloride (2 g) was added to the filtrate, and the mixture was stirred overnight at 80° C. The reaction mixture was concentrated under reduced pressure, the residue was suspended in a small amount of ethanol, and the suspension was filtered. The filtrate was concentrated under reduced pressure to obtain the title compound (2.56 g).

(2) 1-(2-Fluoroethyl)-6-methyl-1H-[1,3,5]triazine-2,4-dione

The title compound (392 mg) was obtained from the compound obtained in Example 70-(1) (1.0 g), by the method similar to Example 68-(2).

$^1$H-NMR (400 MHz, CDCl$_3$); δ 2.52 (s, 3H), 3.88 (bs, 1H), 4.18-4.27 (m, 2H), 4.63-4.77 (m, 2H).

(3) 3-(3-Bromopropyl)-1-(2-fluoroethyl)-6-methyl-1H-[1,3,5]triazine-2,4-dione

The title compound (326 mg) was obtained from the compound obtained in Example 70-(2) (392 mg), by the method similar to Example 69-(1).

$^1$H-NMR (400 MHz, CDCl$_3$); δ 2.27 (quintet, J=6.8 Hz, 2H), 2.52 (s, 3H), 3.44 (t, J=6.8 Hz, 2H), 4.08 (t, J=6.8 Hz, 2H), 4.17-4.26 (m, 2H), 4.63-4.78 (m, 2H).

(4) (Endo)-3-{3-[3-(2-fluorobenzyloxy)-8-azabicyclo[3.2.1]oct-8-yl]propyl}-1-(2-fluoro-ethyl)-6-methyl-1H-[1,3,5]triazine-2,4-dione oxalate The title compound (33 mg) was obtained from the compound obtained in Example 70-(3) (50 mg) and the compound obtained in Production Example 5 (46 mg), by the method similar to Example 69-(2).

$^1$H-NMR (400 MHz, CD$_3$OD); δ 2.08-2.18 (m, 4H), 2.21-2.32 (m, 4H), 2.40-2.45 (m, 2H), 2.48-2.50 (m, 3H), 3.08-3.12 (m, 2H), 3.79 (bs, 1H), 3.94 (bs, 2H), 3.96-4.03 (m, 2H), 4.25-4.33 (m, 2H), 4.57 (s, 2H), 4.63-4.77 (m, 2H), 7.06-7.11 (m, 1H), 7.15-7.19 (m, 1H), 7.31-7.36 (m, 1H), 7.41-7.44 (m, 1H).

Example 71

(Endo)-1,6-dimethyl-3-{2-methyl-3-[3-(2-methylbenzyloxy)-8-azabicyclo[3.2.1]oct-8-yl]propyl}-1H-[1,3,5]triazine-2,4-dione

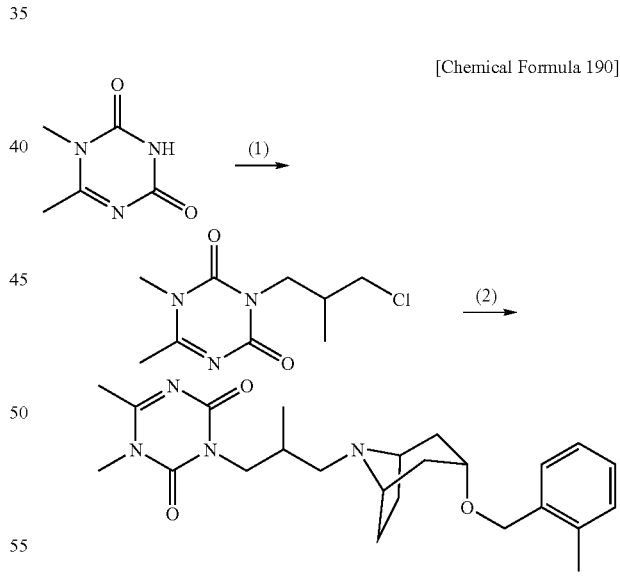

[Chemical Formula 190]

(1) 3-(3-Chloro-2-methylpropyl)-1,6-dimethyl-1H-[1,3,5]triazine-2,4-dione

The title compound (627 mg) was obtained from the compound obtained in Example 12-(1) (500 mg) and 1-bromo-3-chloro-2-methylpropane, by the method similar to Example 69-(1).

$^1$H-NMR (400 MHz, CDCl$_3$); δ 1.06-1.08 (m, 3H), 2.42-2.48 (m, 4H), 3.43-3.55 (m, 5H), 3.87-4.00 (m, 2H).

(2) (Endo)-1,6-dimethyl-3-{2-methyl-3-[3-(2-methylbenzyloxy)-8-azabicyclo[3.2.1]oct-8-yl]propyl}-1H-[1,3,5]triazine-2,4-dione A mixture of the compound obtained in Example 71-(1) (100 mg), the compound obtained in Production Example 3 (106 mg), anhydrous potassium carbonate (155 mg), sodium iodide (56 mg) and N,N-dimethylformamide (2 ml) was stirred at room temperature for 5 days. The reaction mixture was concentrated under reduced pressure, and the residue was purified by preparative thin-layer chromatography to obtain the title compound (5 mg).

$^1$H-NMR (400 MHz, CD$_3$OD); δ 0.89-0.91 (m, 3H), 1.76-1.90 (m, 6H), 1.96-2.02 (m, 2H), 2.17-2.27 (m, 1H), 2.30 (s, 3H), 2.32-2.39 (m, 2H), 2.42-2.44 (m, 3H), 3.06 (bs, 1H), 3.17 (bs, 1H), 3.44 (s, 3H), 3.59 (bs, 1H), 3.71-3.76 (m, 1H), 3.99-4.04 (m, 1H), 4.42 (s, 2H), 7.10-7.17 (m, 3H), 7.27-7.29 (m, 1H).

Example 72

(Endo)-1,6-dimethyl-3-{3-[3-(2-methylbenzyloxy)-8-azabicyclo[3.2.1]oct-8-yl]propyl}-1H-[1,3,5]triazine-2,4-dione oxalate

[Chemical Formula 191]

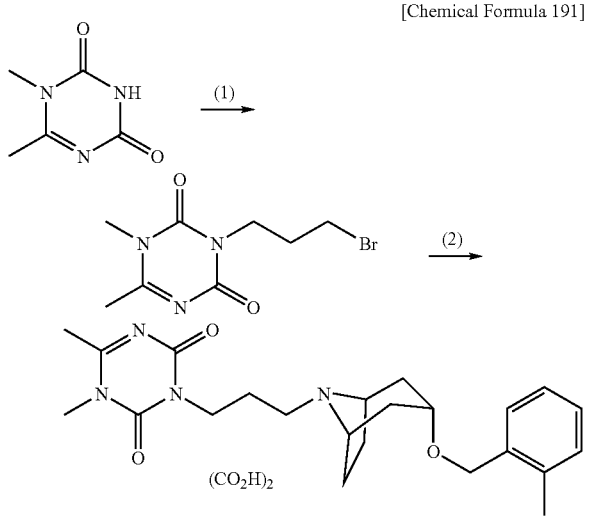

(1) 3-(3-Bromo-propyl)-1,6-dimethyl-1H-[1,3,5]triazine-2,4-dione

The compound obtained in Example 12-(1) (300 mg) and 1,3-dibromopropane (0.66 ml) were dissolved in N,N-dimethylformamide (3 ml), and then sodium hydride (60% in oil) (102 mg) was added and the mixture was stirred at room temperature for 20 hours. A small amount of water was added to the reaction mixture, and the resulting mixture was concentrated under reduced pressure. The residue was purified by NH silica gel column chromatography to obtain the title compound (165 mg).

$^1$H-NMR (400 MHz, CD$_3$OD); δ 2.18-2.22 (m, 2H), 2.44 (s, 3H), 3.44 (s, 3H), 3.45-3.49 (m, 2H), 3.99-4.03 (m, 2H).

(2) (Endo)-1,6-dimethyl-3-{3-[3-(2-methylbenzyloxy)-8-azabicyclo[3.2.1]oct-8-yl]propyl}-1H-[1,3,5]triazine-2,4-dione oxalate A mixture of the compound obtained in Example 72-(1) (80 mg), the compound obtained in Production Example 3 (90 mg), anhydrous potassium carbonate (126 mg) and N,N-dimethylformamide (1 ml) was stirred at room temperature for 15 hours. Water was added to the reaction mixture, and extraction was performed with chloroform. The extract was dried over anhydrous magnesium sulfate and filtered, and then the solvent was distilled off under reduced pressure. The residue was purified by NH silica gel column chromatography to obtain the free form of the title compound (70 mg). This was dissolved in ethanol, oxalic acid (15 mg) was added, and the mixture was concentrated under reduced pressure. Diethyl ether was added to the residue to produce a solid, which was collected by filtration to obtain the title compound (55 mg).

$^1$H-NMR (400 MHz, CD$_3$OD); δ 2.07-2.28 (m, 8H), 2.33 (s, 3H), 2.40-2.46 (m, 5H), 3.08-3.11 (m, 2H), 3.45 (s, 3H), 3.78 (bs, 1H), 3.94 (bs, 2H), 3.97-4.00 (m, 2H), 4.53 (s, 2H), 7.13-7.21 (m, 3H), 7.29-7.30 (m, 1H).

Example 73

(Endo)-6-ethyl-1-methyl-3-{3-[3-(2-methylbenzyloxy)-8-azabicyclo[3.2.1]oct-8-yl]propyl}-1H-[1,3,5]triazine-2,4-dione oxalate

[Chemical Formula 192]

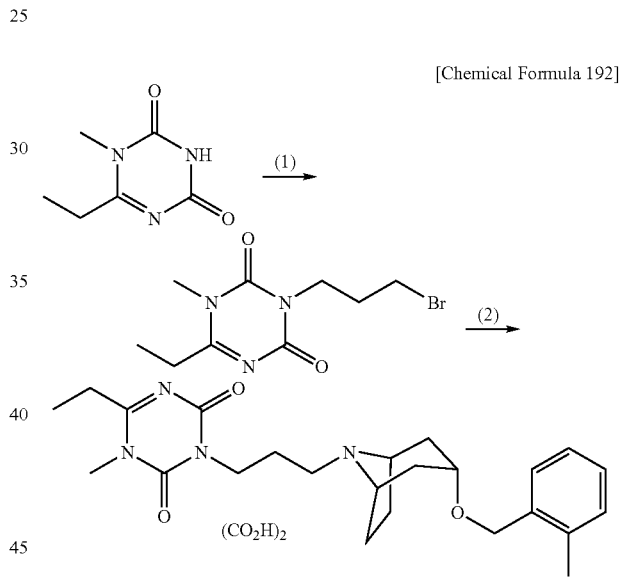

(1) 3-(3-Bromopropyl)-6-ethyl-1-methyl-1H-[1,3,5]triazine-2,4-dione

The title compound (388 mg) was obtained from 6-ethyl-1-methyl-1H-[1,3,5]triazine-2,4-dione (CAS 89465-12-3) (300 mg) and 1,3-dibromopropane by the method similar to Example 69-(1).

$^1$H-NMR (400 MHz, CDCl$_3$); δ 1.33 (t, J=7.2 Hz, 3H), 2.22-2.29 (m, 2H), 2.69 (q, J=7.2 Hz, 2H), 3.41-3.44 (m, 2H), 3.46 (s, 3H), 4.04-4.11 (m, 2H).

(2) (Endo)-6-ethyl-1-methyl-3-{3-[3-(2-methylbenzyloxy)-8-azabicyclo[3.2.1]oct-8-yl]propyl}-1H-[1,3,5]triazine-2,4-dione oxalate The title compound (84 mg) was obtained from the compound obtained in Example 73-(1) (101 mg) and the compound obtained in Production Example 3 (108 mg), by the method similar to Example 72-(2).

$^1$H-NMR (400 MHz, CD$_3$OD); δ 1.27 (t, J=7.2 Hz, 3H), 2.08-2.27 (m, 8H), 2.33 (s, 3H), 2.41-2.46 (m, 2H), 2.77 (q, J=7.2 Hz, 2H), 3.45 (s, 3H), 3.78 (bs, 1H), 3.96-4.01 (m, 4H), 4.54 (s, 2H), 7.13-7.21 (m, 3H), 7.29-7.30 (m, 1H).

Example 74

(Endo)-1-ethyl-3-{3-[3-(2-fluorobenzyloxy)-9-azabicyclo[3.3.1]non-9-yl]propyl}-6-methyl-1H-[1,3,5]triazine-2,4-dione oxalate

[Chemical Formula 193]

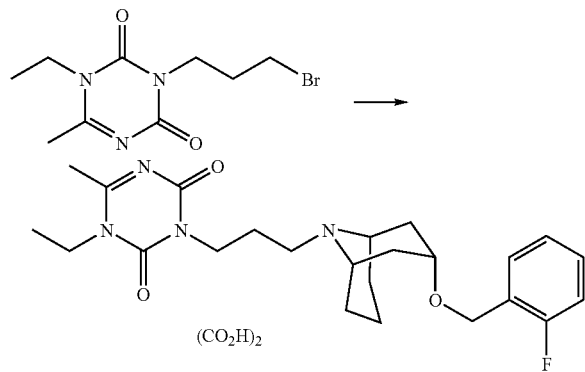

The title compound (57 mg) was obtained from the compound obtained in Example 69-(1) (100 mg) and the compound obtained in Production Example 52 (114 mg), by the method similar to Example 69-(2).

$^1$H-NMR (400 MHz, CD$_3$OD); δ 1.28-1.32 (m, 3H), 1.39-1.46 (m, 2H), 1.64-1.91 (m, 2H), 1.98-2.13 (m, 6H), 2.45-2.52 (m, 5H), 2.87 (bs, 1H), 3.37 (bs, 1H), 3.63 (bs, 2H), 3.83-3.86 (m, 1H), 3.97-4.02 (m, 4H), 4.62 (s, 2H), 7.07-7.11 (m, 1H), 7.15-7.19 (m, 1H), 7.31-7.37 (m, 1H), 7.42-7.46 (m, 1H).

Example 75

(Endo)-3-{3-[3-(2-fluorobenzyloxy)-8-azabicyclo[3.2.1]oct-8-yl]propyl}-6-methyl-1-propyl-1H-[1,3,5]triazine-2,4-dione oxalate

[Chemical Formula 194]

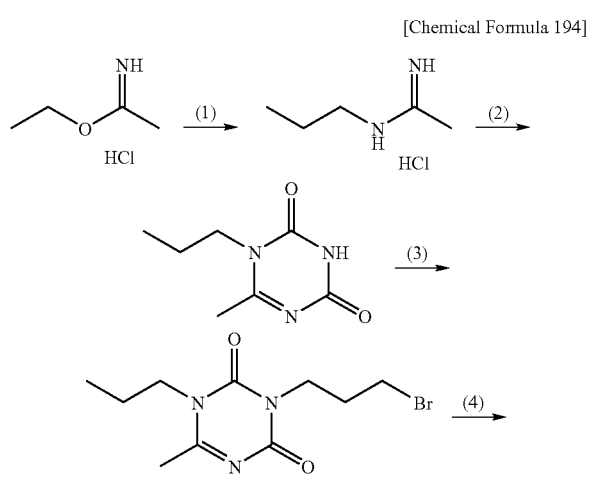

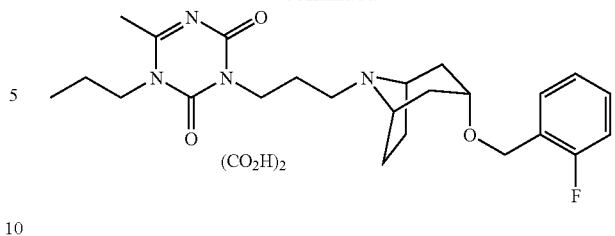

(1) N-Propylacetamidine hydrochloride

The title compound (8.31 g) was obtained from ethyl acetimidate hydrochloride (7.75 g) and propylamine (5 ml) by the method similar to Example 68-(1).

(2) 6-Methyl-1-propyl-1H-[1,3,5]triazine-2,4-dione

The compound obtained in Example 75-(1) (1.0 g) was suspended in ethanol (30 ml), and then potassium tert-butoxide (821 mg) was added and the mixture was stirred at room temperature for 1 hour. The reaction mixture was filtered and the filtrate was concentrated under reduced pressure. The residue was dissolved in acetonitrile (30 ml), and then diphenyl imidodicarbonate (CAS 99911-94-1) (2.07 g) was added and the mixture was stirred at room temperature for 24 hours. The reaction mixture was concentrated under reduced pressure, and the residue was purified by silica gel column chromatography. The title compound (532 mg) was thus obtained.

$^1$H-NMR (400 MHz, DMSO-d$_6$); δ 0.87-0.90 (m, 3H), 1.56-1.62 (m, 2H), 2.39 (s, 3H), 3.69-3.73 (m, 2H), 11.46 (s, 1H).

(3) 3-(3-Bromopropyl)-6-methyl-1-propyl-1H-[1,3,5]triazine-2,4-dione

The title compound (454 mg) was obtained from the compound obtained in Example 75-(2) (300 mg) and 1,3-dibromopropane, by the method similar to Example 72-(1).

$^1$H-NMR (400 MHz, CDCl$_3$); δ 0.99-1.03 (m, 3H), 1.70-1.76 (m, 2H), 2.26 (quintet, J=6.8 Hz, 2H), 2.48 (s, 3H), 3.43 (t, J=6.8 Hz, 2H), 3.81-3.85 (m, 2H), 4.06 (t, J=6.8 Hz, 2H).

(4) (Endo)-3-{3-[3-(2-fluorobenzyloxy)-8-azabicyclo[3.2.1]oct-8-yl]propyl}-6-methyl-1-propyl-1H-[1,3,5]triazine-2,4-dione oxalate The title compound (85 mg) was obtained from the compound obtained in Example 75-(3) (100 mg) and the compound obtained in Production Example 5 (97 mg), by the method similar to Example 69-(2).

$^1$H-NMR (400 MHz, CD$_3$OD); δ 0.97-1.01 (m, 3H), 1.67-1.77 (m, 2H), 2.07-2.18 (m, 4H), 2.27 (bs, 4H), 2.41-2.49 (m, 5H), 3.08-3.13 (m, 2H), 3.79 (bs, 1H), 3.85-3.89 (m, 2H), 3.95-4.00 (m, 4H), 4.57 (s, 2H), 7.06-7.11 (m, 1H), 7.15-7.19 (m, 1H), 7.31-7.36 (m, 1H), 7.41-7.45 (m, 1H).

Example 76

(Endo)-1,6-dimethyl-3-{3-[3-(2-trifluoromethylbenzyloxy)-8-azabicyclo[3.2.1]oct-8-yl]propyl}-1H-[1,3,5]triazine-2,4-dione oxalate

[Chemical Formula 195]

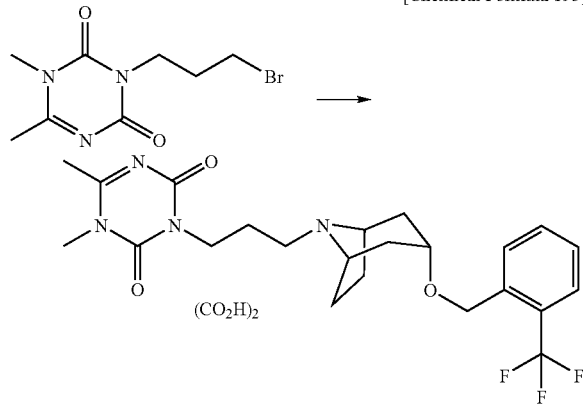

The title compound (102 mg) was obtained from the compound obtained in Example 72-(1) (100 mg) and the compound obtained in Production Example 13 (135 mg), by the method similar to Example 69-(2).

$^1$H-NMR (400 MHz, CD$_3$OD); δ 2.08-2.21 (m, 4H), 2.24-2.35 (m, 4H), 2.40-2.46 (m, 5H), 3.09-3.13 (m, 2H), 3.45 (s, 3H), 3.81 (bs, 1H), 3.97-4.04 (m, 4H), 4.70 (s, 2H), 7.46-7.49 (m, 1H), 7.62-7.65 (m, 1H), 7.68-7.70 (m, 2H).

Example 77

(Exo)-3-{3-[3-(2-fluoro-phenoxymethyl)-8-azabicyclo[3.2.1]oct-8-yl]propyl}-1,6-dimethyl-1H-[113.5]triazine-2,4-dione oxalate

[Chemical Formula 196]

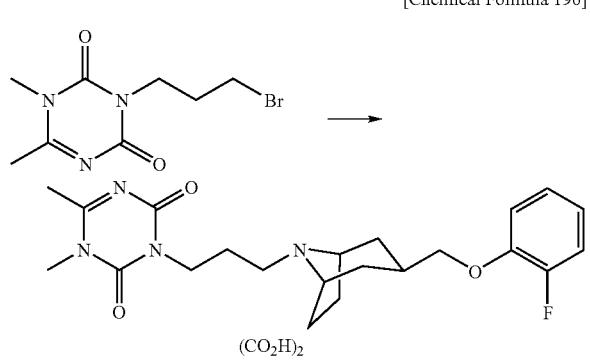

The title compound (75 mg) was obtained from the compound obtained in Example 72-(1) (80 mg) and the compound obtained in Production Example 48 (100 mg), by the method similar to Example 69-(2).

$^1$H-NMR (400 MHz, CD$_3$OD); δ 1.90-2.16 (m, 8H), 2.28-2.31 (m, 2H), 2.42-2.49 (m, 4H), 3.13 (bs, 2H), 3.46 (s, 3H), 3.94-3.96 (m, 2H), 3.98-4.02 (m, 2H), 4.05 (m, 2H), 6.89-6.95 (m, 1H), 7.05-7.10 (m, 3H).

Example 78

(Endo)-3-{3-[3-(2-difluoromethylbenzyloxy)-8-azabicyclo[3.2.1]oct-8-yl]propyl}-1,6-dimethyl-1H-[1,3,5]triazine-2,4-dione oxalate

[Chemical Formula 197]

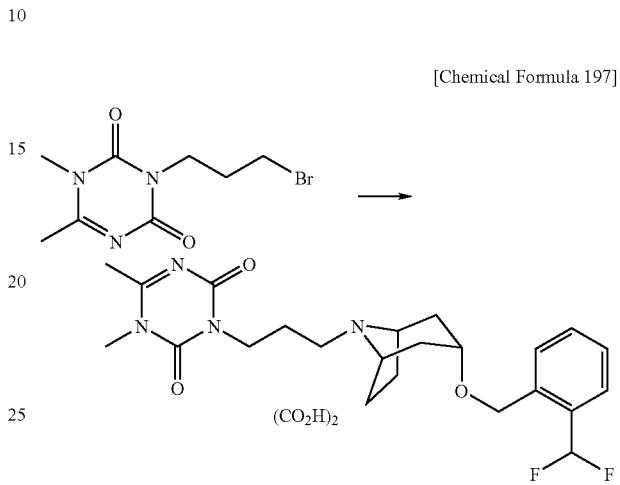

The title compound (63 mg) was obtained from the compound obtained in Example 72-(1) (100 mg) and the compound obtained in Production Example 34 (128 mg), by the method similar to Example 69-(2).

$^1$H-NMR (400 MHz, CD$_3$OD); δ 1.81-2.04 (m, 10H), 2.44-2.48 (m, 5H), 3.20 (bs, 2H), 3.44 (s, 3H), 3.62-3.64 (m, 1H), 3.90-3.94 (m, 2H), 4.60 (s, 2H), 6.86-7.14 (m, 1H), 7.38-7.42 (m, 1H), 7.45-7.50 (m, 2H), 7.57-7.58 (m, 1H).

Example 79

(Endo)-1,6-dimethyl-3-{3-[3-(2-methyl-phenyl)-ethyl)-8-azabicyclo[3.2.1]oct-8-yl]propyl}-1H-[1,3,5]triazine-2,4-dione oxalate

[Chemical Formula 198]

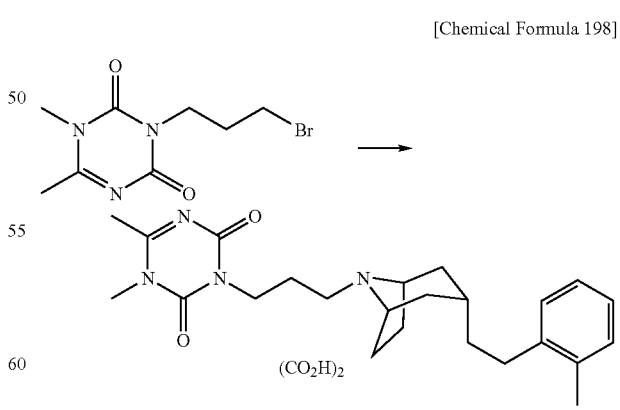

The title compound (73 mg) was obtained from the compound obtained in Example 72-(1) (80 mg) and the compound obtained in Production Example 44 (90 mg), by the method similar to Example 69-(2).

¹H-NMR (400 MHz, CD₃OD); δ 1.84-1.97 (m, 5H), 2.07-2.14 (m, 4H), 2.26-2.38 (m, 7H), 2.44-2.47 (m, 3H), 2.66-2.69 (m, 2H), 3.10 (bs, 2H), 3.46 (s, 3H), 3.95-4.01 (m, 4H), 7.05-7.12 (m, 4H).

Example 80

(Endo)-3-(3-{3-[2-(2-methoxy-phenyl)-ethyl]-8-azabicyclo[3.2.1]oct-8-yl}propyl)-1,6-dimethyl-1H-[1,3,5]triazine-2,4-dione oxalate

[Chemical Formula 199]

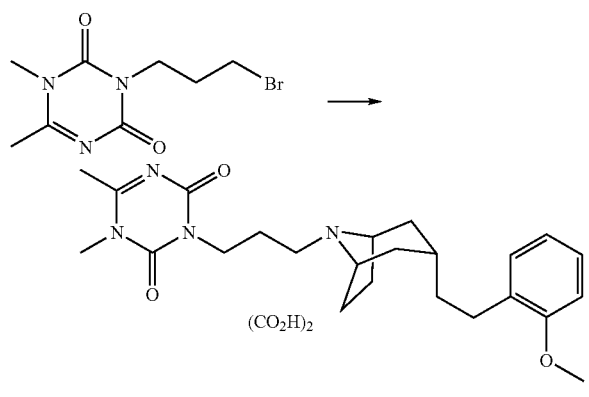

The title compound (83 mg) was obtained from the compound obtained in Example 72-(1) (80 mg) and the compound obtained in Production Example 45 (95 mg), by the method similar to Example 69-(2).
¹H-NMR (400 MHz, CD₃OD); δ 1.85-1.91 (m, 5H), 2.07-2.14 (m, 4H), 2.25-2.34 (m, 4H), 2.45-2.46 (m, 3H), 2.63-2.67 (m, 2H), 3.09 (bs, 2H), 3.46 (s, 3H), 3.81 (s, 3H), 3.93 (bs, 2H), 3.97-4.00 (m, 2H), 6.82-6.86 (m, 1H), 6.90-6.92 (m, 1H), 7.09-7.11 (m, 1H), 7.13-7.17 (m, 1H).

Example 81

(Endo)-3-[3-(3-cyclohexylmethoxy-8-azabicyclo[3.2.1]oct-8-yl)propyl]-1,6-dimethyl-1H-[1,3,5]triazine-2,4-dione

[Chemical Formula 200]

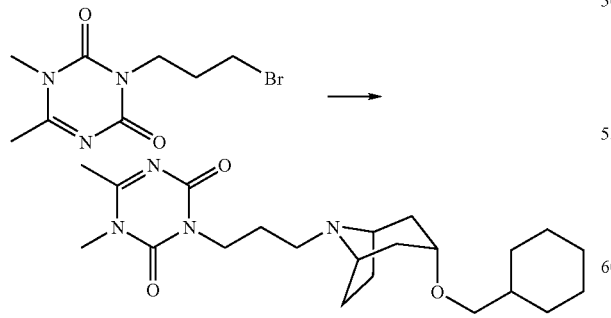

A mixture of the compound obtained in Example 72-(1) (50 mg), the compound obtained in Production Example 11 (55 mg), anhydrous potassium carbonate (80 mg) and N,N-dimethylformamide (1 ml) was stirred at room temperature for 3 days. The reaction mixture was concentrated under reduced pressure, and the residue was purified by NH silica gel column chromatography to obtain the title compound (33 mg).
¹H-NMR (400 MHz, CD₃OD); δ 0.93-1.03 (m, 2H), 1.16-1.32 (m, 3H), 1.47-1.53 (m, 1H), 1.66-1.77 (m, 6H), 1.81-1.92 (m, 7H), 2.00-2.05 (m, 2H), 2.42-2.46 (m, 5H), 3.13-3.16 (m, 4H), 3.40-3.44 (m, 4H), 3.90-3.93 (m, 2H).

Example 82

(Endo)-3-(3-{3-[3-(2-fluorophenyl)-propoxy)-8-azabicyclo[3.2.1]oct-8-yl}propyl)-1,6-dimethyl-1H-[1,3,5]triazine-2,4-dione oxalate

[Chemical Formula 201]

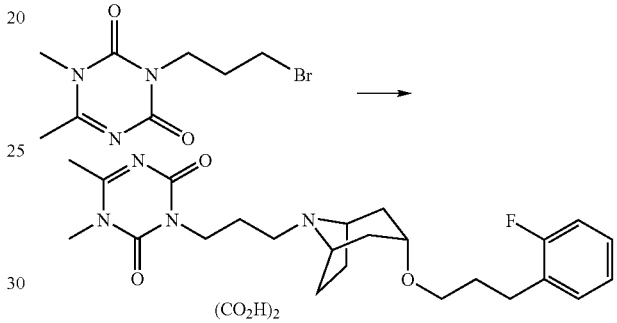

The title compound (81 mg) was obtained from the compound obtained in Example 72-(1) (100 mg) and the compound obtained in Production Example 27 (126 mg), by the method similar to Example 69-(2).
¹H-NMR (400 MHz, CD₃OD); δ 1.84-1.91 (m, 2H), 2.07-2.25 (m, 8H), 2.38-2.46 (m, 5H), 2.73-2.77 (m, 2H), 3.09 (bs, 2H), 3.43-3.46 (m, 5H), 3.60-3.61 (m, 1H), 3.92 (bs, 2H), 3.97-4.00 (m, 2H), 6.99-7.04 (m, 1H), 7.05-7.09 (m, 1H), 7.16-7.21 (m, 1H), 7.22-7.26 (m, 1H).

Example 83

(Exo)-1,6-dimethyl-3-{3-[3-(2-methylbenzyloxy)-8-azabicyclo[3.2.1]oct-8-yl]propyl}-1H-[1,3,5]triazine-2,4-dione oxalate

[Chemical Formula 202]

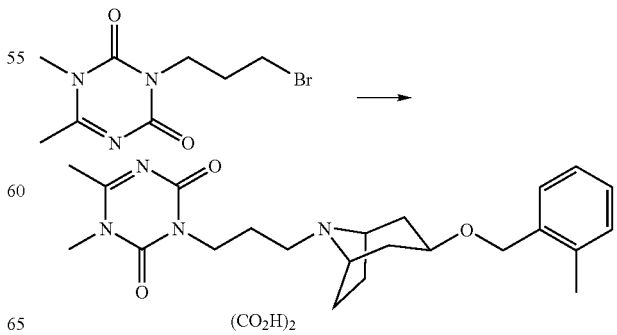

The title compound (58 mg) was obtained from the compound obtained in Example 72-(1) (90 mg) and the compound obtained in Production Example 55 (92 mg), by the method similar to Example 57-(2).

$^1$H-NMR (400 MHz, CD$_3$OD); δ 1.85-1.94 (m, 2H), 1.96-2.13 (m, 2H), 2.05-2.14 (m, 2H), 2.20-2.30 (m, 4H), 2.32 (s, 3H), 2.45 (s, 3H), 3.06-3.13 (m, 2H), 3.44 (s, 3H), 3.92-4.06 (m, 5H), 4.55 (s, 2H), 7.10-7.20 (m, 3H), 7.27 (d, J=7.2 Hz, 1H).

Example 84

(Endo)-6-methyl-3-{3-[3-(2-methylbenzyloxy)-8-azabicyclo[3.2.1]oct-8-yl]propyl}-1-phenyl-1H-[1,3,5]triazine-2,4-dione oxalate

[Chemical Formual 203]

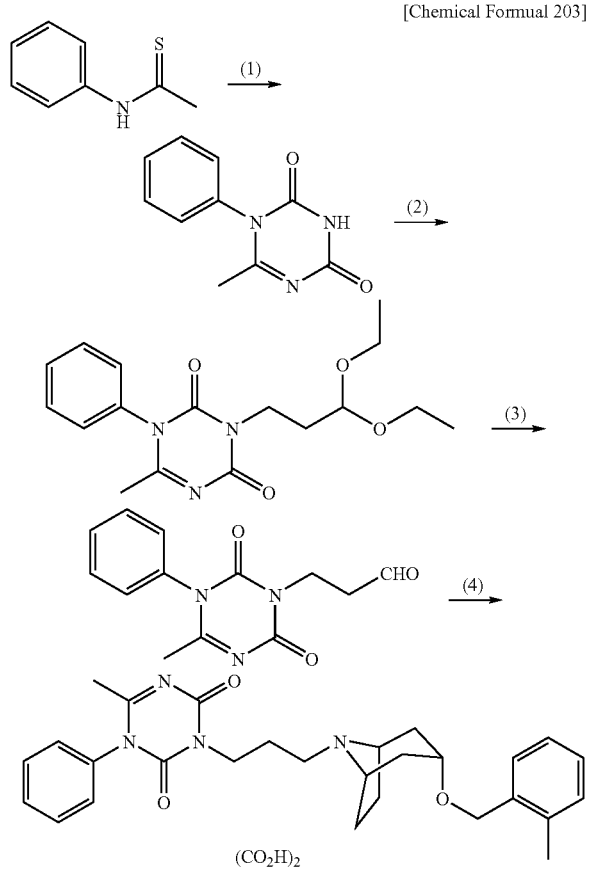

(1) 6-Methyl-1-phenyl-1H-[1,3,5]triazine-2,4-dione

After dissolving N-phenylthioacetamide (5.0 g) and diisopropylethylamine (11.3 ml) in propionitrile (150 ml), silver cyanate (9.92 g) was slowly added while stirring at room temperature. Upon completion of the addition, the mixture was heated to reflux for 2 hours and 30 minutes. The reaction mixture was filtered and the filtrate was concentrated under reduced pressure. The residue was purified by silica gel column chromatography to obtain the title compound (3.11 g).

$^1$H-NMR (400 MHz, CDCl$_3$); δ 2.16 (s, 3H), 3.49 (s, 1H), 7.23-7.31 (m, 2H), 7.51-7.62 (m, 3H).

(2) 3-(3,3-Diethoxypropyl)-6-methyl-1-phenyl-1H-[1,3,5]triazine-2,4-dione

A mixture of the compound obtained in Example 84-(1) (600 mg), 3,3-diethoxy-1-propanol (0.57 ml), triphenylphosphine (929 mg) and tetrahydrofuran (10 ml) was cooled on ice, and then diisopropyl azodicarboxylate (0.81 ml) was added while stirring and the temperature was gradually raised to room temperature. After stirring overnight, the reaction mixture was concentrated under reduced pressure. The residue was purified by silica gel column chromatography to obtain the title compound (984 mg).

(3) 3-(4-Methyl-2,6-dioxo-3-phenyl-3,6-dihydro-2H-[1,3,5]triazin-1-yl)propionaldehyde The compound obtained in Example 84-(2) (984 mg) was dissolved in acetone (20 ml)-water (4 ml), and then Dowex 50W-X4 (1.0 g) was added and the mixture was stirred at room temperature for 20 hours. The reaction mixture was filtered and the filtrate was concentrated under reduced pressure. The residue was purified by silica gel column chromatography to obtain the title compound (140 mg).

$^1$H-NMR (400 MHz, CDCl$_3$); δ 2.13 (s, 3H), 2.85-2.89 (m, 2H), 4.29-4.32 (m, 2H), 7.22-7.26 (m, 2H), 7.52-7.60 (m, 3H), 9.81-9.82 (m, 1H).

(4) (Endo)-6-methyl-3-{3-[3-(2-methylbenzyloxy)-8-azabicyclo[3.2.1]oct-8-yl]propyl}-1-phenyl-1H-[1,3,5]triazine-2,4-dione oxalate Sodium triacetoxyborohydride (443 mg) was added to a mixture of the compound obtained in Example 84-(3) (140 mg), the compound obtained in Production Example 3 (140 mg) and dichloromethane (5 ml), and the mixture was stirred at room temperature for 11 hours and 30 minutes. Water was added to the reaction mixture, and extraction was performed with chloroform. The extract was dried over anhydrous magnesium sulfate and filtered, and then the solvent was distilled off under reduced pressure. The residue was purified by preparative thin-layer chromatography to obtain the free form of the title compound (45 mg). This was dissolved in ethanol, oxalic acid (9 mg) was added, and the mixture was concentrated under reduced pressure. Diethyl ether was added to the residue to produce a solid, which was collected by filtration to obtain the title compound (31 mg).

$^1$H-NMR (400 MHz, CD$_3$OD); δ 2.08-2.25 (m, 8H), 2.33 (s, 3H), 2.42-2.46 (m, 2H), 3.10-3.14 (m, 2H), 3.79 (bs, 1H), 3.99-4.05 (m, 4H), 4.54 (s, 2H), 7.13-7.19 (m, 3H), 7.29-7.30 (m, 1H), 7.39-7.42 (m, 2H), 7.57-7.59 (m, 3H).

Example 85

(Endo)-1-cyclohexyl-6-methyl-3-{3-[3-(2-methylbenzyloxy)-8-azabicyclo[3.2.1]oct-8-yl]propyl}-1H-[1,3,5]triazine-2,4-dione

[Chemical Formula 204]

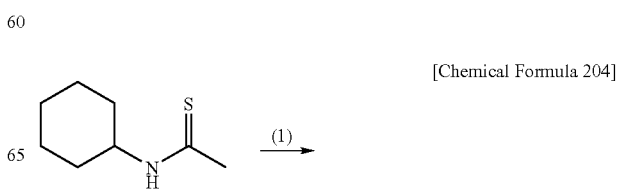

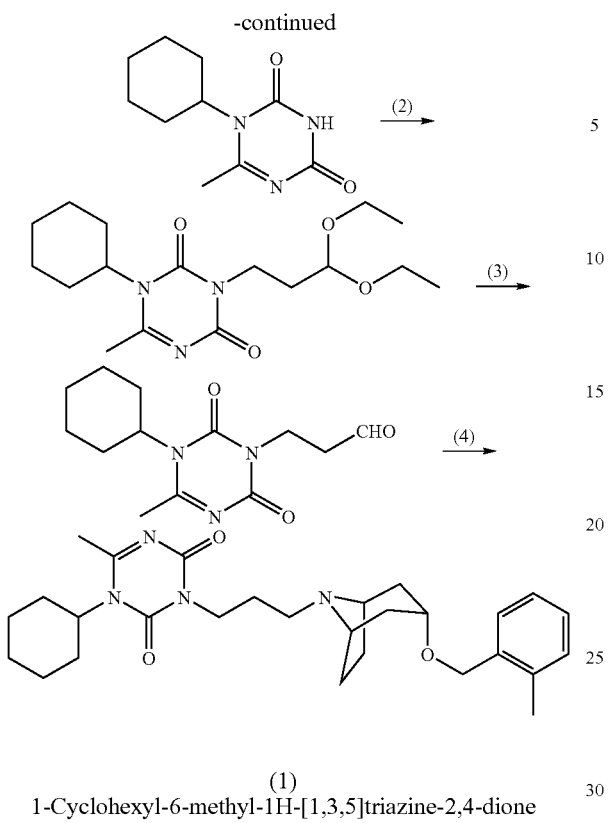

(1) 1-Cyclohexyl-6-methyl-1H-[1,3,5]triazine-2,4-dione

After dissolving N-cyclohexylthioacetamide (CAS 20635-15-8) (6.77 g) and diisopropylethylamine (15 ml) in propionitrile (100 ml), silver cyanate (13.5 g) was slowly added while stirring at room temperature. Upon completion of the addition, the mixture was stirred at 100° C. for 2 hours. The reaction mixture was filtered with Celite, and the filtrate was concentrated under reduced pressure. A small amount of ethyl acetate-methanol was added to the residue, and then n-heptane was further added. The solid was collected by filtration to obtain the title compound (3.23 g).
$^1$H-NMR (400 MHz, CDCl$_3$); δ 1.19-1.36 (m, 3H), 1.69-1.76 (m, 3H), 1.91-1.94 (m, 2H), 2.38-2.47 (m, 2H), 2.50 (s, 3H), 3.93 (m, 1H), 8.05 (br, 1H).

(2) 1-Cyclohexyl-3-(3,3-diethoxypropyl)-6-methyl-1H-[1,3,5]triazine-2,4-dione

The title compound (283 mg) was obtained from the compound obtained in Example 85-(1) (500 mg) and 3,3-diethoxy-1-propanol, by the method similar to Example 84-(2).
$^1$H-NMR (400 MHz, CDCl$_3$); δ 1.16-1.33 (m, 10H), 1.71-1.73 (m, 3H), 1.89-2.00 (m, 4H), 2.43-2.46 (m, 4H), 3.45-3.67 (m, 4H), 3.94-3.97 (m, 3H), 4.61 (t, J=5.6 Hz, 1H).

(3) 3-(3-Cyclohexyl-4-methyl-2,6-dioxo-3,6-dihydro-2H-[1,3,5]triazin-1-yl)propionaldehyde The title compound (188 mg) was obtained from the compound obtained in Example 85-(2) (283 mg), by the method similar to Example 84-(3).

(4) (Endo)-1-cyclohexyl-6-methyl-3-{3-[3-(2-methylbenzyloxy)-8-azabicyclo[3.2.1]oct-8-yl]propyl}-1H-[1,3,5]triazine-2,4-dione Sodium triacetoxyborohydride (52 mg) was added to a mixture of the compound obtained in Example 85-(3) (55 mg), the compound obtained in Production Example 3 (50 mg) and dichloromethane (10 ml) while cooling on ice, and the mixture was stirred overnight at room temperature. After adding a 5N aqueous solution of sodium hydroxide (0.5 ml) to the reaction mixture, anhydrous magnesium sulfate was further added. The reaction mixture was filtered, and then the solvent was distilled off under reduced pressure. The residue was purified by silica gel column chromatography to obtain the title compound (22 mg).
$^1$H-NMR (400 MHz, CD$_3$OD); δ 1.19-1.46 (m, 4H), 1.68-2.06 (m, 14H), 2.16-2.18 (m, 2H), 2.31 (s, 3H), 2.49 (s, 3H), 2.62 (m, 1H), 3.41 (m, 2H), 3.27 (m, 1H), 3.90 (t, J=7.2 Hz, 2H), 4.04-4.08 (m, 1H), 4.47 (s, 2H), 7.11-7.16 (m, 3H), 7.28-7.30 (m, 1H).

Example 86

(Endo)-1-cyclopropyl-6-methyl-3-{3-[3-(2-methylbenzyloxy)-8-azabicyclo[3.2.1]oct-8-yl]propyl}-1H-[1,3,5]triazine-2,4-dione

[Chemical Formula 205]

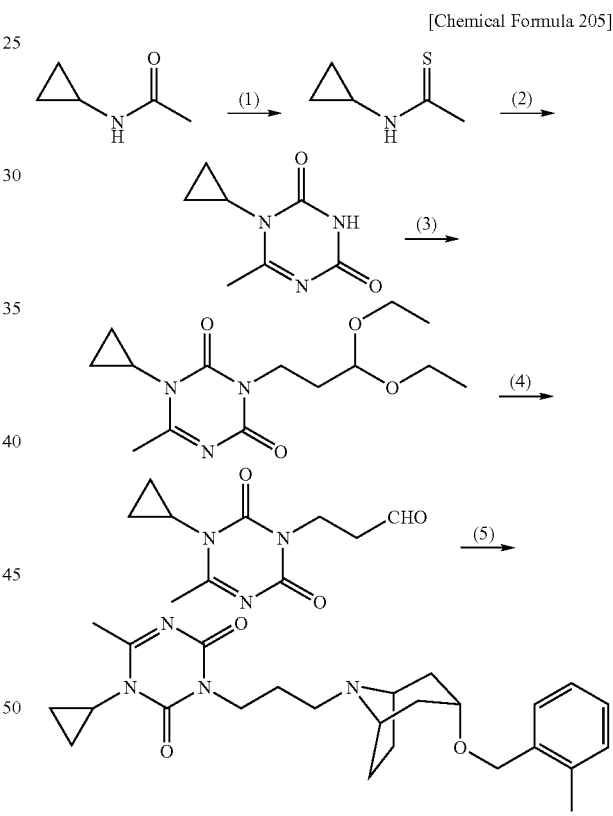

(1) N-Cyclopropylthioacetamide

After dissolving N-cyclopropylacetamide (CAS 29512-07-0) (19 g) in toluene (100 ml), Lawesson's reagent (93.2 g) was added and the mixture was stirred overnight at room temperature. The reaction mixture was filtered and the filtrate was concentrated under reduced pressure. The residue was purified by silica gel column chromatography to obtain the title compound (16.8 g).
$^1$H-NMR (400 MHz, CDCl$_3$); δ 0.65-0.70 (m, 2H), 0.88-0.97 (m, 2H), 2.53 (s, 3H), 3.18-3.24 (m, 1H), 7.21 (br, 1H).

(2) 1-Cyclopropyl-6-methyl-1H-[1,3,5]triazine-2,4-dione

The title compound (2.8 g) was obtained from the compound obtained in Example 86-(1) (16.8 g), by the method similar to Example 84-(1).

¹H-NMR (400 MHz, CDCl₃); δ 1.19-1.36 (m, 3H), 1.69-1.76 (m, 3H), 1.91-1.94 (m, 2H), 2.38-2.47 (m, 2H), 2.50 (s, 3H), 3.93 (m, 1H), 8.05 (br, 1H).

(3) 1-Cyclopropyl-3-(3,3-diethoxypropyl)-6-methyl-1H-[1,3,5]triazine-2,4-dione The title compound (860 mg) was obtained from the compound obtained in Example 86-(2) (600 mg) and 3,3-diethoxy-1-propanol, by the method similar to Example 84-(2).

¹H-NMR (400 MHz, CDCl₃); δ 0.89-0.94 (m, 2H), 1.15-1.31 (m, 8H), 1.95-2.00 (m, 2H), 2.56 (s, 3H), 2.79-2.84 (m, 1H), 3.45-3.67 (m, 4H), 3.97 (t, J=6.8 Hz, 2H), 4.62 (t, J=5.6 Hz, 1H).

(4) 3-(3-Cyclopropyl-4-methyl-2,6-dioxo-3,6-dihydro-2H-[1,3,5]triazin-1-yl)-propionaldehyde The title compound (353 mg) was obtained from the compound obtained in Example 86-(3) (860 mg), by the method similar to Example 84-(3).

¹H-NMR (400 MHz, CDCl₃); δ 0.91-0.95 (m, 2H), 1.23-1.30 (m, 2H), 2.58 (s, 3H), 2.79-2.85 (m, 3H), 4.24 (t, J=6.8 Hz, 2H), 9.80 (s, 1H).

(5) (Endo)-1-cyclopropyl-6-methyl-3-{3-[3-(2-methylbenzyloxy)-8-azabicyclo[3.2.1]oct-8-yl]propyl}-1H-[1,3,5]triazine-2,4-dione The title compound (28 mg) was obtained from the compound obtained in Example 86-(4) (55 mg) and the compound obtained in Production Example 3 (50 mg), by the method similar to Example 85-(4).

¹H-NMR (400 MHz, CDCl₃); δ 0.94 (br, 2H), 1.22-1.28 (m, 2H), 1.86-2.12 (m, 10H), 2.28 (s, 3H), 2.48 (br, 2H), 2.55 (s, 3H), 2.78-2.84 (m, 1H), 3.21 (br, 2H), 3.62 (br, 1H), 3.96 (t, J=6.8 Hz, 2H), 4.40 (s, 2H), 7.12-7.19 (m, 3H), 7.32-7.35 (m, 1H).

Example 87

(Endo)-6-cyclopropyl-1-methyl-3-{3-[3-(2-methylbenzyloxy)-8-azabicyclo[3.2.1]oct-8-yl]propyl}-1H-[1,3,5]triazine-2,4-dione

[Chemical Formula 206]

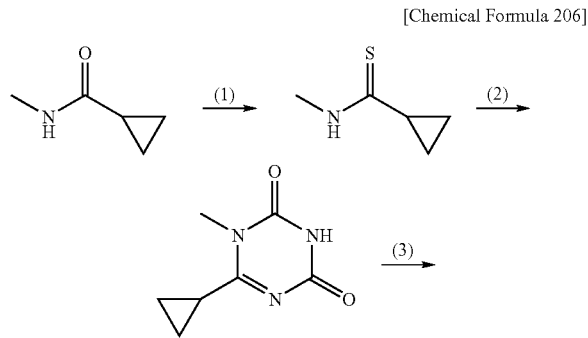

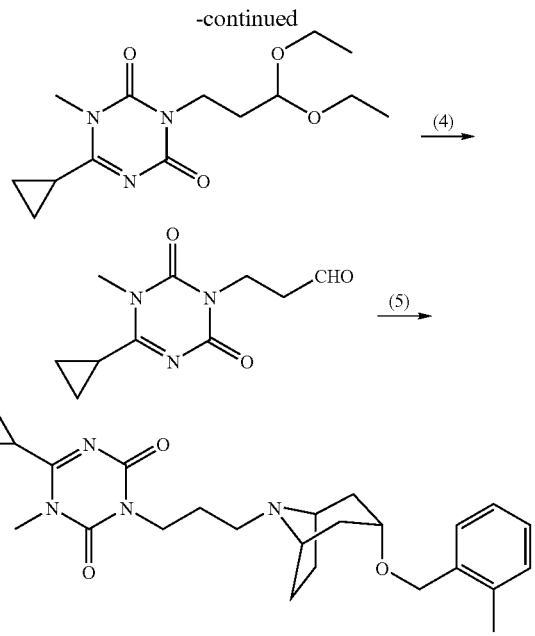

(1) N-Methyl cyclopropanecarbothioamide

The title compound (12.4 g) was obtained from N-methyl cyclopropanecarboxamide (CAS 7108-40-9) (18.9 g) by the method similar to Example 86-(1).

¹H-NMR (400 MHz, CDCl₃); δ 0.89-0.96 (m, 2H), 1.24-1.32 (m, 2H), 1.76-1.83 (m, 1H), 3.22 (d, J=4.8 Hz, 3H), 7.43 (br, 1H).

(2) 6-Cyclopropyl-1-methyl-1H-[1,3,5]triazine-2,4-dione

The title compound (6.0 g) was obtained from the compound obtained in Example 87-(1) (12.4 g), by the method similar to Example 84-(1).

¹H-NMR (400 MHz, CDCl₃); δ 1.20-1.25 (m, 2H), 1.42-1.47 (m, 2H), 1.87-1.94 (m 1H), 3.62 (s, 3H), 8.93 (br, 1H).

(3) 6-Cyclopropyl-3-(3,3-diethoxypropyl)-1-methyl-1H-[1,3,5]triazine-2,4-dione The title compound (882 mg) was obtained from the compound obtained in Example 87-(2) (700 mg) and 3,3-diethoxy-1-propanol, by the method similar to Example 84-(2).

¹H-NMR (400 MHz, CDCl₃); δ 1.14-1.21 (m, 8H), 1.39-1.43 (m, 2H), 1.83-2.00 (m, 3H), 3.45-3.52 (m, 2H), 3.60-3.68 (m, 5H), 4.00 (t, J=6.8 Hz, 2H), 4.63 (t, J=6.0 Hz, 1H).

(4) 3-(4-Cyclopropyl-3-methyl-2,6-dioxo-3,6-dihydro-2H-[1,3,5]triazin-1-yl)propionaldehyde The title compound (434 mg) was obtained from the compound obtained in Example 87-(3) (882 mg), by the method similar to Example 84-(3).

¹H-NMR (400 MHz, CDCl₃); δ 1.18-1.22 (m, 2H), 1.41-1.45 (m, 2H), 1.84-1.91 (m, 1H), 2.79-2.83 (m, 2H), 3.62 (s, 3H), 4.26 (t, J=6.8 Hz, 2H), 9.81 (s, 1H).

(5) (Endo)-6-cyclopropyl-1-methyl-3-{3-[3-(2-methylbenzyloxy)-8-azabicyclo[3.2.1]oct-8-yl]propyl}-1H-[1,3,5]triazine-2,4-dione The title compound (67 mg) was obtained from the compound obtained in Example 87-(4) (55 mg) and the compound obtained in Production Example 3 (50 mg), by the method similar to Example 85-(4).

$^1$H-NMR (400 MHz, CD$_3$OD); δ 1.17-1.30 (m, 4H), 2.06-2.24 (m, 9H), 2.33 (3H), 2.41-2.43 (m, 2H), 3.04-3.08 (m, 2H), 3.63 (s, 3H), 3.78-4.00 (m, 5H), 4.53 (s, 2H), 7.14-7.30 (m, 4H).

Example 88

(Endo)-3-{3-[3-(benzo[b]thiophen-2-ylmethoxy)-8-azabicyclo[3.2.1]oct-8-yl]propyl}-1-ethyl-6-methyl-1H-[1,3,5]triazine-2,4-dione oxalate

[Chemical Formula 207]

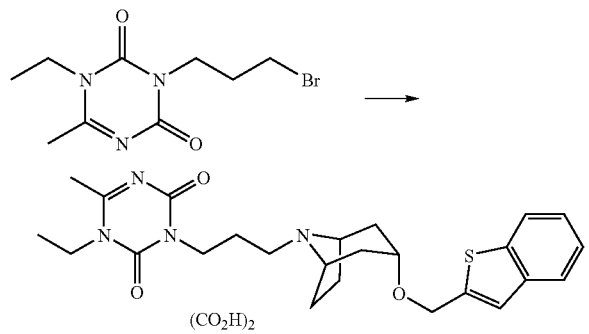

The title compound (67 mg) was obtained from the compound obtained in Example 69-(1) (69 mg) and the compound obtained in Production Example 6 (70 mg), by the method similar to Example 69-(2).

$^1$H-NMR (400 MHz, CD$_3$OD); δ 1.27-1.32 (m, 3H), 2.09-2.52 (m, 13H), 3.07-3.11 (m, 2H), 3.84 (br, 1H), 3.96-4.01 (m, 6H), 4.81-4.82 (m, 2H), 7.27-7.36 (m, 3H), 7.73-7.75 (m, 1H), 7.81-7.83 (m, 1H).

Example 89

(Endo)-3-{3-[3-(benzo[b]thiophen-3-ylmethoxy)-8-azabicyclo[3.2.1]oct-8-yl]propyl}-1-ethyl-6-methyl-1H-[1,3,5]triazine-2,4-dione oxalate

[Chemical Formula 208]

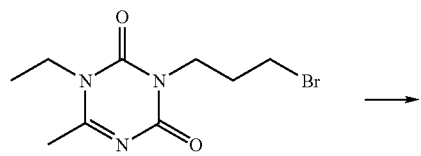

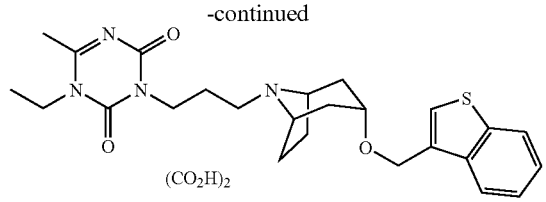

The title compound (16 mg) was obtained from the compound obtained in Example 69-(1) (69 mg) and the compound obtained in Production Example 7 (70 mg), by the method similar to Example 69-(2).

$^1$H-NMR (400 MHz, CD$_3$OD); δ 2.10-2.29 (m, 9H), 2.44-2.49 (m, 4H), 3.05-3.08 (m, 2H), 3.82 (br, 1H), 3.96-3.99 (m, 6H), 4.80 (s, 2H), 7.35-7.42 (m, 2H), 7.53 (s, 1H), 7.87-7.89 (m, 2H).

Example 90

(Endo)-1-ethyl-6-methyl-3-{3-[3-(thiophen-2-ylmethoxy)-8-azabicyclo[3.2.1]oct-8-yl]propyl}-1H-[1,3,5]triazine-2,4-dione oxalate

[Chemical Formula 209]

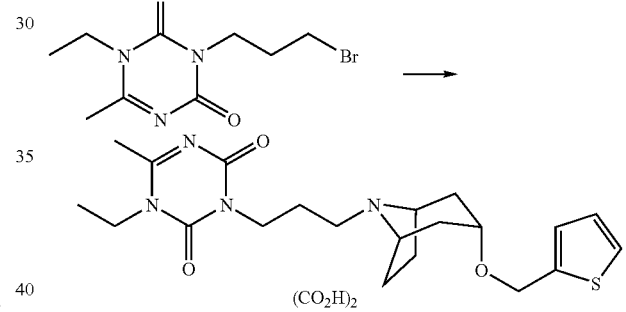

The title compound (109 mg) was obtained from the compound obtained in Example 69-(1) (75 mg) and the compound obtained in Production Example 8 (70 mg), by the method similar to Example 69-(2).

$^1$H-NMR (400 MHz, CD$_3$OD); δ 1.28-1.32 (m, 3H), 2.08-2.50 (m, 13H), 3.05-3.10 (m, 2H), 3.78 (br, 1H), 3.96-4.01 (m, 6H), 4.70 (s, 2H), 6.96-6.98 (m, 1H), 7.02-7.03 (m, 1H), 7.36-7.37 (m, 1H).

Example 91

(Endo)-1-ethyl-3-{3-[3-(3-fluorobiphenyl-2-ylmethoxy)-8-azabicyclo[3.2.1]oct-8-yl]propyl}-6-methyl-1H-[1,3,5]triazine-2,4-dione oxalate

[Chemical Formula 210]

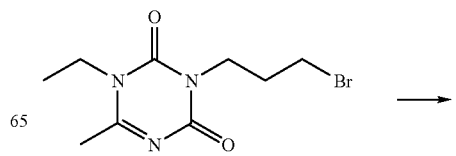

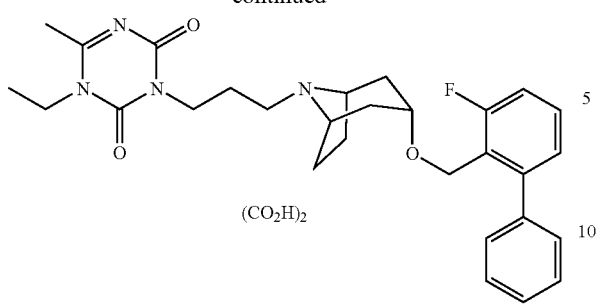

The title compound (87 mg) was obtained from the compound obtained in Example 69-(1) (81 mg) and the compound obtained in Production Example 37 (102 mg), by the method similar to Example 69-(2).

$^1$H-NMR (400 MHz, CD$_3$OD); δ 1.28-1.31 (m, 3H), 2.08-2.31 (m, 10H), 2.39 (s, 3H), 3.03-3.07 (m, 2H), 3.62 (br, 1H), 3.87-4.01 (m, 6H), 4.39-4.40 (m, 2H), 7.12-7.16 (m, 2H), 7.39-7.45 (m, 6H).

Example 92

(Endo)-1-ethyl-3-{3-[3-(2-fluoro-6-pyrazin-2-yl-benzyloxy)-8-azabicyclo[3.2.1]oct-8-yl]propyl}-6-methyl-1H-[1,3,5]triazine-2,4-dione oxalate

[Chemical Formula 211]

The title compound (57 mg) was obtained from the compound obtained in Example 69-(1) (61 mg) and the compound obtained in Production Example 38 (70 mg), by the method similar to Example 69-(2).

$^1$H-NMR (400 MHz, CD$_3$OD); δ 2.06-2.49 (m, 13H), 3.01-3.05 (m, 2H), 3.62-3.64 (m, 1H), 3.90-4.01 (m, 6H), 4.62 (m, 2H), 7.28-7.33 (m, 1H), 7.38-7.40 (m, 1H), 7.51-7.57 (m, 1H), 8.64 (m, 1H), 8.72-8.73 (m, 1H), 8.85-8.86 (m, 1H).

Example 93

(Endo)-1-ethyl-6-methyl-3-{3-[3-(2-morpholin-4-yl-benzyloxy)-8-azabicyclo[3.2.1]oct-8-yl]propyl}-1H-[1,3,5]triazine-2,4-dione oxalate

[Chemical Formula 212]

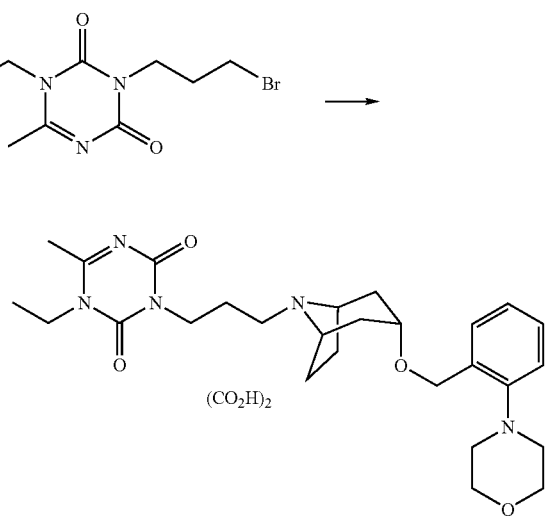

The title compound (65 mg) was obtained from the compound obtained in Example 69-(1) (65 mg) and the compound obtained in Production Example 35 (65 mg), by the method similar to Example 69-(2).

$^1$H-NMR (400 MHz, CD$_3$OD); δ 1.28-1.32 (m, 3H), 2.09-2.50 (m, 13H), 2.89-2.92 (m, 4H), 3.06-3.10 (m, 2H), 3.79-3.83 (m, 5H), 3.98-4.00 (m, 6H), 4.62 (s, 2H), 7.09-7.17 (m, 2H), 7.27-7.31 (m, 1H), 7.41-7.43 (m, 1H).

Example 94

(Endo)-1-ethyl-3-{3-[3-(2-fluoro-6-pyridin-4-yl-benzyloxy)-8-azabicyclo[3.2.1]oct-8-yl]propyl}-6-methyl-1H-[1,3,5]triazine-2,4-dione

[Chemical Formula 213]

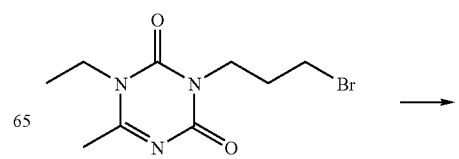

243

-continued

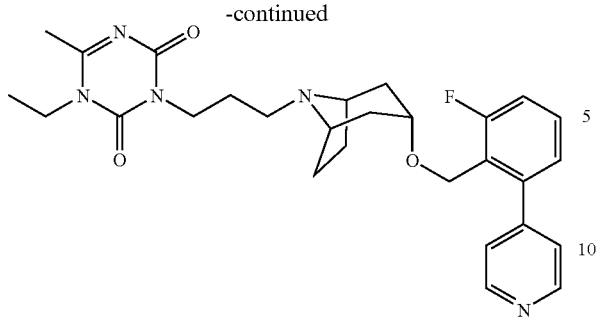

The title compound (87 mg) was obtained from the compound obtained in Example 69-(1) (181 mg) and the compound obtained in Production Example 36 (102 mg), by the method similar to Example 81.

$^1$H-NMR (400 MHz, CDCl$_3$); δ 1.33 (t, J=7.2 Hz, 3H), 1.75-1.95 (m, 10H), 2.38-2.42 (m, 2H), 2.47 (s, 3H), 3.11 (br, 2H), 3.53-3.55 (m, 1H), 3.92-4.00 (m, 4H), 4.23 (m, 2H), 7.09-7.16 (m, 2H), 7.35-7.43 (m, 3H), 8.64-8.66 (m, 2H).

Example 95

(Endo)-3-{3-[3-(2-fluorobenzyloxy)-8-azabicyclo[3.2.1]oct-8-yl]propyl}-6-methoxymethyl-1-methyl-1H-[1,3,5]triazine-2,4-dione oxalate

[Chemical Formula 214]

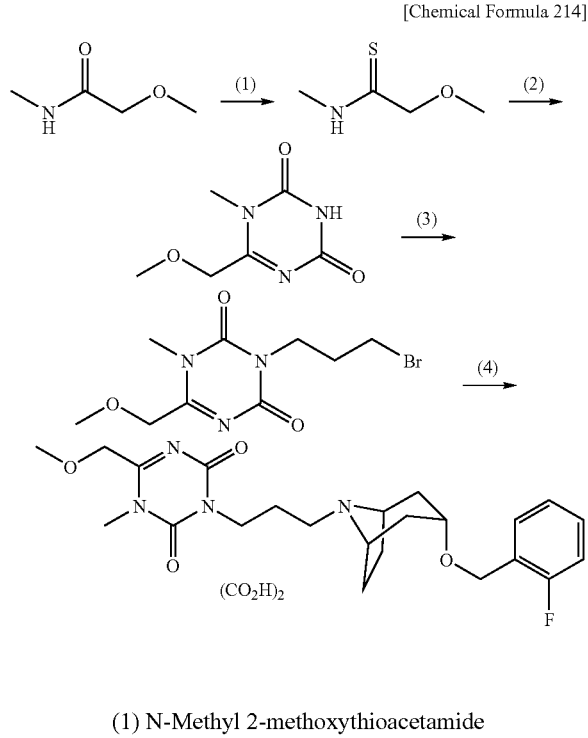

(1) N-Methyl 2-methoxythioacetamide

The title compound (3.75 g) was obtained from N-methyl 2-methoxyacetamide (CAS 57270-75-4) (4.94 g) by the method similar to Example 86-(i).

$^1$H-NMR (400 MHz, CDCl$_3$); δ 3.24-3.25 (m, 3H), 3.44 (s, 3H), 4.31 (m, 2H), 8.37 (br, 1H).

244

(2) 6-Methoxymethyl-1-methyl-1H-[1,3,5]triazine-2,4-dione

The title compound (603 mg) was obtained from the compound obtained in Example 95-(1) (3.75 g), by the method similar to Example 66-(i).

$^1$H-NMR (400 MHz, CD$_3$OD); δ 2.87 (s, 3H), 3.17 (s, 3H), 3.39 (s, 2H).

(3) 3-(3-Bromopropyl)-6-methoxymethyl-1-methyl-1H-[1,3,5]triazine-2,4-dione

The title compound (322 mg) was obtained from the compound obtained in Example 95-(2) (300 mg) and 1,3-dibromopropane, by the method similar to Example 69-(1).

$^1$H-NMR (400 MHz, CDCl$_3$); δ 2.25-2.28 (m, 2H), 3.42-3.45 (m, 2H), 3.47 (s, 3H), 3.53 (s, 3H), 4.06-4.10 (m, 2H), 4.39 (s, 2H).

(4) (Endo)-3-{3-[3-(2-fluorobenzyloxy)-8-azabicyclo[3.2.1]oct-8-yl]propyl}-6-methoxymethyl-1-methyl-1H-[1,3,5]triazine-2,4-dione oxalate The title compound (25 mg) was obtained from the compound obtained in Example 95-(3) (71 mg) and the compound obtained in Production Example 5 (65 mg), by the method similar to Example 69-(2).

$^1$H-NMR (400 MHz, CD$_3$OD); δ 1.98-2.46 (m, 10H), 2.90 (s, 3H), 2.99-3.03 (m, 2H), 3.39 (s, 3H), 3.45-3.48 (m, 1H), 3.72-3.86 (m, 4H), 3.97 (m, 2H), 4.58 (s, 2H), 7.07-7.19 (m, 2H), 7.32-7.45 (m, 2H).

Example 96

(Endo)-3-{3-[3-(2-fluorobenzyloxy)-8-azabicyclo[3.2.1]oct-8-yl]propyl}-1-(2-methoxyethyl)-6-methyl-1H-[1,3,5]triazine-2,4-dione oxalate

[Chemical Formula 215]

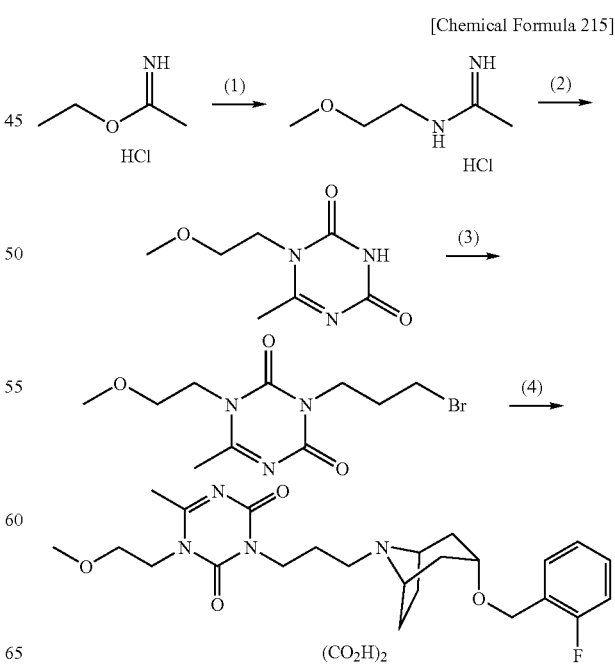

(1) N-(2-Methoxyethyl)-acetamidine hydrochloride

The title compound (8.78 g) was obtained from 2-methoxyethylamine (5 ml) and ethyl acetimidate hydrochloride (7.11 g) by the method similar to Example 68-(1).

(2) 1-(2-Methoxyethyl)-6-methyl-1H-[1,3,5]triazine-2,4-dione

The title compound (557 mg) was obtained from the compound obtained in Example 96-(1) (1.00 g), by the method similar to Example 75-(2).

$^1$H-NMR (400 MHz, DMSO-d$_6$); δ 2.41 (s, 3H), 3.26 (s, 3H), 3.52 (t, J=5.2 Hz, 2H), 3.96 (t, J=5.2 Hz, 2H), 11.52 (s, 1H).

(3) 3-(3-Bromopropyl)-1-(2-methoxyethyl)-6-methyl-1H-[1,3,5]triazine-2,4-dione The title compound (416 mg) was obtained from the compound obtained in Example 96-(2) (300 mg) and 1,3-dibromopropane, by the method similar to Example 72-(1).

$^1$H-NMR (400 MHz, CDCl$_3$); δ 2.23-2.30 (m, 2H), 2.54 (s, 3H), 3.33 (s, 3H), 3.42-3.45 (m, 2H), 3.61-3.64 (m, 2H), 4.05-4.09 (m, 4H).

(4) (Endo)-3-{3-[3-(2-fluorobenzyloxy)-8-azabicyclo[3.2.1]oct-8-yl]propyl}-1-(2-methoxy-ethyl)-6-methyl-1H-[1,3,5]triazine-2,4-dione oxalate The title compound (79 mg) was obtained from the compound obtained in Example 96-(3) (100 mg) and the compound obtained in Production Example 5 (89 mg), by the method similar to Example 69-(2).

$^1$H-NMR (400 MHz, CD$_3$OD); δ 2.06-2.18 (m, 4H), 2.22-2.31 (m, 4H), 2.41-2.46 (m, 2H), 2.51-2.53 (m, 3H), 3.08-3.13 (m, 2H), 3.34 (s, 3H), 3.62-3.65 (m, 2H), 3.79 (bs, 1H), 3.95-4.00 (m, 4H), 4.13-4.15 (m, 2H), 4.57 (s, 2H), 7.06-7.19 (m, 1H), 7.15-7.19 (m, 1H), 7.31-7.36 (m, 1H), 7.41-7.45 (m, 1H).

Example 97

(Endo)-1-ethyl-3-{3-[3-(2-furan-3-ylbenzyloxy)-8-azabicyclo[3.2.1]oct-8-yl]propyl}-6-methyl-1H-[1,3,5]triazine-2,4-dione

[Chemical Formula 216]

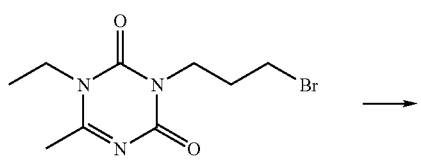

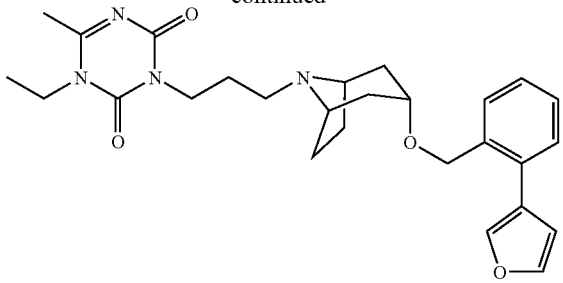

The compound obtained in Example 69-(1) (67 mg) and the compound obtained in Production Example 39 (60 mg) were dissolved in N,N-dimethylformamide (3 ml), and then anhydrous potassium carbonate (57 mg) was added and the mixture was stirred at room temperature for 3 days. Water was added to the reaction mixture, and extraction was performed with ethyl acetate. The extract was dried over anhydrous magnesium sulfate. After filtration, the solvent was distilled off under reduced pressure. The residue was purified by NH silica gel column chromatography to obtain the title compound (15 mg).

$^1$H-NMR (400 MHz, CDCl$_3$); δ 1.33 (t, J=7.2 Hz, 3H), 1.82-2.15 (m, 10H), 2.47 (s, 3H), 2.85-2.51 (m, 2H), 3.18-3.25 (m, 2H), 3.62 (t, J=4.8 Hz, 1H), 3.94 (q, J=7.2 Hz, 2H), 3.99 (t, J=7.2 Hz, 2H), 4.42 (s, 2H), 6.58 (s, 1H), 7.30-7.37 (m, 3H), 7.48-7.52 (m, 2H), 7.59 (s, 1H).

Example 98

(Endo)-1-ethyl-3-(3-{3-[N-(2-fluorobenzyl)-N-methylamino]-8-azabicyclo[3.2.1]oct-8-yl}-propyl)-6-methyl-1H-[1,3,5]triazine-2,4-dione

[Chemical Formula 217]

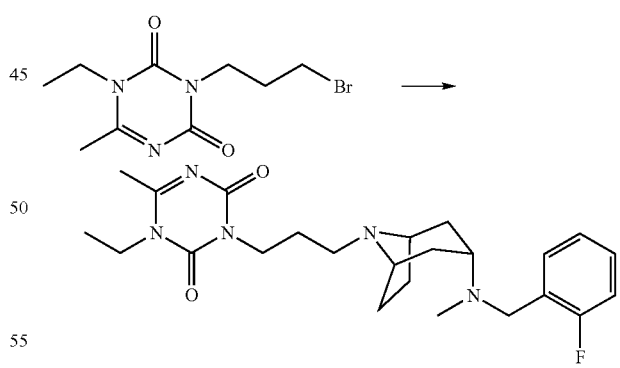

The title compound (35 mg) was obtained from the compound obtained in Example 69-(1) (39 mg) and the compound obtained in Production Example 47 (35 mg), by the method similar to Example 97.

$^1$H-NMR (400 MHz, CDCl$_3$); δ 1.33 (t, J=7.2 Hz, 3H), 1.70-1.77 (m, 2H), 1.78-2.00 (m, 6H), 2.01-2.10 (m, 2H), 2.13 (s, 3H), 2.37 (t, J=7.2 Hz, 2H), 2.46 (s, 3H), 2.54-2.59 (m, 1H), 3.16-3.20 (m, 2H), 3.52 (s, 3H), 3.94 (t, J=7.2 Hz, 2H), 3.98 (q, J=7.2 Hz, 2H), 6.99 (ddd, J=9.8 Hz, 8.6 Hz, 1.6

Hz, 1H), 7.09 (td, J=7.6 Hz, 1.2 Hz, 1H), 7.17-7.23 (m, 1H), 7.39 (td, J=7.4 Hz, 1.6 Hz, 1H).

Example 99

(Endo)-6-{2-fluoro-3-[3-(2-methoxybenzyloxy)-8-azabicyclo[3.2.1]oct-8-yl]-propyl}-2,3-dimethyl-3H-[1,2,4]triazole[1,5-a][1,3,5]triazine-5,7-dione

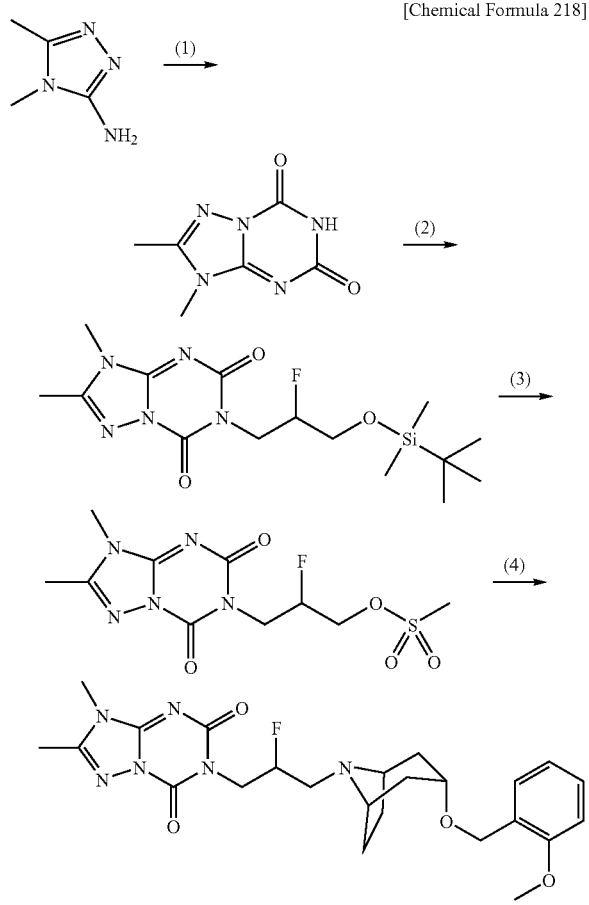

[Chemical Formula 218]

(1) 2,3-Dimethyl-3H-[1,2,4]triazolo[1,5-a][1,3,5]triazine-5,7-dione

After suspending 4,5-dimethyl-4H-[1,2,4]triazol-3-ylamine (CAS 53132-83-5) (7.6 g) in acetonitrile (80 ml), a solution of phenyl isocyanatoformate (5.2 g) in acetonitrile (40 ml) was slowly added dropwise while heating to reflux. After heating to reflux for 6 hours, the reaction mixture was cooled on ice. The insoluble matter was collected by filtration to obtain the title compound (7.98 g).

$^1$H-NMR (400 MHz, DMSO-$d_6$); δ 2.40 (s, 3H), 3.36 (s, 3H), 11.27 (s, 1H).

(2) 6-[3-(tert-Butyldimethylsilanyloxy)-2-fluoropropyl]-2,3-dimethyl-3H-[1,2,4]triazole[1,5-a][1,3,5]triazine-5,7-dione Sodium hydride (60% in oil) (133 mg) was added to a mixture of the compound obtained in Example 99-(1) (500 mg), the compound obtained in Production Example 66 (1.04 g) and N,N-dimethylformamide (10 ml), and the resulting mixture was stirred at room temperature for 44 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (584 mg).

$^1$H-NMR (400 MHz, CDCl$_3$); δ 0.09 (s, 6H), 0.91 (s, 9H), 2.49 (s, 3H), 3.53 (s, 3H), 3.83-4.10 (m, 3H), 4.55-4.64 (m, 1H), 4.81-4.99 (m, 1H).

(3) Methanesulfonic acid 3-(2,3-dimethyl-5,7-dioxo-3,5-dihydro-[1,2,4]triazolo[1,5-a][1,3,5]triazin-6-yl)-2-fluoropropyl ester The compound obtained in Example 99-(2) (3.94 g) was dissolved in tetrahydrofuran (40 ml), and then acetic acid (1.82 ml) and tetra-n-butylammonium fluoride (1 M solution in tetrahydrofuran, 16 ml) was added and the mixture was stirred at room temperature for 11 hours. The reaction mixture was concentrated under reduced pressure, and the residue was purified by silica gel column chromatography.

The obtained compound was dissolved in acetonitrile (50 ml), and then triethylamine (2.21 ml) and trimethylamine hydrochloride (202 mg) were added and methanesulfonyl chloride (1.23 ml) was slowly added while stirring on ice. After stirring for 2 hours, the reaction mixture was concentrated under reduced pressure, acetone was added to the residue, and the mixture was filtered. The filtrate was concentrated under reduced pressure and the residue was purified by silica gel column chromatography. The obtained solid was washed with acetone to obtain the title compound (2.02 g).

$^1$H-NMR (400 MHz, CDCl$_3$); δ 2.51 (s, 3H), 3.12 (s, 3H), 3.55 (s, 3H), 4.09-4.22 (m, 1H), 4.35-4.47 (m, 1H), 4.50-4.62 (m, 2H), 5.05-5.23 (m, 1H).

(4) (Endo)-6-{2-fluoro-3-[3-(2-methoxybenzyloxy)-8-azabicyclo[3.2.1]oct-8-yl]propyl}-2,3-dimethyl-3H-[1,2,4]triazole[1,5-a][1,3,5]triazine-5,7-dione A mixture of the compound obtained in Example 99-(3) (100 mg), the compound obtained in Production Example 10 (85 mg), anhydrous potassium carbonate (91 mg), sodium iodide (catalytic amount) and N,N-dimethylformamide (1 ml) was stirred at 50° C. for 41 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography. It was then solidified with ethyl acetate-diethyl ether and collected by filtration to obtain the title compound (47 mg).

$^1$H-NMR (400 MHz, CDCl$_3$); δ 1.78-2.00 (m, 6H), 2.06-2.13 (m, 2H), 2.49 (s, 3H), 2.58-2.79 (m, 2H), 3.14-3.24 (m, 2H), 3.53 (s, 3H), 3.57-3.64 (m, 1H), 3.82 (s, 3H), 4.10-4.24

(m, 1H), 4.46 (s, 2H), 4.48-4.59 (m, 1H), 4.86-5.06 (m, 1H), 6.82-6.86 (m, 1H), 6.94-6.99 (m, 1H), 7.21-7.28 (m, 1H), 7.40-7.44 (m, 1H).

Example 100

(Endo)-6-{2-fluoro-3-[3-(3-fluoromethylbenzyloxy)-8-azabicyclo[3.2.1]oct-8-yl]propyl}-2,3-dimethyl-3H-[1,2,4]triazole[1,5-a][1,3,5]triazine-5,7-dione

[Chemical Formula 219]

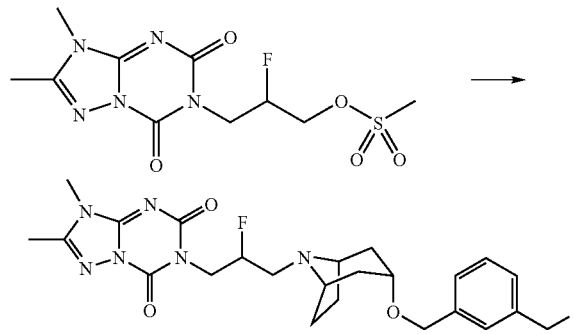

The title compound (61 mg) was obtained from the compound obtained in Example 99-(3) (100 mg) and the compound obtained in Production Example 54 (85 mg), by the method similar to Example 99-(4).

¹H-NMR (400 MHz, CDCl₃); δ 1.82-1.90 (m, 4H), 1.93-2.08 (m, 4H), 2.49 (s, 3H), 2.58-2.78 (m, 2H), 3.18-3.24 (m, 2H), 3.53 (s, 3H), 3.59 (t, J=4.8 Hz, 1H), 4.10-4.23 (m, 1H), 4.46 (s, 2H), 4.50-4.59 (m, 1H), 4.86-5.05 (m, 1H), 5.38 (d, J=48.0 Hz, 2H), 7.26-7.39 (m, 4H).

Example 101

(Endo)-6-{(R)-2-fluoro-3-[3-(3-fluorobenzyloxy)-8-azabicyclo[3.2.1]oct-8-yl]propyl}-2,3-dimethyl-3H-[1,2,4]triazole[1,5-a][1,3,5]triazine-5,7-dione

[Chemical Formula 220]

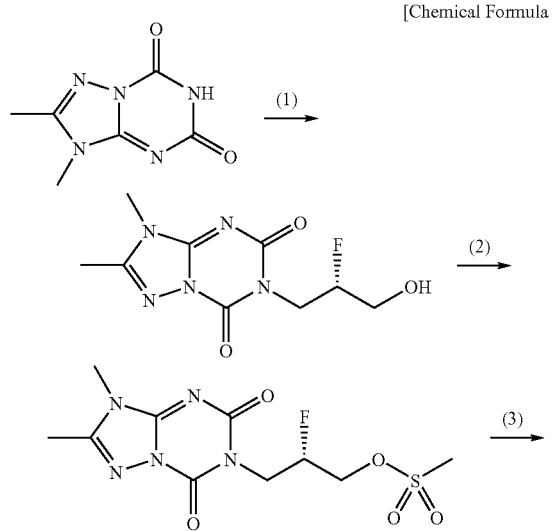

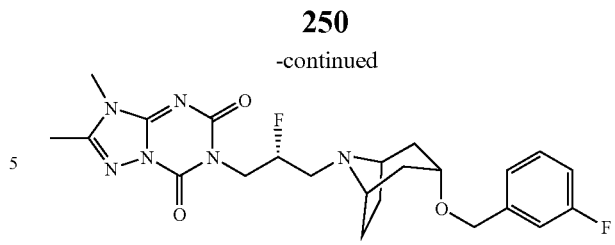

(1) 6-((S)-2-Fluoro-3-hydroxypropyl)-2,3-dimethyl-3H-[1,2,4]triazole[1,5-a][1,3,5]triazine-5,7-dione The compound obtained in Example 99-(1) (500 mg) was suspended in dimethyl sulfoxide (10 ml), and then potassium tert-butoxide (342 mg) was added and the mixture was stirred at room temperature for 1 hour. The compound obtained in Production Example 65 (945 mg) was added dropwise, and the mixture was stirred at room temperature for 13 hours. Water was added to the reaction mixture, and extraction was performed with ethyl acetate. The organic layer was washed with water and brine in that order and then dried over anhydrous magnesium sulfate. After filtration, the solvent was distilled off under reduced pressure.

The obtained compound was dissolved in tetrahydrofuran (10 ml), and then acetic acid (0.48 ml) and tetra-n-butylammonium fluoride (1 M solution in tetrahydrofuran, 4.19 ml) was added and the mixture was stirred at room temperature for 17 hours. The reaction mixture was concentrated under reduced pressure, and the residue was purified by silica gel column chromatography to obtain the title compound (590 mg).

¹H-NMR (400 MHz, CDCl₃); δ 2.51 (s, 3H), 3.55 (s, 3H), 4.18-4.28 (m, 1H), 4.47-4.56 (m, 1H), 4.81-4.99 (m, 1H).

(2) Methanesulfonic acid (S)-3-(2,3-dimethyl-5,7-dioxo-3,5-dihydro-[1,2,4]triazolo[1,5-a][1,3,5]triazin-6-yl)-2-fluoropropyl ester The title compound (450 mg) was obtained from the compound obtained in Example 101-(1) (590 mg), by the method similar to Example 12-(4).

¹H-NMR (400 MHz, CDCl₃); δ 2.51 (s, 3H), 3.12 (s, 3H), 3.55 (s, 3H), 4.09-4.22 (m, 1H), 4.35-4.47 (m, 1H), 4.50-4.62 (m, 2H), 5.05-5.23 (m, 1H).

(3) (Endo)-6-{(R)-2-fluoro-3-[3-(3-fluorobenzyloxy)-8-azabicyclo[3.2.1]oct-8-yl]propyl}-2,3-dimethyl-3H-[1,2,4]triazole[1,5-a][1,3,5]triazine-5,7-dione The title compound (96 mg) was obtained from the compound obtained in Example 101-(2) (150 mg) and the compound obtained in Production Example 2 (121 mg), by the method similar to Example 99-(4).

¹H-NMR (400 MHz, CDCl₃); δ 1.81-2.08 (m, 8H), 2.49 (s, 3H), 2.58-2.78 (m, 2H), 3.17-3.25 (m, 2H), 3.53 (s, 3H), 3.58

Example 102

(Endo)-6-{(R)-3-[3-(3,4-di-fluorobenzyloxy)-8-azabicyclo[3.2.1]oct-8-yl]-2-fluoropropyl}-2,3-dimethyl-3H-[1,2,4]triazole[1,5-a][1,3,5]triazine-5,7-dione

[Chemical Formula 221]

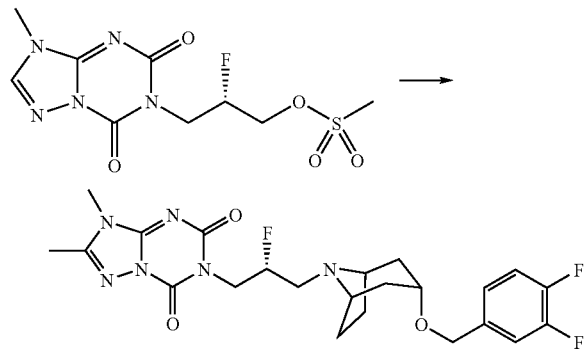

The title compound (54 mg) was obtained from the compound obtained in Example 101-(2) (100 mg) and the compound obtained in Production Example 14 (86 mg), by the method similar to Example 99-(4).

¹H-NMR (400 MHz, CDCl₃); δ 1.80-1.90 (m, 4H), 1.93-2.05 (m, 4H), 2.50 (s, 3H), 2.58-2.77 (m, 2H), 3.18-3.24 (m, 2H), 3.53 (s, 3H), 3.57 (t, J=5.2 Hz, 1H), 4.09-4.22 (m, 1H), 4.38 (s, 2H), 4.50-4.60 (m, 1H), 4.86-5.05 (m, 1H), 6.88-7.03 (m, 1H), 7.07-7.17 (m, 1H).

Example 103

(Endo)-3-{3-[3-(2-fluoro-6-methylbenzyloxy)-8-azabicyclo[3.2.1]oct-8-yl]propyl}-8-methyl-8H-imidazo[1,2-a][1,3,5]triazine-2,4-dione

[Chemical Formula 222]

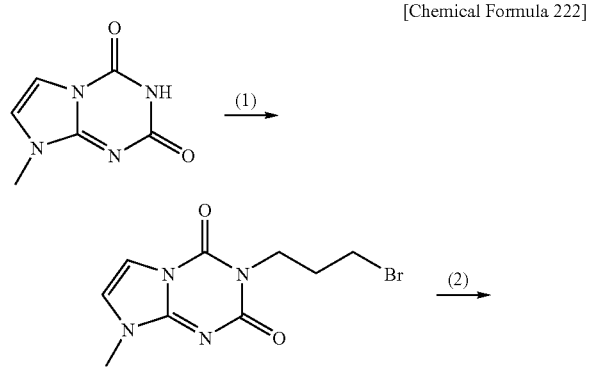

(1) 3-(3-Bromopropyl)-8-methyl-8H-imidazo[1,2-a][1,3,5]triazine-2,4-dione

After suspending 8-methyl-8H-imidazo[1,2-a][1,3,5]triazine-2,4-dione (CAS 67464-13-5) (100 mg) in N,N-dimethylformamide (2 ml), 1,3-dibromopropane (0.18 ml) and sodium hydride (60% in oil) (27 mg) were added and the mixture was stirred at room temperature for 14 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The obtained solid was washed with diethyl ether to obtain the title compound (68 mg).

¹H-NMR (400 MHz, CDCl₃); δ 2.26-2.34 (m, 2H), 3.45 (t, J=6.8 Hz, 2H), 3.58 (s, 3H), 4.15 (t, J=7.2 Hz, 2H), 6.72 (d, J=2.8 Hz, 1H), 7.22 (d, J=2.8 Hz, 1H).

(2) (Endo)-3-{3-[3-(2-fluoro-6-methylbenzyloxy)-8-azabicyclo[3.2.1]oct-8-yl]propyl}-8-methyl-8H-imidazo[1,2-a][1,3,5]triazine-2,4-dione The title compound (44 mg) was obtained from the compound obtained in Example 103-(1) (60 mg) and the compound obtained in Production Example 19 (60 mg), by the method similar to Example 58-(2).

¹H-NMR (400 MHz, CDCl₃); δ 1.81-2.14 (m, 10H), 2.39 (s, 3H), 2.55-2.70 (m, 2H), 3.24-3.41 (m, 2H), 3.56 (s, 3H), 3.57-3.67 (m, 1H), 4.10 (t, J=6.8 Hz, 2H), 4.43-4.50 (m, 2H), 6.70 (d, J=2.8 Hz, 1H), 6.84-6.91 (m, 1H), 6.94-6.99 (m, 1H), 7.03-7.20 (m, 1H), 7.21 (d, J=2.8 Hz, 1H).

Example 104

(Endo)-6-{3-[3-(2-fluorobenzyloxy)-8-azabicyclo[3.2.1]oct-8-yl]propyl}-1,3-dimethyl-1H-[1,2,4]triazolo[4,3-a][1,3,5]triazine-5,7-dione

[Chemical Formula 223]

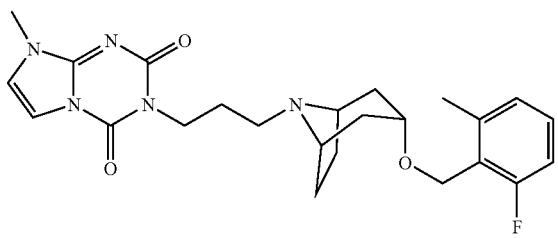

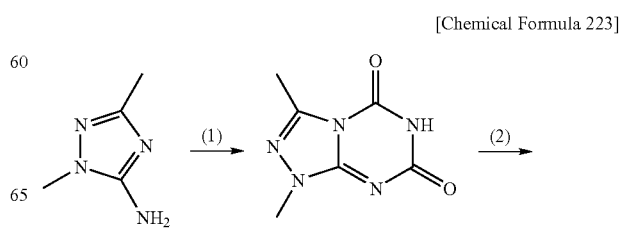

2H), 4.49 (s, 2H), 6.98-7.04 (m, 1H), 7.10-7.16 (m, 1H), 7.21-7.29 (m, 1H), 7.40-7.46 (m, 1H).

Example 105

(Endo)-3-{3-[3-(2-fluorobenzyloxy)-8-azabicyclo[3.2.1]oct-8-yl]propyl}-7-methyl-thiazolo[3,2-a][1,3,5]triazine-2,4-dione

[Chemical Formula 224]

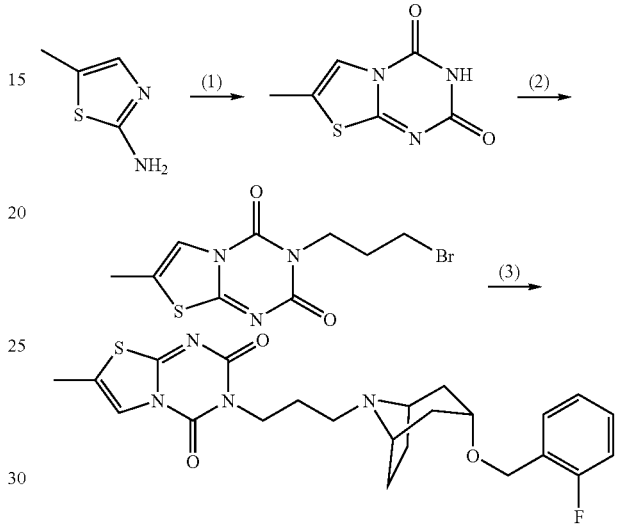

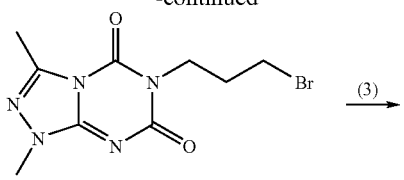

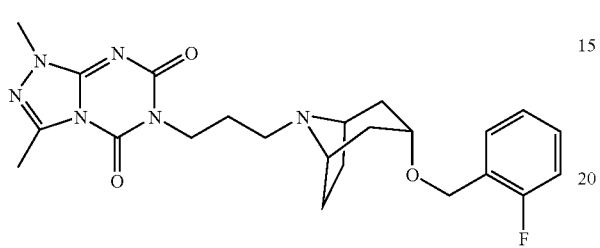

(1) 1,3-Dimethyl-1H-[1,2,4]triazolo[4,3-a][1,3,5]triazine-5,7-dione

The title compound (1.61 g) was obtained from 2,5-dimethyl-2H-[1,2,4]triazol-3-ylamine (CAS 51108-32-8) (1.9 g) by the method similar to Example 99-(1).

$^1$H-NMR (400 MHz, DMSO-$d_6$); δ 2.50 (s, 3H), 3.51 (s, 3H), 11.23 (s, 1H).

(2) 6-(3-Bromo-propyl)-1,3-dimethyl-1H-[1,2,4]triazolo[4,3-a][1,3,5]triazine-5,7-dione The title compound (91 mg) was obtained from the compound obtained in Example 104-(1) (300 mg) and 1,3-dibromopropane, by the method similar to Example 57-(1).

$^1$H-NMR (400 MHz, CDCl$_3$); δ 2.24-2.32 (m, 2H), 2.70 (s, 3H), 3.45 (t, J=6.4 Hz, 2H), 3.68 (s, 3H), 4.09-4.14 (m, 2H).

(3) (Endo)-6-{3-[3-(2-fluorobenzyloxy)-8-azabicyclo[3.2.1]oct-8-yl]propyl}-1,3-dimethyl-1H-[1,2,4]triazolo[4,3-a][1,3,5]triazine-5,7-dione The title compound (77 mg) was obtained from the compound obtained in Example 104-(2) (80 mg) and the compound obtained in Production Example 5 (72 mg), by the method similar to Example 58-(2).

$^1$H-NMR (400 MHz, CDCl$_3$); δ 1.77-1.93 (m, 8H), 1.97-2.04 (m, 2H), 2.45 (t, J=6.8 Hz, 2H), 2.69 (s, 3H), 3.12-3.17 (m, 2H), 3.57-3.61 (m, 1H), 3.66 (s, 3H), 4.07 (t, J=7.2 Hz, (1) 7-Methyl-thiazolo[3,2-a][1,3,5]triazine-2,4-dione A mixture of 2-amino-5-methylthiazole (2.0 g), diphenyl imidodicarbonate (CAS 99911-94-1) (4.5 g) and 1,4-dioxane (40 ml) was heated to reflux for 8 hours. After standing to cool, the precipitate was collected by filtration to obtain the title compound (3.00 g).

$^1$H-NMR (400 MHz, DMSO-$d_6$); δ 2.28 (d, J=1.6 Hz, 3H), 7.51 (d, J=1.2 Hz, 1H), 11.66 (s, 1H).

(2) 3-(3-Bromopropyl)-7-methyl-thiazolo[3,2-a][1,3,5]triazine-2,4-dione

The compound obtained in Example 105-(1) (300 mg) was suspended in dimethyl sulfoxide (5 ml), and then potassium tert-butoxide (202 mg) was added and the mixture was stirred at room temperature for 1 hour. After then adding 1,3-dibromopropane (0.50 ml), the mixture was stirred at room temperature for 19 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The obtained solid was washed with diethyl ether to obtain the title compound (287 mg).

$^1$H-NMR (400 MHz, CDCl$_3$); δ 2.29 (quintet, J=6.8 Hz, 2H), 2.35 (d, J=1.2 Hz, 3H), 3.45 (t, J=6.8 Hz, 2H), 4.19 (t, J=6.8 Hz, 2H), 7.22-7.40 (m, 1H).

(3) (Endo)-3-{3-[3-(2-fluorobenzyloxy)-8-azabicyclo[3.2.1]oct-8-yl]propyl}-7-methyl-thiazolo[3,2-a][1,3,5]triazine-2,4-dione The title compound (63 mg) was obtained from the compound obtained in Example 105-(2) (86 mg) and the compound obtained in Production Example 5 (70 mg), by the method similar to Example 58-(2).

¹H-NMR (400 MHz, CDCl₃); δ 1.76-1.90 (m, 8H), 1.96-2.03 (m, 2H), 2.33 (d, J=1.2 Hz, 3H), 2.45 (t, J=7.2 Hz, 2H), 3.09-3.16 (m, 2H), 3.55-3.60 (m, 1H), 4.09 (t, J=7.2 Hz, 2H), 4.48 (s, 2H), 6.98-7.04 (m, 1H), 7.10-7.16 (m, 1H), 7.21-7.28 (m, 2H), 7.40-7.46 (m, 1H).

Example 106

(Endo)-6-{3-[3-(2-fluorobenzyloxy)-8-azabicyclo[3.2.1]oct-8-yl]propyl}-2-methyl-[1,3,4]thiadiazolo[3,2-a][1,3,5]triazine-5,7-dione

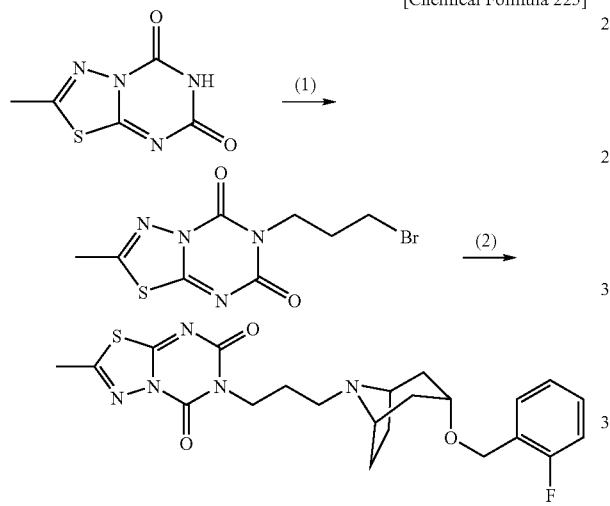

[Chemical Formula 225]

(1) 6-(3-Bromopropyl)-2-methyl-[1,3,4]thiadiazolo[3,2-a][1,3,5]triazine-5,7-dione The title compound (583 mg) was obtained from 2-methyl-[1,3,4]thiadiazolo[3,2-a][1,3,5]triazine-5,7-dione (CAS 110963-15-0) (583 mg) and 1,3-dibromopropane by the method similar to Example 103-(1).

¹H-NMR (400 MHz, DMSO-d₆); δ 2.13 (quintet, J=6.8 Hz, 2H), 2.62 (s, 3H), 3.56 (t, J=6.8 Hz, 2H), 3.91 (t, J=6.8 Hz, 2H).

(2) (Endo)-6-{3-[3-(2-fluorobenzyloxy)-8-azabicyclo[3.2.1]oct-8-yl]propyl}-2-methyl-[1,3,4]thiadiazolo[3,2-a][1,3,5]triazine-5,7-dione The title compound (32 mg) was obtained from the compound obtained in Example 106-(1) (80 mg) and the compound obtained in Production Example 57 (68 mg), by the method similar to Example 58-(2).

¹H-NMR (400 MHz, CDCl₃); δ 1.75-1.92 (m, 8H), 1.96-2.03 (m, 2H), 2.47 (t, J=7.2 Hz, 2H), 2.66 (s, 3H), 3.10-3.18 (m, 2H), 3.55-3.60 (m, 1H), 4.13 (t, J=7.2 Hz, 2H), 4.48 (s, 2H), 6.98-7.04 (m, 1H), 7.10-7.16 (m, 1H), 7.21-7.28 (m, 1H), 7.40-7.46 (m, 1H).

Example 107

(Endo)-2-{3-[3-(2,6-dimethylbenzyloxy)-8-azabicyclo[3.2.1]oct-8-yl]-2-hydroxypropyl}-2,5,6,8-tetrahydro-[1,2,4]triazolo[3,4-c][1,4]oxathin-3-one

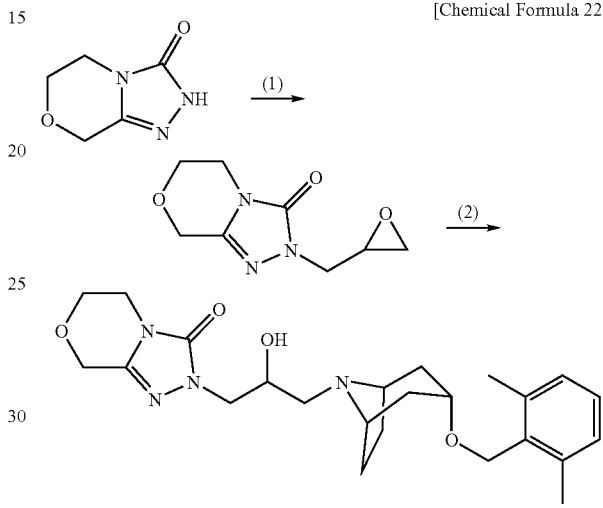

[Chemical Formula 226]

(1) 2-Oxiranylmethyl-2,5,6,8-tetrahydro-[1,2,4]triazolo[3,4-c][1,4]oxathin-3-one The title compound (200 mg) was obtained from 2,5,6,8-tetrahydro-[1,2,4]triazolo[3,4-c][1,4]oxathin-3-one (CAS 133365-36-3) (200 mg) and epibromohydrin by the method similar to Example 66-(2).

¹H-NMR (400 MHz, CDCl₃); δ 2.68 (dd, J=2.4, 4.8 Hz, 1H), 2.85 (dd, J=4.0, 4.8 Hz, 1H), 3.23-3.27 (m, 1H), 3.71 (dd, J=4.8, 6.0 Hz, 2H), 3.87 (dd, J=5.6, 14.8 Hz, 1H), 4.00-4.02 (m, 2H), 4.03 (dd, J=4.0, 14.8 Hz, 1H), 4.65 (s, 2H).

(2) (Endo)-2-{3-[3-(2,6-dimethylbenzyloxy)-8-azabicyclo[3.2.1]oct-8-yl]-2-hydroxypropyl}-2,5,6,8-tetrahydro-[1,2,4]triazolo[3,4-c][14]oxathin-3-one A mixture of the compound obtained in Example 107-(1) (100 mg), the compound obtained in Production Example 20 (143 mg), anhydrous potassium carbonate (140 mg) and N,N-dimethylformamide (2 ml) was stirred at 100° C. for 8 hours and 30 minutes. Water was added to the reaction mixture, and extraction was performed with chloroform. The organic layer was washed with brine and dried over anhydrous magnesium sulfate. After filtration, the solvent was distilled off under reduced pressure. The residue was purified by silica gel column chromatography to obtain the title compound (83 mg).

¹H-NMR (400 MHz, CDCl₃); δ 1.78-2.10 (m, 8H), 2.20-2.30 (m, 1H), 2.38 (s, 6H), 2.53-2.58 (m, 1H), 3.12-3.20 (m,

2H), 3.60-3.65 (m, 1H), 3.69-3.72 (m, 2H), 3.82-3.84 (m, 2H), 3.90-4.01 (m, 2H), 4.41 (s, 2H), 4.65 (s, 2H), 7.00-7.03 (m, 2H), 7.07-7.12 (m, 1H).

Example 108

(Endo)-2-{2-hydroxy-3-[3-(2-methylbenzyloxy)-8-azabicyclo[3.2.1]oct-8-yl]propyl}-3-oxo-2,5,6,8-tetrahydro-3H-[1,2,4]triazolo[4,3-a]pyrazine-7-carboxylic acid tert-butyl ester

[Chemical Formula 227]

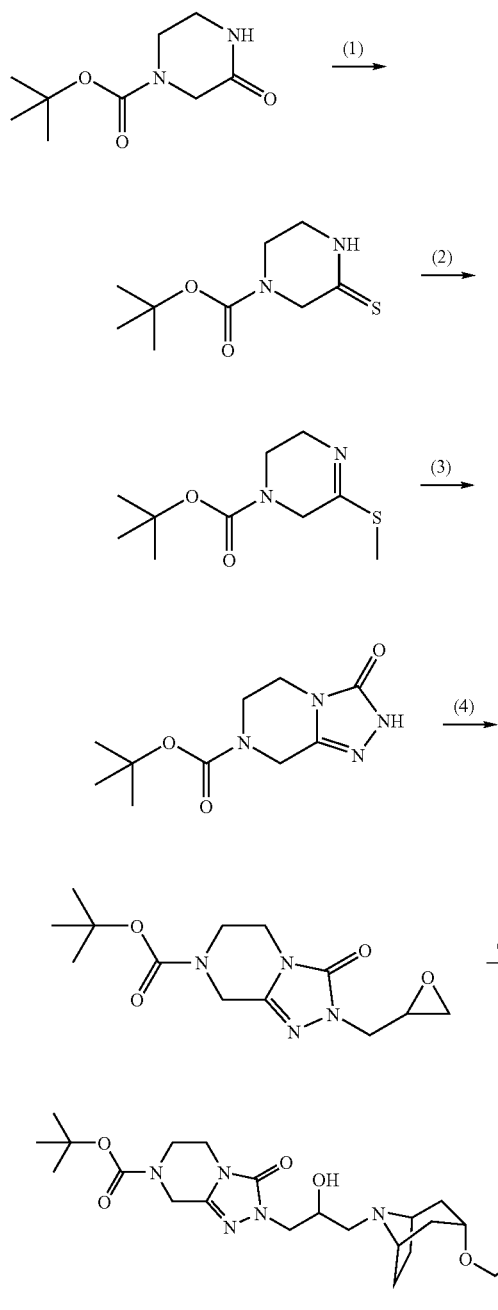

(1) 3-Thioxopiperazine-1-carboxylic acid tert-butyl ester

The title compound (7.26 g) was obtained from 3-oxopiperazine-1-carboxylic acid tert-butyl ester (CAS 76003-29-7) (10.0 g) by the method similar to Example 86-(1).

$^1$H-NMR (400 MHz, CDCl$_3$); δ 1.48 (s, 9H), 3.44 (bs, 2H), 3.67 (t, J=5.2 Hz, 2H), 4.54 (s, 2H), 8.61 (bs, 1H).

(2) 5-Methylsulfanyl-3,6-dihydro-2H-pyrazine-1-carboxylic acid tert-butyl ester

A mixture of the compound obtained in Example 108-(1) (7.26 g), methyl iodide (41.8 ml) and dichloromethane (250 ml) was stirred at room temperature for one day. The reaction mixture was concentrated under reduced pressure, and then a 50% aqueous solution of potassium carbonate was added to the residue and extraction was performed with diethyl ether. The organic layer was washed with water and brine in that order and then dried over anhydrous magnesium sulfate. After filtration, the solvent was distilled off under reduced pressure to obtain the title compound (5.41 g).

$^1$H-NMR (400 MHz, CDCl$_3$); δ 1.46 (s, 9H), 2.33 (s, 3H), 3.42 (t, J=5.2 Hz, 2H), 3.68-3.76 (m, 2H), 4.00 (bs, 2H).

(3) 3-Oxo-2,5,6,8-tetrahydro-3H-[1,2,4]triazolo[4,3-a]pyrazine-7-carboxylic acid tert-butyl ester A mixture of the compound obtained in Example 108-(2) (1.0 g), ethyl carbazate (542 mg) and ethanol (70 ml) was heated to reflux for one day. The reaction mixture was concentrated under reduced pressure, and the residue was purified by silica gel column chromatography. Diethyl ether was then added, and the precipitate was collected by filtration to obtain the title compound (270 mg).

$^1$H-NMR (400 MHz, DMSO-d$_6$); δ 1.41 (s, 9H), 3.47 (t, J=5.6 Hz, 2H), 3.67 (t, J=5.6 Hz, 2H), 4.39 (s, 2H), 11.57 (s, 1H).

(4) 2-Oxiranylmethyl-3-oxo-2,5,6,8-tetrahydro-3H-[1,2,4]triazolo[4,3-a]pyrazine-7-carboxylic acid tert-butyl ester The title compound (890 mg) was obtained from the compound obtained in Example 108-(3) (1.0 g) and epibromohydrin, by the method similar to Example 27-(1).

$^1$H-NMR (400 MHz, CDCl$_3$); δ 1.49 (s, 9H), 2.69 (dd, J=4.8, 2.4 Hz, 1H), 2.85 (t, J=4.4 Hz, 1H), 3.23-3.28 (m, 1H), 3.67 (t, J=5.2 Hz, 2H), 3.78 (t, J=5.2 Hz, 2H), 3.87 (dd, J=14.4, 5.6 Hz, 1H), 4.02 (dd, J=14.4, 4.0 Hz, 1H), 4.54 (s, 2H).

(5) (Endo)-2-{2-hydroxy-3-[3-(2-methylbenzyloxy)-8-azabicyclo[3.2.1]oct-8-yl]propyl}-3-oxo-2,5,6,8-tetrahydro-3H-[1,2,4]triazolo[4,3-a]pyrazine-7-carboxylic acid tert-butyl ester The title compound (323 mg) was obtained from the compound obtained in Example 108-(4) (200 mg) and the compound obtained in Production Example 3 (181 mg), by the method similar to Example 29.

$^1$H-NMR (400 MHz, CD$_3$OD); δ 1.49 (s, 9H), 1.80-2.10 (m, 8H), 2.31 (s, 3H), 2.41-2.52 (m, 2H), 3.14-3.18 (m, 1H), 3.23-3.38 (m, 1H), 3.60-3.67 (m, 3H), 3.75-3.86 (m, 4H), 3.97-4.04 (m, 1H), 4.43 (s, 2H), 4.53 (s, 2H), 7.10-7.17 (m, 3H), 7.27-7.31 (m, 1H).

Example 109

(Endo)-2-{2-hydroxy-3-[3-(2-methylbenzyloxy)-8-azabicyclo[3.2.1]oct-8-yl]propyl}-5,6,7,8-tetrahydro-2H-[1,2,4]triazolo[4,3-a]pyrazin-3-one

[Chemical Formula 228]

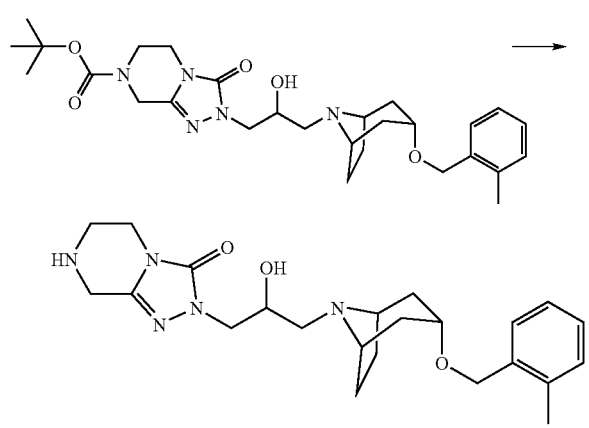

The compound obtained in Example 108 (210 mg) was dissolved in dichloromethane (2 ml), and then trifluoroacetic acid (0.5 ml) and water (0.2 ml) were added and the mixture was stirred overnight at room temperature. The reaction mixture was concentrated under reduced pressure, and the residue was purified by NH silica gel column chromatography to obtain the title compound (170 mg).

$^1$H-NMR (400 MHz, CDCl$_3$); δ 1.86-2.10 (m, 6H), 2.12-2.20 (m, 2H), 2.29 (s, 3H), 2.32-2.40 (m, 1H), 2.61 (dd, J=3.6, 12.8 Hz, 1H), 3.19 (t, J=5.6 Hz, 2H), 3.29 (brs, 2H), 3.62 (t, J=5.6 Hz, 2H), 3.62-3.66 (m, 1H), 3.82-3.84 (m, 2H), 3.92 (s, 2H), 3.98-4.06 (m, 1H), 4.42 (s, 2H), 7.13-7.22 (m, 3H), 7.31-7.35 (m, 1H).

Example 110

(Endo)-2-{2-hydroxy-3-[3-(2-methylbenzyloxy)-8-azabicyclo[3.2.1]oct-8-yl]propyl}-7-methyl-5,6,7,8-tetrahydro-2H-[1,2,4]triazolo[4,3-a]pyrazin-3-one

[Chemical Formula 229]

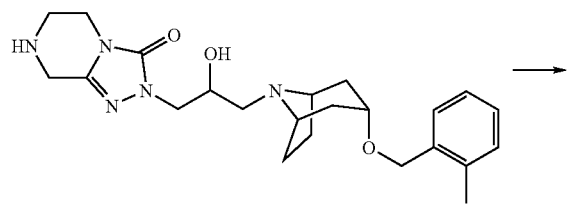

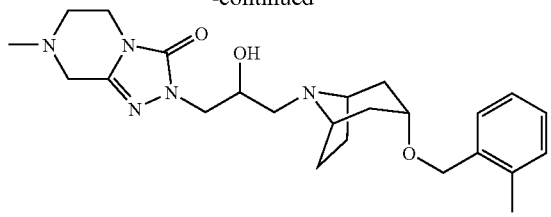

After adding 37% formalin (17 μl) to a mixture of the compound obtained in Example 109 (30 mg), 1N hydrochloric acid (10 μl), sodium cyanoborohydride (13 mg) and methanol (3 ml) while cooling on ice, the mixture was stirred for 5 hours. An aqueous solution of sodium hydrogencarbonate was added to the reaction mixture, and extraction was performed with chloroform. The organic layer was washed with brine and dried over anhydrous magnesium sulfate. After filtration, the solvent was distilled off under reduced pressure and the residue was purified by NH silica gel column chromatography to obtain the title compound (5 mg).

$^1$H-NMR (400 MHz, CDCl$_3$); δ 1.82-2.04 (m, 6H), 2.10-2.14 (m, 2H), 2.26 (dd, J=9.2, 12.4 Hz, 1H), 2.29 (s, 3H), 2.46 (s, 3H), 2.54 (dd, J=4.0, 12.4 Hz, 1H), 2.76-2.79 (m, 2H), 3.16-3.22 (m, 2H), 3.46-3.49 (m, 2H), 3.60-3.66 (m, 2H), 3.66-3.70 (m, 2H), 3.82-3.83 (m, 2H), 3.92-4.00 (m, 1H), 4.41 (s, 2H), 7.13-7.20 (m, 3H), 7.33-7.36 (m, 1H).

Example 111

(Endo)-2-{3-[3-(4-fluorobenzyloxy)-8-azabicyclo[3.2.1]oct-8-yl]-2-hydroxypropyl}-7-methyl-2,5,6,7-tetrahydroimidazo[2,1-c][1,2,4]triazol-3-one

[Chemical Formula 230]

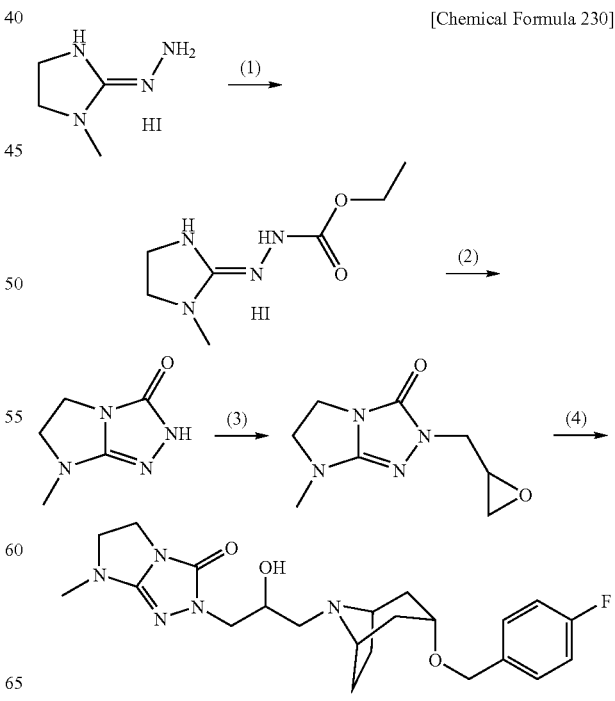

(1) N'-(1-Methyl-4,5-dihydro-1H-imidazol-2-yl)hydrazinecarboxylic acid ethyl ester hydroiodide Ethyl chloroformate (0.95 ml) was added dropwise to a mixture of (1-methyl-4,5-dihydro-1H-imidazol-2-yl)-hydrazine hydroiodide (CAS 49541-82-4) (2 g) and pyridine (40 ml) while stirring, and the mixture was stirred at room temperature for 2 hours. The solvent was distilled off and the residue was purified by silica gel column chromatography. The obtained compound was washed with diethyl ether to obtain the title compound (1.14 g).

$^1$H-NMR (400 MHz, DMSO-$d_6$); δ 1.20 (t, J=7.2 Hz, 3H), 2.89 (s, 3H), 3.55 (m, 2H), 3.70 (m, 1H), 4.10 (q, J=7.2 Hz, 2H), 8.75 (br, 1H), 9.73 (br, 1H), 10.28 (br, 1H).

(2) 7-Methyl-2,5,6,7-tetrahydroimidazo[2,1-c][1,2,4]triazol-3-one

A mixture of the compound obtained in Example 111-(1) (1.13 g) and N,N-dimethylformamide (18 ml) was stirred at 150° C. for 43 hours. An excess of triethylamine was added to the reaction mixture, and the solvent was distilled off. The residue was purified by silica gel column chromatography to obtain the title compound (314 mg).

$^1$H-NMR (400 MHz, DMSO-$d_6$); δ 2.67 (s, 3H), 3.64-3.74 (m, 4H), 10.30 (br, 1H).

(3) 7-Methyl-2-oxiranylmethyl-2,5,6,7-tetrahydroimidazo[2,1-c][1,2,4]triazol-3-one The compound obtained in Example 111-(2) (150 mg) was dissolved in N,N-dimethylformamide (7 ml), and then sodium hydride (60% in oil) (64 mg) was added and the mixture was stirred at room temperature. Epibromohydrin (0.18 ml) was added, and the mixture was stirred overnight. A saturated aqueous solution of sodium hydrogencarbonate was added to the reaction mixture, and extraction was performed with chloroform. The extract was dried over anhydrous magnesium sulfate and filtered, and then the solvent was distilled off under reduced pressure. The residue was purified by silica gel column chromatography to obtain the title compound (139 mg).

$^1$H-NMR (400 MHz, CDCl$_3$); δ 2.70 (m, 1H), 2.83 (m, 1H), 2.85 (s, 3H), 3.23 (m, 1H), 3.73-3.79 (m, 3H), 3.84-3.89 (m, 3H).

(4) (Endo)-2-{3-[3-(4-fluorobenzyloxy)-8-azabicyclo[3.2.1]oct-8-yl]-2-hydroxypropyl}-7-methyl-2,5,6,7-tetrahydroimidazo[2,1-c][1,2,4]triazol-3-one The title compound (264 mg) was obtained from the compound obtained in Example 111-(3) (200 mg) and the compound obtained in Production Example 1 (304 mg), by the method similar to Example 31-(2).

$^1$H-NMR (400 MHz, CDCl$_3$); δ 1.83-2.10 (m, 8H), 2.23 (dd, J=9.2, 12.4 Hz, 1H), 2.52 (dd, J=4.0, 12.4 Hz, 1H), 2.84 (s, 3H), 3.12 (m, 1H), 3.18 (m, 1H), 3.59 (m, 1H), 3.69-3.75 (m, 4H), 3.84-3.94 (m, 3H), 4.40 (s, 2H), 6.99-7.04 (m, 2H), 7.25-7.29 (m, 2H).

Example 112

(Endo)-2-{2-fluoro-3-[3-(4-fluorobenzyloxy)-8-azabicyclo[3.2.1]oct-8-yl]propyl}-7-methyl-2,5,6,7-tetrahydroimidazo[2,1-c][1,2,4]triazol-3-one

[Chemical Formula 231]

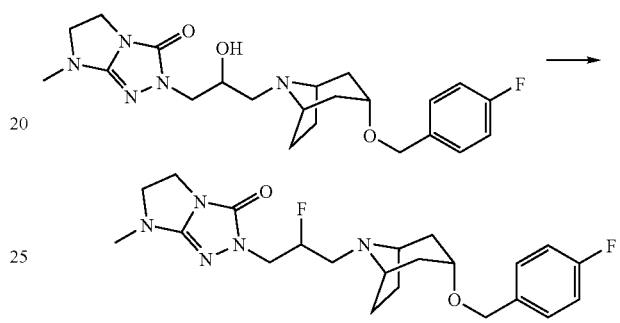

The compound obtained in Example 111 (210 mg) was dissolved in dichloromethane (5 ml), and then (diethylamino)sulfur trifluoride (0.13 ml) was added while stirring on ice and the mixture was stirred overnight at room temperature. A saturated aqueous solution of sodium hydrogencarbonate was added to the reaction mixture, and the resulting mixture was extracted with ethyl acetate and dried over anhydrous magnesium sulfate. After filtration, the solvent was distilled off under reduced pressure. The residue was purified by preparative thin-layer chromatography to obtain the title compound (93 mg).

$^1$H-NMR (400 MHz, CDCl$_3$); δ 1.83-2.05 (m, 8H), 2.60-2.66 (m, 2H), 2.84 (s, 3H), 3.20 (m, 2H), 3.59 (m, 1H), 3.74 (m, 2H), 3.80-3.91 (m, 4H), 3.99 (dt, J=7.2, 15.2 Hz, 1H), 4.40 (s, 2H), 4.87 (m, 1H), 7.01 (m, 2H), 7.28 (m, 2H).

Example 113

2-{2-hydroxy-3-[3β-methoxymethyl-3α-(2-methylbenzyloxy)-8-azabicyclo[3.2.1]oct-8-yl]propyl}-5,6-dihydro-2H-thiazolo[2,3-c][1,2,4]triazol-3-one

[Chemical Formula 232]

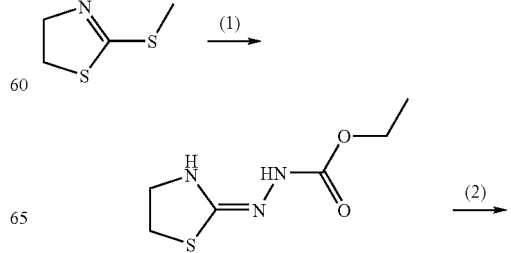

-continued

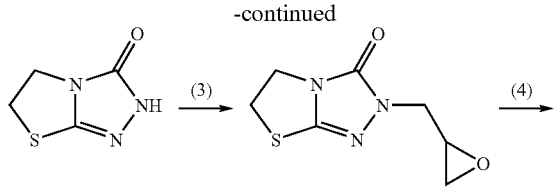

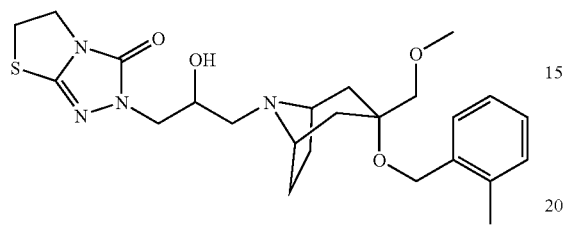

(1) N'-Thiazolidineylidenehydrazinecarboxylic acid ethyl ester

A mixture of ethyl carbazate (23.4 g), 2-(methylthio)-2-thiazoline (25 g) and ethanol (250 ml) was heated to reflux for 3 days. It was then stirred at room temperature for 2 days. The precipitate was collected by filtration and washed with ethanol to obtain the title compound (9.05 g).

$^1$H-NMR (400 MHz, CDCl$_3$); δ 1.24-1.31 (m, 3H), 3.27 (t, J=6.8 Hz, 2H), 3.65 (t, J=6.8 Hz, 2H), 4.20 (q, J=7.2 Hz, 2H).

(2) 5,6-Dihydro-2H-thiazolo[2,3-c][1,2,4]triazol-3-one

The compound obtained in Example 113-(1) (9.05 g) was dissolved in N-methyl-2-pyrrolidinone (10 ml), and then the mixture was stirred at 170° C. for 1 hour and 30 minutes. After stirring at room temperature for one day, the precipitate was collected by filtration. It was then washed with diethyl ether to obtain the title compound (6.5 g).

$^1$H-NMR (400 MHz, DMSO-d$_6$); δ 3.81-3.89 (m, 4H), 11.32 (s, 1H).

(3) 2-Oxiranylmethyl-5,6-dihydro-2H-thiazolo[2,3-c][1,2,4]triazol-3-one

The title compound (1.59 g) was obtained from the compound obtained in Example 113-(2) (2.0 g) and epibromohydrin, by the method similar to Example 27-(1).

$^1$H-NMR (400 MHz, CDCl$_3$); δ 2.69 (dd, J=4.8, 0.8 Hz, 1H), 2.83-2.86 (m, 1H), 3.22-3.27 (m, 1H), 3.78 (dd, J=7.6, 0.4 Hz, 2H), 3.90 (dd, J=14.0, 4.8 Hz, 2H), 3.99 (dd, J=7.6, 0.4 Hz, 2H).

(4) 2-{2-hydroxy-3-[3β-methoxymethyl-3α-(2-methylbenzyloxy)-8-azabicyclo[3.2.1]oct-8-yl]propyl}-5,6-dihydro-2H-thiazolo[2,3-c][1,2,4]triazol-3-one The title compound (125 mg) was obtained from the compound obtained in Example 113-(3) (100 mg) and the compound obtained in Production Example 50 (157 mg), by the method similar to Example 36-(2).

$^1$H-NMR (400 MHz, CD$_3$OD); δ 1.84-2.08 (m, 8H), 2.32 (s, 3H), 2.44-2.68 (m, 2H), 3.30-3.46 (m, 2H), 3.33 (s, 5H), 3.69-3.80 (m, 2H), 3.86-3.91 (m, 2H), 3.96-4.01 (m, 2H), 4.01-4.08 (m, 1H), 4.47 (s, 2H), 7.10-7.16 (m, 3H), 7.33-7.37 (m, 1H).

Example 114

(Endo)-2-{2-hydroxy-3-[3-(2-morpholin-4-yl-benzyloxy)-8-azabicyclo[3.2.1]oct-8-yl]propyl}-5,6-dihydro-2H-thiazolo[2,3-c][1,2,4]triazol-3-one oxalate

[Chemical Formula 233]

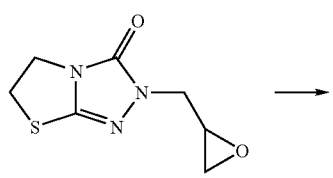

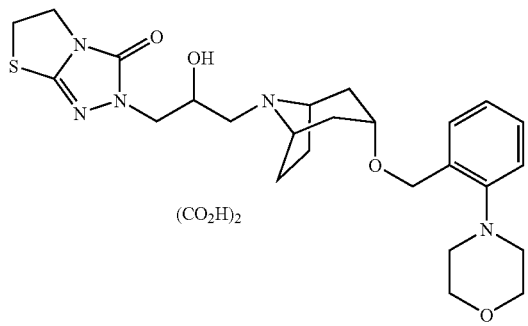

A mixture of the compound obtained in Example 113-(3) (50 mg), the compound obtained in Production Example 35 (78 mg), anhydrous potassium carbonate (69 mg) and N,N-dimethylformamide (2 ml) was stirred overnight at 100° C. The reaction mixture was filtered with Celite, and the filtrate was concentrated under reduced pressure. A saturated aqueous solution of sodium hydrogencarbonate was added to the residue and extraction was performed with ethyl acetate. The organic layer was washed with brine and dried over anhydrous magnesium sulfate. After filtration, the solvent was distilled off under reduced pressure. The residue was purified by preparative thin-layer chromatography. It was then re-purified by preparative thin-layer chromatography (NH silica gel) to obtain the free form of the title compound (30 mg).

This was dissolved in ethanol, oxalic acid (5 mg) was added, and the mixture was concentrated under reduced pressure. Diethyl ether was added to the residue to produce a solid, which was collected by filtration to obtain the title compound (27 mg).

$^1$H-NMR (400 MHz, CD$_3$OD); δ 2.18-2.47 (m, 2H), 2.89-2.92 (m, 4H), 3.05-3.20 (m, 2H), 3.63-3.83 (m, 7H), 3.87-

3.91 (m, 2H), 3.98-4.01 (m, 3H), 4.17 (br, 1H), 4.32 (br, 1H), 4.62 (s, 2H), 7.09-7.17 (m, 2H), 7.27-7.31 (m, 1H), 7.41-7.43 (m, 1H).

Example 115

(Endo)-2-{3-[3-(2,6-dimethylbenzyloxy)-8-azabicyclo[3.2.1]oct-8-yl]-2-hydroxypropyl}-2,5,6,7-tetrahydropyrrolo[2,1-c][1,2,4]triazol-3-one

[Chemical Formula 234]

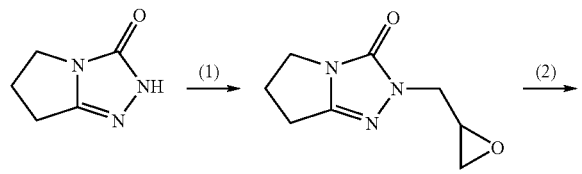

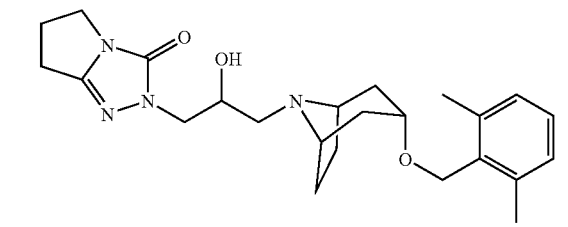

(1) 2-Oxiranylmethyl-2,5,6,7-tetrahydropyrrolo[2,1-c][1,2,4]triazol-3-one

The title compound (1.75 g) was obtained from 2,5,6,7-tetrahydropyrrolo[2,1-c][1,2,4]triazol-3-one (CAS 116056-07-6) (1.61 g) and epibromohydrin by the method similar to Example 27-(1).

$^1$H-NMR (400 MHz, CDCl$_3$); δ 2.55 (m, 2H), 2.70 (m, 1H), 2.79-2.86 (m, 3H), 3.25 (m, 1H), 3.77 (m, 2H), 3.87 (m, 1H), 3.96 (dd, J=4.4, 14.8 Hz, 1H).

(2) (Endo)-2-{3-[3-(2,6-dimethylbenzyloxy)-8-azabicyclo[3.2.1]oct-8-yl]-2-hydroxypropyl}-2,5,6,7-tetrahydropyrrolo[2,1-c][1,2,4]triazol-3-one The title compound (58 mg) was obtained from the compound obtained in Example 115-(1) (72 mg) and the compound obtained in Production Example 20 (113 mg), by the method similar to Example 107-(2).

$^1$H-NMR (400 MHz, CDCl$_3$); δ 1.76-2.05 (m, 8H), 2.22 (dd, J=9.6, 12.4 Hz, 1H), 2.38 (s, 6H), 2.50-2.57 (m, 2H), 2.78-2.82 (m, 2H), 3.07-3.18 (m, 2H), 3.60-3.64 (m, 1H), 3.76-3.82 (m, 4H), 3.88-3.96 (m, 1H), 4.40 (s, 2H), 7.01-7.02 (m, 2H), 7.07-7.11 (m, 1H).

Example 116

(Endo)-2-{3-[3-(2-fluorobenzyloxy)-8-azabicyclo[3.2.1]oct-8-yl]propyl}-5,6-dihydro-2H-thiazolo[2,3-c][1,2,4]triazol-3-one

[Chemical Formula 235]

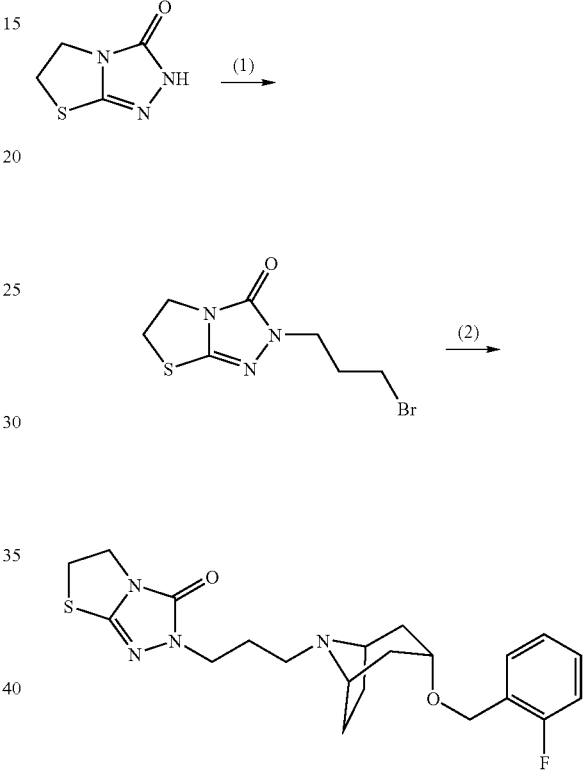

(1) 2-(3-Bromopropyl)-5,6-dihydro-2H-thiazolo[2,3-c][1,2,4]triazol-3-one

The title compound (492 mg) was obtained from the compound obtained in Example 113-(2) (350 mg) and 1,3-dibromopropane, by the method similar to Example 57-(1).

$^1$H-NMR (400 MHz, CDCl$_3$); δ 2.28 (quintet, J=6.8 Hz, 2H), 3.44 (t, J=6.8 Hz, 2H), 3.75-3.80 (m, 2H), 3.87 (t, J=6.8 Hz, 2H), 3.95-4.00 (m, 2H).

(2) (Endo)-2-{3-[3-(2-fluorobenzyloxy)-8-azabicyclo[3.2.1]oct-8-yl]propyl}-5,6-dihydro-2H-thiazolo[2,3-c][1,2,4]triazol-3-one The title compound (61 mg) was obtained from the compound obtained in Example 116-(1) (70 mg) and the compound obtained in Production Example 5 (72 mg), by the method similar to Example 58-(2).

$^1$H-NMR (400 MHz, CDCl$_3$); δ 1.80-2.06 (m, 10H), 2.39 (t, J=7.2 Hz, 2H), 3.12-3.18 (m, 2H), 3.63 (t, J=4.8 Hz, 1H), 3.74-3.83 (m, 4H), 3.97 (t, J=7.2 Hz, 2H), 4.50 (s, 2H), 6.98-7.04 (m, 1H), 7.10-7.16 (m, 1H), 7.21-7.29 (m, 1H), 7.41-7.46 (m, 1H).

Example 117

(Endo)-2-{3-[3-(2-fluorobenzyloxy)-9-azabicyclo[3.3.1]non-9-yl]propyl}-5,6-dihydro-2H-thiazolo[2,3-c][1,2,4]triazol-3-one

[Chemical Formula 236]

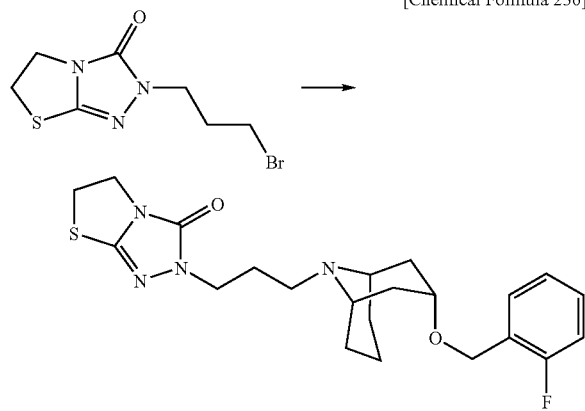

The title compound (30 mg) was obtained from the compound obtained in Example 116-(1) (50 mg) and the compound obtained in Production Example 52 (59 mg), by the method similar to Example 97.

$^1$H-NMR (400 MHz, CDCl$_3$); δ 1.08-1.21 (m, 2H), 1.37-1.64 (m, 3H), 1.74-1.92 (m, 4H), 2.16-2.45 (m, 3H), 2.57-2.70 (m, 2H), 2.98-3.10 (m, 2H), 3.74-3.88 (m, 5H), 3.97 (t, J=6.8 Hz, 2H), 4.59 (s, 2H), 6.99-7.05 (m, 1H), 7.10-7.15 (m, 1H), 7.21-7.28 (m, 1H), 7.41-7.47 (m, 1H).

Example 118

(Endo)-2-fluoro-N-{8-[3-(3-oxo-5,6-dihydro-thiazolo[2,3-c][1,2,4]triazol-2-yl)propyl]-8-azabicyclo[3.2.1]oct-3-yl}benzamide oxalate

[Chemical Formula 237]

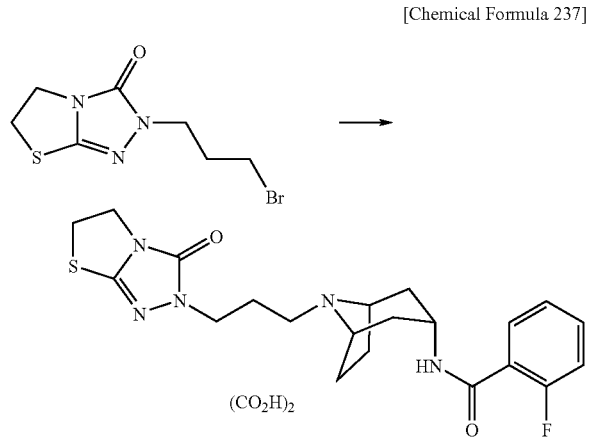

The title compound (8 mg) was obtained from the compound obtained in Example 116-(1) (71 mg) and the compound obtained in Production Example 46 (70 mg), by the method similar to Example 57-(2).

$^1$H-NMR (400 MHz, DMSO-d$_6$); δ 1.85-2.34 (m, 10H), 2.78-2.92 (m, 2H), 3.63-3.98 (m, 9H), 7.2407.32 (m, 2H), 7.49-7.59 (m, 2H), 8.32-8.38 (m, 1H).

Example 119

(Endo)-2-{3-[3-(2-fluoro-pyridin-3-ylmethoxy)-8-azabicyclo[3.2.1]oct-8-yl]propyl}-5,6-dihydro-2H-thiazolo[2,3-c][1,2,4]triazol-3-one oxalate

[Chemical Formula 238]

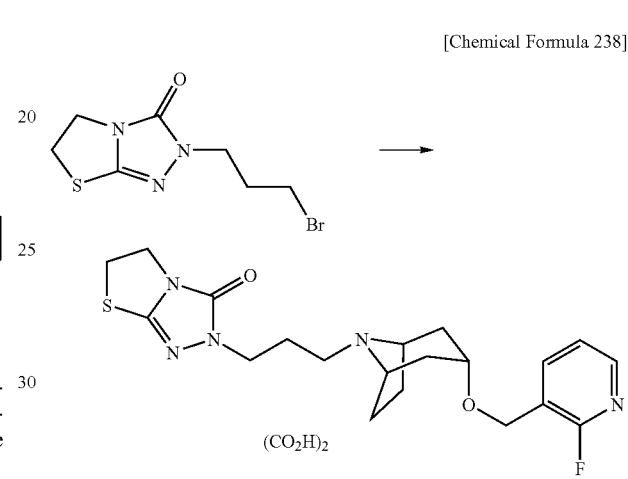

The title compound (59 mg) was obtained from the compound obtained in Example 116-(1) (68 mg) and the compound obtained in Production Example 30 (70 mg), by the method similar to Example 57-(2).

$^1$H-NMR (400 MHz, CD$_3$OD); δ 2.11-2.46 (m, 10H), 3.06-3.17 (m, 2H), 3.79-3.92 (m, 5H), 3.95-4.03 (m, 4H), 4.58 (s, 2H), 7.30-7.36 (m, 1H), 7.95-8.02 (m, 1H), 8.13-8.16 (m, 1H).

Example 120

(Endo)-2-{3-[3-(2-fluorobenzyloxy)-8-azabicyclo[3.2.1]oct-8-yl]propyl}-5,6,7,8-tetrahydro-2H-[1,2,4]triazolo[4,3-a]pyridin-3-one oxalate

[Chemical Formula 239]

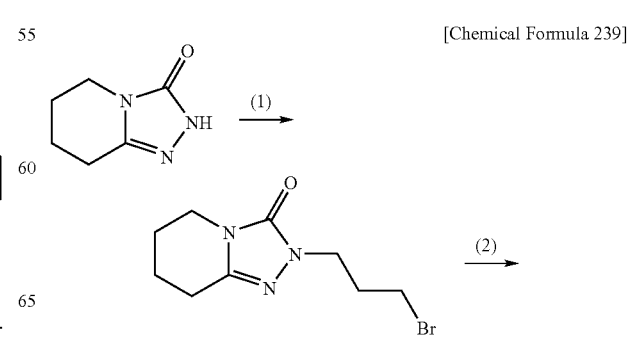

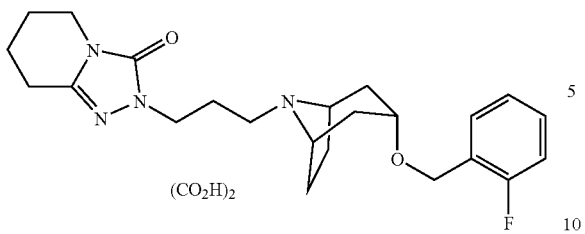

(1) 2-(3-Bromopropyl)-5,6,7,8-tetrahydro-2H-[1,2,4]triazolo[4,3-a]pyridin-3-one

The title compound (728 mg) was obtained from 5,6,7,8-tetrahydro-2H-[1,2,4]triazolo[4,3-a]pyridin-3-one (CAS 118801-67-5) (700 mg) and 1,3-dibromopropane by the method similar to Example 57-(1).
$^1$H-NMR (400 MHz, CDCl$_3$); δ 1.81-1.96 (m, 4H), 2.29 (quintet, J=6.8 Hz, 2H), 2.67 (t, J=6.8 Hz, 2H), 3.44 (t, J=6.8 Hz, 2H), 3.61 (t, J=6.8 Hz, 2H), 3.90 (t, J=6.8 Hz, 2H).

(2) (Endo)-2-{3-[3-(2-fluorobenzyloxy)-8-azabicyclo[3.2.1]oct-8-yl]propyl}-5,6,7,8-tetrahydro-2H-[1,2,4]triazolo[4,3-a]pyridin-3-one oxalate The title compound (60 mg) was obtained from the compound obtained in Example 120-(1) (52 mg) and the compound obtained in Production Example 5 (52 mg), by the method similar to Example 57-(2).
$^1$H-NMR (400 MHz, DMSO-d$_6$); δ 1.68-1.86 (m, 4H), 1.96-2.26 (m, 8H), 2.44-2.53 (m, 2H), 2.57 (t, J=6.4 Hz, 2H), 2.97 (br s, 2H), 3.45 (t, J=5.6 Hz, 2H), 3.64-3.74 (m, 3H), 3.89 (br s, 2H), 4.51 (s, 2H), 7.14-7.24 (m, 2H), 7.32-7.39 (m, 1H), 7.44 (t, J=6.8 Hz, 1H).

Example 121

(Endo)-2-{3-[3-(2-fluorobenzyloxy)-8-azabicyclo[3.2.1]oct-8-yl]propyl}-2,5,6,7,8,9-hexahydro-[1,2,4]triazolo[4,3-a]azepin-3-one oxalate

[Chemical Formula 240]

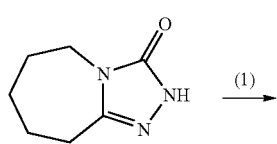

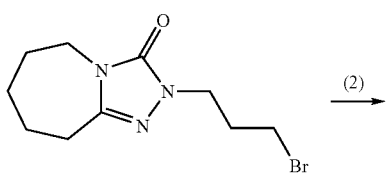

(1) 2-(3-Bromopropyl)-2,5,6,7,8,9-hexahydro-[1,2,4]triazolo[4,3-a]azepin-3-one

The title compound (767 mg) was obtained from 2,5,6,7,8,9-hexahydro-[1,2,4]triazolo[4,3-a]azepin-3-one (CAS 27182-43-0) (700 mg) and 1,3-dibromopropane by the method similar to Example 57-(1).
$^1$H-NMR (400 MHz, CDCl$_3$); δ 1.68-1.76 (m, 4H), 1.80-1.88 (m, 2H), 2.29 (quintet, J=6.8 Hz, 2H), 2.64-2.69 (m, 2H), 3.43 (t, J=6.8 Hz, 2H), 3.72-3.78 (m, 2H), 3.89 (t, J=6.4 Hz, 2H).

(2) (Endo)-2-{3-[3-(2-fluorobenzyloxy)-8-azabicyclo[3.2.1]oct-8-yl]propyl}-2,5,6,7,8,9-hexahydro-[1,2,4]triazolo[4,3-a]azepin-3-one oxalate The title compound (37 mg) was obtained from the compound obtained in Example 121-(1) (60 mg) and the compound obtained in Production Example 5 (59 mg), by the method similar to Example 57-(2).
$^1$H-NMR (400 MHz, DMSO-d$_6$); δ 1.56-1.64 (m, 4H), 1.73-1.80 (m, 2H), 1.96-2.22 (m, 10H), 2.61-2.67 (m, 2H), 2.94 (br s, 2H), 3.63-3.90 (m, 7H), 4.52 (s, 2H), 7.17-7.24 (m, 2H), 7.34-7.41 (m, 1H), 7.42-7.48 (m, 1H).

Example 122

(Endo)-2-{3-[3-(2-fluorobenzyloxymethyl)-8-azabicyclo[3.2.1]oct-8-yl]propyl}-5,6-dihydro-2H-thiazolo[2,3-c][1,2,4]triazol-3-one oxalate

[Chemical Formula 241]

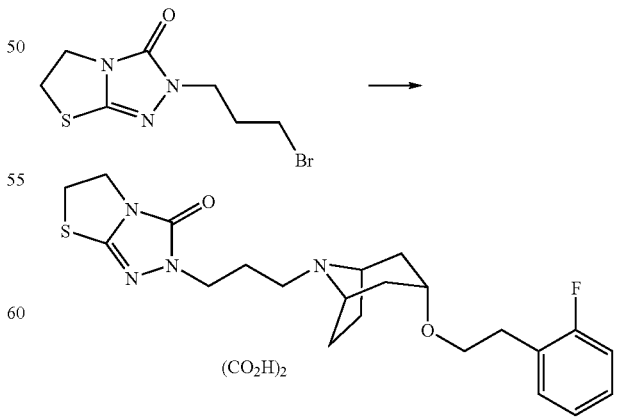

The title compound (137 mg) was obtained from the compound obtained in Example 116-(1) (100 mg) and the compound obtained in Production Example 16 (104 mg), by the method similar to Example 69-(2).

¹H-NMR (400 MHz, CD₃OD); δ 1.85-1.91 (m, 4H), 2.09-2.31 (m, 7H), 3.08 (bs, 2H), 3.55-3.57 (m, 2H), 3.79-3.82 (m, 2H), 3.86-3.90 (m, 4H), 3.96-4.00 (m, 2H), 4.61 (s, 2H), 7.07-7.12 (m, 1H), 7.15-7.19 (m, 1H), 7.31-7.37 (m, 1H), 7.41-7.46 (m, 1H).

Example 123

(Endo)-2-(3-{3-[(2-fluoro-benzyl)-methyl-amino]-8-azabicyclo[3.2.1]oct-8-yl}propyl)-5,6-dihydro-2H-thiazolo[2,3-c][1,2,4]triazol-3-one

[Chemical Formula 242]

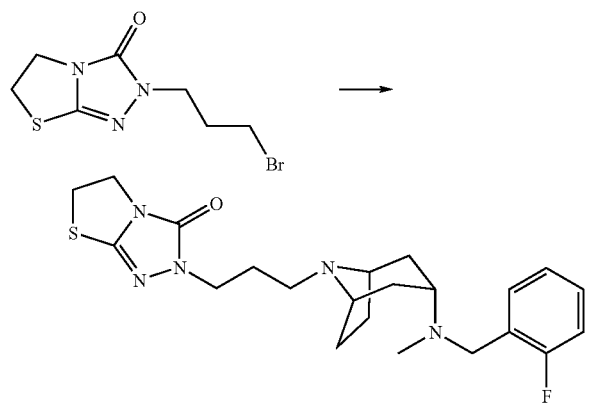

The title compound (40 mg) was obtained from the compound obtained in Example 116-(1) (27 mg) and the compound obtained in Production Example 47 (25 mg), by the method similar to Example 97.

¹H-NMR (400 MHz, CDCl₃); δ 1.74-1.79 (m, 2H), 1.87-1.98 (m, 6H), 2.04-2.11 (m, 2H), 2.14 (s, 3H), 2.39 (t, J=7.2 Hz, 2H), 2.57-2.62 (m, 1H), 3.22 (brs, 2H), 3.53 (s, 2H), 3.77 (t, J=7.2 Hz, 2H), 3.79 (t, J=7.0 Hz, 2H), 3.96 (t, J=7.0 Hz, 2H), 7.00 (t, J=9.2 Hz, 1H), 7.08-7.12 (m, 1H), 7.16-7.24 (m, 1H), 7.36-7.41 (m, 1H).

Example 124

(Endo)-2-{2-[3-(2-fluorobenzyloxy)-8-azabicyclo[3.2.1]oct-8-yl]-1-methyl-ethyl}-2,5,6,7-tetrahydro-pyrrolo[2,1-c][1,2,4]triazol-3-one oxalate

[Chemical Formula 243]

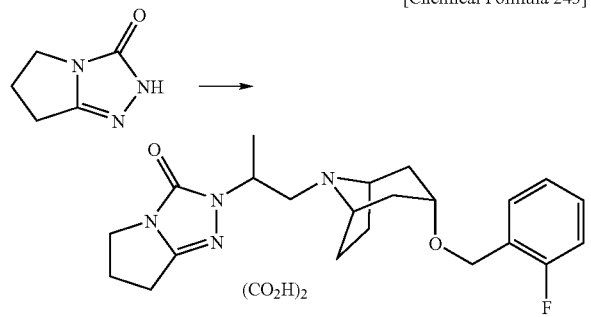

A mixture of 2,5,6,7-tetrahydropyrrolo[2,1-c][1,2,4]triazol-3-one (CAS 116056-07-6) (1.5 g), 1,2-dibromopropane (3.75 ml), anhydrous potassium carbonate (2.49 g) and N,N-dimethylformamide (12 ml) was stirred overnight at 90° C. Water was added to the reaction mixture, and extraction was performed with ethyl acetate. The organic layer was washed with brine and dried over anhydrous magnesium sulfate. After filtration, the solvent was distilled off under reduced pressure. The residue was purified by NH silica gel column chromatography to obtain an oil (210 mg).

The oil was dissolved in N,N-dimethylformamide (3 ml), and then the compound obtained in Example 5 (232 mg), anhydrous potassium carbonate (259 mg) and sodium iodide (128 mg) were added and the mixture was stirred overnight at 90° C. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography to obtain the free form of the title compound (32 mg).

This was dissolved in ethanol, and then oxalic acid (7 mg) was added. The mixture was concentrated under reduced pressure to obtain the title compound (41 mg).

¹H-NMR (400 MHz, CD₃OD); δ 1.41 (d, J=6.4 Hz, 3H), 2.10-2.36 (m, 6H), 2.40-2.50 (m, 2H), 2.52-2.62 (m, 2H), 2.76-2.86 (m, 2H), 3.16-3.24 (m, 1H), 3.40-3.52 (m, 1H), 3.70-3.80 (m, 3H), 4.16-4.34 (m, 2H), 4.57 (s, 2H), 4.60-4.70 (m, 1H), 7.06-7.11 (m, 1H), 7.14-7.20 (m, 1H), 7.30-7.38 (m, 1H), 7.39-7.46 (m, 1H).

Example 125

(Endo)-2-{5-[3-(2-fluoro-6-methylbenzyloxy)-8-azabicyclo[3.2.1]oct-8-yl]pentyl}-2,5,6,7-tetrahydro-pyrrolo[2,1-c][1,2,4]triazol-3-one oxalate

[Chemical Formula 244]

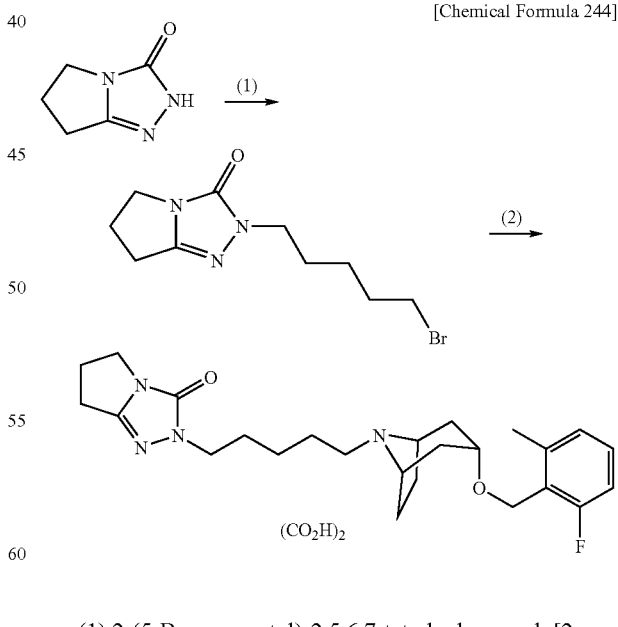

(1) 2-(5-Bromo-pentyl)-2,5,6,7-tetrahydropyrrolo[2,1-c][1,2,4]triazol-3-one

The title compound (221 mg) was obtained from 2,5,6,7-tetrahydropyrrolo[2,1-c][1,2,4]triazol-3-one (CAS 116056-

07-6) (200 mg) and 1,5-dibromopropane (0.65 ml) by the method similar to Example 69-(1).

¹H-NMR (400 MHz, CDCl₃); δ 1.44-1.54 (m, 2H), 1.72-1.82 (m, 2H), 1.86-1.95 (m, 2H), 2.51-2.58 (m, 2H), 2.77-2.81 (m, 2H), 3.39-3.42 (m, 2H), 3.72-3.78 (m, 4H).

(2) (Endo)-2-{5-[3-(2-fluoro-6-methylbenzyloxy)-8-azabicyclo[3.2.1]oct-8-yl]pentyl}-2,5,6,7-tetrahydro-pyrrolo[2,1-c][1,2,4]triazol-3-one oxalate The title compound (62 mg) was obtained from the compound obtained in Example 125-(1) (80 mg) and the compound obtained in Production Example 19 (84 mg), by the method similar to Example 72-(2).

¹H-NMR (400 MHz, CD₃OD); δ 1.34-1.44 (m, 2H), 1.70-1.82 (m, 4H), 2.08-2.30 (m, 6H), 2.32-2.39 (m, 2H), 2.42 (s, 3H), 2.50-2.60 (m, 2H), 2.77-2.81 (m, 2H), 2.90-3.00 (m, 2H), 3.70-3.78 (m, 5H), 3.90-3.98 (m, 2H), 4.59 (s, 2H), 6.88-6.96 (m, 1H), 7.02-7.06 (m, 1H), 7.18-7.26 (m, 1H).

Example 126

(Endo)-2-{2,2-difluoro-3-[3-(2-fluorobenzyloxy)-8-azabicyclo[3.2.1]oct-8-yl]propyl}-2,5,6,7-tetrahydropyrrolo[2,1-c][1,2,4]triazol-3-one

[Chemical Formula 245]

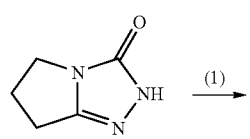
(1)

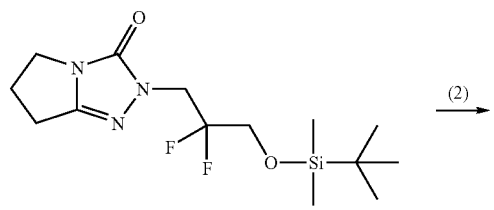
(2)

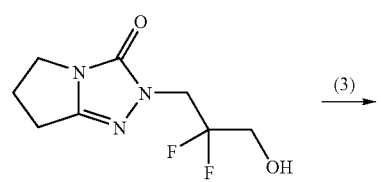
(3)

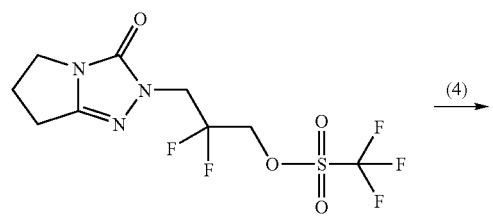
(4)

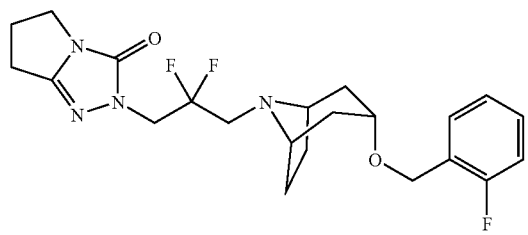

(1) 2-[3-(tert-Butyldimethyl silanyloxy)-2,2-difluoro-propyl]-2,5,6,7-tetrahydropyrrolo[2,1-c][1,2,4]triazol-3-one The title compound (628 mg) was obtained from 2,5,6,7-tetrahydropyrrolo[2,1-c][1,2,4]triazol-3-one (CAS 116056-07-6) (300 mg) and the compound obtained in Production Example 68 (946 mg) by the method similar to Example 1-(1).

¹H-NMR (400 MHz, CDCl₃); δ 0.10 (s, 6H), 0.91 (s, 9H), 2.50-2.58 (m, 2H), 2.79-2.83 (m, 2H), 3.75-3.78 (m, 2H), 3.83-3.89 (m, 2H), 4.16-4.23 (m, 2H).

(2) 2-(2,2-Difluoro-3-hydroxypropyl)-2,5,6,7-tetrahydropyrrolo[2,1-c][1,2,4]triazol-3-one The compound obtained in Example 126-(1) (628 mg) was dissolved in methanol (20 ml), and then Dowex 50W-X4 (628 mg) was added and the mixture was stirred at room temperature for 2 days. The reaction mixture was filtered and the filtrate was concentrated under reduced pressure to obtain the title compound (444 mg).

¹H-NMR (400 MHz, CDCl₃); δ 2.55-2.62 (m, 2H), 2.82-2.86 (m, 2H), 3.49 (s, 1H), 3.73-3.76 (m, 2H), 3.79-3.83 (m, 2H), 4.21-4.27 (m, 2H).

(3) Trifluoromethanesulfonic acid 2,2-difluoro-3-(3-oxo-6,7-dihydro-5H-pyrrolo[2,1-c][1,2,4]triazol-2-yl)propyl ester The title compound (646 mg) was obtained from the compound obtained in Example 126-(2) (444 mg) and trifluoromethanesulfonic anhydride, by the method similar to Example 22-(3).

¹H-NMR (400 MHz, CDCl₃); δ 2.53-2.61 (m, 2H), 2.80-2.84 (m, 2H), 3.77-3.80 (m, 2H), 4.21-4.27 (m, 2H), 4.68-4.74 (m, 2H).

(4) (Endo)-2-{2,2-difluoro-3-[3-(2-fluorobenzyloxy)-8-azabicyclo[3.2.1]oct-8-yl]propyl}-2,5,6,7-tetrahydropyrrolo[2,1-c][1,2,4]triazol-3-one The title compound (9 mg) was obtained from the compound obtained in Example 126-(3) (100 mg) and the compound obtained in Production Example 5 (80 mg), by the method similar to Example 81.

¹H-NMR (400 MHz, CDCl₃); δ 1.81-1.94 (m, 4H), 1.99-2.08 (m, 4H), 2.51-2.59 (m, 2H), 2.72-2.83 (m, 4H), 3.22 (bs, 2H), 3.61-3.64 (m, 1H), 3.73-3.77 (m, 2H), 4.24-4.31 (m,

2H), 4.49 (s, 2H), 7.02-7.07 (m, 1H), 7.13-7.17 (m, 1H), 7.26-7.32 (m, 1H), 7.41-7.45 (m, 1H).

Example 127

(Endo)-3-{2-fluoro-3-[3-(4-methylbenzyloxy)-8-azabicyclo[3.2.1]oct-8-yl]propyl}-8-methyl-7,8-dihydro-6H-imidazo[1,2-a][1,3,5]triazine-2,4-dione

[Chemical Formula 246]

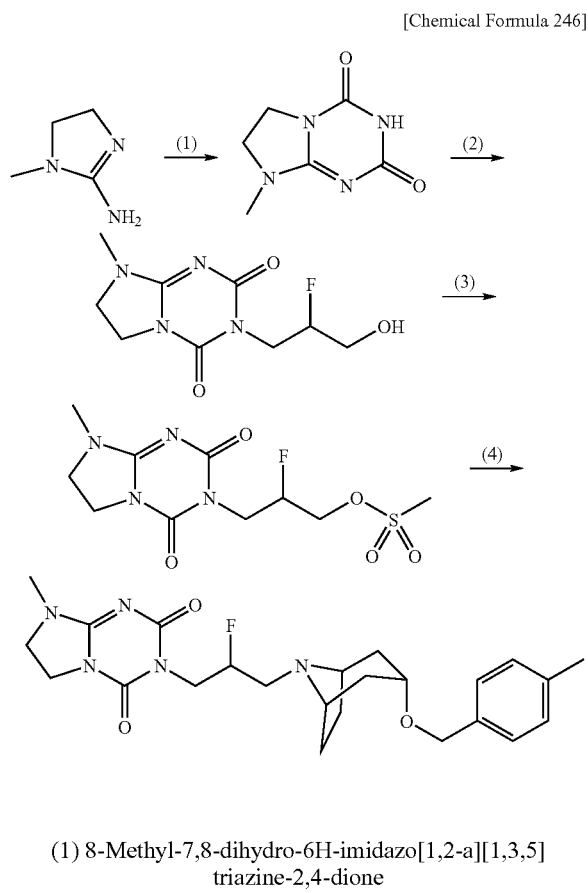

(1) 8-Methyl-7,8-dihydro-6H-imidazo[1,2-a][1,3,5]triazine-2,4-dione

After dissolving 1-methyl-4,5-dihydro-1H-imidazo-2-ylamine (CAS 45435-70-9) (2.5 g) in acetonitrile (50 ml), diphenyl imidodicarbonate (CAS 99911-94-1) (6.49 g) was added and the mixture was stirred at room temperature for 19 hours. The precipitate was collected by filtration to obtain the title compound (3.34 g).

$^1$H-NMR (400 MHz, DMSO-$d_6$); δ 2.88 (s, 3H), 3.61-3.68 (m, 2H), 3.81-3.87 (m, 2H), 10.50 (s, 1H).

(2) 3-(2-Fluoro-3-hydroxypropyl)-8-methyl-7,8-dihydro-6H-imidazo[1,2-a][1,3,5]triazine-2,4-dione The title compound (651 mg) was obtained from the compound obtained in Example 127-(1) (1.0 g) and the compound obtained in Production Example 66 (2.03 g), by the method similar to Example 101-(1).

$^1$H-NMR (400 MHz, CDCl$_3$); δ 2.95 (t, J=7.2 Hz, 1H), 3.08 (s, 3H), 3.62-3.85 (m, 4H), 4.47-4.19 (m, 3H), 4.26-4.35 (m, 1H), 4.71-4.88 (m, 1H).

(3) Methanesulfonic acid 2-fluoro-3-(8-methyl-2,4-dioxo-2,6,7,8-tetrahydroimidazo[1,2-a][1,3,5]triazin-3-yl)propyl ester The title compound (779 mg) was obtained from the compound obtained in Example 127-(2) (651 mg) and methanesulfonyl chloride, by the method similar to Example 65-(3).

$^1$H-NMR (400 MHz, CDCl$_3$); δ 3.08 (s, 3H), 3.10 (s, 3H), 3.74-3.80 (m, 2H), 3.98-4.12 (m, 3H), 4.33-4.55 (m, 3H), 4.98-5.16 (m, 1H).

(4) (Endo)-3-{2-fluoro-3-[3-(4-methylbenzyloxy)-8-azabicyclo[3.2.1]oct-8-yl]propyl}-8-methyl-7,8-dihydro-6H-imidazo[1,2-a][1,3,5]triazine-2,4-dione The title compound (66 mg) was obtained from the compound obtained in Example 127-(3) (100 mg) and the compound obtained in Production Example 60 (79 mg), by the method similar to Example 99-(4).

$^1$H-NMR (400 MHz, CDCl$_3$); δ 1.80-2.09 (m, 8H), 2.33 (s, 3H), 2.55-2.74 (m, 2H), 3.06 (s, 3H), 3.16-3.22 (m, 2H), 3.58 (t, J=4.8 Hz, 1H), 3.71-3.77 (m, 2H), 3.93-4.12 (m, 3H), 4.34-4.43 (m, 1H), 4.40 (s, 2H), 4.81-4.99 (m, 1H), 7.02-7.06 (m, 2H), 7.19-7.23 (m, 2H).

Example 128

(Endo)-3-{(R)-2-fluoro-3-[3-(4-fluorobenzyloxy)-8-azabicyclo[3.2.1]oct-8-yl]propyl}-7,8-dihydro-6H-pyrrolo[1,2-a][1,3,5]triazine-2,4-dione oxalate

[Chemical Formula 247]

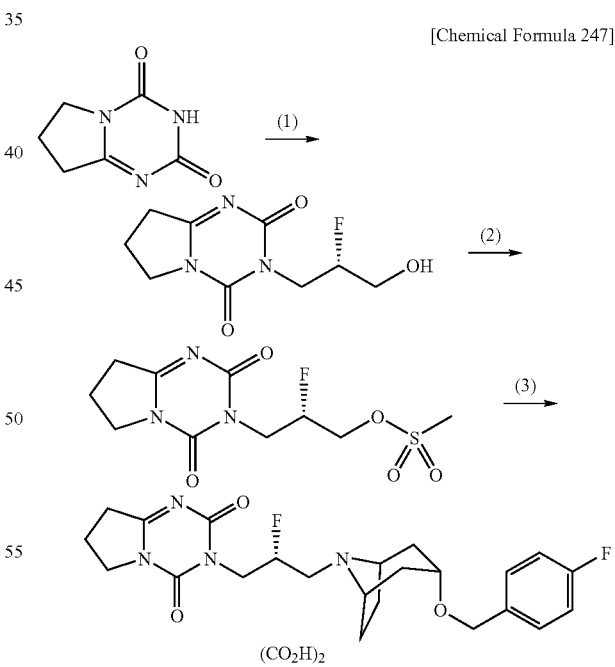

(1) 3-((S)-2-Fluoro-3-hydroxypropyl)-7,8-dihydro-6H-pyrrolo[1,2-a][1,3,5]triazine-2,4-dione The title compound (443 mg) was obtained from 7,8-dihydro-6H-pyrrolo[1,2-a][1,3,5]triazine-2,4-dione (CAS 133365-44-3) (500 mg) and the compound obtained in Production Example 65 (1.11 g), by the method similar to Example 101-(1).

(2) Methanesulfonic acid (S)-3-(2,4-dioxo-2,6,7,8-tetrahydropyrrolo[1,2-a][1,3,5]triazin-3-yl)-2-fluoropropyl ester A mixture of the compound obtained in Example 128-(1) (443 mg), triethylamine (0.81 ml), trimethylamine hydrochloride (55 mg) and acetonitrile (6 ml) was cooled on ice, and then methanesulfonyl chloride (0.45 ml) was added dropwise while stirring. After stirring for 1 hour, the reaction mixture was concentrated under reduced pressure. Acetone was added to the residue, and the mixture was filtered. The filtrate was concentrated under reduced pressure, and the residue was purified by silica gel column chromatography to obtain the title compound (558 mg).

$^1$H-NMR (400 MHz, CDCl$_3$); δ 2.25-2.34 (m, 2H), 3.03-3.41 (m, 2H), 3.10 (s, 3H), 4.00-4.15 (m, 3H), 4.33-4.57 (m, 3H), 5.01-5.19 (m, 1H).

(3) (Endo)-3-{(R)-2-fluoro-3-[3-(4-fluorobenzyloxy)-8-azabicyclo[3.2.1]oct-8-yl]propyl}-7,8-dihydro-6H-pyrrolo[1,2-a][1,3,5]triazine-2,4-dione oxalate A mixture of the compound obtained in Example 128-(2) (558 mg), the compound obtained in Production Example 1 (492 mg), anhydrous potassium carbonate (550 mg), sodium iodide (catalytic amount) and N,N-dimethylformamide (6 ml) was stirred at 50° C. for 63 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the free form of the title compound (274 mg).

This was dissolved in ethanol, oxalic acid (55 mg) was added, and the mixture was concentrated under reduced pressure. The residue was solidified with diethyl ether and collected by filtration to obtain the title compound (291 mg).

$^1$H-NMR (400 MHz, CD$_3$OD); δ 2.11-2.32 (m, 8H), 2.35-2.44 (m, 2H), 3.02 (t, J=8.0 Hz, 2H), 3.28-3.42 (m, 2H), 3.71-3.75 (m, 1H), 3.85-3.90 (m, 1H), 3.93-3.98 (m, 1H), 4.00-4.13 (m, 3H), 4.31 (td, J=6.8, 14.0 Hz, 1H), 4.49 (s, 2H), 5.18-5.37 (m, 1H), 7.03-7.10 (m, 2H), 7.33-7.39 (m, 2H).

Example 129

(Endo)-3-(3-{3-[2-(2-fluorophenyl)ethyl]-8-azabicyclo[3.2.1]oct-8-yl}propyl]-6,7,8,9-tetrahydropyrido[1,2-a][1,3,5]triazine-2,4-dione oxalate

[Chemical Formula 248]

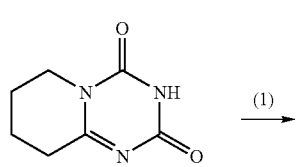

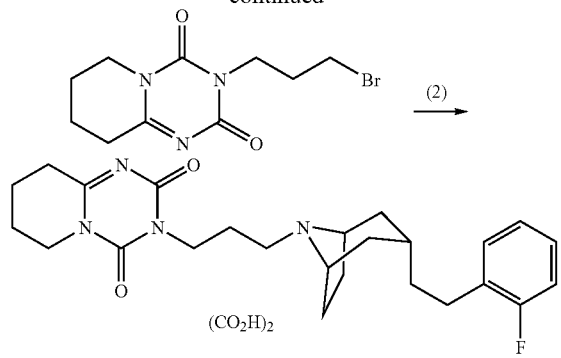

(1) 3-(3-Bromopropyl)-6,7,8,9-tetrahydropyrido[1,2-a][1,3,5]triazine-2,4-dione

The title compound (375 mg) was obtained from 6,7,8,9-tetrahydropyrido[1,2-a][1,3,5]triazine-2,4-dione (CAS 133365-43-2) (500 mg) and 1,3-dibromopropane (0.91 ml) by the method similar to Example 57-(1).

$^1$H-NMR (400 MHz, CDCl$_3$); δ 1.86-2.02 (m, 4H), 2.26 (quintet, J=6.8 Hz, 2H), 2.82 (t, J=6.8 Hz, 2H), 3.43 (t, J=6.8 Hz, 2H), 3.84 (t, J=6.8 Hz, 2H), 4.05 (t, J=6.8 Hz, 2H).

(2) (Endo)-3-(3-{3-[2-(2-fluoro-phenyl)-ethyl)-8-azabicyclo[3.2.1]oct-8-yl}propyl]-6,7,8,9-tetrahydropyrido[1,2-a][1,3,5]triazine-2,4-dione oxalate The title compound (42 mg) was obtained from the compound obtained in Example 129-(1) (64 mg) and the compound obtained in Production Example 42 (60 mg), by the method similar to Example 57-(2).

$^1$H-NMR (400 MHz, DMSO-d$_6$); δ 1.66-2.02 (m, 13H), 2.06-2.30 (m, 4H), 2.60-2.72 (m, 4H), 2.88-3.04 (m, 2H), 3.68 (t, J=6.0 Hz, 2H), 3.74-3.92 (m, 4H), 7.07-7.15 (m, 2H), 7.19-7.33 (m, 2H).

Example 130

(Endo)-3-{3-[3-(2-methyl-phenoxymethyl)-8-azabicyclo[3.2.1]oct-8-yl]propyl}-6,7,8,9-tetrahydropyrido[1,2-a][1,3,5]triazine-2,4-dione oxalate

[Chemical Formula 249]

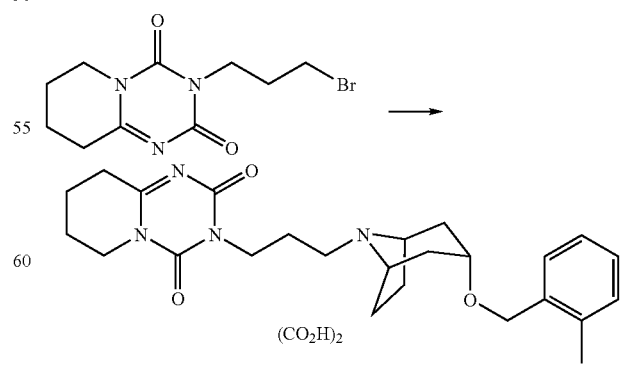

The title compound (73 mg) was obtained from the compound obtained in Example 129-(1) (95 mg) and the compound obtained in Production Example 18 (80 mg), by the method similar to Example 57-(2).

$^1$H-NMR (400 MHz, CD$_3$OD); δ 1.84-2.18 (m, 10H), 2.20 (s, 3H), 2.28-2.47 (m, 6H), 2.75-2.82 (m, 1H), 3.06-3.14 (m, 2H), 3.83 (t, J=6.4 Hz, 2H), 3.98-4.09 (m, 6H), 6.84 (d, J=7.2 Hz, 1H), 6.91 (d, J=7.6 Hz, 1H), 7.10-7.16 (m, 2H).

Example 131

3-{3-[3β-methoxymethyl-3α-(2-methylbenzyloxy)-8-azabicyclo[3.2.1]oct-8-yl]propyl}-6,7,8,9-tetrahydropyrido[1,2-a][1,3,5]triazine-2,4-dione oxalate

[Chemical Formula 250]

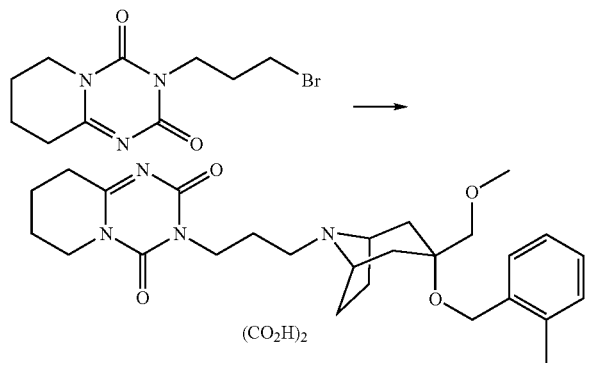

The title compound (74 mg) was obtained from the compound obtained in Example 129-(1) (74 mg) and the compound obtained in Production Example 50 (80 mg), by the method similar to Example 57-(2).

$^1$H-NMR (400 MHz, CD$_3$OD); δ 1.84-1.90 (m, 2H), 1.93-2.01 (m, 2H), 2.06-2.36 (m, 12H), 2.34 (s, 3H), 3.05-3.15 (m, 2H), 3.36 (s, 3H), 3.41 (s, 2H), 3.82 (t, J=6.0 Hz, 2H), 3.95-4.03 (m, 4H), 4.54 (s, 2H), 7.12-7.20 (m, 3H), 7.32-7.36 (m, 1H).

Example 132

(Endo)-3-{3-[3-(2-methylbenzyloxy)-8-azabicyclo[3.2.1]oct-8-yl]propyl}-6,7-dihydrothiazolo[3,2-a][1,3,5]triazine-2,4-dione

[Chemical Formula 251]

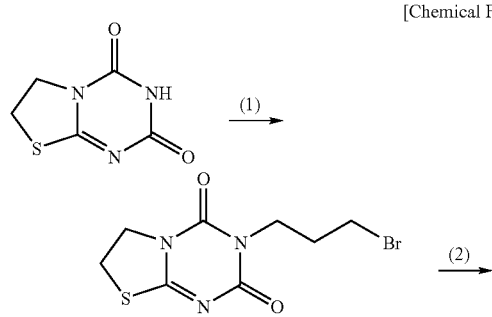

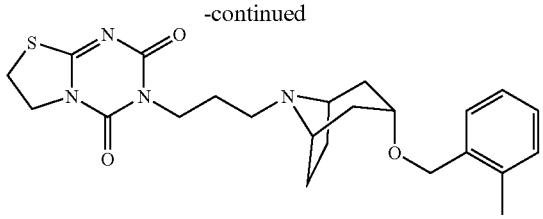

(1) 3-(3-Bromo-propyl)-6,7-dihydro-thiazolo[3,2-a][1,3,5]triazine-2,4-dione

The title compound (1.21 g) was obtained from 6,7-dihydro-thiazolo[3,2-a][1,3,5]triazine-2,4-dione (CAS 133365-66-9) (1.00 g) and 1,3-dibromopropane by the method similar to Example 103-(1).

$^1$H-NMR (400 MHz, CD$_3$OD); δ 2.14-2.25 (m, 2H), 3.47 (t, J=6.8 Hz, 2H), 3.55 (t, J=7.6 Hz, 2H), 3.97 (t, J=6.8 Hz, 2H), 4.36 (t, J=7.6 Hz, 2H).

(2) (Endo)-3-{3-[3-(2-methylbenzyloxy)-8-azabicyclo[3.2.1]oct-8-yl]propyl}-6,7-dihydrothiazolo[3,2-a][1,3,5]triazine-2,4-dione The title compound (6 mg) was obtained from the compound obtained in Example 132-(1) (87 mg) and the compound obtained in Production Example 3 (80 mg), by the method similar to Example 97.

$^1$H-NMR (400 MHz, DMSO-d$_6$); δ 1.78-1.98 (m, 8H), 2.01-2.07 (m, 2H), 2.29 (s, 3H), 2.45 (t, J=7.2 Hz, 2H), 3.13-3.19 (m, 2H), 3.46 (t, J=7.6 Hz, 2H), 3.62 (t, J=4.8 Hz, 1H), 3.98 (t, J=7.2 Hz, 2H), 4.36 (t, J=7.6 Hz, 2H), 4.41 (s, 2H), 7.12-7.21 (m, 3H), 7.33-7.38 (m, 1H).

Example 133

3-{3-[3β-methyl-3α-(2-methylbenzyloxy)-8-azabicyclo[3.2.1]oct-8-yl]propyl}-6,7,8,9-tetrahydropyrido[1,2-a][1,3,5]triazine-2,4-dione oxalate

[Chemical Formula 252]

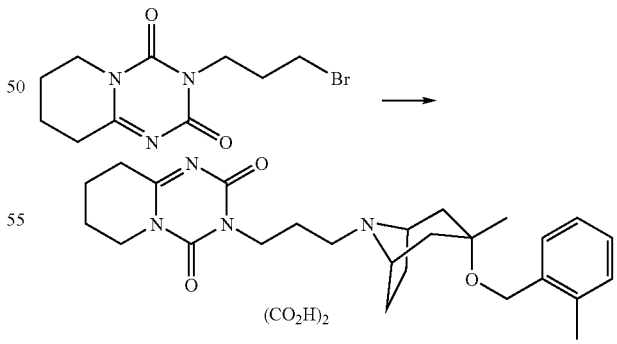

The title compound (103 mg) was obtained from the compound obtained in Example 129-(1) (90 mg) and the compound obtained in Production Example 23 (80 mg), by the method similar to Example 57-(2).

$^1$H-NMR (400 MHz, CD$_3$OD); δ 1.34 (s, 3H), 1.84-2.16 (m, 10H), 2.29-2.44 (m, 4H), 2.34 (s, 3H), 2.79 (t, J=6.0 Hz,

2H), 3.06-3.14 (m, 2H), 3.82 (t, J=6.0 Hz, 2H), 3.92-3.98 (m, 2H), 4.00 (t, J=6.4 Hz, 2H), 4.49 (s, 2H), 7.12-7.20 (m, 3H), 7.32-7.36 (m, 1H).

Example 134

(Endo)-3-{3-[3-(5-methyl-isoxazol-3-ylmethoxy)-8-azabicyclo[3.2.1]oct-8-yl]propyl}-7,8-dihydro-6H-pyrrolo[1,2-a][1,3,5]triazine-2,4-dione oxalate

[Chemical Formula 253]

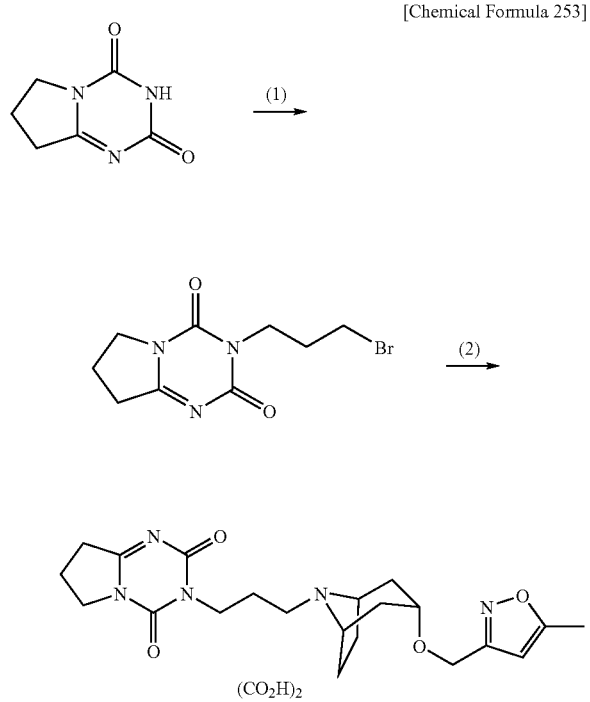

(1) 3-(3-Bromopropyl)-7,8-dihydro-6H-pyrrolo[1,2-a][1,3,5]triazine-2,4-dione

The title compound (386 mg) was obtained from 7,8-dihydro-6H-pyrrolo[1,2-a][1,3,5]triazine-2,4-dione (CAS 133365-44-3) (400 mg) and 1,3-dibromopropane by the method similar to Example 57-(1).

$^1$H-NMR (400 MHz, CDCl$_3$); δ 2.21-2.32 (m, 4H); 3.04 (t, J=8.0 Hz, 2H), 3.43 (t, J=6.8 Hz, 2H), 4.05 (t, J=7.2 Hz, 4H).

(2) (Endo)-3-{3-[3-(5-methyl-isoxazol-3-ylmethoxy)-8-azabicyclo[3.2.1]oct-8-yl]propyl}-7,8-dihydro-6H-pyrrolo[1,2-a][1,3,5]triazine-2,4-dione oxalate The title compound (74 mg) was obtained from the compound obtained in Example 134-(1) (85 mg) and the compound obtained in Production Example 29 (80 mg), by the method similar to Example 57-(2).

$^1$H-NMR (400 MHz, CD$_3$OD); δ 2.06-2.29 (m, 10H), 2.38-2.45 (m, 2H), 2.42 (d, J=1.3 Hz, 3H), 3.02 (t, J=8.0 Hz, 2H), 3.05-3.12 (m, 2H), 3.74-3.79 (m, 1H), 3.92-4.04 (m, 6H), 4.54 (s, 2H), 6.16-6.18 (m, 1H).

Example 135

(Endo)-3-{3-[3-(2-fluorobenzyloxy)-8-azabicyclo[3.2.1]oct-8-yl]propyl}-5,6-dihydro-8H-7-oxa-1,3,4a-triazanaphthalene-2,4-dione oxalate

[Chemical Formula 254]

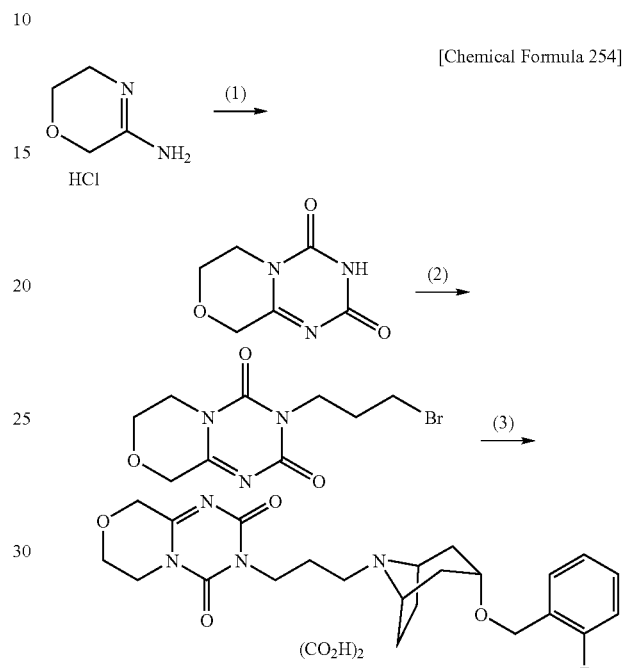

(1) 5,6-Dihydro-8H-7-oxa-1,3,4a-triazanaphthalene-2,4-dione

After suspending 5,6-dihydro-2H-[1,4]oxathin-3-ylamine hydrochloride (CAS 623564-41-0) (1.38 g) in ethanol (20 ml), potassium tert-butoxide (1.13 g) was added and the mixture was stirred at room temperature for 30 minutes. The reaction mixture was filtered and the filtrate was concentrated under reduced pressure. The residue was suspended in acetonitrile (20 ml), and then diphenyl imidodicarbonate (CAS 99911-94-1) (2.6 g) was added and the mixture was stirred at room temperature for 13 hours. The precipitate was collected by filtration. The filtrate was concentrated under reduced pressure, the residue was purified by silica gel column chromatography and the obtained solid was washed with diethyl ether.

This was combined with the previously collected compound, suspended in acetonitrile and heated to 60° C. After standing to cool, the mixture was filtered and the filtrate was concentrated under reduced pressure. The obtained solid was washed with diethyl ether to obtain the title compound (920 mg).

$^1$H-NMR (400 MHz, DMSO-d$_6$); δ 3.63 (t, J=5.6 Hz, 2H), 3.98 (t, J=5.6 Hz, 2H), 4.46 (s, 2H), 11.47-11.60 (m, 1H).

(2) 3-(3-Bromopropyl)-5,6-dihydro-8H-7-oxa-1,3,4a-triazanaphthalene-2,4-dione

The title compound (440 mg) was obtained from the compound obtained in Example 135-(1) (400 mg) and 1,3-dibromopropane, by the method similar to Example 57-(1).

$^1$H-NMR (400 MHz, CDCl$_3$); δ 2.23-2.31 (m, 2H), 3.44 (t, J=6.8 Hz, 2H), 3.85-3.90 (m, 2H), 4.05-4.11 (m, 4H), 4.57 (s, 2H).

(3) (Endo)-3-{3-[3-(2-fluorobenzyloxy)-8-azabicyclo[3.2.1]oct-8-yl]propyl}-5,6-dihydro-8H-7-oxa-1,3,4a-triazanaphthalene-2,4-dione oxalate The title compound (77 mg) was obtained from the compound obtained in Example 135-(2) (80 mg) and the compound obtained in Production Example 5 (75 mg), by the method similar to Example 57-(2).
$^1$H-NMR (400 MHz, CD$_3$OD); δ 2.08-2.46 (m, 10H), 3.06-3.15 (m, 2H), 3.76-3.84 (m, 3H), 3.90-4.03 (m, 4H), 4.07 (t, J=5.2 Hz, 2H), 4.54 (s, 2H), 4.57 (s, 2H), 7.05-7.12 (m, 1H), 7.14-7.20 (m, 1H), 7.29-7.36 (m, 1H), 7.40-7.46 (m, 1H).

Example 136

(Endo)-3-{3-[3-(2-fluoro-6-methylbenzyloxy)-8-azabicyclo[3.2.1]oct-8-yl]propyl}-7,8,9,10-tetrahydro-6H-[1,3,5]triazino[1,2-a]azepine-2,4-dione oxalate

[Chemical Formula 255]

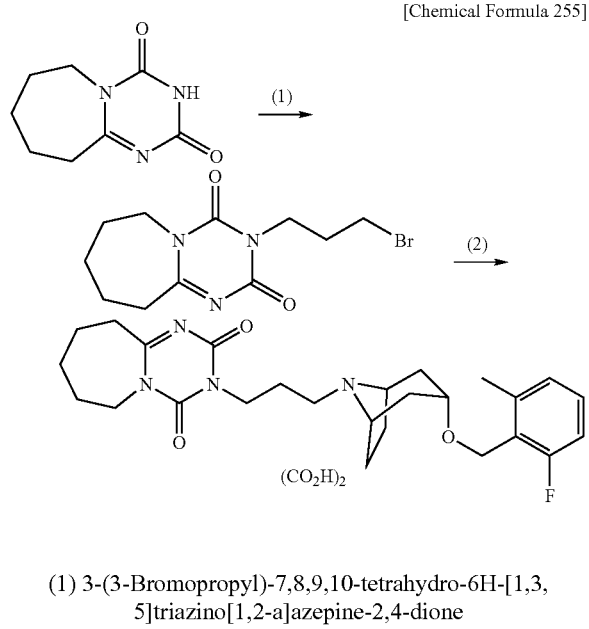

(1) 3-(3-Bromopropyl)-7,8,9,10-tetrahydro-6H-[1,3,5]triazino[1,2-a]azepine-2,4-dione The title compound (440 mg) was obtained from 7,8,9,10-tetrahydro-6H-[1,3,5]triazino[1,2-a]azepine-2,4-dione (CAS 133365-45-4) (400 mg) and 1,3-dibromopropane by the method similar to Example 57-(1).
$^1$H-NMR (400 MHz, CDCl$_3$); δ 1.78-1.85 (m, 6H), 2.05-2.30 (m, 2H), 2.86-2.89 (m, 2H), 3.42-3.46 (m, 2H), 4.10-4.17 (m, 4H)

(2) (Endo)-3-{3-[3-(2-fluoro-6-methylbenzyloxy)-8-azabicyclo[3.2.1]oct-8-yl]propyl}-7,8,9,10-tetrahydro-6H-[1,3,5]triazino[1,2-a]azepine-2,4-dione oxalate The title compound (86 mg) was obtained from the compound obtained in Example 136-(1) (100 mg) and the compound obtained in Production Example 19 (81 mg), by the method similar to Example 57-(2).
$^1$H-NMR (400 MHz, CD$_3$OD); δ 1.75 (bs, 2H), 1.84 (bs, 4H), 2.07-2.15 (m, 4H), 2.19-2.31 (m, 4H), 2.33-2.39 (m, 2H), 2.42 (s, 3H), 2.89-2.90 (m, 2H), 3.07-3.11 (m, 2H), 3.76 (bs, 1H), 3.92 (bs, 2H), 3.96-4.00 (m, 2H), 4.18-4.20 (m, 2H), 4.59 (m, 2H), 6.90-6.94 (m, 1H), 7.02-7.04 (m, 1H), 7.20-7.25 (m, 1H).

Example 137

(Endo)-3-{3-[3-(thiophen-3-ylmethoxy)-8-azabicyclo[3.2.1]oct-8-yl]propyl}-6,7,8,9-tetrahydropyrido[1,2-a][1,3,5]triazine-2,4-dione oxalate

[Chemical Formula 256]

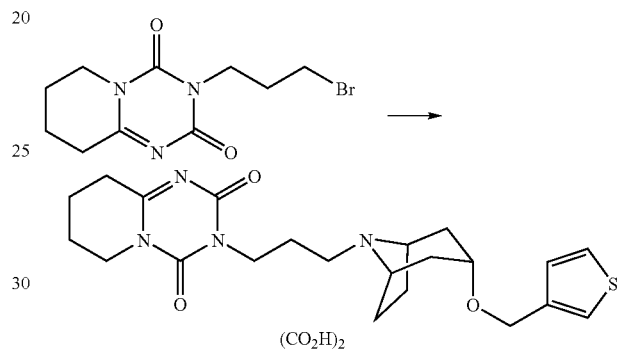

A mixture of the compound obtained in Example 129-(1) (85 mg), the compound obtained in Production Example 26 (70 mg), anhydrous potassium carbonate (112 mg) and N,N-dimethylformamide (10 ml) was stirred overnight at room temperature. The reaction mixture was filtered with Celite, and the filtrate was concentrated under reduced pressure. The residue was purified by NH silica gel column chromatography to obtain the free form of the title compound (38 mg). This was dissolved in ethanol, and then oxalic acid (8 mg) was added. The mixture was concentrated under reduced pressure to obtain the title compound (46 mg).
$^1$H-NMR (400 MHz, CD$_3$OD); δ 1.85-2.28 (m, 14H), 2.44-2.48 (m, 2H), 3.06-3.10 (m, 2H), 3.75 (m, 1H), 3.81-3.84 (m, 2H), 3.96-4.01 (m, 4H), 4.54 (s, 2H), 7.07-7.09 (m, 1H), 7.30-7.31 (m, 1H), 7.38-7.40 (m, 1H).

Example 138

(Endo)-3-{3-[3-(2-methylbenzyloxy)-8-azabicyclo[3.2.1]oct-8-yl]propyl}-6,7,8,9-tetrahydropyrido[1,2-a][1,3,5]triazine-2,4-dione

[Chemical Formula 257]

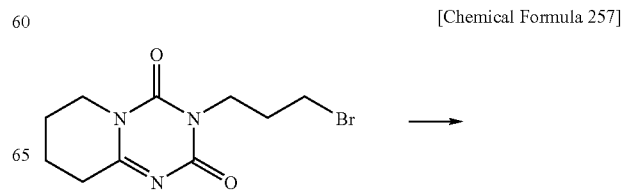

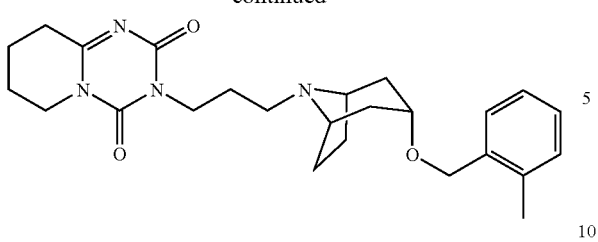

The title compound (73 mg) was obtained from the compound obtained in Example 129-(1) (104 mg) and the compound obtained in Production Example 3 (90 mg), by the method similar to Example 97.

$^1$H-NMR (400 MHz, CDCl$_3$); δ 1.99-1.80 (m, 12H), 2.05-1.99 (m, 2H), 2.28 (s, 3H), 2.44 (t, J=7.2 Hz, 2H), 2.80 (t, J=6.6 Hz, 2H), 3.15-3.14 (m, 2H), 3.61 (t, J=4.8 Hz, 1H), 3.83 (t, J=6.2 Hz, 2H), 4.01 (t, J=7.4 Hz, 2H), 4.41 (s, 2H), 7.21-7.12 (m, 3H), 7.37-7.33 (m, 1H).

Example 139

(Endo)-3-{3-[3-(2-trifluoromethoxybenzyloxy)-8-azabicyclo[3.2.1]oct-8-yl]propyl}-6,7,8,9-tetrahydropyrido[1,2-a][1,3,5]triazine-2,4-dione

[Chemical Formula 258]

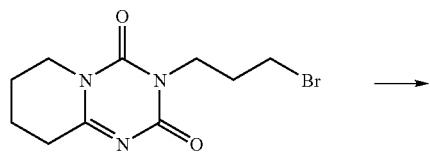

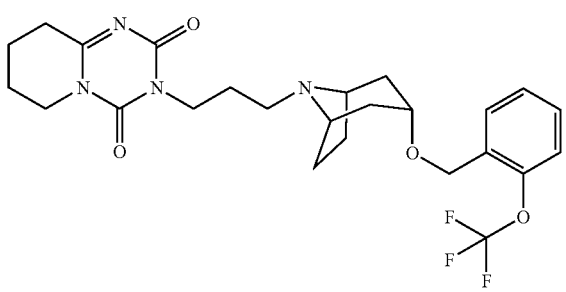

The title compound (101 mg) was obtained from the compound obtained in Example 129-(1) (82 mg) and the compound obtained in Production Example 12 (90 mg), by the method similar to Example 97.

$^1$H-NMR (400 MHz, CDCl$_3$); δ 1.86-2.01 (m, 10H), 2.06-2.17 (m, 4H), 2.57 (t, J=7.6 Hz, 2H), 2.81 (t, J=6.8 Hz, 2H), 3.31 (brs, 2H), 3.66 (t, J=4.8 Hz, 1H), 3.85 (t, J=6.0 Hz, 2H), 4.01 (t, J=7.2 Hz, 2H), 4.50 (s, 2H), 7.20-7.25 (m, 1H), 7.27-7.33 (m, 2H), 7.49-7.54 (m, 1H).

Example 140

(Endo)-3-{5-[3-(2-methylbenzyloxy)-8-azabicyclo[3.2.1]oct-8-yl]pentyl}-6,7,8,9-tetrahydropyrido[1,2-a][1,3,5]triazine-2,4-dione

[Chemical Formula 259]

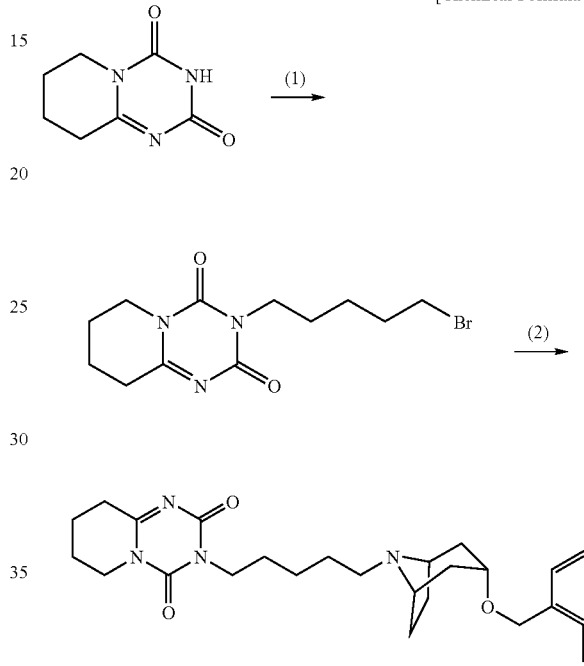

(1) 3-(5-Bromopentyl)-6,7,8,9-tetrahydropyrido[1,2-a][1,3,5]triazine-2,4-dione The title compound (470 mg) was obtained from 6,7,8,9-tetrahydropyrido[1,2-a][1,3,5]triazine-2,4-dione (CAS 133365-43-2) (250 mg) and 1,5-dibromopentane by the method similar to Example 57-(1).

$^1$H-NMR (400 MHz, CDCl$_3$); δ 1.46-1.54 (m, 2H), 1.66-1.74 (m, 2H), 1.86-2.01 (m, 6H), 2.82 (t, J=6.8 Hz, 2H), 3.41 (t, J=6.8 Hz, 2H), 3.84 (t, J=6.4 Hz, 2H), 3.92 (t, J=7.6 Hz, 2H).

(2) (Endo)-3-{5-[3-(2-methylbenzyloxy)-8-azabicyclo[3.2.1]oct-8-yl]pentyl}-6,7,8,9-tetrahydropyrido[1,2-a][1,3,5]triazine-2,4-dione The title compound (120 mg) was obtained from the compound obtained in Example 140-(1) (104 mg) and the compound obtained in Production Example 3 (90 mg), by the method similar to Example 97.

$^1$H-NMR (400 MHz, CDCl$_3$); δ 1.38 (q, J=7.6 Hz, 2H), 1.64-1.73 (m, 4H), 1.87-2.01 (m, 8H), 2.18 (dd, J=13.6 Hz, 6.4 Hz, 2H), 2.30 (s, 3H), 2.27-2.31 (m, 2H), 2.50-2.54 (m, 2H), 2.81 (t, J=6.8 Hz, 2H), 3.41 (brs, 2H), 3.70 (t, J=4.8 Hz, 1H), 3.84 (t, J=6.0 Hz, 2H), 3.91 (t, J=8.0 Hz, 2H), 4.43 (s, 2H), 7.13-7.21 (m, 3H), 7.30-7.35 (m, 1H).

Example 141

(Endo)-3-{2-[3-(2-methylbenzyloxy)-8-azabicyclo[3.2.1]oct-8-yl]ethyl}-6,7,8,9-tetrahydropyrido[1,2-a][1,3,5]triazine-2,4-dione

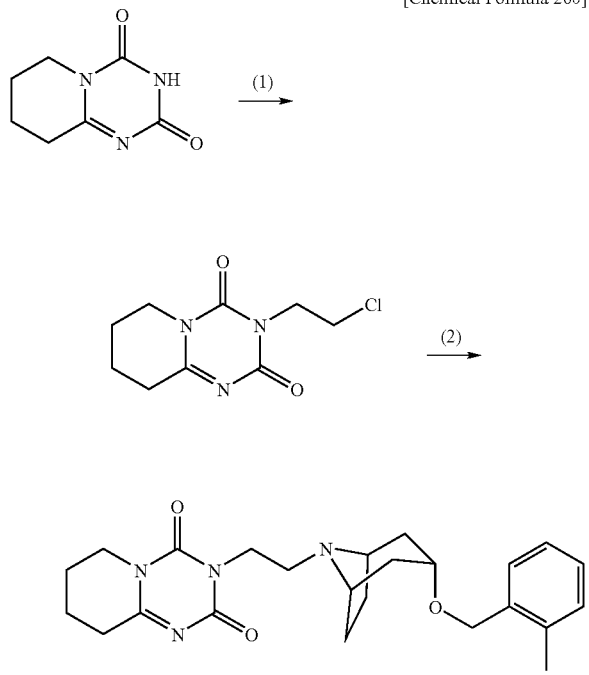

[Chemical Formula 260]

(1) 3-(2-Chloroethyl)-6,7,8,9-tetrahydropyrido[1,2-a][1,3,5]triazine-2,4-dione

The title compound (204 mg) was obtained from 6,7,8,9-tetrahydropyrido[1,2-a][1,3,5]triazine-2,4-dione (CAS 133365-43-2) (200 mg) and 1-bromo-2-chloroethane (516 mg) by the method similar to Example 57-(1).

$^1$H-NMR (400 MHz, CDCl$_3$); δ 1.88-2.03 (m, 4H), 2.83 (t, J=6.8 Hz, 2H), 3.77 (t, J=6.8 Hz, 2H), 3.86 (t, J=6.4 Hz, 2H), 4.27 (t, J=6.8 Hz, 2H).

(2) (Endo)-3-{2-[3-(2-methylbenzyloxy)-8-azabicyclo[3.2.1]oct-8-yl]ethyl}-6,7,8,9-tetrahydropyrido[1,2-a][1,3,5]triazine-2,4-dione A mixture of the compound obtained in Example 141-(1) (77 mg), the compound obtained in Production Example 3 (90 mg), anhydrous potassium carbonate (102 mg) and N,N-dimethylformamide (1 ml) was stirred overnight at 80° C. Water was added to the reaction mixture, and extraction was performed with ethyl acetate. The extract was dried over anhydrous magnesium sulfate. After filtration, the solvent was distilled off under reduced pressure. The residue was purified by silica gel column chromatography to obtain the title compound (54 mg).

$^1$H-NMR (400 MHz, CDCl$_3$); δ 1.86-2.23 (m, 6H), 2.90 (s, 3H), 2.76-2.85 (m, 6H), 3.60-3.91 (m, 5H), 3.98-4.33 (m, 4H), 4.41 (s, 2H), 7.13-7.22 (m, 3H), 7.31-7.34 (m, 1H).

Example 142

(Endo)-3-(3-{3-[2-(2-fluorophenyl)ethyl]-8-azabicyclo[3.2.1]oct-8-yl}-2-hydroxypropyl)-6,7,8,9-tetrahydropyrido[1,2-a][1,3,5]triazine-2,4-dione

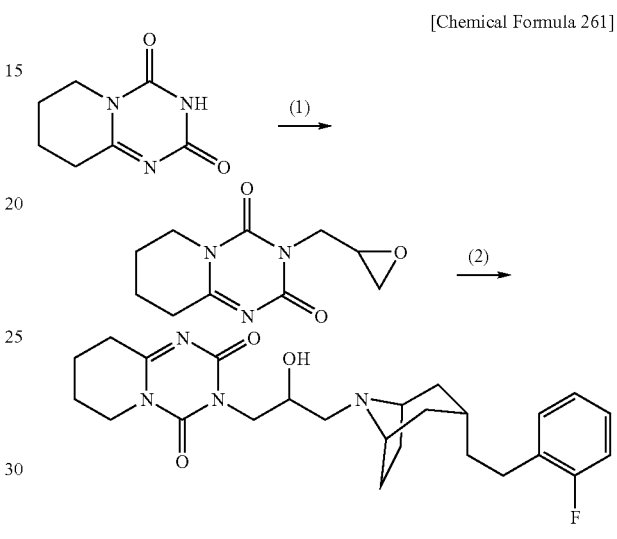

[Chemical Formula 261]

(1) 3-Oxiranylmethyl-6,7,8,9-tetrahydropyrido[1,2-a][1,3,5]triazine-2,4-dione

After dissolving 6,7,8,9-tetrahydropyrido[1,2-a][1,3,5]triazine-2,4-dione (CAS 133365-43-2) (195 mg) and epibromohydrin (321 mg) in N,N-dimethylformamide (1 ml), sodium hydride (60% in oil) (52 mg) was added and the mixture was stirred overnight at room temperature. The reaction mixture was concentrated under reduced pressure, and the residue was purified by NH silica gel column chromatography. The title compound (189 mg) was thus obtained.

$^1$H-NMR (400 MHz, CDCl$_3$); δ 1.94-1.87 (m, 2H), 2.02-1.95 (m, 2H), 2.72 (dd, J=4.8 Hz, 2.4 Hz, 1H), 2.82-2.78 (m, 1H), 2.84 (t, J=6.6 Hz, 2H), 3.33-3.28 (m, 1H), 3.86 (t, J=6.0 Hz, 2H), 4.05 (dd, J=13.8 Hz, 4.6 Hz, 1H), 4.20 (dd, J=13.8 Hz, 5.4 Hz, 1H).

(2) (Endo)-3-(3-{3-[2-(2-fluorophenyl)ethyl]-8-azabicyclo[3.2.1]oct-8-yl}-2-hydroxypropyl)-6,7,8,9-tetrahydropyrido[1,2-a][1,3,5]triazine-2,4-dione The compound obtained in Example 142-(1) (85 mg) and the compound obtained in Production Example 42 (113 mg) were dissolved in N,N-dimethylformamide (2 ml), and then anhydrous potassium carbonate (58 mg) was added and the mixture was stirred overnight at room temperature. The reaction mixture was concentrated under reduced pressure, and the residue was purified by NH silica gel column chromatography. The title compound (33 mg) was thus obtained.

$^1$H-NMR (400 MHz, CDCl$_3$); δ 1.45 (d, J=14.4 Hz, 2H), 1.80-1.68 (m, 4H), 1.92-1.83 (m, 2H), 2.04-1.93 (m, 4H), 2.43-2.17 (m, 3H), 2.67-2.57 (m, 3H), 2.82 (t, J=6.6 Hz, 2H), 3.31 (brs, 2H), 3.92-3.80 (m, 3H), 4.16-4.07 (m, 2H), 7.06-6.97 (m, 2H), 7.19-7.12 (m, 2H).

Example 143

(Endo)-3-(3-{3-[2-(2-fluoro-phenyl)ethyl]-8-azabi-cyclo[3.2.1]oct-8-yl}-2-oxopropyl)-6,7,8,9-tetrahy-dropyrido[1,2-a][1,3,5]triazine-2,4-dione

[Chemical Formula 262]

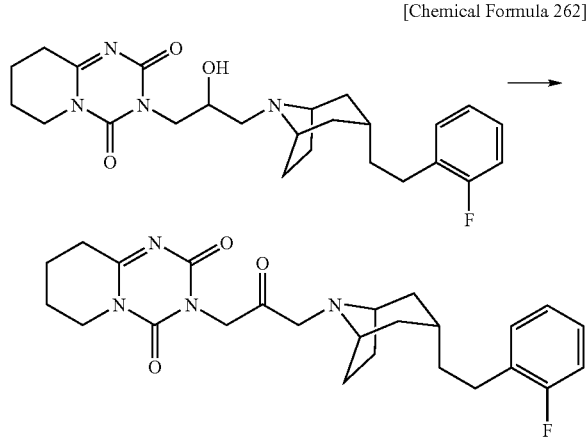

Oxalyl chloride (22 μl) was dissolved in dichloromethane (2 ml), and then dimethyl sulfoxide (35 μl) was slowly added at −50 to −60° C. and the mixture was stirred for 10 minutes. A solution of the compound obtained in Example 142 (55 mg) in dichloromethane (2 ml) was added, and stirring was continued for 40 minutes. Triethylamine (0.14 ml) was added, and the cooling bath was removed to allow the temperature to rise to room temperature. After stirring for 5 hours, water was added to the reaction mixture and extraction was performed with ethyl acetate. The extract was dried over anhydrous magnesium sulfate. After filtration, the solvent was distilled off under reduced pressure. The residue was purified by silica gel column chromatography to obtain the title compound (31 mg).

$^1$H-NMR (400 MHz, CDCl$_3$); δ 1.40 (brd, J=14.0 Hz, 2H), 1.55-1.79 (m, 5H), 1.88-2.05 (m, 6H), 2.16-2.32 (m, 3H), 2.58-2.67 (m, 3H), 2.85 (t, J=6.8 Hz, 2H), 3.16-3.22 (m, 2H), 3.25 (s, 2H), 3.83 (t, J=6.4 Hz, 2H), 5.04 (s, 2H), 6.59-7.06 (m, 2H), 7.12-7.19 (m, 2H).

Example 144

(Endo)-2-{3-[3-(2-fluorobenzyloxy)-8-azabicyclo[3.2.1]oct-8-yl]-2-hydroxypropyl}-2H-[1,2,4]tria-zolo[4,3-a]pyridin-3-one

[Chemical Formula 263]

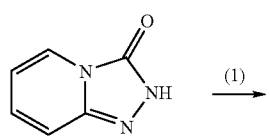

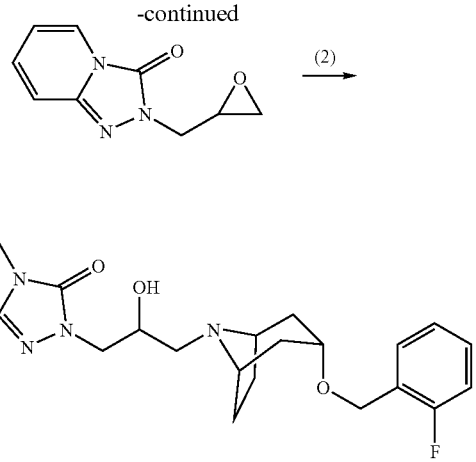

(1) 2-Oxiranylmethyl-2H-[1,2,4]triazolo[4,3-a]pyridin-3-one

After dissolving 2H-[1,2,4]triazolo[4,3-a]pyridin-3-one (CAS 6969-71-7) (1.0 g) and epibromohydrin (1.27 ml) in N,N-dimethylformamide (10 ml), sodium hydride (60% in oil) (326 mg) was added and the mixture was stirred at room temperature for 14 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography. The obtained solid was washed with n-heptane to obtain the title compound (290 mg).

$^1$H-NMR (400 MHz, CDCl$_3$); δ 2.74 (dd, J=4.4, 2.4 Hz, 1H), 2.88 (t, J=4.4 Hz, 1H), 3.33-3.38 (m, 1H), 4.12 (dd, J=14.4, 1.6 Hz, 1H), 4.23 (dd, J=14.4, 4.4 Hz, 1H), 6.46-6.53 (m, 1H), 7.07-7.12 (m, 2H), 7.75 (dt, J=6.8, 1.2 Hz, 1H).

(2) (Endo)-2-{3-[3-(2-fluorobenzyloxy)-8-azabicy-clo[3.2.1]oct-8-yl]-2-hydroxypropyl}-2H-[1,2,4]triazolo[4,3-a]pyridin-3-one After dissolving the compound obtained in Example 144-(1) (77 mg) and the compound obtained in Production Example 5 (100 mg) in N,N-dimethylformamide (3 ml), anhydrous potassium carbonate (56 mg) was added and the mixture was stirred at 100° C. for 5 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography. Ethanol was added to the obtained oil to produce a solid, which was then collected by filtration to obtain the title compound (87 mg).

$^1$H-NMR (400 MHz, CDCl$_3$); δ 1.78-2.13 (m, 8H), 2.26 (dd, J=12.4, 8.4 Hz, 1H), 2.58 (dd, J=12.4, 4.0 Hz, 1H), 3.09-3.20 (m, 2H), 3.59-3.64 (m, 1H), 3.99-4.09 (m, 3H), 4.38 (br s, 1H), 4.49 (s, 2H), 6.45-6.51 (m, 1H), 6.97-7.15 (m, 4H), 7.20-7.28 (m, 1H), 7.38-7.44 (m, 1H), 7.76 (dt, J=7.2, 1.2 Hz, 1H).

Example 145

(Endo)-2-{3-[3-(2-fluorobenzyloxy)-8-azabicyclo[3.2.1]oct-8-yl]propyl}-2H-[1,2,4]triazolo[4,3-a]pyridin-3-one

[Chemical Formula 264]

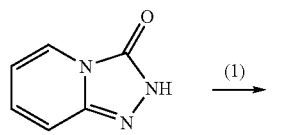

(1)

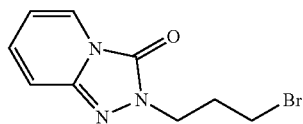

(2)

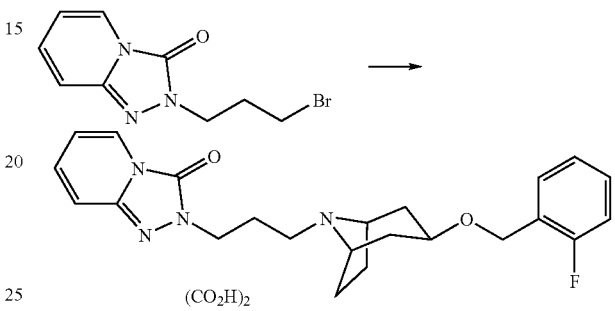

(1) 2-(3-Bromopropyl)-2H-[1,2,4]triazolo[4,3-a]pyridin-3-one

The title compound (2.39 g) was obtained from 2H-[1,2,4]triazolo[4,3-a]pyridin-3-one (CAS 6969-71-7) (2.0 g) and 1,3-dibromopropane by the method similar to Example 57-(1).

$^1$H-NMR (400 MHz, CDCl$_3$); δ 2.41 (quintet, J=6.8 Hz, 2H), 3.46 (t, J=6.8 Hz, 2H), 4.17 (t, J=6.8 Hz, 2H), 6.46-6.53 (m, 1H), 7.06-7.12 (m, 2H), 7.74-7.77 (m, 1H).

(2) (Endo)-2-{3-[3-(2-fluorobenzyloxy)-8-azabicyclo[3.2.1]oct-8-yl]propyl}-2H-[1,2,4]triazolo[4,3-a]pyridin-3-one The title compound (107 mg) was obtained from the compound obtained in Example 145-(1) (100 mg) and the compound obtained in Production Example 5 (128 mg), by the method similar to Example 58-(2).

$^1$H-NMR (400 MHz, CDCl$_3$); δ 1.78-2.04 (m, 10H), 2.42 (t, J=7.2 Hz, 1H), 3.12-3.18 (m, 2H), 3.59 (t, J=4.8 Hz, 1H), 4.09 (t, J=7.2 Hz, 2H), 4.48 (s, 2H), 6.44-6.49 (m, 1H), 6.97-7.14 (m, 4H), 7.19-7.26 (m, 1H), 7.39-7.44 (m, 1H), 7.74 (dt, J=7.2, 1.2 Hz, 1H).

Example 146

(Exo)-2-{3-[3-(2-fluorobenzyloxy)-8-azabicyclo[3.2.1]oct-8-yl]propyl}-2H-[1,2,4]triazolo[4,3-a]pyridin-3-one oxalate

[Chemical Formula 265]

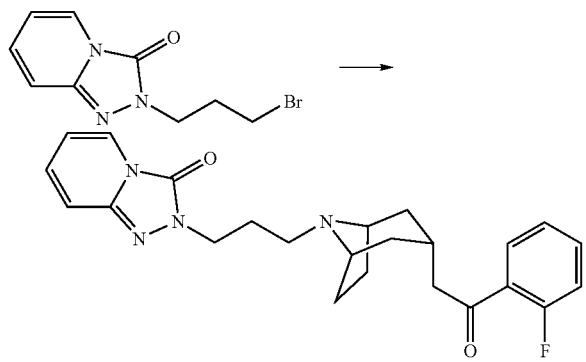

The title compound (139 mg) was obtained from the compound obtained in Example 145-(1) (100 mg) and the compound obtained in Production Example 56 (106 mg), by the method similar to Example 57-(2).

$^1$H-NMR (400 MHz, DMSO-d$_6$); δ 1.72-1.90 (m, 4H), 2.02-2.20 (m, 6H), 2.93-3.03 (m, 2H), 3.85-4.02 (m, 5H), 4.53 (s, 2H), 6.59-6.65 (m, 1H), 7.14-7.26 (m, 4H), 7.32-7.44 (m, 2H), 7.85 (dt, J=7.2, 1.2 Hz, 1H).

Example 147

(Endo)-2-(3-{3-[2-(2-fluorophenyl)-2-oxo-ethyl]-8-azabicyclo[3.2.1]oct-8-yl}propyl)-2H-[1,2,4]triazolo[4,3-a]pyridin-3-one

[Chemical Formula 266]

The title compound (9 mg) was obtained from the compound obtained in Example 145-(1) (70 mg) and the compound obtained in Production Example 40 (218 mg), by the method similar to Example 58-(2).

$^1$H-NMR (400 MHz, CDCl$_3$); δ 1.20-1.30 (m, 2H), 1.54-1.69 (m, 2H), 1.88-2.19 (m, 7H), 3.36-2.70 (m, 2H), 3.10-

3.24 (m, 4H), 4.08 (t, J=6.8 Hz, 2H), 6.44-6.49 (m, 1H), 7.03-7.14 (m, 3H), 7.18-7.26 (m, 1H), 7.45-7.52 (m, 1H), 7.72-7.81 (m, 2H).

Example 148

(Endo)-2-(3-{3-[(E)-2-(2-fluorophenyl)vinyl]-8-azabicyclo[3.2.1]oct-8-yl}propyl)-2H-[1,2,4]triazolo[4,3-a]pyridin-3-one

[Chemical Formula 267]

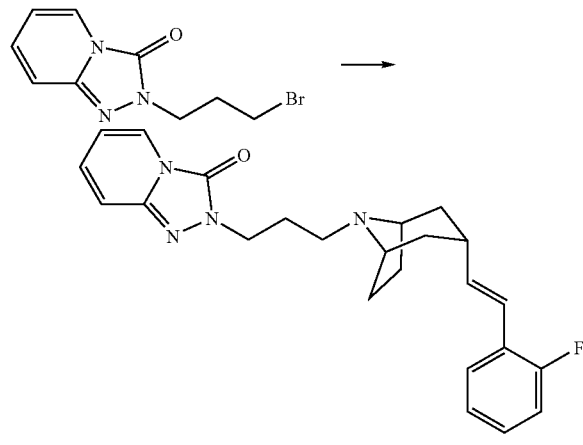

The title compound (48 mg) was obtained from the compound obtained in Example 145-(1) (76 mg) and the compound obtained in Production Example 43 (80 mg), by the method similar to Example 58-(2).

$^1$H-NMR (400 MHz, CDCl$_3$); δ 1.58-1.72 (m, 4H), 1.84-1.93 (m, 2H), 1.97-2.05 (m, 2H), 2.12-2.20 (m, 2H), 2.44 (t, J=7.2 Hz, 2H), 2.56-2.64 (m, 1H), 3.20 (br s, 2H), 4.11 (t, J=7.2 Hz, 2H), 6.44-6.58 (m, 3H), 6.98-7.19 (m, 5H), 7.37-7.43 (m, 1H), 7.75-7.79 (m, 1H).

Example 149

(Endo)-2-(3-{3-[2-(2-fluorophenyl)ethyl]-8-azabicyclo[3.2.1]oct-8-yl}propyl]-2H-[1,2,4]triazolo[4,3-a]pyridin-3-one

[Chemical Formula 268]

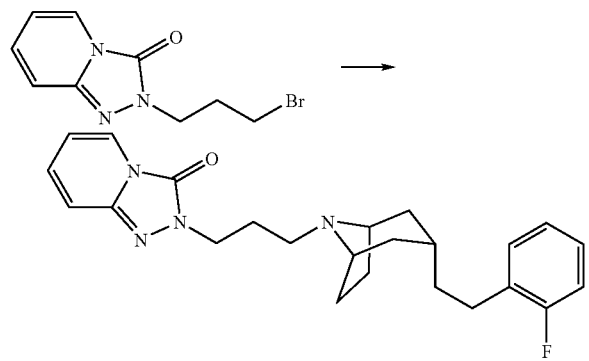

The title compound (40 mg) was obtained from the compound obtained in Example 145-(1) (57 mg) and the compound obtained in Production Example 42 (60 mg), by the method similar to Example 58-(2).

$^1$H-NMR (400 MHz, CDCl$_3$); δ 1.28-1.35 (m 2H), 1.56-1.75 (m, 5H), 1.84-1.94 (m, 2H), 1.95-2.12 (m, 4H), 2.42 (t, J=7.2 Hz, 2H), 2.56-2.64 (m, 2H), 3.12-3.22 (m, 2H), 4.08 (t, J=7.2 Hz, 2H), 6.44-6.59 (m, 1H), 6.94-7.17 (m, 6H), 7.74 (dt, J=7.2, 1.2 Hz, 1H).

Example 150

(Endo)-2-(3-{3-[3-(2-fluorophenyl)-2-oxo-propyl]-8-azabicyclo[3.2.1]oct-8-yl}propyl)-2H-[1,2,4]triazolo[4,3-a]pyridin-3-one

[Chemical Formula 269]

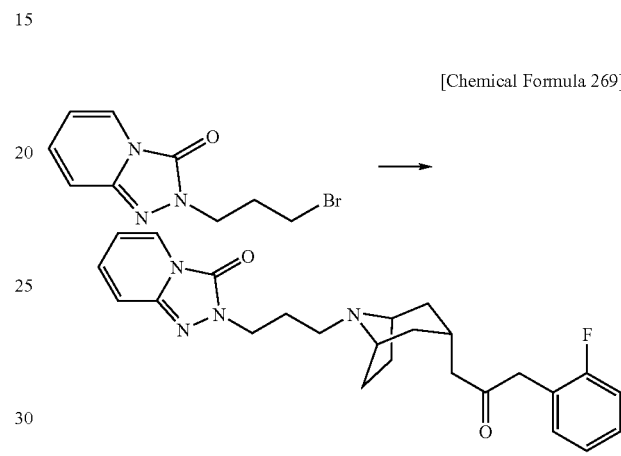

The title compound (50 mg) was obtained from the compound obtained in Example 145-(1) (95 mg) and the compound obtained in Production Example 41 (100 mg), by the method similar to Example 58-(2).

$^1$H-NMR (400 MHz, CDCl$_3$); δ 1.09-1.20 (m, 2H), 1.46-1.57 (m, 2H), 1.85-2.24 (m, 6H), 2.29-2.52 (m, 3H), 2.65 (d, J=8.0 Hz, 2H), 3.12-3.24 (m, 2H), 3.68 (s, 2H), 4.08 (t, J=6.8 Hz, 2H), 6.45-6.51 (m, 1H), 7.03-7.20 (m, 5H), 7.22-7.29 (m, 1H), 7.73-7.77 (m, 1H).

Example 151

2-{3-[3α-(2-fluorobenzyloxy)-3β-methyl-8-azabicyclo[3.2.1]oct-8-yl]propyl}-2H-[1,2,4]triazolo[4,3-a]pyridin-3-one

[Chemical Formula 270]

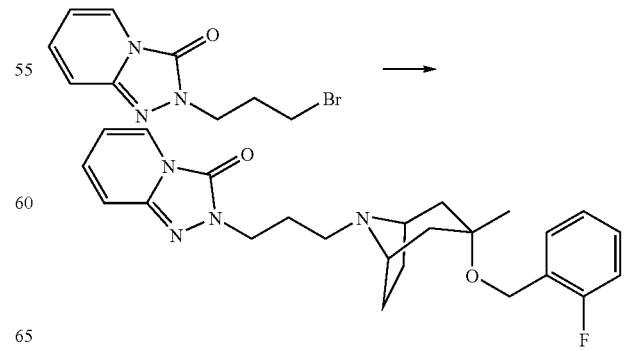

The title compound (62 mg) was obtained from the compound obtained in Example 145-(1) (59 mg) and the compound obtained in Production Example 24 (60 mg), by the method similar to Example 58-(2).

$^1$H-NMR (400 MHz, CDCl$_3$); δ 1.16 (br s, 3H), 1.66-1.82 (m, 4H), 1.88-2.06 (m, 6H), 2.38-2.52 (m, 2H), 3.09-3.22 (m, 2H), 4.10 (t, J=6.8 Hz, 2H), 4.45 (s, 2H), 6.46-6.51 (m, 1H), 6.97-7.15 (m, 4H), 7.19-7.27 (m, 1H), 7.43-7.50 (m, 1H), 7.76 (dt, J=6.8, 1.2 Hz, 1H).

Example 152

2-{3-[3α-(2-fluorobenzyloxy)-3β-methoxymethyl-8-azabicyclo[3.2.1]oct-8-yl]propyl}-2H-[1,2,4]triazolo[4,3-a]pyridin-3-one oxalate

[Chemical Formula 271]

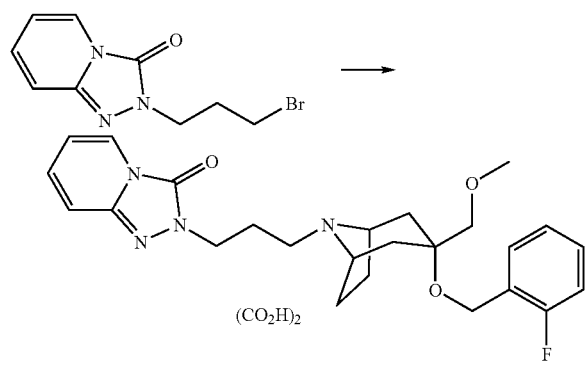

The title compound (86 mg) was obtained from the compound obtained in Example 145-(1) (71 mg) and the compound obtained in Production Example 51 (80 mg), by the method similar to Example 57-(2).

$^1$H-NMR (400 MHz, CD$_3$OD); δ 2.08-2.36 (m, 10H), 3.10-3.21 (m, 2H), 3.33 (s, 3H), 3.39 (s, 2H), 3.97-4.03 (m, 2H), 4.12 (t, J=6.4 Hz, 2H), 4.59 (s, 2H), 6.66-6.71 (m, 1H), 7.05-7.11 (m, 1H), 7.14-7.22 (m, 2H), 7.25-7.36 (m, 2H), 7.42-7.48 (m, 1H), 7.81-7.85 (m, 1H).

Example 153

(Exo)-2-{4-[3-(2-methylphenoxymethyl)-8-azabicyclo[3.2.1]oct-8-yl]butyl}-2H-[1,2,4]triazolo[4,3-a]pyridin-3-one oxalate

[Chemical Formula 272]

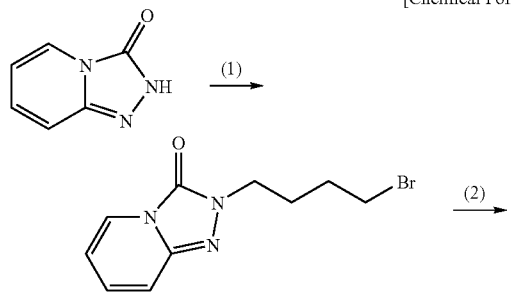

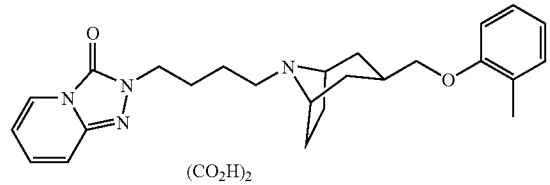

(1) 2-(4-Bromobutyl)-2H-[1,2,4]triazolo[4,3-a]pyridin-3-one

The title compound (363 mg) was obtained from 2H-[1,2,4]triazolo[4,3-a]pyridin-3-one (CAS 6969-71-7) (240 mg) and 1,4-dibromobutane by the method similar to Example 57-(1).

$^1$H-NMR (400 MHz, CDCl$_3$); δ 1.88-2.07 (m, 4H), 3.45 (t, J=6.4 Hz, 2H), 4.04 (t, J=6.8 Hz, 2H), 6.45-6.53 (m, 1H), 7.06-7.10 (m, 2H), 7.73-7.77 (m, 1H).

(2) (Exo)-2-{4-[3-(2-methylphenoxymethyl)-8-azabicyclo[3.2.1]oct-8-yl]butyl}-2H-[1,2,4]triazolo[4,3-a]pyridin-3-one oxalate The title compound (46 mg) was obtained from the compound obtained in Example 153-(1) (100 mg) and the compound obtained in Production Example 49 (109 mg), by the method similar to Example 69-(2).

$^1$H-NMR (400 MHz, CD$_3$OD); δ 1.73-1.81 (m, 2H), 1.88-1.98 (m, 6H), 2.04-2.10 (m, 2H), 2.19 (s, 3H), 2.30 (bs, 2H), 2.44-2.49 (m, 1H), 3.10 (bs, 2H), 3.87-3.88 (m, 2H), 4.06-4.09 (m, 4H), 6.65-6.69 (m, 1H), 6.80-6.86 (m, 2H), 7.09-7.12 (m, 2H), 7.17-7.19 (m, 1H), 7.24-7.28 (m, 1H), 7.81-7.82 (m, 1H).

Example 154

(Endo)-2-{3-[3-(2-fluorophenoxymethyl)-8-azabicyclo[3.2.1]oct-8-yl]propyl}-2H-[1,2,4]triazolo[4,3-a]pyridin-3-one

[Chemical Formula 273]

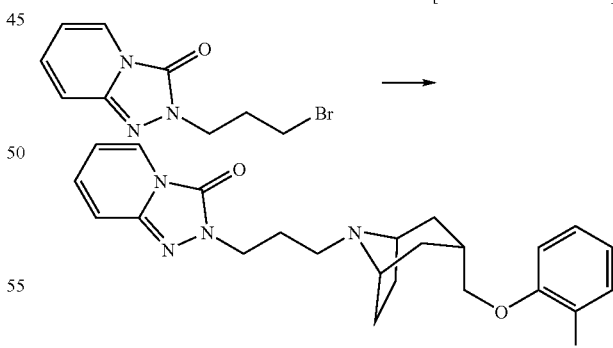

A mixture of the compound obtained in Example 145-(1) (45 mg), the compound obtained in Production Example 17 (41 mg), anhydrous potassium carbonate (27 mg) and N,N-dimethylformamide (1 ml) was stirred at 100° C. for one day. The reaction mixture was filtered and the filtrate was concentrated under reduced pressure. The residue was purified by silica gel column chromatography to obtain the title compound (38 mg).

¹H-NMR (400 MHz, CDCl₃); δ 1.50-2.40 (m, 9H), 2.50-2.66 (m, 2H), 2.96-3.20 (m, 2H), 3.85 (bs, 2H), 3.99 (d, J=7.2 Hz, 2H), 4.14 (t, J=6.4 Hz, 2H), 6.50-6.71 (m, 1H), 6.91-6.97 (m, 2H), 7.02-7.15 (m, 4H), 7.73-7.77 (m, 1H).

Example 155

(Endo)-2-{(S)-4-[3-(2-fluorobenzyloxy)-8-azabicyclo[3.2.1]oct-8-yl]-3-hydroxybutyl}-2H-[1,2,4]triazolo[4,3-a]pyridin-3-one

[Chemical Formula 274]

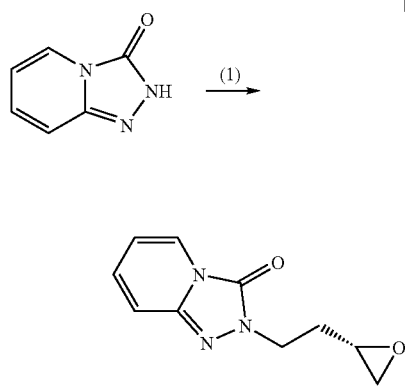

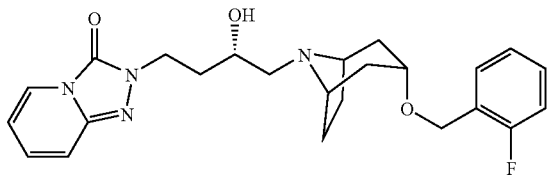

(1) 2-((S)-2-Oxiranylethyl)-2H-[1,2,4]triazolo[4,3-a]pyridin-3-one

The title compound (1.47 g) was obtained from 2H-[1,2,4]triazolo[4,3-a]pyridin-3-one (CAS 6969-71-7) (1.0 g) and (S)-4-bromo-1,2-epoxybutane by the method similar to Example 27-(1).

¹H-NMR (400 MHz, CDCl₃); δ 2.00-2.20 (m, 2H), 2.49 (dd, J=4.8, 2.4 Hz, 1H), 2.76 (td, J=4.8, 0.4 Hz, 1H), 3.02-3.08 (m, 1H), 4.19 (t, J=6.8 Hz, 2H), 6.46-6.54 (m, 1H), 7.08-7.11 (m, 2H), 7.77 (dt, J=7.2, 1.2 Hz, 1H).

(2) (Endo)-2-{(S)-4-[3-(2-fluorobenzyloxy)-8-azabicyclo[3.2.1]oct-8-yl]-3-hydroxybutyl}-2H-[1,2,4]triazolo[4,3-a]pyridin-3-one The title compound (165 mg) was obtained from the compound obtained in Example 155-(1) (300 mg) and the compound obtained in Production Example 5 (397 mg), by the method similar to Example 154.

¹H-NMR (400 MHz, DMSO-d₆); δ 1.62-2.04 (m, 10H), 2.18-2.28 (m, 2H), 3.04 (bs, 2H), 3.47-3.59 (m, 2H), 3.90-4.06 (m, 2H), 4.42 (s, 2H), 6.58 (ddd, J=9.6, 4.8, 2.4 Hz, 1H), 7.12-7.22 (m, 4H), 7.29-7.35 (m, 1H), 7.38-7.44 (m, 1H), 7.82 (dt, J=7.2, 1.2 Hz, 1H).

Example 156

(Endo)-2-{2-fluoro-3-[3-(2-fluorobenzyloxy)-8-azabicyclo[3.2.1]oct-8-yl]propyl}-2H-[1,2,4]triazolo[4,3-a]pyridin-3-one

[Chemical Formula 275]

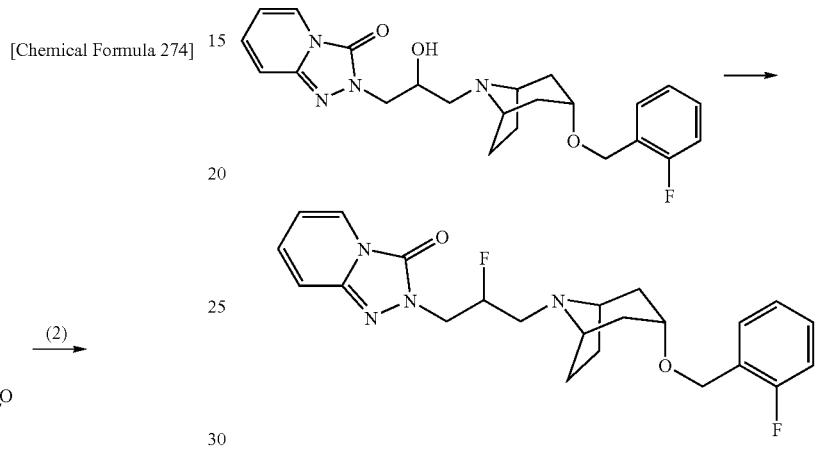

The compound obtained in Example 144 (70 mg) was dissolved in dichloromethane (1 ml), and then dimethylaminosulfur trifluoride (32 μl) was added while stirring on ice and the mixture was stirred at room temperature for one day. Water was added to the reaction mixture, and extraction was performed with ethyl acetate. The organic layer was washed with a saturated aqueous solution of sodium hydrogencarbonate and brine in that order, and dried over anhydrous magnesium sulfate. After filtration, the solvent was distilled off under reduced pressure. The residue was purified by silica gel column chromatography to obtain the title compound (24 mg).

¹H-NMR (400 MHz, CDCl₃); δ 1.80-2.15 (m, 8H), 2.60-2.80 (m, 2H), 3.15-3.30 (bs, 2H), 3.62 (bs, 1H), 4.22-4.45 (m, 2H), 4.49 (s, 2H), 5.01 (d, J=47.2 Hz, 1H), 6.46-6.52 (m, 1H), 6.98-7.04 (m, 1H), 7.06-7.16 (m, 3H), 7.21-7.28 (m, 1H), 7.39-7.45 (m, 1H), 7.74-7.78 (m, 1H).

Example 157

(Endo)-2-{3-[3-(2-fluorobenzyloxy)-8-azabicyclo[3.2.1]oct-8-yl]-2-methoxypropyl}-2H-[1,2,4]triazolo[4,3-a]pyridin-3-one

[Chemical Formula 276]

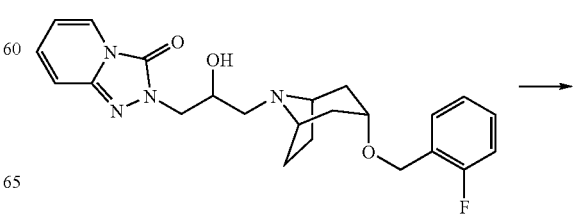

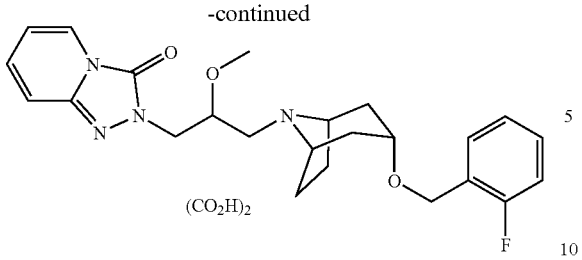

(CO₂H)₂

The compound obtained in Example 144 (50 mg) was dissolved in N,N-dimethylformamide (1 ml), and then sodium hydride (60% in oil) (6 mg) and methyl iodide (8 μl) were added and the mixture was stirred at room temperature for 1 hour. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography to obtain the free form of the title compound. This was dissolved in methanol, and then oxalic acid (5 mg) was added. The mixture was concentrated under reduced pressure to obtain the title compound (32 mg).

$^1$H-NMR (400 MHz, CD₃OD); δ 2.14-2.46 (m, 8H), 3.26-3.40 (m, 2H), 3.53 (s, 3H), 3.75-3.80 (m, 1H), 3.93-3.98 (m, 1H), 4.01-4.06 (m, 1H), 4.08-4.17 (m, 2H), 4.32-4.38 (m, 1H), 4.56 (s, 2H), 6.64-6.70 (m, 1H), 7.05-7.11 (m, 1H), 7.14-7.20 (m, 2H), 7.23-7.36 (m, 2H), 7.39-7.45 (m, 1H), 7.79-7.83 (m, 1H).

Example 158

(Endo)-2-{3-[3-(2-fluorobenzyloxy)-8-azabicyclo[3.2.1]oct-8-yl]-2-oxopropyl}-2H-[1,2,4]triazolo[4,3-a]pyridin-3-one

[Chemical Formula 277]

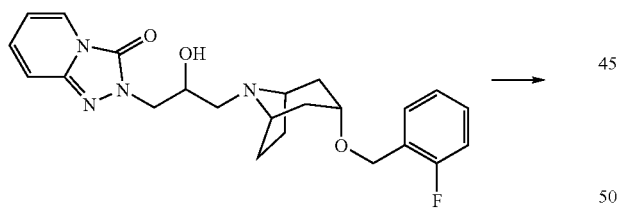

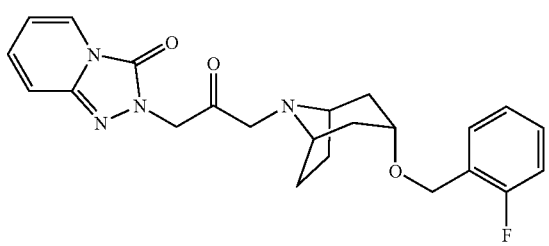

The title compound (70 mg) was obtained from the compound obtained in Example 144 (100 mg), by the method similar to Example 56.

$^1$H-NMR (400 MHz, CDCl₃); δ 1.84-2.14 (m, 8H), 3.12-3.18 (m, 2H), 3.26 (s, 2H), 3.63-3.69 (m, 1H), 4.51 (s, 2H), 5.13 (s, 2H), 6.46-6.54 (m, 1H), 6.99-7.05 (m, 1H), 7.07-7.16 (m, 3H), 7.22-7.29 (m, 1H), 7.39-7.45 (m, 1H), 7.74-7.78 (m, 1H).

Example 159

(Endo)-3-[3-(2-fluorobenzyloxy)-8-azabicyclo[3.2.1]oct-8-yl]-2-(3-oxo-[1,2,4]triazolo[4,3-a]pyridin-2-ylmethyl)propionitrile

[Chemical Formula 278]

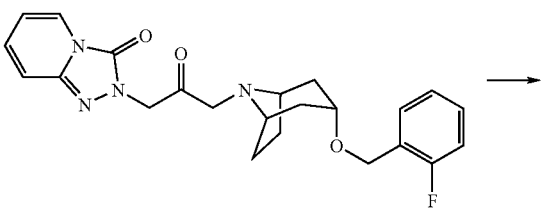

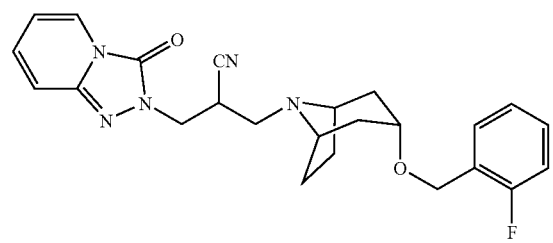

After dissolving the compound obtained in Example 158 (100 mg) and p-toluenesulfonylmethyl isocyanide (69 mg) in a mixed solvent of 1,2-dimethoxyethane (1 ml) and tert-butanol (0.1 ml), a suspension of potassium tert-butoxide (58 mg) in 1,2-dimethoxyethane (1 ml) was added dropwise while stirring on ice. The mixture was stirred on ice for 30 minutes and then at room temperature for 2 hours. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography. The obtained solid was washed with diethyl ether to obtain the title compound (30 mg).

$^1$H-NMR (400 MHz, CDCl₃); δ 1.75-2.12 (m, 8H), 2.64 (d, J=6.4 Hz, 2H), 3.15-3.25 (m, 2H), 3.26-3.34 (m, 1H), 3.58-3.64 (m, 1H), 4.29-4.44 (m, 2H), 4.49 (s, 2H), 6.49-6.54 (m,

1H), 6.98-7.04 (m, 1H), 7.07-7.16 (m, 3H), 7.22-7.28 (m, 1H), 7.38-7.44 (m, 1H), 7.74-7.78 (m, 1H).

Example 160

(Endo)-2-{2-amino-3-[3-(2-fluorobenzyloxy)-8-azabicyclo[3.2.1]oct-8-yl]propyl}-2H-[1,2,4]triazolo[4,3-a]pyridin-3-one

[Chemical Formula 279]

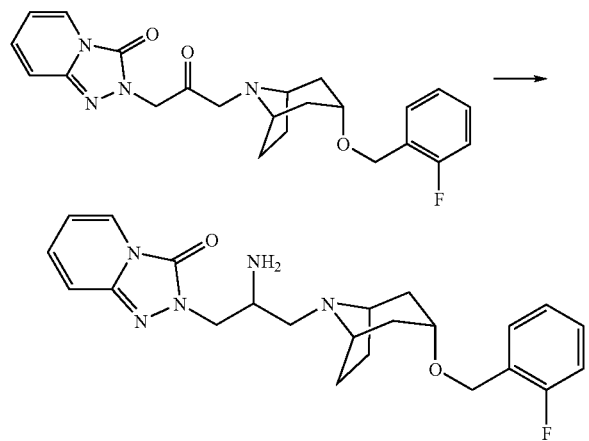

The compound obtained in Example 158 (200 mg) was dissolved in methanol (10 ml), and then ammonium acetate (726 mg) and sodium cyanoborohydride (156 mg) were added and the mixture was stirred at room temperature for 2 hours. Water was added to the reaction mixture, and extraction was performed with ethyl acetate. The organic layer was washed with brine and dried over anhydrous magnesium sulfate. After filtration, the solvent was distilled off under reduced pressure. The residue was purified by NH silica gel column chromatography to obtain the title compound (55 mg).
$^1$H-NMR (400 MHz, CDCl$_3$); δ 1.80-2.10 (m, 10H), 2.28 (dd, J=12.4, 8.4 Hz, 1H), 2.49 (dd, J=12.4, 4.8 Hz, 1H), 3.16 (bs, 2H), 3.32-3.40 (m, 1H), 3.60-3.65 (m, 1H), 3.91 (dd, J=14.0, 7.6 Hz, 1H), 4.09 (dd, J=14.0, 4.4 Hz, 1H), 4.49 (s, 2H), 6.46-6.54 (m, 1H), 6.98-7.05 (m, 1H), 7.06-7.16 (m, 3H), 7.21-7.28 (m, 1H), 7.40-7.46 (m, 1H), 7.75-7.79 (m, 1H).

Example 161

(Endo)-N-[2-[3-(2-fluorobenzyloxy)-8-azabicyclo[3.2.1]oct-8-yl]-1-(3-oxo-[1,2,4]triazolo[4,3-a]pyridin-2-ylmethyl)ethyl]acetamide

[Chemical Formula 280]

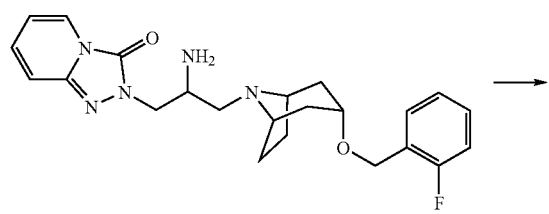

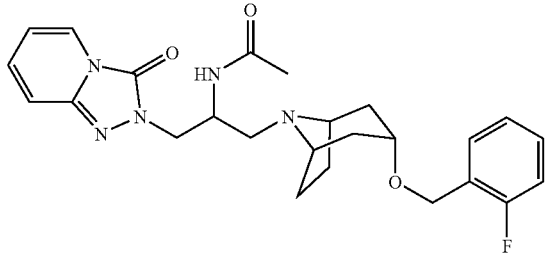

The compound obtained in Example 160 (40 mg) was dissolved in pyridine (2 ml), and then acetic anhydride (18 µl) was added and the mixture was stirred at room temperature for 30 minutes. The reaction mixture was concentrated under reduced pressure, and then a saturated aqueous solution of sodium carbonate was added to the residue and extraction was performed with ethyl acetate. The organic layer was washed with brine and dried over anhydrous magnesium sulfate. After filtration, the solvent was distilled off under reduced pressure. The obtained solid was washed with diethyl ether to obtain the title compound (35 mg).
$^1$H-NMR (400 MHz, CDCl$_3$); δ 1.76-2.08 (m, 8H), 1.87 (s, 3H), 2.50-2.60 (m, 2H), 3.16-3.28 (m, 2H), 3.57-3.62 (m, 2H), 4.04 (dd, J=14.0, 7.2 Hz, 1H), 4.29 (dd, J=14.0, 4.8 Hz, 1H), 4.34-4.42 (m, 1H), 4.48 (s, 2H), 6.62-6.68 (m, 1H), 7.01-7.08 (m, 1H), 7.11-7.32 (m, 4H), 7.39-7.44 (m, 1H), 7.79 (d, J=7.2 Hz, 1H).

Example 162

(Endo)-N-[2-[3-(2-fluorobenzyloxy)-8-azabicyclo[3.2.1]oct-8-yl]-1-(3-oxo-[1,2,4]triazolo[4,3-a]pyridin-2-ylmethyl)ethyl]methanesulfonamide

[Chemical Formula 281]

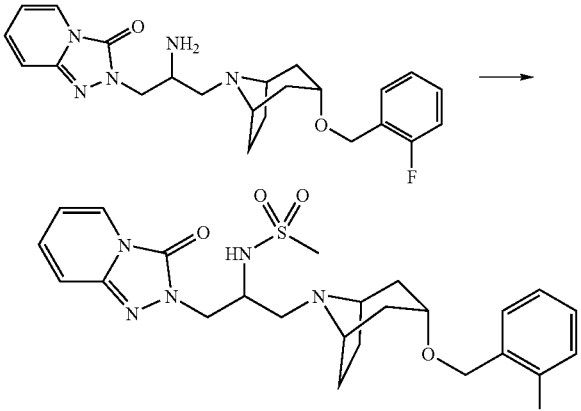

The title compound (29 mg) was obtained from the compound obtained in Example 160 (50 mg) and methanesulfonyl chloride, by the method similar to Example 161.
$^1$H-NMR (400 MHz, CDCl$_3$); δ 1.75-2.12 (m, 8H), 2.40-2.60 (m, 2H), 2.96 (s, 3H), 3.10-3.20 (m, 2H), 3.60-3.65 (m, 1H), 3.88-3.97 (m, 1H), 4.14-4.30 (m, 2H), 4.49 (s, 2H), 6.50-6.54 (m, 1H), 7.01 (t, J=8.8 Hz, 1H), 7.07-7.15 (m, 3H), 7.21-7.28 (m, 1H), 7.40 (t, J=7.2 Hz, 1H), 7.76 (d, J=7.2 Hz, 1H).

Example 163

(Endo)-2-{3-[3-(2-fluorobenzyloxy)-8-azabicyclo [3.2.1]oct-8-yl]-2-[(Z)-methoxyimino]propyl}-2H-[1,2,4]triazolo[4,3-a]pyridin-3-one and (endo)-2-{3-[3-(2-fluorobenzyloxy)-8-azabicyclo [3.2.1]oct-8-yl]-2-[(E)-methoxyimino]propyl}-2H-[1,2,4]triazolo[4,3-a]pyridin-3-one

[Chemical Formula 282]

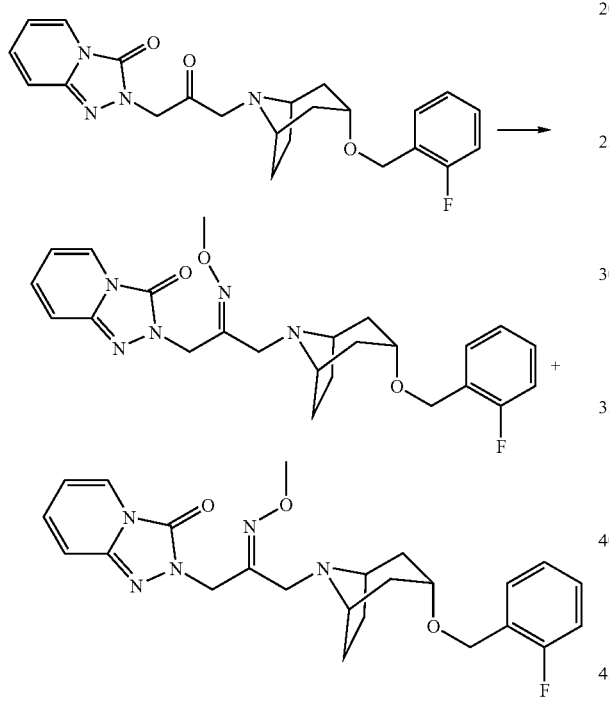

A mixture of the compound obtained in Example 158 (50 mg), methoxyamine hydrochloride (15 mg), sodium acetate (19 mg), ethanol (1 ml) and water (0.3 ml) was stirred at room temperature for one day. Water was added to the reaction mixture, and extraction was performed with ethyl acetate. The organic layer was washed with brine and dried over anhydrous magnesium sulfate. After filtration, the solvent was distilled off under reduced pressure. The residue was purified by preparative thin-layer chromatography (NH silica gel) to obtain the title compound as a lower polarity isomer (26 mg) and a higher polarity isomer (6 mg).
Lower Polarity Isomer (Endo)-2-{3-[3-(2-fluorobenzyloxy)-8-azabicyclo [3.2.1]oct-8-yl]-2-[(Z)-methoxyimino]propyl}-2H-[1,2,4]triazolo[4,3-a]pyridin-3-one $^1$H-NMR (400 MHz, CDCl$_3$); δ 1.57-1.77 (m, 6H), 1.88-1.95 (m, 2H), 2.88 (bs, 2H), 3.05 (s, 2H), 3.45-3.49 (m, 1H), 3.90 (s, 3H), 4.42 (s, 2H), 5.01 (s, 2H), 6.45-6.50 (m, 1H), 6.96-7.02 (m, 1H), 7.04-7.14 (m, 3H), 7.19-7.26 (m, 1H), 7.36-7.41 (m, 1H), 7.72-7.76 (m, 1H).
Higher Polarity Isomer (Endo)-2-{3-[3-(2-fluorobenzyloxy)-8-azabicyclo [3.2.1]oct-8-yl]-2-[(E)-methoxyimino]propyl}-2H-[1,2,4]triazolo[4,3-a]pyridin-3-one $^1$H-NMR (400 MHz, CDCl$_3$); δ 1.75-1.92 (m, 6H), 1.95-2.02 (m, 2H), 2.95 (bs, 2H), 3.25 (s, 2H), 3.50-3.54 (m, 1H), 3.84 (s, 3H), 4.46 (s, 2H), 4.88 (s, 2H), 6.45-6.50 (m, 1H), 6.97-7.14 (m, 4H), 7.20-7.28 (m, 1H), 7.38-7.44 (m, 1H), 7.74-7.78 (m, 1H).

Example 164

(Endo)-2-{3-[3-(2-fluorobenzyloxy)-8-azabicyclo [3.2.1]oct-8-yl]-2-[(E)-hydroxyimino]propyl}-2H-[1, 2,4]triazolo[4,3-a]pyridin-3-one and (Endo)-2-{3-[3-(2-fluorobenzyloxy)-8-azabicyclo [3.2.1]oct-8-yl]-2-[(Z)-hydroxyimino]propyl}-2H-[1, 2,4]triazolo[4,3-a]pyridin-3-one

[Chemical Formula 283]

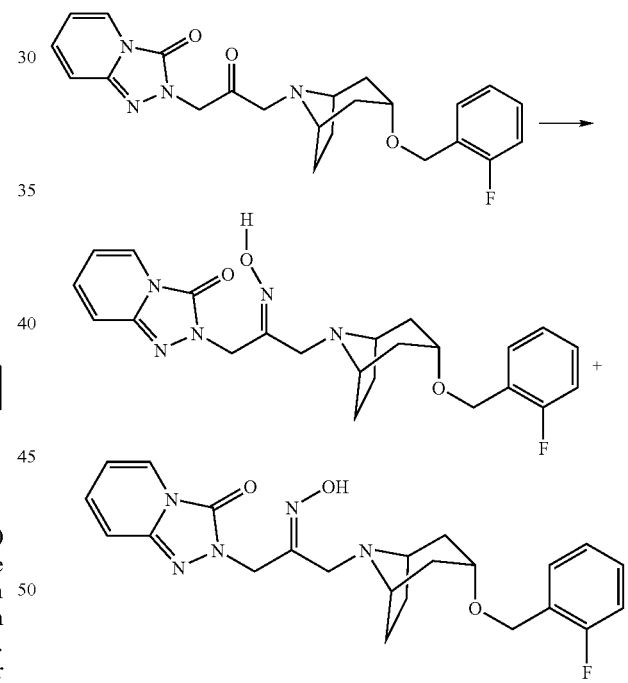

The title compound was obtained as a lower polarity isomer (15 mg) and a higher polarity isomer (27 mg) from the compound obtained in Example 158 (50 mg) and hydroxylamine hydrochloride (12 mg), by the method similar to Example 163.
Lower Polarity Isomer (Endo)-2-{3-[3-(2-fluorobenzyloxy)-8-azabicyclo [3.2.1]oct-8-yl]-2-[(E)-hydroxyimino]propyl}-2H-[1, 2,4]triazolo[4,3-a]pyridin-3-one $^1$H-NMR (400 MHz, CDCl$_3$); δ 1.65-1.88 (m, 8H), 2.90 (bs, 2H), 3.18 (s, 2H), 3.44-3.48 (m, 1H), 4.39 (s, 2H), 4.72 (s, 2H), 6.54-6.60 (m, 1H), 7.12-7.24 (m, 4H), 7.29-7.43 (m, 2H), 7.80-7.85 (m, 1H), 11.00 (s, 1H).
Higher Polarity Isomer (Endo)-2-{3-[3-(2-fluorobenzyloxy)-8-azabicyclo [3.2.1]oct-8-yl]-2-[(Z)-hydroxyimino]propyl}-2H-[1,2,4]triazolo[4,3-a]pyridin-3-one ¹H-NMR (400 MHz, CDCl₃); δ 1.38-1.79 (m, 8H), 2.70 (bs, 2H), 2.94 (s, 2H), 3.32-3.39 (m, 1H), 4.34 (s, 2H), 4.85 (s, 2H), 6.55-6.61 (m, 1H), 7.10-7.24 (m, 4H), 7.26-7.38 (m, 2H), 7.79-7.84 (m, 1H), 11.11 (s, 1H).

Example 165

(Endo)-2-{3-[3-(2-fluorobenzyloxy)-8-azabicyclo [3.2.1]oct-8-yl]-2-hydroxymethylpropyl}-2H-[1,2,4]triazolo[4,3-a]pyridin-3-one

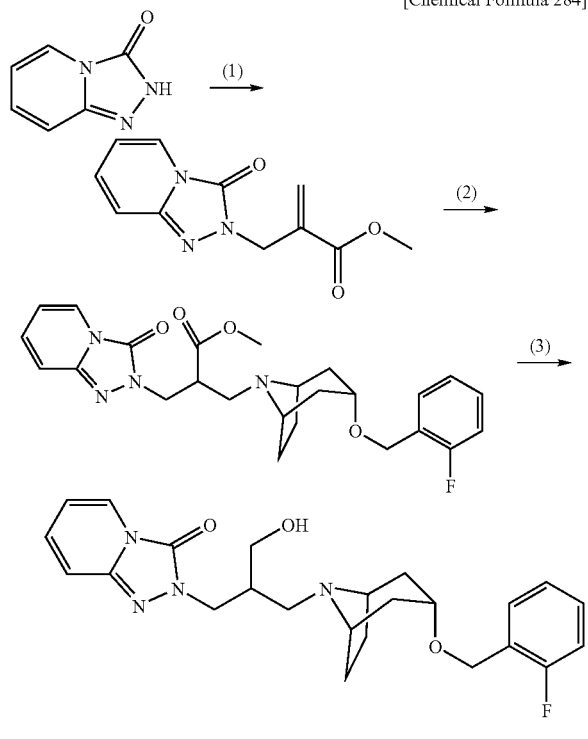

[Chemical Formula 284]

(1) 2-(3-Oxo-[1,2,4]triazolo[4,3-a]pyridin-2-ylmethyl)acrylic acid methyl ester

After dissolving 2H-[1,2,4]triazolo[4,3-a]pyridin-3-one (CAS 6969-71-7) (1.0 g) in N,N-dimethylformamide (50 ml), sodium hydride (60% in oil) (355 mg) was added while stirring on ice. After stirring for 20 minutes, methyl 3-bromo-2-(bromomethyl)propionate (2.11 ml) was added dropwise. Stirring was continued for 1 hour and 30 minutes, and then sodium hydride (60% in oil) (200 mg) was added and the mixture was stirred for 3 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (400 mg).

¹H-NMR (400 MHz, CDCl₃); δ 3.79 (s, 3H), 4.88 (s, 2H), 5.64 (s, 1H), 6.41 (s, 1H), 6.49-6.52 (m, 1H), 7.10-7.11 (m, 2H), 7.77-7.80 (m, 1H).

(2) (Endo)-3-[3-(2-fluorobenzyloxy)-8-azabicyclo [3.2.1]oct-8-yl]-2-(3-oxo-[1,2,4]triazolo[4,3-a]pyridin-2-ylmethyl)propionic acid methyl ester The compound obtained in Example 165-(1) (170 mg) and the compound obtained in Production Example 5 (198 mg) were dissolved in ethanol (20 ml), and the mixture was stirred overnight at 90° C. The reaction mixture was concentrated under reduced pressure, and the residue was purified by preparative thin-layer chromatography to obtain the title compound (32 mg).

(3) (Endo)-2-{3-[3-(2-fluorobenzyloxy)-8-azabicyclo[3.2.1]oct-8-yl]-2-hydroxymethylpropyl}-2H-[1,2,4]triazolo[4,3-a]pyridin-3-one The compound obtained in Example 165-(2) (32 mg) was dissolved in toluene (15 ml), and then diisobutylaluminum hydride (0.99 M solution in toluene, 0.17 ml) was added dropwise while stirring on ice. After stirring for 30 minutes, water was added to the reaction mixture and extraction was performed with ethyl acetate. The organic layer was washed with water and brine in that order and then dried over anhydrous magnesium sulfate. After filtration, the solvent was distilled off under reduced pressure. The residue was then dissolved in ethyl acetate and filtered with NH silica gel. The filtrate was concentrated under reduced pressure to obtain the title compound (6 mg).

¹H-NMR (400 MHz, CD₃OD); & 1.82-2.08 (m, 8H), 2.34-2.58 (m, 3H), 3.19 (br, 2H), 3.56-3.67 (m, 3H), 3.93-4.00 (m, 1H), 4.47-4.50 (m. 3H), 6.64-6.71 (m, 1H), 7.02-7.42 (m, 6H), 7.79-7.81 (m, 1H).

Example 166

(Endo)-6-chloro-2-{3-[3-(2-fluorobenzyloxy)-8-azabicyclo[3.2.1]oct-8-yl]propyl}-2H-[1,2,4]triazolo [4,3-b]pyridazin-3-one oxalate

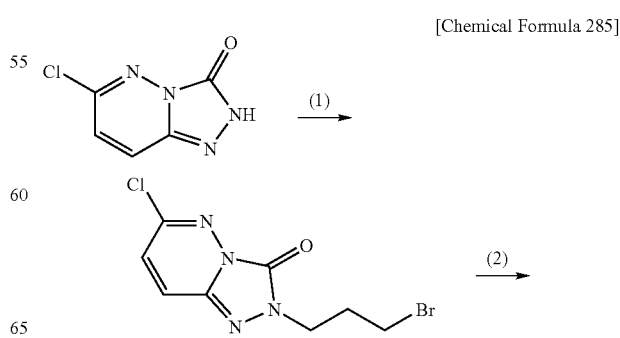

[Chemical Formula 285]

-continued

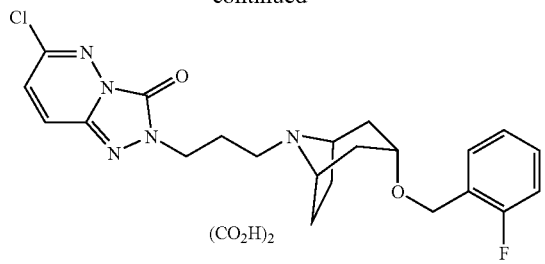

(1) 2-(3-Bromopropyl)-6-chloro-2H-[1,2,4]triazolo[4,3-b]pyridazin-3-one

The title compound (72 mg) was obtained from 6-chloro-2H-[1,2,4]triazolo[4,3-b]pyridazin-3-one (CAS 33050-32-7) (500 mg) and 1,3-dibromopropane by the method similar to Example 57-(1).

$^1$H-NMR (400 MHz, CDCl$_3$); δ 2.41 (quintet, J=6.8 Hz, 2H), 3.45 (t, J=6.8 Hz, 2H), 4.21 (t, J=6.8 Hz, 2H), 6.91 (d, J=9.6 Hz, 1H), 7.47 (d, J=9.6 Hz, 1H).

(2) (Endo)-6-chloro-2-{3-[3-(2-fluorobenzyloxy)-8-azabicyclo[3.2.1]oct-8-yl]propyl}-2H-[1,2,4]triazolo[4,3-b]pyridazin-3-one oxalate The title compound (88 mg) was obtained from the compound obtained in Example 166-(1) (72 mg) and the compound obtained in Production Example 5 (67 mg), by the method similar to Example 57-(2).

$^1$H-NMR (400 MHz, DMSO-d$_6$); δ 1.98-2.26 (m, 10H), 2.98 (br s, 2H), 3.68-3.74 (m, 1H), 3.85 (br s, 2H), 4.01 (t, J=6.4 Hz, 2H), 4.51 (s, 2H), 7.15-7.23 (m, 2H), 7.29 (d, J=10.0 Hz, 1H), 7.32-7.39 (m, 1H), 7.41-7.46 (m, 1H), 7.94 (d, J=10.0 Hz, 1H).

Example 167

(Endo)-2-{3-[3-(2-fluorobenzyloxy)-8-azabicyclo[3.2.1]oct-8-yl]propyl}-2H-[1,2,4]triazolo[4,3-a]pyrimidin-3-one

[Chemical Formula 286]

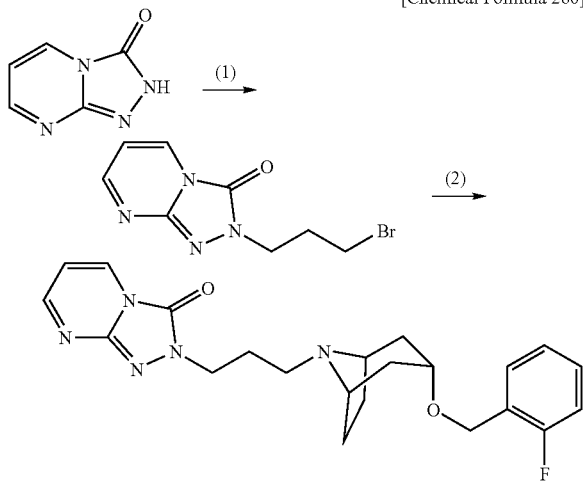

(1) 2-(3-Bromopropyl)-2H-[1,2,4]triazolo[4,3-a]pyrimidin-3-one

A mixture of 2H-[1,2,4]triazolo[4,3-a]pyrimidin-3-one (CAS 63206-77-9) (1.0 g), 1,3-dibromopropane (1.55 ml), sodium hydride (60% in oil) (353 mg) and N,N-dimethylformamide (20 ml) was stirred at room temperature for one day. After further addition of 1,3-dibromopropane (3.88 ml) and sodium hydride (60% in oil) (353 mg), stirring was continued at 80° C. for 2 hours. Water was added to the reaction mixture, and extraction was performed with ethyl acetate. The organic layer was washed with brine and dried over anhydrous magnesium sulfate. After filtration, the solvent was distilled off under reduced pressure. The residue was purified by silica gel column chromatography to obtain the title compound (190 mg).

$^1$H-NMR (400 MHz, CDCl$_3$); δ 2.45 (qn, J=6.8 Hz, 2H), 3.47 (t, J=6.8 Hz, 2H), 4.22 (t, J=6.8 Hz, 2H), 7.16 (dd, J=6.4, 4.8 Hz, 1H), 8.46 (dd, J=4.8, 1.6 Hz, 1H), 8.55 (dd, J=6.4, 1.6 Hz, 1H).

(2) (Endo)-2-{3-[3-(2-fluorobenzyloxy)-8-azabicyclo[3.2.1]oct-8-yl]propyl}-2H-[1,2,4]triazolo[4,3-a]pyrimidin-3-one A mixture of the compound obtained in Example 167-(1) (90 mg), the compound obtained in Production Example 5 (95 mg), anhydrous potassium carbonate (102 mg) and N,N-dimethylformamide (2 ml) was stirred at 100° C. for one day. The reaction mixture was filtered and the filtrate was concentrated under reduced pressure. A saturated aqueous solution of sodium hydrogencarbonate was added to the residue and extraction was performed with ethyl acetate. The organic layer was washed with brine and dried over anhydrous magnesium sulfate. After filtration, the solvent was distilled off under reduced pressure. The residue was purified by preparative thin-layer chromatography. The obtained solid was washed with diethyl ether to obtain the title compound (7 mg).

$^1$H-NMR (400 MHz, CD$_3$OD); δ 1.79-1.91 (m, 6H), 1.99-2.09 (m, 4H), 2.51 (t, J=7.2 Hz, 2H), 3.11-3.19 (m, 2H), 3.56-3.61 (m, 1H), 4.12 (t, J=6.8 Hz, 2H), 4.47 (s, 2H), 7.01-7.46 (m, 5H), 8.64 (dd, J=4.8, 2.0 Hz, 1H), 8.85 (dd, J=6.4, 2.0 Hz, 1H).

Example 168

(Endo)-2-{trans-2-[3-(2-fluoro-6-methylbenzyloxy)-8-azabicyclo[3.2.1]oct-8-ylmethyl]cyclopropylmethyl}-2,5,6,7-tetrahydropyrrolo[2,1-c][1,2,4]triazol-3-one

[Chemical Formula 287]

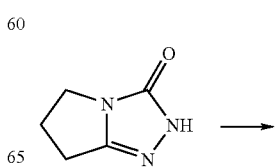

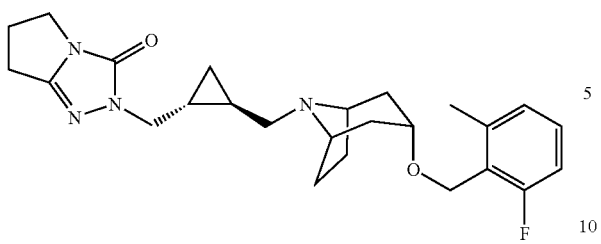

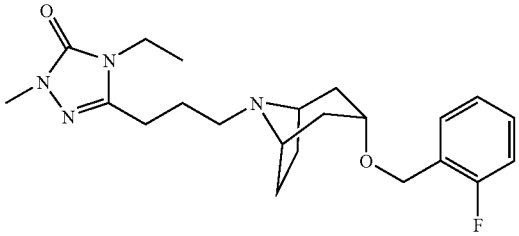

Sodium hydride (60% in oil) (9 mg) was added to a mixture of 2,5,6,7-tetrahydropyrrolo[2,1-c][1,2,4]triazol-3-one (CAS 116056-07-6) (27 mg), the compound obtained in Production Example 69 (80 mg), sodium iodide (32 mg) and N,N-dimethylformamide (2 ml). The mixture was stirred at room temperature for 1 hour and 30 minutes and then overnight at 60° C. A saturated aqueous solution of sodium hydrogencarbonate was added to the reaction mixture, and extraction was performed with ethyl acetate. The organic layer was washed with brine and dried over anhydrous magnesium sulfate. After filtration, the solvent was distilled off under reduced pressure. The residue was purified by NH silica gel column chromatography to obtain the title compound (41 mg).

$^1$H-NMR (400 MHz, CDCl$_3$); δ 0.38 (m, 1H), 0.58 (m, 1H), 0.96-1.08 (m, 2H), 1.72-2.38 (m, 10H), 2.40 (s, 3H), 2.53 (m, 2H), 2.79 (m, 2H), 3.29 (m, 2H), 3.59 (m, 1H), 3.64 (m, 2H), 3.76 (m, 2H), 4.46 (d, J=1.6 Hz, 2H), 6.87 (m, 1H), 6.96 (d, J=7.6 Hz, 1H), 7.15 (m, 1H).

Example 169

(Endo)-4-ethyl-5-{3-[3-(2-fluorobenzyloxy)-8-azabicyclo[3.2.1]oct-8-yl]propyl}-2-methyl-2,4-dihydro[1,2,4]triazol-3-one

[Chemical Formula 288]

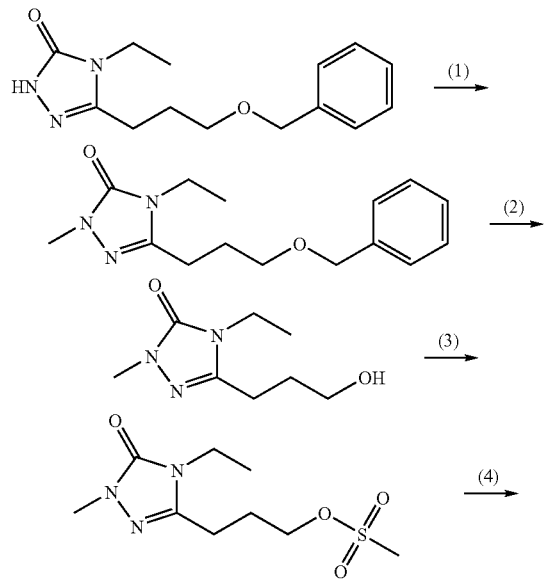

(1) 5-(3-Benzyloxypropyl)-4-ethyl-2-methyl-2,4-dihydro[1,2,4]triazol-3-one

The title compound (1.2 g) was obtained from 5-(3-benzyloxy-propyl)-4-ethyl-2,4-dihydro[1,2,4]triazol-3-one (CAS 425676-20-6) (1.16 g) and methyl iodide by the method similar to Example 33.

$^1$H-NMR (400 MHz, CDCl$_3$); δ 1.26 (t, J=7.2 Hz, 3H), 1.98-2.05 (m, 2H), 2.62 (t, J=7.6 Hz, 2H), 3.41 (s, 3H), 3.57 (t, J=5.8 Hz, 2H), 3.66 (q, J=7.2 Hz, 2H), 4.51 (s, 2H), 7.26-7.35 (m, 5H).

(2) 4-Ethyl-5-(3-hydroxypropyl)-2-methyl-2,4-dihydro[1,2,4]triazol-3-one

The compound obtained in Example 169-(1) (418 mg) was dissolved in methanol (10 ml), and then 20% palladium hydroxide on carbon (50% wet) (730 mg) was added and the mixture was stirred overnight at room temperature under a hydrogen atmosphere (1 atm). The reaction mixture was filtered and the filtrate was concentrated under reduced pressure to obtain the title compound (244 mg).

$^1$H-NMR (400 MHz, CDCl$_3$); δ 1.25 (t, J=7.2 Hz, 3H), 1.91-1.98 (m, 1H), 2.63 (t, J=7.4 Hz, 2H), 3.39 (s, 3H), 3.65 (q, J=7.2 Hz, 2H), 3.71 (t, J=6.0 Hz, 2H).

(3) Methanesulfonic acid 3-(4-ethyl-1-methyl-5-oxo-4,5-dihydro-1H-[1,2,4]triazol-3-yl)propyl ester The compound obtained in Example 169-(2) (100 mg) was dissolved in dichloromethane (0.7 ml), and then triethylamine (0.12 ml) was added and methanesulfonyl chloride (63 μl) was also added while stirring on ice. The mixture was further stirred for 1 hour at room temperature. After then adding water to the reaction mixture, it was extracted with ethyl acetate and dried over anhydrous magnesium sulfate. After filtration, the solvent was distilled off under reduced pressure to obtain the title compound (148 mg).

$^1$H-NMR (400 MHz, CDCl$_3$); δ 1.28 (t, J=7.2 Hz, 3H), 2.17-2.24 (m, 2H), 2.67 (t, J=7.2 Hz, 2H), 3.05 (s, 3H), 3.42 (s, 3H), 3.70 (q, J=7.2 Hz, 2H), 4.38 (t, J=5.8 Hz, 2H).

(4) (Endo)-4-ethyl-5-{3-[3-(2-fluorobenzyloxy)-8-azabicyclo[3.2.1]oct-8-yl]propyl}-2-methyl-2,4-dihydro[1,2,4]triazol-3-one A mixture of the compound obtained in Example 169-(3) (96 mg), the compound obtained in Production Example 5 (90 mg), sodium iodide (50 mg), anhydrous potassium carbonate (101 mg) and N,N-dimethylformamide (1 ml) was stirred at 90° C. for 5 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by preparative silica gel chromatography to obtain the title compound (63 mg).

¹H-NMR (400 MHz, CDCl₃); δ 1.28 (t, J=7.2 Hz, 3H), 1.84-2.14 (m, 10H), 2.46 (t, J=7.0 Hz, 2H), 2.60 (t, J=7.6 Hz, 2H), 3.15-3.24 (m, 2H), 3.42 (s, 3H), 3.65 (t, J=4.8 Hz, 1H), 3.69 (q, J=7.2 Hz, 2H), 4.50 (s, 2H), 6.98-7.05 (m, 1H), 7.11-7.16 (m, 1H), 7.22-7.29 (m, 1H), 7.40-7.46 (m, 1H).

Example 170

(Endo-4-{3-[3-(2-fluorobenzyloxy)-8-azabicyclo[3.2.1]oct-8-yl]-2-hydroxypropyl}-2,5-dimethyl-2,4-dihydro[1,2,4]triazol-3-one oxalate

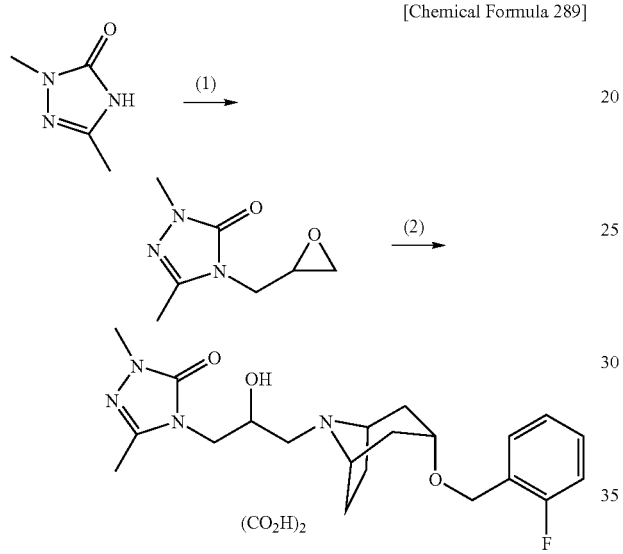

(1) 2,5-Dimethyl-4-oxiranylmethyl-2,4-dihydro[1,2,4]triazol-3-one

The title compound (521 mg) was obtained from 2,5-dimethyl-2,4-dihydro[1,2,4]triazol-3-one (CAS 4114-21-0) (500 mg) and epibromohydrin by the method similar to Example 27-(1).

¹H-NMR (400 MHz, CDCl₃); δ 2.25 (s, 3H), 2.53-2.58 (m, 1H), 2.81-2.86 (m, 1H), 3.18-3.24 (m, 1H), 3.43 (s, 3H), 3.57-3.66 (m, 1H), 4.05-4.12 (m, 1H).

(2) (Endo)-4-{3-[3-(2-fluorobenzyloxy)-8-azabicyclo[3.2.1]oct-8-yl]-2-hydroxypropyl}-2,5-dimethyl-2,4-dihydro[1,2,4]triazol-3-one oxalate The compound obtained in Example 170-(1) (70 mg) was dissolved in N,N-dimethylformamide (1 ml), and then the compound obtained in Production Example 5 (124 mg) and anhydrous potassium carbonate (63 mg) were added and the mixture was stirred at 100° C. for 41 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the free form of the title compound (110 mg). This was dissolved in ethanol, oxalic acid (25 mg) was added, and the mixture was concentrated under reduced pressure. Diethyl ether was added to the residue to produce a solid which was collected by filtration. The title compound (108 mg) was thus obtained.

¹H-NMR (400 MHz, CD₃OD); δ 2.14-2.50 (m, 8H), 2.27 (s, 3H), 3.02-3.12 (m, 1H), 3.16-3.26 (m, 1H), 3.38 (s, 3H), 3.66 (dd, J=15.2, 3.2 Hz, 1H), 3.73-3.82 (m, 2H), 3.86-4.02 (m, 1H), 4.06-4.14 (m, 1H), 4.24-4.32 (m, 1H), 4.58 (s, 2H), 7.06-7.12 (m, 1H), 7.15-7.20 (m, 1H), 7.30-7.37 (m, 1H), 7.41-7.46 (m, 1H).

Example 171

(Endo)-5-{3-[3-(2-fluorobenzyloxy)-8-azabicyclo[3.2.1]oct-8-yl]propyl}-1,2-dimethyl-1,2-dihydro-[1,2,4]triazol-3-one oxalate

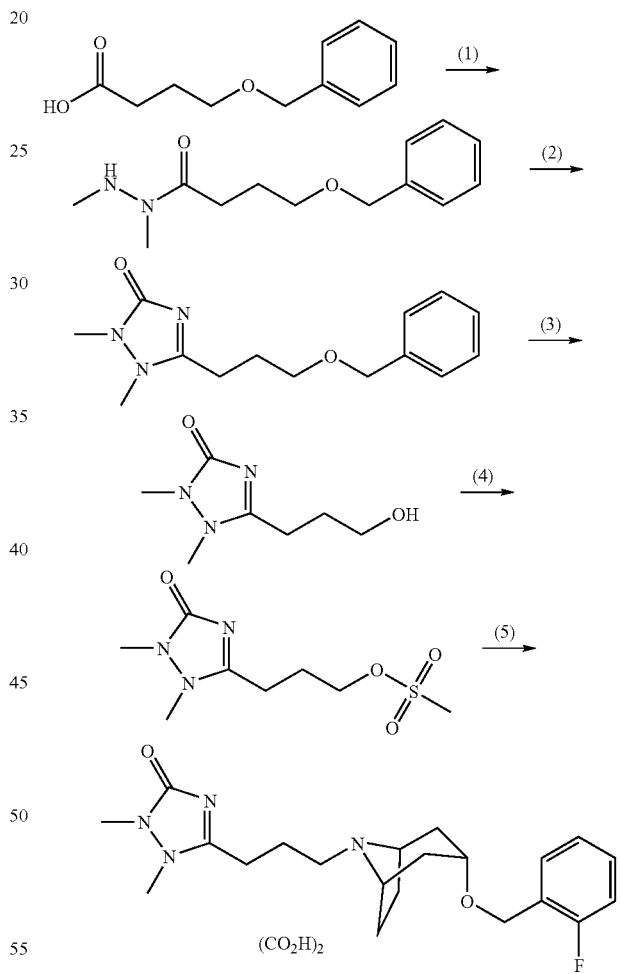

(1) 4-Benzyloxybutyric acid N,N'-dimethyl hydrazide

After dissolving 4-benzylbutyric acid (500 mg) in N,N-dimethylformamide (10 ml), 1,1'-carbonyldiimidazole (628 mg) was added and the mixture was stirred at room temperature for 1 hour. After then adding 1,2-dimethylhydrazine hydrochloride (515 mg), the mixture was stirred at room temperature for 62 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (357 mg).

$^1$H-NMR (400 MHz, CDCl$_3$); δ 1.90-2.02 (m, 2H), 2.39-2.66 (m, 5H), 3.08 and 3.13 (s, 3H), 3.24-3.32 and 5.52-5.57 (m, 1H), 3.54 (t, J=6.4 Hz, 2H), 4.51 (s, 2H), 7.24-7.38 (m, 5H).

(2) 5-(3-Benzyloxypropyl)-1,2-dimethyl-1,2-dihydro-[1,2,4]triazol-3-one

The compound obtained in Example 171-(1) (357 mg) was dissolved in tetrahydrofuran (5 ml), and then trimethylsilyl isocyanate (0.24 ml) was added and the mixture was stirred at room temperature for 2 hours. Trimethylsilyl isocyanate (2.41 ml) was further added, and stirring was continued at room temperature for 1 hour and then at 70° C. for 2 hours. The reaction mixture was concentrated under reduced pressure, water was added to the residue, and extraction was performed with ethyl acetate. The organic layer was washed with water and brine in that order and then dried over anhydrous magnesium sulfate. After filtration, the solvent was distilled off under reduced pressure to obtain a solid (360 mg).

The obtained solid was dissolved in ethanol (5 ml) and a 1N aqueous solution of sodium hydroxide (3.9 ml), and the mixture was heated to reflux for 30 minutes. The reaction mixture was concentrated under reduced pressure, water was added to the residue, and the mixture was extracted with chloroform and dried over anhydrous magnesium sulfate. After filtration, the solvent was distilled off under reduced pressure and the residue was purified by silica gel column chromatography to obtain the title compound (233 mg).

$^1$H-NMR (400 MHz, CDCl$_3$); δ 2.05-2.13 (m, 2H), 2.68 (t, J=7.2 Hz, 2H), 3.33 (s, 3H), 3.41 (s, 3H), 3.56 (t, J=5.6 Hz, 2H), 4.48 (s, 2H), 7.25-7.38 (m, 5H).

(3) 5-(3-Hydroxypropyl)-1,2-dimethyl-1,2-dihydro-[2,4]triazol-3-one

The title compound (158 mg) was obtained from the compound obtained in Example 171-(2) (233 mg), by the method similar to Example 169-(2).

$^1$H-NMR (400 MHz, CDCl$_3$); δ 1.98-2.06 (m, 2H), 2.73 (t, J=6.8 Hz, 2H), 3.39 (s, 3H), 3.53 (s, 3H), 3.73 (t, J=5.6 Hz, 2H).

(4) Methanesulfonic acid 3-(1,2-dimethyl-5-oxo-2,5-dihydro-1H-[1,2,4]triazol-3-yl)propyl ester The compound obtained in Example 171-(3) (158 mg) was dissolved in dichloromethane (5 ml), and then triethylamine (0.19 ml) was added and methanesulfonyl chloride (0.11 ml) was also added while stirring on ice. After stirring on ice for 2 hours, the reaction mixture was purified by silica gel column chromatography to obtain the title compound (25 mg).

$^1$H-NMR (400 MHz, CDCl$_3$); δ 2.26-2.33 (m, 2H), 2.73 (t, J=6.8 Hz, 2H), 3.02 (s, 3H), 3.41 (s, 3H), 3.53 (s, 3H), 4.37 (t, J=5.6 Hz, 2H).

(5) (Endo)-5-{3-[3-(2-fluorobenzyloxy)-8-azabicyclo[3.2.1]oct-8-yl]propyl}-1,2-dimethyl-1,2-dihydro-[1,2,4]triazol-3-one oxalate The free form of the title compound (19 mg) was obtained from the compound obtained in Example 171-(4) (81 mg) and the compound obtained in Production Example 57 (81 mg), by the method similar to Example 169-(4). This was dissolved in ethanol, oxalic acid (4.6 mg) was added, and the mixture was concentrated under reduced pressure. Diethyl ether was added to the residue to produce a solid which was collected by filtration. The title compound (5 mg) was thus obtained.

$^1$H-NMR (400 MHz, CD$_3$OD); δ 2.12-2.48 (m, 10H), 2.82-2.89 (m, 2H), 3.09-3.17 (m, 2H), 3.45 (s, 3H), 3.64 (s, 3H), 3.81-3.87 (m, 1H), 3.92-4.00 (m, 2H), 4.58 (s, 2H), 7.06-7.12 (m, 1H), 7.15-7.20 (m, 1H), 7.30-7.37 (m, 1H), 7.40-7.47 (m, 1H).

Example 172

(Endo)-3-{3-[3-(2-fluorobenzyloxy)-8-azabicyclo[3.2.1]oct-8-yl]propyl}-pyrido[1,2-a][1,3,5]triazine-2,4-dione

[Chemical Formula 291]

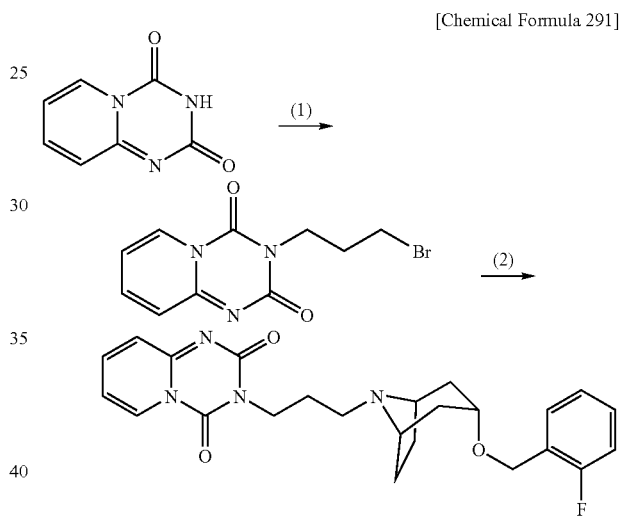

(1) 3-(3-Bromopropyl)-pyrido[1,2-a][1,3,5]triazine-2,4-dione

The title compound (44 mg) was obtained from pyrido[1,2-a][1,3,5]triazine-2,4-dione (CAS 26737-41-7) (500 mg) and 1,3-dibromopropane by the method similar to Example 57-(1).

$^1$H-NMR (400 MHz, CDCl$_3$); δ 2.13-2.21 (m, 2H), 3.58 (t, J=6.8 Hz, 2H), 3.98 (t, J=6.8 Hz, 2H), 6.90-6.95 (m, 1H), 7.04-7.08 (m, —H), 7.78-7.84 (m, 1H), 8.38-8.42 (m, 1H).

(2) (Endo)-3-{3-[3-(2-fluorobenzyloxy)-8-azabicyclo[3.2.1]oct-8-yl]propyl}-pyrido[1,2-a][1,3,5]triazine-2,4-dione The title compound (14 mg) was obtained from the compound obtained in Example 172-(1) (44 mg) and the compound obtained in Production Example 5 (46 mg), by the method similar to Example 58-(2).

$^1$H-NMR (400 MHz, CDCl$_3$); δ 1.75-2.05 (m, 10H), 2.28 (s, 3H), 2.48 (t, J=7.2 Hz, 2H), 3.09-3.18 (m, 2H), 3.52-3.57

(m, 1H), 4.19 (t, J=7.2 Hz, 2H), 4.38 (s, 2H), 6.76-6.82 (m, 1H), 7.11-7.21 (m, 4H), 7.32-7.38 (m, 1H), 7.60-7.66 (m, 1H), 8.41-8.46 (m, 1H).

Example 173

(Endo)-3-{3-[3-(2-fluorobenzyloxy)-8-azabicyclo[3.2.1]oct-8-yl]propyl}-8H-imidazo[1,2-a][1,3,5]triazine-2,4-dione

[Chemical Formula 292]

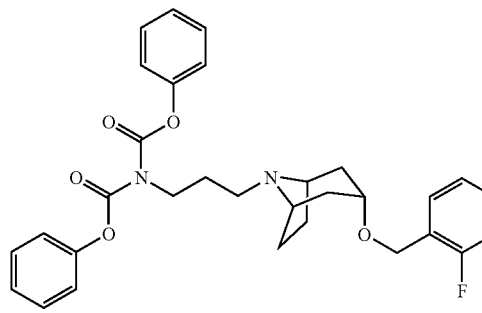

After dissolving 2-aminoimidazole sulfate (121 mg) in water (2 ml), sodium carbonate (146 mg) was added. After then stirring at room temperature for 30 minutes, the reaction mixture was concentrated under reduced pressure. Ethanol was added to the residue and the mixture was filtered. The filtrate was concentrated under reduced pressure, and then a solution of the compound obtained in Production Example 61 (488 mg) in acetonitrile (5 ml) was added to the residue and the mixture was heated to reflux for 9 hours. Ethyl acetate was added to the reaction mixture and the mixture was filtered. The filtrate was concentrated under reduced pressure and the residue was purified by silica gel column chromatography. The purified product was solidified with diethyl ether and a small amount of water, and then collected by filtration to obtain the title compound (175 mg).

$^1$H-NMR (400 MHz, CD$_3$OD); δ 2.08-2.42 (m, 10H), 3.01 (t, J=7.2 Hz, 2H), 3.77-3.82 (m, 1H), 3.85-3.92 (m, 2H), 4.07 (t, J=6.4 Hz, 2H), 4.56 (s, 2H), 6.88 (d, J=2.0 Hz, 1H), 7.05-7.11 (m, 1H), 7.14-7.20 (m, 1H), 7.19 (d, J=2.0 Hz, 1H), 7.29-7.36 (m, 1H), 7.40-7.46 (m, 1H).

Example 174

(Endo)-3-{3-[3-(2-fluorobenzyloxy)-8-azabicyclo[3.2.1]oct-8-yl]propyl}-8-methyl-8H-imidazo[1,2-a][1,3,5]triazine-2,4-dione

[Chemical Formula 293]

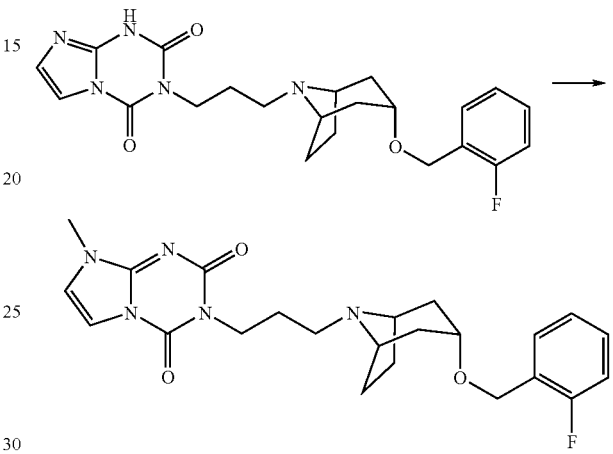

The compound obtained in Example 173 (80 mg) was dissolved in N,N-dimethylformamide (2 ml), and then sodium hydride (60% in oil) (8 mg) was added and the mixture was stirred at room temperature for 30 minutes. Methyl iodide (13 μl) was added, and stirring was continued at room temperature for 3 hours. Water was added to the reaction mixture, and extraction was performed with ethyl acetate. The organic layer was washed with a 1N aqueous solution of sodium hydroxide, water and brine in that order and dried over anhydrous magnesium sulfate. After filtration, the solvent was distilled off under reduced pressure. The residue was purified by silica gel column chromatography. The purified product was solidified with diethyl ether and then collected by filtration to obtain the title compound (18 mg).

$^1$H-NMR (400 MHz, CDCl$_3$); δ 1.70-2.02 (m, 10H), 2.47 (t, J=6.4 Hz, 2H), 3.06-3.14 (m, 2H), 3.50-3.55 (m, 1H), 3.61 (s, 3H), 4.15 (t, J=6.8 Hz, 2H), 4.47 (s, 2H), 6.98-7.04 (m, 1H), 7.01 (d, J=1.6 Hz, 1H), 7.10-7.15 (m, 1H), 7.20-7.29 (m, 1H), 7.35 (d, J=1.6 Hz, 1H), 7.39-7.44 (m, 1H).

Example 175

(Endo)-6-{3-[3-(2-fluorobenzyloxy)-8-azabicyclo[3.2.1]oct-8-yl]propyl}-2,4-dimethyl-3a,4-dihydro[1,2,4]triazole[1,5-a][1,3,5]triazine-5,7-dione oxalate

[Chemical Formula 294]

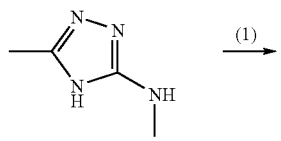 (1)

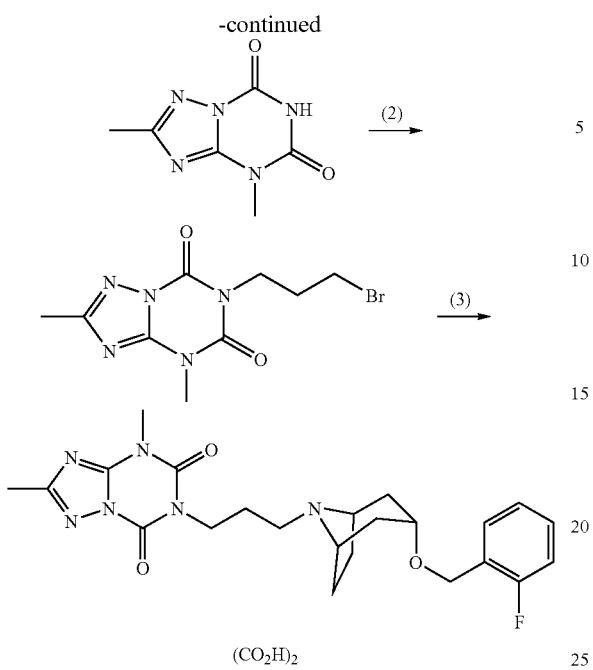

(1) 2,4-Dimethyl-3a,4-dihydro[1,2,4]triazole[1,5-a]
[1,3,5]triazine-5,7-dione

The title compound (237 mg) was obtained from methyl-(5-methyl-4H-[1,2,4]triazol-3-yl)amine (CAS 57561-15-6) (227 mg) and diphenyl imidodicarbonate (CAS 99911-94-1) by the method similar to Example 105-(1).

$^1$H-NMR (400 MHz, DMSO-d$_6$); δ 2.30 (s, 3H), 3.34 (s, 3H), 12.10 (s, 1H).

(2) 6-(3-Bromopropyl)-2,4-dimethyl-3a,4-dihydro[1,2,4]triazole[1,5-a][1,3,5]triazine-5,7-dione The title compound (60 mg) was obtained from the compound obtained in Example 175-(1) (100 mg) and 1,3-dibromopropane (16811), by the method similar to Example 57-(1).

$^1$H-NMR (400 MHz, CDCl$_3$); δ 2.31 (quintet, J=6.8 Hz, 2H), 2.45 (s, 3H), 3.46 (t, J=6.8 Hz, 2H), 3.63 (s, 3H), 4.20 (t, J=6.8 Hz, 2H).

(3) (Endo)-6-{3-[3-(2-fluorobenzyloxy)-8-azabicyclo[3.2.1]oct-8-yl]propyl}-2,4-dimethyl-3a,4-dihydro[1,2,4]triazole[1,5-a][1,3,5]triazine-5,7-dione oxalate The title compound (59 mg) was obtained from the compound obtained in Example 175-(2) (60 mg) and the compound obtained in Production Example 57 (52 mg), by the method similar to Example 57-(2).

$^1$H-NMR (400 MHz, CD$_3$OD); δ 2.12-2.30 (m, 8H), 2.39 (s, 3H), 2.40-2.47 (m, 2H), 3.08-3.19 (m, 2H), 3.56 (s, 3H), 3.77-3.82 (m, 1H), 3.93-3.99 (m, 2H), 4.11 (t, J=6.8 Hz, 2H), 4.54 (s, 2H), 7.06-7.12 (m, 1H), 7.15-7.20 (m, 1H), 7.30-7.37 (m, 1H), 7.40-7.46 (m, 1H).

Example 176

(Endo)-4-{3-[3-(2-fluorobenzyloxy)-8-azabicyclo[3.2.1]oct-8-yl]propyl}-2,6-dimethyl-3a,4-dihydro[1,2,4]triazole[1,5-a][1,3,5]triazine-5,7-dione oxalate

[Chemical Formula 295]

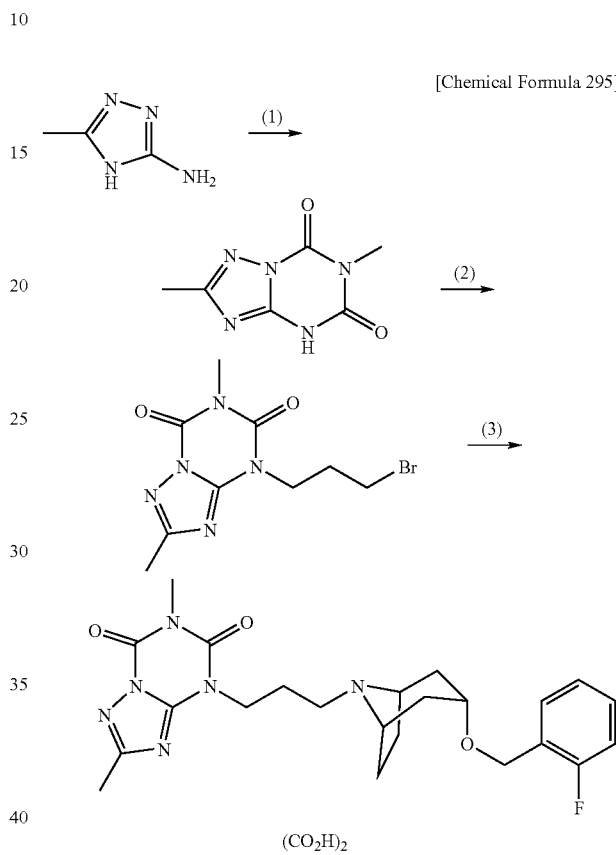

(1) 2,6-Dimethyl-3a,4-dihydro[1,2,4]triazole[1,5-a]
[1,3,5]triazine-5,7-dione

The title compound (2.05 g) was obtained from 5-methyl-4H-[1,2,4]triazol-3-ylamine (CAS 4923-01-7) (1.69 g) and N-methyl diphenyl imidodicarbonate (CAS 79658-69-8) (4.65 g) by the method similar to Example 105-(1).

(2) 4-(3-Bromopropyl)-2,6-dimethyl-3a,4-dihydro[1,2,4]triazolo[1,5-a][1,3,5]triazine-5,7-dione The title compound (974 mg) was obtained from the compound obtained in Example 176-(1) (2.05 g) and 1,3-dibromopropane, by the method similar to Example 105-(2).

$^1$H-NMR (400 MHz, CDCl$_3$); δ 2.35-2.44 (m, 2H), 2.45 (s, 3H), 3.47 (t, J=6.8 Hz, 2H), 3.50 (s, 3H), 4.28 (t, J=7.2 Hz, 2H).

(3) (Endo)-4-{3-[3-(2-fluorobenzyloxy)-8-azabicyclo[3.2.1]oct-8-yl]-propyl}-2,6-dimethyl-3a,4-dihydro[1,2,4]triazole[1,5-a][1,3,5]triazine-5,7-dione oxalate The title compound (80 mg) was obtained from the compound obtained in Example 176-(2) (70 mg) and the compound obtained in Production Example 5 (69 mg), by the method similar to Example 57-(2).

¹H-NMR (400 MHz, CD₃OD); δ 2.14-2.34 (m, 8H), 2.37-2.44 (m, 2H), 2.38 (s, 3H), 3.11-3.17 (m, 2H), 3.41 (s, 3H), 3.76-3.81 (m, 1H), 3.90-3.95 (m, 2H), 4.18 (t, J=6.8 Hz, 2H), 4.57 (s, 2H), 7.05-7.11 (m, 1H), 7.14-7.19 (m, 1H), 7.30-7.36 (m, 1H), 7.40-7.45 (m, 1H).

Example 177

(Endo)-3,6-dimethyl-1-{3-[3-(2-methylbenzyloxy)-8-azabicyclo[3.2.1]oct-8-yl]propyl}-1H-[1,3,5]triazine-2,4-dione oxalate

[Chemical Formula 296]

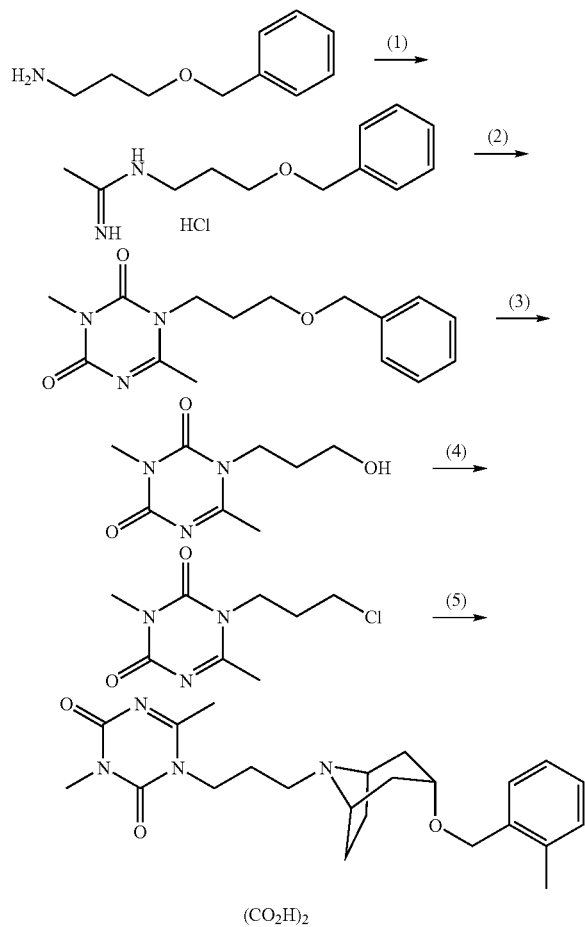

(1) N-(3-Benzyloxypropyl)acetamidine hydrochloride

The title compound (5.31 g) was obtained from 3-benzyloxy-propylamine (CAS 16728-64-6) (3.10 g) and ethyl acetimidate hydrochloride (2.4 g) by the method similar to Example 68-(1).

(2) 1-(3-Benzyloxypropyl)-3,6-dimethyl-1H-[1,3,5]triazine-2,4-dione

The title compound (546 mg) was obtained from the compound obtained in Example 177-(1) (871 mg) and N-methyl diphenyl imidodicarbonate (CAS 79658-69-8) (974 mg) by the method similar to Example 75-(2).

¹H-NMR (400 MHz, CDCl₃); δ 1.97-2.03 (m, 2H), 2.47 (s, 3H), 3.32 (s, 3H), 3.53-3.56 (m, 2H), 4.00-4.04 (m, 2H), 4.50 (s, 2H), 7.28-7.38 (m, 5H).

(3) 1-(3-Hydroxypropyl)-3,6-dimethyl-1H-[1,3,5]triazine-2,4-dione

The compound obtained in Example 177-(2) (536 mg) was dissolved in acetonitrile (10 ml), and then trimethylsilyl iodide (2.63 ml) was added and the mixture was stirred at room temperature for 3 days. After adding tert-butyl methyl ether to the reaction mixture, stirring was continued for 5 hours. The reaction mixture was concentrated under reduced pressure, and the residue was dissolved in methanol and filtered with NH silica gel. The filtrate was concentrated under reduced pressure and the residue was purified by NH silica gel column chromatography.

The title compound (265 mg) was thus obtained.

¹H-NMR (400 MHz, CDCl₃); δ 1.91-1.97 (m, 2H), 2.14-2.17 (m, 1H), 2.53 (s, 3H), 3.37 (s, 3H), 3.68-3.72 (m, 2H), 4.05-4.09 (m, 2H).

(4) 1-(3-Chloropropyl)-3,6-dimethyl-1H-[1,3,5]triazine-2,4-dione

The compound obtained in Example 177-(3) (265 mg) was dissolved in dichloromethane (5 ml), and then triethylamine (0.37 ml) and methanesulfonyl chloride (0.15 ml) were added and the mixture was stirred at room temperature for 9 hours. The reaction mixture was concentrated under reduced pressure, and the residue was purified by silica gel column chromatography to obtain the title compound (217 mg).

¹H-NMR (400 MHz, CDCl₃+CD₃OD); δ 2.16-2.22 (m, 2H), 2.52 (s, 3H), 3.10 (s, 3H), 4.07-4.11 (m, 2H), 4.36-4.38 (m, 2H).

(5) (Endo)-3,6-dimethyl-1-{3-[3-(2-methylbenzyloxy)-8-azabicyclo[3.2.1]oct-8-yl]propyl}-1H-[1,3,5]triazine-2,4-dione oxalate The title compound (53 mg) was obtained from the compound obtained in Example 177-(4) (50 mg) and the compound obtained in Production Example 3 (68 mg), by the method similar to Example 69-(2).

¹H-NMR (400 MHz, CD₃OD); δ 2.10-2.33 (m, 10H), 2.41-2.49 (m, 3H), 3.11-3.15 (m, 2H), 3.30 (s, 3H), 3.78 (bs, 1H), 3.96-4.02 (m, 4H), 4.54 (s, 2H), 7.13-7.21 (m, 3H), 7.29-7.31 (m, 1H).

Example 178

(Endo)-3-{2-[3-(2-fluorobenzyloxy)-8-azabicyclo[3.2.1]oct-8-yl]ethyl}-2-methyl-6,7,8,9-tetrahydropyrido[1,2-a]pyrimidin-4-one oxalate

[Chemical Formula 297]

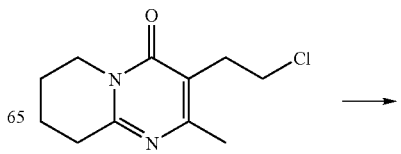

-continued

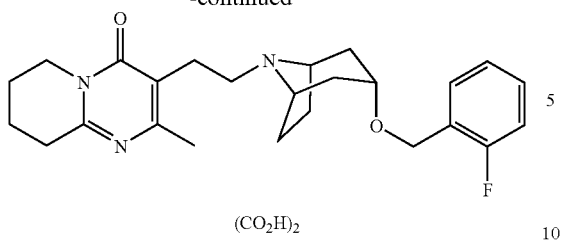

(CO₂H)₂

After dissolving 3-(2-chloroethyl)-2-methyl-6,7,8,9-tetrahydropyrido[1,2-a]pyrimidin-4-one (CAS 63234-80-0) (100 mg) in N,N-dimethylformamide (3 ml), the compound obtained in Production Example 5 (120 mg), anhydrous potassium carbonate (134 mg) and sodium iodide (66 mg) were added and the mixture was stirred at 90° C. for 12 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the free form of the title compound (124 mg). This was dissolved in ethanol, and then oxalic acid (28 mg) was added. Diethyl ether was then added to produce a solid, which was collected by filtration to obtain the title compound (137 mg).

$^1$H-NMR (400 MHz, DMSO-d$_6$); δ 1.72-1.90 (m, 4H), 2.00-2.30 (m, 11H), 2.74-2.86 (m, 4H), 2.90-3.02 (m, 2H), 3.72-3.82 (m, 3H), 4.04 (br s, 2H), 4.53 (s, 2H), 7.16-7.24 (m, 2H), 7.33-7.40 (m, 1H), 7.42-7.48 (m, 1H).

Example 179

(Endo)-3-{2-[3-(2-fluorobenzyloxy)-8-azabicyclo[3.2.1]oct-8-yl]ethyl}-2-methylpyrido[1,2-a]pyrimidin-4-one oxalate

[Chemical Formula 298]

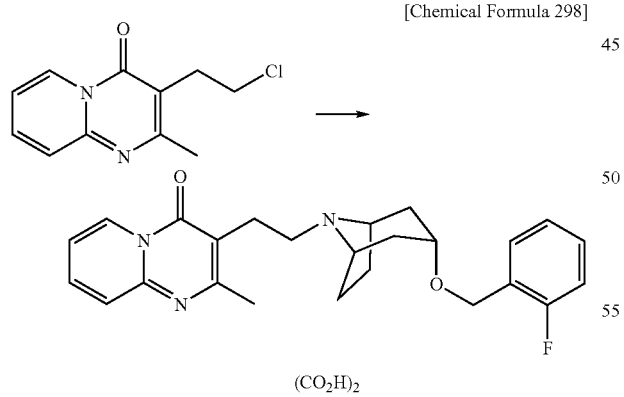

(CO₂H)₂

The title compound (119 mg) was obtained from 3-(2-chloroethyl)-2-methyl-pyrido[1,2-a]pyrimidin-4-one (CAS 41078-70-0) (70 mg) and the compound obtained in Production Example 5 (85 mg), by the method similar to Example 178.

$^1$H-NMR (400 MHz, DMSO-d$_6$); δ 2.04-2.34 (m, 8H), 2.50 (s, 3H), 2.98-3.14 (m, 4H), 3.73-3.80 (m, 1H), 4.04-4.16 (m, 2H), 4.54 (s, 2H), 7.17-7.24 (m, 2H), 7.30-7.40 (m, 2H), 7.43-7.48 (m, 1H), 7.60-7.64 (m, 1H), 7.88-7.94 (m, 1H), 8.87-8.92 (m, 1H).

Example 180

(Endo)-3-{2-[3-(2-fluorobenzyloxy)-8-azabicyclo[3.2.1]oct-8-yl]ethyl}-2-methyl-5,6,7,8-tetrahydro-3H-quinazolin-4-one oxalate

[Chemical Formula 299]

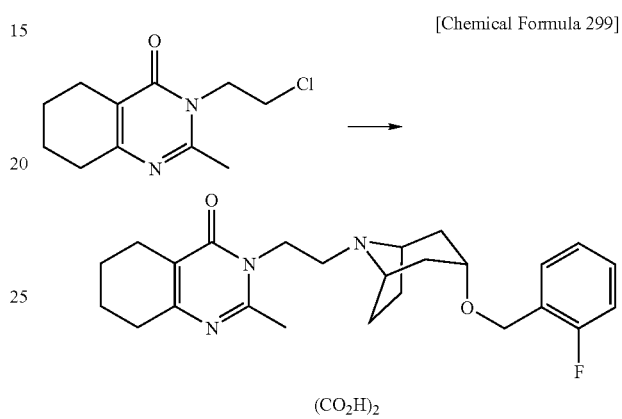

(CO₂H)₂

The title compound (52 mg) was obtained from 3-(2-chloroethyl)-2-methyl-5,6,7,8-tetrahydro-3H-quinazolin-4-one (CAS 142221-86-1) (80 mg) and the compound obtained in Production Example 5 (96 mg), by the method similar to Example 178.

$^1$H-NMR (400 MHz, DMSO-d$_6$); δ 1.50-1.74 (m, 4H), 1.98-2.24 (m, 8H), 2.30-2.37 (m, 2H), 2.43-2.53 (m, 5H), 3.06-3.18 (m, 2H), 3.50-3.56 (m, 1H), 3.84-3.96 (m, 2H), 4.18-4.26 (m, 2H), 4.52 (s, 2H), 7.16-7.23 (m, 2H), 7.32-7.39 (m 1H), 7.42-7.47 (m, 1H).

Example 181

(Endo)-6-{2-[3-(2-fluorobenzyloxy)-8-azabicyclo[3.2.1]oct-8-yl]ethyl}-7-methyl-2,3-dihydrothiazolo[3,2-a]pyrimidin-5-one oxalate

[Chemical Formula 300]

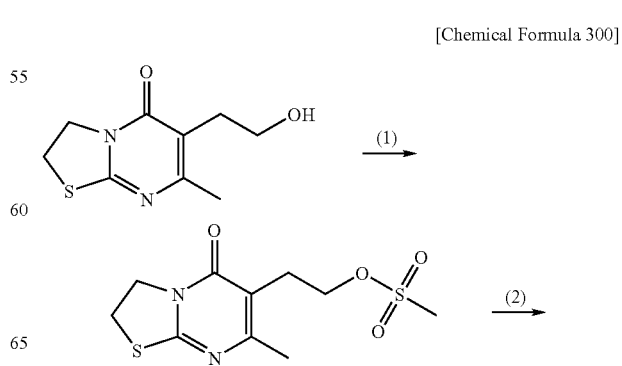

323
-continued

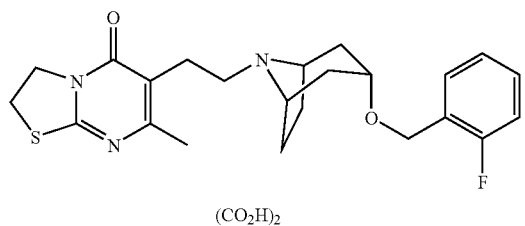

(CO₂H)₂

(1) Methanesulfonic acid 2-(7-methyl-5-oxo-2,3-dihydro-5H-thiazolo[3,2-a]pyrimidin-6-yl)ethyl ester After dissolving 6-(2-hydroxy-ethyl)-7-methyl-2,3-dihydro-thiazolo[3,2-a]pyrimidin-5-one (CAS 86487-53-8) (225 mg) in dichloromethane (10 ml), triethylamine (0.44 ml) was added, and then methanesulfonyl chloride (0.20 ml) was added dropwise while stirring on ice. After stirring for 10 minutes, ethyl acetate was added to the reaction mixture and the resulting mixture was filtered. The filtrate was concentrated under reduced pressure, and the residue was purified by NH silica gel column chromatography to obtain the title compound (264 mg).

¹H-NMR (400 MHz, CDCl₃); δ 2.31 (s, 3H), 2.95 (t, J=6.8 Hz, 2H), 2.99 (s, 3H), 3.46 (t, J=7.6 Hz, 2H), 4.37 (t, J=6.8 Hz, 2H), 4.45 (t, J=7.6 Hz, 2H).

(2) (Endo)-6-{2-[3-(2-fluorobenzyloxy)-8-azabicyclo[3.2.1]oct-8-yl]ethyl}-7-methyl-2,3-dihydrothiazolo[3,2-a]pyrimidin-5-one oxalate The title compound (137 mg) was obtained from the compound obtained in Example 181-(1) (106 mg) and the compound obtained in Production Example 5 (90 mg), by the method similar to Example 178.

¹H-NMR (400 MHz, DMSO-d₆); δ 2.00-2.27 (m, 11H), 2.75-2.82 (m, 2H), 2.88-3.01 (m, 2H), 3.52 (t, J=7.6 Hz, 2H), 3.72-3.78 (m, 1H), 3.95-4.07 (m, 2H), 4.33 (t, J=7.6 Hz, 2H), 4.54 (s, 2H), 7.18-7.25 (m, 2H), 7.34-7.41 (m, 1H), 7.43-7.49 (m, 1H).

Example 182

(Endo)-7-{3-[3-(2-fluorobenzyloxy)-8-azabicyclo[3.2.1]oct-8-yl]propyl}-1,3-dimethyl-3,7-dihydropurine-2,6-dione

[Chemical Formula 301]

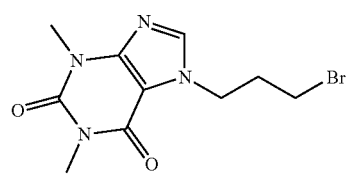

324
-continued

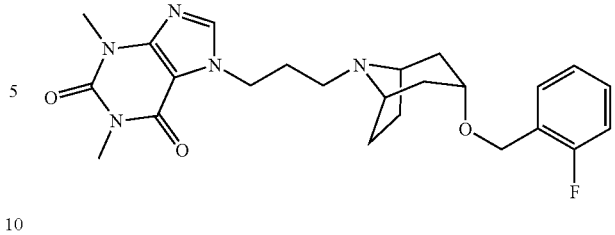

The title compound (62 mg) was obtained from 7-(3-bromopropyl)-1,3-dimethyl-3,7-dihydro-purine-2,6-dione (CAS 23146-06-7) (97 mg) and the compound obtained in Production Example 5 (80 mg), by the method similar to Example 58-(2).

¹H-NMR (400 MHz, CDCl₃); δ 1.79-2.12 (m, 10H), 2.23-2.34 (m, 2H), 3.06-3.16 (m, 2H), 3.41 (s, 3H), 3.60 (s, 3H), 3.63-3.68 (m, 1H), 4.44 (t, J=6.4 Hz, 2H), 4.51 (s, 2H), 6.99-7.05 (m, 1H), 7.11-7.16 (m, 1H), 7.22-7.28 (m, 1H), 7.40-7.46 (m, 1H), 7.63 (s, 1H).

Example 183

(Endo)-1-{3-[3-(2-fluorobenzyloxy)-8-azabicyclo[3.2.1]oct-8-yl]propyl}-3,7-dimethyl-3,7-dihydropurine-2,6-dione

[Chemical Formula 302]

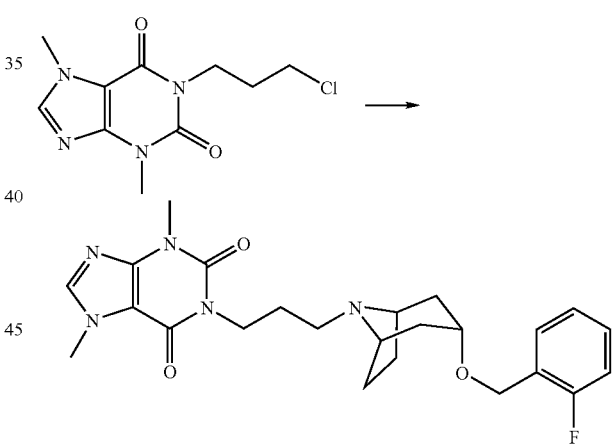

A mixture of 1-(3-chloropropyl)-3,7-dimethyl-3,7-dihydro-purine-2,6-dione (CAS 74409-52-2) (83 mg), the compound obtained in Production Example 5 (80 mg), anhydrous potassium carbonate (90 mg), benzyltriethylammonium bromide (80 mg) and N,N-dimethylformamide (1 ml) was stirred at room temperature for 5 days. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography. The obtained solid was washed with diethyl ether/n-heptane to obtain the title compound (52 mg).

¹H-NMR (400 MHz, CDCl₃); δ 1.80-2.06 (m, 10H), 2.46 (t, J=7.2 Hz, 2H), 3.15-3.23 (m, 2H), 3.57 (s, 3H), 3.57-3.64 (m, 1H), 3.99 (s, 3H), 4.10 (t, J=7.2 Hz, 2H), 4.49 (s, 2H), 6.98-7.04 (m, 1H), 7.10-7.16 (m, 1H), 7.21-7.28 (m, 1H), 7.40-7.46 (m, 1H), 7.49 (s, 1H).

Example 184

(Endo)-5-{2-[3-(2-fluorobenzyloxy)-8-azabicyclo[3.2.1]oct-8-yl]ethyl}-2,3,6-trimethyl-3H-pyrimidin-4-one oxalate

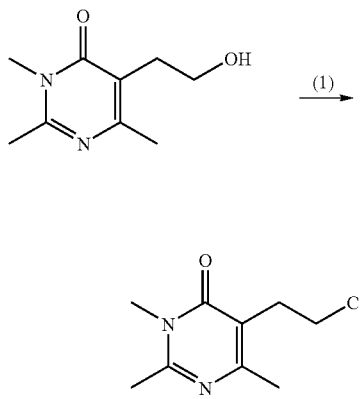

[Chemical Formula 303]

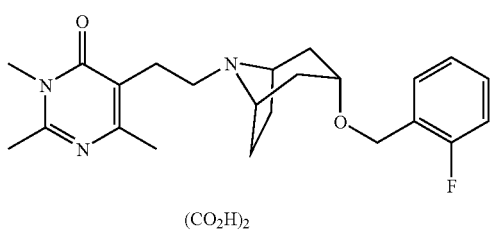

(1) 5-(2-Chloroethyl)-2,36-trimethyl-3H-pyrimidin-4-one

After dissolving 5-(2-hydroxyethyl)-2,3,6-trimethyl-3H-pyrimidin-4-one (CAS 181525-32-6) (120 mg) in dichloromethane (5 ml), triethylamine (0.29 ml) was added, and then methanesulfonyl chloride (0.13 ml) was added dropwise while stirring on ice. After stirring for 14 hours at room temperature, the reaction mixture was concentrated under reduced pressure. The residue was purified by silica gel column chromatography to obtain the title compound (208 mg).

$^1$H-NMR (400 MHz, CDCl$_3$); δ 2.33 (s, 3H), 2.50 (s, 3H), 2.99 (t, J=6.8 Hz, 2H), 3.51 (s, 3H), 3.75 (t, J=6.8 Hz, 2H).

(2) (Endo)-5-{2-[3-(2-fluorobenzyloxy)-8-azabicyclo[3.2.1]oct-8-yl]ethyl}-2,3,6-trimethyl-3H-pyrimidin-4-one oxalate The title compound (131 mg) was obtained from the compound obtained in Example 184-(1) (100 mg) and the compound obtained in Production Example 5 (136 mg), by the method similar to Example 178.

$^1$H-NMR (400 MHz, DMSO-d$_6$); δ 2.00-2.30 (m, 1H), 2.45 (s, 3H), 2.77-2.85 (m, 2H), 2.90-3.00 (m, 2H), 3.42 (s, 3H), 3.72-3.77 (m, 1H), 3.86-4.04 (m, 2H), 4.54 (s, 2H), 7.17-7.25 (m, 2H), 7.34-7.41 (m, 1H), 7.43-7.49 (m, 1H).

Example 185

(Endo)-5-[2-(3-cyclohexylmethoxy-8-azabicyclo[3.2.1]oct-8-yl)ethyl]-2,3,6-trimethyl-3H-pyrimidin-4-one oxalate

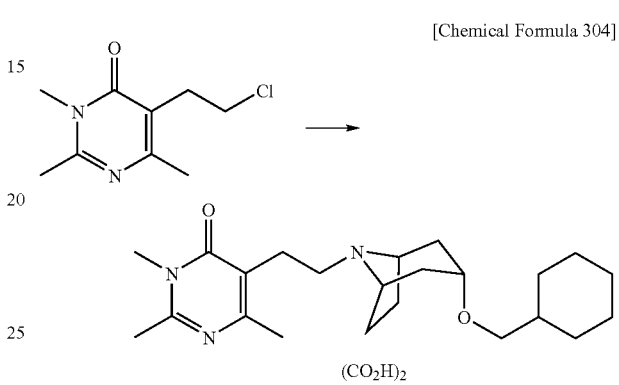

[Chemical Formula 304]

The title compound (99 mg) was obtained from the compound obtained in Example 184-(1) (68 mg) and the compound obtained in Production Example 11 (80 mg), by the method similar to Example 178.

$^1$H-NMR (400 MHz, DMSO-d$_6$); δ 0.88-1.00 (m, 2H), 1.09-1.28 (m, 3H), 1.44-1.56 (m, 1H), 1.59-1.74 (m, 5H), 1.96-2.21 (m, 8H), 2.23 (s, 3H), 2.45 (s, 3H), 2.76-2.83 (m, 2H), 2.87-3.00 (m, 2H), 3.17 (d, J=6.0 Hz, 2H), 3.42 (s, 3H), 3.51-3.60 (m, 1H), 3.93-4.03 (m, 2H).

Example 186

(Endo)-5-{2-[3-(2-fluorobenzyloxy)-8-azabicyclo[3.2.1]oct-8-yl]ethyl}-1,3,6-trimethyl-1H-pyrimidine-2,4-dione oxalate

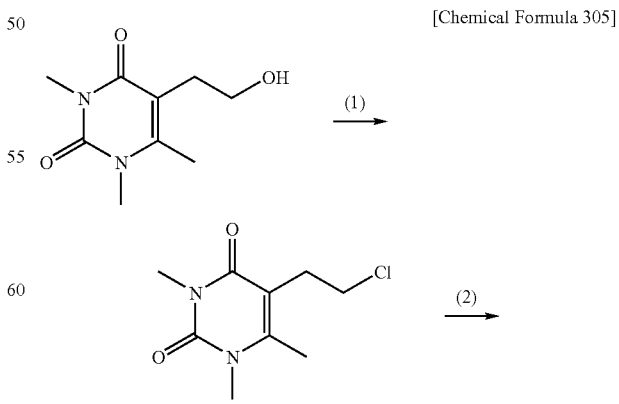

[Chemical Formula 305]

-continued

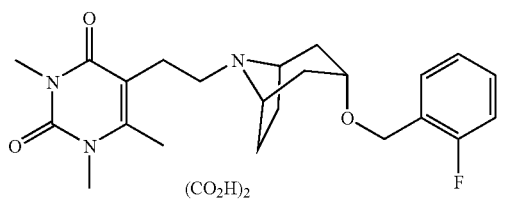

(CO₂H)₂

(1) 5-(2-Chloroethyl)-1,3,6-trimethyl-1H-pyrimidine-2,4-dione

The title compound (504 mg) was obtained from 5-(2-hydroxy-ethyl)-1,3,6-trimethyl-1H-pyrimidine-2,4-dione (CAS 14181-48-7) (500 mg) by the method similar to Example 184-(1).

$^1$H-NMR (400 MHz, CDCl$_3$); δ 2.33 (s, 3H), 2.93 (t, J=6.4 Hz, 2H), 3.36 (s, 3H), 3.47 (s, 3H), 3.71 (t, J=6.4 Hz, 2H).

(2) (Endo)-5-{2-[3-(2-fluorobenzyloxy)-8-azabicyclo[3.2.1]oct-8-yl]ethyl}-1,3,6-trimethyl-1H-pyrimidine-2,4-dione oxalate The title compound (127 mg) was obtained from the compound obtained in Example 186-(1) (88 mg) and the compound obtained in Production Example 5 (100 mg), by the method similar to Example 178.

$^1$H-NMR (400 MHz, DMSO-d$_6$); δ 1.96-2.23 (m, 8H), 2.30 (s, 3H), 2.50-2.86 (m, 4H), 3.19 (s, 3H), 3.37 (s, 3H), 3.70-3.75 (m, 1H), 3.83-3.94 (m, 2H), 4.52 (s, 2H), 7.17-7.25 (m, 2H), 7.34-7.41 (m, 1H), 7.43-7.49 (m, 1H).

Example 187

(Endo)-3-{3-[3-(2-fluorobenzyloxy)-8-azabicyclo[3.2.1]oct-8-yl]propyl}-2-methoxy-5,6,7,8-tetrahydro-3H-quinazolin-4-one

[Chemical Formula 306]

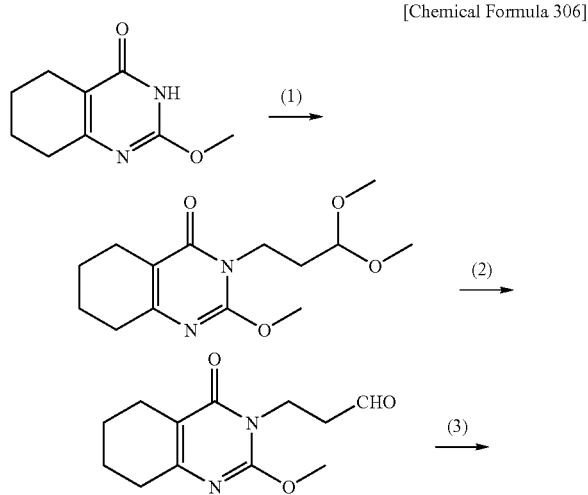

-continued

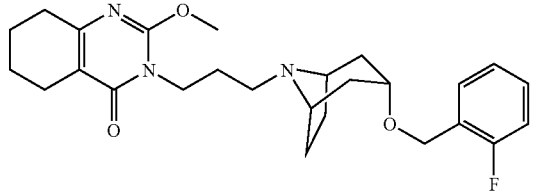

(1) 3-(3,3-Dimethoxypropyl)-2-methoxy-5,6,7,8-tetrahydro-3H-quinazolin-4-one After dissolving 2-methoxy-5,6,7,8-tetrahydro-3H-quinazolin-4-one (CAS 94815-67-5) (2.0 g) and 3-bromopropionaldehyde dimethylacetal (2.44 g) in N,N-dimethylformamide (30 ml), sodium hydride (60% in oil) (533 mg) was added, and the mixture was stirred at room temperature for 30 minutes and at 100° C. for 5 hours. Water was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (640 mg).

$^1$H-NMR (400 MHz, CDCl$_3$); δ 1.67-1.80 (m, 4H), 1.91-1.97 (m, 2H), 2.41-2.46 (m, 2H), 2.47-2.52 (m, 2H), 3.33 (s, 6H), 3.96 (s, 3H), 4.01-4.06 (m, 2H), 4.49 (t, J=5.6 Hz, 1H).

(2) 3-(2-Methoxy-4-oxo-5,6,7,8-tetrahydro-4H-quinazolin-3-yl)propionaldehyde The title compound (466 mg) was obtained from the compound obtained in Example 187-(1) (640 mg), by the method similar to Example 84-(3).

$^1$H-NMR (400 MHz, CDCl$_3$); δ 1.67-1.80 (m, 4H), 2.40-2.52 (m, 4H), 2.78 (td, J=7.2, 1.6 Hz, 2H), 3.96 (s, 3H), 4.32 (t, J=7.2 Hz, 2H), 9.80 (t, J=1.6 Hz, 1H).

(3) (Endo)-3-{3-[3-(2-fluorobenzyloxy)-8-azabicyclo[3.2.1]oct-8-yl]propyl}-2-methoxy-5,6,7,8-tetrahydro-3H-quinazolin-4-one Sodium triacetoxyborohydride (331 mg) was added to a mixture of the compound obtained in Example 187-(2) (230 mg), the compound obtained in Production Example 5 (291 mg) and dichloromethane (5 ml), and the mixture was stirred at room temperature for 20 hours. A saturated aqueous solution of sodium hydrogencarbonate was added to the reaction mixture, and extraction was performed with ethyl acetate. The organic layer was washed with water and brine in that order and then dried over anhydrous magnesium sulfate. After filtration, the solvent was distilled off under reduced pressure. The residue was purified by NH silica gel column chromatography to obtain the title compound (354 mg).

$^1$H-NMR (400 MHz, CDCl$_3$); δ 1.66-2.06 (m, 14H), 2.38-2.52 (m, 6H), 3.12-3.18 (m, 2H), 3.62 (t, J=4.8 Hz, 1H), 3.95

(s, 3H), 4.05 (t, J=7.6 Hz, 2H), 4.50 (s, 2H), 6.98-7.05 (m, 1H), 7.11-7.16 (m, 1H), 7.21-7.28 (m, 1H), 7.42-7.47 (m, 1H).

Example 188

(Endo)-1-{3-[3-(2-fluorobenzyloxy)-8-azabicyclo[3.2.1]oct-8-yl]propyl}-3-methyl-5,6,7,8-tetrahydro-1H-quinazoline-2,4-dione

[Chemical Formula 307]

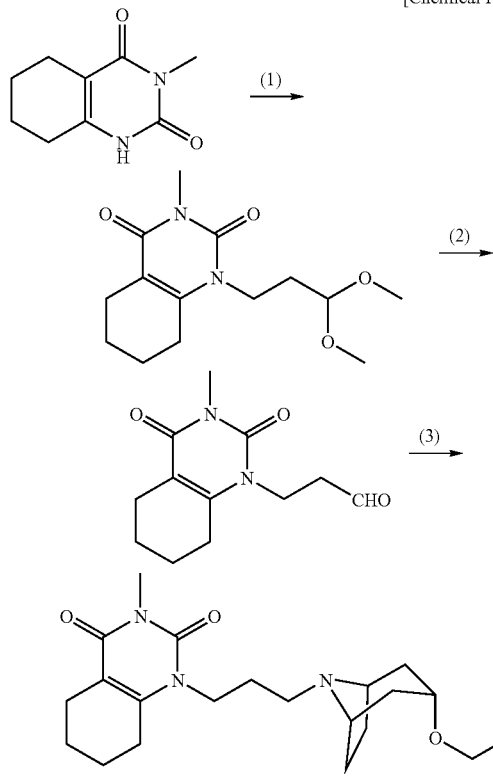

(1) 1-(3,3-Dimethoxypropyl)-3-methyl-5,6,7,8-tetrahydro-1H-quinazoline-2,4-dione After suspending 3-methyl-5,6,7,8-tetrahydro-1H-quinazoline-2,4-dione (CAS 85458-77-1) (500 mg) in methanol (10 ml), potassium tert-butoxide (342 mg) was added and the mixture was stirred at room temperature for 30 minutes. After then adding 3-bromopropionaldehyde dimethylacetal (0.57 ml), the mixture was heated to reflux for 5 hours. The reaction mixture was concentrated under reduced pressure, water was added to the residue, and extraction was performed with ethyl acetate. The organic layer was washed with water and brine in that order and then dried over anhydrous magnesium sulfate. After filtration, the solvent was distilled off under reduced pressure. The residue was purified by silica gel column chromatography to obtain the title compound (235 mg).

$^1$H-NMR (400 MHz, CDCl$_3$); δ 1.64-1.71 (m, 2H), 1.78-1.85 (m, 2H), 1.93-1.99 (m, 2H), 2.41-2.46 (m, 2H), 2.51-2.56 (m, 2H), 3.36 (s, 3H), 3.60 (s, 6H), 3.38-3.94 (m, 2H), 4.45 (t, J=5.6 Hz, 1H).

(2) 3-(3-Methyl-2,4-dioxo-3,4,5,6,7,8-hexahydro-2H-quinazolin-1-yl)propionaldehyde The title compound (212 mg) was obtained from the compound obtained in Example 188-(1) (235 mg), by the method similar to Example 84-(3).

$^1$H-NMR (400 MHz, CDCl$_3$); δ 1.63-1.71 (m, 2H), 1.78-1.86 (m, 2H), 2.40-2.46 (m, 2H), 2.51-2.56 (m, 2H), 2.90 (td, J=7.2, 0.8 Hz, 2H), 3.34 (s, 3H), 4.14 (t, J=7.2 Hz, 2H), 9.81 (d, J=0.8 Hz, 1H).

(3) (Endo)-1-{3-[3-(2-fluorobenzyloxy)-8-azabicyclo[3.2.1]oct-8-yl]propyl}-3-methyl-5,6,7,8-tetrahydro-1H-quinazoline-2,4-dione The title compound (73 mg) was obtained from the compound obtained in Example 188-(2) (77 mg) and the compound obtained in Production Example 5 (80 mg), by the method similar to Example 187-(3).

$^1$H-NMR (400 MHz, CDCl$_3$); δ 1.63-2.14 (m, 12H), 2.33-2.47 (m, 4H), 2.59-2.66 (m, 2H), 3.09-3.20 (m, 2H), 3.36 (s, 3H), 3.60-3.68 (m, 1H), 3.90-3.97 (m, 2H), 4.50 (s, 2H), 6.99-7.06 (m, 1H), 7.11-7.16 (m, 1H), 7.21-7.29 (m, 1H), 7.40-7.46 (m, 1H).

Example 189

(Endo)-3-{3-[3-(2-fluorobenzyloxy)-8-azabicyclo[3.2.1]oct-8-yl]propyl}-1,5,6-trimethyl-1H-pyrimidine-2,4-dione oxalate

[Chemical Formula 308]

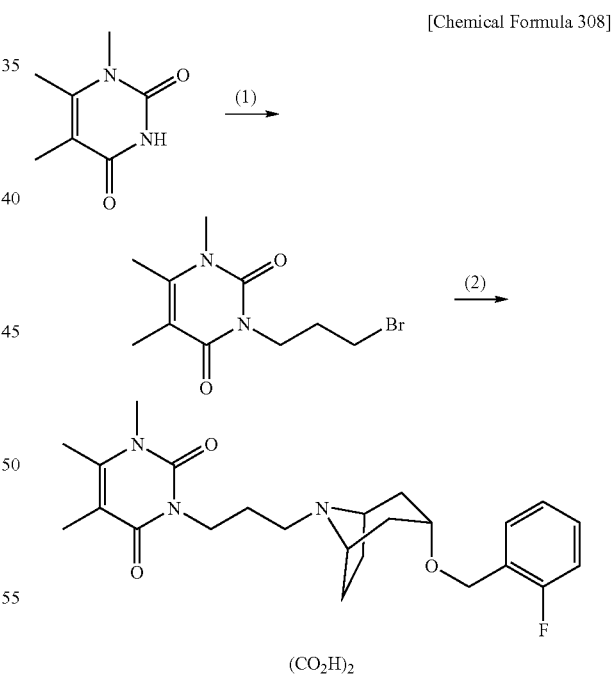

(1) 3-(3-Bromopropyl)-1,5,6-trimethyl-1H-pyrimidine-2,4-dione

The title compound (1.27 g) was obtained from 1,5,6-trimethyl-1H-pyrimidine-2,4-dione (CAS 31111-40-7) (1.0 g) and 1,3-dibromopropane by the method similar to Example 69-(1).

¹H-NMR (400 MHz, CDCl₃); δ 1.99 (s, 3H), 2.21-2.26 (m, 5H), 3.41-3.44 (m, 5H), 4.09-4.12 (m, 2H).

(2) (Endo)-3-{3-[3-(2-fluorobenzyloxy)-8-azabicyclo[3.2.1]oct-8-yl]propyl}-1,5,6-trimethyl-1H-pyrimidine-2,4-dione oxalate The title compound (147 mg) was obtained from the compound obtained in Example 189-(1) (100 mg) and the compound obtained in Production Example 5 (109 mg), by the method similar to Example 69-(2).

¹H-NMR (400 MHz, CD₃OD); δ 1.98 (s, 3H), 2.05-2.12 (m, 2H), 2.16-2.19 (m, 2H), 2.28 (bs, 4H), 2.33 (s, 3H), 2.42-2.47 (m, 2H), 3.06 (bs, 2H), 3.45 (s, 3H), 3.81-3.82 (m, 1H), 3.96 (bs, 2H), 4.03-4.07 (m, 2H), 4.58 (s, 2H), 7.07-7.11 (m, 1H), 7.15-7.19 (m, 1H), 7.31-7.37 (m, 1H), 7.41-7.45 (m, 1H).

Example 190

(Endo)-1-{3-[3-(2-fluorobenzyloxy)-8-azabicyclo[3.2.1]oct-8-yl]-2-hydroxypropyl}-4-phenyl-1,4-dihydro-tetrazol-5-one

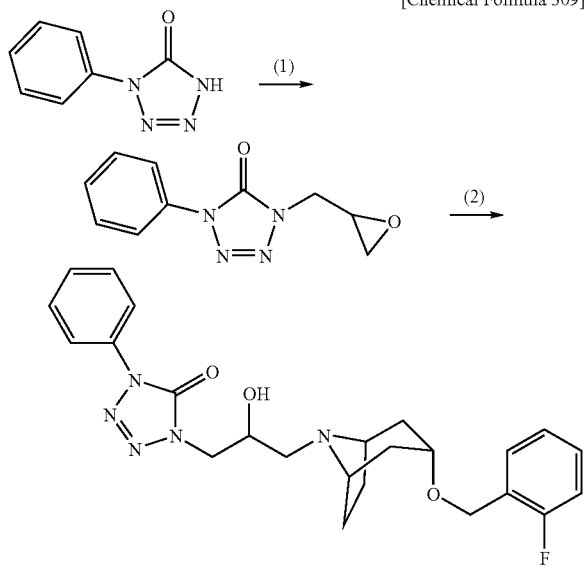

[Chemical Formula 309]

(1) 1-Oxiranylmethyl-4-phenyl-1,4-dihydro-tetrazol-5-one

The title compound (1.22 g) was obtained from 1-phenyl-1,2-dihydro-tetrazol-5-one (CAS 5097-82-5) (2.0 g) and epibromohydrin by the method similar to Example 27-(1).

¹H-NMR (400 MHz, CDCl₃); δ 2.77 (dd, J=4.4, 2.0 Hz, 1H), 2.93 (t, J=4.4 Hz, 1H), 3.38-3.42 (m, 1H), 4.21 (d, J=3.2 Hz, 1H), 4.22 (d, J=2.4 Hz, 1H), 7.35-7.40 (m, 1H), 7.47-7.53 (m, 2H), 7.91-7.95 (m, 2H).

(2) (Endo)-1-{3-[3-(2-fluorobenzyloxy)-8-azabicyclo[3.2.1]oct-8-yl]-2-hydroxypropyl}-4-phenyl-1,4-dihydro-tetrazol-5-one The title compound (100 mg) was obtained from the compound obtained in Example 190-(1) (100 mg) and the compound obtained in Production Example 5 (124 mg), by the method similar to Example 36-(2).

¹H-NMR (400 MHz, CD₃OD); δ 1.81-2.12 (m, 8H), 2.51 (dd, J=14.4, 5.6 Hz, 1H), 2.55 (dd, J=14.4, 6.0 Hz, 1H), 3.16-3.21 (m, 1H), 3.23-3.28 (m, 1H), 3.58 (t, J=4.8 Hz, 1H), 4.06 (dd, J=14.4, 7.2 Hz, 1H), 4.08-4.16 (m, 1H), 4.20 (dd, J=14.4, 3.6 Hz, 1H), 4.48 (s, 2H), 7.01-7.08 (m, 1H), 7.14 (td, J=7.2, 1.2 Hz, 1H), 7.25-7.32 (m, 1H), 7.38-7.44 (m, 2H), 7.50-7.56 (m, 2H), 7.87-7.92 (m, 2H).

Example 191

(Endo)-5-ethanesulfonyl-4-ethyl-2-{3-[3-(2-fluorobenzyloxy)-8-azabicyclo[3.2.1]oct-8-yl]propyl}-2,4-dihydro[1,2,4]triazol-3-one oxalate

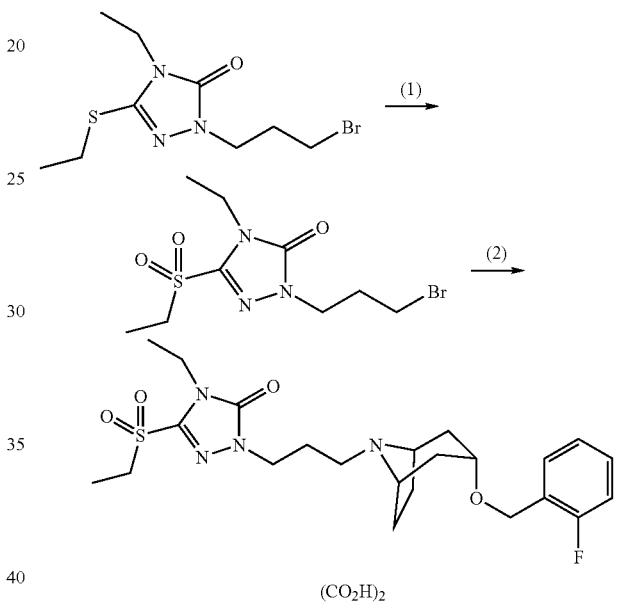

[Chemical Formula 310]

(1) 2-(3-Bromopropyl)-5-ethanesulfonyl-4-ethyl-2,4-dihydro[1,2,4]triazol-3-one

After dissolving the compound obtained in Example 60-(1) (120 mg) in dichloromethane (10 ml), m-chloroperbenzoic acid (194 mg) was added while stirring on ice. The mixture was stirred for 30 minutes on ice, and then for 30 minutes at room temperature. After further adding m-chloroperbenzoic acid (97 mg), stirring was continued at room temperature for another 30 minutes. A saturated aqueous solution of sodium hydrogencarbonate was added to the reaction mixture, and extraction was performed with dichloromethane. The organic layer was dried over anhydrous magnesium sulfate and filtered, and then the solvent was distilled off under reduced pressure. The residue was purified by NH silica gel column chromatography to obtain the title compound (118 mg).

¹H-NMR (400 MHz, CD₃OD); δ 1.39 (t, J=7.6 Hz, 3H), 1.47 (t, J=7.6 Hz, 3H), 2.33 (quintet, J=6.8 Hz, 2H), 3.40-3.49 (m, 4H), 4.00-4.08 (m, 4H).

(2) (Endo)-5-ethanesulfonyl-4-ethyl-2-{3-[3-(2-fluorobenzyloxy)-8-azabicyclo[3.2.1]oct-8-yl]propyl}-2,4-dihydro[1,2,4]triazol-3-one oxalate A mixture of the compound obtained in Example 191-(1) (50 mg), the compound obtained in Production Example 5 (54 mg), anhydrous potassium carbonate (102 mg), sodium iodide (55 mg) and N,N-dimethylformamide (2 ml) was stirred overnight at room temperature. Water was added to the reaction mixture and extraction was performed with diethyl ether. The organic layer was washed with water and brine in that order and then dried over anhydrous magnesium sulfate. After filtration, the solvent was distilled off under reduced pressure. The residue was purified by NH silica gel column chromatography to obtain the free form of the title compound (39 mg).

This was dissolved in methanol (2 ml), and then oxalic acid (7 mg) was added and the solvent was distilled off under reduced pressure. Diethyl ether was added to the residue to produce a solid which was collected by filtration. The title compound (32 mg) was thus obtained.

$^1$H-NMR (400 MHz, CD$_3$OD); δ 1.35 (t, J=7.6 Hz, 3H), 1.38 (t, J=7.6 Hz, 3H), 2.12-2.38 (m, 8H), 2.40-2.50 (m, 2H), 3.12 (brs, 2H), 3.50 (q, J=7.6 Hz, 2H), 3.80 (brs, 1H), 3.95-4.05 (m, 4H), 4.58 (s, 2H), 7.06-7.12 (m, 1H), 7.15-7.20 (m, 1H), 7.30-7.38 (m, 1H), 7.40-7.45 (m, 1H).

Example 192

(Endo)-1,6-dimethyl-3-{3-[3-(naphthalen-2-yl-methoxy)-8-azabicyclo[3.2.1]oct-8-yl]propyl}-1H-[1,3,5]triazine-2,4-dione

[Chemical Formula 311]

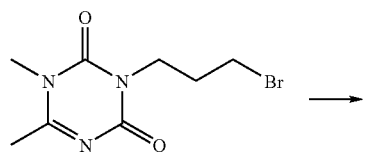

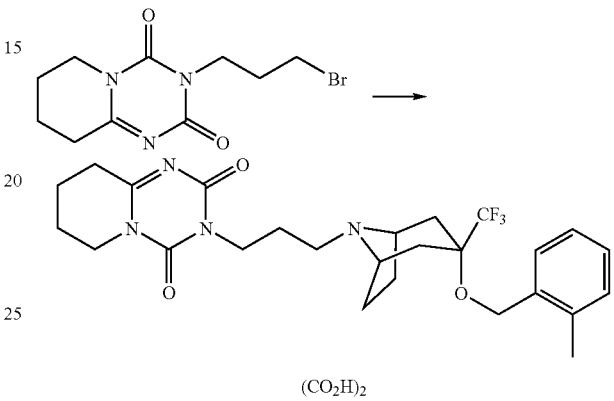

A mixture of the compound obtained in Example 72-(1) (100 mg), the compound obtained in Production Example 70 (116 mg), anhydrous potassium carbonate (116 mg) and N,N-dimethylformamide (1 ml) was stirred at room temperature for 22 hours. Ethyl acetate was added to the reaction mixture and the mixture was filtered. The filtrate was concentrated under reduced pressure and the residue was purified by silica gel column chromatography. The obtained solid was washed with diethyl ether to obtain the title compound (140 mg).

$^1$H-NMR (400 MHz, CDCl$_3$); δ 1.79-1.93 (m, 8H), 2.05-2.10 (m, 2H), 2.41-2.46 (m, 2H), 2.44 (s, 3H), 3.13-3.19 (m, 2H), 3.45 (s, 3H), 3.63-3.67 (m, 1H), 4.01 (t, J=7.2 Hz, 2H), 4.60 (s, 2H), 7.43-7.49 (m, 3H9, 7.76 (s, 1H), 7.80-7.84 (m, 3H).

Example 193

3-{3-[3α-(2-methylbenzyloxy)-3β-trifluoromethyl-8-azabicyclo[3.2.1]oct-8-yl]propyl}-6,7,8,9-tetrahydropyrido[1,2-a][1,3,5]triazine-2,4-dione oxalate

[Chemical Formula 312]

The title compound (53 mg) was obtained from the compound obtained in Example 129-(1) (75 mg) and the compound obtained in Production Example 71 (80 mg), by the method similar to Example 57-(2).

$^1$H-NMR (400 MHz, CD$_3$OD); δ 1.84-1.91 (m, 2H), 1.92-2.00 (m, 2H), 2.08-2.25 (m, 6H), 2.36 (s, 3H), 2.38-2.53 (m, 4H), 2.74-2.81 (m, 2H), 3.09-3.14 (m, 2H), 3.82 (t, J=6.0 Hz, 2H), 4.00 (t, J=6.8 Hz, 2H), 4.05-4.10 (m, 2H), 4.74 (s, 2H), 7.15-7.25 (m, 3H), 7.35-7.38 (m, 1H).

Example 194

2-{3-[3α-(2-methylbenzyloxy)-3β-trifluoromethyl-8-azabicyclo[3.2.1]oct-8-yl]propyl}-2H-[1,2,4]triazolo[4,3-a]pyridin-3-one

[Chemical Formula 313]

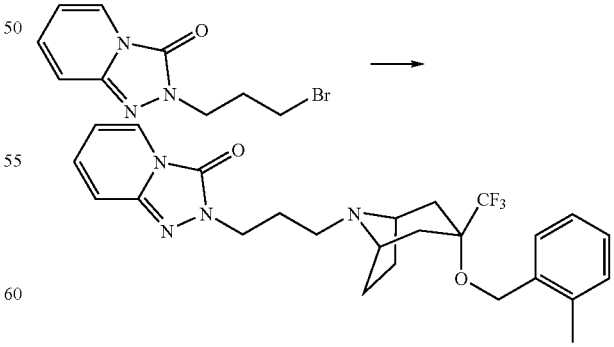

The title compound (42 mg) was obtained from the compound obtained in Example 145-(1) (50 mg) and the compound obtained in Production Example 71 (60 mg), by the method similar to Example 58-(2).

¹H-NMR (400 MHz, CD₃OD); δ 1.76-2.11 (m, 10H), 2.32 (s, 3H), 2.45-2.55 (m, 2H), 3.22-3.32 (m, 2H), 4.11 (t, J=6.8 Hz, 2H), 4.59 (s, 2H), 6.45-6.53 (m, 1H), 7.05-7.11 (m, 2H), 7.15-7.24 (m, 3H), 7.34-7.39 (m, 1H), 7.76 (dt, J=7.2, 1.2 Hz, 1H).

Example 195

(Exo)-3-{3-[3-(4-methoxybenzylsulfanyl)-8-azabicyclo[3.2.1]oct-8-yl]propyl}-1,6-dimethyl-1H-[1,3,5]triazine-2,4-dione oxalate

[Chemical Formula 314]

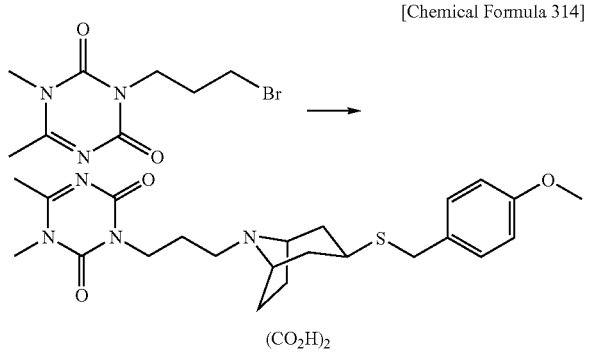

The title compound (124 mg) was obtained from the compound obtained in Example 72-(1) (100 mg) and the compound obtained in Production Example 72 (101 mg), by the method similar to Example 137.

¹H-NMR (400 MHz, CD₃OD); δ 1.86-2.12 (m, 8H), 2.18-2.24 (m, 2H), 2.46 (s, 3H), 3.06-3.08 (m, 3H), 3.45 (s, 3H), 3.76 (s, 2H), 3.77 (s, 3H), 3.93-3.99 (m, 4H), 6.84-6.88 (m, 2H), 7.24-7.28 (m, 2H).

Example 196

(Endo)-3-{3-[3-(4-methoxybenzylsulfanyl)-8-azabicyclo[3.2.1]oct-8-yl]propyl}-1,6-dimethyl-1H-[1,3,5]triazine-2,4-dione oxalate

[Chemical Formula 315]

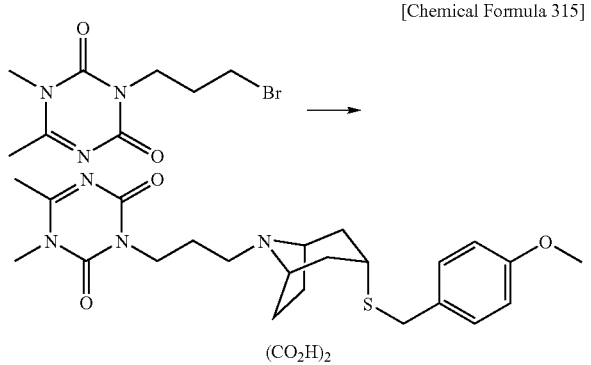

The title compound (124 mg) was obtained from the compound obtained in Example 72-(i) (80 mg) and the compound obtained in Production Example 73 (92 mg), by the method similar to Example 137.

¹H-NMR (400 MHz, CD₃OD); δ 2.02-2.12 (m, 4H), 2.20-2.28 (m, 2H), 2.43-2.56 (m, 4H), 2.46 (s, 3H), 3.02 (t, J=7.6 Hz, 1H), 3.05-3.12 (m, 3H), 3.45 (s, 3H), 3.76 (s, 3H), 3.79 (s, 2H), 3.93-4.00 (m, 4H), 6.84-6.88 (m, 2H), 7.22-7.26 (m, 2H).

Example 197

(Endo)-2-((R)-2-fluoro-3-{3-[2-(2-fluorophenyl)-ethyl]-8-azabicyclo[3.2.1]oct-8-yl}propyl)-4,5-dimethyl-2,4-dihydro[1,2,4]triazol-3-one

[Chemical Formula 316]

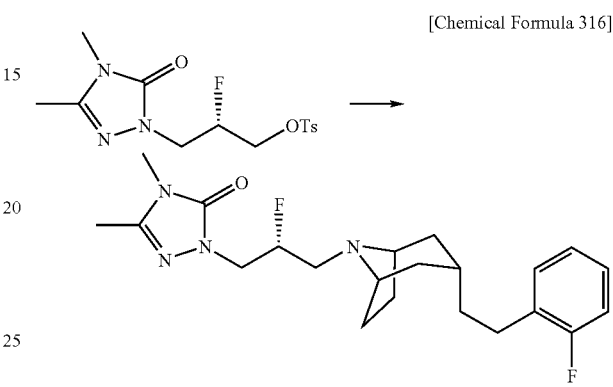

The title compound (71 mg) was obtained from the compound obtained in Example 1-(3) (100 mg) and the compound obtained in Production Example 42 (79 mg), by the method similar to Example 1-(4).

¹H-NMR (400 MHz, CD₃OD); δ1.37-1.45 (m, 2H), 1.62-1.81 (m, 5H), 1.94-2.02 (m, 2H), 2.09-2.20 (m, 2H), 2.23 (s, 3H), 2.58-2.76 (m, 2H), 3.18-3.34 (m, 2H), 3.23 (s, 3H), 3.85-4.10 (m, 2H), 4.78-4.98 (m, 1H), 6.95-7.09, 7.12-7.24 (m, 2H).

Example 198

(Exo)-2-{(R)-2-fluoro-3-[3-(2-fluorobenzyloxy)-8-azabicyclo[3.2.1]oct-8-yl]propyl}-4,5-dimethyl-2,4-dihydro[1,2,4]triazol-3-one

[Chemical Formula 317]

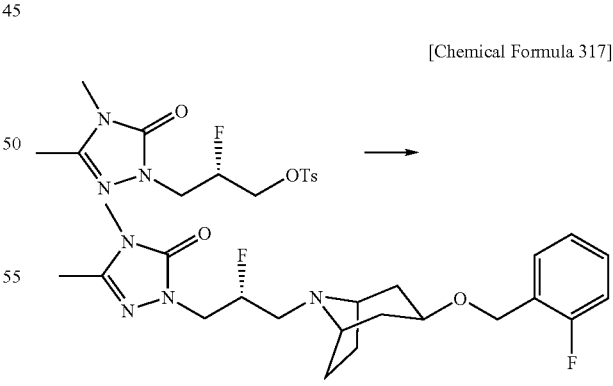

The title compound (71 mg) was obtained from the compound obtained in Example 1-(3) (100 mg) and the compound obtained in Production Example 56 (79 mg), by the method similar to Example 1-(4).

¹H-NMR (400 MHz, CD₃OD); δ 1.54-1.70 (m, 4H), 1.84-2.00 (m, 4H), 2.23 (s, 3H), 2.70-2.80 (m, 2H), 3.22 (s, 3H), 3.26-3.39 (m, 2H), 3.70-3.89 (m, 1H), 3.87-4.13 (m, 2H), 4.56 (s, 2H), 4.78-4.97 (m, 1H), 7.03-7.09 (m, 1H), 7.14 (td, J=7.6, 1.2 Hz, 1H), 7.27-7.34 (m, 1H), 7.41 (td, J=7.6, 1.6 Hz, 1H).

Example 199

(Endo)-2-{(R)-2-fluoro-3-[3-(2-trifluoromethylbenzyloxy)-8-azabicyclo[3.2.1]oct-8-yl]propyl}-4,5-dimethyl-2,4-dihydro[1,2,4]triazol-3-one

[Chemical Formula 318]

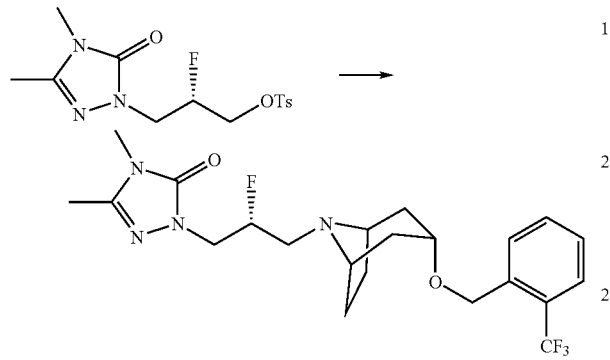

The title compound (79 mg) was obtained from the compound obtained in Example 1-(3) (100 mg) and the compound obtained in Production Example 13 (94 mg), by the method similar to Example 1-(4).

$^1$H-NMR (400 MHz, CD$_3$OD); δ1.85-2.15 (m, 8H), 2.24 (s, 3H), 2.59-2.76 (m, 2H), 3.19-3.33 (m, 2H); 3.23 (s, 3H), 3.65 (t, J=4.8 Hz, 1H), 3.87-4.11 (m, 2H), 4.62 (s, 2H), 4.79-4.98 (m, 1H), 7.43 (t, J=7.6 Hz, 1H), 7.61 (t, J=7.6 Hz, 1H), 7.66 (d, J=7.6 Hz, 1H), 7.73 (t, J=7.6 Hz, 1H).

Example 200

(Endo)-2-{(R)-2-fluoro-3-[3β-methyl-3α-(2-methylbenzyloxy)-8-azabicyclo[3.2.1]oct-8-yl]propyl}-4,5-dimethyl-2,4-dihydro[1,2,4]triazol-3-one

[Chemical Formula 319]

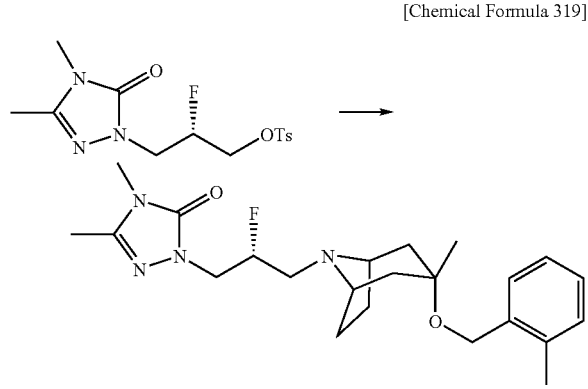

The title compound (75 mg) was obtained from the compound obtained in Example 1-(3) (100 mg) and the compound obtained in Production Example 23 (82 mg), by the method similar to Example 1-(4).

$^1$H-NMR (400 MHz, CD$_3$OD); δ 1.21 (s, 3H), 1.75-1.87 (m, 4H), 1.95-2.04 (m, 4H), 2.24 (s, 3H), 2.31 (s, 3H), 2.59-2.76 (m, 2H), 3.16-3.37 (m, 2H), 3.23 (s, 3H), 3.86-4.11 (m, 2H), 4.61 (s, 2H), 4.77-4.98 (m, 1H), 7.09-7.18 (m, 3H), 7.31-7.37 (m, 1H).

Example 201

(Endo)-2-{(R)-2-fluoro-3-[3-(3-naphthalen-2-ylmethoxy)-8-azabicyclo[3.2.1]oct-8-yl]propyl}-4,5-dimethyl-2,4-dihydro[1,2,4]triazol-3-one

[Chemical Formula 320]

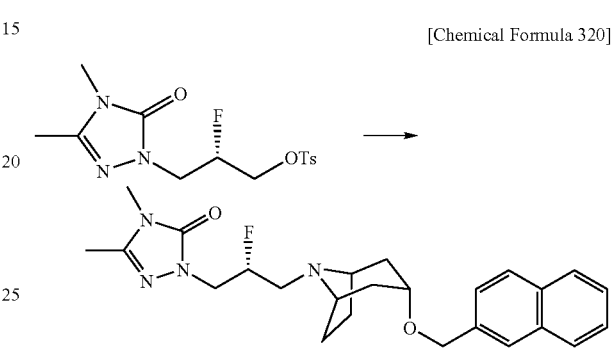

The title compound (81 mg) was obtained from the compound obtained in Example 1-(3) (100 mg) and the compound obtained in Production Example 70 (89 mg), by the method similar to Example 1-(4).

$^1$H-NMR (400 MHz, CD$_3$OD); δ 1.84-2.20 (m, 8H), 2.23 (s, 3H), 2.59-2.76 (m, 2H), 3.18-3.38 (m, 2H), 3.23 (s, 3H), 3.67 (t, J=4.8 Hz, 1H), 3.87-4.11 (m, 2H), 4.62 (s, 2H), 4.78-4.98 (m, 1H), 7.41-7.50 (m, 3H), 7.75-7.88 (m, 4H).

Example 202

(Endo)-2-{(R)-2-fluoro-3-[3-(4-methoxybenzylsulfanyl)-8-azabicyclo[3.2.1]oct-8-yl]propyl}-4,5-dimethyl-2,4-dihydro[1,2,4]triazol-3-one

[Chemical Formula 321]

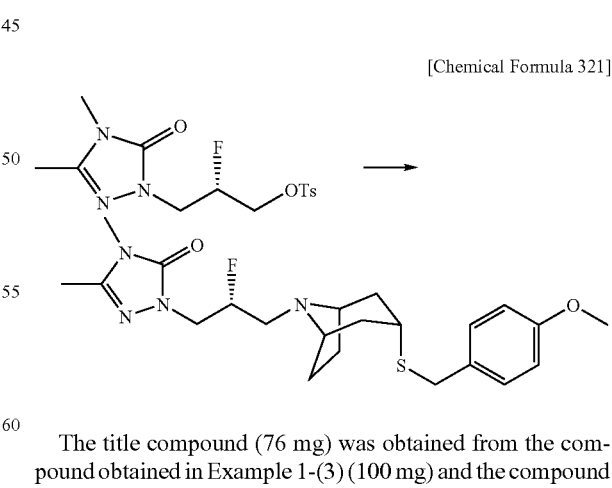

The title compound (76 mg) was obtained from the compound obtained in Example 1-(3) (100 mg) and the compound obtained in Production Example 73 (88 mg), by the method similar to Example 1-(4).

$^1$H-NMR (400 MHz, CD$_3$OD); δ 1.65-1.73 (m, 2H), 1.88-2.00 (m, 2H), 2.08-2.28 (m, 4H), 2.23 (s, 3H), 2.56-2.70 (m, 2H), 2.87 (t, J=7.6 Hz, 1H), 3.17-3.37 (m, 2H), 3.22 (s, 3H), 3.68 (s, 2H), 3.76 (s, 3H), 3.84-4.09 (m, 2H), 4.75-4.95 (m, 1H), 6.80-6.86 (m, 2H), 7.16-7.24 (m, 2H).

TEST EXAMPLES

Test Example 1

Pharmacological Effects on TTX-Resistant Na Channels in Cells Expressing Human Nav1.8 Gene A cell line expressing human Nav1.8 gene was used to evaluate the pharmacological effects of compounds of the invention.

Specifically, a test compound was pre-added to cells expressing human Nav1.8, and approximately 15 minutes thereafter, deltamethrin, a Nav1.8 channel stimulant, was added in the presence of tetrodotoxin (TTX) to increase the membrane potential via TTX-resistant Na channels, and the membrane potential increase-inhibitory action of the test compound was evaluated.

1. A membrane potential-sensitive dye containing TTX (final concentration: 0.25 µM) was added to cells expressing human Nav1.8, prior to incubation at 37° C. for 30-60 minutes.
2. The test compound was added to the cells, and the mixture was stationed for 15-30 minutes at room temperature while shielded from light.
3. Deltamethrin (final concentration: 50 µM), a Nav1.8 channel stimulant, was added, and the change in fluorescence intensity due to increased membrane potential was measured.

Pharmacological Evaluation

The Nav1.8 channel inhibition of the test compound was determined by the following equation.

Nav1.8 channel inhibition (%)=100×[(AUC in the case of deltamethrin stimulation alone in absence of a test compound)−(AUC in the case of deltamethrin stimulation in the presence of a test compound)/(AUC in the case of deltamethrin stimulation alone in the absence of a test compound)−(AUC in the case of deltamethrin stimulation in the presence of 30 µM desipramine which completely inhibits Nav1.8 channels)]

Test Results

Table 1 shows the Nav1.8 channel-inhibitory activity ($IC_{50}$) of the example compounds used in Test Example 1.

TABLE 1

| Example | IC50 (µM) |
| --- | --- |
| 1 | 3.2 |
| 4 | 5.0 |
| 6 | 5.2 |
| 7 | 4.3 |
| 12 | 8.7 |
| 13 | 10 |
| 15 | 2.4 |
| 21 | 4.0 |
| 23 | 5.3 |
| 24 | 3.7 |
| 25 | 0.71 |
| 31 | 1.0 |
| 34 | 16 |
| 35 | 14 |
| 47 | 1.3 |
| 48 | 0.20 |
| 55 | 12 |
| 57 | 0.080 |
| 58 | 0.13 |
| 66 | 5.4 |
| 91 | 0.17 |

TABLE 1-continued

| Example | IC50 (µM) |
| --- | --- |
| 101 | 2.7 |
| 102 | 2.8 |
| 112 | 12 |
| 116 | 5.8 |
| 128 | 3.7 |
| 129 | 9.8 |
| 136 | 4.9 |
| 145 | 0.53 |
| 149 | 0.28 |
| 153 | 3.7 |
| 155 | 1.3 |
| 157 | 1.2 |
| 158 | 0.93 |
| 169 | 12 |
| 174 | 0.89 |
| 179 | 8.7 |
| 180 | 4.8 |
| 182 | 6.7 |
| 184 | 7.6 |
| 189 | 3.8 |
| 190 | 0.030 |

Test Example 2

Suppression of Ectopic Firing (1) The suppressing effect on ectopic firing was evaluated by the following method, with reference to Burchiel, K J., Exp. Neurol., 102, 249-253 (1988).
(2) Using rats that exhibited ectopic firing, the left saphenous nerve was cut near the knee joint one week prior to the test, removing approximately 3 mm to prevent reattachment of the nerve. The left saphenous nerve was exposed under urethane anesthesia (1 g/kg body weight), and an area approximately 1 cm adjacent to the cutting site was removed from the surrounding tissue. A catheter was inserted into the right cervical vein for administration of the compound.
(3) The removed nerve was placed on a platinum hook electrode and covered with liquid paraffin to avoid drying of the nerve. The electrode was connected to a microelectrode amp, and the change in potential was recorded on a computer from an oscilloscope, via an A/D converter. The recorded nerve firing was evaluated based on the number of firings every 10 seconds, using analysis software (Acq-Knowledge).

Test Results

Table 2 shows the suppressing activities of the example compounds on ectopic firing in Test Example 2.

TABLE 2

| Example | ED50 (mg/kg) |
| --- | --- |
| 1 | 0.14 |
| 4 | 0.23 |
| 6 | 0.27 |
| 12 | 0.28 |
| 25 | <0.10 |
| 47 | 0.18 |
| 58 | 0.18 |
| 112 | 0.29 |
| 116 | 0.15 |
| 129 | 0.13 |
| 145 | 0.28 |
| 149 | 0.15 |
| 157 | 0.28 |
| 174 | 0.21 |

TABLE 2-continued

| Example | ED50 (mg/kg) |
|---|---|
| 179 | 0.14 |
| 184 | 0.19 |

As explained above, the present invention can provide novel bicycloamine compounds and pharmaceutically acceptable salts thereof that have excellent sodium channel inhibitory activity, and high utility as drugs when comprehensively considered from the viewpoint of pharmacological activity, as well as novel pharmaceutical compositions comprising the same. The compounds of the invention and pharmaceutical compositions comprising the same can exhibit excellent therapeutic effect for diseases for which sodium channel inhibition is effective, and are promising as therapeutic agents and analgesics for various kinds of neuralgia (for example, diabetic neuralgia, HIV-induced neuralgia, postherpetic neuralgia, trigeminal neuralgia, stump pain, post-spinal cord injury pain, thalamic pain and post-apoplectic pain), neuropathy, epilepsy, insomnia, premature ejaculation and the like.

What is claimed is:

1. A compound represented by the formula (I) or pharmaceutically acceptable salt thereof:

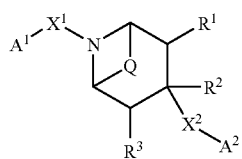

(I)

wherein
Q represents ethylene or trimethylene,
$R^1$, $R^2$ and $R^3$ each independently represents hydrogen, halogen or hydroxy, or $C_{1-6}$ alkyl or $C_{1-6}$ alkoxy each optionally having one or more substituents selected from the group consisting of Group A,
$X^1$ represents, cyclopropane-1,2-dimethylene, or $C_{1-6}$ alkylene or $C_{2-6}$ alkenylene each optionally having one or more substituents selected from the group consisting of Group B,
$X^2$ represents $C_{1-6}$ alkylene, $C_{1-6}$ alkyleneoxy, oxy$C_{1-6}$ alkylene, $C_{1-6}$ alkylenethio, thio-$C_{1-6}$ alkylene, $C_{1-6}$ alkyleneoxy-$C_{1-6}$ alkylene, $C_{2-6}$ alkenylene, oxycarbonyl, carbonyloxy, $C_{1-6}$ alkyleneamnino, amino-$C_{1-6}$ alkylene, aminocarbonyl, carbonylamino, $C_{1-6}$ alkyleneaminocarbonyl, carbonylamino-$C_{1-6}$ alkylene, oxycarbonylamino, aminocarbonyloxy or ureylene each optionally having one or more substituents selected from the group consisting of Group C,
$A^1$ is a group represented by the formula:

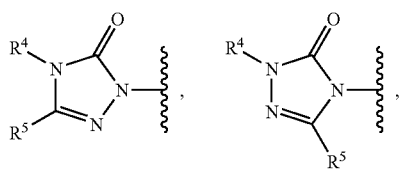

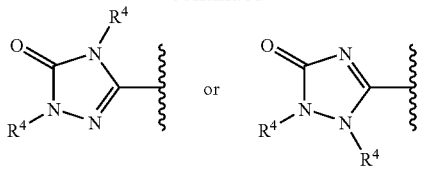

wherein
$R^4$ independently repesents hydrogen or $C_{1-6}$ alkyl, $C_{2-6}$ alkenyl, $C_{3-8}$ cycloalkyl, $C_{3-8}$ cycloalkylmethyl, $C_{6-10}$ aryl, $C_{7-11}$ aralkyl or a 5- to 6-membered aromatic heterocyclic group each optionally having one or more substituents selected from the group consigting of Group D1, and
$R^5$ represents hydrogen, halogen, hydroxy, or amino optionally having one or two $C_{1-6}$ alkyl, or $C_{1-6}$ alkyl, $C_{2-6}$ alkenyl, $C_{3-8}$ cycloalkyl, $C_{3-8}$ cycloalkylmethyl, $C_{1-6}$ alkylthio, $C_{1-6}$ alkylsulfonyl, $C_{6-10}$ aryl, $C_{7-11}$ aralkyl or a 5- to 6-membered aromatic heterocyclic group each optionally having one or more-substituents selected from the group consisting of Group D1,
$A^2$ represents $C_{3-8}$ cycloalkyl, $C_{6-14}$ aryl, a 5- to 6-membered aromatic heterocyclic group or a 9- to 11-membered benzo-fused heterocyclic group each optionally having one or more substituents selected from Group E,
Group A: halogen, hydroxy and $C_{1-6}$ alkoxy,
Group B: halogen, hydroxy, oxo, cyano, amino, $C_{1-6}$ alkyl, halo-$C_{1-6}$ alkyl, hydroxy-$C_{1-6}$ alkyl, $C_{1-6}$ alkoxy-$C_{1-6}$ alkyl, $C_{1-6}$ alkoxy, $C_{1-6}$ alkylcarbonylamino, $C_{1-6}$ alkoxycarbonylamino, $C_{1-6}$ alkylsulfonylamino, hydroxyimino and $C_{1-6}$ alkoxyimino,
Group C: halogen, hydroxy, $C_{1-6}$ alkoxy, oxo and $C_{1-6}$ alkyl,
Group D1: halogen, hydroxy, $C_{1-6}$ alkyl and $C_{1-6}$ alkoxy,
Group E: halogen, cyano, hydroxy, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl, and $C_{6-10}$ aryl, a 5- to 6-membered heterocyclic group and a 5- to 6-membered aromatic heterocyclic group each optionally having one or more substituents selected from the group consisting of Group E1, and
Group E1: halogen, $C_{1-6}$ alkyl, halo-$C_{1-6}$ alkyl, $C_{1-6}$ alkoxy and halo-$C_{1-6}$ alkoxy.

2. The compound or pharmaceutically acceptable salt thereof of claim 1, wherein
$A^2$ is phenyl, thienyl, benzothienyl or naphthyl each optionally having one or more substituents selected from the group consisting of Group E2,
Group E2: halogen, cyano, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl, and phenyl, furyl, pyridyl, pyrazinyl, pyrrolidinyl, piperidinyl and morpholinyl each optionally having one or more substituents selected from the group consisting Group E3, and
Group E3: halogen, $C_{1-6}$ alkyl, halo-$C_{1-6}$ alkyl, $C_{1-6}$ alkoxy and halo-$C_{1-6}$ alkoxy.

3. The compound or pharmaceutically acceptable salt thereof of claim 1, wherein
$X^2$ is $C_{1-6}$ alkylene, $C_{1-6}$ alkyleneoxy or oxy-$C_{1-6}$ alkylene each optionally having one or more substituents selected from the group consisting of Group C1, and
Group C1: halogen, hydroxy, $C_{1-6}$ alkoxy, oxo and $C_{1-6}$ alkyl.

4. The compound or pharmaceutically acceptable salt of claim 1, wherein Q is ethylene.

5. The compound or pharmaceutically acceptable salt thereof of claim 1, wherein
$A^1$ is a group represented by the formula:

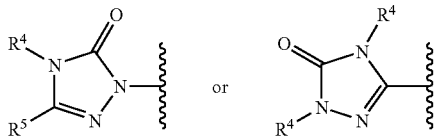

or wherein $R^4$ and $R^5$ have the same definitions as in claim 1.

6. The compound or pharmaceutically acceptable salt thereof of claim 5, wherein
- $X^1$ is $C_{2-6}$ alkylene optionally having one or more substituents selected from the group consisting of Group B1,
- Group B1: halogen, amino, acetamide, methoxyacetamide, methanesulfonylamide, hydroxy, oxo, cyano, $C_{1-6}$ alkyl, hydroxy-$C_{1-6}$ alkyl, halo-$C_{1-6}$ alkyl, $C_{1-6}$ alkoxy-$C_{1-6}$ alkyl and $C_{1-6}$ alkoxy,
- $X^2$ is $C_{1-6}$ alkylene, $C_{1-6}$ alkyleneoxy or oxy-$C_{1-6}$ alkylene each optionally having one or more substituents selected from the group consisting of Group C1,
- Group C1: halogen, hydroxy, $C_{1-6}$ alkoxy, oxo and $C_{1-6}$ alkyl,
- $A^2$ is phenyl or thienyl each optionally having one or more substituents selected from the group consisting of Group E2, and
- Group E2: halogen, cyano, $C_{1-6}$ alkyl, halo-$C_{1-6}$ alkyl, $C_{1-6}$ alkoxy-$C_{1-6}$ alkyl, $C_{1-6}$ alkoxy, halo-$C_{1-6}$ alkoxy and $C_{2-7}$ acyl.

7. The compound or pharmaceutically acceptable salt thereof of claim 1, wherein the compound represented by formula (I) is a compound represented by the formula:

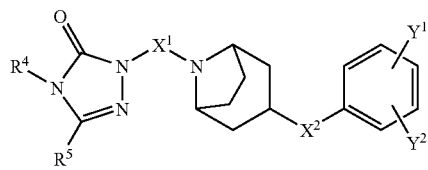

wherein
- $Y^1$ and $Y^2$ each independently represents hydrogen, halogen, hydroxy, $C_{1-6}$ alkyl, halo-$C_{1-6}$ alkyl, $C_{1-6}$ alkoxy-$C_{1-6}$ alkyl, $C_{1-6}$ alkoxy or halo-$C_{1-6}$ alkoxy,
- $X^1$ represents $C_{2-6}$ alkylene optionally having one or more substituents selected from the group consisting of halogen, amino, acetamide, methoxyacetamide, methanesulfonylamide, hydroxy, oxo, cyano, $C_{1-6}$ alkyl, hydroxy-$C_{1-6}$ alkyl, halo-$C_{1-6}$ alkyl, $C_{1-6}$ alkoxy-$C_{1-6}$ alkyl and $C_{1-6}$ alkoxy,
- $X^2$ represents $C_{1-6}$ alkylene, $C_{1-6}$ alkyleneoxy or oxy-$C_{1-6}$ alkylene each optionally having one or more substituents selected from the group consisting of halogen, hydroxy, $C_{1-6}$ alkoxy, oxo and $C_{1-6}$ alkyl, and
- $R^4$ and $R^5$ have the same definitions as in claim 1.

8. The compound or pharmaceutically acceptable salt thereof of claim 7, wherein
$X^1$ is $C_{2-6}$ alkylene optionally having one or more substituents selected from the group consisting of B2, and
Group B2: halogen and hydroxy.

9. A pharmaceutical composition comprising
the compound or pharmaceutically acceptable salt thereof of claim 1 and
a pharmaceutically acceptable carrier.

* * * * *